United States Patent
Haq et al.

(10) Patent No.: US 9,980,964 B2
(45) Date of Patent: *May 29, 2018

(54) ERK INHIBITORS AND USES THEREOF

(71) Applicant: Celgene CAR LLC, Pembroke (BM)

(72) Inventors: Nadia Haq, Lexington, MA (US);
Deqiang Niu, Lexington, MA (US);
Russell C. Petter, Stow, MA (US);
Lixin Qiao, Andover, MA (US);
Juswinder Singh, Southborough, MA (US); Zhendong Zhu, Westborough, MA (US)

(73) Assignee: CELGENE CAR LLC, Pembroke (BM)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/422,617

(22) Filed: Feb. 2, 2017

(65) Prior Publication Data

US 2017/0210729 A1    Jul. 27, 2017

Related U.S. Application Data

(62) Division of application No. 14/768,190, filed as application No. PCT/US2014/015256 on Feb. 7, 2014, now Pat. No. 9,561,228.

(Continued)

(51) Int. Cl.

| A61K 31/506 | (2006.01) |
| A61K 31/505 | (2006.01) |
| C07D 405/12 | (2006.01) |
| C07D 401/12 | (2006.01) |
| C07D 239/48 | (2006.01) |
| C07D 403/12 | (2006.01) |
| C07D 401/14 | (2006.01) |
| C07D 239/47 | (2006.01) |

(52) U.S. Cl.
CPC .......... *A61K 31/505* (2013.01); *A61K 31/506* (2013.01); *C07D 239/47* (2013.01); *C07D 239/48* (2013.01); *C07D 401/12* (2013.01); *C07D 401/14* (2013.01); *C07D 403/12* (2013.01); *C07D 405/12* (2013.01)

(58) Field of Classification Search
CPC ... A61K 31/505; A61K 31/506; C07D 239/48
USPC .......................................... 514/275; 544/323
See application file for complete search history.

(56) References Cited

U.S. PATENT DOCUMENTS 3,609,152 A    9/1971  Hess et al.
4,337,341 A    6/1982  Zimmerman
(Continued)

FOREIGN PATENT DOCUMENTS

AU    2009251863 A1    12/2009
CA       2375182 A1    12/2000
(Continued)

OTHER PUBLICATIONS

U.S. Appl. No. 13/518,833, filed Jun. 22, 2012, Gray et al.
(Continued)

*Primary Examiner* — Craig D Ricci
*Assistant Examiner* — Janet L. Coppins
(74) *Attorney, Agent, or Firm* — Choate, Hall & Stewart LLP; Kristen C. Buteau

(57) ABSTRACT

The present invention provides compounds, compositions thereof, and methods of using the same.

28 Claims, 2 Drawing Sheets

Amino Acid Sequence of ERK1
SEQ ID NO. 1

```
           10         20         30         40         50         60
    MAAAAAQGGG GGEPRRTEGV GPGVPGEVEM VKGQPFDVGP RYTQLQYIGE GAYGMVSSAY 70         80         90        100        110        120
    DHVRKTRVAI KKISPFEHQT YCQRTLREIQ ILLRFRHENV IGIRDILRAS TLEAMRDVYI 130        140        150        160        170        180
    VQDLMETDLY KLLKSQQLSN DHICYFLYQI LRGLKYIHSA NVLHRDLKPS NLLINTTCDL 190        200        210        220        230        240
    KICDFGLARI ADPEHDHTGF LTEYVATRWY RAPEIMLNSK GYTKSIDIWS VGCILAEMLS 250        260        270        280        290        300
    NRPIFPGKHY LDQLNHILGI LGSPSQEDLN CIINMKARNY LQSLPSKTKV AWAKLFPKSD 310        320        330        340        350        360
    SKALDLLDRM LTFNPNKRIT VEEALAHPYL EQYYDPTDEP VAEEPFTFAM ELDDLPKERL

370
    KELIFQETAR FQPGVLEAP
```

Related U.S. Application Data

(60) Provisional application No. 61/785,126, filed on Mar. 14, 2013, provisional application No. 61/762,408, filed on Feb. 8, 2013.

(56) References Cited

U.S. PATENT DOCUMENTS

| | | | |
|---|---|---|---|
| 4,879,303 | A | 11/1989 | Davison et al. |
| 5,786,476 | A | 7/1998 | Fuso |
| 5,958,935 | A | 9/1999 | Davis et al. |
| 6,093,716 | A | 7/2000 | Davis et al. |
| 6,114,333 | A | 9/2000 | Davis et al. |
| 6,127,376 | A | 10/2000 | Davey et al. |
| 6,160,010 | A | 12/2000 | Uckun et al. |
| 6,262,088 | B1 | 7/2001 | Phillips |
| 6,469,168 | B1 | 10/2002 | Ratzne Simonek et al. |
| 6,579,983 | B1 | 6/2003 | Batchelor et al. |
| 6,593,326 | B1 | 7/2003 | Bradbury et al. |
| 6,838,464 | B2 | 1/2005 | Pease et al. |
| 6,878,717 | B2 | 4/2005 | De Corte et al. |
| 6,908,906 | B2 | 6/2005 | Takita et al. |
| 6,939,874 | B2 | 9/2005 | Harmange et al. |
| 7,037,917 | B2 | 5/2006 | De Corte et al. |
| 7,060,827 | B2 | 6/2006 | Singh et al. |
| 7,122,542 | B2 | 10/2006 | Singh et al. |
| 7,125,879 | B2 | 10/2006 | Guillemont et al. |
| 7,176,212 | B2 | 2/2007 | Breault et al. |
| 7,202,033 | B2 | 4/2007 | Prescott et al. |
| 7,241,769 | B2 | 7/2007 | Stadtmueller et al. |
| 7,276,510 | B2 | 10/2007 | Kukla et al. |
| 7,282,504 | B2 | 10/2007 | Armistead et al. |
| 7,288,547 | B2 | 10/2007 | Lucking et al. |
| 7,329,671 | B2 | 2/2008 | Singh et al. |
| 7,329,672 | B2 | 2/2008 | Singh et al. |
| 7,332,484 | B2 | 2/2008 | Singh et al. |
| 7,432,377 | B2 | 10/2008 | Chew et al. |
| 7,435,814 | B2 | 10/2008 | Singh et al. |
| 7,449,458 | B2 | 11/2008 | Bhamidipati et al. |
| 7,452,879 | B2 | 11/2008 | Singh et al. |
| 7,485,724 | B2 | 2/2009 | Singh et al. |
| 7,491,732 | B2 | 2/2009 | Li et al. |
| 7,498,435 | B2 | 3/2009 | Singh et al. |
| 7,500,137 | B2 | 3/2009 | Park |
| 7,504,396 | B2 | 3/2009 | Nunes et al. |
| 7,514,444 | B2 | 4/2009 | Honigberg et al. |
| 7,514,445 | B2 | 4/2009 | Freyne et al. |
| 7,514,446 | B2 | 4/2009 | Davis-Ward et al. |
| 7,517,886 | B2 | 4/2009 | Singh et al. |
| 7,528,143 | B2 | 5/2009 | Noronha et al. |
| 7,531,548 | B2 | 5/2009 | Guillemont et al. |
| 7,540,908 | B2 | 6/2009 | Sao et al. |
| 7,540,909 | B2 | 6/2009 | Sao et al. |
| 7,550,460 | B2 | 6/2009 | Singh et al. |
| 7,553,357 | B2 | 6/2009 | Sao et al. |
| 7,557,207 | B2 | 7/2009 | Cooper et al. |
| 7,557,210 | B2 | 7/2009 | Singh et al. |
| 7,582,648 | B2 | 9/2009 | Singh et al. |
| 7,589,200 | B2 | 9/2009 | Singh et al. |
| 7,642,351 | B2 | 1/2010 | Singh et al. |
| 7,655,797 | B2 | 2/2010 | Singh et al. |
| 7,659,280 | B2 | 2/2010 | Clough et al. |
| 7,713,987 | B2 | 5/2010 | Bhamidipati et al. |
| 7,718,662 | B1 | 5/2010 | Chen et al. |
| 7,741,330 | B1 | 6/2010 | Chen et al. |
| 7,803,939 | B2 | 9/2010 | Singh et al. |
| 7,812,029 | B1 | 10/2010 | Singh et al. |
| 7,820,819 | B2 | 10/2010 | Singh et al. |
| 7,825,116 | B2 | 11/2010 | Singh et al. |
| 7,834,024 | B2 | 11/2010 | Li et al. |
| 7,858,633 | B2 | 12/2010 | Li et al. |
| 7,863,286 | B2 | 1/2011 | Argade et al. |
| 7,879,984 | B2 | 2/2011 | Martin et al. |
| 7,884,111 | B2 | 2/2011 | Argade et al. |
| 7,893,074 | B2 | 2/2011 | Garcia-Echeverria et al. |
| 7,906,644 | B2 | 3/2011 | Singh et al. |
| 7,915,273 | B2 | 3/2011 | Argade et al. |
| 7,947,698 | B2 | 5/2011 | Atuegbu et al. |
| 7,989,465 | B2 | 8/2011 | Singh et al. |
| 8,003,789 | B2 | 8/2011 | De Corte et al. |
| 8,088,781 | B2 | 1/2012 | Honigberg et al. |
| 8,133,900 | B2 | 3/2012 | Hood et al. |
| 8,148,525 | B2 | 4/2012 | Singh et al. |
| 8,153,640 | B2 | 4/2012 | Guillemont et al. |
| 8,158,621 | B2 | 4/2012 | Singh et al. |
| 8,163,902 | B2 | 4/2012 | Bhamidipati et al. |
| 8,188,276 | B2 | 5/2012 | Singh et al. |
| 8,193,197 | B2 | 6/2012 | Li et al. |
| 8,206,711 | B2 | 6/2012 | White et al. |
| 8,263,590 | B2 | 9/2012 | Garcia-Echeverria et al. |
| 8,299,087 | B2 | 10/2012 | Li et al. |
| 8,304,422 | B2 | 11/2012 | Atuegbu et al. |
| 8,334,296 | B2 | 12/2012 | Singh et al. |
| 8,338,439 | B2 | 12/2012 | Singh et al. |
| 8,399,433 | B2 | 3/2013 | Appari et al. |
| 8,399,450 | B2 | 3/2013 | Michellys et al. |
| 8,399,472 | B2 | 3/2013 | Li et al. |
| 8,410,266 | B2 | 4/2013 | Singh et al. |
| 8,415,365 | B2 | 4/2013 | Li et al. |
| 8,450,335 | B2 | 5/2013 | Singh et al. |
| 8,501,751 | B2 | 8/2013 | Honigberg et al. |
| 8,530,466 | B2 | 9/2013 | Masuda et al. |
| 8,530,655 | B2 | 9/2013 | De Corte et al. |
| 8,557,806 | B2 | 10/2013 | Singh et al. |
| 8,563,568 | B2 | 10/2013 | Witowski et al. |
| 8,609,679 | B2 | 12/2013 | Singh et al. |
| 8,697,694 | B2 | 4/2014 | Arasappan et al. |
| 8,710,222 | B2 | 4/2014 | Singh et al. |
| 8,735,404 | B2 | 5/2014 | Honigberg et al. |
| 8,748,438 | B2 | 6/2014 | Honigberg et al. |
| 8,748,597 | B2 | 6/2014 | Singh et al. |
| 8,796,255 | B2 | 8/2014 | Lee et al. |
| 8,822,685 | B2 | 9/2014 | Singh et al. |
| 8,835,430 | B2 | 9/2014 | Singh et al. |
| 8,853,397 | B2 | 10/2014 | Singh et al. |
| 8,883,435 | B2 | 11/2014 | Honigberg et al. |
| 8,883,803 | B2 | 11/2014 | Honigberg et al. |
| 8,975,249 | B2 | 3/2015 | Lee et al. |
| 9,012,462 | B2 | 4/2015 | Wang et al. |
| 9,145,387 | B2 * | 9/2015 | Haq .................. C07D 401/12 |
| 9,504,686 | B2 | 11/2016 | Haq et al. |
| 9,561,228 | B2 | 2/2017 | Haq et al. |
| 2002/0147339 | A1 | 10/2002 | Batchelor et al. |
| 2004/0002395 | A1 | 1/2004 | Poynor |
| 2004/0019067 | A1 | 1/2004 | Armistead et al. |
| 2004/0023957 | A1 | 2/2004 | Wang et al. |
| 2004/0077661 | A1 | 4/2004 | Arbiser |
| 2004/0180914 | A1 | 9/2004 | Batchelor et al. |
| 2005/0004125 | A1 | 1/2005 | Freyne et al. |
| 2005/0014753 | A1 | 1/2005 | Ding et al. |
| 2005/0085637 | A1 | 4/2005 | Cheung et al. |
| 2005/0209221 | A1 | 9/2005 | Nunes et al. |
| 2005/0272083 | A1 | 12/2005 | Seshagiri |
| 2006/0030018 | A1 | 2/2006 | Zuccola et al. |
| 2006/0079543 | A1 | 4/2006 | Sum et al. |
| 2006/0084644 | A1 | 4/2006 | Pal et al. |
| 2006/0084645 | A1 | 4/2006 | Pal et al. |
| 2006/0100227 | A1 | 5/2006 | Baenteli et al. |
| 2006/0148800 | A1 | 7/2006 | Stadtmueller et al. |
| 2006/0160803 | A1 | 7/2006 | Adams et al. |
| 2006/0247241 | A1 | 11/2006 | Garcia-Echeverria et al. |
| 2006/0247262 | A1 | 11/2006 | Baenteli et al. |
| 2006/0270694 | A1 | 11/2006 | Wong |
| 2006/0293311 | A1 | 12/2006 | Li et al. |
| 2007/0010668 | A1 | 1/2007 | Davis-Ward et al. |
| 2007/0032493 | A1 | 2/2007 | Foley et al. |
| 2007/0066658 | A1 | 3/2007 | Chappell |
| 2007/0141143 | A1 | 6/2007 | Smithey et al. |
| 2007/0203161 | A1 | 8/2007 | Argade et al. |
| 2007/0203162 | A1 | 8/2007 | Li et al. |
| 2007/0208022 | A1 | 9/2007 | Guillemont et al. |
| 2007/0208034 | A1 | 9/2007 | Stadlwieser |
| 2007/0259904 | A1 | 11/2007 | Noronha et al. |
| 2008/0009484 | A1 | 1/2008 | Argade et al. |
| 2008/0009494 | A1 | 1/2008 | Li et al. |

(56) References Cited

U.S. PATENT DOCUMENTS

| | | |
|---|---|---|
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0176866 A1 | 7/2008 | Jautelat et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0207913 A1 | 8/2008 | Breitenkamp et al. |
| 2008/0214501 A1 | 9/2008 | Pan et al. |
| 2008/0221089 A1 | 9/2008 | Argade et al. |
| 2008/0260754 A1 | 10/2008 | Li et al. |
| 2008/0261977 A1 | 10/2008 | Eatherton et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0030197 A1 | 1/2009 | Chew et al. |
| 2009/0088371 A1 | 4/2009 | Grossbard |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0144706 A1 | 6/2010 | Zahn et al. |
| 2010/0173285 A1 | 7/2010 | Varmus et al. |
| 2010/0197918 A1 | 8/2010 | Singh et al. |
| 2010/0249092 A1* | 9/2010 | Singh .............. C07D 239/47 514/210.18 |
| 2010/0254905 A1 | 10/2010 | Honigberg et al. |
| 2011/0027856 A1 | 2/2011 | Li et al. |
| 2011/0028405 A1 | 2/2011 | Harrison et al. |
| 2011/0039868 A1 | 2/2011 | Honigberg et al. |
| 2011/0071158 A1 | 3/2011 | Sapountzis et al. |
| 2011/0098280 A1 | 4/2011 | Garcia-Echeverria et al. |
| 2011/0098288 A1 | 4/2011 | Major et al. |
| 2011/0105472 A1 | 5/2011 | Greul et al. |
| 2011/0144330 A1 | 6/2011 | Singh et al. |
| 2011/0190261 A1 | 8/2011 | Dong et al. |
| 2011/0207736 A1 | 8/2011 | Gray et al. |
| 2011/0212077 A1 | 9/2011 | Noronha et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0021434 A1 | 1/2012 | Foley et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1 | 3/2012 | Witowski et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0142667 A1 | 6/2012 | Ramsden et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2012/0165328 A1 | 6/2012 | Honigberg et al. |
| 2012/0165332 A1 | 6/2012 | Major et al. |
| 2012/0172385 A1 | 7/2012 | Harrison et al. |
| 2012/0184013 A1 | 7/2012 | Honigberg et al. |
| 2012/0184567 A1 | 7/2012 | Honigberg et al. |
| 2012/0190697 A1 | 7/2012 | Guillemont et al. |
| 2012/0202264 A1 | 8/2012 | Honigberg et al. |
| 2012/0213795 A1 | 8/2012 | Li et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0109709 A1 | 5/2013 | Witowski et al. |
| 2013/0137708 A1 | 5/2013 | Garske et al. |
| 2013/0142807 A1 | 6/2013 | Li et al. |
| 2013/0150349 A1 | 6/2013 | Singh et al. |
| 2013/0165462 A1 | 6/2013 | Singh et al. |
| 2013/0231306 A1 | 9/2013 | Crew et al. |
| 2013/0267530 A1 | 10/2013 | Lai |
| 2013/0267531 A1 | 10/2013 | Lai et al. |
| 2014/0057929 A1 | 2/2014 | Witowski et al. |
| 2014/0134265 A1 | 5/2014 | Buggy et al. |
| 2014/0140991 A1 | 5/2014 | Daniel et al. |
| 2014/0142123 A1 | 5/2014 | Honigberg et al. |
| 2014/0142128 A1 | 5/2014 | Daniel et al. |
| 2014/0142129 A1 | 5/2014 | Daniel et al. |
| 2014/0163027 A1 | 6/2014 | Verner et al. |
| 2014/0163046 A1 | 6/2014 | Honigberg et al. |
| 2014/0179720 A1 | 6/2014 | Tester et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2014/0228322 A1 | 8/2014 | Haq et al. |
| 2014/0303154 A1 | 10/2014 | Singh et al. |
| 2014/0303191 A1 | 10/2014 | Buggy et al. |
| 2014/0330007 A1 | 11/2014 | Singh et al. |
| 2014/0371241 A1 | 12/2014 | Buggy et al. |
| 2015/0005297 A1 | 1/2015 | Singh et al. |
| 2015/0025055 A1 | 1/2015 | Lee et al. |
| 2015/0038518 A1 | 2/2015 | Balasubramanian |
| 2016/0002176 A1 | 1/2016 | Haq et al. |
| 2016/0082008 A1 | 3/2016 | Haq et al. |

FOREIGN PATENT DOCUMENTS

| | | |
|---|---|---|
| CA | 2463822 A1 | 5/2003 |
| CA | 2553729 A1 | 8/2005 |
| CA | 2608367 A1 | 12/2006 |
| CA | 2673125 A1 | 4/2008 |
| CA | 2710118 A1 | 7/2009 |
| CA | 2717529 A1 | 9/2009 |
| CA | 2757671 A1 | 10/2010 |
| CA | 2760061 A1 | 11/2010 |
| CA | 2763720 A1 | 12/2010 |
| CN | 102558149 A | 7/2012 |
| CN | 103159742 A | 6/2013 |
| CN | 103664878 A | 3/2014 |
| EP | 1 054 004 A1 | 11/2000 |
| EP | 1187816 A1 | 3/2002 |
| EP | 1448556 A1 | 8/2004 |
| EP | 1597251 A2 | 11/2005 |
| EP | 1904457 A2 | 4/2008 |
| EP | 1990342 A1 | 11/2008 |
| EP | 2089369 A2 | 8/2009 |
| EP | 2234986 A2 | 10/2010 |
| EP | 2276747 A1 | 1/2011 |
| EP | 2414337 A1 | 2/2012 |
| EP | 2428508 A1 | 3/2012 |
| EP | 2443095 A1 | 4/2012 |
| JP | H0741461 A | 2/1995 |
| WO | WO-96/28427 A1 | 9/1996 |
| WO | WO-97/19065 A1 | 5/1997 |
| WO | WO-99/31073 A1 | 6/1999 |
| WO | WO-00/027825 A1 | 5/2000 |

(56) References Cited

FOREIGN PATENT DOCUMENTS

| | | |
|---|---|---|
| WO | WO-00/046203 A2 | 8/2000 |
| WO | WO-00/078731 A1 | 12/2000 |
| WO | WO-01/047897 A1 | 7/2001 |
| WO | WO-01/060816 A1 | 8/2001 |
| WO | WO-01/064654 A1 | 9/2001 |
| WO | WO-01/064655 A1 | 9/2001 |
| WO | WO-01/085699 A2 | 11/2001 |
| WO | WO-02/064586 A2 | 8/2002 |
| WO | WO-02/083653 A1 | 10/2002 |
| WO | WO-03/016306 A1 | 2/2003 |
| WO | WO-03/030909 A1 | 4/2003 |
| WO | WO-03/037891 A1 | 5/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A2 | 11/2004 |
| WO | WO-2005/013996 A2 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2005/118544 A2 | 12/2005 |
| WO | WO-2006/021544 A1 | 3/2006 |
| WO | WO-2006/038001 A1 | 4/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/098507 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/093687 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2008/147831 A1 | 12/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A2 | 10/2009 |
| WO | WO-2009/136995 A2 | 11/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/077740 A2 | 7/2010 |
| WO | WO-2010/081679 A2 | 7/2010 |
| WO | WO-2010/112210 A1 | 10/2010 |
| WO | WO-2010/128659 A1 | 11/2010 |
| WO | WO-2010/129053 A2 | 11/2010 |
| WO | WO-2010/141406 A2 | 12/2010 |
| WO | WO-2010/146132 A1 | 12/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2011/153553 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/078492 A2 | 6/2012 |
| WO | WO-2012/100459 A1 | 8/2012 |
| WO | WO-2012/135801 A1 | 10/2012 |
| WO | WO-2012/151561 A1 | 11/2012 |
| WO | WO-2012/158843 A2 | 11/2012 |
| WO | WO-2013/063401 A1 | 5/2013 |
| WO | WO-2013/138495 A1 | 9/2013 |
| WO | WO-2013/138502 A1 | 9/2013 |
| WO | WO-2013/173518 A1 | 11/2013 |
| WO | WO-2014/025128 A1 | 2/2014 |
| WO | WO-2014/039452 A1 | 3/2014 |
| WO | WO-2014/074580 A1 | 5/2014 |
| WO | WO-2014/081709 A2 | 5/2014 |
| WO | WO-2014/081712 A2 | 5/2014 |
| WO | WO-2014/081714 A2 | 5/2014 |
| WO | WO-2014/100748 A1 | 6/2014 |
| WO | WO-2014/124230 A2 | 8/2014 |
| WO | WO-PCT/US15/44783 | 8/2015 |
| WO | WO-PCT/US15/44793 | 8/2015 |
| WO | WO-PCT/US15/44890 | 8/2015 |
| WO | WO-PCT/US15/44917 | 8/2015 |
| WO | WO-PCT/US15/44918 | 8/2015 |
| WO | WO-PCT/US15/44919 | 8/2015 |
| WO | WO-PCT/US15/44928 | 8/2015 |
| WO | WO-PCT/US15/44929 | 8/2015 |
| WO | WO-PCT/US15/44930 | 8/2015 |
| WO | WO-PCT/US15/44931 | 8/2015 |
| WO | WO-PCT/US15/44932 | 8/2015 |
| WO | WO-PCT/US15/44936 | 8/2015 |

OTHER PUBLICATIONS

U.S. Appl. No. 13/882,958, filed Jul. 8, 2013, Pandey et al.
U.S. Appl. No. 15/361,590, filed Nov. 28, 2016, Haq et al.
Adult Non-Hodgkin Lymphoma Treatment (PDQ®), Nat. Can. Inst., retreived Jul. 28, 2014 from web: http://www.cancer.gov/cancertopics/pdq/treatment/adult-non-hodgkins/HealthProfessional/page1.
Advani, R.H. et al., Bruton Tyrosine Kinase Inhibitor Ibrutinib (PCI-32765) Has Significant Activity in Patients With Relapsed/Refractory B-Cell Malignancies, J. Clin. Oncol., pp. 1-9 (2012).
Aliagas-Martin, I. et al., A class of 2,4-bisanilinopyrimidine Aurora A inhibitors with unusually high selectivity against Aurora B, J. Med. Chem. 52:3300-3307 (2009).

(56) References Cited

OTHER PUBLICATIONS

Andrulis, I. et al., Neu/ErbB-2 amplification identifies a poor-prognosis group of women with node-negative breast cancer, J Clin Oncol 16:1340-9 (1998).

Aronov, A.M. et al., Flipped out: structure-guided design of selective pyrazolylpyrrole ERK inhibitors, J. Med. Chem., 50(6)1280-7 (2007).

Aronov, A.M. et al., Structure-guided design of potent and selective pyrimidylpyrrole inhibitors of extracellular signal-regulated kinase (ERK) using conformational control, J. Med. Chem., 52(20):6362-8 (2009).

Balmana et al., BRCA in breast cancer: ESMO Clinical Recommendations, Annals of Oncology, 20(Supplement 4): iv19-iv20 (2009).

Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).

Brown, J.R. et al., Phase Ib trial of AVL-292, a covalent inhibitor of Bruton's tyrosine kinase (Btk), in chronic lymphocytic leukemia (CLL) and B-non-Hodgkin lymphoma (B-NHL), J. Clin. Oncol., 30, (2012).

Brunton, L.L. et al., eds., Chemotherapy of Neoplastic Diseases, in Goodman & Gilman's: The Pharmacological Basis of Therapeutics, 11th edition, pp. 853-908 (2008).

Buggy, J.J. et al., Bruton tyrosine kinase (BTK) and its role in B-cell malignancy, Int. Rev. Immunol., 31(2): 119-32 (2012).

Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).

Carter, T. et al, Inhibition of drug-resistant mutants of ABL, KIT, and EGF receptor kinases, Proc. Natl. Acad. Sci. USA 102(31):11011-11016 (2005).

Chabner, B.A. et al., Chemotherapy of Neoplastic Diseases, Neoplastic Agents, Goodman & Gilman's: The Pharmacological Basis of Therapeutics, 11th edition, Brunton, L.L. et al., eds., pp. 1315-1403 (2006).

Clovis Oncology, Press Release, "Clovis Oncology's CO-1686 Demonstrates Compelling Clinical Activity and Progression-free Survival (PFS) in Updated Phase 1/2 Study Results in Patients with EGFR-Mutant Non-small Cell Lung Cancer (NSCLS)", May 31, 2014.

Cohen, M. et al., Structural bioinformatics-based design of selective, irreversible inhibitors, Science 308:1318-1321 (2005).

Curto, M. et al., Contact-dependent inhibition of EGFR signaling by Nf2/Merlin, J Cell Biol 177:893-903 (2007).

Dickson, M.A., and Schwartz, G.K., Development of cell-cycle inhibitors for cancer therapy, Current Oncology, 16(2): 36-43 (2009).

Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).

Evans, E. et al., Clinical Development of AVL-292; A Potent, Selective Covalent Btk Inhibitor for the Treatment of B Cell Malignancies, Blood (ASH Annual Meeting Abstracts), 118: 3485 (2011).

Eve, H.E. et al., Single-agent lenalidomide in relapsed/refractory mantle cell lymphoma: results from a UK phase II study suggest activity and possible gender differences, Br. J. Haematol., 159(2): 154-63 (2012).

Extended European Search Report for EP11816874.9, 5 pages (dated Dec. 12, 2013).

Extended European Search Report for EP11838624.2, 5 pages (dated Jun. 6, 2014).

Extended European Search Report for EP11838628.3, 7 pages (dated Jun. 20, 2014).

Extended European Search Report for EP11839800.7, 8 pages (dated Jun. 24, 2014).

Fabian, M. et al., A small molecule-kinase interaction map for clinical kinase inhibitors, Nature Biotechnology, 23(3): 329 (2005).

Fallon, K. et al., Constitutive activation of the neuregulin-1/erbB signaling pathway promotes the proliferation of a human peripheral neuroepithelioma cell line, J Neuro Oncol 66:273-84 (2004).

Frank, D., STAT signaling in the pathogenesis and treatment of cancer, Mol. Med. 5 :432-456 (1999).

Friday, B.B., and Adjei, A.A., Advances in targeting the Ras/Raf/MEK/Erk mitogen-activated protein kinase cascade with MEK inhibitors for cancer therapy, Clinical Cancer Research, 14(2): 342-346 (2008).

Friedberg, J.W. et al., Inhibition of Syk with fostamatinib disodium has significant clinical activity in non-Hodgkin lymphoma and chronic lymphocytic leukemia, Blood, 115(13): 2578-85 (2010).

Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).

Galustian, C. et al., Thalidomide-derived immunomodulatory drugs as therapeutic agents, Expert. Opin. Biol. Ther., 4(12): 1963-70 (2004).

Ghoneim, K., Synthesis and evaluation of some 2-, 4-, di-substituted-6-methylpyrimidine derivatives for antimicrobial activity, J. Indian Chem. Soc. 63(10):914-917 (1986).

Ghosh, D., 2-4-bis (arylamino)-5-methylpyrimidines as antimicrobial agents, J. Med. Chem. 10(5):974 (1967).

Ghosh, D., 2-4-bis (arylamino)-6-methylpyrimidines as antimicrobial agents, J. Indian Chem. Soc. 58(5):512-573 (1981).

Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).

Gunnellini, M. and Falchi, L., Therapeutic Activity of Lenalidomide in Mantle Cell Lymphoma and Indolent Non-Hodgkin's Lymphomas, Adv. Hematol., Article ID 523842, 7 pages (2012).

Hacken, E.T. and Burger, J.A., Microenvironment dependency in Chronic Lymphocytic Leukemia: The basis for new targeted therapies, Pharmacology & Therapeutics, http://dx.doi.org/10.1016/j.pharmthera.2014.07.003, (2014).

Harris N.L. et al., Lymphoma classification: from REAL to WHO and beyond. In: DeVita VT, Hellman S, Rosenberg SA, eds. Cancer: Principles and Practice of Oncology Updates. Philadelphia, Pa: Lippincott-Raven, 13(3): 1-14 (1999).

Hernandez-Ilizaliturri, F.J. et al., Higher response to lenalidomide in relapsed/refractory diffuse large B-cell lymphoma in nongerminal center B-cell-like than in germinal center B-cell-like phenotype, Cancer, 117(22): 5058-66 (2011).

Hur, W. et al., Clinical stage EGFR inhibitors irreversibly alkylate Bmx kinase, Bioorg. Med. Chem. Lett. 18:5916-5919 (2008).

International Search Report for PCT/US09/48784, 8 pages (dated Nov. 16, 2009).

International Search Report for PCT/US10/31714, 4 pages (dated Aug. 13, 2010).

International Search Report for PCT/US10/62432, 4 pages (dated May 26, 2011).

International Search Report for PCT/US11/58610, 4 pages (dated Mar. 27, 2012).

International Search Report for PCT/US11/58616, 3 pages (dated Mar. 27, 2012).

International Search Report for PCT/US11/59726, 3 pages (dated Mar. 20, 2012).

International Search Report for PCT/US13/70772, 3 pages (dated Mar. 25, 2014).

International Search Report for PCT/US13/70776, 4 pages (dated Mar. 25, 2014).

International Search Report for PCT/US2014/015256, 6 pages (dated Aug. 5, 2014).

International Search Report of PCT/US09/48784, 8 pages (dated Nov. 16, 2009).

International Search Report of PCT/US11/46926, 2 pages (dated Dec. 22, 2011).

International Search Report of PCT/US13/30982, 2 pages (dated May 30, 2013).

(56) References Cited

OTHER PUBLICATIONS

International Search Report of PCT/US13/30996, 2 pages (dated May 30, 2013).

International Search Report of PCT/US13/70766, 4 pages (dated Mar. 25, 2014).

Irish, J. et al., Altered B-cell receptor signaling kinetics distinguish human follicular lymphoma B cells from tumor-infiltrating nonmalignant B cells, Blood, 108(9): 3135-42 (2006).

Jaffe E.S. and Pittaluga S., Aggressive B-cell lymphomas: a review of new and old entities in the WHO classification, Hematology Am. Soc. Hematol. Educ. Program, 506-14 (2011).

Jemal, A. et al., Cancer statistics, CA Cancer J. Clin., 53(1): 5-26 (2003).

Johnson, J. et al., Relationships between drug activity in NCI preclinical in vitro and in vivo models and early clinical trials, British Journal of Cancer, 84(10): 1424-1431 (2001).

Kataja V. and Castiglione M., Primary breast cancer: ESMO clinical recommendations for diagnosis, treatment and follow-up, Annals of Oncology, 20(Supplement 4): iv10-iv14 (2009).

Kiesewetter, B. et al., A phase II study of lenalidomide in patients with extranodal marginal zone B-cell lymphoma of the mucosa associated lymphoid tissue (MALT-lymphoma), Haematologica, 98(3):353-6 (2013).

Kirken, R., Targeting Jak3 for immune suppression and allograft acceptance, Transplant. Proc. 33: 3268-3270 (2001).

Kumar, A., et al, Structure and Clinical Relevance of the Epidermal Growth Factor Receptor in Human Cancer, Journal of Clinical Oncology 26(10):1742-1751 (2008).

Kuster, B., ed., Chapters 1 and 2, Kinase Inhibitors: Methods and Protocols, Methods in Molecular Biology, vol. 795, Humana Press, 46 pages (2012).

Kwak, E. et al., Irreversible inhibitors of the EGF receptor may circumvent acquired resistance to gefitinib, Proc. Natl. Acad. Sci. USA 102:7665-7670 (2005).

Lajeunesse, D. et al., A systematic screen for dominant second-site modifiers of Merlin/NF2 phenotypes reveals an interaction with blistered/DSRF and scribbler, Genetics 158:667-79 (2001).

Leonard, J. et al., A randomized trial of lenalidomide alone versus lenalidomide plus rituximab in patients with recurrent follicular lymphoma, J. Clin. Oncol., 30 (2012).

Li, D. et al., BIBW2992, an irreversible EGFR/HER2 inhibitor highly effective in preclinical lung cancer models, Oncogene 27:4702-4711 (2008).

Liddle, J. et al., Discovery of GSK143, a highly potent, selective and orally efficacious spleen tyrosine kinase inhibitor, Bioorg. Med. Chem. Lett., 21(20):6188-94 (2011).

Lin, N. and Winer, E., New targets for therapy in breast cancer: Small molecule tyrosine kinase inhibitors, Breast Cancer Res 6:204-210 (2004).

Malaviya, R. et al., Targeting Janus Kinase 3 in Mast Cells Prevents Immediate Hypersensitivity Reactions and Anaphylaxis, J. Biol. Chem. 274 :27028-27038 (1999).

McClatchey, A. and Giovannini, M., Membrane organization and tumorigenesis—the NF2 tumor suppressor, Merlin, Genes Dev 19:2265-77 (2005).

McCubrey, J.A. et al., Targeting survival cascades induced by activation of Ras/Raf/MEK/ERK, PI3K/PTEN/Akt/mTOR and Jak/STAT pathways for effective leukemia therapy, Leukemia, 22(4): 708-722 (2008).

McDaniel J.M. et al., Molecular action of lenalidomide in lymphocytes and hematologic malignancies, Adv. Hematol., Article ID 513702, 9 pages (2012).

Merriam-Webster's Online Directory, "Prevent" download on Apr. 7, 2008 from "http//www.merriam-webster.com/dictionary/prevent", p. 1 of 1.

Minkovsky, N. and Berezov, A., BIBW-2992, a dual receptor tyrosine kinase inhibitor for the treatment of solid tumors, Curr Opin Invest Drugs 9:1336-1346 (2008).

Montagut, C. and Settleman, J., Targeting the RAF-MEK-ERK pathway in cancer therapy, Cancer Letters, 283(2): 125-134 (2009).

Nastoupil, L.J. et al., Diffuse large B-cell lymphoma: current treatment approaches, Oncology, 26(5): 488-95 (2012).

Nelson et al., Screening for breast cancer: an update for the U.S. Preventive Services Task Force, Ann. Intern Med, 151(10): 727-737 (2009).

Ogiso, et al., Crystal Structure of the Complex of Human Epidermal Growth Factor and Receptor Extracellular Domains, Cell, vol. 110, 775-787 (2002).

Pearce, H.L. et al., Failure modes in anticancer drug discovery and development, Cancer Drug Design and Discovery Edited by Stephen Neidle, 18: 424-435 (2008).

Pelton, P. et al., Ruffling membrane, stress fiber, cell spreading and proliferation abnormalities in human Schwann cells, Oncogene 17:2195-2209 (1998).

PubChem CID 44594695. Feb. 1, 2010. [Retrieved from the Internet May 15, 2011: http://pubchem.ncbi.nlm.nih.gov/summary.cgi?cid=44594695&loc=ec_rcs].

Readinger, J. et al., Selective Targeting of ITK Blocks Multiple Steps of HIV Replication, Proc. Natl. Acad. Sci. USA 105: 6684-6689 (2008).

Rinaldi, A. et al., Genomic and expression profiling identifies the B-cell associated tyrosine kinase Syk as a possible therapeutic target in mantle cell lymphoma, Br. J. Haematol., 132(3): 303-16 (2006).

Roberts, P.J., and Der, C.J., Targeting the Raf-MEK-ERK mitogen-activated protein kinase cascade for the treatment of cancer, Oncogene, 26(22): 3291-3310 (2007).

Ruiz-Ballesteros, E. et al., Splenic marginal zone lymphoma: proposal of new diagnostic and prognostic markers identified after tissue and cDNA microarray analysis. Blood, 106(5): 1831-8 (2005).

Sakamoto, T. et al., Blockade of the ERK pathway enhances the therapeutic efficacy of the histone deacetylase inhibitor MS-275 in human tumor xenograft models, Biochem. Biophys. Res. Commun., 433(4):456-62 (2013).

Schlessingerman, Mass of an Adult Male, The Physics Factbook (2003), retreived Jul. 22, 2014 from web: http://hypertextbook.com/facts/2003/AlexSchleesingerman.shtml.

Seidel, H. et al., Pharmaceutical intervention in the JAK/STAT signaling pathway, Oncogene 19: 2645-2656 (2000).

Seipelt, I et al., Dual Inhibition of PI3K and Erk1/2 shows synergy and efficacy in human tumor cells, either by using drug combinations or novel dual PI3K/Erk inhibitors, Aeterna Zentaris GmbH, AACR Poster, Abstract #871 (2012).

Sequist, L., Second-Generation Epidermal Growth Factor Receptor Tyrosine Kinase Inhibitors in Non-Small Cell Lung Cancer, The Oncologist 12(3):325-330 (2007).

Simone, J.V., Oncology: Introduction, Cecil Textbook of Medicine, 20th Edition, 1: 1004-1010 (1995).

Singh, J. et al, Structure-based design of a potent, selective, and irreversible inhibitor of the catalytic domain of the erbB receptor subfamily of protein tyrosine kinases, J. Med. Chem. 40:1130-1135 (1997).

Soria, J-C. et al., "Abstract # 1354: First-In-Human Evaluation of CO-1686, an Irreversible, Highly Selective Tyrosine Kinase Inhibitor of Mutations of EGFR (Activating and T790M)," 15th World Conference on Lung Cancer, Oct. 27, 2013.

Steelman, L.S. et al., Contributions of the Raf/MEK/ERK, PI3K/PTEN/Akt/mTOR and Jak/STAT pathways to leukemia, Leukemia, 22(4): 686-707 (2008).

Steelman, L.S. et al., Roles of the Ras/Raf/MEK/ERK pathway in leukemia therapy, Leukemia, 25(7): 1080-1097 (2011).

Steinhardt, J.J. and Gartenhaus, R.B., Promising Personalized Therapeutic Options for Diffuse Large B-cell Lymphoma Subtypes with Oncogene Addictions, Clin. Cancer Res., 18(17): 4538-48 (2012).

Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).

Sudbeck, E. et al., Structure-based Design of Specific Inhibitors of Janus Kinase 3 as Apoptosis-inducing Antileukemic Agents, Clin. Cancer Res. 5: 1569-1582 (1999).

(56) References Cited

OTHER PUBLICATIONS

Supplementary European Search Report for EP10844293.0, 8 pages (dated Jun. 27, 2013).
Tohnya, T.M. et al., A phase I study of oral CC-5013 (lenalidomide, Revlimid), a thalidomide derivative, in patients with refractory metastatic cancer, Clin Prostate Cancer, 2(4): 241-3 (2004).
Trieu, V. et al., A specific inhibitor of janus kinase-3 increases survival in a transgenic mouse model of amyotrophic lateral sclerosis, Biochem. Biophys. Res. Commun. 267 :22-25 (2000).
Walter, A. O. et al., "Discovery of a mutant-selective covalent inhibitor of EGFR that overcomes T790M-mediated resistance in NSCLC," *Cancer Discov.* Dec. 2013; 3(12): 1404-1415.
Westlin, W. et al., Translational medicine enables rapid early clinical development of AVL-292, a highly selective, orally available inhibitor of Bruton's tyrosine kinase, in a phase 1b clinical trial, Cancer Res., 72 (2012).
Wiernik, P.H. et al., Lenalidomide monotherapy in relapsed or refractory aggressive non-Hodgkin's lymphoma, J. Clin. Oncol., 26(30): 4952-7 (2008).
Winer, E.S. et al., A novel Bruton's tyrosine kinase inhibitor for the treatment of lymphoid malignancies, Expert Opin. Investig. Drugs, 21(3): 355-61 (2012).
Witzig, T.E. et al., Lenalidomide oral monotherapy produces durable responses in relapsed or refractory indolent non-Hodgkin's Lymphoma, J. Clin. Oncol., 27(32): 5404-5409 (2009).
Wong, K-K., Recent developments in anti-cancer agents targeting the Ras/Raf/ MEK/ERK pathway, Recent Patents on Anti-Cancer Drug Discovery, 4(1): 28-35 (2009).
Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US09/48784, 9 pages (dated Nov. 16, 2009).
Written Opinion for PCT/US10/31714, 7 pages (dated Aug. 13, 2010).
Written Opinion for PCT/US10/62432, 14 pages (dated May 26, 2011).
Written Opinion for PCT/US11/46926, 9 pages (dated Dec. 22, 2011).
Written Opinion for PCT/US11/58610, 8 pages (dated Mar. 27, 2012).
Written Opinion for PCT/US11/58616, 9 pages (dated Mar. 27, 2012).
Written Opinion for PCT/US11/59726, 7 pages (dated Mar. 20, 2012).
Written Opinion for PCT/US13/70772, 10 pages (dated Mar. 25, 2014).
Written Opinion for PCT/US13/70776, 11 pages (dated Mar. 25, 2014).
Written Opinion for PCT/US2013/070766, 11 pages (dated Mar. 25, 2014).
Written Opinion for PCT/US2014/015256, 6 pages (dated Aug. 5, 2014).
Written Opinion of PCT/US13/30982, 12 pages (dated May 30, 2013).
Written Opinion of PCT/US13/30996, 12 pages (dated May 30, 2013).
Yang, Y. et al., Exploiting Synthetic Lethality for the Therapy of ABC Diffuse Large B Cell Lymphoma, Cancer Cell, 21: 723-737 (2012).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).
Zhu, D. et al., Immunomodulatory drugs Revlimid (lenalidomide) and CC-4047 induce apoptosis of both hematological and solid tumor cells through NK cell activation. Cancer Immunol. Immunother., 57(12): 1849-59 (2008).

\* cited by examiner

Amino Acid Sequence of ERK1

SEQ ID NO. 1

```
         10         20         30         40         50         60
MAAAAAQGGG GGEPRRTEGV GPGVPGEVEM VKGQPFDVGP RYTQLQYIGE GAYGMVSSAY 70         80         90        100        110        120
DHVRKTRVAI KKISPFEHQT YCQRTLREIQ ILLRFRHENV IGIRDILRAS TLEAMRDVYI 130        140        150        160        170        180
VQDLMETDLY KLLKSQQLSN DHICYFLYQI LRGLKYIHSA NVLHRDLKPS NLLINTTCDL 190        200        210        220        230        240
KICDFGLARI ADPEHDHTGF LTEYVATRWY RAPEIMLNSK GYTKSIDIWS VGCILAEMLS 250        260        270        280        290        300
NRPIFPGKHY LDQLNHILGI LGSPSQEDLN CIINMKARNY LQSLPSKTKV AWAKLFPKSD 310        320        330        340        350        360
SKALDLLDRM LTFNPNKRIT VEEALAHPYL EQYYDPTDEP VAEEPFTFAM ELDDLPKERL

370
KELIFQETAR FQPGVLEAP
```

FIGURE 1

Amino Acid Sequence of ERK2

SEQ ID NO. 3

```
          10         20         30         40         50         60
  MAAAAAAGAG PEMVRGQVFD VGPRYTNLSY IGEGAYGMVC SAYDNVNKVR VAIKKISPFE 70         80         90        100        110        120
  HQTYCQRTLR EIKILLRFRH ENIIGINDII RAPTIEQMKD VYIVQDLMET DLYKLLKTQH 130        140        150        160        170        180
  LSNDHICYFL YQILRGLKYI HSANVLHRDL KPSNLLLNTT CDLKICDFGL ARVADPDHDH 190        200        210        220        230        240
  TGFLTEYVAT RWYRAPEIML NSKGYTKSID IWSVGCILAE MLSNRPIFPG KHYLDQLNHI 250        260        270        280        290        300
  LGILGSPSQE DLNCIINLKA RNYLLSLPHK NKVPWNRLFP NADSKALDLL DKMLTFNPHK 310        320        330        340        350        360
  RIEVEQALAH PYLEQYYDPS DEPIAEAPFK FDMELDDLPK EKLKELIFEE TARFQPGYRS
```

FIGURE 2

ERK INHIBITORS AND USES THEREOF

CROSS-REFERENCE TO RELATED APPLICATIONS

The present application is a divisional application of U.S. non-provisional application Ser. No. 14/768,190, filed Aug. 14, 2015, which is a U.S. National Stage Entry of international PCT application number US14/15256, filed Feb. 7, 2014, which claims priority to U.S. provisional application No. 61/785,126, filed Mar. 14, 2013, and U.S. provisional application No. 61/762,408, filed Feb. 8, 2013, the entirety of each of which is hereby incorporated by reference.

TECHNICAL FIELD OF THE INVENTION

The present invention relates to compounds useful as inhibitors of ERK kinases, for example one or both of ERK1 and ERK2 kinases. The invention also provides pharmaceutically acceptable compositions comprising compounds of the present invention and methods of using said compositions in the treatment of various disorders.

SEQUENCE LISTING

In accordance with 37 CFR 1.52(e)(5), the present specification makes reference to a Sequence Listing submitted electronically in the form of a text file (entitled "Sequence_Listing.txt," created on Mar. 17, 2014, 7.37 KB in size). The entire contents of the Sequence Listing are herein incorporated by reference, with the intention that, upon publication (including issuance), this incorporated sequence listing will be inserted in the published document immediately before the claims.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates one or both of ERK1 and ERK2. When activated, one or both of ERK1 and ERK2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of one or both of ERK1 and ERK2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers.

Many diseases are associated with abnormal cellular responses triggered by protein kinase-mediated events as described above. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of one or both of ERK1 and ERK2. Such compounds have general formula I:

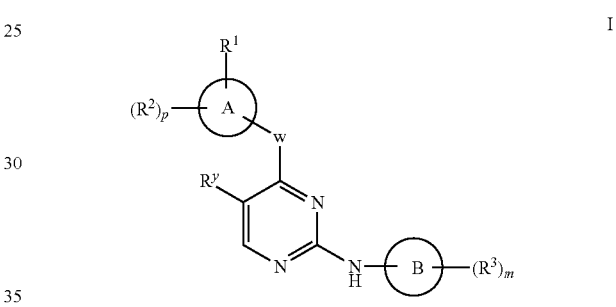

or a pharmaceutically acceptable salt thereof, wherein each of Ring A, Ring B, $R^1$, $R^2$, $R^3$, $R^y$, W, m, and p, with respect to the formula above, is as defined and described in embodiments herein. In certain embodiments, $R^1$ is a warhead group.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

BRIEF DESCRIPTION OF THE FIGURES

FIG. 1 provides SEQ ID NO. 1, which is the amino acid sequence of ERK1.

FIG. 2 provides SEQ ID NO. 3, which is the amino acid sequence of ERK2.

DETAILED DESCRIPTION OF CERTAIN EMBODIMENTS

1. General Description of Compounds of the Invention

In certain embodiments, the present invention provides irreversible inhibitors of one or both of ERK1 and ERK2 and conjugates thereof. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

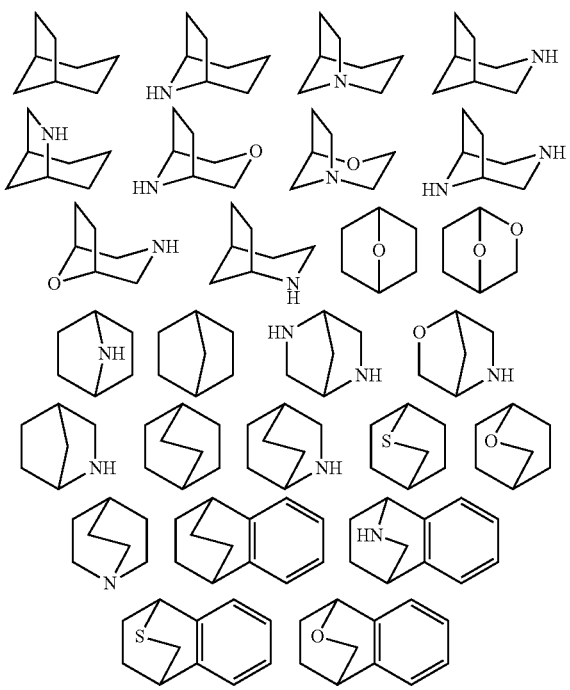

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

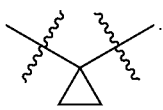 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or ⁺NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure

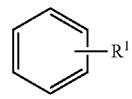

refers to at least

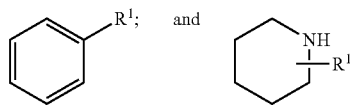

refers to at least

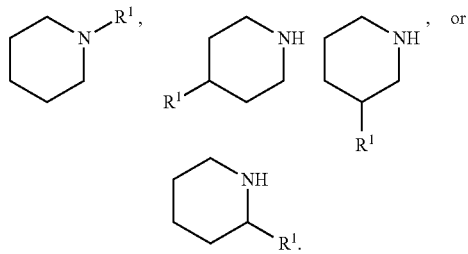

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "irreversible" or "irreversible inhibitor" refers to an inhibitor (i.e. a compound) that is able to be covalently bonded to a kinase in a substantially non-reversible manner. That is, whereas a reversible inhibitor is able to bind to (but is generally unable to form a covalent bond with) a kinase, and therefore can become dissociated from the a kinase, an irreversible inhibitor will remain substantially bound to a kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with a kinase, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein. In certain instances, a "pro-warhead group" is used in place of a warhead group. Such a pro-warhead group converts to a warhead group in vivo or in vitro.

As used herein, the term "inhibitor" is defined as a compound that binds to and/or inhibits a kinase with measurable affinity. In certain embodiments, an inhibitor has an $IC_{50}$ and/or binding constant of less about 50 μM, less than about 1 μM, less than about 500 nM, less than about 100 nM, less than about 10 nM, or less than about 1 nM.

The terms "measurable affinity" and "measurably inhibit," as used herein, means a measurable change in a kinase activity between a sample comprising a compound of the present invention, or composition thereof, and a kinase, and an equivalent sample comprising a kinase, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Embodiments

As described herein, the present invention provides irreversible inhibitors of one or both of ERK1 and ERK2 kinase. The compounds of the invention comprise a warhead group, designated as $R^1$, as described herein. Without wishing to be bound by any particular theory, it is believed that such $R^1$ groups, i.e. warhead groups, are particularly suitable for covalently binding to a key cysteine residue in the binding domain of one or both of ERK1 and ERK2 kinase. One of ordinary skill in the art will appreciate that one or both of ERK1 and ERK2 kinase, and mutants thereof, have a cysteine residue in the binding domain. Without wishing to be bound by any particular theory, it is believed that proximity of a warhead group to the cysteine of interest facilitates covalent modification of that cysteine by the warhead group.

The cysteine residues of interest can also be described by an identifying portion of the Target's amino acid sequence which includes the cysteine of interest. Thus, in certain embodiments, Cys183 of ERK1 is characterized in that Cys183 is the cysteine embedded in the amino acid sequence of ERK1. FIG. 1 provides SEQ ID NO. 1, which is the amino acid sequence of ERK1. Cys183 is more clearly provided in the abbreviated amino acid sequence below where Cysteine 183 is highlighted in bold with underlining:

SEQ ID NO. 2: NLLINTTCDL KIC(183)DFGLARI.

Cys166 of ERK2 is characterized in that Cys166 is the cysteine embedded in the amino acid sequence of ERK2. FIG. 2 provides SEQ ID NO. 3, which is the amino acid sequence of ERK2. Cys166 is more clearly provided in the abbreviated amino acid sequence below where Cysteine 166 is highlighted in bold with underlining:

SEQ ID NO. 4: KPSNLLLNTT CDLKIC(166)DFGL.

In some embodiments, compounds of the present invention include a warhead group characterized in that provided compounds covalently modify one or more of Cys 183 of ERK1 or Cys166 of ERK2.

In certain embodiments, compounds of the present invention include a warhead group characterized in that provided compounds bind to a target of Cys183 of ERK1 or Cys166 of ERK2, thereby irreversibly inhibiting the kinase.

Thus, in some embodiments, the $R^1$ warhead group is characterized in that the -L-Y moiety, as defined and described below, is capable of covalently binding to a cysteine residue thereby irreversibly inhibiting the enzyme. In some embodiments, the cysteine residue is Cys183 of ERK1. In some embodiments, the cysteine residue is Cys166 of ERK2. In some embodiments, it is both Cys183 of ERK1 and Cys166 of ERK2. One of ordinary skill in the art will recognize that a variety of warhead groups, as defined herein, are suitable for such covalent bonding. Such $R^1$ groups include, but are not limited to, those described herein and depicted infra.

According to one aspect, the present invention provides a compound of formula I,

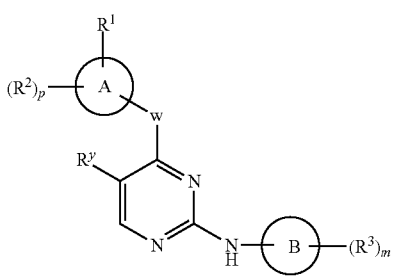

I or a pharmaceutically acceptable salt thereof, wherein:

Ring A is an optionally substituted group selected from phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur; or Ring A is selected from

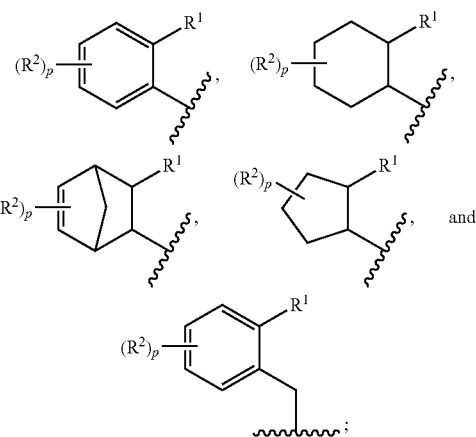

$R^1$ is a warhead group, wherein when Ring A is a monocyclic ring, then $R^1$ is attached to an atom adjacent to where W is attached;

each $R^2$ is independently hydrogen, an optionally substituted $C_{1-6}$ aliphatic, halogen, or —OR;

Ring B (a) is an optionally substituted group selected from phenyl, a 3-7 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-12 membered bicyclic saturated, partially unsaturated or aryl ring, a 7-12 membered bicyclic saturated or partially unsaturated heterocyclic ring having 1-5 heteroatoms independently selected from nitrogen, oxygen, or sulfur, or an 8-12 membered bicyclic heteroaryl ring having 1-5 heteroatoms independently selected from nitrogen, oxygen, or sulfur; or (b) is absent and $(R^3)_m$ is attached to —NH—;

each —$R^3$ is independently selected from —R, —Cy, halogen, —OR, —SR, —CN, —NO$_2$, —SO$_2$NR, —SO$_2$R, —SOR, —C(O)R, —C(O)OR, —OC(O)R, —OC(O)N(R)$_2$, —C(O)N(R)$_2$, —C(O)N(R)—OR —C(O)C(O)R, —P(O)(R)$_2$, —NRC(O)OR, —NRC(O)R, —NRC(O)N(R)$_2$, —NRSO$_2$R, or —N(R)$_2$; or two $R^3$ groups on the same carbon atom together form —C(O)—, —C(S)—, or —C(N—R)—;

each R is independently hydrogen or an optionally substituted group selected from $C_{1-6}$ aliphatic, phenyl, a 3-8 membered saturated or partially unsaturated carbocyclic ring, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

Cy is an optionally substituted 5-6 membered monocyclic heteroaryl ring having 1-4 heteroatoms independently selected from nitrogen, oxygen, or sulfur, or an optionally substituted 4-7 membered saturated or partially unsaturated heterocyclic ring having 1-3 heteroatoms independently selected from nitrogen, oxygen, or sulfur;

R$^y$ is hydrogen, optionally substituted —C$_{1-6}$ aliphatic, halogen, haloalkyl, —CN, —C(O)R', —C(O)N(R')$_2$, —C(=N—R")R' or —N(R')$_2$;

each R' is independently hydrogen or an optionally substituted C$_{1-6}$ aliphatic;

R" is hydrogen or —OR;

W is —O—, —NH—, —S—, —CH$_2$—, or —C(O)—; and m and p are each independently 0-4;

wherein:

(a) when R$^y$ is Cl and Ring B is phenyl para-substituted with morpholine, then R$^1$ is not

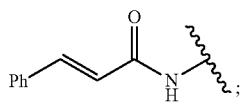 [SMILES: *NC(=O)/C=C/c1ccccc1]

(b) when R$^y$ is Cl and Ring B is phenyl di-substituted with methoxy, then R$^1$ is not

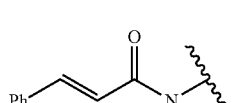

(c) when R$^y$ is Cl and Ring B is a 7-12 membered bicyclic saturated or partially unsaturated heterocyclic ring having 1-5 heteroatoms independently selected from nitrogen, oxygen, or sulfur, then R$^1$ is not

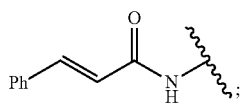 [SMILES: *NC(=O)/C=C/c1ccccc1]

or (d) when R$^y$ is F and Ring B is phenyl tri-substituted with methoxy, then R$^1$ is not

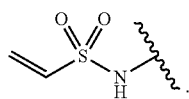

According to one aspect, the present invention provides a compound of formula I',

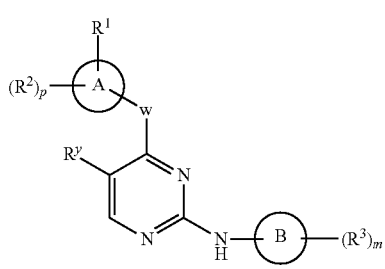

or a pharmaceutically acceptable salt thereof, wherein:

Ring A is an optionally substituted group selected from phenyl, a 3-8 membered saturated or partially unsaturated carbocyclic ring, a 4-7 membered heterocyclic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur; or Ring A is selected from

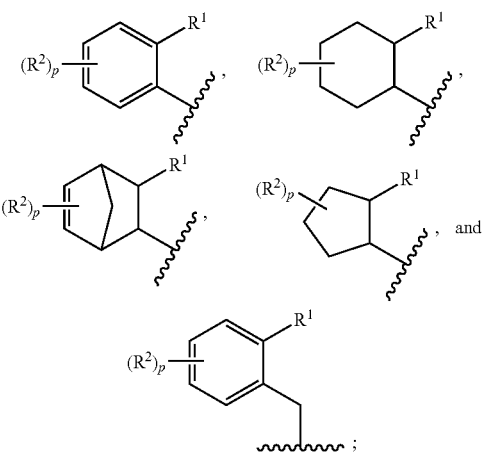

R$^1$ is a warhead group, wherein when Ring A is a monocyclic ring, then R$^1$ is attached to an atom adjacent to where W is attached;

each R$^2$ is independently hydrogen, an optionally substituted C$_{1-6}$ aliphatic, —CN, halogen, —OR, or -L$^1$-R$^x$;

L$^1$ is a C$_{1-6}$ saturated straight or branched hydrocarbon chain wherein one or two methylene units of L$^1$ is optionally and independently replaced by -Hy-, —N(R$^z$)—, —S—, —O—, —C(O)—, —OC(O)—, —C(O)O—, —SO—, or —SO$_2$—, —N(R$^z$)C(O)—, —C(O)N(R$^z$)—, —N(R$^z$)SO$_2$—, or —SO$_2$N(R$^z$)—;

-Hy- is a bivalent saturated 6-membered heterocyclic ring having 1-2 nitrogens;

each R$^z$ is independently hydrogen or C$_{1-6}$ alkyl;

R$^x$ is a 4-8 membered saturated, partially unsaturated, or heteroaromatic ring having 1-4 heteroatoms independently selected from nitrogen, oxygen, or sulfur, wherein R$^x$ is optionally substituted with 1-3 groups selected from C$_{1-6}$ alkyl, —C(O)R$^z$, —C(O)CH$_2$OR$^z$, —C(O)OR$^z$, —OC(O)C$_{1-6}$ alkyl, —C(O)N(R$^z$)$_2$, —OR$^z$, —SR$^z$, —SO$_2$R$^z$, —N(R$^z$)$_2$, —N(R$^z$)C(O)R$^z$, —N(R$^z$)S(O)$_2$C$_{1-6}$ alkyl, or —SO$_2$N(R$^z$)$_2$;

Ring B (a) is an optionally substituted group selected from phenyl, a 3-7 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-12 membered bicyclic saturated, partially unsaturated or aryl ring, a 7-12 membered bicyclic saturated or partially unsaturated heterocyclic ring having 1-5 heteroatoms independently selected from nitrogen, oxygen, or sulfur, or an 8-12 membered bicyclic heteroaryl ring having 1-5 heteroatoms independently selected from nitrogen, oxygen, or sulfur; or (b) is absent and $(R^3)_m$ is attached to —NH—;

each —$R^3$ is independently selected from —R, —Cy, halogen, —OR, —SR, —CN, —NO$_2$, —SO$_2$NR, —SO$_2$R, —SOR, —C(O)R, —C(O)OR, —OC(O)R, —OC(O)N(R)$_2$, —C(O)N(R)$_2$, —C(O)N(R)—OR —C(O)C(O)R, —P(O)(R)$_2$, —NRC(O)OR, —NRC(O)R, —NRC(O)N(R)$_2$, —NRSO$_2$R, or —N(R)$_2$; or two $R^3$ groups on the same carbon atom together form —C(O)—, —C(S)—, or —C(N—R)—;

each R is independently hydrogen or an optionally substituted group selected from $C_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or
  two R groups on the same nitrogen are taken together with the nitrogen atom to which they are attached to form a 4-7 membered heterocylic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

Cy is an optionally substituted 5-6 membered monocyclic heteroaryl ring having 1-4 heteroatoms independently selected from nitrogen, oxygen, or sulfur, or an optionally substituted 4-7 membered saturated or partially unsaturated heterocyclic ring having 1-3 heteroatoms independently selected from nitrogen, oxygen, or sulfur;

$R^y$ is hydrogen, optionally substituted $C_{1-6}$ aliphatic, halogen, haloalkyl, —CN, —OR, —C(O)R', —C(O)N(R')$_2$, —C(=N—R")R' or —N(R')$_2$;

each R' is independently hydrogen or an optionally substituted $C_{1-6}$ aliphatic;

R" is hydrogen or —OR;

W is —O—, —NH—, —S—, —CH$_2$—, or —C(O)—; and m and p are each independently 0-4;

wherein:

(a) when $R^y$ is Cl and Ring B is phenyl para-substituted with morpholine, then $R^1$ is not

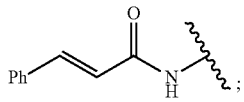

(b) when $R^y$ is Cl and Ring B is phenyl di-substituted with methoxy, then $R^1$ is not

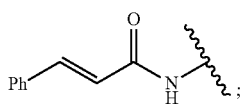

(c) when $R^y$ is Cl and Ring B is a 7-12 membered bicyclic saturated or partially unsaturated heterocyclic ring having 1-5 heteroatoms independently selected from nitrogen, oxygen, or sulfur, then $R^1$ is not

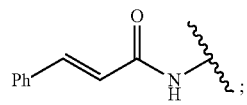

or (d) when $R^y$ is F and Ring B is phenyl tri-substituted with methoxy, then $R^1$ is not

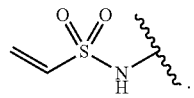

In certain embodiments, Ring A is an optionally substituted group selected from phenyl, a 3-8 membered saturated or partially unsaturated carbocyclic ring, a 4-7 membered heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur; or Ring A is selected from

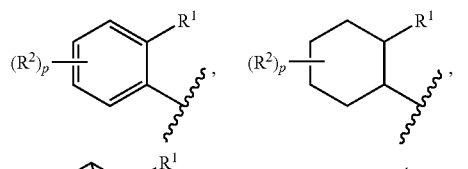

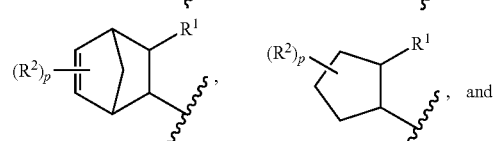

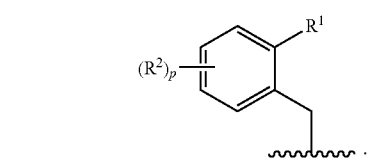

In certain embodiments, Ring A is phenyl.

In certain embodiments, Ring A is an optionally substituted 3-8 membered saturated or partially unsaturated carbocyclic ring, an optionally substituted 4-7 membered heterocylic ring having 1-2 heteroatoms independently selected from nitrogen, oxygen, or sulfur, an optionally substituted 5-6 membered monocyclic heteroaryl ring having 1-4 heteroatoms independently selected from nitrogen, oxygen, or sulfur, a 7-10 membered bicyclic saturated, partially unsaturated or aryl ring which is optionally bridged, an 8-10 membered bicyclic heteroaryl ring having 1-5 heteroatoms independently selected from nitrogen, oxygen, or sulfur, or a 7-10 membered bicyclic saturated or partially unsaturated heterocyclic ring having 1-5 heteroatoms independently selected from nitrogen, oxygen, or sulfur.

In some embodiments, Ring A is an optionally substituted group selected from phenyl, a 3-8 membered saturated or partially unsaturated monocyclic carbocyclic ring, a 4-7 membered monocyclic heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or Ring A is selected from

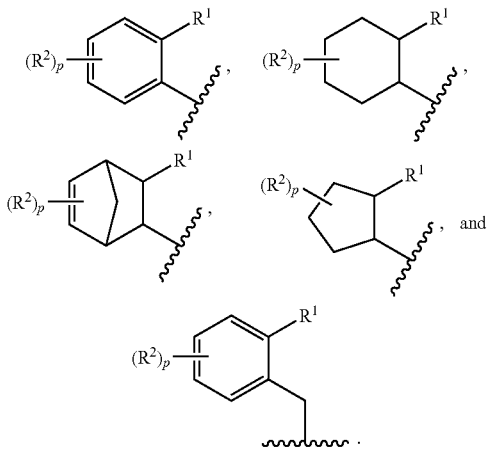

As defined above, $R^1$ is a warhead group. In some embodiments, $R^1$ is attached to an atom adjacent to where W is attached.

In various embodiments, Ring A is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

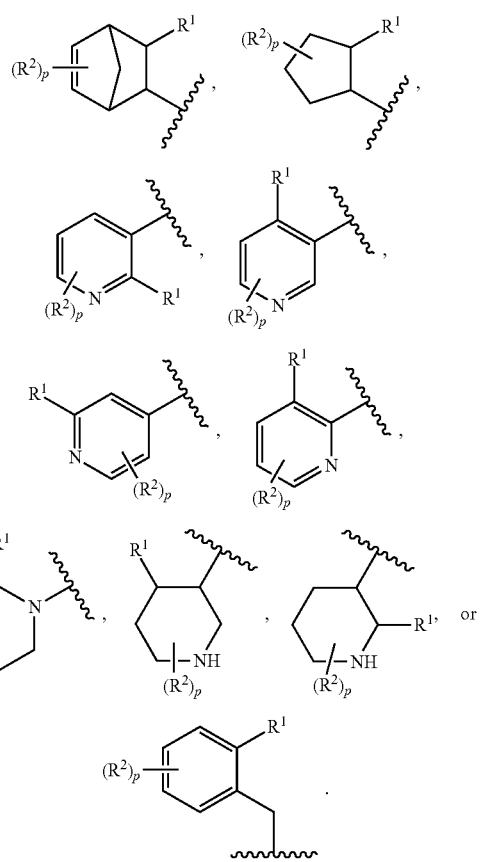

In certain embodiments, Ring A is

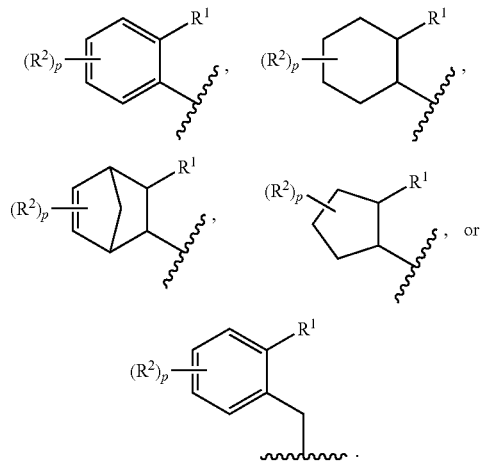

In certain embodiments, Ring A is

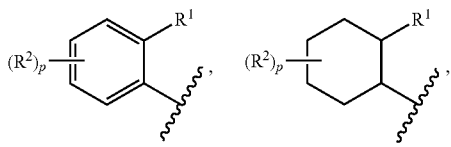

In some embodiments, Ring A is a 4-7 membered saturated or partially unsaturated heterocylic ring having 1-2 heteroatoms independently selected from nitrogen, oxygen, sulfur, or —P(O)R—. In some embodiments, Ring A is a 4-7 membered saturated or partially unsaturated heterocylic ring having a —P(O)R— ring moiety. An exemplary Ring A group having a —P(O)R-ring moiety is

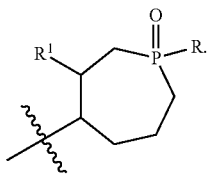

In some embodiments, Ring A is

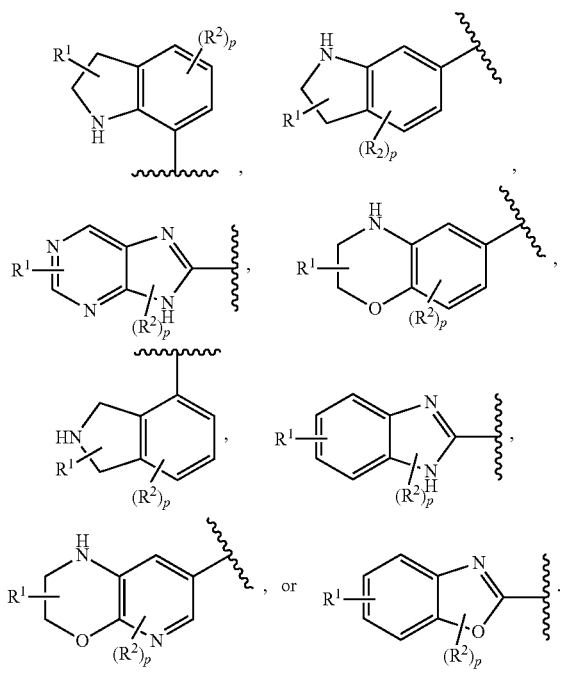

In certain embodiments, each $R^2$ is independently hydrogen.

In certain embodiments, each $R^2$ is independently an optionally substituted $C_1$ aliphatic, halogen, or —OR.

In certain embodiments, each $R^2$ is independently an optionally substituted methyl, ethyl, propyl, i-propyl, butyl, s-butyl, t-butyl, straight or branched pentyl, or a straight or branched hexyl.

In certain embodiments, each $R^2$ is independently F, Cl, Br, or I.

In certain embodiments, each $R^2$ is independently —OMe, —OEt, —O-i-Pr, —O-t-Bu,

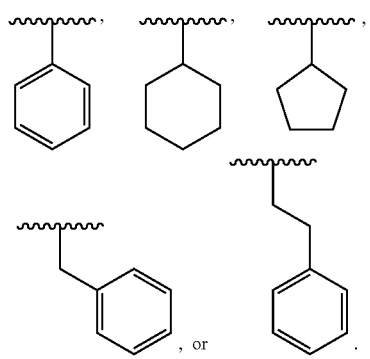

In certain embodiments, each $R^2$ is independently hydrogen, F, Cl, Me, $CF_3$, or OMe.

In certain embodiments, Ring B is phenyl.

As defined above for formula I', in some embodiments, $L^1$ is a $C_{1-6}$ saturated straight or branched hydrocarbon chain wherein one or two methylene units of $L^1$ is optionally and independently replaced by -Hy-, —N($R^z$)—, —S—, —O—, —C(O)—, —OC(O)—, —C(O)O—, —SO—, or —SO$_2$—, —N($R^z$)C(O)—, —C(O)N($R^z$)—, —N($R^z$)SO$_2$—, or —SO$_2$N($R^z$)—; wherein -Hy- is a bivalent saturated 6-membered heterocyclic ring having 1-2 nitrogens; each $R^z$ is independently hydrogen or $C_{1-6}$ alkyl; and $R^x$ is a 4-8 membered saturated, partially unsaturated, or heteroaromatic ring having 1-4 heteroatoms independently selected from nitrogen, oxygen, or sulfur, wherein $R^x$ is optionally substituted with 1-3 groups selected from $C_{1-6}$ alkyl, —C(O)$R^z$, —C(O)CH$_2$O$R^z$, —C(O)O$R^z$, —OC(O)$C_{1-6}$ alkyl, —C(O)N($R^z$)$_2$, —O$R^z$, —S$R^z$, —SO$_2$$R^z$, —N($R^z$)$_2$, —N($R^z$)C(O)$R^z$, —N($R^z$)S(O)$_2$$C_{1-6}$ alkyl, or —SO$_2$N($R^z$)$_2$.

In some embodiments, $R^2$ is —CN. In some embodiments, $R^2$ is -$L^1$-$R^x$ wherein $L^1$ is —CH$_2$-piperazin-4-yl-, —CH$_2$—, —C(O)—, or —O—CH$_2$C(O)—. In some embodiments, $R^x$ is piperazin-4-yl or pyridazinyl. Exemplary $R^2$ groups are set forth in Table 3, below.

In certain embodiments, Ring B is an optionally substituted group selected from phenyl, a 3-7 membered saturated or partially unsaturated carbocyclic ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-12 membered bicyclic saturated, partially unsaturated or aryl ring, a 7-12 membered bicyclic saturated or partially unsaturated heterocyclic ring having 1-5 heteroatoms independently selected from nitrogen, oxygen, or sulfur, or an 8-12 membered bicyclic heteroaryl ring having 1-5 heteroatoms independently selected from nitrogen, oxygen, or sulfur.

In various embodiments, Ring B is cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, Ring B is selected from:

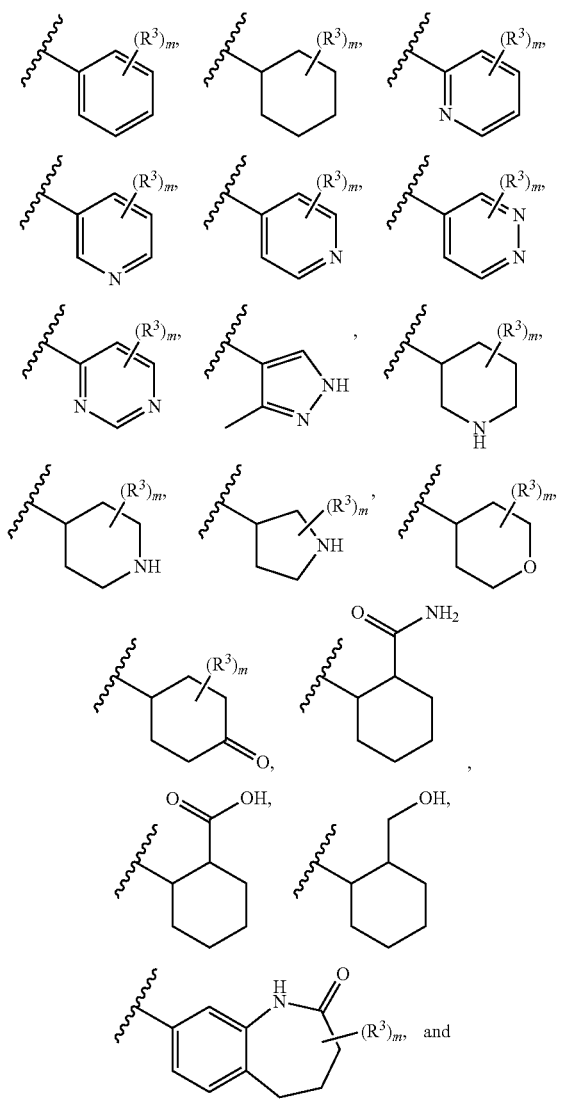

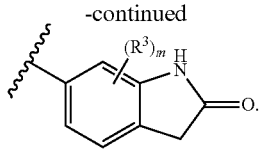

In certain embodiments, Ring B is absent and $(R^3)_m$ is attached to —NH.

As defined above, each $R^3$ is independently selected from —R, —Cy, halogen, —OR, —SR, —CN, —NO$_2$, —SO$_2$NR, —SO$_2$R, —SOR, —C(O)R, —C(O)OR, —OC(O)R, —OC(O)N(R)$_2$, —C(O)N(R)$_2$, —C(O)N(R)—OR —C(O)C(O)R, —P(O)(R)$_2$, —NRC(O)OR, —NRC(O)R, —NRC(O)N(R)$_2$, —NRSO$_2$R, or —N(R)$_2$; or two $R^3$ groups on the same carbon atom together form —C(O)—, —C(S)—, or —C(N—R)—.

In certain embodiments, each $R^3$ is independently hydrogen.

In certain embodiments, each $R^3$ is independently —R. In other embodiments, one $R^3$ is —Cy.

In certain embodiments, each $R^3$ is independently an optionally substituted $C_{1-6}$ aliphatic.

In certain embodiments, each $R^3$ is independently an optionally substituted 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, each $R^3$ is independently halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each —$R^3$ is independently halogen, —OR, —CN, —SO$_2$R, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^3$ is independently -Me, -Et, -t-Bu, —CH$_2$OH, —CF$_3$, —(CH$_2$)$_3$NHBoc, —(CH$_2$)$_3$NH$_2$, —CN, —F, —Cl, —Br, —OH, —OMe, —OEt, —OCH$_2$CH$_2$OMe, —NHCH$_2$CH$_2$OMe, —OCH$_2$F, —OCHF$_2$, —OCF$_3$, —OCH$_2$CCH, —NH(Me), or —P(O)(Me)$_2$.

In certain embodiments, each $R^3$ is independently

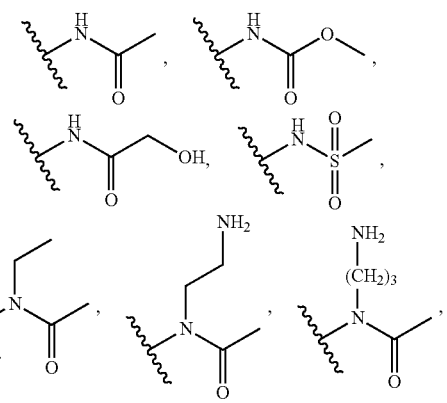

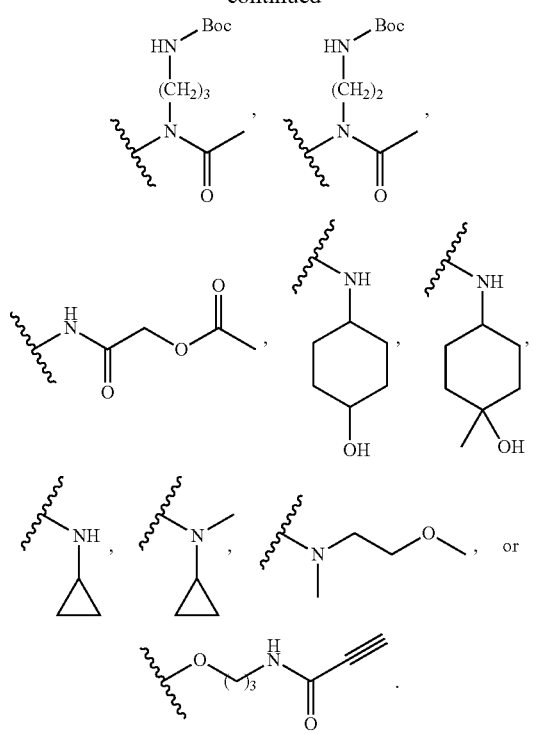

In certain embodiments, each R³ is independently

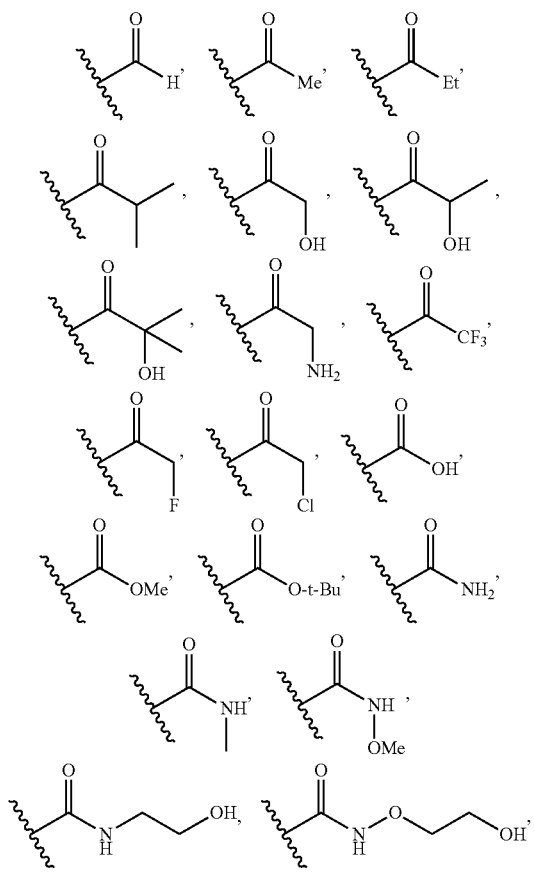

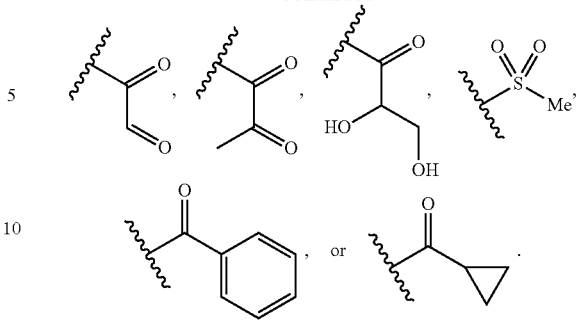

In certain embodiments, each R³ is independently an optionally substituted ring selected from cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, or xanthenyl.

In certain embodiments, each R³ is independently an optionally substituted ring selected from piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, or azetidinyl. In some embodiments, R³ is optionally substituted morpholinyl or thiomorpholinyl. In certain embodiments, the ring is substituted with Me, Et, OH, C(O)NH₂, or C(O)Me. In certain embodiments, the ring is substituted with C(O)Me.

In certain embodiments, each R³ is independently

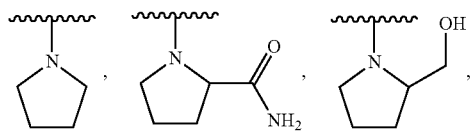

-continued

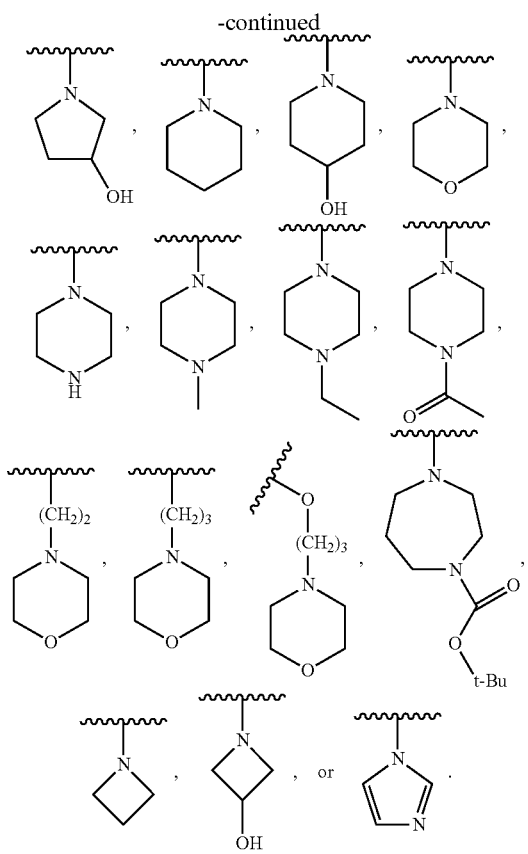

In certain embodiments, each R³ is independently -Me, —OMe, —NHCH₂CH₂OMe,

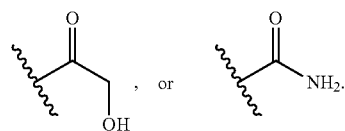

In some embodiments, each R³ is independently selected from those depicted in Table 3, below.

In certain embodiments, $R^y$ is hydrogen, optionally substituted $C_{1-6}$ aliphatic, halogen, —Cl, —CF₃, —CN, —C(O)R', —C(O)N(R')₂, —C(=N—R")R' or —N(R')₂; wherein each R' is independently hydrogen or an optionally substituted $C_{1-4}$ aliphatic; and R" is hydrogen or —OR. In certain embodiments, each R' is independently hydrogen, Me, or Et.

In certain embodiments, $R^y$ is hydrogen.

In certain embodiments, $R^y$ is -Me, —Cl, —F, —CF₃, —CN, C(O)Me, —C(O)NH₂, —C(O)NH(Me), —C(O)NH(Et), —C(=N—OH)Me, —C(=N—OMe)Me, or —NH₂.

In some embodiments, $R^y$ is haloaliphatic. In certain embodiments, $R^y$ is —CF₃.

In certain embodiments, $R^y$ is halogen. In certain embodiments, $R^y$ is —Cl.

In some embodiments, $R^y$ is selected from those depicted in Table 3, below.

In certain embodiments, W is NH. In certain embodiments, W is O.

In certain embodiments, R' is independently hydrogen, Me, or Et.

In various embodiments, the invention provides a compound of formula I, wherein each of Ring A, Ring B, R¹, R², R³, $R^y$, W, m and p is as defined above and described in embodiments, classes and subclasses above and herein, singly or in combination.

In various embodiments, the invention provides a compound of formula I-a:

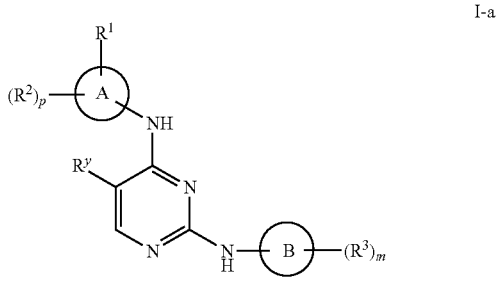

or a pharmaceutically acceptable salt thereof, wherein each of $R^y$, Ring A, Ring B, R¹, R², R³, m and p is as defined above and described in embodiments, classes and subclasses above and herein, singly or in combination.

In various embodiments, the invention provides a compound of formula I-b:

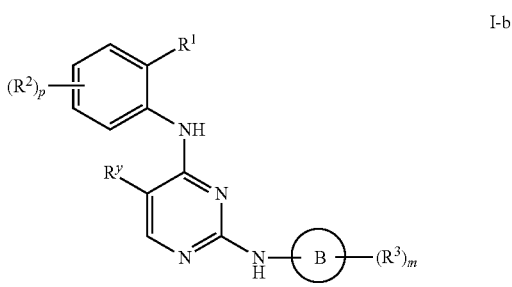

or a pharmaceutically acceptable salt thereof, wherein each of $R^y$, Ring B, R¹, R², R³, m and p is as defined above and described in embodiments, classes and subclasses above and herein, singly or in combination.

In various embodiments, the invention provides a compound of formula I-c:

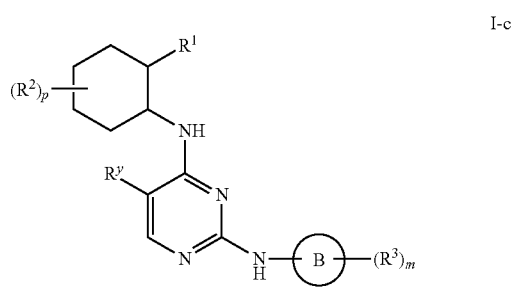

or a pharmaceutically acceptable salt thereof, wherein each of $R^y$, Ring B, R¹, R², R³, m and p is as defined above and described in embodiments, classes and subclasses above and herein, singly or in combination.

In various embodiments, the invention provides a compound of formula I-e:

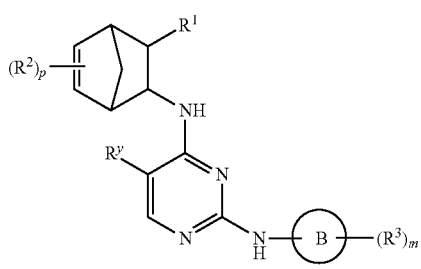

I-d

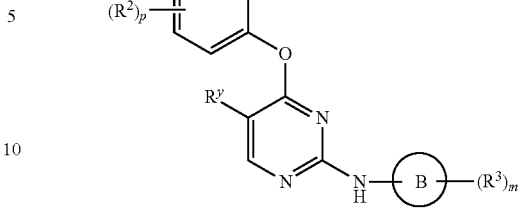

I-g or a pharmaceutically acceptable salt thereof, wherein each of $R^y$, Ring B, $R^1$, $R^2$, $R^3$, m and p is as defined above and described in embodiments, classes and subclasses above and herein, singly or in combination.

In various embodiments, the invention provides a compound of formula I-e:

or a pharmaceutically acceptable salt thereof, wherein each of $R^y$, Ring B, $R^1$, $R^2$, $R^3$, m and p is as defined above and described in embodiments, classes and subclasses above and herein, singly or in combination.

In various embodiments, the invention provides a compound of formula I-h:

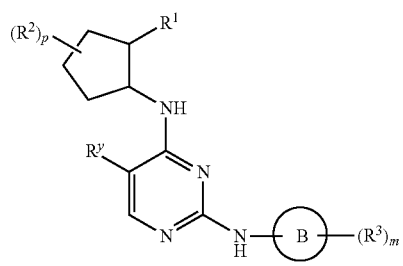

I-e

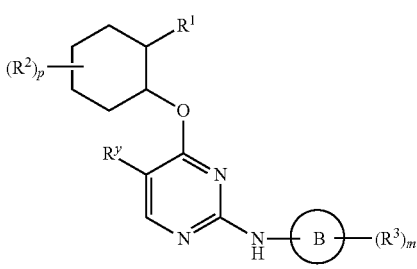

I-h or a pharmaceutically acceptable salt thereof, wherein each of $R^y$, Ring B, $R^1$, $R^2$, $R^3$, m and p is as defined above and described in embodiments, classes and subclasses above and herein, singly or in combination.

In various embodiments, the invention provides a compound of formula I-f:

or a pharmaceutically acceptable salt thereof, wherein each of $R^y$, Ring B, $R^1$, $R^2$, $R^3$, m and p is as defined above and described in embodiments, classes and subclasses above and herein, singly or in combination.

In various embodiments, the invention provides a compound of formula I-j:

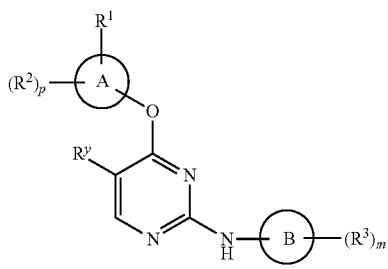

I-f

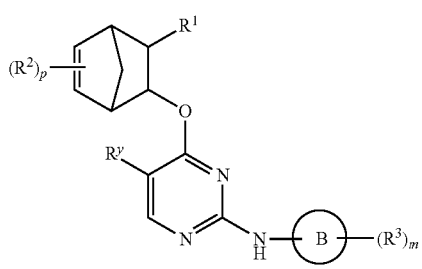

I-j or a pharmaceutically acceptable salt thereof, wherein each of $R^y$, Ring A, Ring B, $R^1$, $R^2$, $R^3$, m and p is as defined above and described in embodiments, classes and subclasses above and herein, singly or in combination.

In various embodiments, the invention provides a compound of formula I-g:

or a pharmaceutically acceptable salt thereof, wherein each of $R^y$, Ring B, $R^1$, $R^2$, $R^3$, m and p is as defined above and described in embodiments, classes and subclasses above and herein, singly or in combination.

In various embodiments, the invention provides a compound of formula I-k:

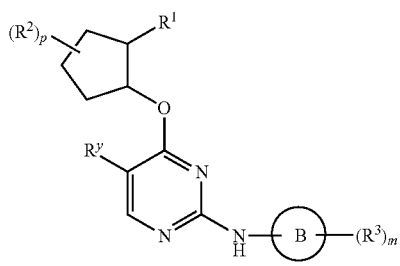

I-k


II-a


II-b


II-c

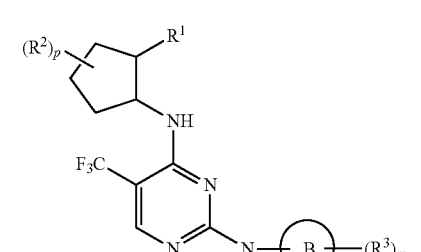

II-d or a pharmaceutically acceptable salt thereof, wherein each of $R^y$, Ring B, $R^1$, $R^2$, $R^3$, m and p is as defined above and described in embodiments, classes and subclasses above and herein, singly or in combination.

In various embodiments, the invention provides a compound selected from formula I-a, I-b, I-c, I-d, I-e, I-f, I-g, I-h, I-j, and I-k, wherein $R^y$ is haloaliphatic. In various embodiments, the invention provides a compound selected from formula I-a, I-b, I-c, I-d, I-e, I-f, I-g, I-h, I-j, and I-k, wherein $R^y$ is —$CF_3$. In various embodiments, the invention provides a compound of formula I', wherein $R^y$ is haloaliphatic. In various embodiments, the invention provides a compound of formula I', wherein $R^y$ is —$CF_3$.

In various embodiments, the invention provides a compound selected from formula I-a, I-b, I-c, I-d, I-e, I-f, I-g, I-h, I-j, and I-k, wherein $R^y$ is halogen. In various embodiments, the invention provides a compound selected from formula I-a, I-b, I-c, I-d, I-e, I-f, I-g, I-h, I-j, and I-k, wherein $R^y$ is —Cl. In various embodiments, the invention provides a compound of formula I', wherein $R^y$ is halogen. In various embodiments, the invention provides a compound of formula I', wherein $R^y$ is —Cl.

In various embodiments, the invention provides a compound of formula II:

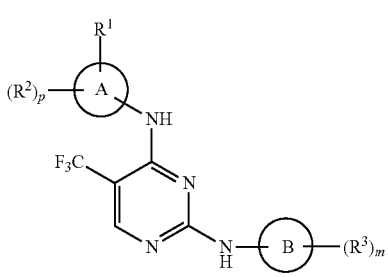

II or a pharmaceutically acceptable salt thereof, wherein each of Ring A, Ring B, $R^1$, $R^2$, $R^3$, m and p is as defined above and described in embodiments, classes and subclasses above and herein, singly or in combination.

In various embodiments, the invention provides a compound of any of formula II-a, II-b, II-c, or II-d:

or a pharmaceutically acceptable salt thereof, wherein each of Ring B, $R^1$, $R^2$, $R^3$, m and p is as defined above and described in embodiments, classes and subclasses above and herein, singly or in combination.

According to another embodiment, the present invention provides a compound of formula III:

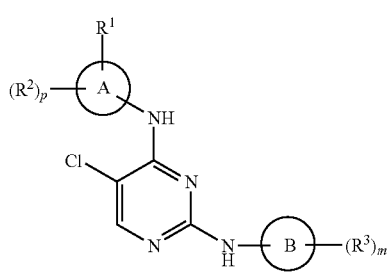

III or a pharmaceutically acceptable salt thereof, wherein, each of Ring A, Ring B, $R^1$, $R^2$, $R^3$, m and p is as defined above and described in embodiments, classes and subclasses above and herein, singly or in combination.

According to another embodiment, the present invention provides a compound of any of formula III-a, III-b, III-c, or III-d:

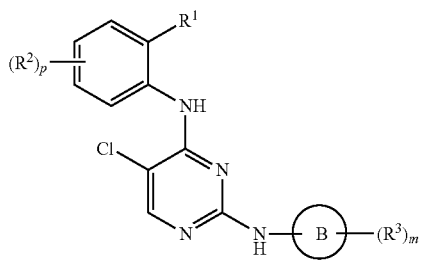

III-a

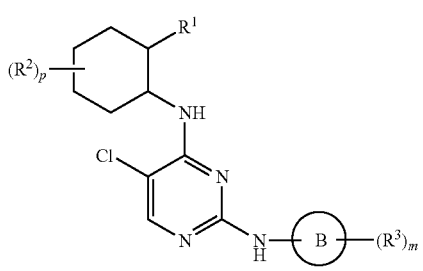

III-b

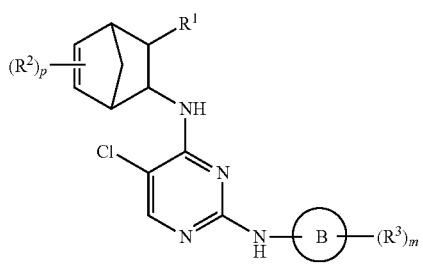

III-c

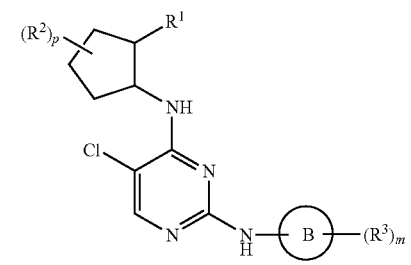

III-d or a pharmaceutically acceptable salt thereof,
wherein each of Ring B, $R^1$, $R^2$, $R^3$, m and p is as defined above and described in embodiments, classes and subclasses above and herein, singly or in combination.

According to another embodiment, the present invention provides a compound of formula IV:

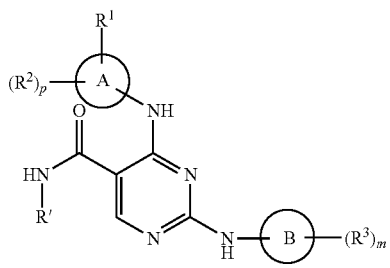

IV or a pharmaceutically acceptable salt thereof,
wherein each of Ring B, $R^1$, $R^2$, $R^3$, R', m and p is as defined above and described in embodiments, classes and subclasses above and herein, singly or in combination.

According to another embodiment, the present invention provides a compound of any of formula IV-a, IV-b, IV-c, or IV-d:

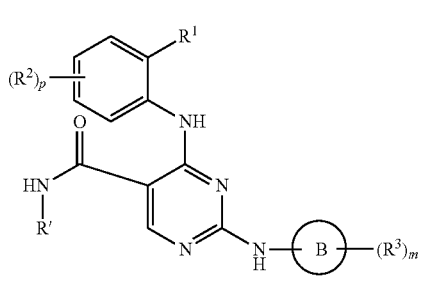

IV-a

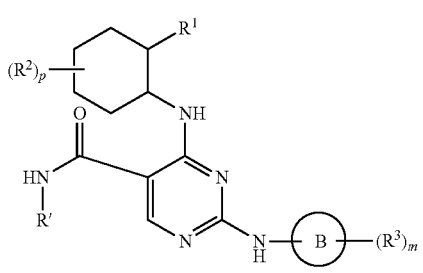

IV-b

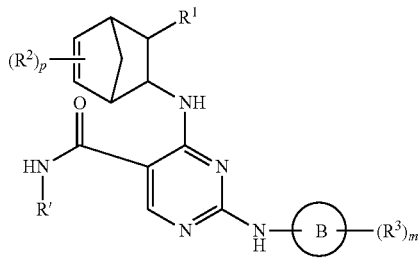

IV-c

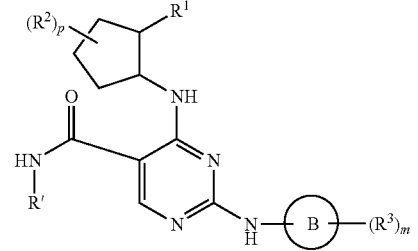

IV-d or a pharmaceutically acceptable salt thereof, wherein each of Ring B, $R^1$, $R^2$, $R^3$, R', m and p is as defined above and described in embodiments, classes and subclasses above and herein, singly or in combination.

According to another embodiment, the present invention provides a compound of formula V:

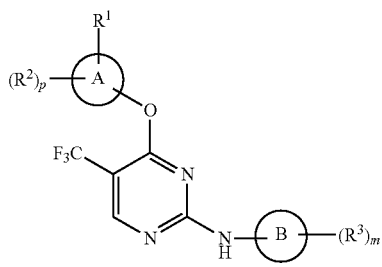

V or a pharmaceutically acceptable salt thereof, wherein each of Ring A, Ring B, $R^1$, $R^2$, $R^3$, m and p is as defined above and described in embodiments, classes and subclasses above and herein, singly or in combination.

According to another embodiment, the present invention provides a compound of any of formula V-a, V-b, V-c, or V-d:

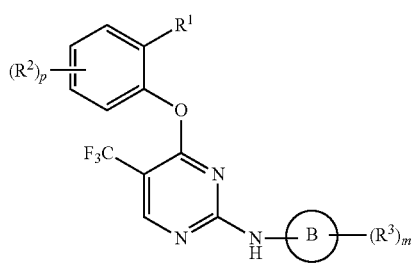

V-a

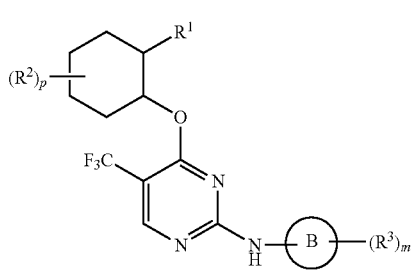

V-b

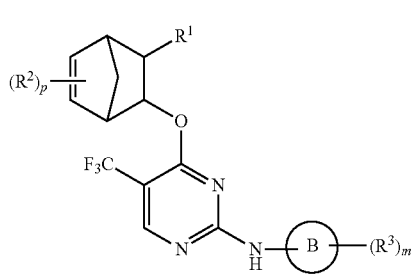

V-c

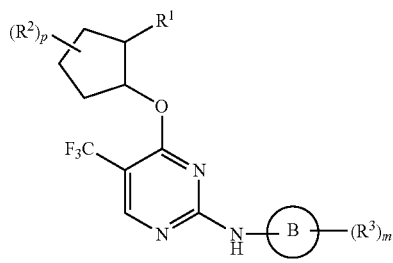

V-d or a pharmaceutically acceptable salt thereof, wherein each of Ring B, $R^1$, $R^2$, $R^3$, m and p is as defined above and described in embodiments, classes and subclasses above and herein, singly or in combination.

According to another embodiment, the present invention provides a compound of formula VI:

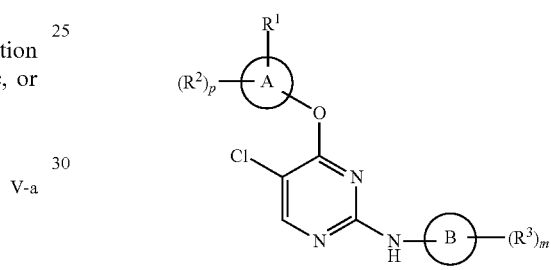

VI or a pharmaceutically acceptable salt thereof, wherein each of Ring A, Ring B, $R^1$, $R^2$, $R^3$, m and p is as defined above and described in embodiments, classes and subclasses above and herein, singly or in combination.

According to another embodiment, the present invention provides a compound of any of formula VI-a, VI-b, VI-c, or VI-d:

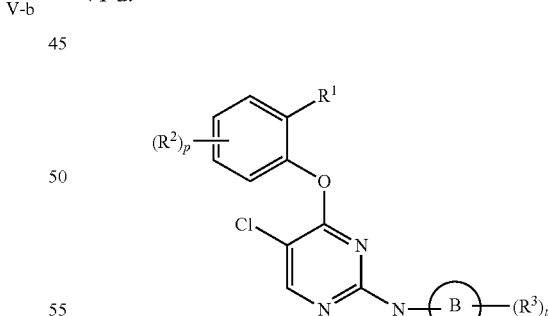

VI-a

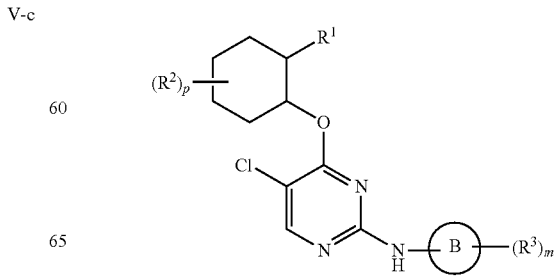

VI-b

-continued

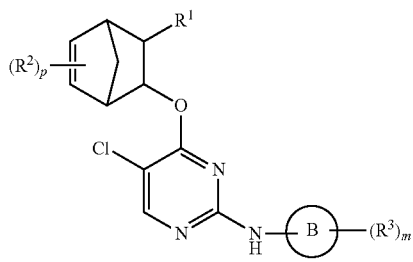
VI-c

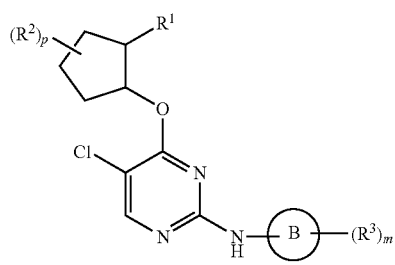
VI-d or a pharmaceutically acceptable salt thereof, wherein each of Ring B, $R^1$, $R^2$, $R^3$, m and p is as defined above and described in embodiments, classes and subclasses above and herein, singly or in combination.

According to another embodiment, the present invention provides a compound of formula VII:

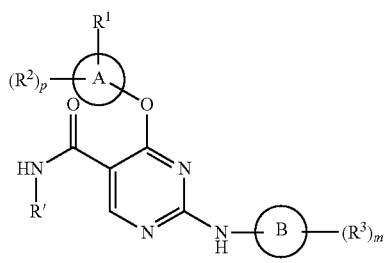
VII or a pharmaceutically acceptable salt thereof, wherein each of Ring A, Ring B, $R^1$, $R^2$, $R^3$, R', m and p is as defined above and described in embodiments, classes and subclasses above and herein, singly or in combination.

According to another embodiment, the present invention provides a compound of any of formula VII-a, VII-b, VII-c, or VII-d:

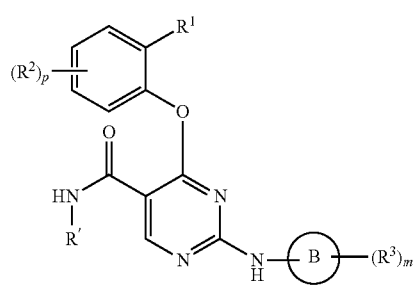
VII-a

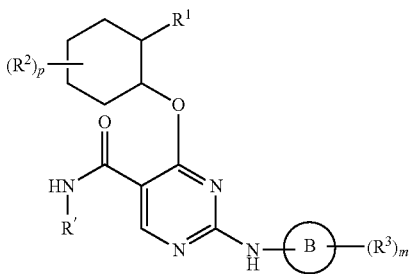
VII-b

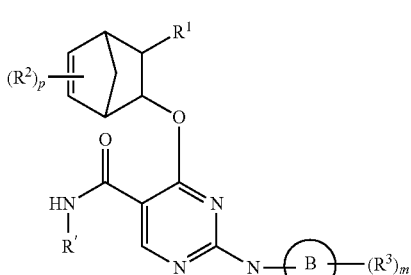
VII-c

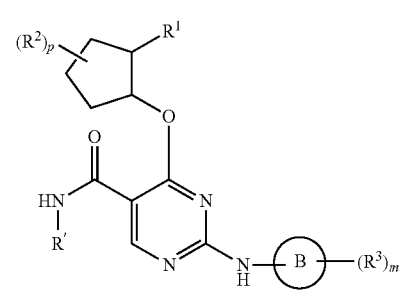
VII-d or a pharmaceutically acceptable salt thereof, wherein each of Ring B, $R^1$, $R^2$, $R^3$, R', m and p is as defined above and described in embodiments, classes and subclasses above and herein, singly or in combination.

In certain embodiments, the present invention provides a compound of any of formula I, II, III, IV, V, VI, or VII wherein Ring B is phenyl. In other embodiments, the present invention provides a compound of any of formula I, II, III, IV, V, VI, or VII wherein Ring B is pyridyl. In other embodiments, the present invention provides a compound of any of formula I, II, III, IV, V, VI, or VII wherein Ring B is piperdinyl. In other embodiments, the present invention provides a compound of any of formula I, II, III, IV, V, VI, or VII wherein Ring B is cyclohexyl.

In certain embodiments, the present invention provides a compound of formula I' wherein Ring B is phenyl. In other embodiments, the present invention provides a compound of formula I' wherein Ring B is pyridyl. In other embodiments, the present invention provides a compound of formula I' wherein Ring B is piperdinyl. In other embodiments, the present invention provides a compound of formula I' wherein Ring B is cyclohexyl.

In some embodiments, the present invention provides a compound of formula VIII:

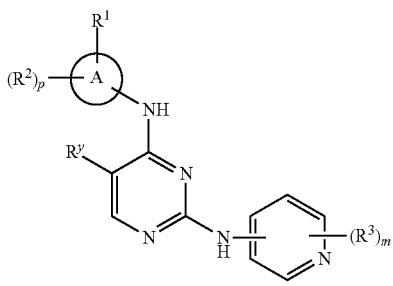

VIII or a pharmaceutically acceptable salt thereof, wherein each of Ring A, $R^1$, $R^2$, $R^3$, $R^y$, m and p is as defined above and described in embodiments, classes and subclasses above and herein, singly or in combination.

In some embodiments, the present invention provides a compound of formula VIII wherein $R^y$ is haloaliphatic. In certain embodiments, the present invention provides a compound of formula VIII wherein $R^y$ is —$CF_3$.

In some embodiments, the present invention provides a compound of formula VIII wherein $R^y$ is halogen. In certain embodiments, the present invention provides a compound of formula VIII wherein $R^y$ is —Cl.

In certain embodiments, the present invention provides a compound of formula VIII wherein at least one $R^3$ is —OMe.

In some embodiments, the present invention provides a compound of any of formula VIII-a, VIII-b, VIII-c, or VIII-d:

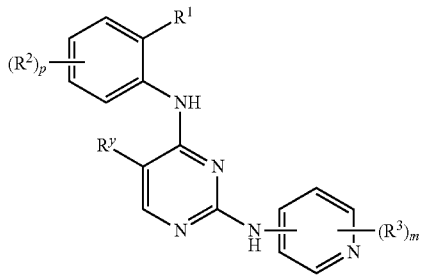

VIII-a

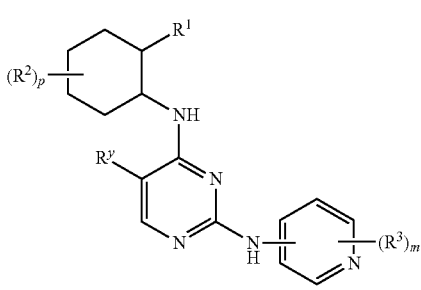

VIII-b

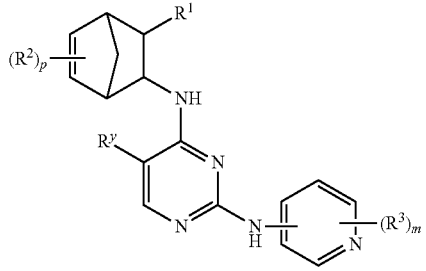

VIII-c

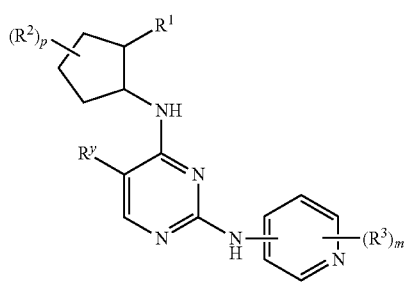

VIII-d or a pharmaceutically acceptable salt thereof, wherein each of $R^1$, $R^2$, $R^3$, $R^y$, m and p is as defined above and described in embodiments, classes and subclasses above and herein, singly or in combination.

In some embodiments, the present invention provides a compound of any of formula VIII-a, VIII-b, VIII-c, or VIII-d wherein $R^y$ is haloaliphatic. In certain embodiments, the present invention provides a compound of formula VIII wherein $R^y$ is —$CF_3$.

In some embodiments, the present invention provides a compound of any of formula VIII-a, VIII-b, VIII-c, or VIII-d wherein $R^y$ is halogen. In certain embodiments, the present invention provides a compound of formula VIII wherein $R^y$ is —Cl.

In certain embodiments, the present invention provides a compound of any of formula VIII-a, VIII-b, VIII-c, or VIII-d wherein at least one $R^3$ is —OMe.

As defined generally above, the $R^1$ group of any of formula I, I', II, III, IV, V, VI, VII, or VIII is a warhead group. In certain embodiments, $R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or C$_{1-6}$ aliphatic optionally substituted with oxo, halogen, NO$_2$, or CN.

In certain embodiments, L is a covalent bond.

In certain embodiments, L is a bivalent C$_{1-8}$ saturated or unsaturated, straight or branched, hydrocarbon chain. In certain embodiments, L is —CH$_2$—.

In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.

In certain embodiments, L is a bivalent C$_{1-8}$ hydrocarbon chain wherein at least one methylene unit of L is replaced by —C(O)—. In certain embodiments, L is a bivalent C$_{1-8}$ hydrocarbon chain wherein at least two methylene units of L are replaced by —C(O)—. In some embodiments, L is —C(O)CH$_2$CH$_2$C(O)—, —C(O)CH$_2$NHC(O)—, —C(O)CH$_2$NHC(O)CH$_2$CH$_2$C(O)—, or —C(O)CH$_2$CH$_2$CH$_2$NHC(O)CH$_2$CH$_2$C(O)—.

In certain embodiments, L is a bivalent C$_{1-8}$ hydrocarbon chain wherein at least one methylene unit of L is replaced by —S(O)$_2$—. In certain embodiments, L is a bivalent C$_{1-8}$ hydrocarbon chain wherein at least one methylene unit of L is replaced by —S(O)$_2$— and at least one methylene unit of L is replaced by —C(O)—. In certain embodiments, L is a bivalent C$_{1-8}$ hydrocarbon chain wherein at least one methylene unit of L is replaced by —S(O)$_2$— and at least two methylene units of L are replaced by —C(O)—. In some embodiments, L is —S(O)$_2$CH$_2$CH$_2$NHC(O)CH$_2$CH$_2$C(O)— or —S(O)$_2$CH$_2$CH$_2$NHC(O)—.

In some embodiments, L is a bivalent C$_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—.

In certain embodiments, L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In some embodiments, L is a bivalent C$_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent C$_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent C$_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent C$_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —CH$_2$C(O)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent C$_{2-8}$ straight or branched, hydrocarbon chain wherein L has at least one double bond and at least one methylene unit of L is replaced by —OC(O)—.

In some embodiments, L is a bivalent C$_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH2OC(O)CH=CHCH2-, —CH2-OC(O)CH=CH—, or —CH(CH=CH2)OC(O)CH=CH—.

In certain embodiments, L is —NRC(O)CH=CH—, —NRC(O)CH=CHCH2N(CH3)-, —NRC(O)CH=CHCH2O—, —CH2NRC(O)CH=CH—, —NRSO2CH=CH—, —NRSO2CH=CHCH2-, —NRC(O)(C=N$_2$)C(O)—, —NRC(O)CH=CHCH$_2$N(CH$_3$)—, —NRC(O)CH=CHCH$_2$O—, —NRC(O)C(=CH$_2$)CH$_2$—, —CH$_2$NRC(O)—, —CH$_2$CH$_2$NRC(O)—, or —CH$_2$NRC(O)cyclopropylene-, wherein each R is independently hydrogen or optionally substituted C$_{1-6}$ aliphatic.

In certain embodiments, L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)C(O)—, —NHC(O)C(=CH$_2$)CH$_2$—, —CH$_2$NHC(O)—, —CH$_2$CH$_2$NHC(O)—, or —CH$_2$NHC(O)cyclopropylene-.

In some embodiments, L is a bivalent C$_{2-8}$ straight or branched, hydrocarbon chain wherein L has at least one triple bond. In certain embodiments, L is a bivalent C$_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—.

In some embodiments, L is a bivalent C$_{2-8}$ straight or branched, hydrocarbon chain wherein has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In certain embodiments, L is a bivalent C$_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—. Exemplary L groups include —NHC(O)-cyclopropylene-SO$_2$— and —NHC(O)— cyclopropylene-.

As defined generally above, Y is hydrogen, C$_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 R$^e$ groups, each R$^e$ is independently selected from -Q-Z, oxo, NO$_2$, halogen, CN, a suitable leaving group, or C$_{1-6}$ aliphatic, wherein Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and, Z is hydrogen or C$_{1-6}$ aliphatic optionally substituted with oxo, halogen, NO$_2$, or CN.

In certain embodiments, Y is hydrogen.

In certain embodiments, Y is C$_{1-6}$ aliphatic optionally substituted with oxo, halogen, NO$_2$, or CN. In some embodiments, Y is C$_{2-6}$ alkenyl optionally substituted with oxo, halogen, NO$_2$, or CN. In other embodiments, Y is C$_{2-6}$ alkynyl optionally substituted with oxo, halogen, NO$_2$, or CN. In some embodiments, Y is C$_{2-6}$ alkenyl. In other embodiments, Y is C$_{2-4}$ alkynyl. In certain embodiments, Y is hydrogen or C$_{1-6}$ aliphatic optionally substituted with oxo, halogen, NO$_2$, or CN.

In other embodiments, Y is C$_{1-6}$ alkyl substituted with oxo, halogen, NO$_2$, or CN. Such Y groups include —CH$_2$F, —CH$_2$Cl, —CH$_2$CN, and —CH$_2$NO$_2$.

In certain embodiments, Y is a saturated 3-6 membered monocyclic ring having 0-3 heteroatoms independently selected from nitrogen, oxygen, or sulfur, wherein Y is substituted with 1-4 R$^e$ groups, wherein each R$^e$ is as defined above and described herein.

In some embodiments, Y is a saturated 3-4 membered heterocyclic ring having 1 heteroatom selected from oxygen or nitrogen wherein said ring is substituted with 1-2 R$^e$ groups, wherein each R$^e$ is as defined above and described herein. Exemplary such rings are epoxide and oxetane rings, wherein each ring is substituted with 1-2 R$^e$ groups, wherein each R$^e$ is as defined above and described herein.

In other embodiments, Y is a saturated 5-6 membered heterocyclic ring having 1-2 heteroatom selected from oxygen or nitrogen wherein said ring is substituted with 1-4 R$^e$ groups, wherein each R$^e$ is as defined above and described herein. Such rings include piperidine and pyrrolidine, wherein each ring is substituted with 1-4 R$^e$ groups, wherein each R$^e$ is as defined above and described herein. In certain embodiments, Y is

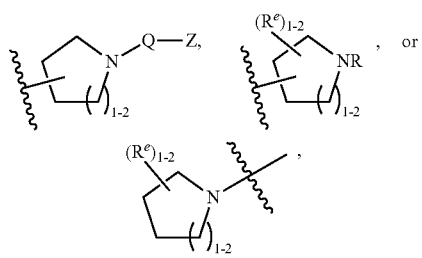

wherein each R, Q, Z, and R$^e$ is as defined above and described herein. In certain embodiments, Y is piperazine.

In some embodiments, Y is a saturated 3-6 membered carbocyclic ring, wherein said ring is substituted with 1-4 R$^e$ groups, wherein each R$^e$ is as defined above and described herein. In certain embodiments, Y is cyclopropyl, cyclobutyl, cyclopentyl, or cyclohexyl, wherein each ring is substituted with 1-4 R$^e$ groups, wherein each R$^e$ is as defined above and described herein. In certain embodiments, Y is

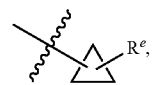

wherein R$^e$ is as defined above and described herein. In certain embodiments, Y is cyclopropyl optionally substituted with halogen, CN or NO$_2$. In certain embodiments, Y is cyclopropyl substituted with halogen, CN or NO$_2$.

In certain embodiments, Y is a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein.

In some embodiments, Y is a partially unsaturated 3-6 membered carbocyclic ring, wherein said ring is substituted with 1-4 R$^e$ groups, wherein each R$^e$ is as defined above and described herein. In some embodiments, Y is cyclopropenyl, cyclobutenyl, cyclopentenyl, or cyclohexenyl wherein each ring is substituted with 1-4 R$^e$ groups, wherein each R$^e$ is as defined above and described herein. In certain embodiments, Y is

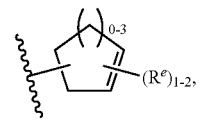

wherein each R$^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein. In certain embodiments, Y is selected from:

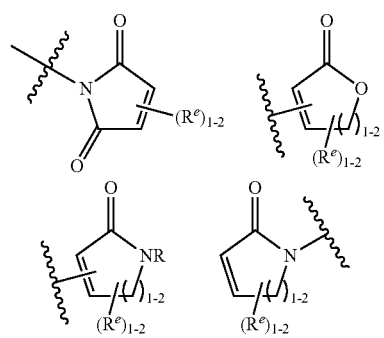

wherein each R and R$^e$ is as defined above and described herein.

In certain embodiments, Y is a 6-membered aromatic ring having 0-2 nitrogens wherein said ring is substituted with 1-4 R$^e$ groups, wherein each R$^e$ group is as defined above and described herein. In certain embodiments, Y is phenyl, pyridyl, or pyrimidinyl, wherein each ring is substituted with 1-4 R$^e$ groups, wherein each R$^e$ is as defined above and described herein. In certain embodiments, Y is phenyl, pyridyl, or pyrimidinyl, wherein each ring is substituted with 1-4 R$^e$ groups, wherein each R$^e$ is -Q-Z wherein Q is a bivalent C$_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —SO$_2$—. In some embodiments, -Q-Z is —NHC(O)CH=CH$_2$ or —C(O)CH=CH$_2$. In certain embodiments, each R$^e$ is independently selected from from —NHC(O)CH=CH$_2$, —C(O)CH=CH$_2$, —CH$_2$CH=CH$_2$, —C≡CH, —C(O)OCH$_2$Cl, —C(O)OCH$_2$F, —C(O)OCH$_2$CN, —C(O)CH$_2$Cl, —C(O)CH$_2$F, or —C(O)CH$_2$CN.

In some embodiments, Y is selected from:

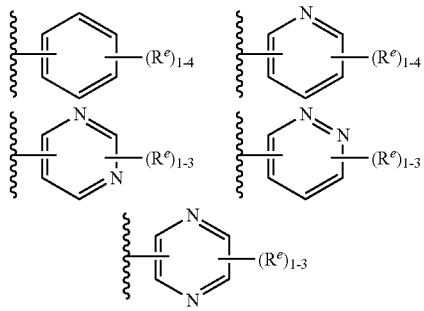

wherein each R$^e$ is as defined above and described herein. In some embodiments, Y is selected from:

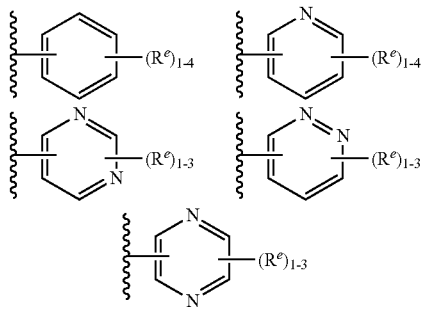

wherein each R$^e$ is -Q-Z wherein Q is a bivalent C$_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —SO$_2$—. In some embodiments, -Q-Z is —NHC(O)CH=CH$_2$ or —C(O)CH=CH$_2$. In certain embodiments, each R$^e$ is independently selected from from —NHC(O)CH=CH$_2$, —C(O)CH=CH$_2$, —CH$_2$CH=CH$_2$, —C≡CH, —C(O)OCH$_2$Cl, —C(O)OCH$_2$F, —C(O)OCH$_2$CN, —C(O)CH$_2$Cl, —C(O)CH$_2$F, or —C(O)CH$_2$CN.

In other embodiments, Y is a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 R$^e$ groups, wherein each R$^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 R$^e$ groups, wherein each R$^e$ group is as defined above and described herein. In certain embodiments, Y is selected from:

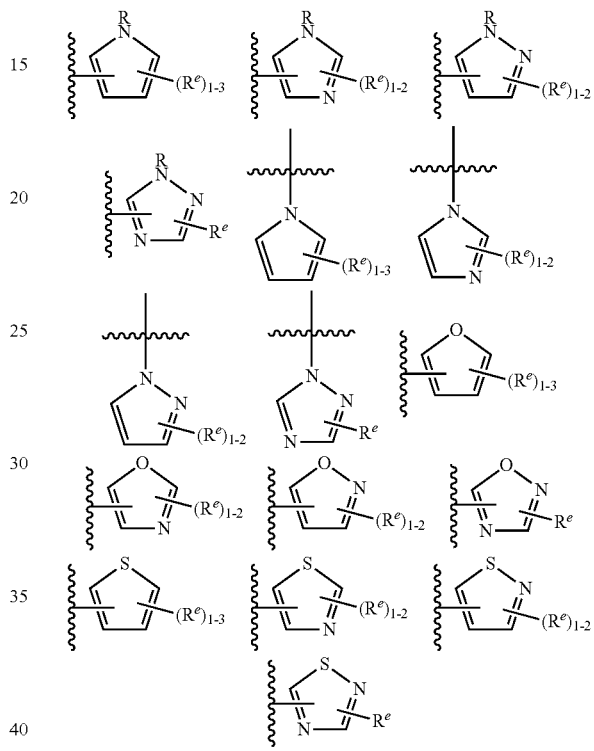

wherein each R and R$^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 R$^e$ groups, wherein R$^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 R$^e$ groups, wherein R$^e$ is as defined above and described herein. Exemplary such bicyclic rings include 2,3-dihydrobenzo[d]isothiazole, wherein said ring is substituted with 1-4 R$^e$ groups, wherein R$^e$ is as defined above and described herein.

As defined generally above, each R$^e$ group is independently selected from -Q-Z, oxo, NO$_2$, halogen, CN, a suitable leaving group, or C$_{1-6}$ aliphatic optionally substituted with oxo, halogen, NO$_2$, or CN, wherein Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or C$_{1-6}$ aliphatic optionally substituted with oxo, halogen, NO$_2$, or CN.

In certain embodiments, R$^e$ is C$_{1-6}$ aliphatic optionally substituted with oxo, halogen, NO$_2$, or CN. In other embodiments, R$^e$ is oxo, NO$_2$, halogen, or CN.

In some embodiments, R$^e$ is -Q-Z, wherein Q is a covalent bond and Z is hydrogen (i.e., R$^e$ is hydrogen). In other embodiments, R$^e$ is -Q-Z, wherein Q is a bivalent C$_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —SO$_2$—. In other embodiments, Q is a bivalent C$_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —SO$_2$—. In certain embodiments, the Z moiety of the R$^e$ group is hydrogen. In some embodiments, -Q-Z is —NHC(O)CH=CH$_2$ or —C(O)CH=CH$_2$.

In certain embodiments, each R$^e$ is independently selected from from oxo, NO$_2$, CN, fluoro, chloro, —NHC(O)CH=CH$_2$, —C(O)CH=CH$_2$, —CH$_2$CH=CH$_2$, —C≡CH, —C(O)OCH$_2$Cl, —C(O)OCH$_2$F, —C(O)OCH$_2$CN, —C(O)CH$_2$Cl, —C(O)CH$_2$F, —C(O)CH$_2$CN, or —CH$_2$C(O)CH$_3$.

In certain embodiments, R$^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyloxy, and diazonium moieties. Examples of suitable leaving groups include chloro, iodo, bromo, fluoro, acetoxy, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:
(a) L is a bivalent C$_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or C$_{1-6}$ aliphatic optionally substituted with oxo, halogen, NO$_2$, or CN; or
(b) L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or
(c) L is a bivalent C$_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or
(d) L is a bivalent C$_{2-8}$ straight or branched, hydrocarbon chain wherein L has at least one double bond and at least one methylene unit of L is replaced by —C(O)—; and Y is hydrogen or C$_{1-6}$ aliphatic optionally substituted with oxo, halogen, NO$_2$, or CN; or
(e) L is a bivalent C$_{2-8}$ straight or branched, hydrocarbon chain wherein L has at least one double bond and at least one methylene unit of L is replaced by —OC(O)—; and Y is hydrogen or C$_{1-6}$ aliphatic optionally substituted with oxo, halogen, NO$_2$, or CN; or
(f) L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-; wherein R is H or optionally substituted C$_{1-6}$ aliphatic; and Y is hydrogen or C$_{1-6}$ aliphatic optionally substituted with oxo, halogen, NO$_2$, or CN; or
(g) L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-; and Y is hydrogen or C$_{1-6}$ aliphatic optionally substituted with oxo, halogen, NO$_2$, or CN; or
(h) L is a bivalent C$_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—; and Y is hydrogen or C$_{1-6}$ aliphatic optionally substituted with oxo, halogen, NO$_2$, or CN; or
(i) is a bivalent C$_{2-8}$ straight or branched, hydrocarbon chain wherein L has at least one triple bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, or —C(O)O—, and Y is hydrogen or C$_{1-6}$ aliphatic optionally substituted with oxo, halogen, NO$_2$, or CN; or
(j) L is —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—; and Y is hydrogen or C$_{1-6}$ aliphatic optionally substituted with oxo, halogen, NO$_2$, or CN; or
(k) L is a bivalent C$_{2-8}$ straight or branched, hydrocarbon chain wherein one methylene unit of L is replaced by cyclopropylene and one or two additional methylene units of L are independently replaced by —NRC(O)—, —C(O)NR—, —N(R)SO$_2$—, —SO$_2$N(R)—, —S—, —S(O)—, —SO$_2$—, —OC(O)—, or —C(O)O—; and Y is hydrogen or C$_{1-6}$ aliphatic optionally substituted with oxo, halogen, NO$_2$, or CN; or
(l) L is a covalent bond and Y is selected from:
(i) C$_{1-6}$ alkyl substituted with oxo, halogen, NO$_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

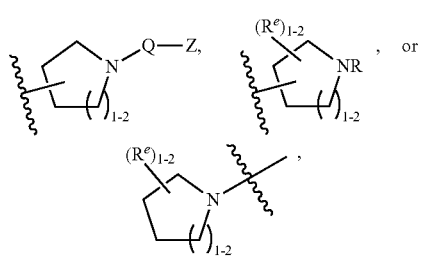

(vi)

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or

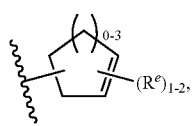

(x)

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

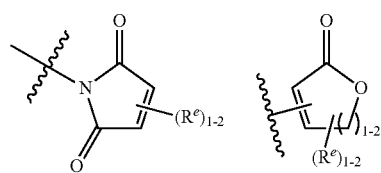

(xii)

-continued

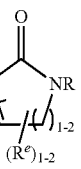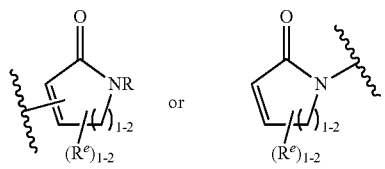

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or

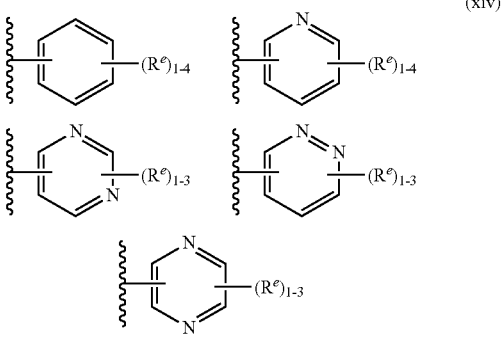

(xiv)

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

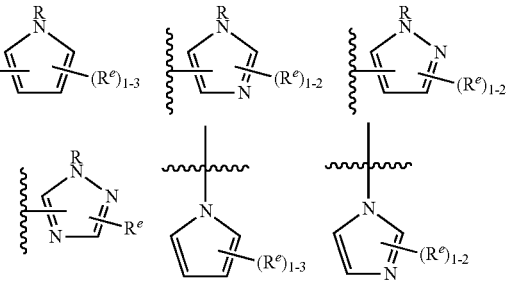

(xvi)

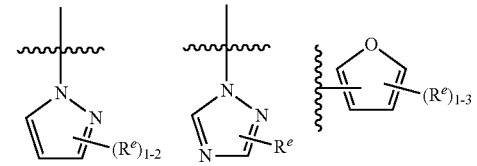

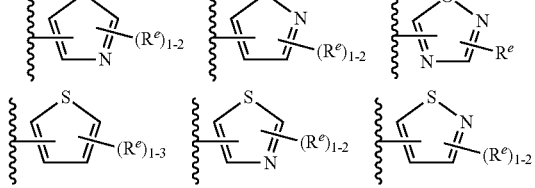

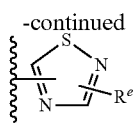

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:

(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

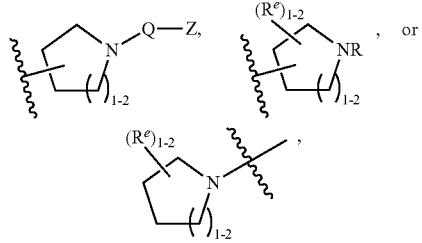
(vi)

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or

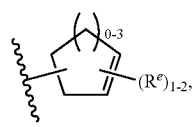
(x)

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

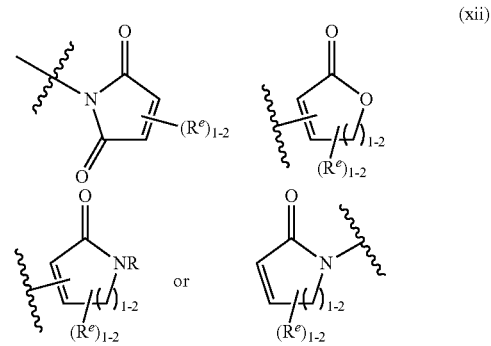
(xii)

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or

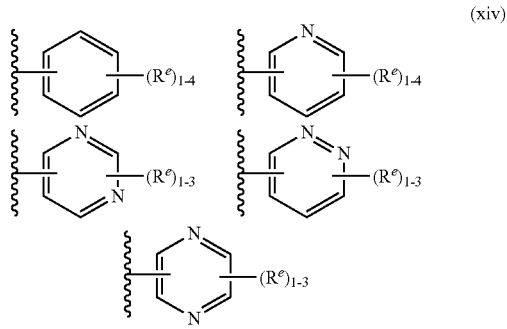
(xiv)

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or

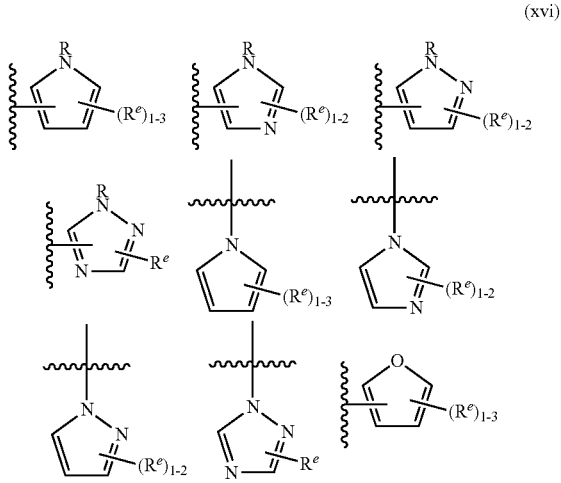
(xvi)

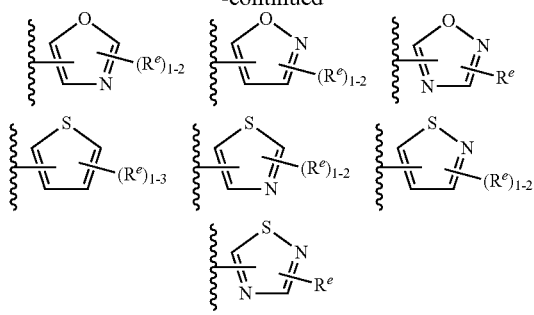

wherein each R and R$^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 R$^e$ groups, wherein R$^e$ is as defined above and described herein;

(n) L is —N(R)C(O)— and Y is selected from:

(i) C$_{1-6}$ alkyl substituted with oxo, halogen, NO$_2$, or CN; or (ii) C$_{2-6}$ alkenyl optionally substituted with oxo, halogen, NO$_2$, or CN; or (iii) C$_{2-6}$ alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or

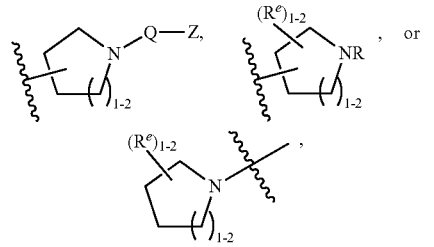

wherein each R, Q, Z, and R$^e$ is as defined above and described herein; or (vii) a saturated 3-6 membered carbocyclic ring, wherein said ring is substituted with 1-4 R$^e$ groups, wherein each R$^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or (ix) a partially unsaturated 3-6 membered carbocyclic ring, wherein said ring is substituted with 1-4 R$^e$ groups, wherein each R$^e$ is as defined above and described herein; or

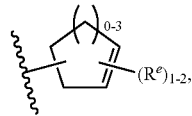

wherein each R$^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein; or

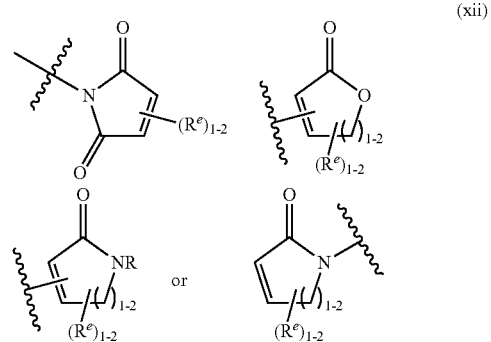

wherein each R and R$^e$ is as defined above and described herein; or (xiii) a 6-membered aromatic ring having 0-2 nitrogens wherein said ring is substituted with 1-4 R$^e$ groups, wherein each R$^e$ group is as defined above and described herein; or

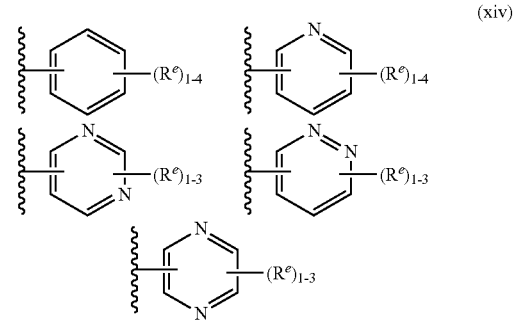

wherein each R$^e$ is as defined above and described herein; or (xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein; or

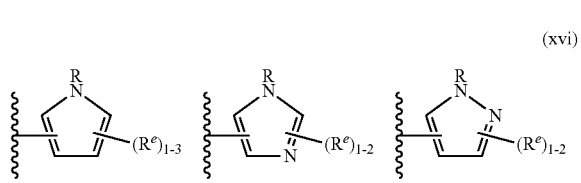

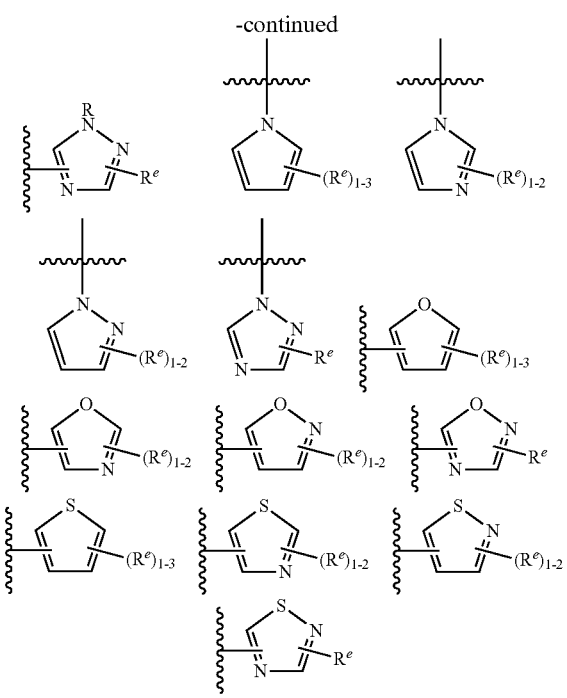

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or

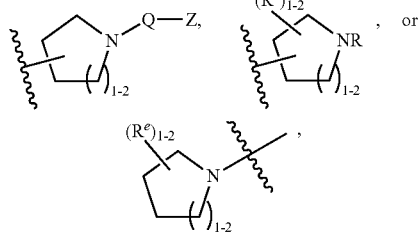

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or

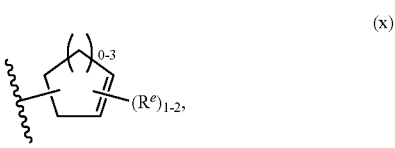

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or

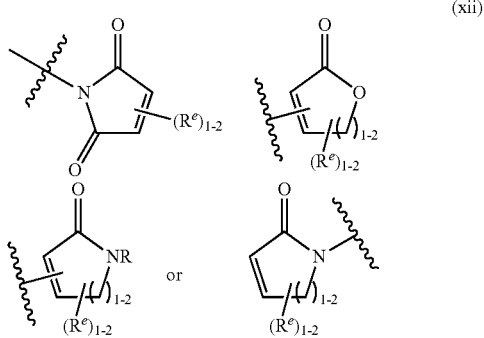

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or

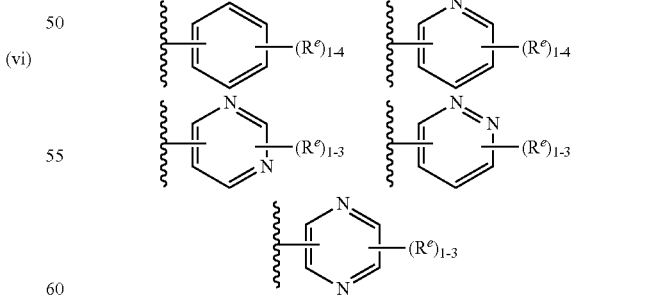

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

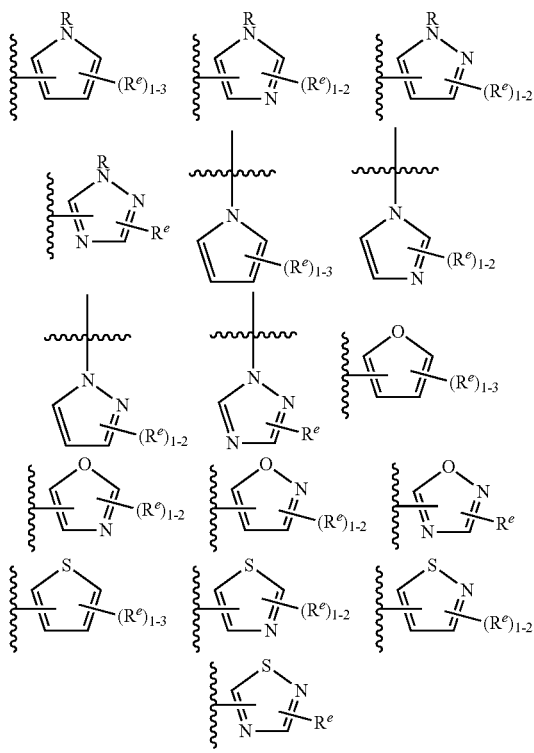

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—; and Y is selected from:

(i) C$_{1-6}$ alkyl substituted with oxo, halogen, NO$_2$, or CN; or (ii) C$_{2-6}$ alkenyl optionally substituted with oxo, halogen, NO$_2$, or CN; or (iii) C$_{2-6}$ alkynyl optionally substituted with oxo, halogen, NO$_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

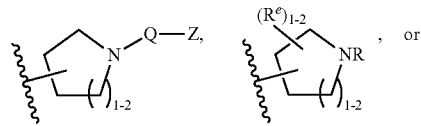

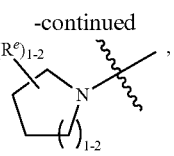

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

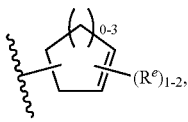

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

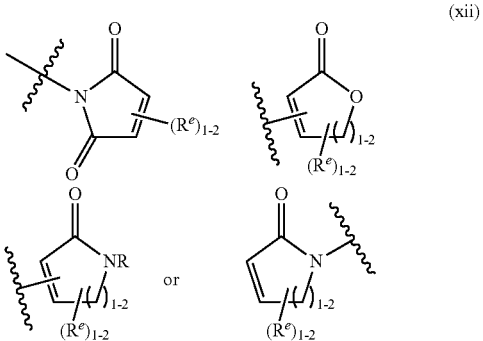

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

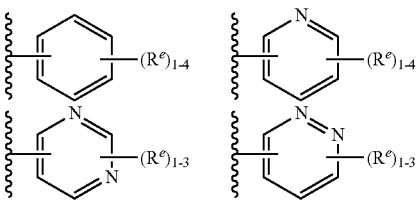

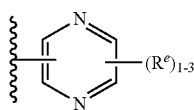

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

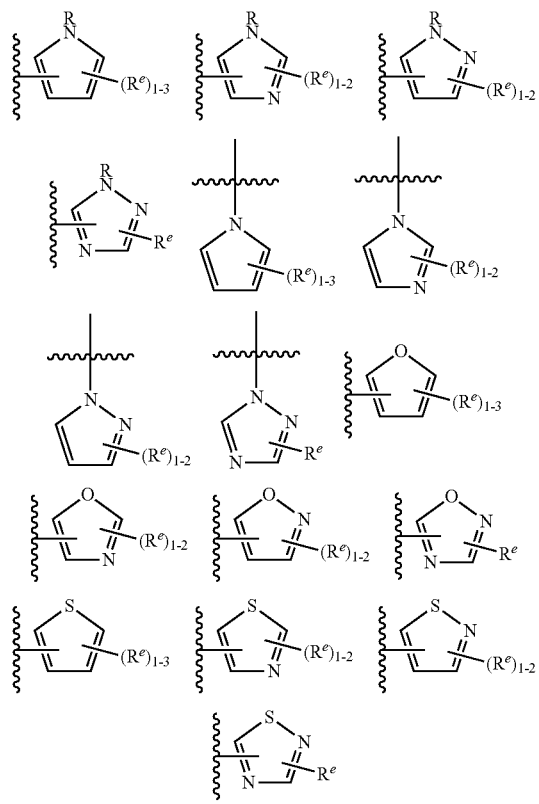

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

(q) L is a bivalent $C_{2-8}$ straight or branched, hydrocarbon chain wherein two or three methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen or $C_{1-6}$ aliphatic optionally substituted with oxo, halogen, NO$_2$, or CN.

(r) L-Y is "pro-warhead" that is converted in vitro or in vivo to an irreversible warhead.

In certain embodiments, L-Y is

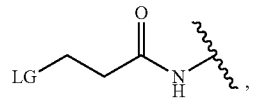

wherein LG is a leaving group as understood by one of ordinary skill in the art. In certain embodiments, L-Y is

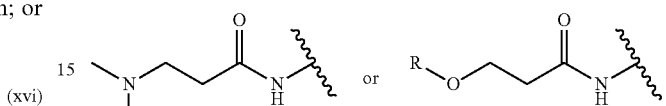

wherein R is as defined and described above and herein. In certain embodiments, the "pro-warhead" is converted to a warhead group (e.g., an acrylamide group) according to the following:

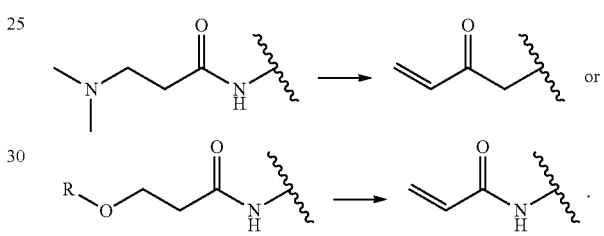

Such "pro-warheads" are applicable to any α,β unsaturated system, e.g.,

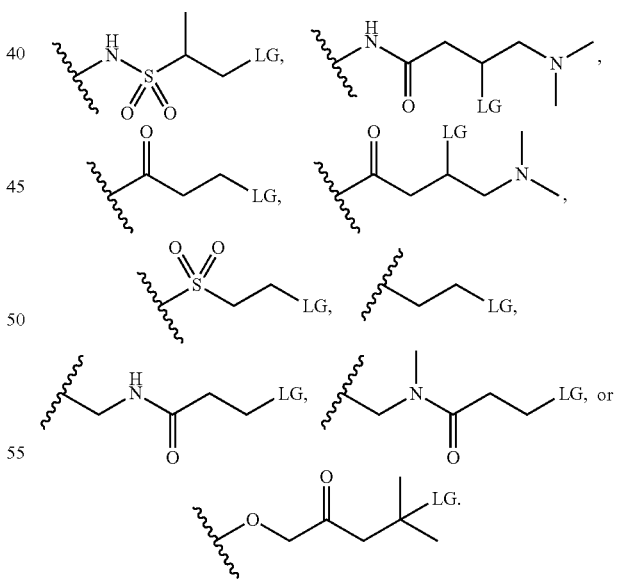

In certain embodiments, $R^1$ is -L-Y, wherein:
L is a covalent bond or a bivalent $C_{1-8}$ saturated or unsaturated, straight or branched, hydrocarbon chain, wherein one, two, or three methylene units of L are optionally and independently replaced by —N(R)C(O)—, —N(R)SO$_2$—, —O—, —C(O)—, or —SO$_2$—; and Y is hydrogen, or $C_{1-6}$ aliphatic optionally substituted with oxo, halogen, $N(R)_2$, $NO_2$, or CN.
In certain embodiments, the Y group of $R^1$ group, -L-Y, is selected from those set forth in Table 1, below, wherein each wavy line indicates the point of attachment to the rest of the molecule.
TABLE 1
| Exemplary Y groups: | |
|---|---|
| 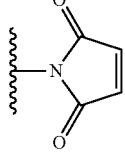 | a |
| 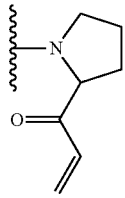 [SMILES: *N1CCCC1C(=O)C=C] | b |
| 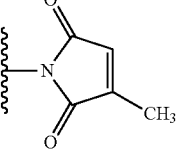 | c |
| 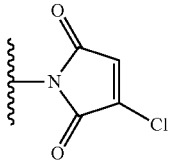 [SMILES: *N1C(=O)C=C(Cl)C1=O] | d |
| 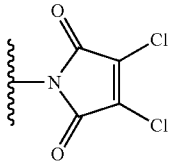 [SMILES: *N1C(=O)C(Cl)=C(Cl)C1=O] | e |
| 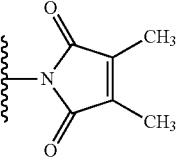 [SMILES: *N1C(=O)C(C)=C(C)C1=O] | f |
| 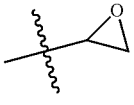 [SMILES: *C1CO1] | g |
| 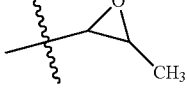 | h |
TABLE 1-continued
| Exemplary Y groups: | |
|---|---|
| 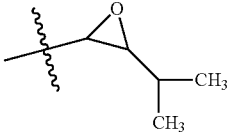 | i |
| 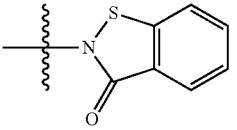 [SMILES: *n1sc2ccccc2c1=O] | j |
| 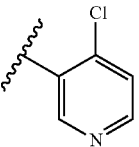 [SMILES: *c1cnccc1Cl] | k |
| 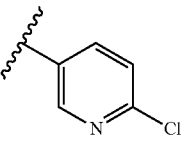 [SMILES: *c1ccc(Cl)nc1] | l |
| 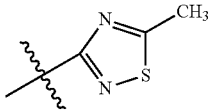 [SMILES: *c1nsc(C)n1] | m |
| 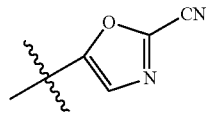 [SMILES: *c1cnc(C#N)o1] | n |
| 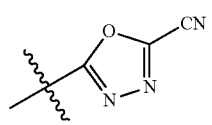 | o |
| 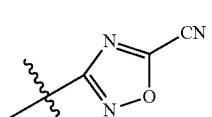 | p |
| 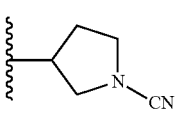 | q |
| 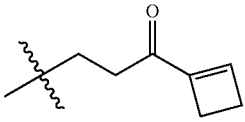 [SMILES: *CCC(=O)C1=CCC1] | r |
| 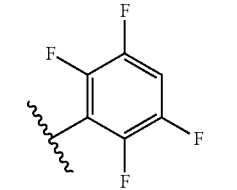 [SMILES: *c1c(F)c(F)cc(F)c1F] | s |

TABLE 1-continued
Exemplary Y groups:
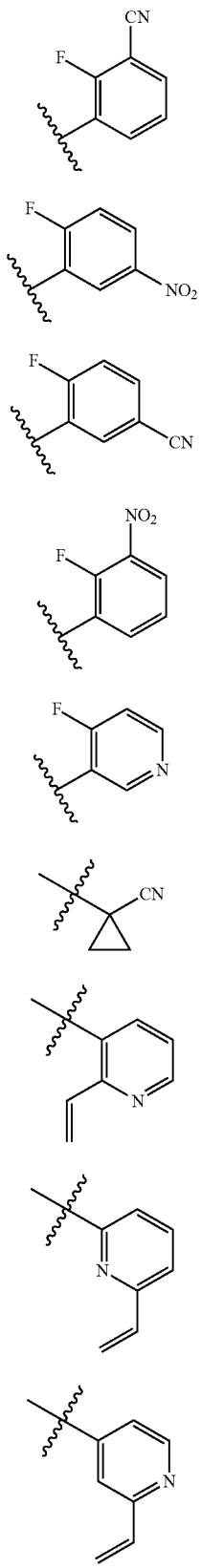
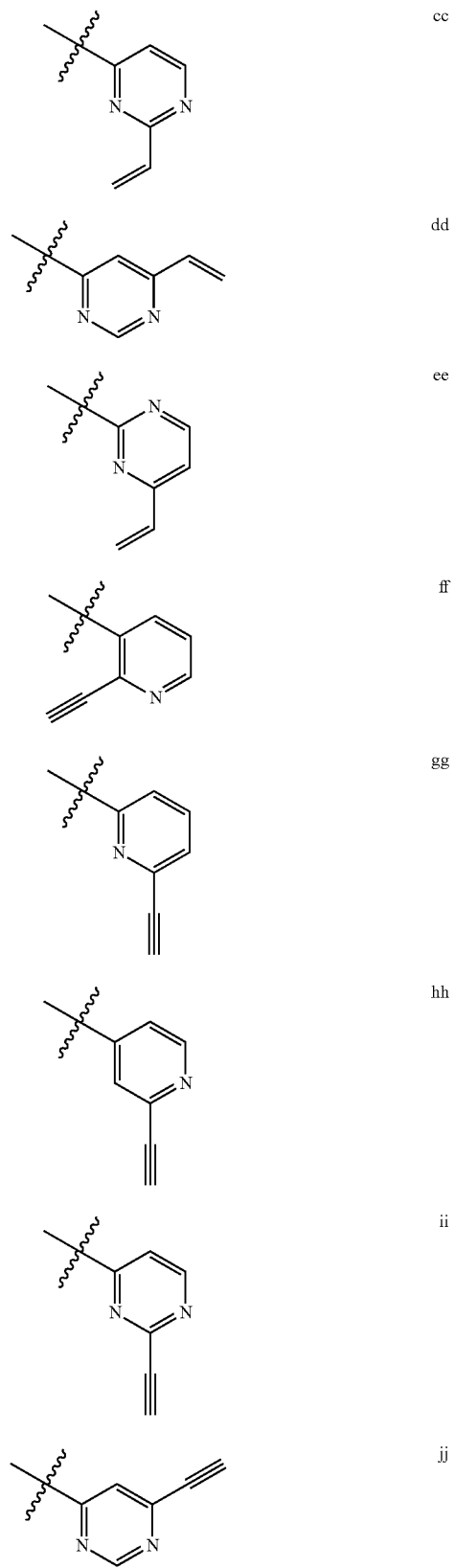

TABLE 1-continued
Exemplary Y groups:
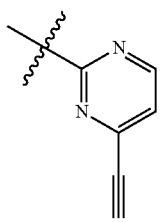 kk
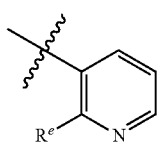 ll
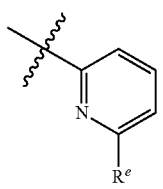 mm
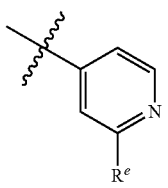 nn
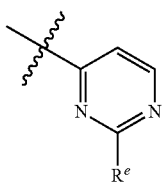 oo
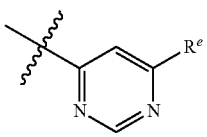 pp
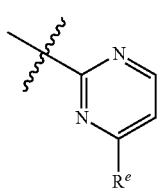 qq
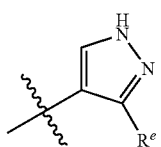 rr
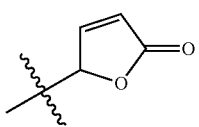 [SMILES: *C1C=CC(=O)O1] ss
TABLE 1-continued
Exemplary Y groups:
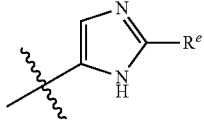 tt
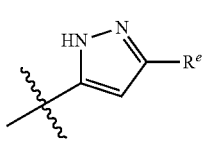 uu
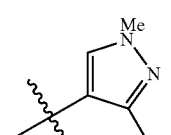 vv
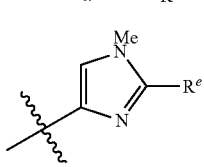 ww
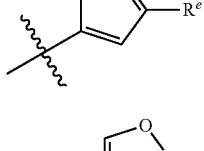 xx
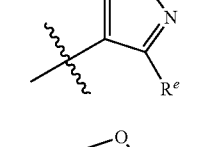 yy
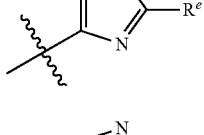 zz
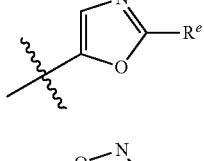 aaa
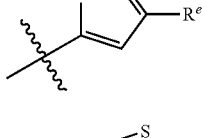 bbb
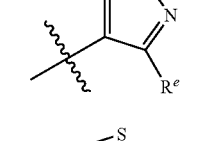 ccc
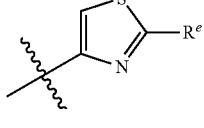 ddd TABLE 1-continued
Exemplary Y groups:
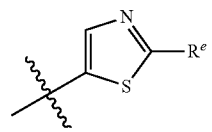 eee
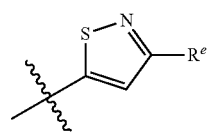 fff
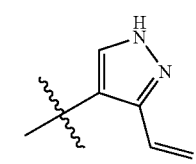 [SMILES: *c1c[nH]nc1C=C] ggg
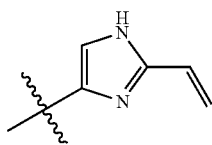 [SMILES: *c1c[nH]c(C=C)n1] hhh
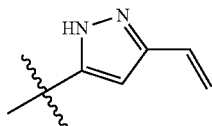 [SMILES: *c1cc(C=C)n[nH]1] iii
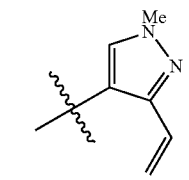 [SMILES: *c1cn(C)nc1C=C] jjj
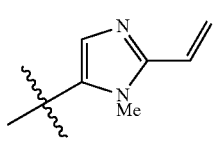 [SMILES: *c1cnc(C=C)n1C] kkk
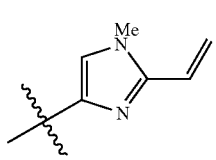 [SMILES: *c1cn(C)c(C=C)n1] lll
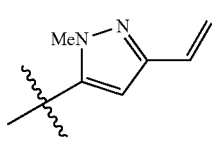 [SMILES: *c1cc(C=C)nn1C] mmm
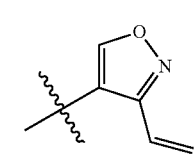 [SMILES: *c1conc1C=C] nnn
TABLE 1-continued
Exemplary Y groups:
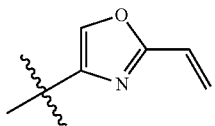 [SMILES: *c1coc(C=C)n1] ooo
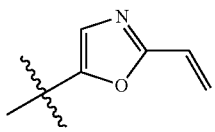 [SMILES: *c1cnc(C=C)o1] ppp
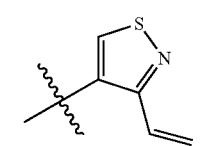 [SMILES: *c1csnc1C=C] qqq
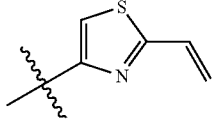 rrr
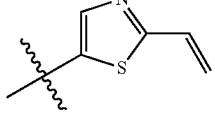 sss
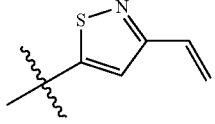 [SMILES: *c1cc(C=C)no1] ttt
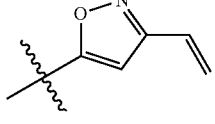 uuu
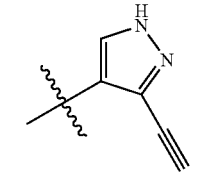 [SMILES: *c1c[nH]nc1C#C] vvv
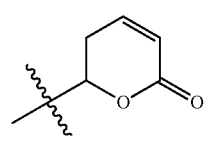 [SMILES: *C1CC=CC(=O)O1] qqq
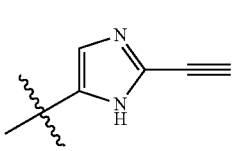 www TABLE 1-continued Exemplary Y groups:

| Structure | Label |
|---|---|
| 1-methyl-pyrazole with ethynyl | xxx |
| 1H-pyrazole with ethynyl | yyy |
| dihydropyridinone | zzz |
| 1-methyl-imidazole with ethynyl | aaaa |
| 1-methyl-pyrazole with ethynyl (isomer) | bbbb |
| isoxazole with ethynyl | cccc |
| isoxazole with ethynyl (isomer) | dddd |
| oxazole with ethynyl | eeee |
| oxazole with ethynyl (isomer) | ffff |
| dihydropyrrolone | gggg |

TABLE 1-continued

Exemplary Y groups:

| Structure | Label |
|---|---|
| isothiazole with ethynyl | hhhh |
| thiazole with ethynyl | iiii |
| N-linked pyrazole with ethynyl | jjjj |
| cyclohexenone | kkkk |
| imidazole with ethynyl (N-linked) | llll |
| pyrrolidine with acryloyl | mmmm |
| isothiazole with ethynyl (isomer) | nnnn |
| thiazole with ethynyl (isomer) | oooo |
| N-linked pyrazole with $R^e$ | pppp |
| cyclohexenone (isomer) | qqqq |

TABLE 1-continued

| Exemplary Y groups: | |
|---|---|
| 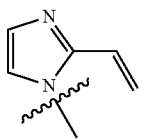 | rrrr |
| 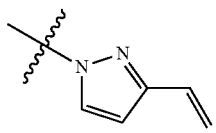 [SMILES: *n1ccc(C=C)n1] | ssss |
| 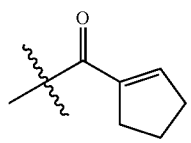 [SMILES: *C(=O)C1=CCCC1] | tttt |
| 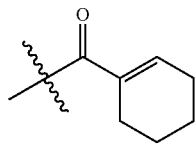 [SMILES: *C(=O)C1=CCCCC1] | uuuu |
| 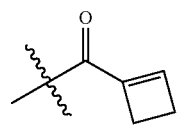 [SMILES: *C(=O)C1=CCC1] | vvvv |
| 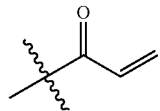 [SMILES: *C(=O)C=C] | wwww |
| 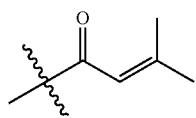 [SMILES: *C(=O)C=C(C)C] | xxxx |
| 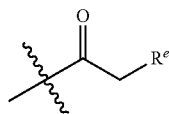 | yyyy |
| 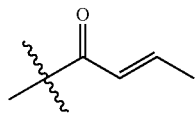 [SMILES: *C(=O)/C=C/C] | zzzz |
| 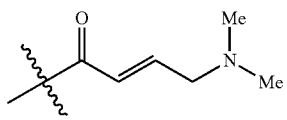 [SMILES: *C(=O)/C=C/CN(C)C] | aaaaa |
| 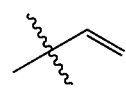 | bbbbb |

TABLE 1-continued

| Exemplary Y groups: | |
|---|---|
|  | ccccc | wherein each $R^e$ is independently a suitable leaving group, $NO_2$, CN, or oxo.

In certain embodiments, $R^1$ is —C≡CH, —C≡CCH$_2$NH(isopropyl), —NHC(O)C≡CCH$_2$CH$_3$, —CH$_2$—C≡C—CH$_3$, —C≡CCH$_2$OH, —CH$_2$C(O)C≡CH, —C(O)C≡CH, or —CH$_2$OC(═O)C≡CH. In some embodiments, $R^1$ is selected from —NHC(O)CH═CH$_2$, —NHC(O)CH═CHCH$_2$N(CH$_3$)$_2$, or —CH$_2$NHC(O)CH═CH$_2$.

In some embodiments, $R^1$ is 6-12 atoms long. In certain embodiments, $R^1$ is 6-9 atoms long. In certain embodiments, $R^1$ is 10-12 atoms long. In certain embodiments, $R^1$ is at least 8 atoms long.

In certain embodiments, $R^1$ is —C(O)CH$_2$CH$_2$C(O)CH═C(CH$_3$)$_2$, —C(O)CH$_2$CH$_2$C(O)CH═CH(cyclopropyl), —C(O)CH$_2$CH$_2$C(O)CH═CHCH$_3$, —C(O)CH$_2$CH$_2$C(O)CH═CHCH$_2$CH$_3$, or —C(O)CH$_2$CH$_2$C(O)C(═CH$_2$)CH$_3$. In certain embodiments, $R^1$ is —C(O)CH$_2$NHC(O)CH═CH$_2$, —C(O)CH$_2$NHC(O)CH$_2$CH$_2$C(O)CH═CHCH$_3$, or —C(O)CH$_2$NHC(O)CH$_2$CH$_2$C(O)C(═CH$_2$)CH$_3$. In certain embodiments, $R^1$ is —S(O)$_2$CH$_2$CH$_2$NHC(O)CH$_2$CH$_2$C(O)CH═C(CH$_3$)$_2$, —S(O)$_2$CH$_2$CH$_2$NHC(O)CH$_2$CH$_2$C(O)CH═CHCH$_3$, or —S(O)$_2$CH$_2$CH$_2$NHC(O)CH$_2$CH$_2$C(O)CH═CH$_2$. In certain embodiments, $R^1$ is —C(O)(CH$_2$)$_3$NHC(O)CH$_2$CH$_2$C(O)CH═CHCH$_3$ or —C(O)(CH$_2$)$_3$NHC(O)CH$_2$CH$_2$C(O)CH═CH$_2$.

In certain embodiments, $R^1$ is selected from those set forth in Table 2, below, wherein each wavy line indicates the point of attachment to the rest of the molecule.

TABLE 2

| Exemplary $R^1$ Groups | |
|---|---|
| 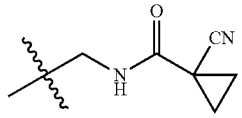 [SMILES: *CNC(=O)C1(C#N)CC1] | a |
| 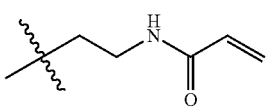 [SMILES: *CCNC(=O)C=C] | b |
| 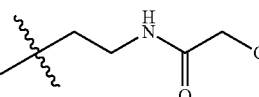 | c |
| 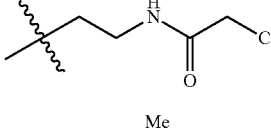 | d |
| 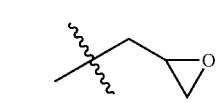 | e |

TABLE 2-continued

Exemplary R¹ Groups

| | |
|---|---|
| (epoxide structure) | f |
| N-H crotonamide | g |
| N-H acrylamide | h |
| N-H (E)-4-(dimethylamino)but-2-enamide | i |
| N-H chloroacetamide | j |
| benzisothiazolinone-N-methyl | k |
| N-Me acrylamide (propyl linker) | l |
| N-H (S)-2-chloropropanamide | m |
| N-H (R)-2-chloropropanamide | n |
| N-H 2-chloropropanamide (racemic) | o |
| N-Me acrylamide | p |

TABLE 2-continued

Exemplary R¹ Groups

| | |
|---|---|
| N-H methacrylamide | q |
| N-H 2-(trifluoromethyl)acrylamide | r |
| pent-1-en-3-one | s |
| (E)-hex-4-en-3-one linker | t |
| (E)-7-(dimethylamino)hept-5-en-4-one | u |
| 6-methylhept-5-en-4-one | v |
| 5-methylhex-4-en-3-one | w |
| acrylate ester | x |
| acrylate ester (branched) | y |
| crotonate ester | z |
| crotonate ester (branched) | aa |
| N-Et acrylamide | bb |

TABLE 2-continued
Exemplary R¹ Groups
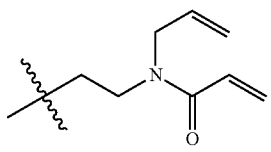 [SMILES: *CCN(CC=C)C(=O)C=C] cc
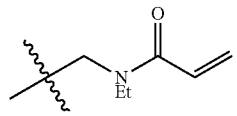 dd
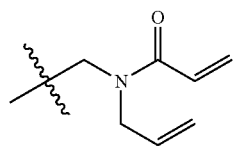 [SMILES: *CN(CC=C)C(=O)C=C] ee
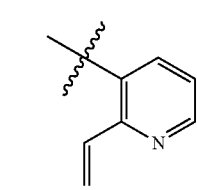 [SMILES: *c1cccnc1C=C] ff
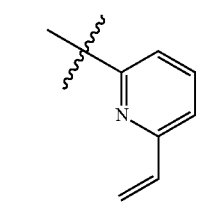 [SMILES: *c1cccc(C=C)n1] gg
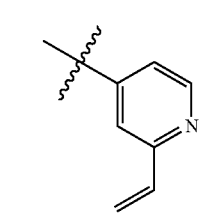 hh
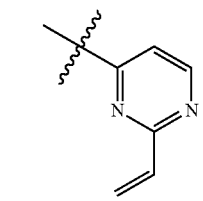 [SMILES: *c1ccnc(C=C)n1] ii
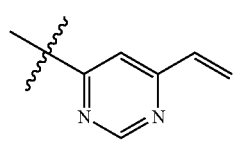 [SMILES: *c1cc(C=C)ncn1] jj
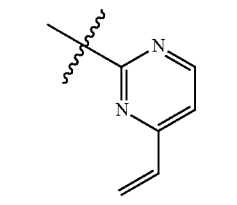 [SMILES: *c1nccc(C=C)n1] kk
TABLE 2-continued
Exemplary R¹ Groups
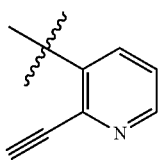 [SMILES: *c1cccnc1C#C] ll
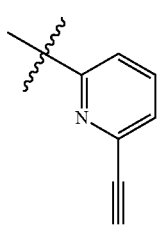 [SMILES: *c1cccc(C#C)n1] mm
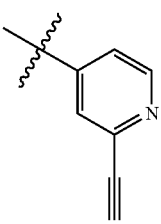 [SMILES: *c1ccnc(C#C)c1] nn
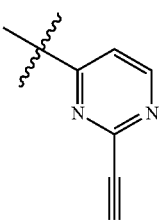 oo
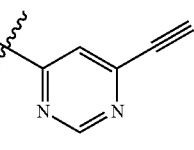 pp
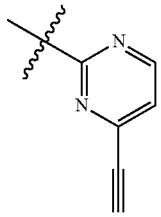 [SMILES: *c1nccc(C#C)n1] qq
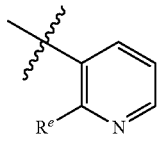 rr
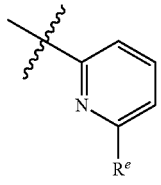 ss TABLE 2-continued
Exemplary R¹ Groups
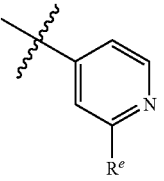 tt
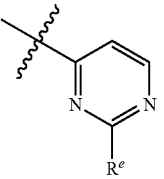 uu
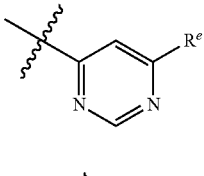 vv
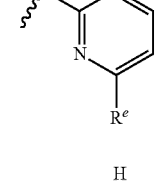 ww
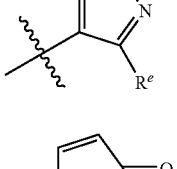 xx
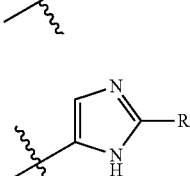 yy
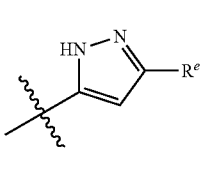 zz
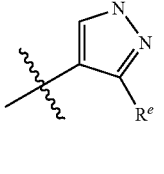 aaa
 bbb
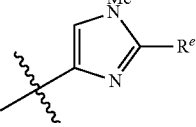 ccc
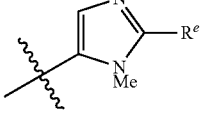 ddd
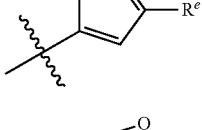 eee
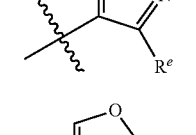 fff
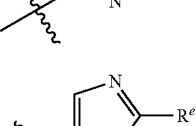 ggg
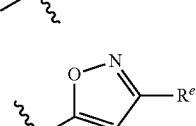 hhh
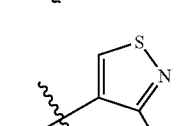 iii
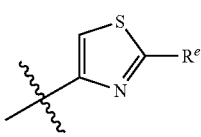 jjj
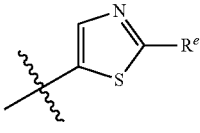 kkk
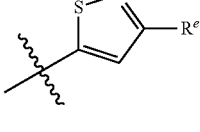 lll
 mmm TABLE 2-continued
Exemplary R¹ Groups
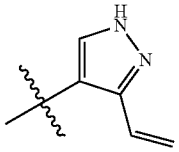 [SMILES: *c1c[nH]nc1C=C] nnn
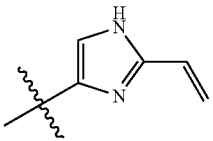 [SMILES: *c1c[nH]c(C=C)n1] ooo
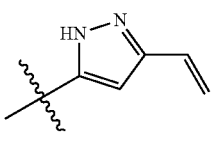 ppp
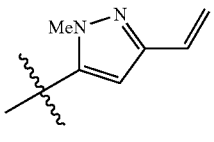 qqq
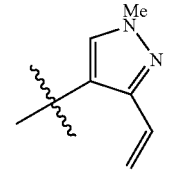 [SMILES: *c1cn(C)nc1C=C] rrr
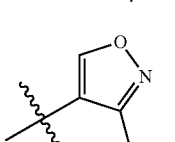 sss
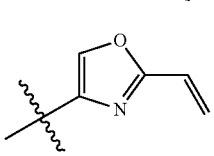 ttt
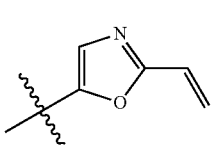 uuu
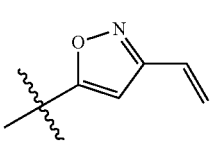 [SMILES: *c1cc(C=C)no1] vvv
TABLE 2-continued
Exemplary R¹ Groups
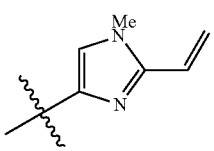 [SMILES: *c1cn(C)c(C=C)n1] www
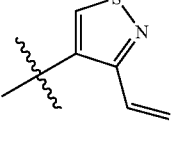 xxx
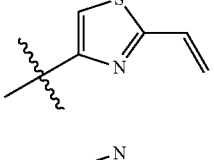 yyy
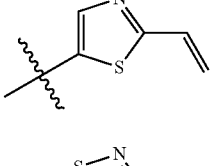 zzz
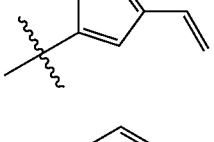 aaaa
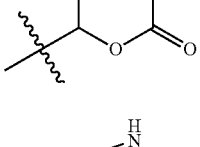 bbbb
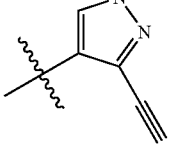 cccc
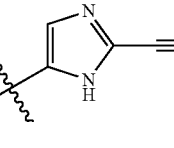 dddd
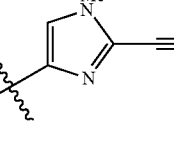 eeee
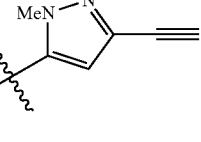 ffff TABLE 2-continued
Exemplary R¹ Groups
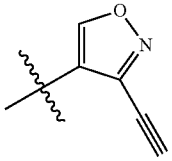 [SMILES: *c1conc1C#C] gggg
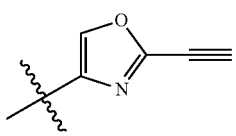 hhhh
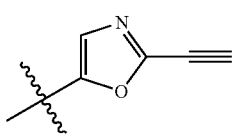 iiii
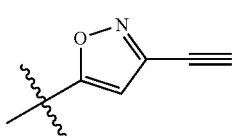 [SMILES: *c1cc(C#C)no1] jjjj
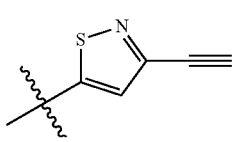 kkkk
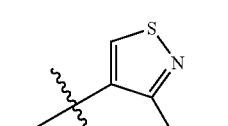 llll
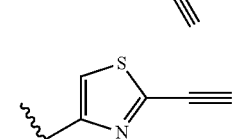 mmmm
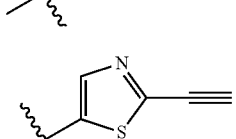 nnnn
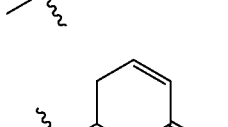 oooo
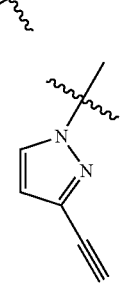 pppp
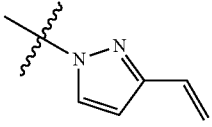 qqqq
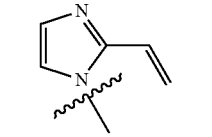 rrrr
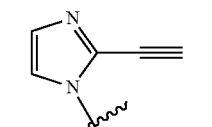 ssss
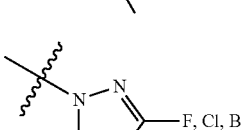 tttt
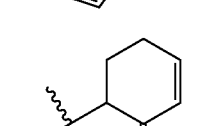 uuuu
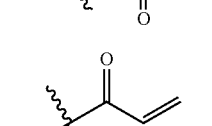 vvvv
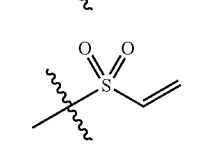 wwww
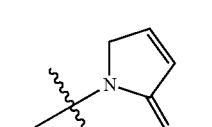 xxxx
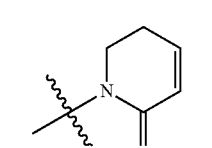 yyyy
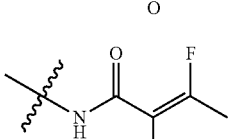 zzzz
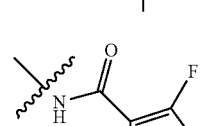 aaaaa TABLE 2-continued Exemplary R¹ Groups

| | |
|---|---|
| bbbbb | lllll |
| ccccc | mmmmm |
| ddddd | nnnnn |
| eeeee | ooooo |
| fffff | ppppp |
| ggggg | qqqqq |
| hhhhh | rrrrr |
| iiiii | sssss |
| jjjjj | ttttt |
| kkkkk | uuuuu |
| | vvvvv |

TABLE 2-continued
Exemplary R¹ Groups
 wwwww
 xxxxx
 yyyyy
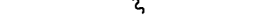 zzzzz
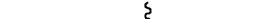 aaaaaa
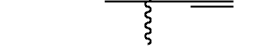 bbbbbb
 cccccc
 dddddd
 eeeeee
 fffff
 gggggg
 hhhhhh
TABLE 2-continued
Exemplary R¹ Groups
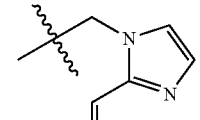 iiiiii
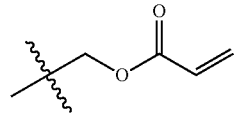 [SMILES: *COC(=O)C=C] jjjjjj
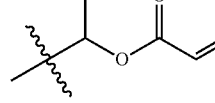 kkkkkk
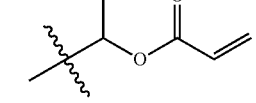 llllll
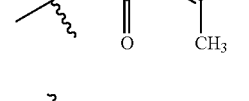 mmmmmm
 nnnnnn
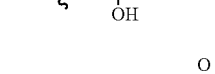 oooooo
 pppppp
 qqqqqq
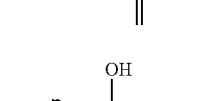 rrrrrr
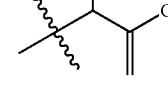 ssssss TABLE 2-continued Exemplary R¹ Groups

| Structure | Label |
|---|---|
| (enone, methyl) | tttttt |
| (enone, F-methyl) | uuuuuu |
| (thiazole-F amide) | vvvvvv |
| (O-CH2-CH=CH-C(O)OMe) | wwwwww |
| (enone, dimethyl) | xxxxxx |
| (diketone, prenyl) | yyyyyy |
| (diketone, cyclopropyl vinyl) | zzzzzz |
| (diketone, propyl enone) | aaaaaaa |
| (diketone, methyl enone) | bbbbbbb |
| (diketone, methyl vinyl) | ccccccc |
| (ketone-CH2-NH-acryloyl) | ddddddd |
| (ketone-CH2-NH-C(O)-enone) | eeeeeee |
| (ketone-CH2-NH-C(O)-methylene ketone) | fffffff |
| (acyl piperazine-acryloyl) | ggggggg |
| (sulfonyl-ethyl-NH-C(O)-methyl enone) | hhhhhhh |
| (sulfonyl-ethyl-NH-C(O)-enone) | iiiiiii |
| (sulfonyl-ethyl-NH-C(O)-vinyl ketone) | jjjjjjj |
| (ketone-propyl-NH-C(O)-enone) | kkkkkkk |
| (ketone-propyl-NH-C(O)-vinyl ketone) | lllllll |
| (diketone, dimethyl vinyl) | mmmmmmm |
| (diketone, prenyl extended) | nnnnnnn |

TABLE 2-continued
Exemplary R¹ Groups
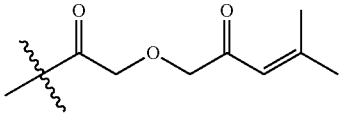 [SMILES: *C(=O)COCC(=O)C=C(C)C] ooooooo
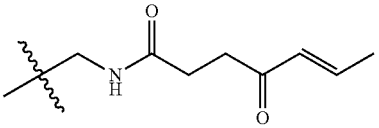 [SMILES: *CNC(=O)CCC(=O)/C=C/C] ppppppp
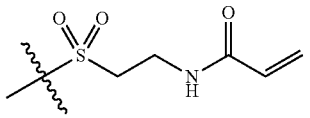 [SMILES: *S(=O)(=O)CCNC(=O)C=C] qqqqqqq
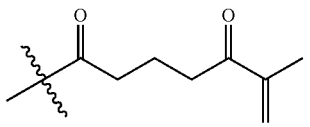 [SMILES: *C(=O)CCCC(=O)C(=C)C] rrrrrrr
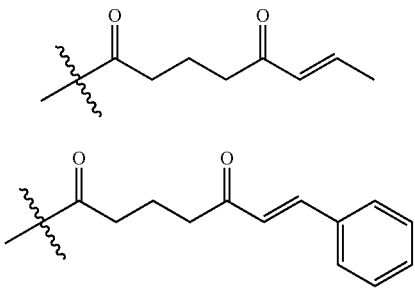 sssssss
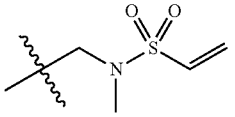 [SMILES: *CN(C)S(=O)(=O)C=C] ttttttt
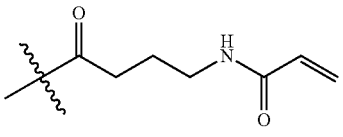 [SMILES: *C(=O)CCCNC(=O)C=C] uuuuuuu
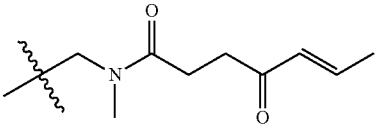 [SMILES: *CN(C)C(=O)CCC(=O)/C=C/C] vvvvvvv
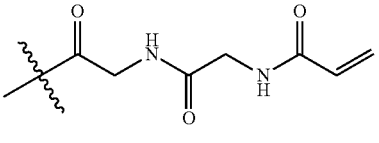 [SMILES: *C(=O)CNC(=O)CNC(=O)C=C] wwwwwww
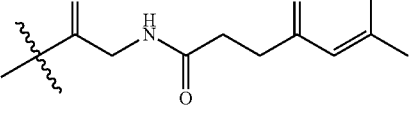 xxxxxxx
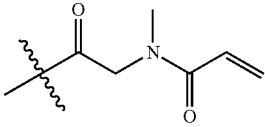 [SMILES: *C(=O)CN(C)C(=O)C=C] yyyyyyy
TABLE 2-continued
Exemplary R¹ Groups
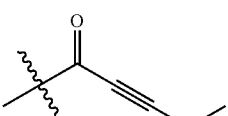 zzzzzzz
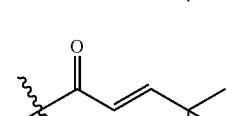 aaaaaaaa
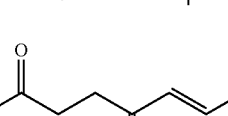 bbbbbbbb
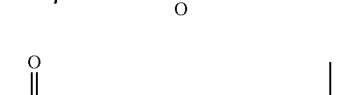 cccccccc
 dddddddd
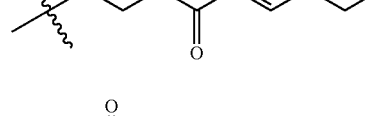 eeeeeeee
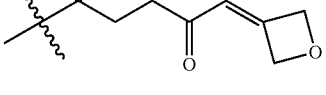 ffffffff
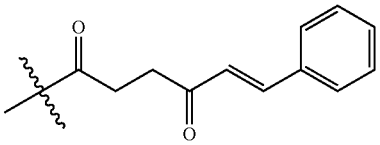 [SMILES: *C(=O)CCC(=O)/C=C/c1ccccc1] gggggggg
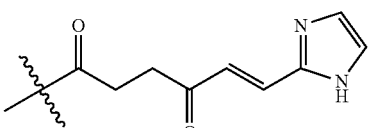 hhhhhhhh
iiiiiiii TABLE 2-continued
Exemplary R¹ Groups
| | |
|---|---|
| 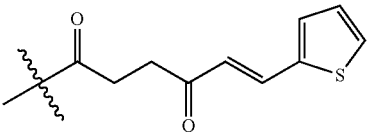 [SMILES: *C(=O)CCC(=O)/C=C/c1cccs1] | jjjjjjjj |
| 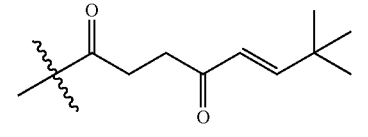 [SMILES: *C(=O)CCC(=O)/C=C/C(C)(C)C] | kkkkkkkk |
| 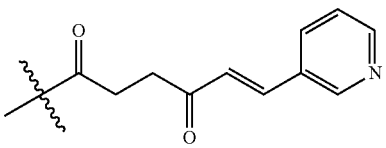 [SMILES: *C(=O)CCC(=O)/C=C/c1cccnc1] | llllllll |
| 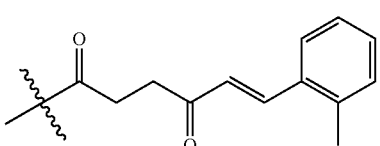 | mmmmmmmm |
| 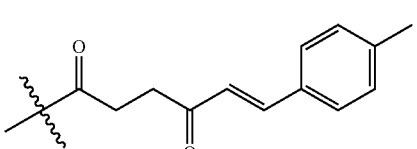 | nnnnnnnn |
| 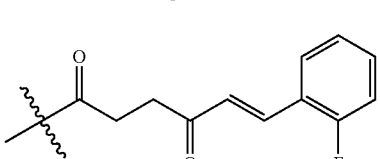 | oooooooo |
| 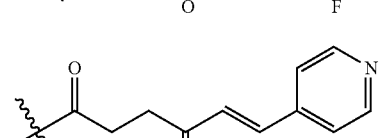 | pppppppp |
| 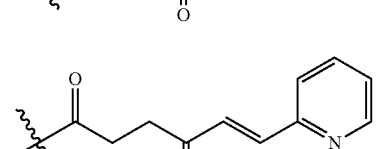 | qqqqqqqq |
| 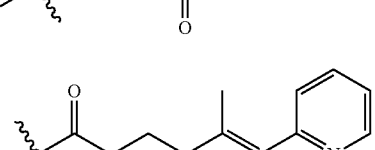 | rrrrrrrr |
| 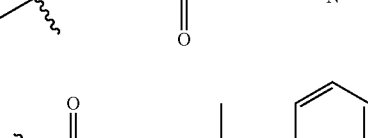 | ssssssss |
TABLE 2-continued
Exemplary R¹ Groups
| | |
|---|---|
| 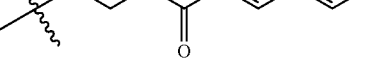 | tttttttt |
| 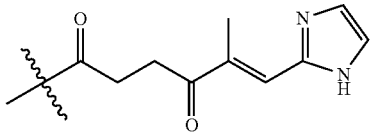 [SMILES: *C(=O)CCC(=O)/C(C)=C/c1ncc[nH]1] | uuuuuuuu |
| 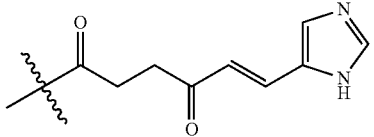 [SMILES: *C(=O)CCC(=O)/C=C/c1cnc[nH]1] | vvvvvvvv |
| 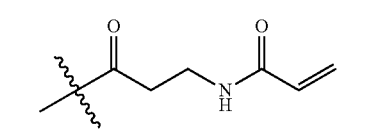 [SMILES: *C(=O)CCNC(=O)C=C] | wwwwwwww |
| 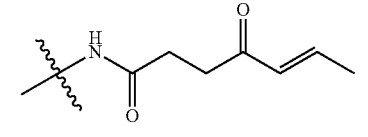 [SMILES: *NC(=O)CCC(=O)/C=C/C] | xxxxxxxx |
| 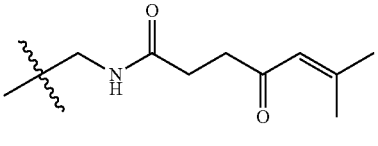 [SMILES: *CNC(=O)CCC(=O)C=C(C)C] | yyyyyyyy |
| 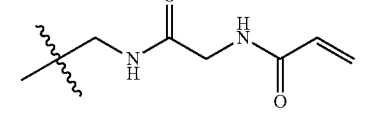 | zzzzzzzz |
| 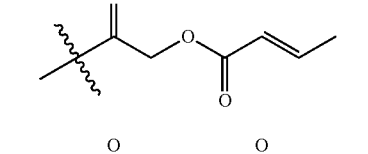 | aaaaaaaaa |
| 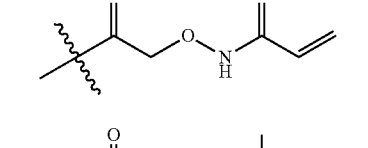 | bbbbbbbbb |
| 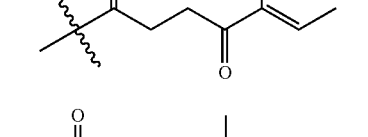 | ccccccccc |
| 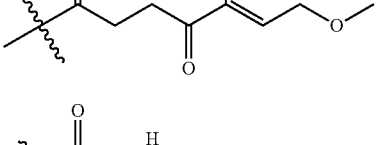 | ddddddddd |

TABLE 2-continued
Exemplary R¹ Groups
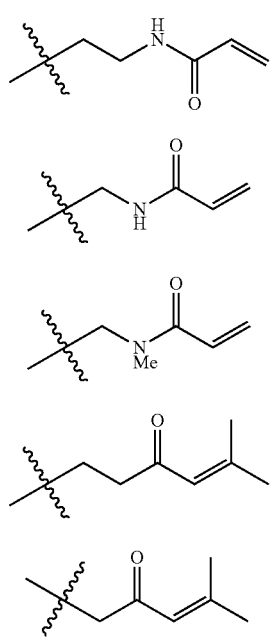
wherein each $R^e$ is independently a suitable leaving group, $NO_2$, CN, or oxo.
In certain embodiments, $R^1$ is selected from:
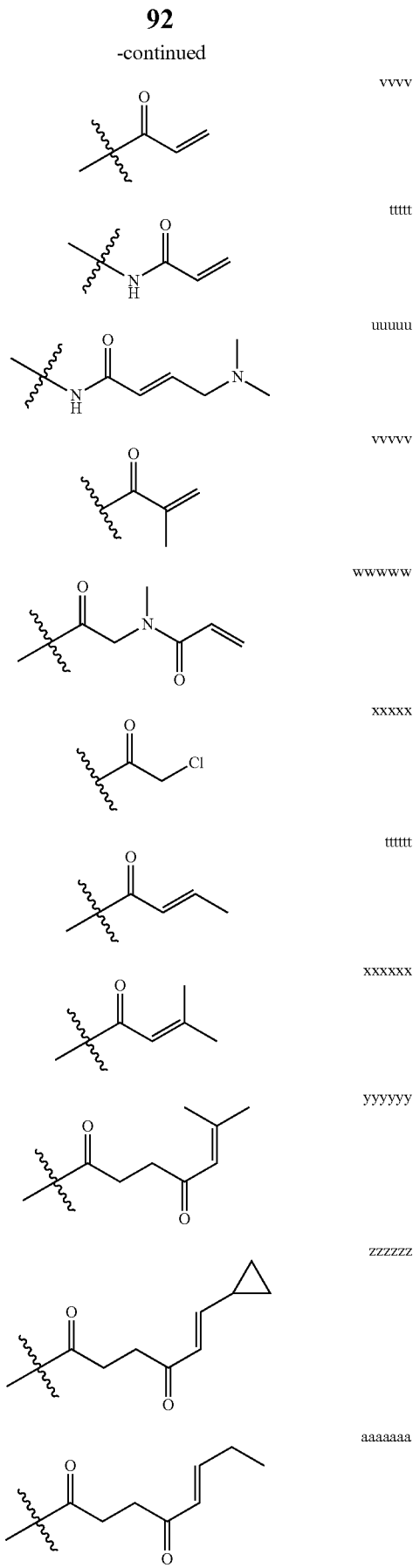

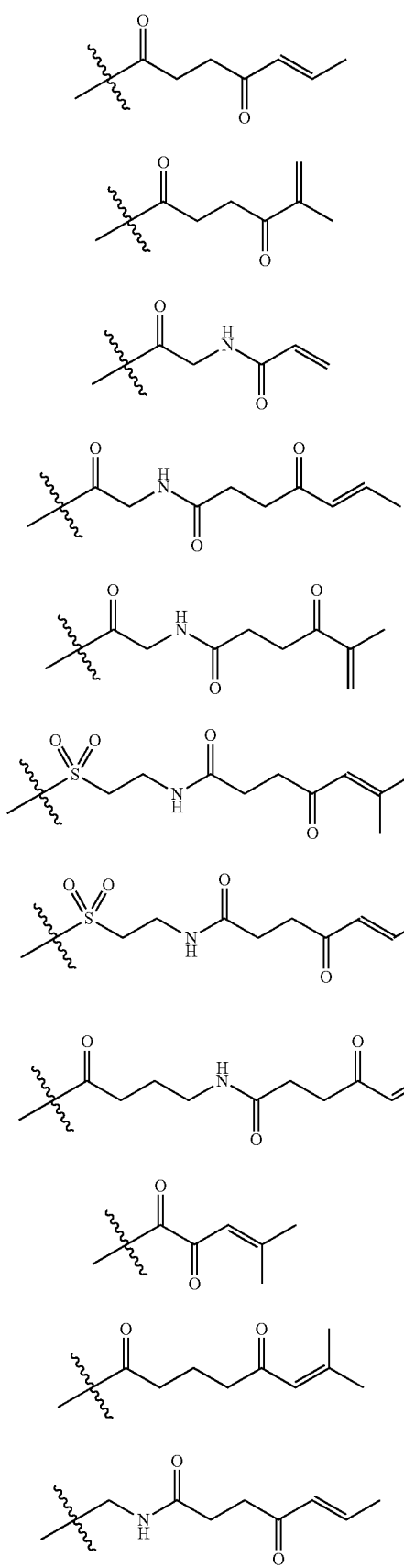
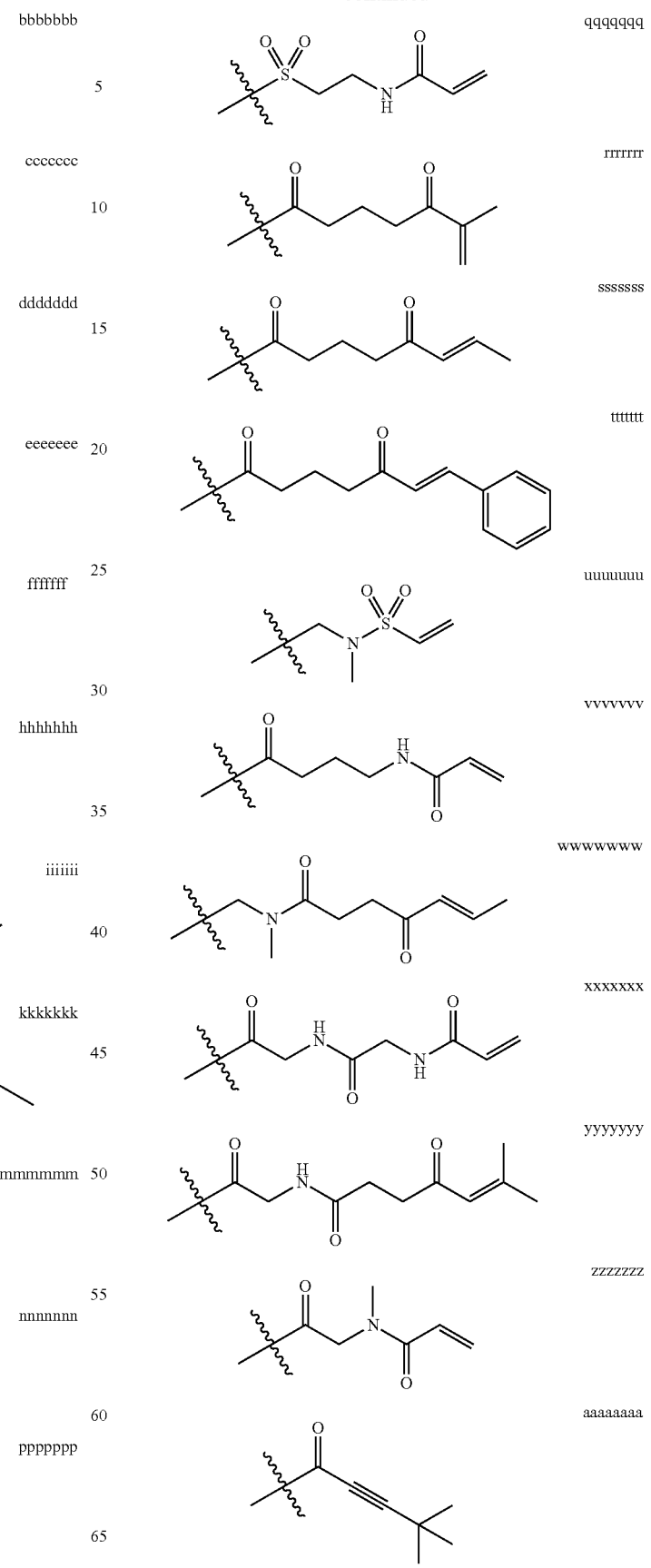

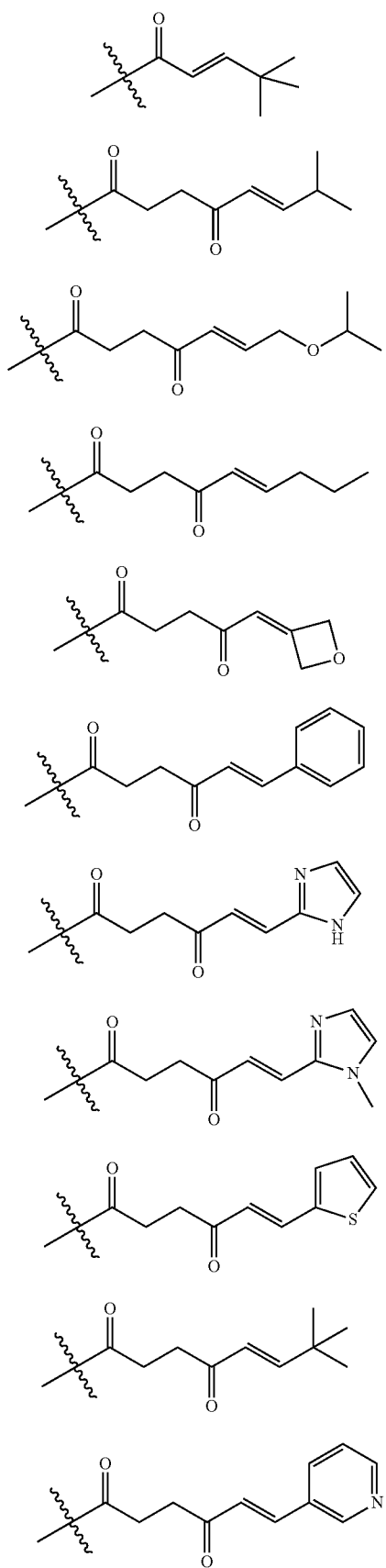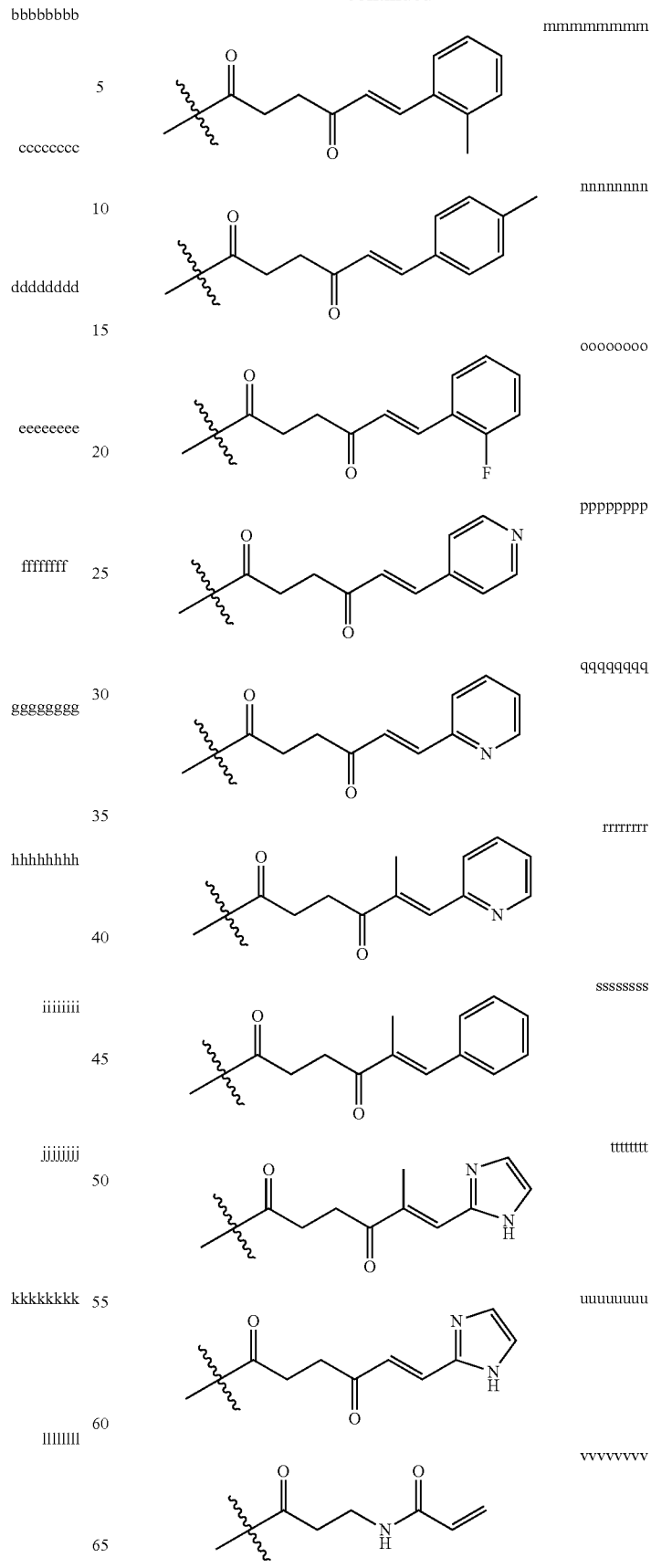

97
-continued
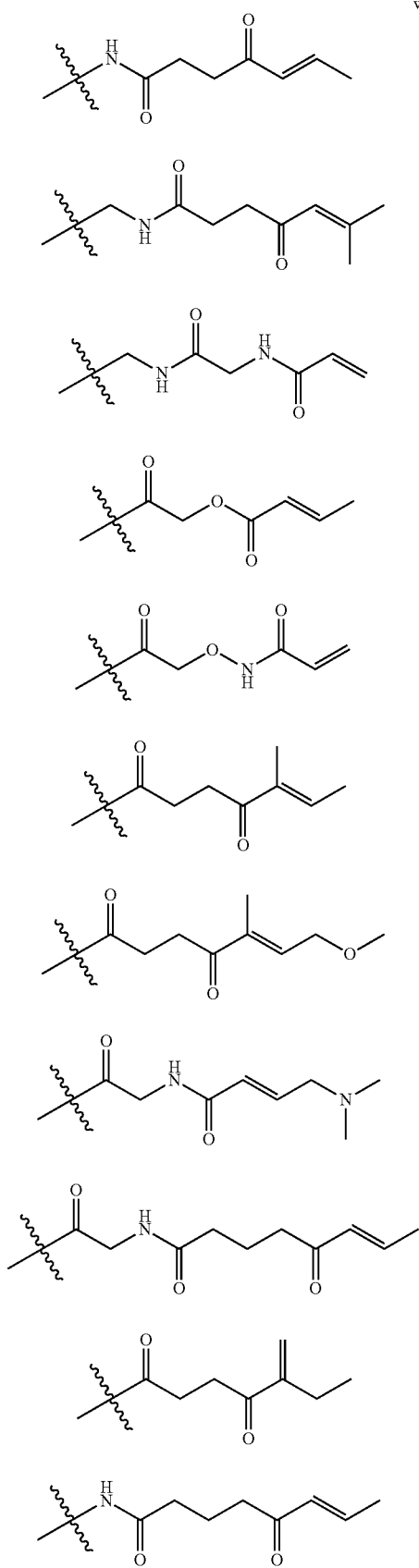
wwwwwwww
xxxxxxxx
yyyyyyy
zzzzzzzz
aaaaaaaaa
bbbbbbbb
cccccccc
dddddddd
eeeeeeee
ffffffff
gggggggg
98
-continued
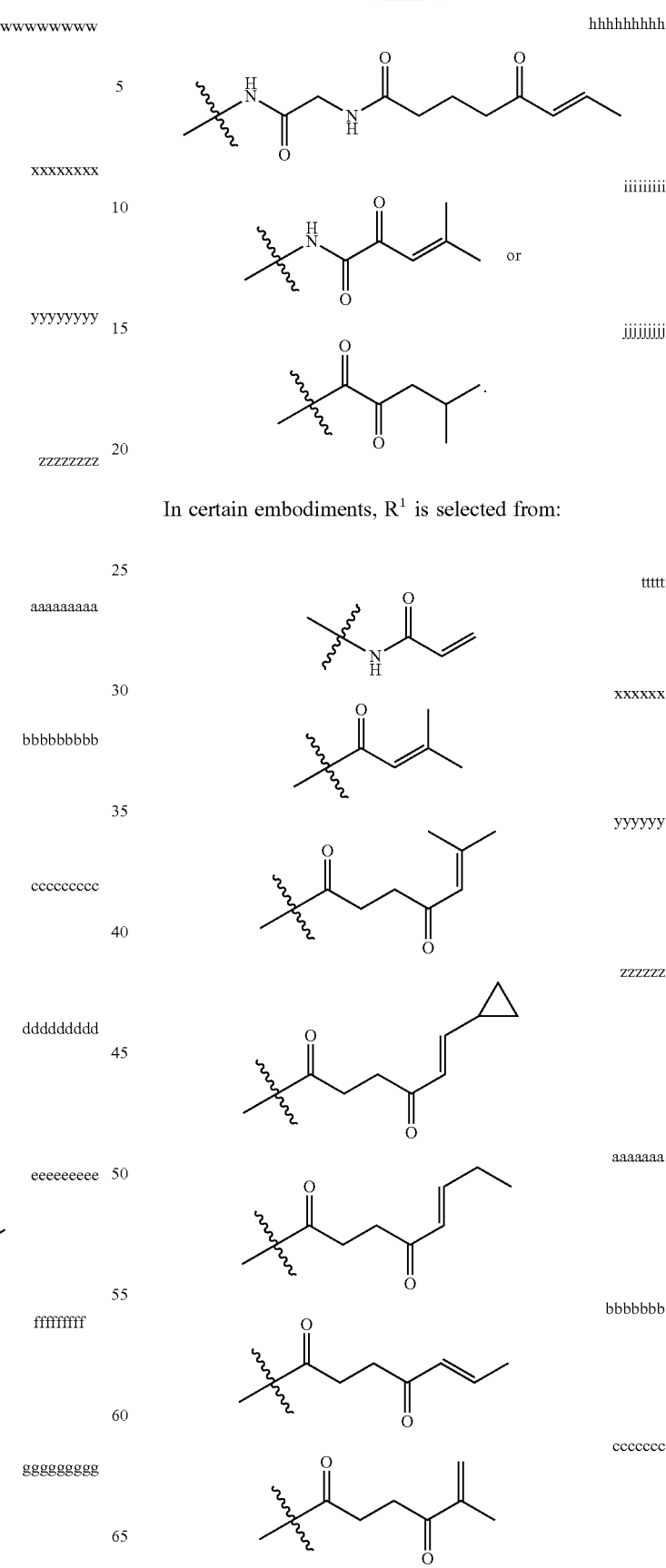
hhhhhhhh
iiiiiiiii
jjjjjjjjj
In certain embodiments, $R^1$ is selected from:
ttttt
xxxxxx
yyyyyy
zzzzzz
aaaaaaa
bbbbbbb
ccccccc -continued
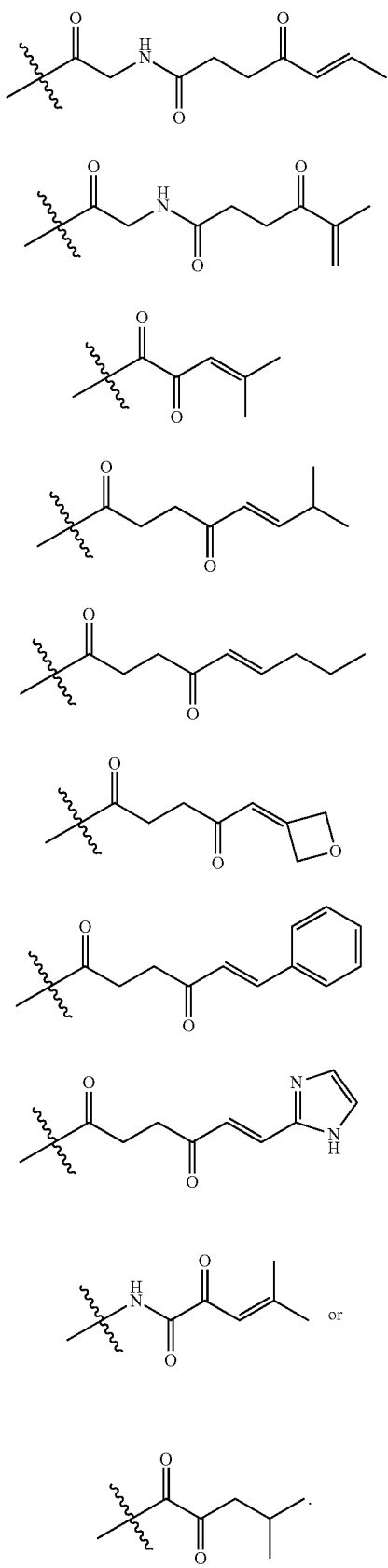
In certain embodiments, R¹ is selected from
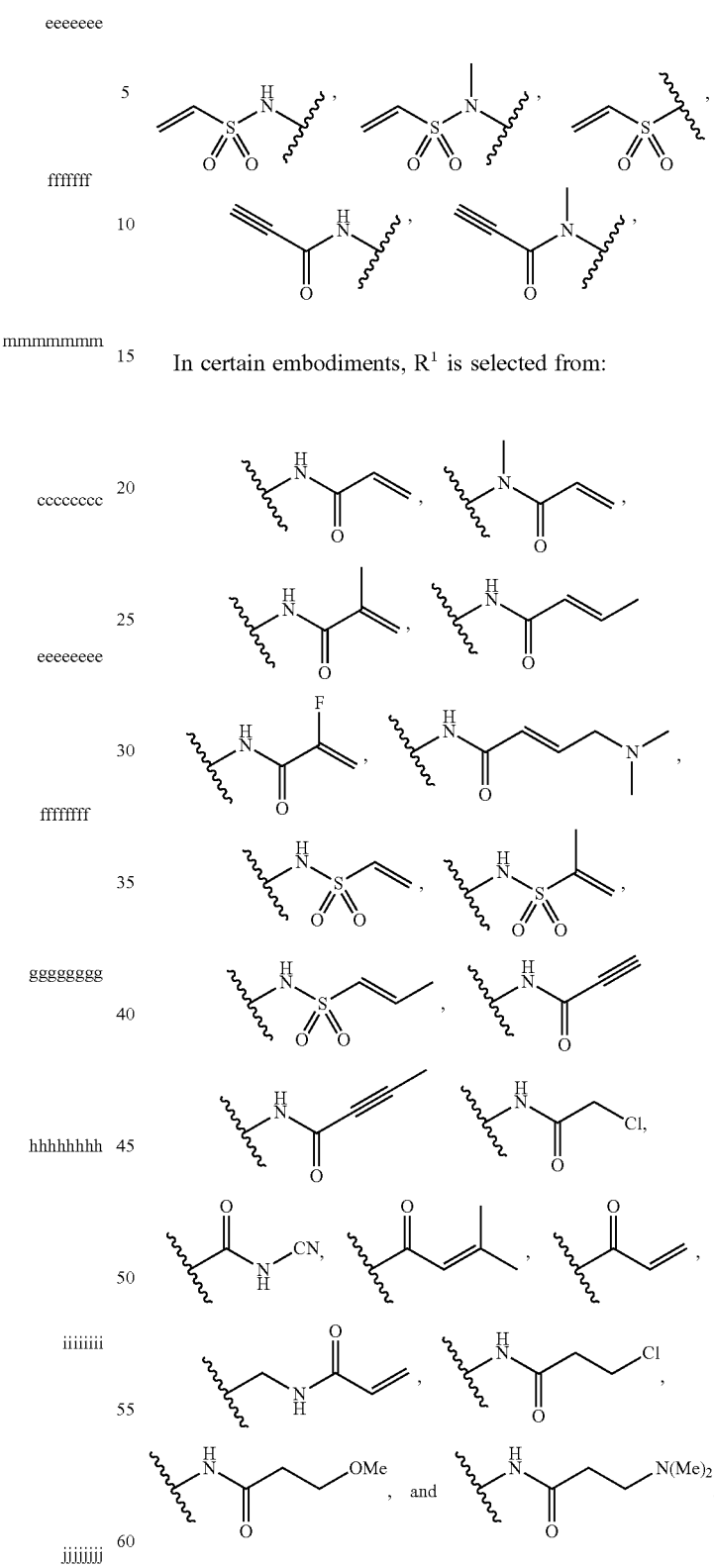
In some embodiments, R¹ is selected from those depicted in Table 3, below.
In certain embodiments, the invention provides a compound selected from the group consisting of those set forth in Table 3, below:

TABLE 3
Exemplary Compounds of Formula I
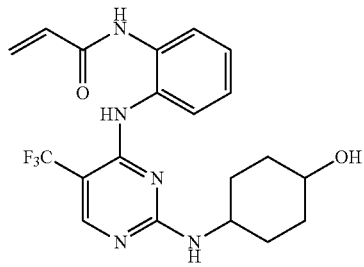 [SMILES: C=CC(=O)Nc1ccccc1Nc1nc(NC2CCC(O)CC2)ncc1C(F)(F)F]
I-1
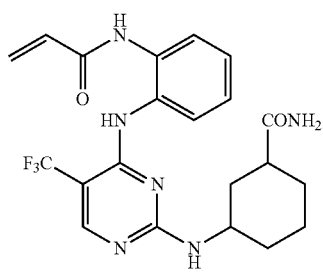 [SMILES: C=CC(=O)Nc1ccccc1Nc1nc(NC2CCCC(C(N)=O)C2)ncc1C(F)(F)F]
I-2
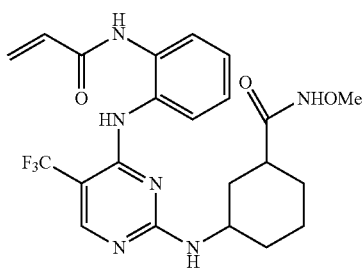
I-3
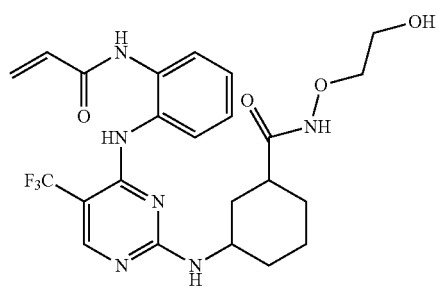 [SMILES: C=CC(=O)Nc1ccccc1Nc1nc(NC2CCCC(C(=O)NOCCO)C2)ncc1C(F)(F)F]
I-4
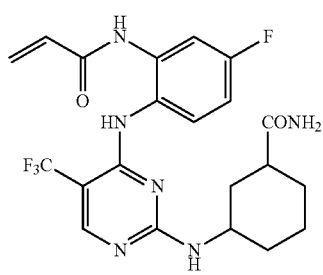 [SMILES: C=CC(=O)Nc1cc(F)ccc1Nc1nc(NC2CCCC(C(N)=O)C2)ncc1C(F)(F)F]
I-5

TABLE 3-continued
Exemplary Compounds of Formula I
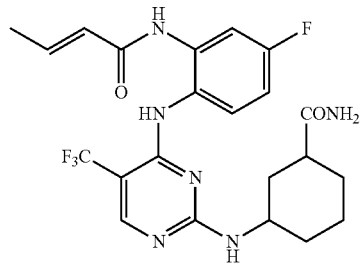 [SMILES: C/C=C/C(=O)Nc1cc(F)ccc1Nc1nc(NC2CCCC(C(N)=O)C2)ncc1C(F)(F)F]
I-6
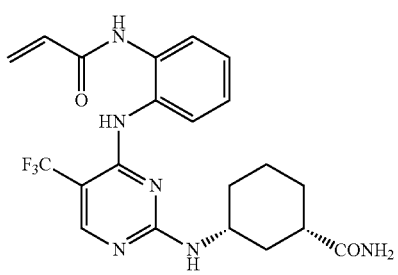 [SMILES: C=CC(=O)Nc1ccccc1Nc1nc(N[C@@H]2CCC[C@H](C(N)=O)C2)ncc1C(F)(F)F]
I-7
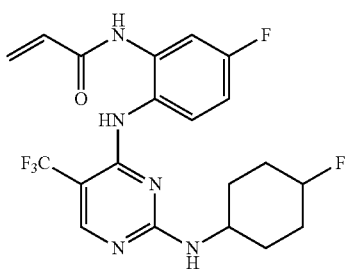 [SMILES: C=CC(=O)Nc1cc(F)ccc1Nc1nc(NC2CCC(F)CC2)ncc1C(F)(F)F]
I-8
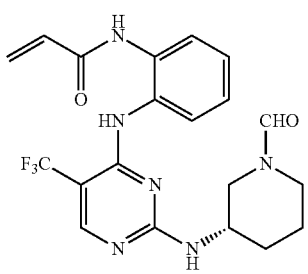 [SMILES: C=CC(=O)Nc1ccccc1Nc1nc(N[C@H]2CCCN(C=O)C2)ncc1C(F)(F)F]
I-9
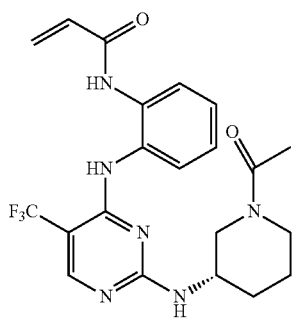 [SMILES: C=CC(=O)Nc1ccccc1Nc1nc(N[C@H]2CCCN(C(C)=O)C2)ncc1C(F)(F)F]
I-10

TABLE 3-continued
Exemplary Compounds of Formula I
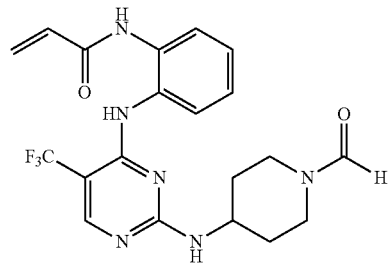 [SMILES: C=CC(=O)Nc1ccccc1Nc1nc(NC2CCN(C=O)CC2)ncc1C(F)(F)F]
I-11
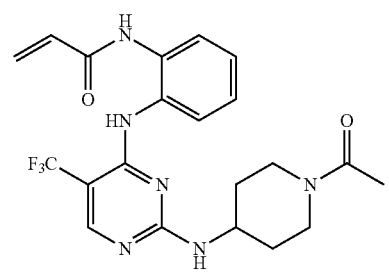 [SMILES: C=CC(=O)Nc1ccccc1Nc1nc(NC2CCN(C(C)=O)CC2)ncc1C(F)(F)F]
I-12
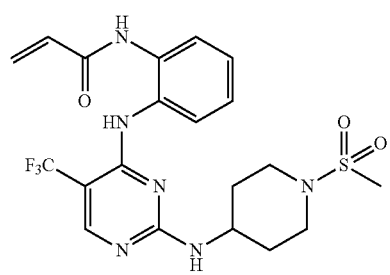 [SMILES: C=CC(=O)Nc1ccccc1Nc1nc(NC2CCN(S(C)(=O)=O)CC2)ncc1C(F)(F)F]
I-13
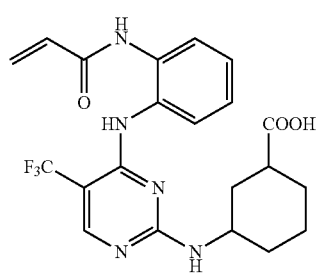 [SMILES: C=CC(=O)Nc1ccccc1Nc1nc(NC2CCCC(C(=O)O)C2)ncc1C(F)(F)F]
I-14
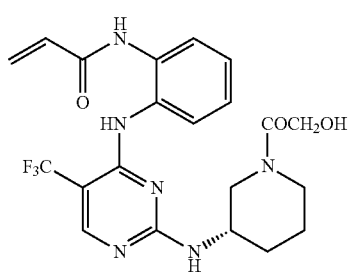
I-15

TABLE 3-continued
Exemplary Compounds of Formula I
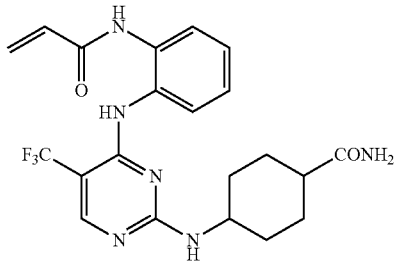 [SMILES: C=CC(=O)Nc1ccccc1Nc1nc(NC2CCC(C(N)=O)CC2)ncc1C(F)(F)F]
I-16
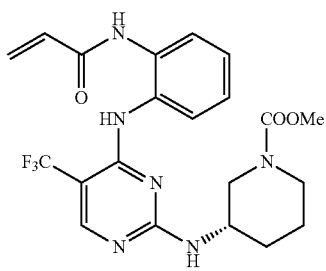 [SMILES: C=CC(=O)Nc1ccccc1Nc1nc(N[C@H]2CCCN(C(=O)OC)C2)ncc1C(F)(F)F]
I-17
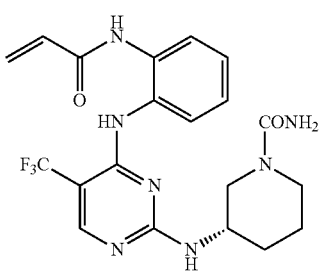 [SMILES: C=CC(=O)Nc1ccccc1Nc1nc(N[C@H]2CCCN(C(N)=O)C2)ncc1C(F)(F)F]
I-18
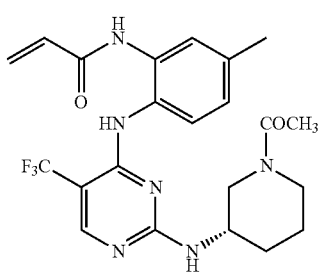 [SMILES: C=CC(=O)Nc1cc(C)ccc1Nc1nc(N[C@H]2CCCN(C(C)=O)C2)ncc1C(F)(F)F]
I-19
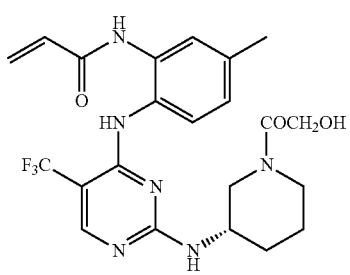
I-20

TABLE 3-continued
Exemplary Compounds of Formula I
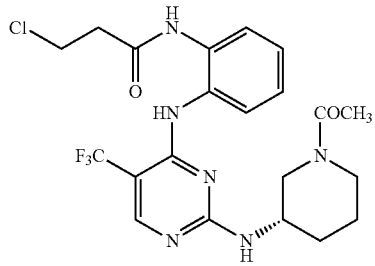 [SMILES: CC(=O)N1CCC[C@H](Nc2ncc(C(F)(F)F)c(Nc3ccccc3NC(=O)CCCl)n2)C1]
I-21
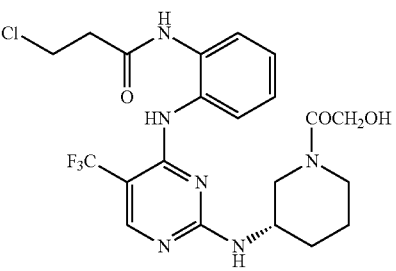
I-22
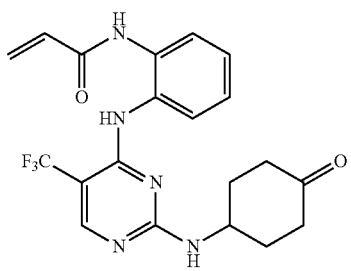 [SMILES: C=CC(=O)Nc1ccccc1Nc1nc(NC2CCC(=O)CC2)ncc1C(F)(F)F]
I-23
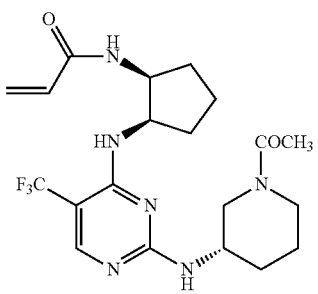 [SMILES: C=CC(=O)N[C@H]1CCC[C@H]1Nc1nc(N[C@H]2CCCN(C(C)=O)C2)ncc1C(F)(F)F]
I-24
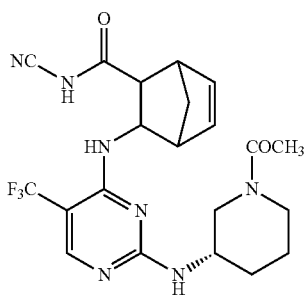 [SMILES: CC(=O)N1CCC[C@H](Nc2ncc(C(F)(F)F)c(NC3C4C=CC(C4)C3C(=O)NC#N)n2)C1]
I-25

TABLE 3-continued
Exemplary Compounds of Formula I
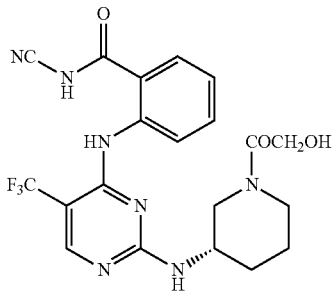
I-26
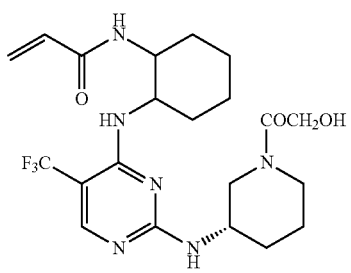
I-27
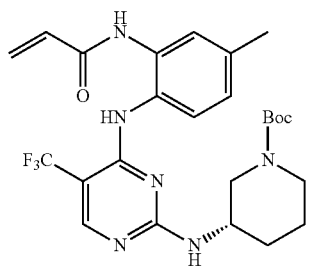 [SMILES: C=CC(=O)Nc1cc(C)ccc1Nc1nc(N[C@H]2CCCN(C(=O)OC(C)(C)C)C2)ncc1C(F)(F)F]
I-28
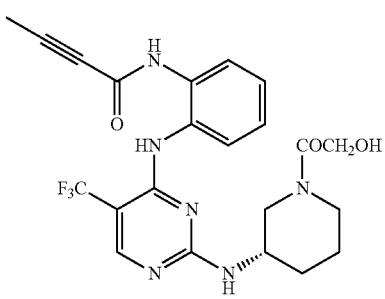
I-29
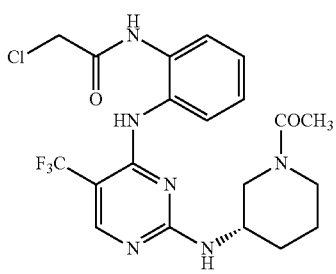 [SMILES: CC(=O)N1CCC[C@H](Nc2ncc(C(F)(F)F)c(Nc3ccccc3NC(=O)CCl)n2)C1]
I-30

TABLE 3-continued
Exemplary Compounds of Formula I
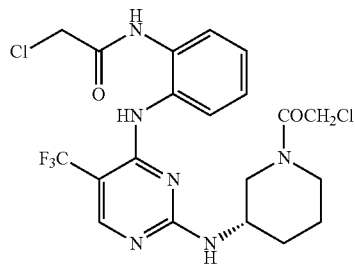
I-31
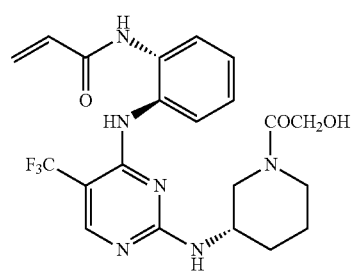
I-32
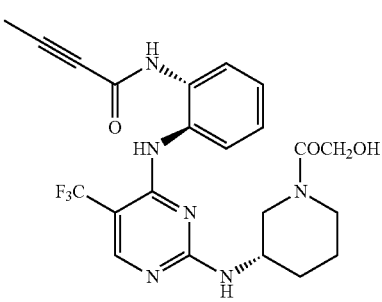
I-33
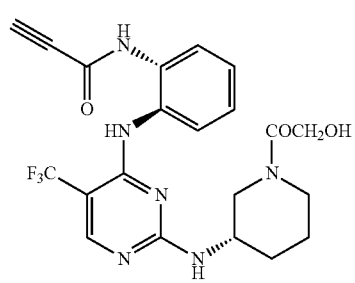
I-34
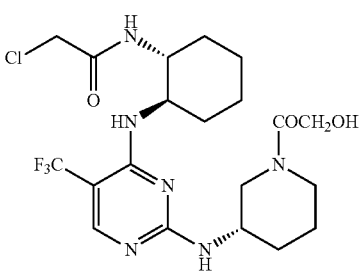
I-35

TABLE 3-continued
Exemplary Compounds of Formula I
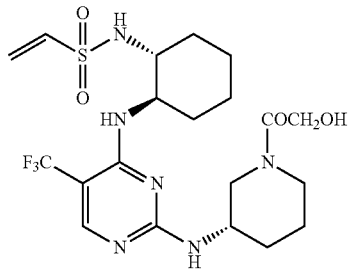
I-36
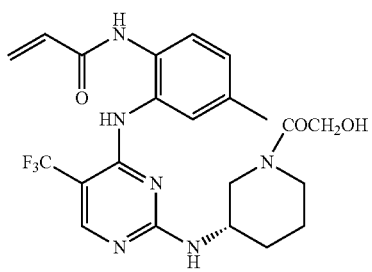
I-37
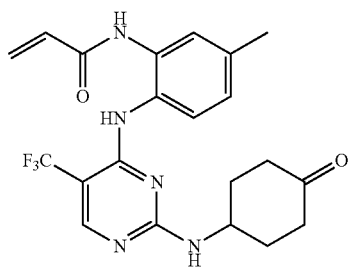 [SMILES: C=CC(=O)Nc1cc(C)ccc1Nc1nc(NC2CCC(=O)CC2)ncc1C(F)(F)F]
I-38
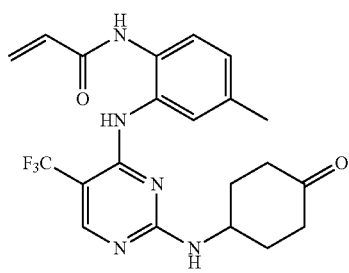 [SMILES: C=CC(=O)Nc1ccc(C)cc1Nc1nc(NC2CCC(=O)CC2)ncc1C(F)(F)F]
I-39
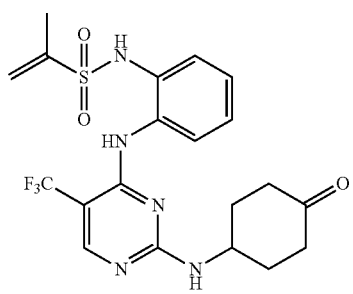 [SMILES: C=C(C)S(=O)(=O)Nc1ccccc1Nc1nc(NC2CCC(=O)CC2)ncc1C(F)(F)F]
I-40

TABLE 3-continued
Exemplary Compounds of Formula I
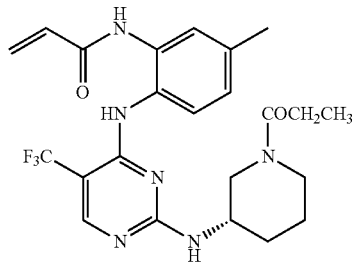
I-41
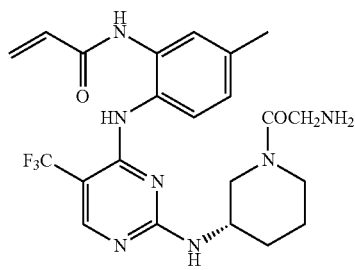
I-42
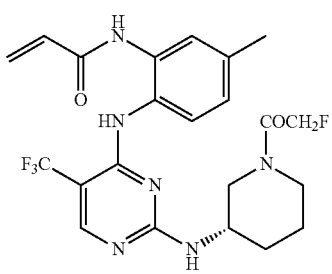
I-43
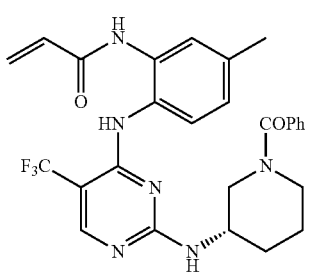
I-44
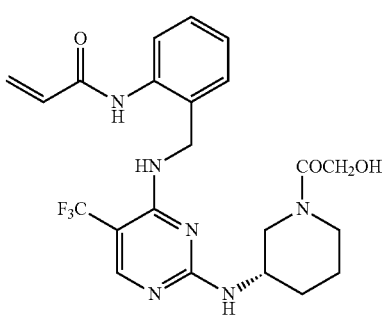
I-45

TABLE 3-continued
Exemplary Compounds of Formula I
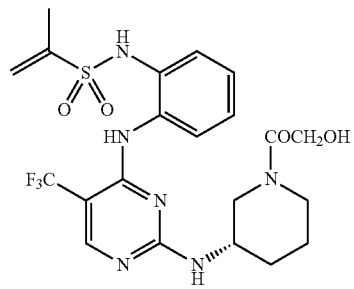
I-46
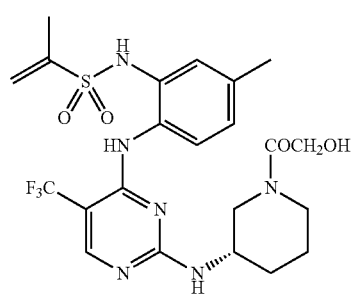
I-47
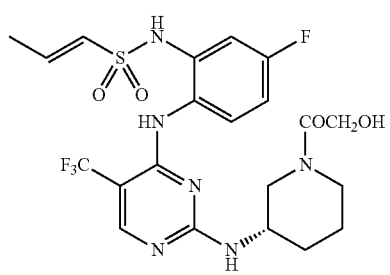
I-48
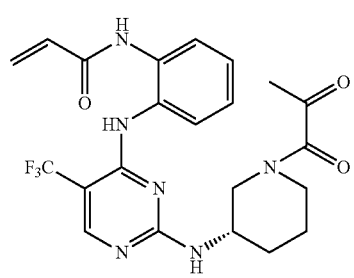 [SMILES: C=CC(=O)Nc1ccccc1Nc1nc(N[C@H]2CCCN(C(=O)C(C)=O)C2)ncc1C(F)(F)F]
I-49
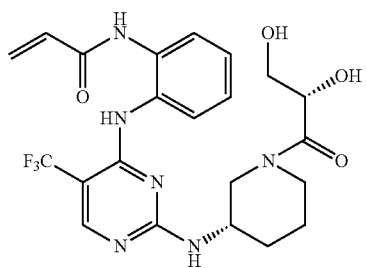 [SMILES: C=CC(=O)Nc1ccccc1Nc1nc(N[C@H]2CCCN(C(=O)[C@@H](O)CO)C2)ncc1C(F)(F)F]
I-50

TABLE 3-continued
Exemplary Compounds of Formula I
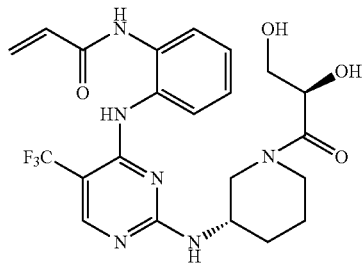 [SMILES: C=CC(=O)Nc1ccccc1Nc1nc(N[C@H]2CCCN(C(=O)[C@H](O)CO)C2)ncc1C(F)(F)F]
I-51
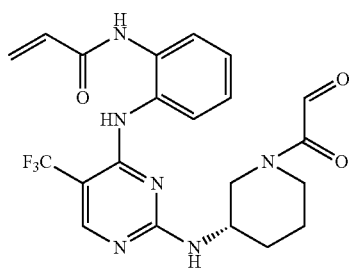 [SMILES: C=CC(=O)Nc1ccccc1Nc1nc(N[C@H]2CCCN(C(=O)C=O)C2)ncc1C(F)(F)F]
I-52
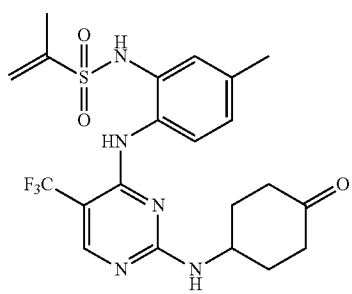 [SMILES: C=C(C)S(=O)(=O)Nc1cc(C)ccc1Nc1nc(NC2CCC(=O)CC2)ncc1C(F)(F)F]
I-53
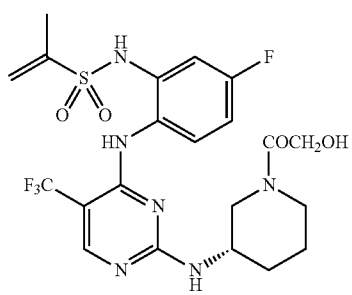
I-54
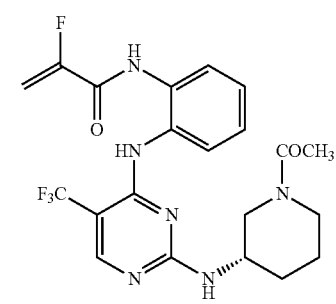 [SMILES: C=C(F)C(=O)Nc1ccccc1Nc1nc(N[C@H]2CCCN(C(C)=O)C2)ncc1C(F)(F)F]
I-55

TABLE 3-continued
Exemplary Compounds of Formula I
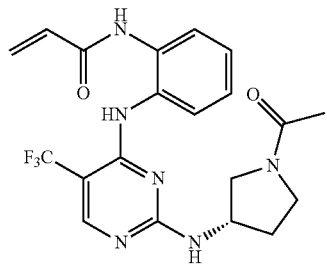 [SMILES: C=CC(=O)Nc1ccccc1Nc1nc(N[C@H]2CCN(C(C)=O)C2)ncc1C(F)(F)F] I-56
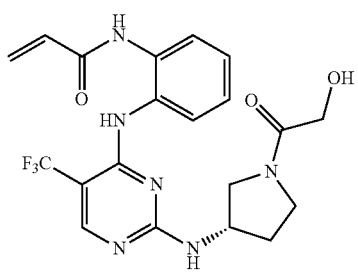 [SMILES: C=CC(=O)Nc1ccccc1Nc1nc(N[C@H]2CCN(C(=O)CO)C2)ncc1C(F)(F)F] I-57
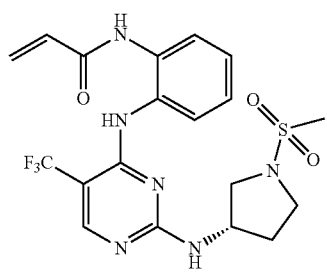 [SMILES: C=CC(=O)Nc1ccccc1Nc1nc(N[C@H]2CCN(S(C)(=O)=O)C2)ncc1C(F)(F)F] I-58
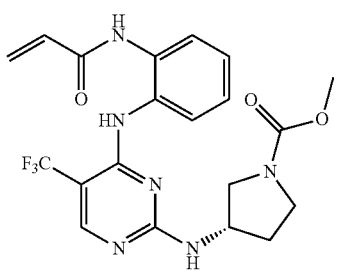 [SMILES: C=CC(=O)Nc1ccccc1Nc1nc(N[C@H]2CCN(C(=O)OC)C2)ncc1C(F)(F)F] I-59
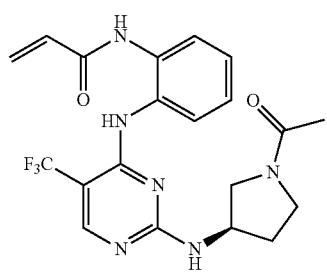 [SMILES: C=CC(=O)Nc1ccccc1Nc1nc(N[C@@H]2CCN(C(C)=O)C2)ncc1C(F)(F)F] I-60

TABLE 3-continued
Exemplary Compounds of Formula I
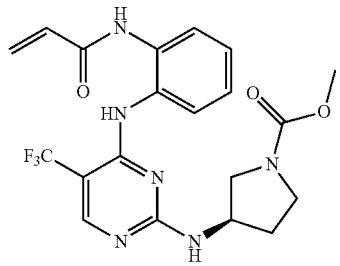 [SMILES: C=CC(=O)Nc1ccccc1Nc1nc(N[C@@H]2CCN(C(=O)OC)C2)ncc1C(F)(F)F]
I-61
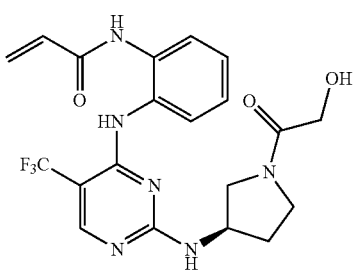 [SMILES: C=CC(=O)Nc1ccccc1Nc1nc(N[C@@H]2CCN(C(=O)CO)C2)ncc1C(F)(F)F]
I-62
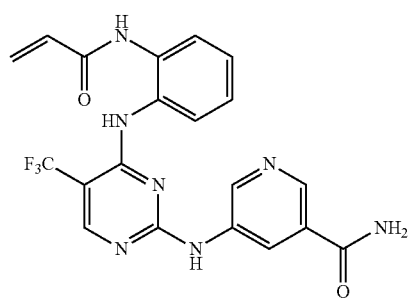 [SMILES: C=CC(=O)Nc1ccccc1Nc1nc(Nc2cncc(C(N)=O)c2)ncc1C(F)(F)F]
I-63
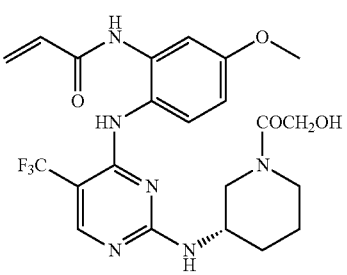
I-64
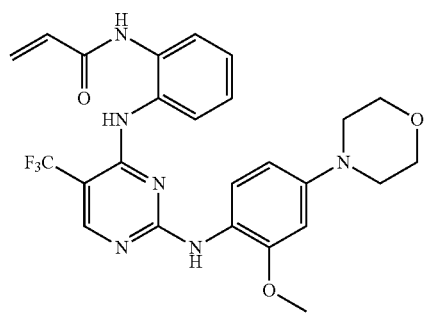 [SMILES: C=CC(=O)Nc1ccccc1Nc1nc(Nc2ccc(N3CCOCC3)cc2OC)ncc1C(F)(F)F]
I-65

TABLE 3-continued
Exemplary Compounds of Formula I
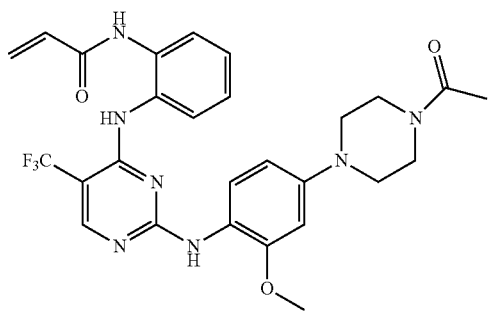 [SMILES: C=CC(=O)Nc1ccccc1Nc1nc(Nc2ccc(N3CCN(C(C)=O)CC3)cc2OC)ncc1C(F)(F)F]
I-66
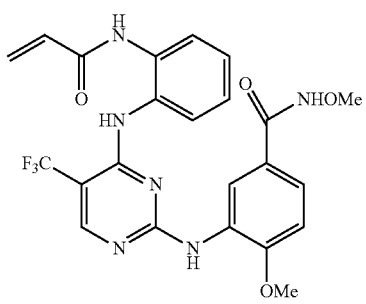
I-67
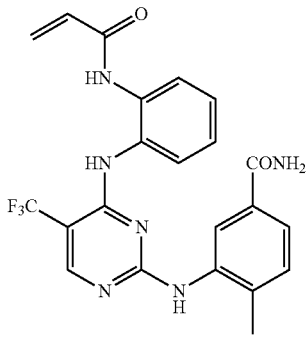 [SMILES: C=CC(=O)Nc1ccccc1Nc1nc(Nc2cc(C(N)=O)ccc2C)ncc1C(F)(F)F]
I-68
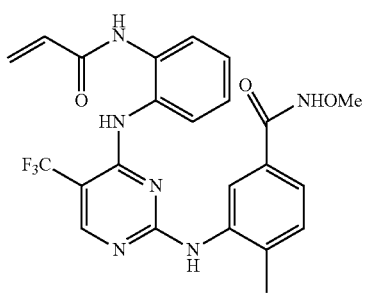
I-69
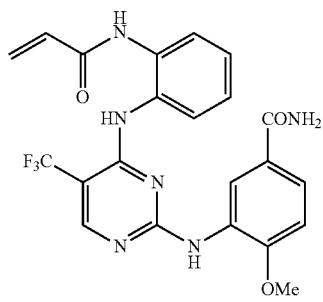 [SMILES: C=CC(=O)Nc1ccccc1Nc1nc(Nc2cc(C(N)=O)ccc2OC)ncc1C(F)(F)F]
I-70

TABLE 3-continued
Exemplary Compounds of Formula I
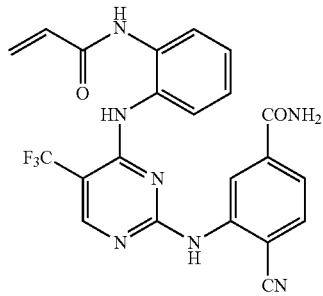 [SMILES: C=CC(=O)Nc1ccccc1Nc1nc(Nc2cc(C(N)=O)ccc2C#N)ncc1C(F)(F)F]
I-71
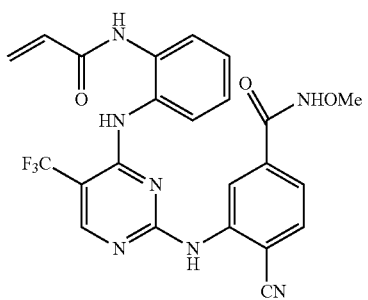
I-72
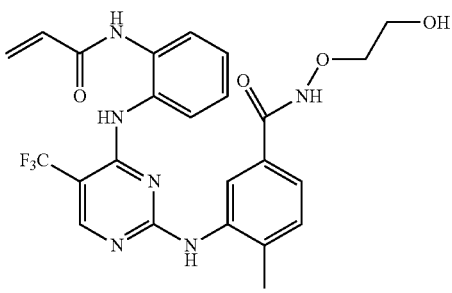
I-73
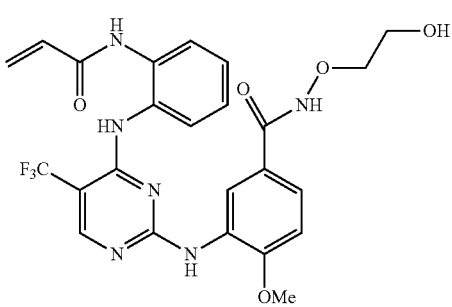 [SMILES: C=CC(=O)Nc1ccccc1Nc1nc(Nc2cc(C(=O)NOCCO)ccc2OC)ncc1C(F)(F)F]
I-74
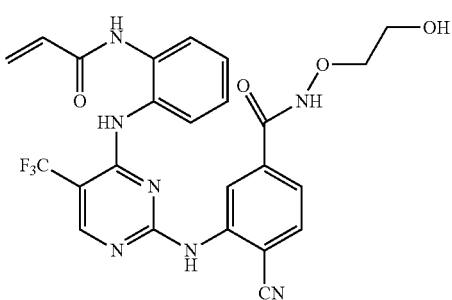
I-75

TABLE 3-continued
Exemplary Compounds of Formula I
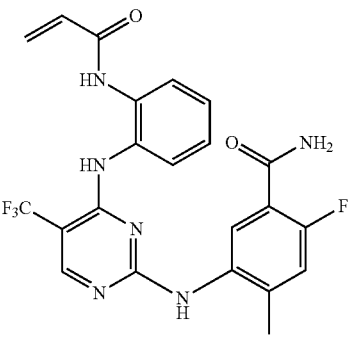 [SMILES: C=CC(=O)Nc1ccccc1Nc1nc(Nc2cc(C(N)=O)c(F)cc2C)ncc1C(F)(F)F]
I-76
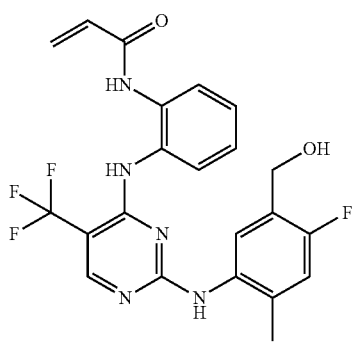 [SMILES: C=CC(=O)Nc1ccccc1Nc1nc(Nc2cc(CO)c(F)cc2C)ncc1C(F)(F)F]
I-77
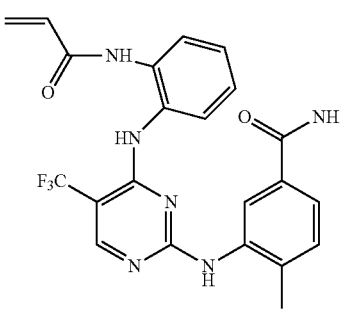 [SMILES: C=CC(=O)Nc1ccccc1Nc1nc(Nc2cc(C(N)=O)ccc2C)ncc1C(F)(F)F]
I-78
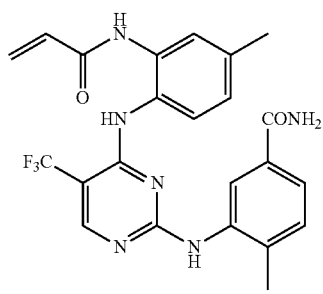 [SMILES: C=CC(=O)Nc1cc(C)ccc1Nc1nc(Nc2cc(C(N)=O)ccc2C)ncc1C(F)(F)F]
I-79
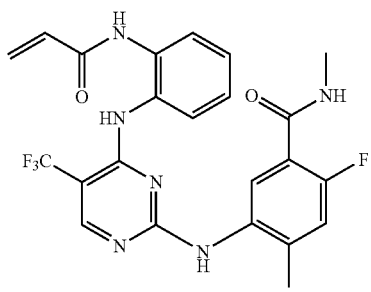 [SMILES: C=CC(=O)Nc1ccccc1Nc1nc(Nc2cc(C(=O)NC)c(F)cc2C)ncc1C(F)(F)F]
I-80

TABLE 3-continued
Exemplary Compounds of Formula I
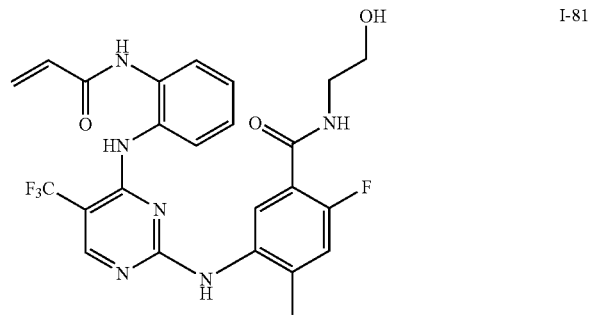
I-81
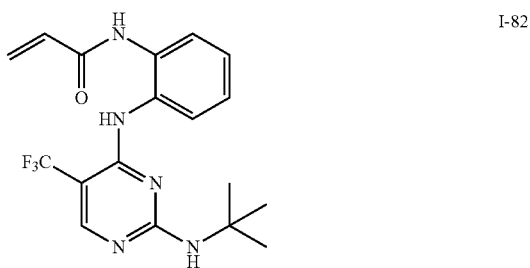
I-82
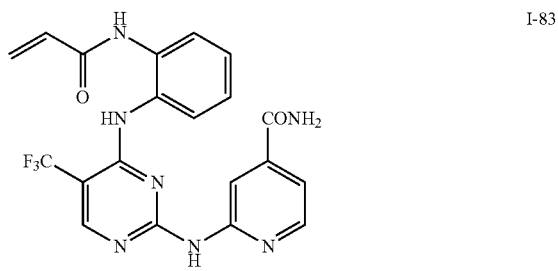
I-83
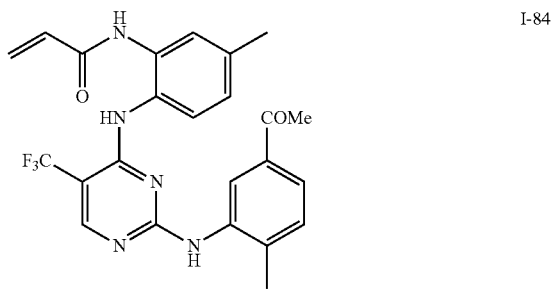
I-84
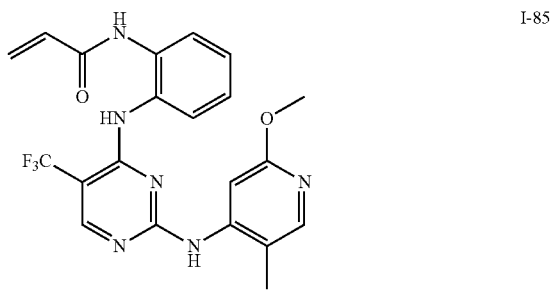
I-85

TABLE 3-continued
Exemplary Compounds of Formula I
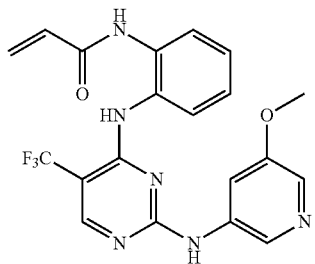 [SMILES: C=CC(=O)Nc1ccccc1Nc1nc(Nc2cncc(OC)c2)ncc1C(F)(F)F]
I-86
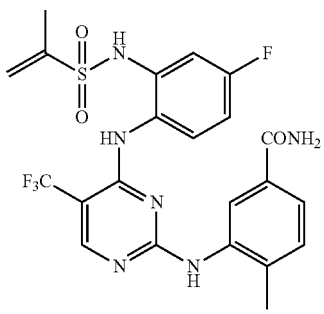 [SMILES: C=C(C)S(=O)(=O)Nc1cc(F)ccc1Nc1nc(Nc2cc(C(N)=O)ccc2C)ncc1C(F)(F)F]
I-87
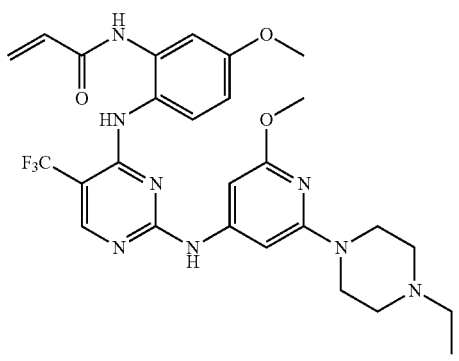 [SMILES: C=CC(=O)Nc1cc(OC)ccc1Nc1nc(Nc2cc(OC)nc(N3CCN(CC)CC3)c2)ncc1C(F)(F)F]
I-88
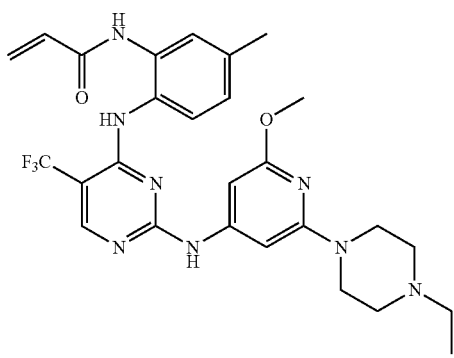 [SMILES: C=CC(=O)Nc1cc(C)ccc1Nc1nc(Nc2cc(OC)nc(N3CCN(CC)CC3)c2)ncc1C(F)(F)F]
I-89
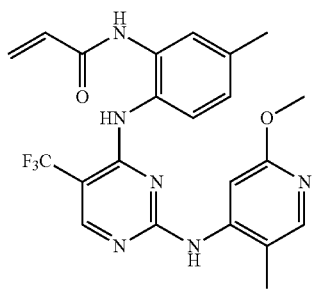 [SMILES: C=CC(=O)Nc1cc(C)ccc1Nc1nc(Nc2cc(OC)ncc2C)ncc1C(F)(F)F]
I-90

TABLE 3-continued
Exemplary Compounds of Formula I
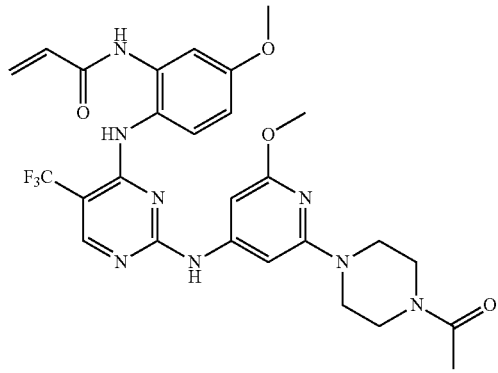 [SMILES: C=CC(=O)Nc1cc(OC)ccc1Nc1nc(Nc2cc(OC)nc(N3CCN(C(C)=O)CC3)c2)ncc1C(F)(F)F]
I-91
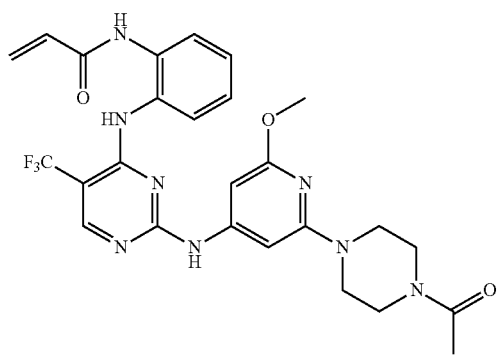 [SMILES: C=CC(=O)Nc1ccccc1Nc1nc(Nc2cc(OC)nc(N3CCN(C(C)=O)CC3)c2)ncc1C(F)(F)F]
I-92
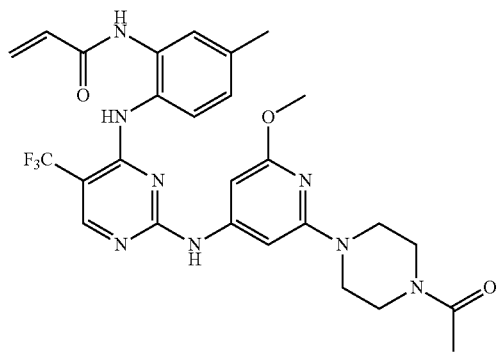 [SMILES: C=CC(=O)Nc1cc(C)ccc1Nc1nc(Nc2cc(OC)nc(N3CCN(C(C)=O)CC3)c2)ncc1C(F)(F)F]
I-93
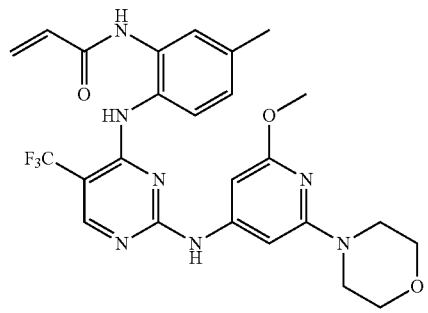 [SMILES: C=CC(=O)Nc1cc(C)ccc1Nc1nc(Nc2cc(OC)nc(N3CCOCC3)c2)ncc1C(F)(F)F]
I-94

TABLE 3-continued
Exemplary Compounds of Formula I
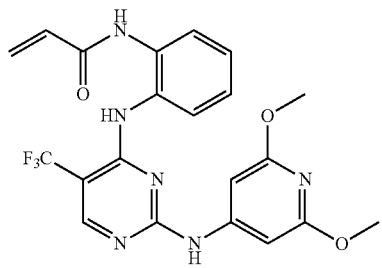 [SMILES: C=CC(=O)Nc1ccccc1Nc1nc(Nc2cc(OC)nc(OC)c2)ncc1C(F)(F)F]
I-95
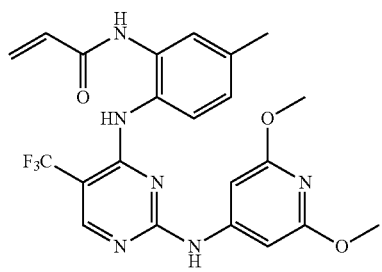 [SMILES: C=CC(=O)Nc1cc(C)ccc1Nc1nc(Nc2cc(OC)nc(OC)c2)ncc1C(F)(F)F]
I-96
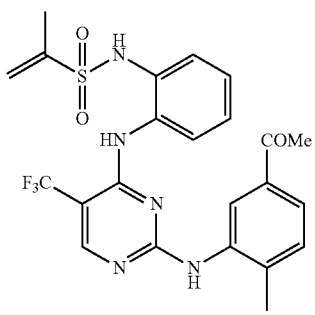
I-97
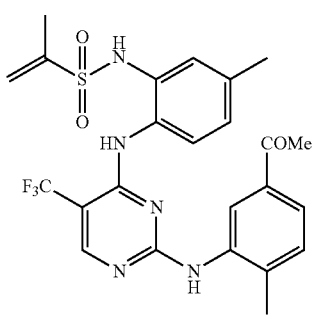
I-98
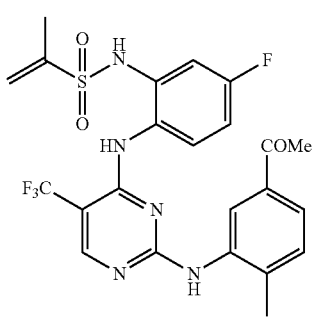
I-99

TABLE 3-continued
Exemplary Compounds of Formula I
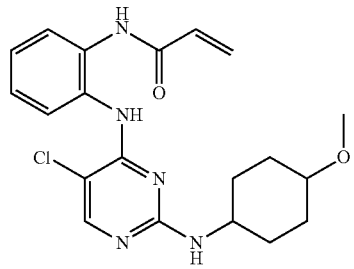 [SMILES: C=CC(=O)Nc1ccccc1Nc1nc(NC2CCC(OC)CC2)ncc1Cl] I-100
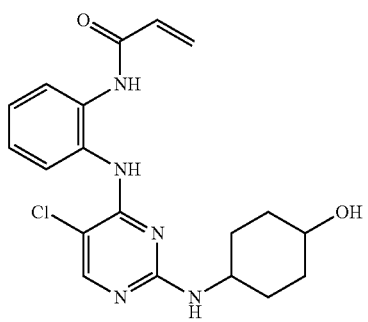 [SMILES: C=CC(=O)Nc1ccccc1Nc1nc(NC2CCC(O)CC2)ncc1Cl] I-101
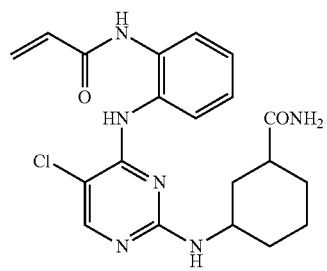 [SMILES: C=CC(=O)Nc1ccccc1Nc1nc(NC2CCCC(C(N)=O)C2)ncc1Cl] I-102
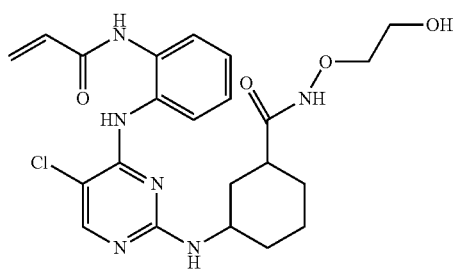 [SMILES: C=CC(=O)Nc1ccccc1Nc1nc(NC2CCCC(C(=O)NOCCO)C2)ncc1Cl] I-103
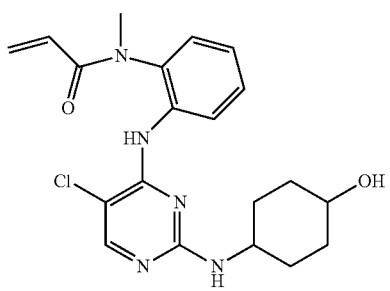 [SMILES: C=CC(=O)N(C)c1ccccc1Nc1nc(NC2CCC(O)CC2)ncc1Cl] I-104

TABLE 3-continued
Exemplary Compounds of Formula I
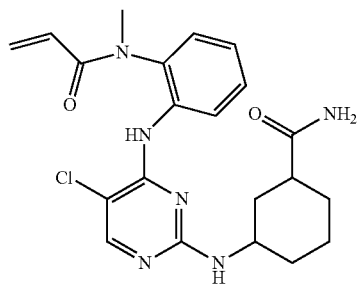 [SMILES: C=CC(=O)N(C)c1ccccc1Nc1nc(NC2CCCC(C(N)=O)C2)ncc1Cl]
I-105
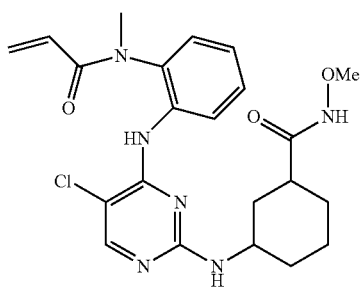 [SMILES: C=CC(=O)N(C)c1ccccc1Nc1nc(NC2CCCC(C(=O)NOC)C2)ncc1Cl]
I-106
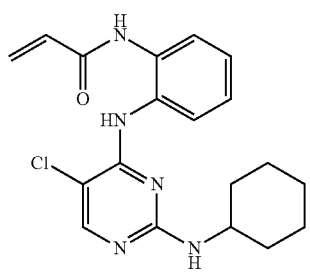 [SMILES: C=CC(=O)Nc1ccccc1Nc1nc(NC2CCCCC2)ncc1Cl]
I-107
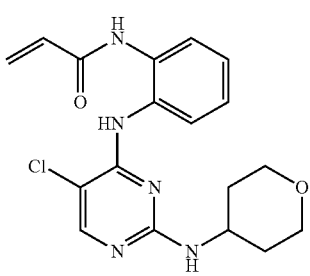 [SMILES: C=CC(=O)Nc1ccccc1Nc1nc(NC2CCOCC2)ncc1Cl]
I-108
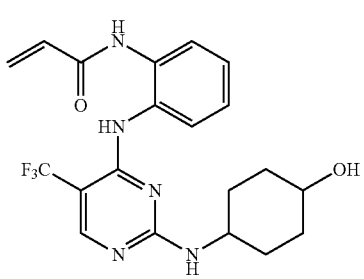 [SMILES: C=CC(=O)Nc1ccccc1Nc1nc(NC2CCC(O)CC2)ncc1C(F)(F)F]
I-109

TABLE 3-continued
Exemplary Compounds of Formula I
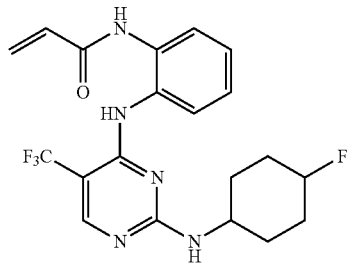 [SMILES: C=CC(=O)Nc1ccccc1Nc1nc(NC2CCC(F)CC2)ncc1C(F)(F)F]
I-110
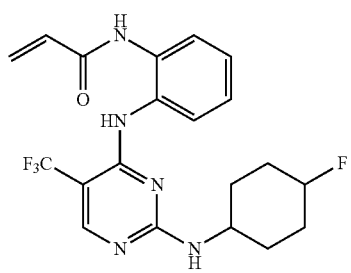 [SMILES: C=CC(=O)Nc1ccccc1Nc1nc(NC2CCC(F)CC2)ncc1C(F)(F)F]
I-111
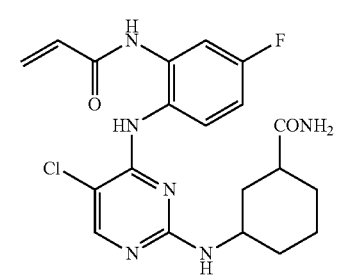 [SMILES: C=CC(=O)Nc1cc(F)ccc1Nc1nc(NC2CCCC(C(N)=O)C2)ncc1Cl]
I-112
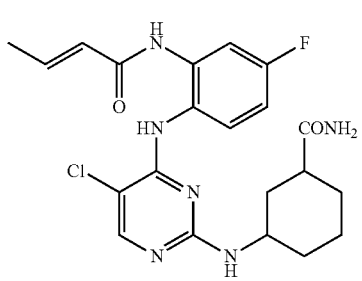 [SMILES: C/C=C/C(=O)Nc1cc(F)ccc1Nc1nc(NC2CCCC(C(N)=O)C2)ncc1Cl]
I-113
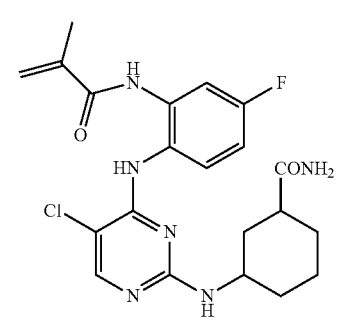 [SMILES: C=C(C)C(=O)Nc1cc(F)ccc1Nc1nc(NC2CCCC(C(N)=O)C2)ncc1Cl]
I-114

TABLE 3-continued
Exemplary Compounds of Formula I
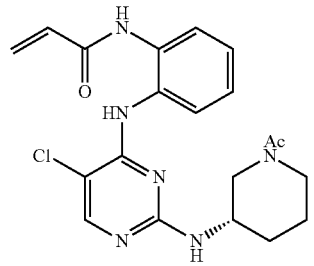
I-115
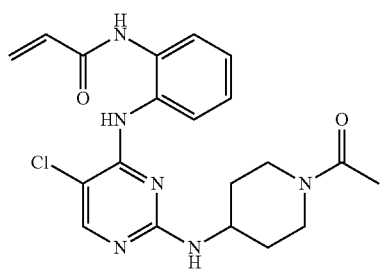 [SMILES: C=CC(=O)Nc1ccccc1Nc1nc(NC2CCN(C(C)=O)CC2)ncc1Cl]
I-116
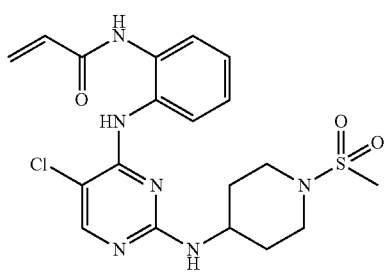 [SMILES: C=CC(=O)Nc1ccccc1Nc1nc(NC2CCN(S(C)(=O)=O)CC2)ncc1Cl]
I-117
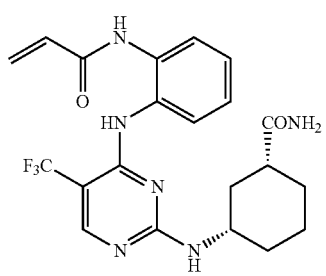
I-118
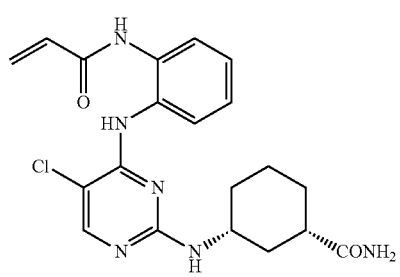 [SMILES: C=CC(=O)Nc1ccccc1Nc1nc(N[C@@H]2CCC[C@H](C(N)=O)C2)ncc1Cl]
I-119

TABLE 3-continued
Exemplary Compounds of Formula I
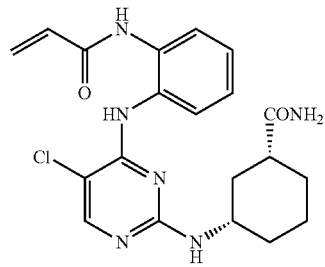 [SMILES: C=CC(=O)Nc1ccccc1Nc1nc(N[C@H]2CCC[C@@H](C(N)=O)C2)ncc1Cl]
I-120
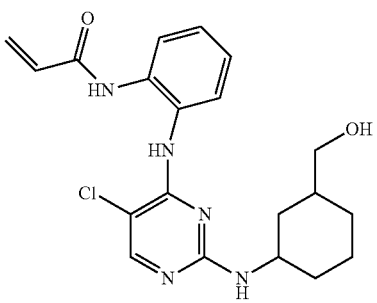 [SMILES: C=CC(=O)Nc1ccccc1Nc1nc(NC2CCCC(CO)C2)ncc1Cl]
I-121
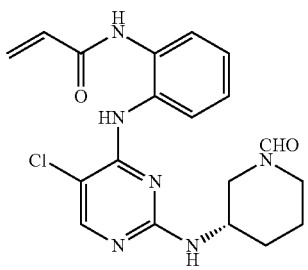
I-122
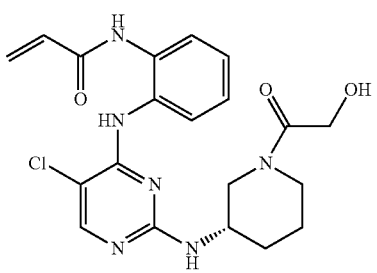 [SMILES: C=CC(=O)Nc1ccccc1Nc1nc(N[C@H]2CCCN(C(=O)CO)C2)ncc1Cl]
I-123
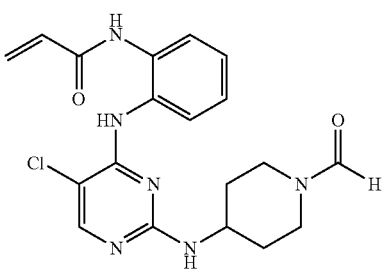 [SMILES: C=CC(=O)Nc1ccccc1Nc1nc(NC2CCN(C=O)CC2)ncc1Cl]
I-124

TABLE 3-continued
Exemplary Compounds of Formula I
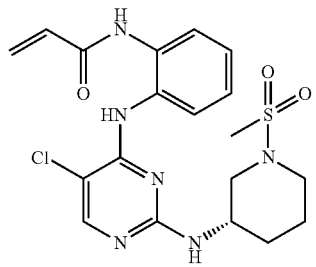 [SMILES: C=CC(=O)Nc1ccccc1Nc1nc(N[C@H]2CCCN(S(C)(=O)=O)C2)ncc1Cl]
I-125
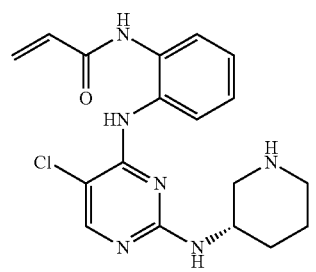 [SMILES: C=CC(=O)Nc1ccccc1Nc1nc(N[C@H]2CCCNC2)ncc1Cl]
I-126
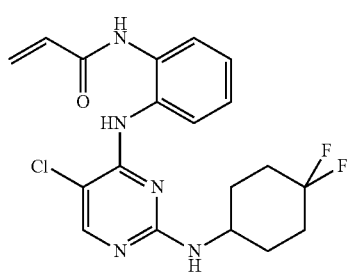 [SMILES: C=CC(=O)Nc1ccccc1Nc1nc(NC2CCC(F)(F)CC2)ncc1Cl]
I-127
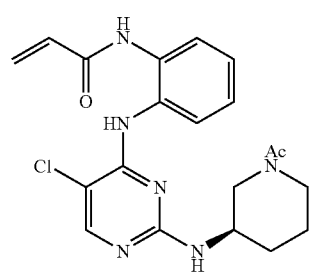
I-128
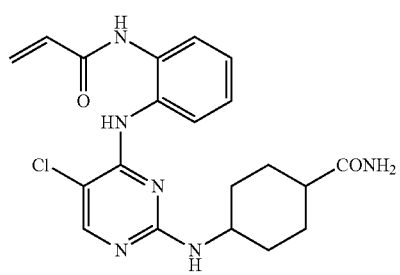 [SMILES: C=CC(=O)Nc1ccccc1Nc1nc(NC2CCC(C(N)=O)CC2)ncc1Cl]
I-129

TABLE 3-continued
Exemplary Compounds of Formula I
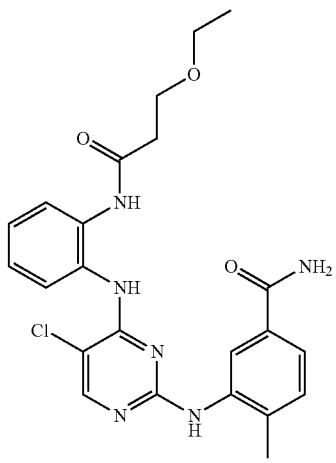 [SMILES: CCOCCC(=O)Nc1ccccc1Nc1nc(Nc2cc(C(N)=O)ccc2C)ncc1Cl]
I-130
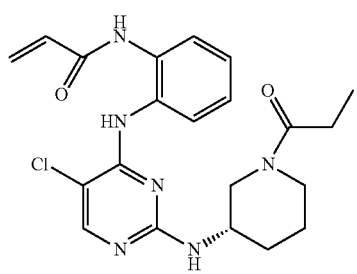 [SMILES: C=CC(=O)Nc1ccccc1Nc1nc(N[C@H]2CCCN(C(=O)CC)C2)ncc1Cl]
I-131
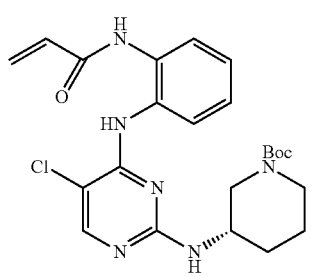 [SMILES: C=CC(=O)Nc1ccccc1Nc1nc(N[C@H]2CCCN(C(=O)OC(C)(C)C)C2)ncc1Cl]
I-132
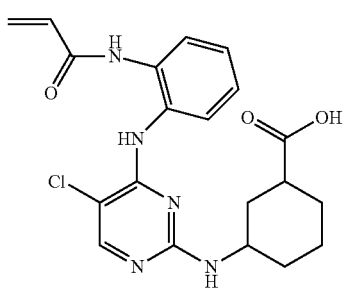 [SMILES: C=CC(=O)Nc1ccccc1Nc1nc(NC2CCCC(C(=O)O)C2)ncc1Cl]
I-133

TABLE 3-continued
Exemplary Compounds of Formula I
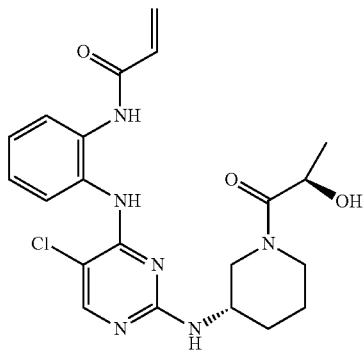 [SMILES: C=CC(=O)Nc1ccccc1Nc1nc(N[C@H]2CCCN(C(=O)[C@@H](C)O)C2)ncc1Cl]
I-134
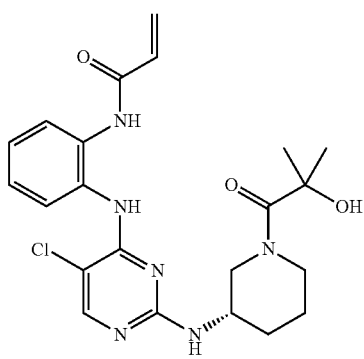 [SMILES: C=CC(=O)Nc1ccccc1Nc1nc(N[C@H]2CCCN(C(=O)C(C)(C)O)C2)ncc1Cl]
I-135
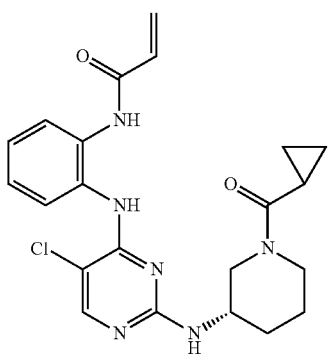 [SMILES: C=CC(=O)Nc1ccccc1Nc1nc(N[C@H]2CCCN(C(=O)C3CC3)C2)ncc1Cl]
I-136
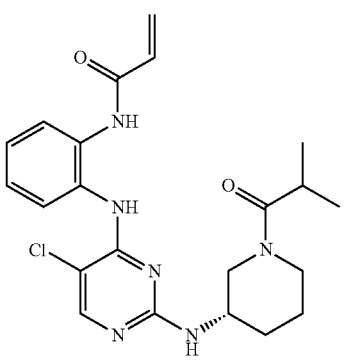 [SMILES: C=CC(=O)Nc1ccccc1Nc1nc(N[C@H]2CCCN(C(=O)C(C)C)C2)ncc1Cl]
I-137

TABLE 3-continued
Exemplary Compounds of Formula I
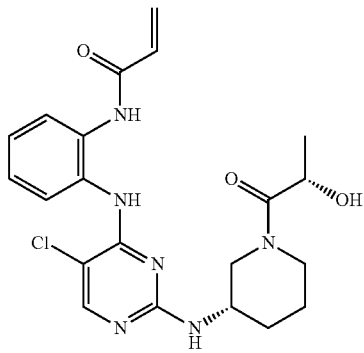 [SMILES: C=CC(=O)Nc1ccccc1Nc1nc(N[C@H]2CCCN(C(=O)[C@H](C)O)C2)ncc1Cl]
I-138
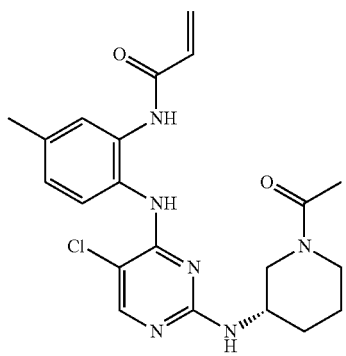 [SMILES: C=CC(=O)Nc1cc(C)ccc1Nc1nc(N[C@H]2CCCN(C(C)=O)C2)ncc1Cl]
I-139
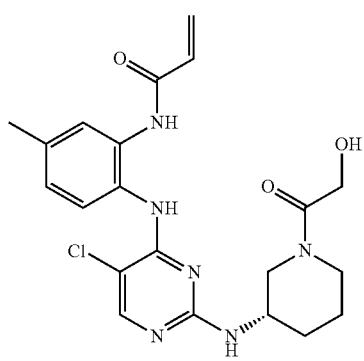 [SMILES: C=CC(=O)Nc1cc(C)ccc1Nc1nc(N[C@H]2CCCN(C(=O)CO)C2)ncc1Cl]
I-140
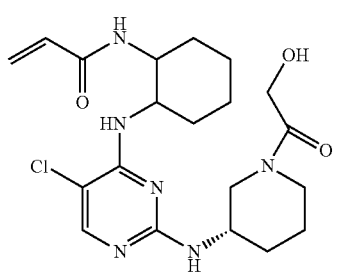 [SMILES: C=CC(=O)NC1CCCCC1Nc1nc(N[C@H]2CCCN(C(=O)CO)C2)ncc1Cl]
I-141

TABLE 3-continued
Exemplary Compounds of Formula I
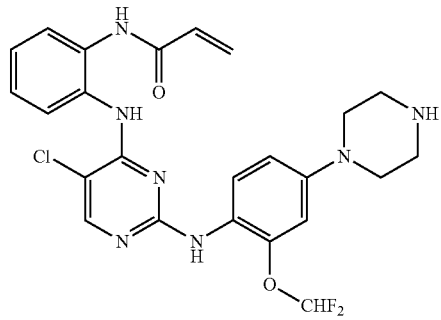 [SMILES: C=CC(=O)Nc1ccccc1Nc1nc(Nc2ccc(N3CCNCC3)cc2OC(F)F)ncc1Cl]
I-142
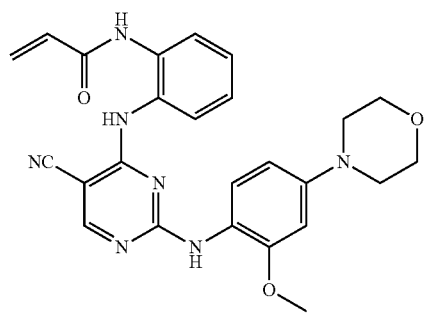 [SMILES: C=CC(=O)Nc1ccccc1Nc1nc(Nc2ccc(N3CCOCC3)cc2OC)ncc1C#N]
I-143
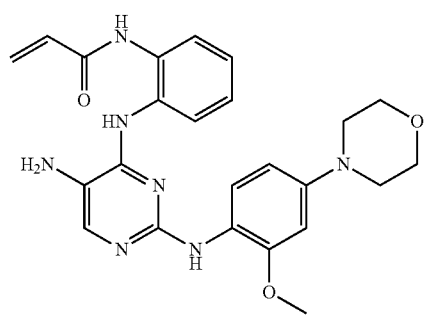 [SMILES: C=CC(=O)Nc1ccccc1Nc1nc(Nc2ccc(N3CCOCC3)cc2OC)ncc1N]
I-144
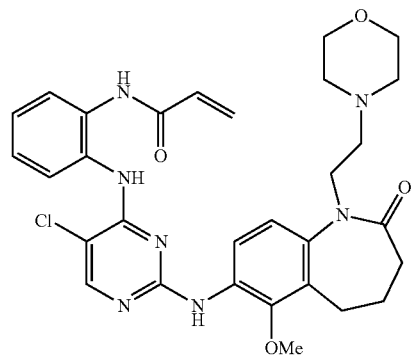 [SMILES: C=CC(=O)Nc1ccccc1Nc1nc(Nc2ccc3c(c2OC)CCCC(=O)N3CCN2CCOCC2)ncc1Cl]
I-145

TABLE 3-continued
Exemplary Compounds of Formula I
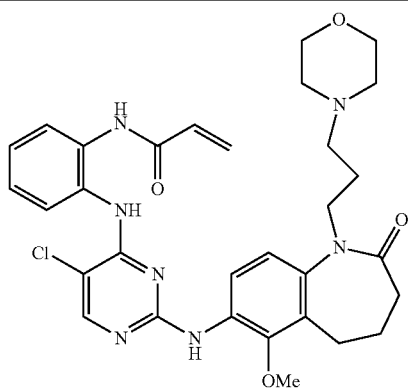
I-146
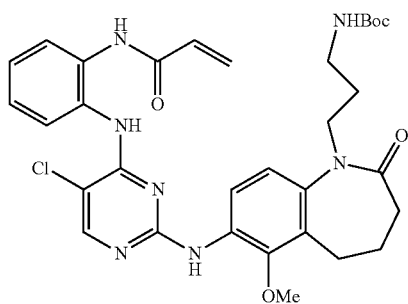 [SMILES: C=CC(=O)Nc1ccccc1Nc1nc(Nc2ccc3c(c2OC)CCCC(=O)N3CCCNC(=O)OC(C)(C)C)ncc1Cl]
I-147
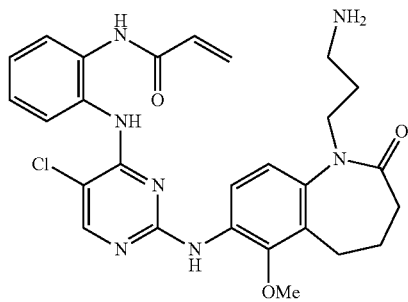 [SMILES: C=CC(=O)Nc1ccccc1Nc1nc(Nc2ccc3c(c2OC)CCCC(=O)N3CCCN)ncc1Cl]
I-148
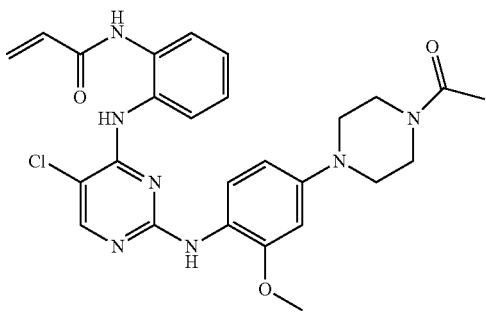 [SMILES: C=CC(=O)Nc1ccccc1Nc1nc(Nc2ccc(N3CCN(C(C)=O)CC3)cc2OC)ncc1Cl]
I-149
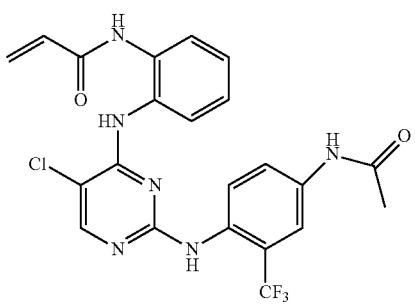 [SMILES: C=CC(=O)Nc1ccccc1Nc1nc(Nc2ccc(NC(C)=O)cc2C(F)(F)F)ncc1Cl]
I-150

TABLE 3-continued
Exemplary Compounds of Formula I
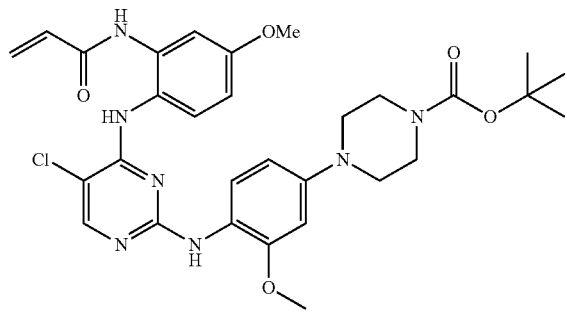 [SMILES: C=CC(=O)Nc1cc(OC)ccc1Nc1nc(Nc2ccc(N3CCN(C(=O)OC(C)(C)C)CC3)cc2OC)ncc1Cl]
I-151
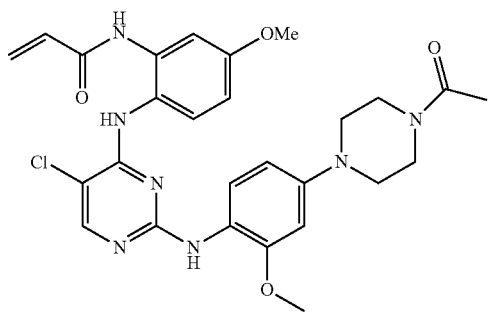 [SMILES: C=CC(=O)Nc1cc(OC)ccc1Nc1nc(Nc2ccc(N3CCN(C(C)=O)CC3)cc2OC)ncc1Cl]
I-152
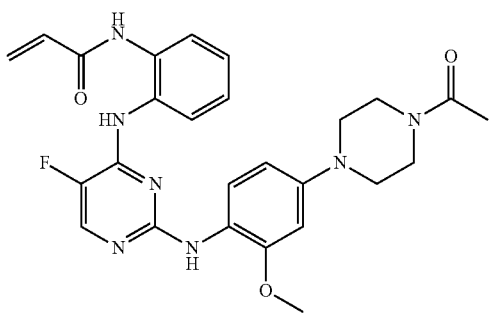 [SMILES: C=CC(=O)Nc1ccccc1Nc1nc(Nc2ccc(N3CCN(C(C)=O)CC3)cc2OC)ncc1F]
I-153
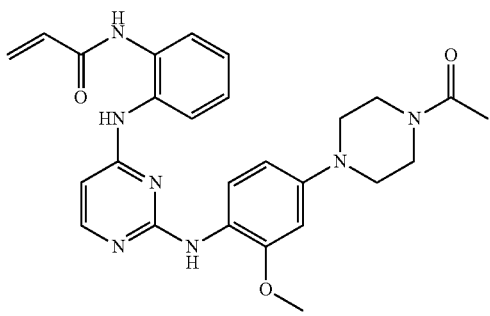 [SMILES: C=CC(=O)Nc1ccccc1Nc1ccnc(Nc2ccc(N3CCN(C(C)=O)CC3)cc2OC)n1]
I-154
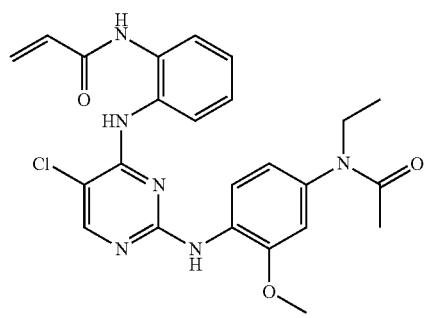 [SMILES: C=CC(=O)Nc1ccccc1Nc1nc(Nc2ccc(N(CC)C(C)=O)cc2OC)ncc1Cl]
I-155

TABLE 3-continued
Exemplary Compounds of Formula I
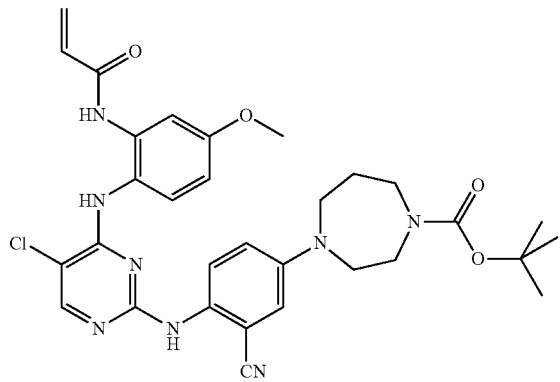 [SMILES: C=CC(=O)Nc1cc(OC)ccc1Nc1nc(Nc2ccc(N3CCCN(C(=O)OC(C)(C)C)CC3)cc2C#N)ncc1Cl]
I-156
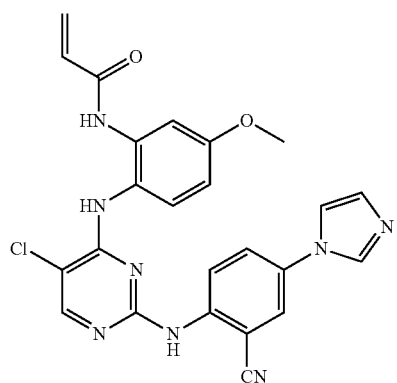 [SMILES: C=CC(=O)Nc1cc(OC)ccc1Nc1nc(Nc2ccc(-n3ccnc3)cc2C#N)ncc1Cl]
I-157
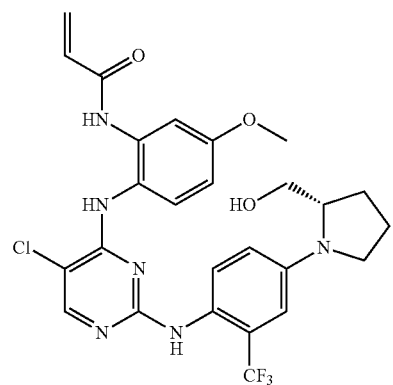 [SMILES: C=CC(=O)Nc1cc(OC)ccc1Nc1nc(Nc2ccc(N3CCC[C@H]3CO)cc2C(F)(F)F)ncc1Cl]
I-158
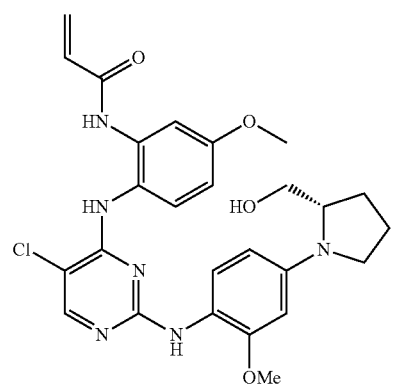 [SMILES: C=CC(=O)Nc1cc(OC)ccc1Nc1nc(Nc2ccc(N3CCC[C@H]3CO)cc2OC)ncc1Cl]
I-159

TABLE 3-continued
Exemplary Compounds of Formula I
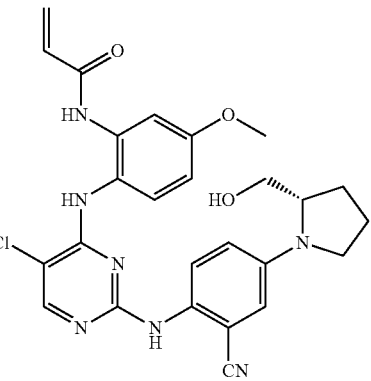
I-160
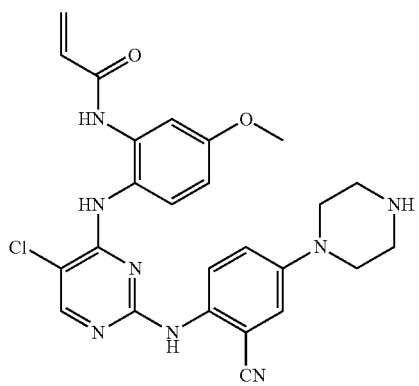 [SMILES: C=CC(=O)Nc1cc(OC)ccc1Nc1nc(Nc2ccc(N3CCNCC3)cc2C#N)ncc1Cl]
I-161
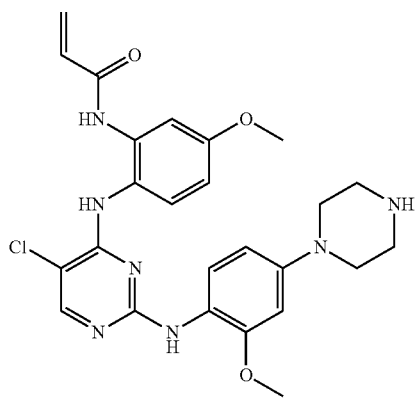 [SMILES: C=CC(=O)Nc1cc(OC)ccc1Nc1nc(Nc2ccc(N3CCNCC3)cc2OC)ncc1Cl]
I-162
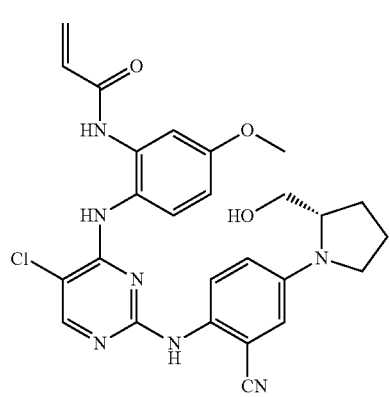 [SMILES: C=CC(=O)Nc1cc(OC)ccc1Nc1nc(Nc2ccc(N3CCC[C@H]3CO)cc2C#N)ncc1Cl]
I-163

TABLE 3-continued
Exemplary Compounds of Formula I
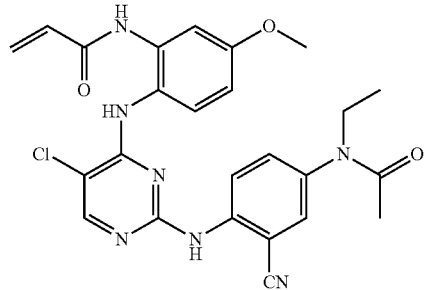 [SMILES: C=CC(=O)Nc1cc(OC)ccc1Nc1nc(Nc2ccc(N(CC)C(C)=O)cc2C#N)ncc1Cl]
I-164
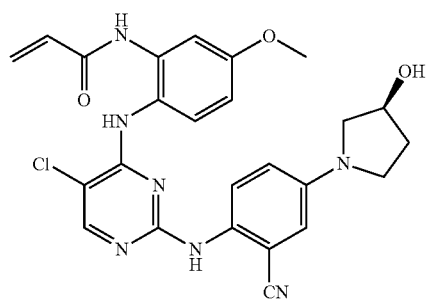 [SMILES: C=CC(=O)Nc1cc(OC)ccc1Nc1nc(Nc2ccc(N3CC[C@H](O)C3)cc2C#N)ncc1Cl]
I-165
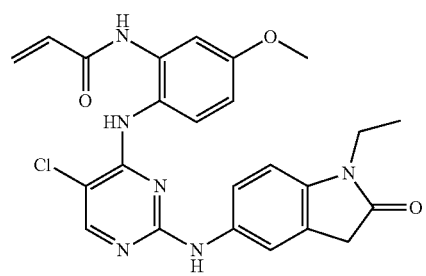 [SMILES: C=CC(=O)Nc1cc(OC)ccc1Nc1nc(Nc2ccc3c(c2)CC(=O)N3CC)ncc1Cl]
I-166
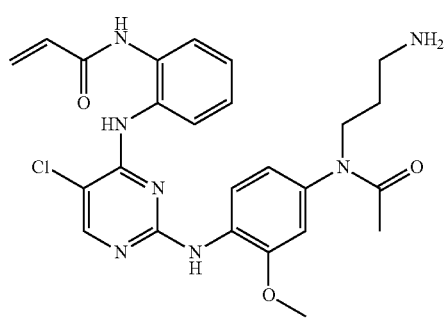 [SMILES: C=CC(=O)Nc1ccccc1Nc1nc(Nc2ccc(N(CCCN)C(C)=O)cc2OC)ncc1Cl]
I-167
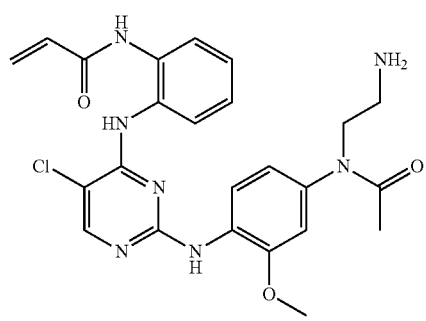 [SMILES: C=CC(=O)Nc1ccccc1Nc1nc(Nc2ccc(N(CCN)C(C)=O)cc2OC)ncc1Cl]
I-168

TABLE 3-continued
Exemplary Compounds of Formula I
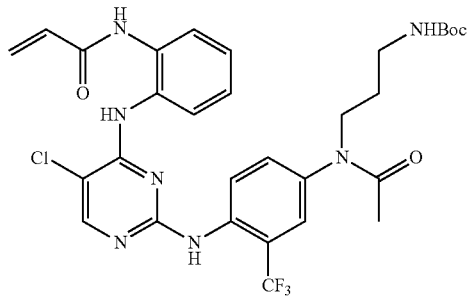 [SMILES: C=CC(=O)Nc1ccccc1Nc1nc(Nc2ccc(N(CCCNC(=O)OC(C)(C)C)C(C)=O)cc2C(F)(F)F)ncc1Cl]
I-169
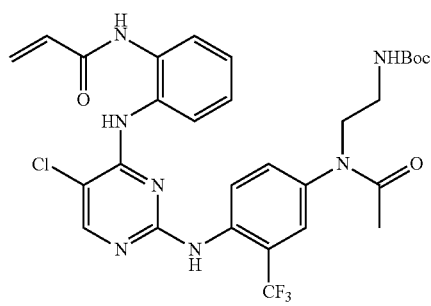 [SMILES: C=CC(=O)Nc1ccccc1Nc1nc(Nc2ccc(N(CCNC(=O)OC(C)(C)C)C(C)=O)cc2C(F)(F)F)ncc1Cl]
I-170
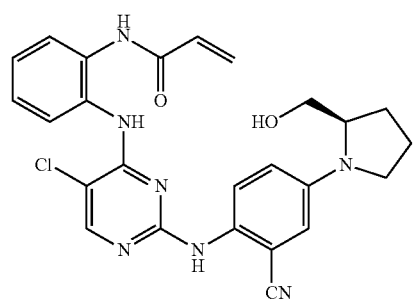 [SMILES: C=CC(=O)Nc1ccccc1Nc1nc(Nc2ccc(N3CCC[C@@H]3CO)cc2C#N)ncc1Cl]
I-171
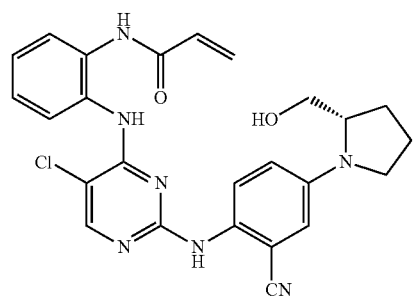 [SMILES: C=CC(=O)Nc1ccccc1Nc1nc(Nc2ccc(N3CCC[C@H]3CO)cc2C#N)ncc1Cl]
I-172
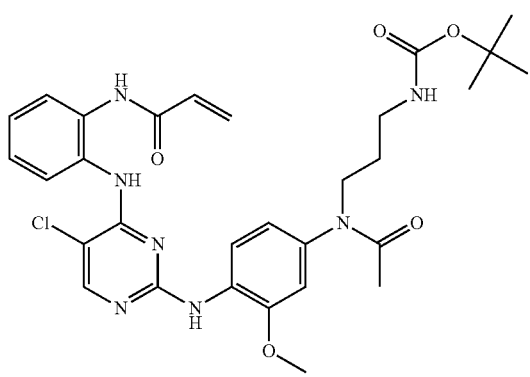 [SMILES: C=CC(=O)Nc1ccccc1Nc1nc(Nc2ccc(N(CCCNC(=O)OC(C)(C)C)C(C)=O)cc2OC)ncc1Cl]
I-173

TABLE 3-continued
Exemplary Compounds of Formula I
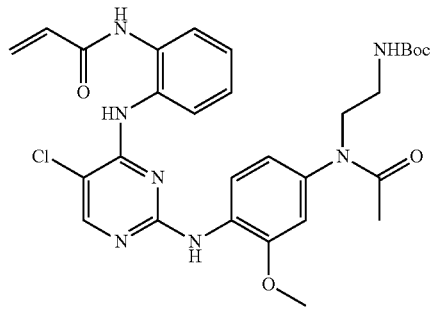 [SMILES: C=CC(=O)Nc1ccccc1Nc1nc(Nc2ccc(N(CCNC(=O)OC(C)(C)C)C(C)=O)cc2OC)ncc1Cl]
I-174
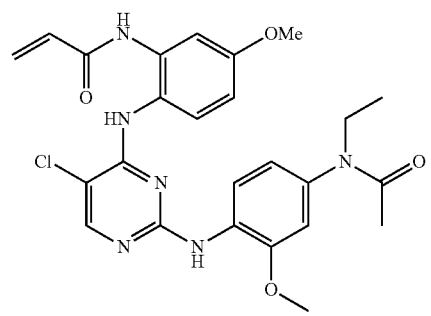 [SMILES: C=CC(=O)Nc1cc(OC)ccc1Nc1nc(Nc2ccc(N(CC)C(C)=O)cc2OC)ncc1Cl]
I-175
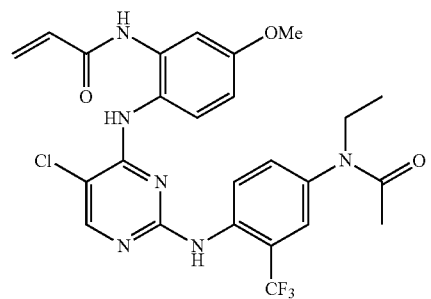 [SMILES: C=CC(=O)Nc1cc(OC)ccc1Nc1nc(Nc2ccc(N(CC)C(C)=O)cc2C(F)(F)F)ncc1Cl]
I-176
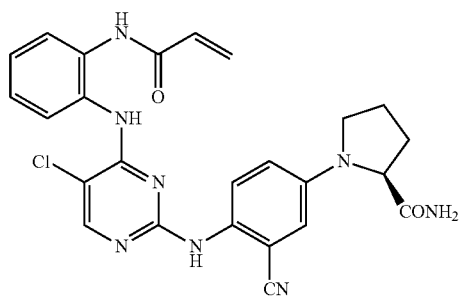 [SMILES: C=CC(=O)Nc1ccccc1Nc1nc(Nc2ccc(N3CCC[C@H]3C(N)=O)cc2C#N)ncc1Cl]
I-177
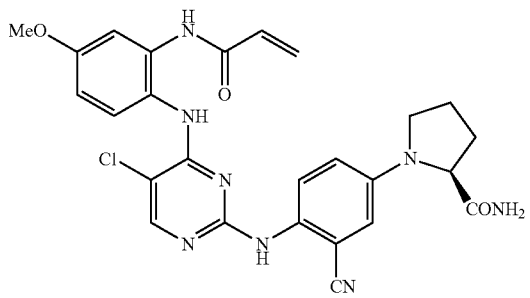 [SMILES: C=CC(=O)Nc1cc(OC)ccc1Nc1nc(Nc2ccc(N3CCC[C@H]3C(N)=O)cc2C#N)ncc1Cl]
I-178

TABLE 3-continued
Exemplary Compounds of Formula I
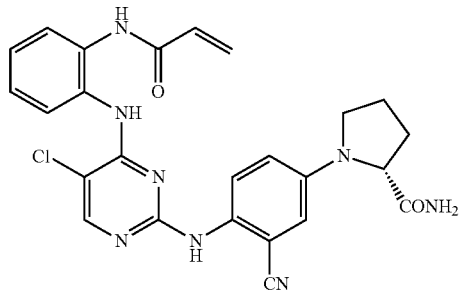 [SMILES: C=CC(=O)Nc1ccccc1Nc1nc(Nc2ccc(N3CCC[C@@H]3C(N)=O)cc2C#N)ncc1Cl]
I-179
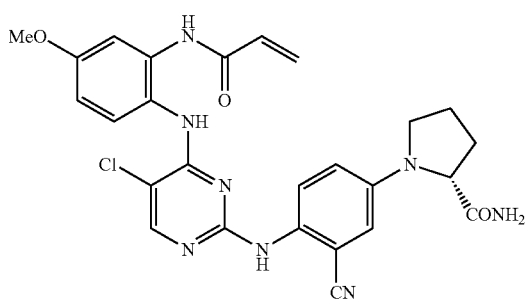 [SMILES: C=CC(=O)Nc1cc(OC)ccc1Nc1nc(Nc2ccc(N3CCC[C@@H]3C(N)=O)cc2C#N)ncc1Cl]
I-180
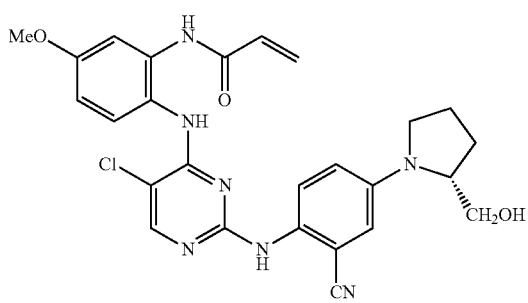 [SMILES: C=CC(=O)Nc1cc(OC)ccc1Nc1nc(Nc2ccc(N3CCC[C@@H]3CO)cc2C#N)ncc1Cl]
I-181
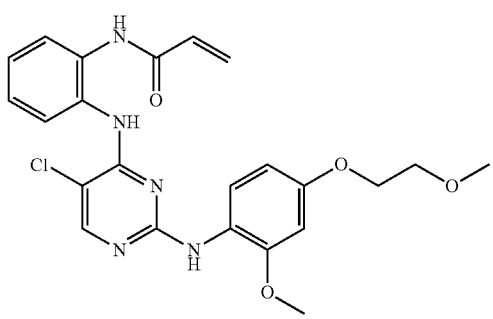 [SMILES: C=CC(=O)Nc1ccccc1Nc1nc(Nc2ccc(OCCOC)cc2OC)ncc1Cl]
I-182
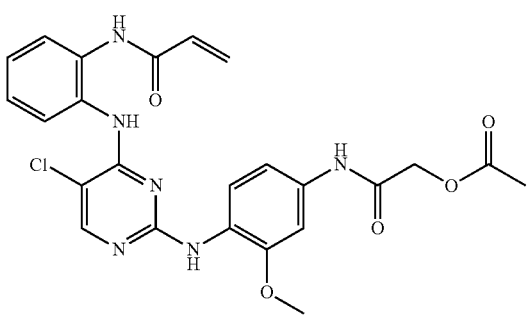
I-183

TABLE 3-continued
Exemplary Compounds of Formula I
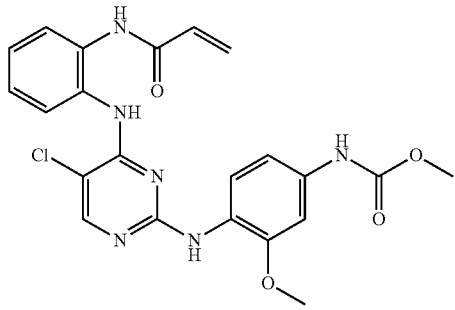 [SMILES: C=CC(=O)Nc1ccccc1Nc1nc(Nc2ccc(NC(=O)OC)cc2OC)ncc1Cl]
I-184
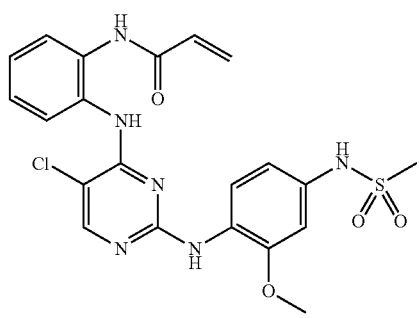 [SMILES: C=CC(=O)Nc1ccccc1Nc1nc(Nc2ccc(NS(C)(=O)=O)cc2OC)ncc1Cl]
I-185
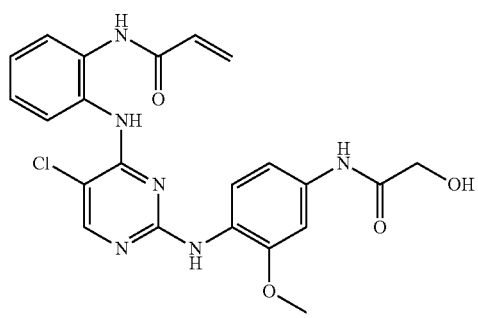 [SMILES: C=CC(=O)Nc1ccccc1Nc1nc(Nc2ccc(NC(=O)CO)cc2OC)ncc1Cl]
I-186
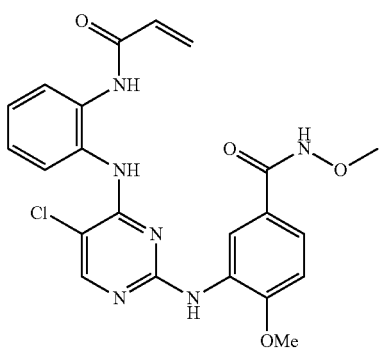 [SMILES: C=CC(=O)Nc1ccccc1Nc1nc(Nc2cc(C(=O)NOC)ccc2OC)ncc1Cl]
I-187

TABLE 3-continued
Exemplary Compounds of Formula I
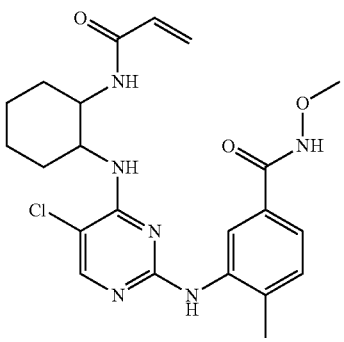 [SMILES: C=CC(=O)NC1CCCCC1Nc1nc(Nc2cc(C(=O)NOC)ccc2C)ncc1Cl]
I-188
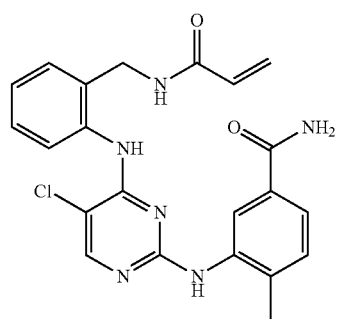 [SMILES: C=CC(=O)NCc1ccccc1Nc1nc(Nc2cc(C(N)=O)ccc2C)ncc1Cl]
I-189
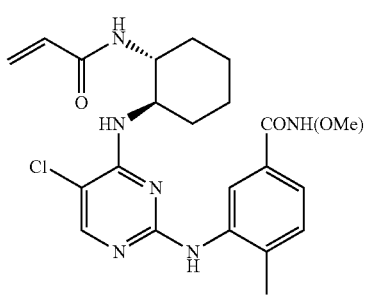
I-190
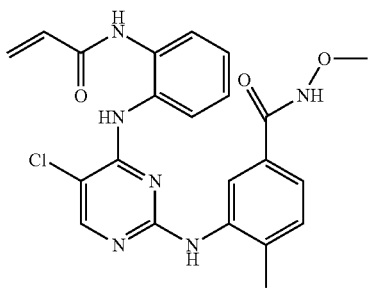 [SMILES: C=CC(=O)Nc1ccccc1Nc1nc(Nc2cc(C(=O)NOC)ccc2C)ncc1Cl]
I-191
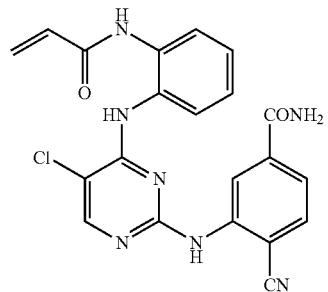
I-192

TABLE 3-continued
Exemplary Compounds of Formula I
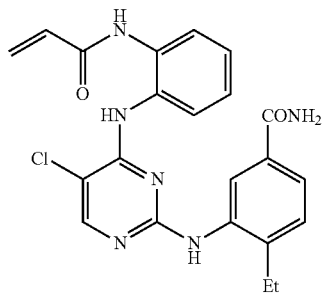 [SMILES: C=CC(=O)Nc1ccccc1Nc1nc(Nc2cc(C(N)=O)ccc2CC)ncc1Cl]
I-193
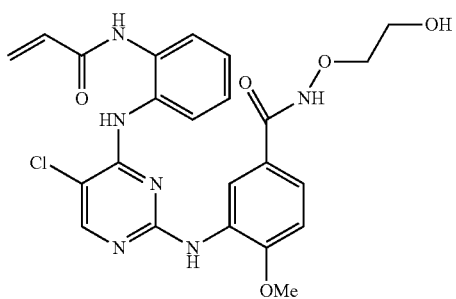
I-194
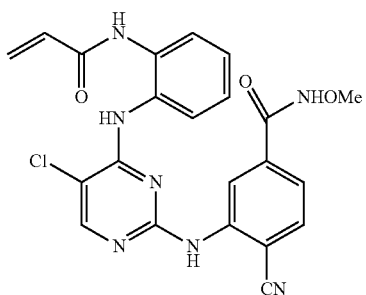
I-195
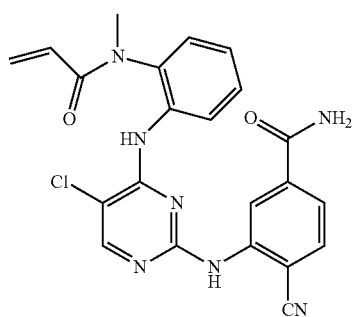 [SMILES: C=CC(=O)N(C)c1ccccc1Nc1nc(Nc2cc(C(N)=O)ccc2C#N)ncc1Cl]
I-196
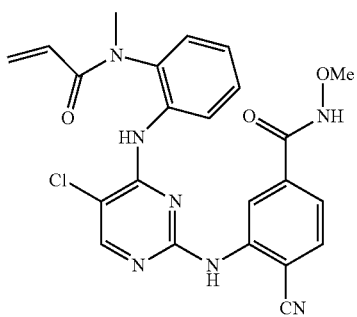 [SMILES: C=CC(=O)N(C)c1ccccc1Nc1nc(Nc2cc(C(=O)NOC)ccc2C#N)ncc1Cl]
I-197

TABLE 3-continued
Exemplary Compounds of Formula I
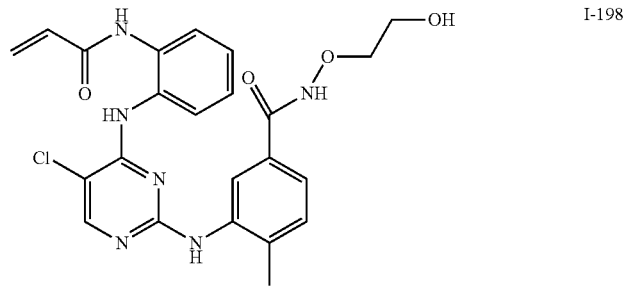 I-198
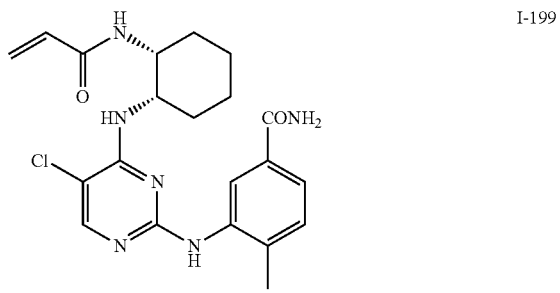 I-199
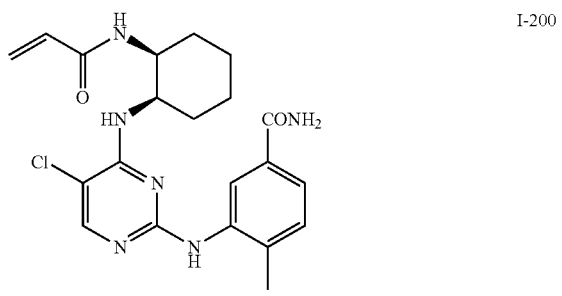 I-200
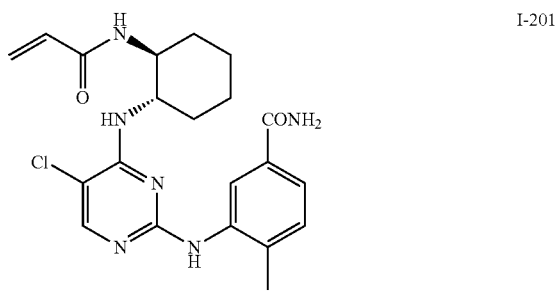 I-201
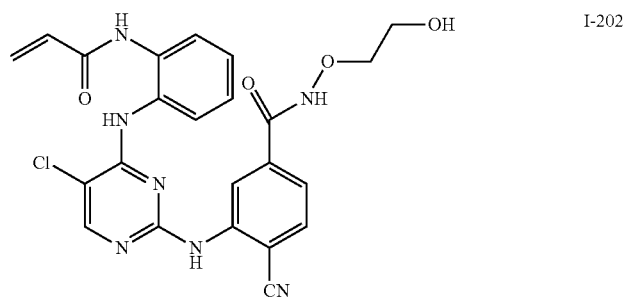 I-202

TABLE 3-continued
Exemplary Compounds of Formula I
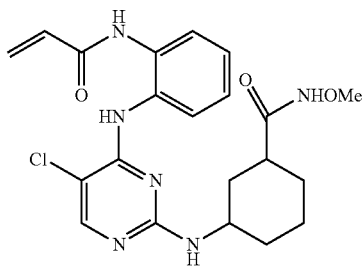
I-203
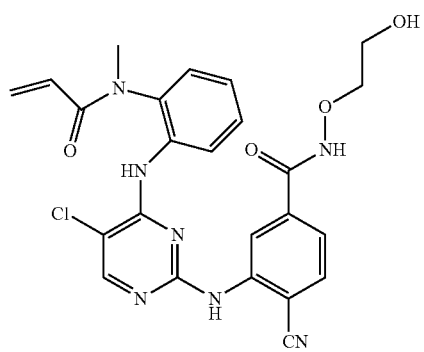 [SMILES: C=CC(=O)N(C)c1ccccc1Nc1nc(Nc2cc(C(=O)NOCCO)ccc2C#N)ncc1Cl]
I-204
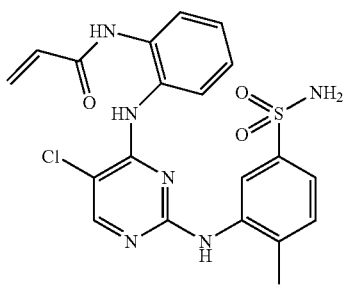 [SMILES: C=CC(=O)Nc1ccccc1Nc1nc(Nc2cc(S(N)(=O)=O)ccc2C)ncc1Cl]
I-205
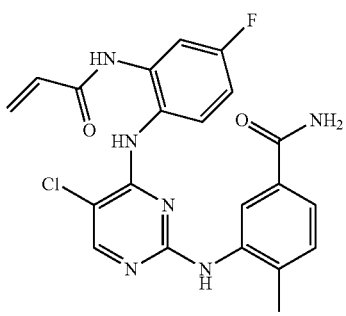 [SMILES: C=CC(=O)Nc1cc(F)ccc1Nc1nc(Nc2cc(C(N)=O)ccc2C)ncc1Cl]
I-206
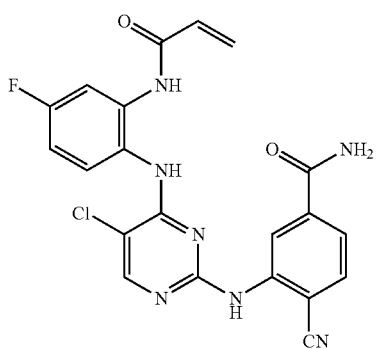 [SMILES: C=CC(=O)Nc1cc(F)ccc1Nc1nc(Nc2cc(C(N)=O)ccc2C#N)ncc1Cl]
I-207

TABLE 3-continued
Exemplary Compounds of Formula I
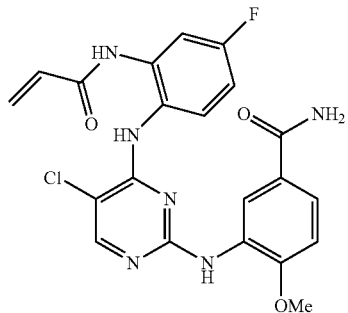 [SMILES: C=CC(=O)Nc1cc(F)ccc1Nc1nc(Nc2cc(C(N)=O)ccc2OC)ncc1Cl]
I-208
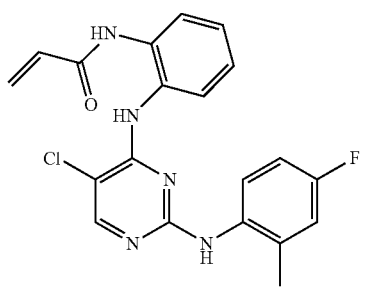 [SMILES: C=CC(=O)Nc1ccccc1Nc1nc(Nc2ccc(F)cc2C)ncc1Cl]
I-209
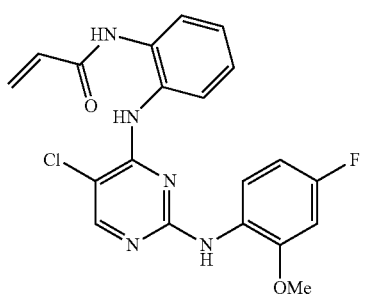 [SMILES: C=CC(=O)Nc1ccccc1Nc1nc(Nc2ccc(F)cc2OC)ncc1Cl]
I-210
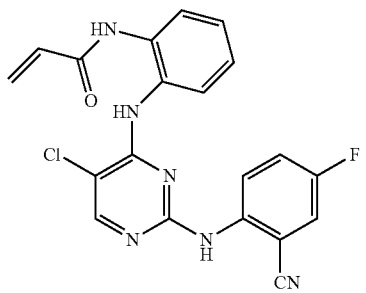 [SMILES: C=CC(=O)Nc1ccccc1Nc1nc(Nc2ccc(F)cc2C#N)ncc1Cl]
I-211
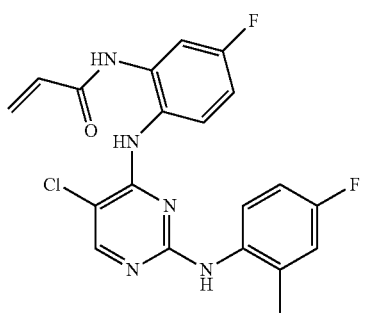 [SMILES: C=CC(=O)Nc1cc(F)ccc1Nc1nc(Nc2ccc(F)cc2C)ncc1Cl]
I-212

TABLE 3-continued
Exemplary Compounds of Formula I
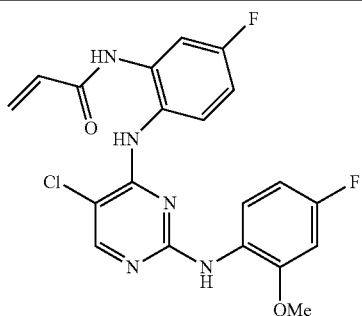
I-213
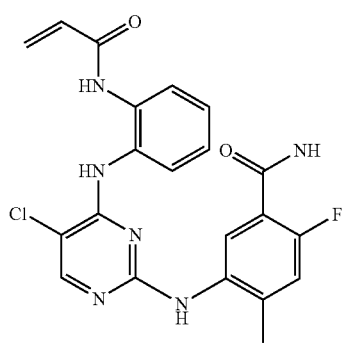 [SMILES: C=CC(=O)Nc1ccccc1Nc1nc(Nc2cc(C(N)=O)c(F)cc2C)ncc1Cl]
I-214
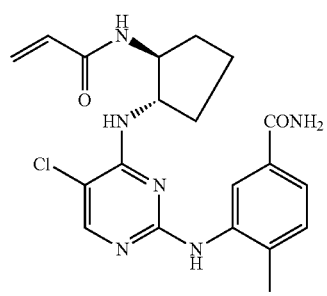 [SMILES: C=CC(=O)N[C@H]1CCC[C@@H]1Nc1nc(Nc2cc(C(N)=O)ccc2C)ncc1Cl]
I-215
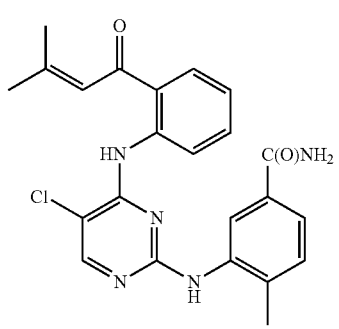
I-216
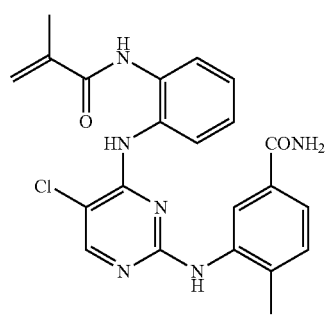 [SMILES: C=C(C)C(=O)Nc1ccccc1Nc1nc(Nc2cc(C(N)=O)ccc2C)ncc1Cl]
I-217

TABLE 3-continued
Exemplary Compounds of Formula I
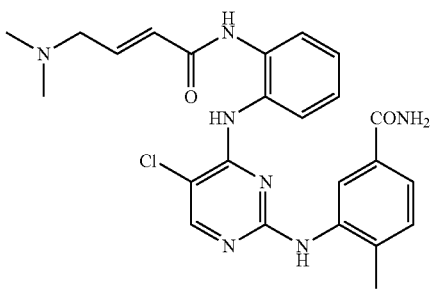 [SMILES: Cc1ccc(C(N)=O)cc1Nc1ncc(Cl)c(Nc2ccccc2NC(=O)/C=C/CN(C)C)n1]
I-218
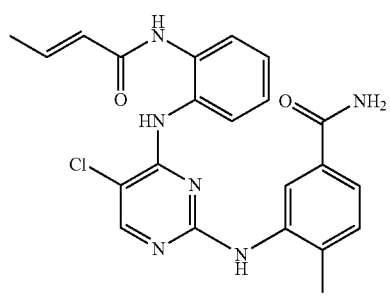 [SMILES: C/C=C/C(=O)Nc1ccccc1Nc1nc(Nc2cc(C(N)=O)ccc2C)ncc1Cl]
I-219
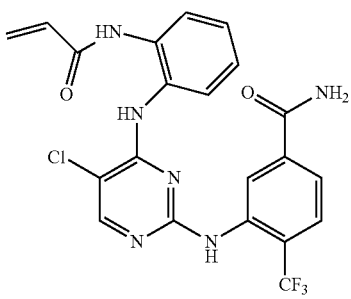 [SMILES: C=CC(=O)Nc1ccccc1Nc1nc(Nc2cc(C(N)=O)ccc2C(F)(F)F)ncc1Cl]
I-220
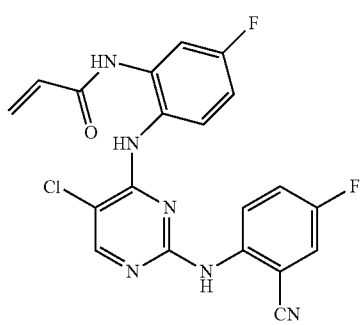 [SMILES: C=CC(=O)Nc1cc(F)ccc1Nc1nc(Nc2ccc(F)cc2C#N)ncc1Cl]
I-221
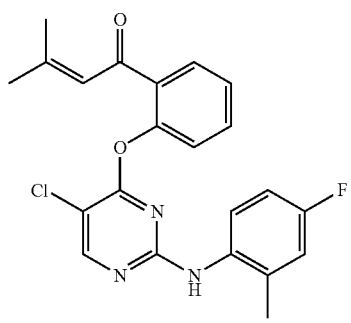 [SMILES: CC(C)=CC(=O)c1ccccc1Oc1nc(Nc2ccc(F)cc2C)ncc1Cl]
I-222

TABLE 3-continued
Exemplary Compounds of Formula I
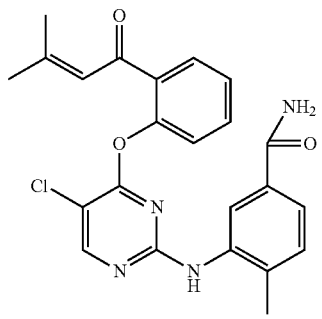 [SMILES: CC(C)=CC(=O)c1ccccc1Oc1nc(Nc2cc(C(N)=O)ccc2C)ncc1Cl]
I-223
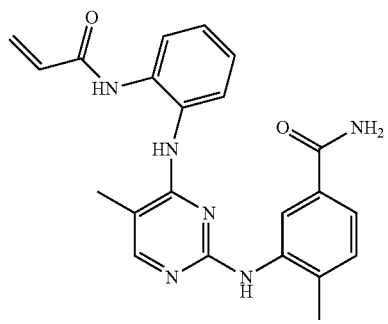 [SMILES: C=CC(=O)Nc1ccccc1Nc1nc(Nc2cc(C(N)=O)ccc2C)ncc1C]
I-224
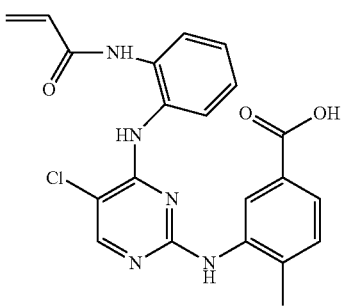 [SMILES: C=CC(=O)Nc1ccccc1Nc1nc(Nc2cc(C(=O)O)ccc2C)ncc1Cl]
I-225
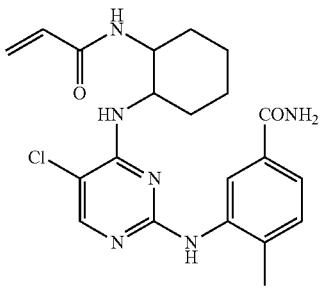 [SMILES: C=CC(=O)NC1CCCCC1Nc1nc(Nc2cc(C(N)=O)ccc2C)ncc1Cl]
I-226
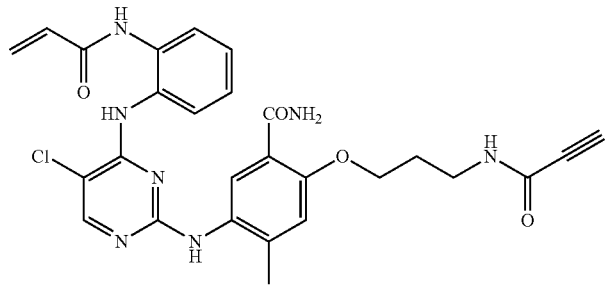 [SMILES: C#CC(=O)NCCCOc1cc(C)c(Nc2ncc(Cl)c(Nc3ccccc3NC(=O)C=C)n2)cc1C(N)=O]
I-227

TABLE 3-continued
Exemplary Compounds of Formula I
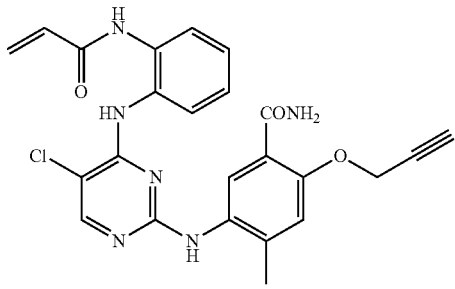 [SMILES: C#CCOc1cc(C)c(Nc2ncc(Cl)c(Nc3ccccc3NC(=O)C=C)n2)cc1C(N)=O]
I-228
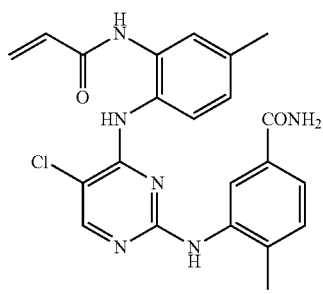 [SMILES: C=CC(=O)Nc1cc(C)ccc1Nc1nc(Nc2cc(C(N)=O)ccc2C)ncc1Cl]
I-229
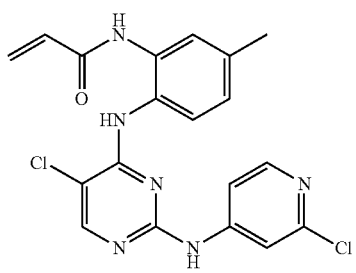 [SMILES: C=CC(=O)Nc1cc(C)ccc1Nc1nc(Nc2ccnc(Cl)c2)ncc1Cl]
I-230
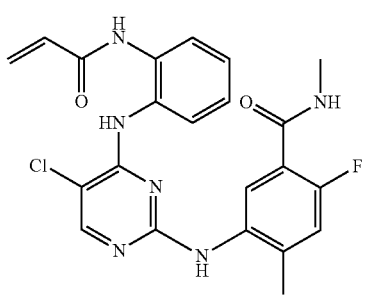 [SMILES: C=CC(=O)Nc1ccccc1Nc1nc(Nc2cc(C(=O)NC)c(F)cc2C)ncc1Cl]
I-231
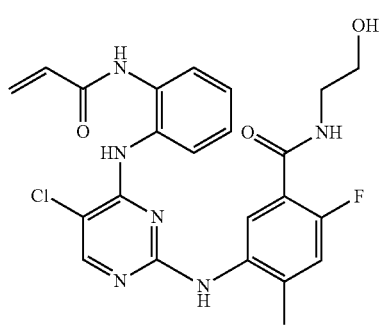 [SMILES: C=CC(=O)Nc1ccccc1Nc1nc(Nc2cc(C(=O)NCCO)c(F)cc2C)ncc1Cl]
I-232

TABLE 3-continued
Exemplary Compounds of Formula I
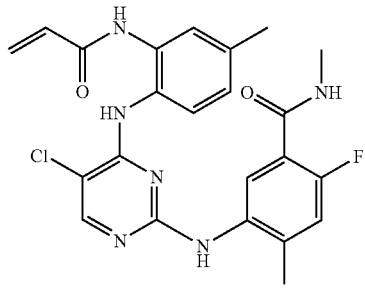 [SMILES: C=CC(=O)Nc1cc(C)ccc1Nc1nc(Nc2cc(C(=O)NC)c(F)cc2C)ncc1Cl]
I-233
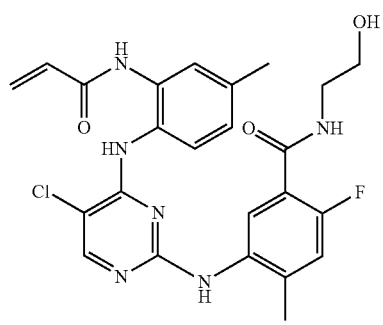 [SMILES: C=CC(=O)Nc1cc(C)ccc1Nc1nc(Nc2cc(C(=O)NCCO)c(F)cc2C)ncc1Cl]
I-234
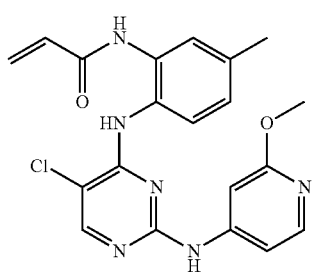 [SMILES: C=CC(=O)Nc1cc(C)ccc1Nc1nc(Nc2ccnc(OC)c2)ncc1Cl]
I-235
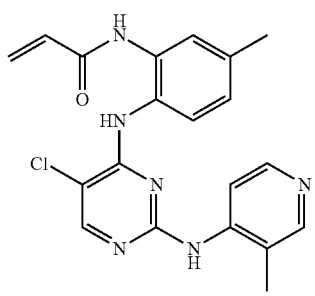 [SMILES: C=CC(=O)Nc1cc(C)ccc1Nc1nc(Nc2ccncc2C)ncc1Cl]
I-236
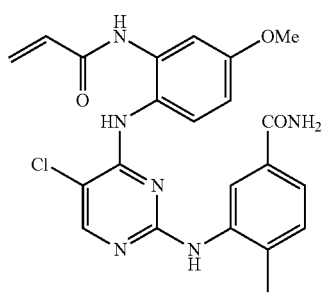 [SMILES: C=CC(=O)Nc1cc(OC)ccc1Nc1nc(Nc2cc(C(N)=O)ccc2C)ncc1Cl]
I-237

TABLE 3-continued
Exemplary Compounds of Formula I
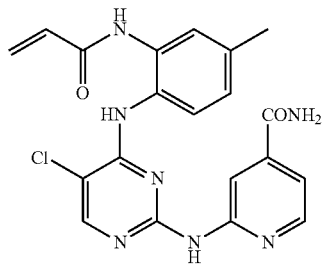 [SMILES: C=CC(=O)Nc1cc(C)ccc1Nc1nc(Nc2cc(C(N)=O)ccn2)ncc1Cl]
I-238
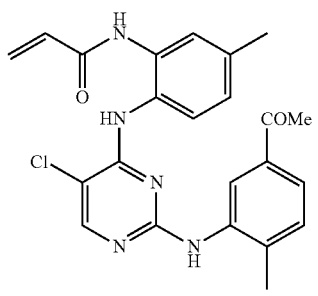
I-239
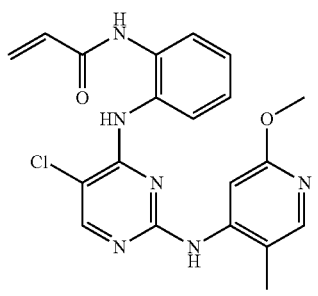 [SMILES: C=CC(=O)Nc1ccccc1Nc1nc(Nc2cc(OC)ncc2C)ncc1Cl]
I-240
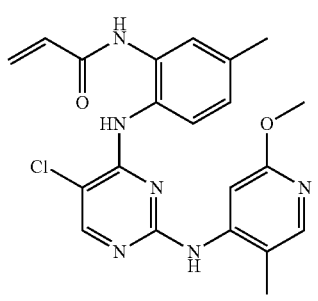 [SMILES: C=CC(=O)Nc1cc(C)ccc1Nc1nc(Nc2cc(OC)ncc2C)ncc1Cl]
I-241
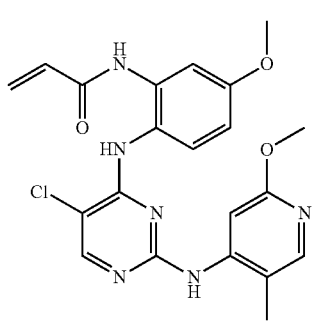 [SMILES: C=CC(=O)Nc1cc(OC)ccc1Nc1nc(Nc2cc(OC)ncc2C)ncc1Cl]
I-242

TABLE 3-continued
Exemplary Compounds of Formula I
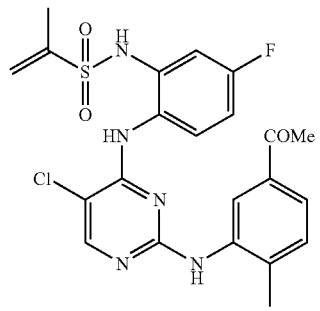
I-243
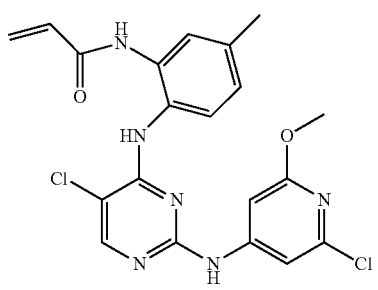 [SMILES: C=CC(=O)Nc1cc(C)ccc1Nc1nc(Nc2cc(Cl)nc(OC)c2)ncc1Cl]
I-244
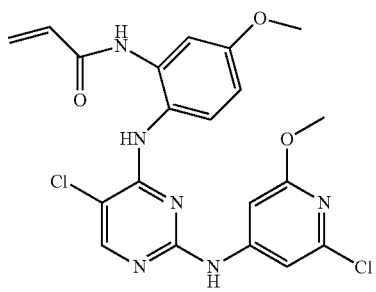 [SMILES: C=CC(=O)Nc1cc(OC)ccc1Nc1nc(Nc2cc(Cl)nc(OC)c2)ncc1Cl]
I-245
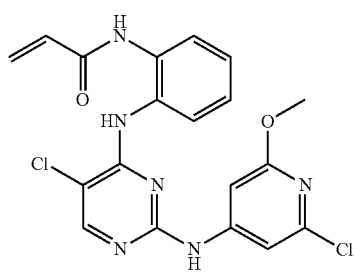 [SMILES: C=CC(=O)Nc1ccccc1Nc1nc(Nc2cc(Cl)nc(OC)c2)ncc1Cl]
I-246
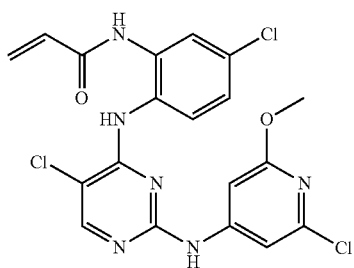 [SMILES: C=CC(=O)Nc1cc(Cl)ccc1Nc1nc(Nc2cc(Cl)nc(OC)c2)ncc1Cl]
I-247

US 9,980,964 B2
TABLE 3-continued
Exemplary Compounds of Formula I
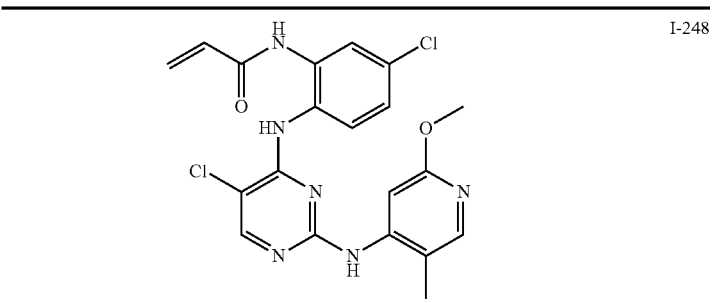 I-248
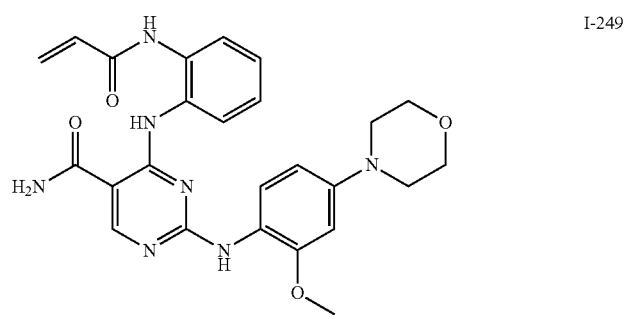 I-249
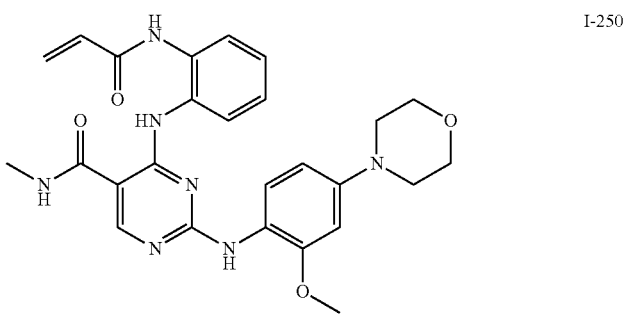 I-250
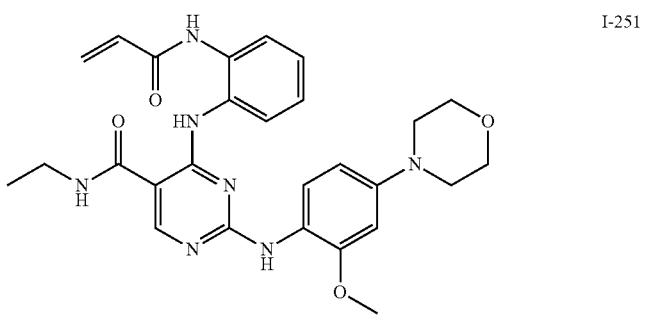 I-251
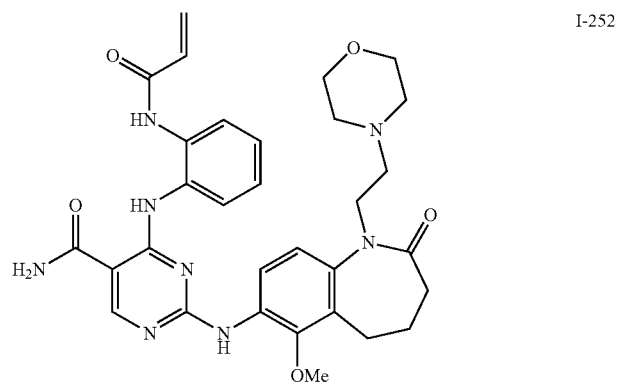 I-252

TABLE 3-continued
Exemplary Compounds of Formula I
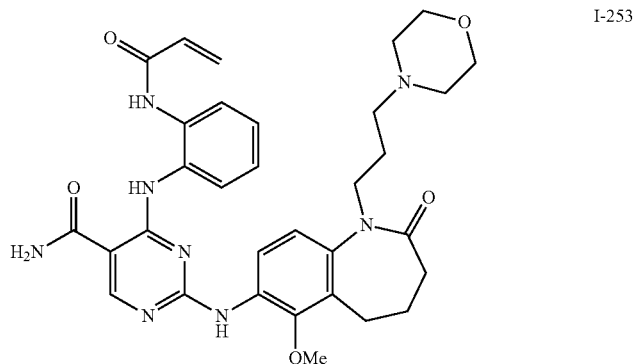
I-253
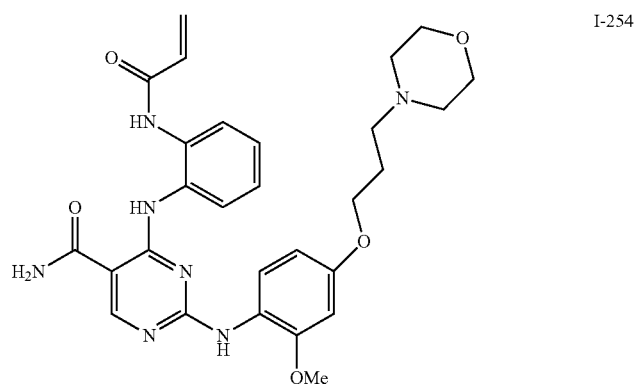
I-254
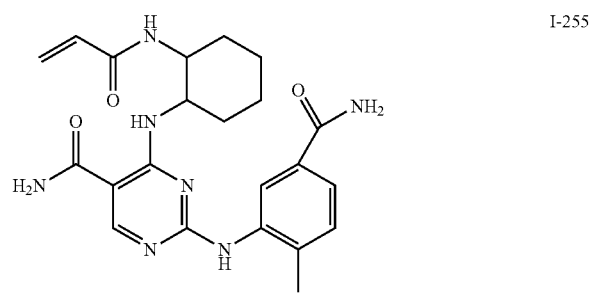
I-255
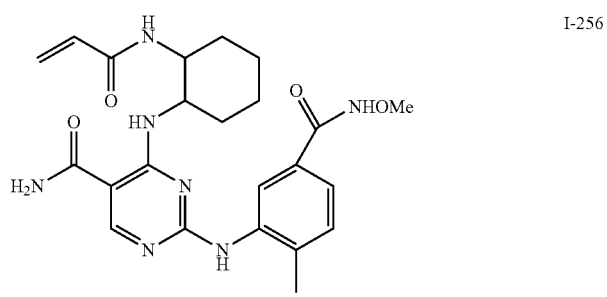
I-256

TABLE 3-continued
Exemplary Compounds of Formula I
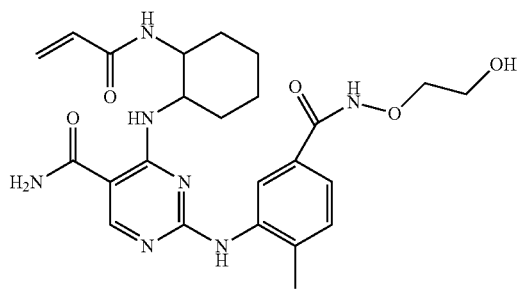 [SMILES: C=CC(=O)NC1CCCCC1Nc1nc(Nc2cc(C(=O)NOCCO)ccc2C)ncc1C(N)=O]
I-257
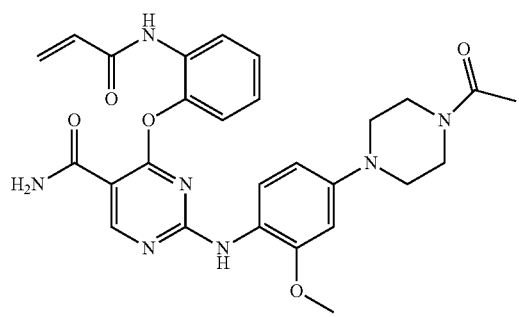 [SMILES: C=CC(=O)Nc1ccccc1Oc1nc(Nc2ccc(N3CCN(C(C)=O)CC3)cc2OC)ncc1C(N)=O]
I-258
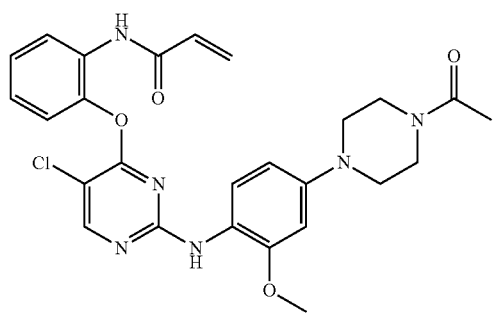 [SMILES: C=CC(=O)Nc1ccccc1Oc1nc(Nc2ccc(N3CCN(C(C)=O)CC3)cc2OC)ncc1Cl]
I-259
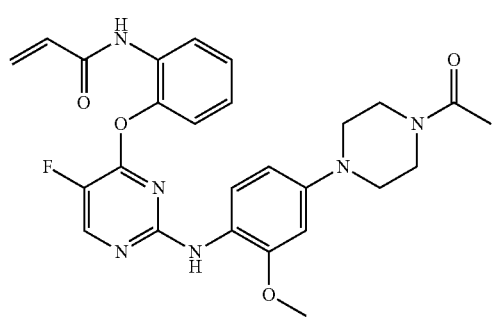 [SMILES: C=CC(=O)Nc1ccccc1Oc1nc(Nc2ccc(N3CCN(C(C)=O)CC3)cc2OC)ncc1F]
I-260
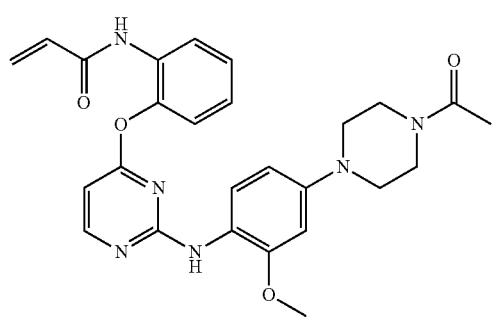 [SMILES: C=CC(=O)Nc1ccccc1Oc1ccnc(Nc2ccc(N3CCN(C(C)=O)CC3)cc2OC)n1]
I-261

TABLE 3-continued
Exemplary Compounds of Formula I
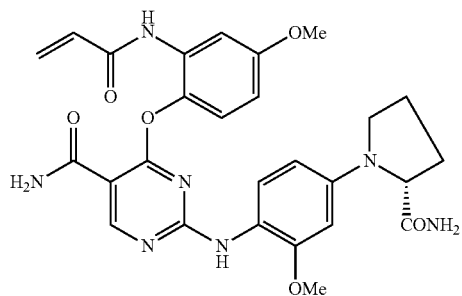 [SMILES: C=CC(=O)Nc1cc(OC)ccc1Oc1nc(Nc2ccc(N3CCC[C@@H]3C(N)=O)cc2OC)ncc1C(N)=O]
I-262
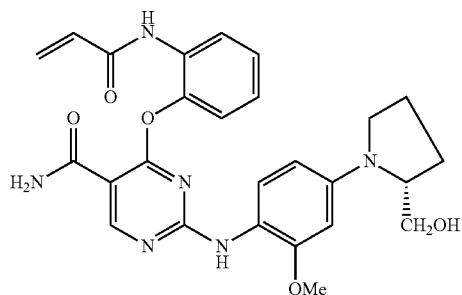
I-263
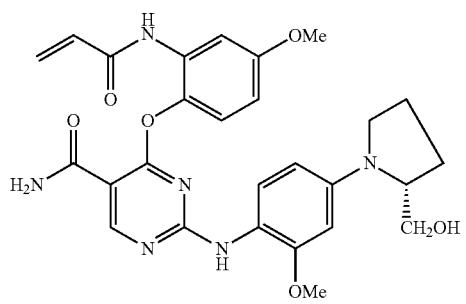
I-264
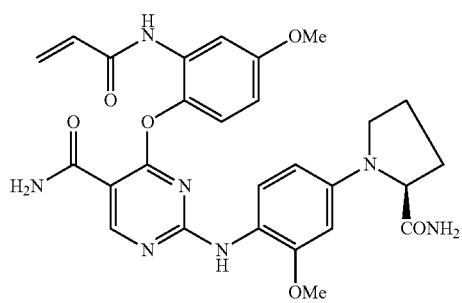 [SMILES: C=CC(=O)Nc1cc(OC)ccc1Oc1nc(Nc2ccc(N3CCC[C@H]3C(N)=O)cc2OC)ncc1C(N)=O]
I-265
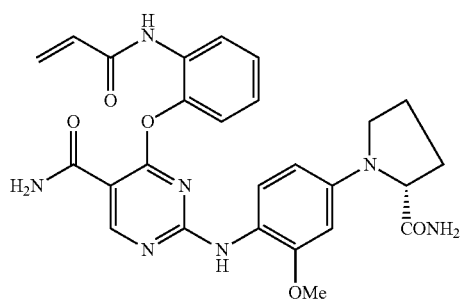 [SMILES: C=CC(=O)Nc1ccccc1Oc1nc(Nc2ccc(N3CCC[C@@H]3C(N)=O)cc2OC)ncc1C(N)=O]
I-266

TABLE 3-continued
Exemplary Compounds of Formula I
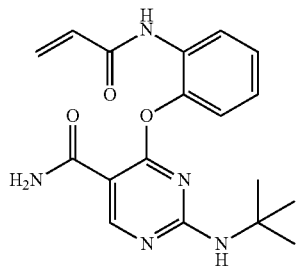 [SMILES: C=CC(=O)Nc1ccccc1Oc1nc(NC(C)(C)C)ncc1C(N)=O]  I-267
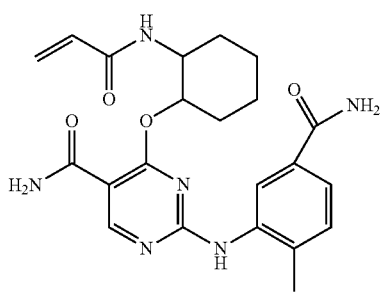 [SMILES: C=CC(=O)NC1CCCCC1Oc1nc(Nc2cc(C(N)=O)ccc2C)ncc1C(N)=O]  I-268
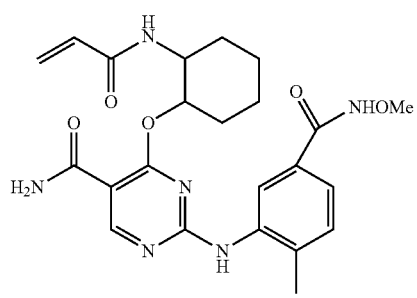  I-269
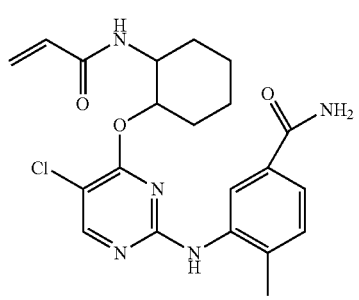 [SMILES: C=CC(=O)NC1CCCCC1Oc1nc(Nc2cc(C(N)=O)ccc2C)ncc1Cl]  I-270
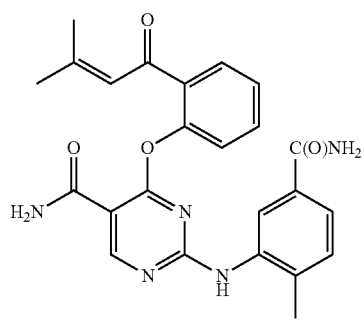  I-271

TABLE 3-continued
Exemplary Compounds of Formula I
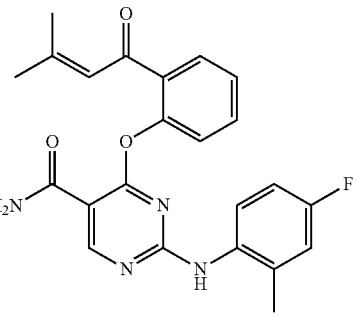
I-272
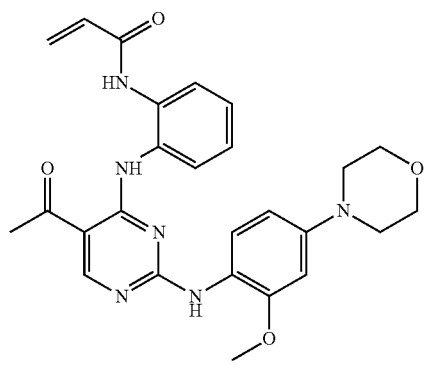 [SMILES: C=CC(=O)Nc1ccccc1Nc1nc(Nc2ccc(N3CCOCC3)cc2OC)ncc1C(C)=O]
I-273
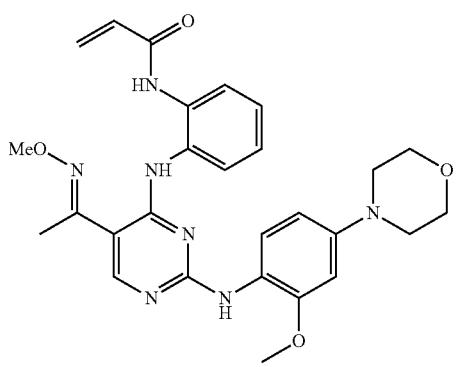 [SMILES: C=CC(=O)Nc1ccccc1Nc1nc(Nc2ccc(N3CCOCC3)cc2OC)ncc1/C(C)=N/OC]
I-274
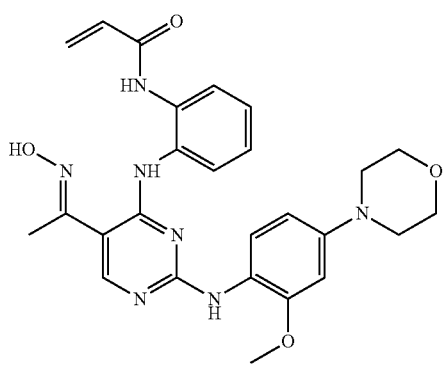 [SMILES: C=CC(=O)Nc1ccccc1Nc1nc(Nc2ccc(N3CCOCC3)cc2OC)ncc1/C(C)=N/O]
I-275

TABLE 3-continued
Exemplary Compounds of Formula I
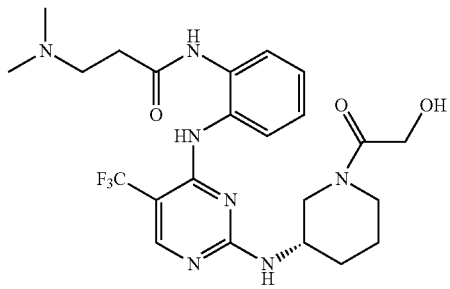 [SMILES: CN(C)CCC(=O)Nc1ccccc1Nc1nc(N[C@H]2CCCN(C(=O)CO)C2)ncc1C(F)(F)F]
I-276
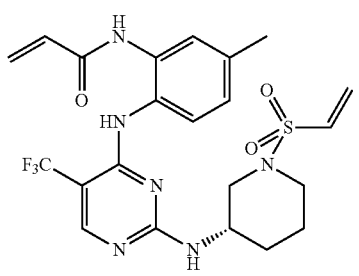 [SMILES: C=CC(=O)Nc1cc(C)ccc1Nc1nc(N[C@H]2CCCN(S(=O)(=O)C=C)C2)ncc1C(F)(F)F]
I-277
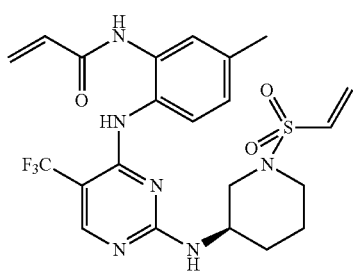 [SMILES: C=CC(=O)Nc1cc(C)ccc1Nc1nc(N[C@@H]2CCCN(S(=O)(=O)C=C)C2)ncc1C(F)(F)F]
I-278
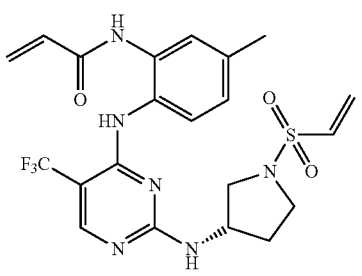
I-279
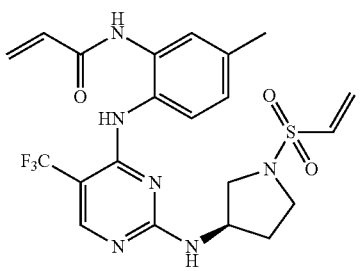 [SMILES: C=CC(=O)Nc1cc(C)ccc1Nc1nc(N[C@@H]2CCN(S(=O)(=O)C=C)C2)ncc1C(F)(F)F]
I-280

TABLE 3-continued
Exemplary Compounds of Formula I
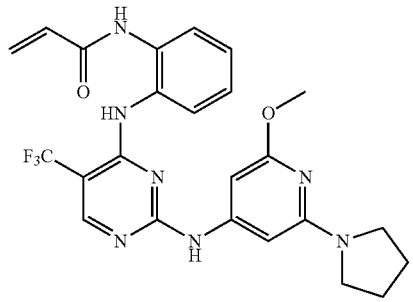 [SMILES: C=CC(=O)Nc1ccccc1Nc1nc(Nc2cc(OC)nc(N3CCCC3)c2)ncc1C(F)(F)F]
I-281
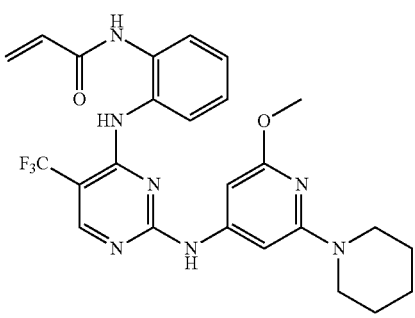 [SMILES: C=CC(=O)Nc1ccccc1Nc1nc(Nc2cc(OC)nc(N3CCCCC3)c2)ncc1C(F)(F)F]
I-282
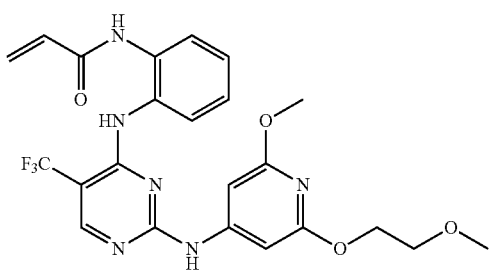 [SMILES: C=CC(=O)Nc1ccccc1Nc1nc(Nc2cc(OC)nc(OCCOC)c2)ncc1C(F)(F)F]
I-283
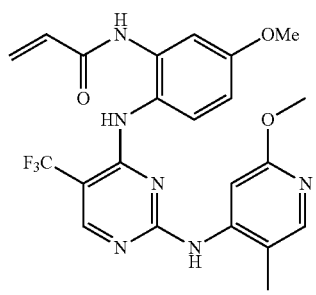 [SMILES: C=CC(=O)Nc1cc(OC)ccc1Nc1nc(Nc2cc(OC)ncc2C)ncc1C(F)(F)F]
I-284
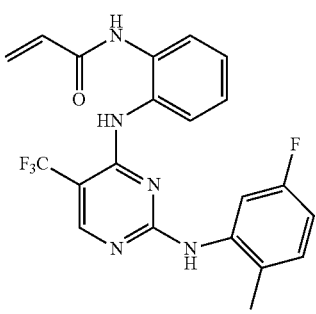 [SMILES: C=CC(=O)Nc1ccccc1Nc1nc(Nc2cc(F)ccc2C)ncc1C(F)(F)F]
I-285

TABLE 3-continued
Exemplary Compounds of Formula I
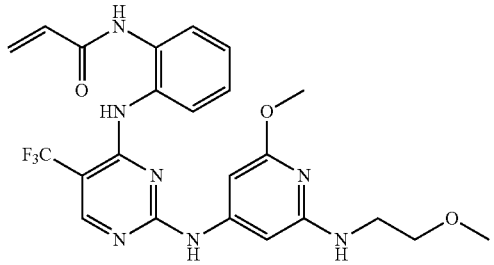
I-286
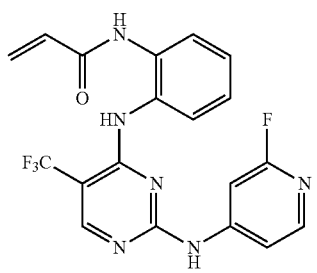 [SMILES: C=CC(=O)Nc1ccccc1Nc1nc(Nc2ccnc(F)c2)ncc1C(F)(F)F]
I-287
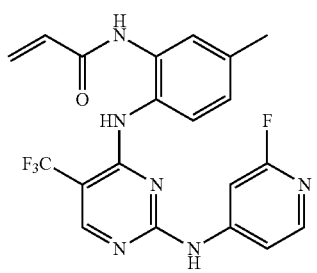
I-288
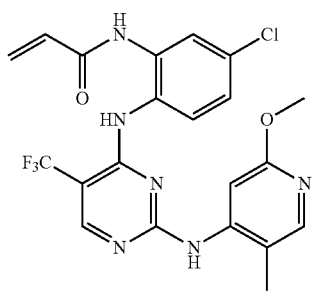
I-289
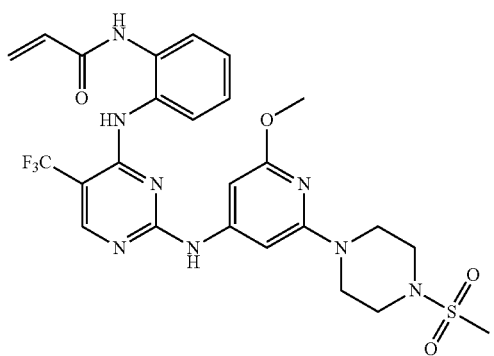 [SMILES: C=CC(=O)Nc1ccccc1Nc1nc(Nc2cc(OC)nc(N3CCN(S(C)(=O)=O)CC3)c2)ncc1C(F)(F)F]
I-290

TABLE 3-continued
Exemplary Compounds of Formula I
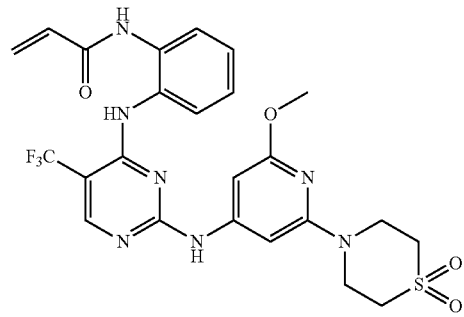 [SMILES: C=CC(=O)Nc1ccccc1Nc1nc(Nc2cc(OC)nc(N3CCS(=O)(=O)CC3)c2)ncc1C(F)(F)F]
I-291
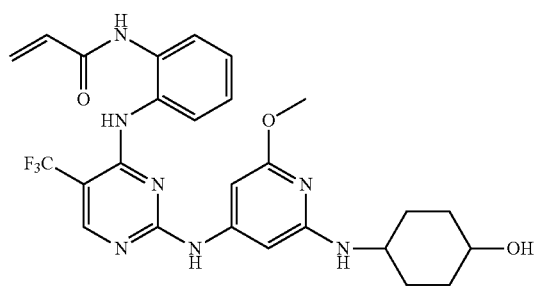 [SMILES: C=CC(=O)Nc1ccccc1Nc1nc(Nc2cc(NC3CCC(O)CC3)nc(OC)c2)ncc1C(F)(F)F]
I-292
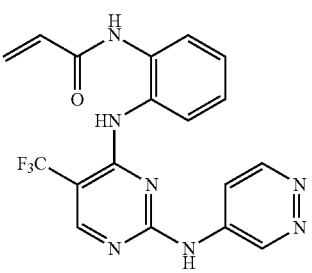 [SMILES: C=CC(=O)Nc1ccccc1Nc1nc(Nc2ccnnc2)ncc1C(F)(F)F]
I-293
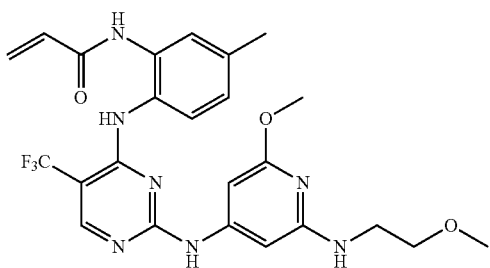 [SMILES: C=CC(=O)Nc1cc(C)ccc1Nc1nc(Nc2cc(NCCOC)nc(OC)c2)ncc1C(F)(F)F]
I-294
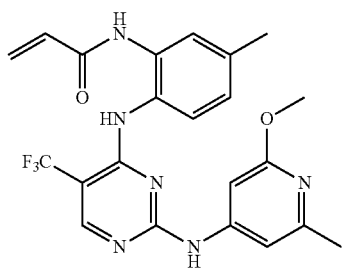 [SMILES: C=CC(=O)Nc1cc(C)ccc1Nc1nc(Nc2cc(C)nc(OC)c2)ncc1C(F)(F)F]
I-295

TABLE 3-continued
Exemplary Compounds of Formula I
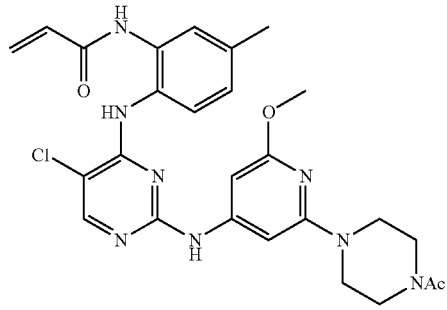
I-296
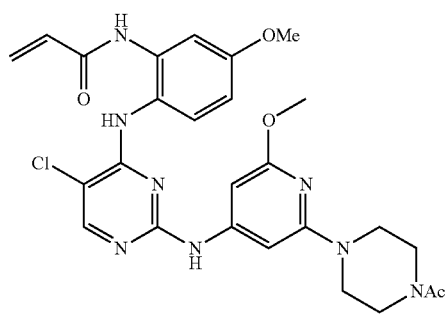
I-297
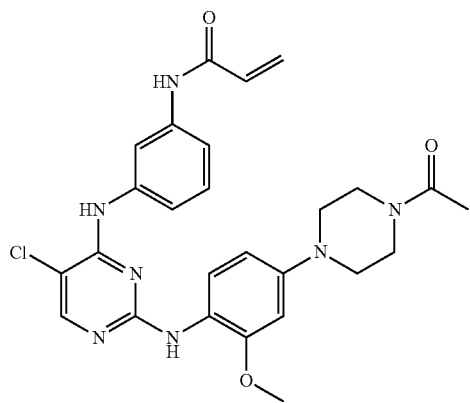 [SMILES: C=CC(=O)Nc1cccc(Nc2nc(Nc3ccc(N4CCN(C(C)=O)CC4)cc3OC)ncc2Cl)c1]
I-298
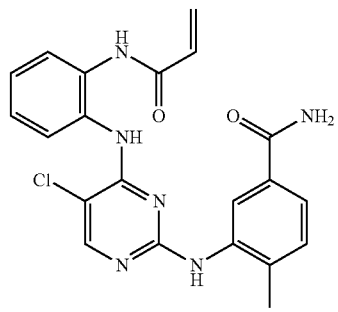 [SMILES: C=CC(=O)Nc1ccccc1Nc1nc(Nc2cc(C(N)=O)ccc2C)ncc1Cl]
I-319

TABLE 3-continued
Exemplary Compounds of Formula I
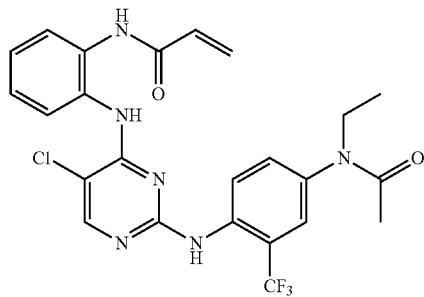 [SMILES: C=CC(=O)Nc1ccccc1Nc1nc(Nc2ccc(N(CC)C(C)=O)cc2C(F)(F)F)ncc1Cl]
I-320
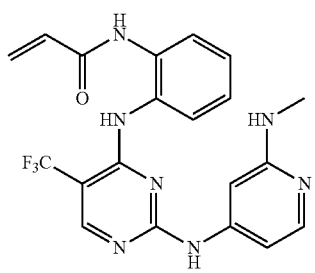 [SMILES: C=CC(=O)Nc1ccccc1Nc1nc(Nc2ccnc(NC)c2)ncc1C(F)(F)F]
I-321
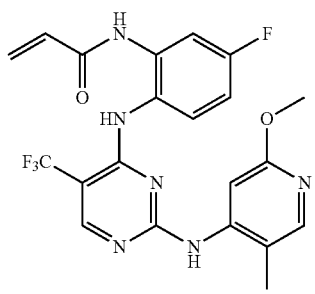
I-322
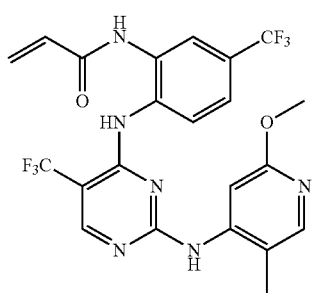 [SMILES: C=CC(=O)Nc1cc(C(F)(F)F)ccc1Nc1nc(Nc2cc(OC)ncc2C)ncc1C(F)(F)F]
I-323
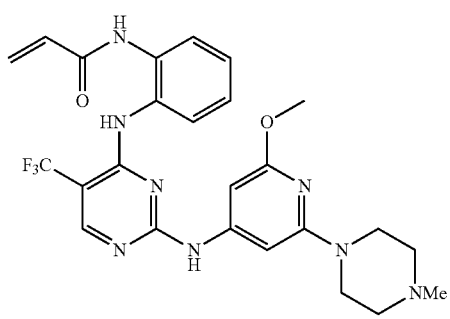 [SMILES: C=CC(=O)Nc1ccccc1Nc1nc(Nc2cc(OC)nc(N3CCN(C)CC3)c2)ncc1C(F)(F)F]
I-324

TABLE 3-continued
Exemplary Compounds of Formula I
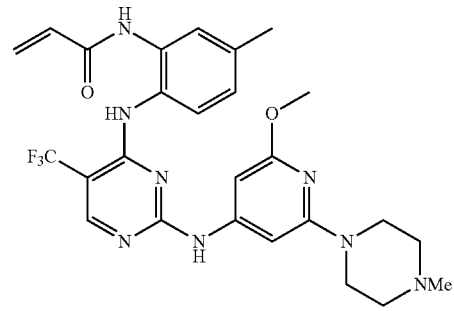 [SMILES: C=CC(=O)Nc1cc(C)ccc1Nc1nc(Nc2cc(OC)nc(N3CCN(C)CC3)c2)ncc1C(F)(F)F] I-325
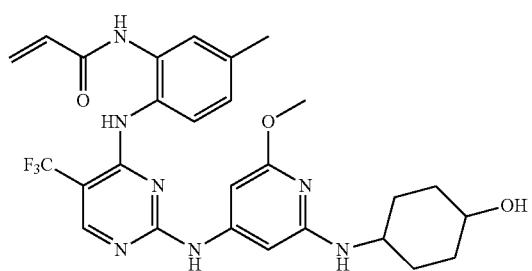 [SMILES: C=CC(=O)Nc1cc(C)ccc1Nc1nc(Nc2cc(NC3CCC(C)(O)CC3)nc(OC)c2)ncc1C(F)(F)F] I-326
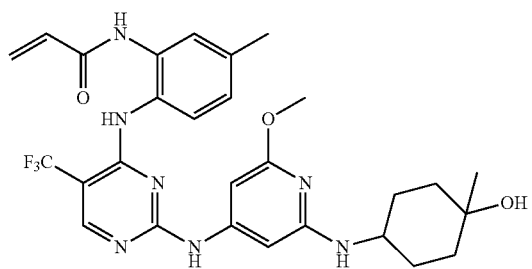 I-327
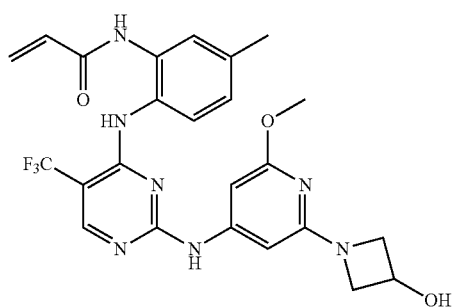 [SMILES: C=CC(=O)Nc1cc(C)ccc1Nc1nc(Nc2cc(OC)nc(N3CC(O)C3)c2)ncc1C(F)(F)F] I-328
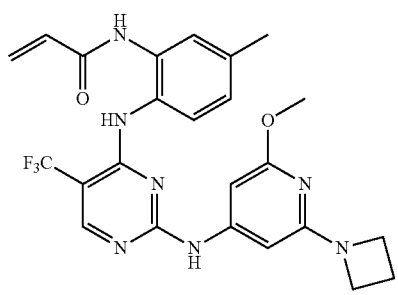 [SMILES: C=CC(=O)Nc1cc(C)ccc1Nc1nc(Nc2cc(OC)nc(N3CCC3)c2)ncc1C(F)(F)F] I-329

TABLE 3-continued
Exemplary Compounds of Formula I
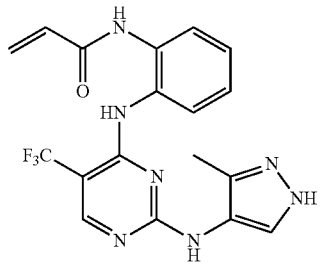 [SMILES: C=CC(=O)Nc1ccccc1Nc1nc(Nc2c[nH]nc2C)ncc1C(F)(F)F]
I-330
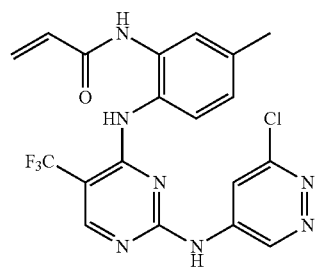 [SMILES: C=CC(=O)Nc1cc(C)ccc1Nc1nc(Nc2cnnc(Cl)c2)ncc1C(F)(F)F]
I-331
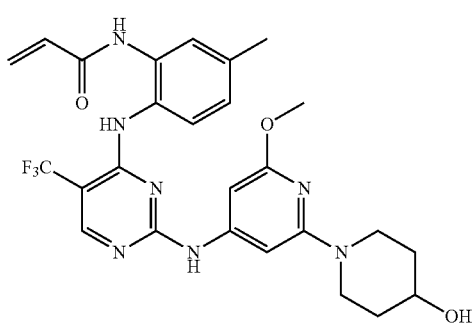 [SMILES: C=CC(=O)Nc1cc(C)ccc1Nc1nc(Nc2cc(OC)nc(N3CCC(O)CC3)c2)ncc1C(F)(F)F]
I-332
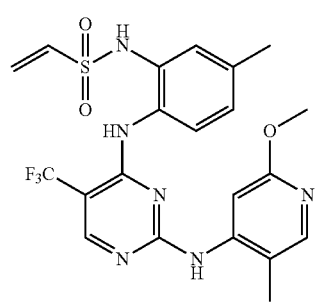 [SMILES: C=CS(=O)(=O)Nc1cc(C)ccc1Nc1nc(Nc2cc(OC)ncc2C)ncc1C(F)(F)F]
I-333
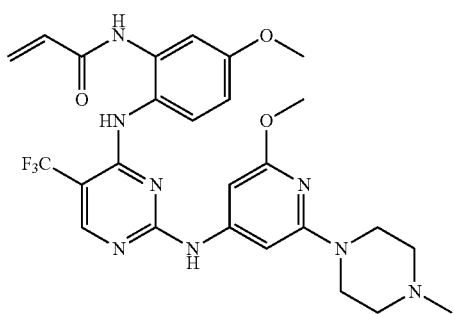 [SMILES: C=CC(=O)Nc1cc(OC)ccc1Nc1nc(Nc2cc(OC)nc(N3CCN(C)CC3)c2)ncc1C(F)(F)F]
I-334

TABLE 3-continued
Exemplary Compounds of Formula I
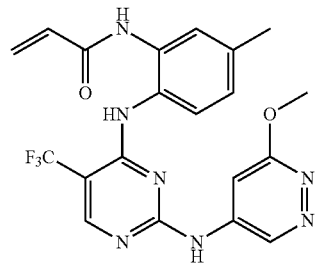 [SMILES: C=CC(=O)Nc1cc(C)ccc1Nc1nc(Nc2cnnc(OC)c2)ncc1C(F)(F)F]
I-335
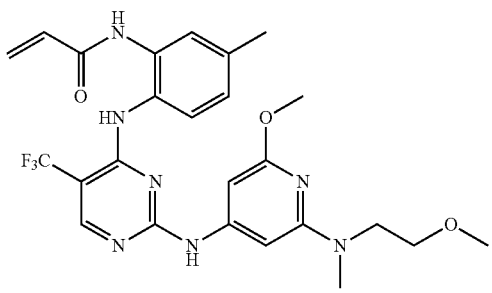 [SMILES: C=CC(=O)Nc1cc(C)ccc1Nc1nc(Nc2cc(OC)nc(N(C)CCOC)c2)ncc1C(F)(F)F]
I-336
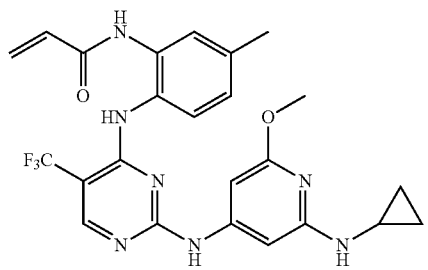 [SMILES: C=CC(=O)Nc1cc(C)ccc1Nc1nc(Nc2cc(NC3CC3)nc(OC)c2)ncc1C(F)(F)F]
I-337
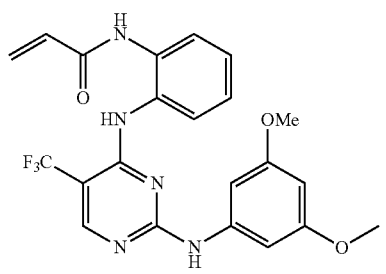 [SMILES: C=CC(=O)Nc1ccccc1Nc1nc(Nc2cc(OC)cc(OC)c2)ncc1C(F)(F)F]
I-338
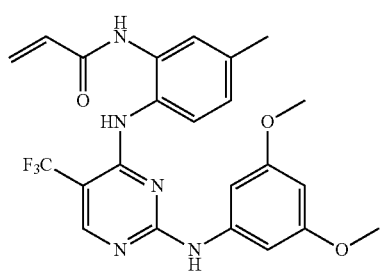 [SMILES: C=CC(=O)Nc1cc(C)ccc1Nc1nc(Nc2cc(OC)cc(OC)c2)ncc1C(F)(F)F]
I-339

TABLE 3-continued
Exemplary Compounds of Formula I
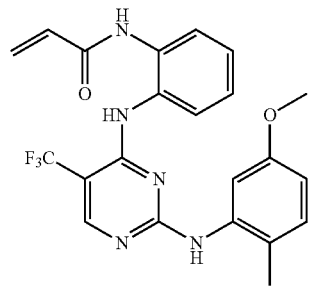 [SMILES: C=CC(=O)Nc1ccccc1Nc1nc(Nc2cc(OC)ccc2C)ncc1C(F)(F)F]
I-340
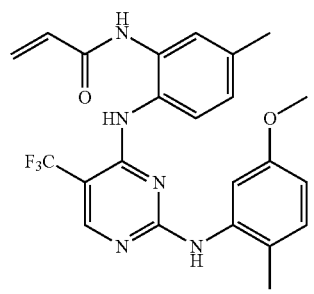 [SMILES: C=CC(=O)Nc1cc(C)ccc1Nc1nc(Nc2cc(OC)ccc2C)ncc1C(F)(F)F]
I-341
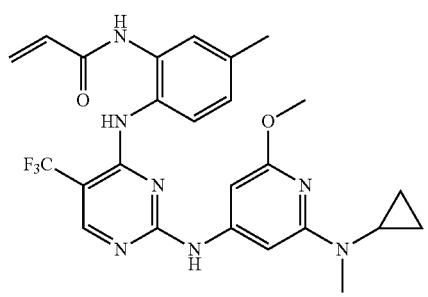 [SMILES: C=CC(=O)Nc1cc(C)ccc1Nc1nc(Nc2cc(OC)nc(N(C)C3CC3)c2)ncc1C(F)(F)F]
I-342
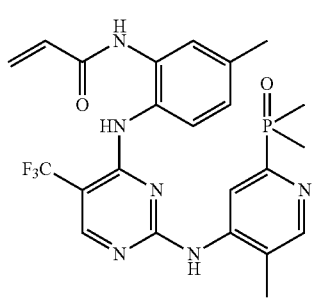 [SMILES: C=CC(=O)Nc1cc(C)ccc1Nc1nc(Nc2cc(P(C)(C)=O)ncc2C)ncc1C(F)(F)F]
I-343
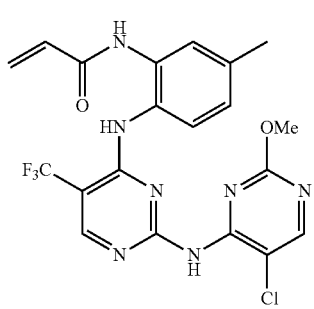
I-344

TABLE 3-continued
Exemplary Compounds of Formula I
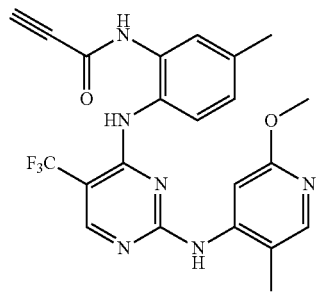 [SMILES: C#CC(=O)Nc1cc(C)ccc1Nc1nc(Nc2cc(OC)ncc2C)ncc1C(F)(F)F]
I-345
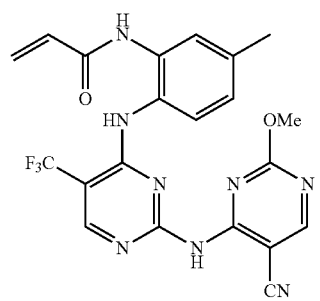 [SMILES: C=CC(=O)Nc1cc(C)ccc1Nc1nc(Nc2nc(OC)ncc2C#N)ncc1C(F)(F)F]
I-346
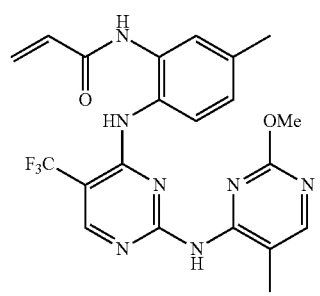 [SMILES: C=CC(=O)Nc1cc(C)ccc1Nc1nc(Nc2nc(OC)ncc2C)ncc1C(F)(F)F]
I-347
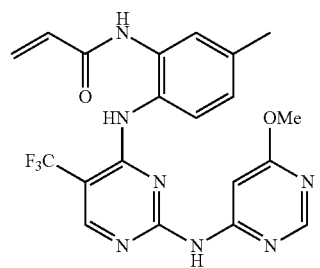 [SMILES: C=CC(=O)Nc1cc(C)ccc1Nc1nc(Nc2cc(OC)ncn2)ncc1C(F)(F)F]
I-348
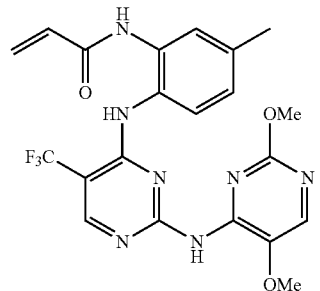 [SMILES: C=CC(=O)Nc1cc(C)ccc1Nc1nc(Nc2nc(OC)ncc2OC)ncc1C(F)(F)F]
I-349

TABLE 3-continued
Exemplary Compounds of Formula I
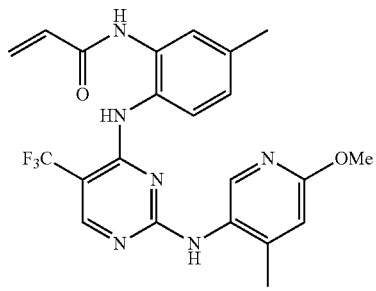 [SMILES: C=CC(=O)Nc1cc(C)ccc1Nc1nc(Nc2cnc(OC)cc2C)ncc1C(F)(F)F]
I-350
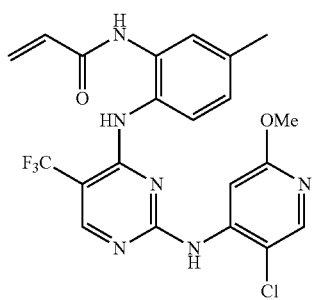 [SMILES: C=CC(=O)Nc1cc(C)ccc1Nc1nc(Nc2cc(OC)ncc2Cl)ncc1C(F)(F)F]
I-351
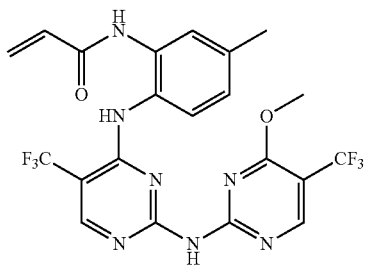 [SMILES: C=CC(=O)Nc1cc(C)ccc1Nc1nc(Nc2ncc(C(F)(F)F)c(OC)n2)ncc1C(F)(F)F]
I-354
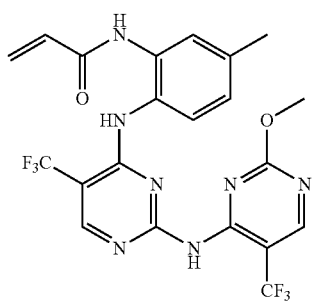 [SMILES: C=CC(=O)Nc1cc(C)ccc1Nc1nc(Nc2nc(OC)ncc2C(F)(F)F)ncc1C(F)(F)F]
I-355
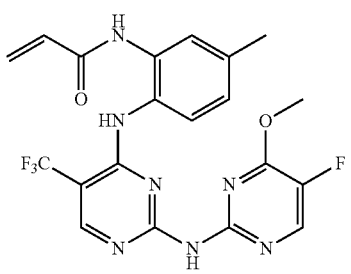 [SMILES: C=CC(=O)Nc1cc(C)ccc1Nc1nc(Nc2ncc(F)c(OC)n2)ncc1C(F)(F)F]
I-356

TABLE 3-continued
Exemplary Compounds of Formula I
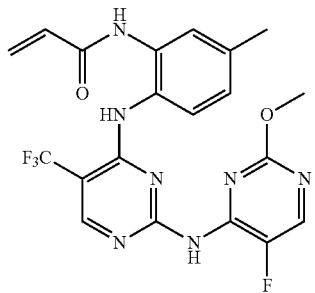 [SMILES: C=CC(=O)Nc1cc(C)ccc1Nc1nc(Nc2nc(OC)ncc2F)ncc1C(F)(F)F]
I-357
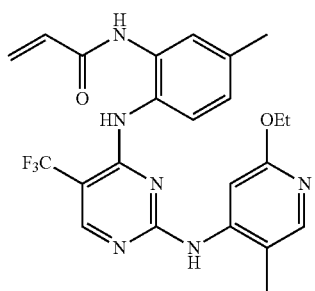
I-358
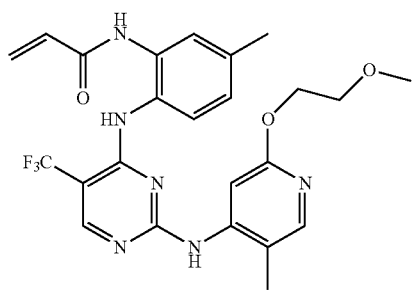 [SMILES: C=CC(=O)Nc1cc(C)ccc1Nc1nc(Nc2cc(OCCOC)ncc2C)ncc1C(F)(F)F]
I-359
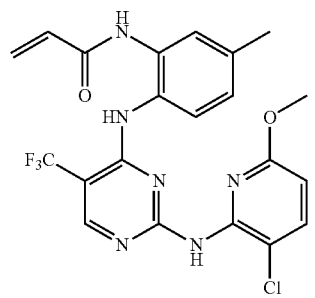 [SMILES: C=CC(=O)Nc1cc(C)ccc1Nc1nc(Nc2nc(OC)ccc2Cl)ncc1C(F)(F)F]
I-360
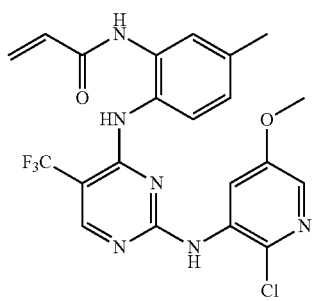 [SMILES: C=CC(=O)Nc1cc(C)ccc1Nc1nc(Nc2cc(OC)cnc2Cl)ncc1C(F)(F)F]
I-361

TABLE 3-continued
Exemplary Compounds of Formula I
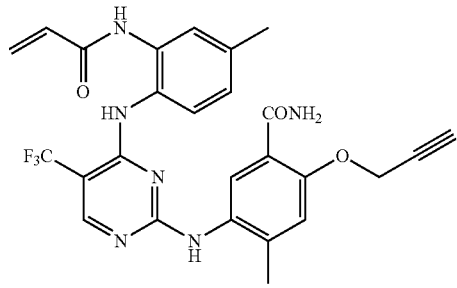 [SMILES: C#CCOc1cc(C)c(Nc2ncc(C(F)(F)F)c(Nc3ccc(C)cc3NC(=O)C=C)n2)cc1C(N)=O]
I-362
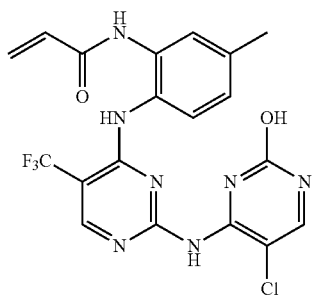 [SMILES: C=CC(=O)Nc1cc(C)ccc1Nc1nc(Nc2nc(O)ncc2Cl)ncc1C(F)(F)F]
I-363
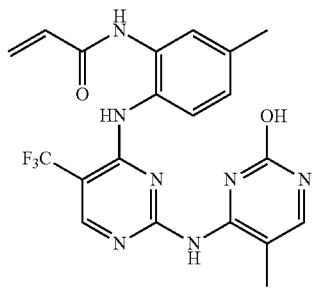 [SMILES: C=CC(=O)Nc1cc(C)ccc1Nc1nc(Nc2nc(O)ncc2C)ncc1C(F)(F)F]
I-364
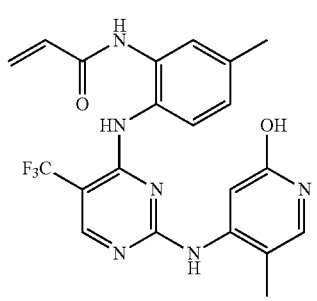 [SMILES: C=CC(=O)Nc1cc(C)ccc1Nc1nc(Nc2cc(O)ncc2C)ncc1C(F)(F)F]
I-365
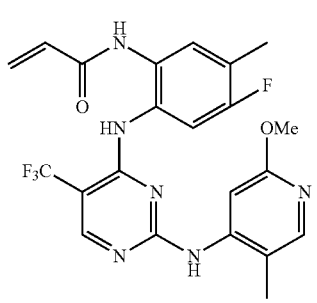 [SMILES: C=CC(=O)Nc1cc(C)c(F)cc1Nc1nc(Nc2cc(OC)ncc2C)ncc1C(F)(F)F]
I-366

TABLE 3-continued
Exemplary Compounds of Formula I
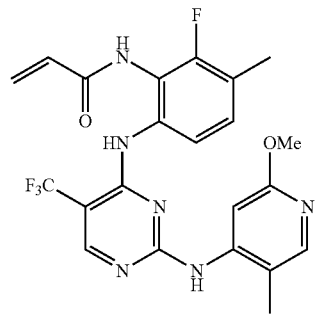 [SMILES: C=CC(=O)Nc1c(Nc2nc(Nc3cc(OC)ncc3C)ncc2C(F)(F)F)ccc(C)c1F]
I-367
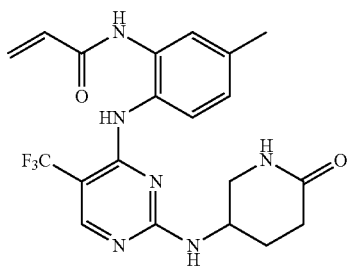 [SMILES: C=CC(=O)Nc1cc(C)ccc1Nc1nc(NC2CCC(=O)NC2)ncc1C(F)(F)F]
I-368
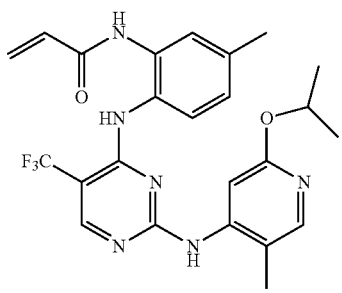 [SMILES: C=CC(=O)Nc1cc(C)ccc1Nc1nc(Nc2cc(OC(C)C)ncc2C)ncc1C(F)(F)F]
I-369
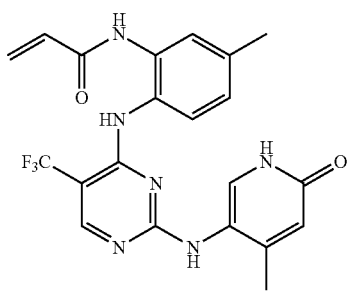 [SMILES: C=CC(=O)Nc1cc(C)ccc1Nc1nc(Nc2c[nH]c(=O)cc2C)ncc1C(F)(F)F]
I-370
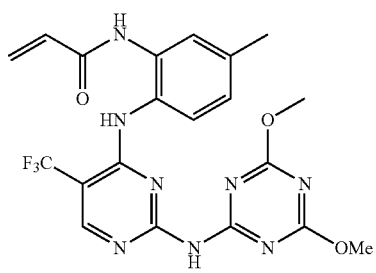 [SMILES: C=CC(=O)Nc1cc(C)ccc1Nc1nc(Nc2nc(OC)nc(OC)n2)ncc1C(F)(F)F]
I-371

TABLE 3-continued
Exemplary Compounds of Formula I
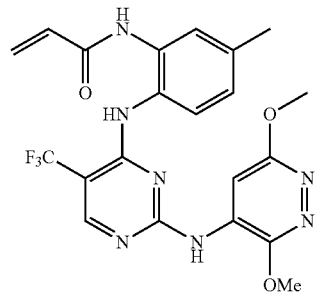 [SMILES: C=CC(=O)Nc1cc(C)ccc1Nc1nc(Nc2cc(OC)nnc2OC)ncc1C(F)(F)F]
I-372
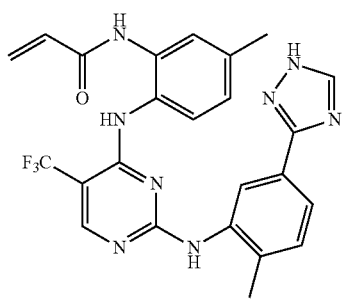 [SMILES: C=CC(=O)Nc1cc(C)ccc1Nc1nc(Nc2cc(-c3nc[nH]n3)ccc2C)ncc1C(F)(F)F]
I-373
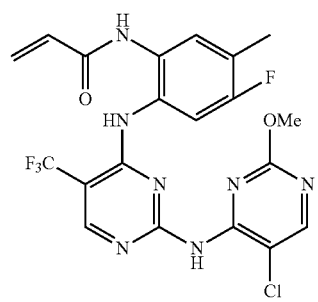 [SMILES: C=CC(=O)Nc1cc(C)c(F)cc1Nc1nc(Nc2nc(OC)ncc2Cl)ncc1C(F)(F)F]
I-374
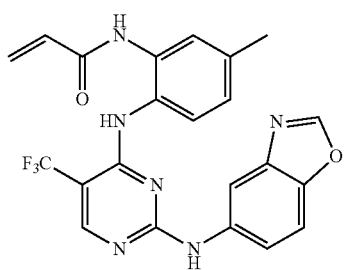 [SMILES: C=CC(=O)Nc1cc(C)ccc1Nc1nc(Nc2ccc3ocnc3c2)ncc1C(F)(F)F]
I-375
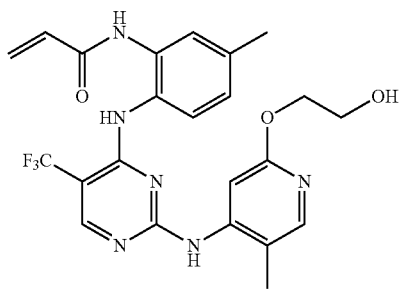 [SMILES: C=CC(=O)Nc1cc(C)ccc1Nc1nc(Nc2cc(OCCO)ncc2C)ncc1C(F)(F)F]
I-376

TABLE 3-continued
Exemplary Compounds of Formula I
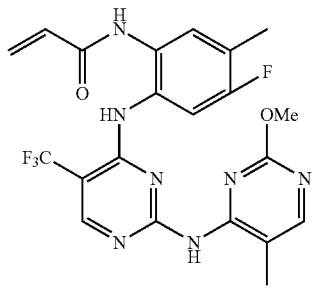
I-377
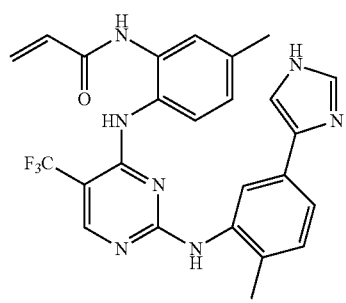 [SMILES: C=CC(=O)Nc1cc(C)ccc1Nc1nc(Nc2cc(-c3c[nH]cn3)ccc2C)ncc1C(F)(F)F]
I-378
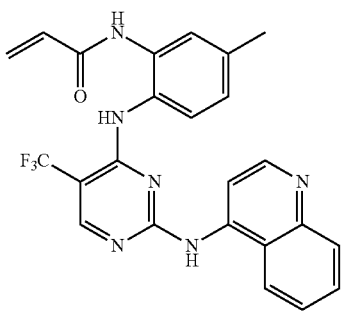 [SMILES: C=CC(=O)Nc1cc(C)ccc1Nc1nc(Nc2ccnc3ccccc23)ncc1C(F)(F)F]
I-379
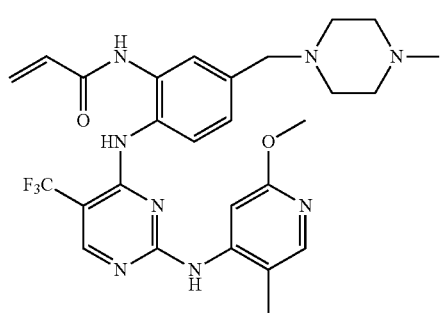 [SMILES: C=CC(=O)Nc1cc(CN2CCN(C)CC2)ccc1Nc1nc(Nc2cc(OC)ncc2C)ncc1C(F)(F)F]
I-380
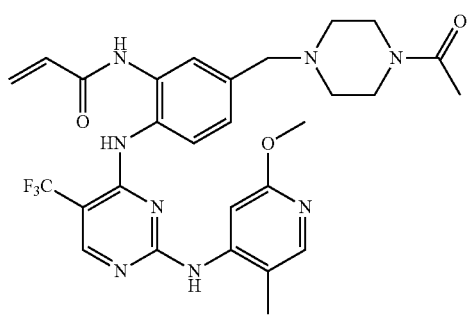 [SMILES: C=CC(=O)Nc1cc(CN2CCN(C(C)=O)CC2)ccc1Nc1nc(Nc2cc(OC)ncc2C)ncc1C(F)(F)F]
I-381

TABLE 3-continued
Exemplary Compounds of Formula I
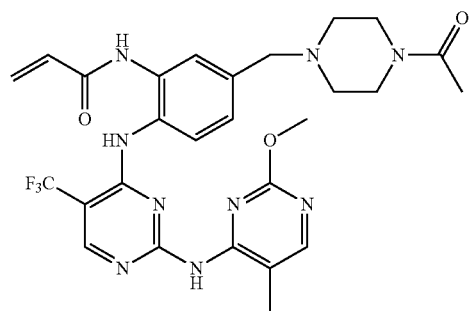 [SMILES: C=CC(=O)Nc1cc(CN2CCN(C(C)=O)CC2)ccc1Nc1nc(Nc2nc(OC)ncc2C)ncc1C(F)(F)F]
I-382
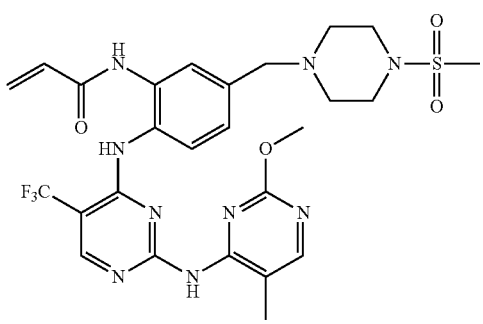 [SMILES: C=CC(=O)Nc1cc(CN2CCN(S(C)(=O)=O)CC2)ccc1Nc1nc(Nc2nc(OC)ncc2C)ncc1C(F)(F)F]
I-383
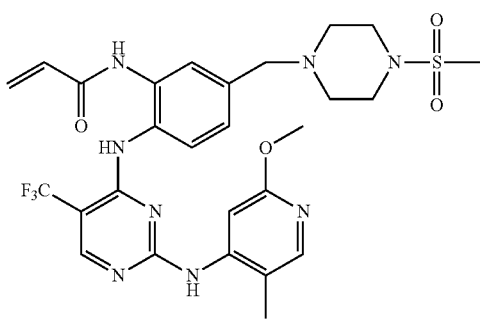 [SMILES: C=CC(=O)Nc1cc(CN2CCN(S(C)(=O)=O)CC2)ccc1Nc1nc(Nc2cc(OC)ncc2C)ncc1C(F)(F)F]
I-384
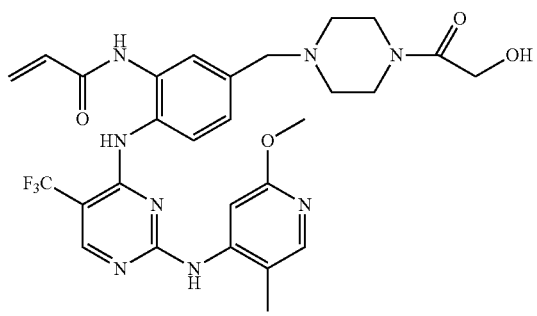
I-385
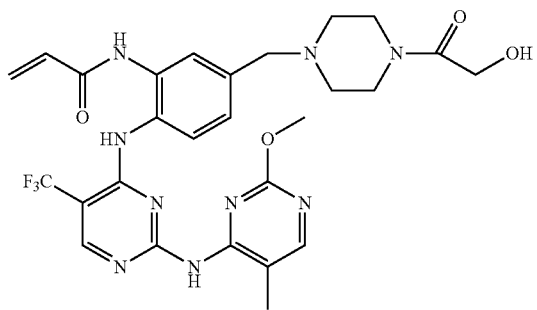 [SMILES: C=CC(=O)Nc1cc(CN2CCN(C(=O)CO)CC2)ccc1Nc1nc(Nc2nc(OC)ncc2C)ncc1C(F)(F)F]
I-386

TABLE 3-continued
Exemplary Compounds of Formula I
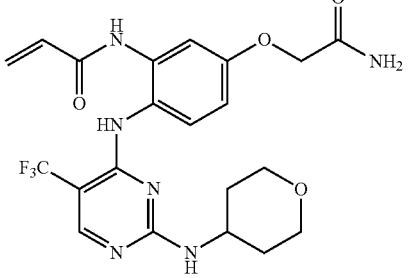 I-387
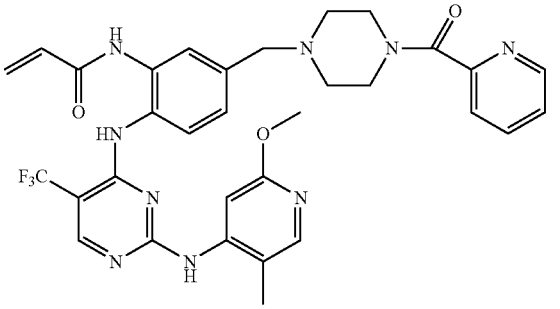 [SMILES: C=CC(=O)Nc1cc(CN2CCN(C(=O)c3ccccn3)CC2)ccc1Nc1nc(Nc2cc(OC)ncc2C)ncc1C(F)(F)F] I-388
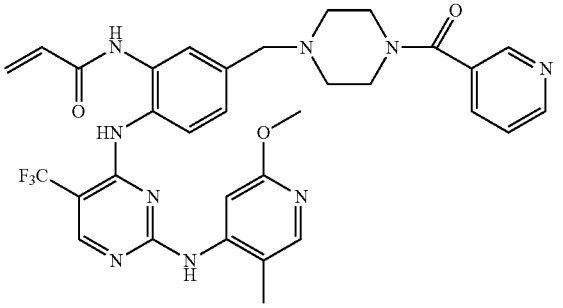 [SMILES: C=CC(=O)Nc1cc(CN2CCN(C(=O)c3cccnc3)CC2)ccc1Nc1nc(Nc2cc(OC)ncc2C)ncc1C(F)(F)F] I-389
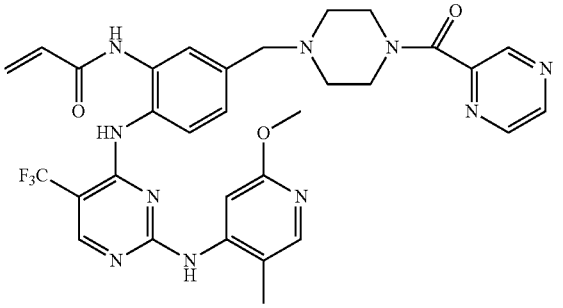 [SMILES: C=CC(=O)Nc1cc(CN2CCN(C(=O)c3cnccn3)CC2)ccc1Nc1nc(Nc2cc(OC)ncc2C)ncc1C(F)(F)F] I-390
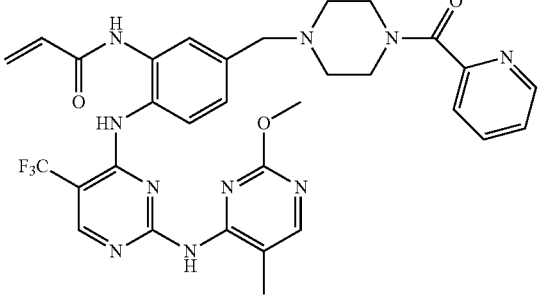 I-391

TABLE 3-continued
Exemplary Compounds of Formula I
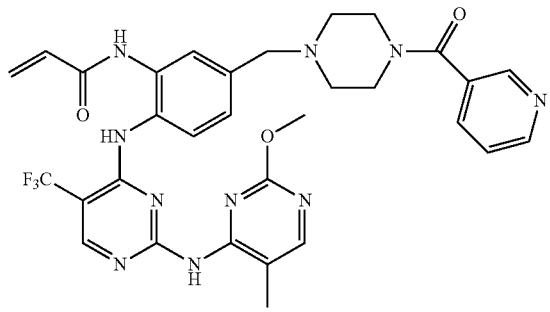 [SMILES: C=CC(=O)Nc1cc(CN2CCN(C(=O)c3cccnc3)CC2)ccc1Nc1nc(Nc2nc(OC)ncc2C)ncc1C(F)(F)F]
I-392
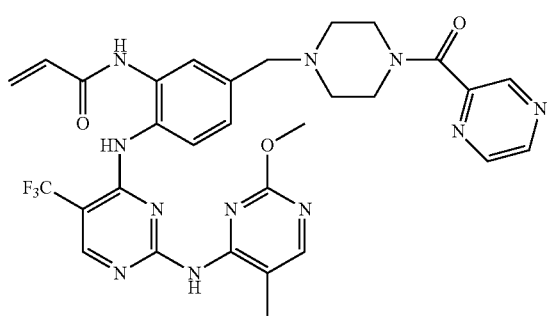
I-393
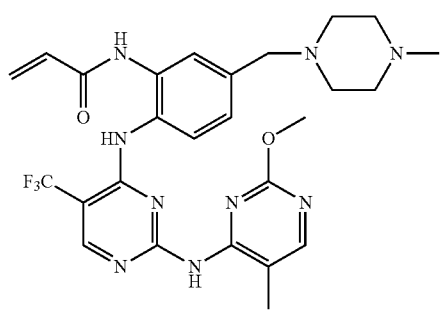 [SMILES: C=CC(=O)Nc1cc(CN2CCN(C)CC2)ccc1Nc1nc(Nc2nc(OC)ncc2C)ncc1C(F)(F)F]
I-394
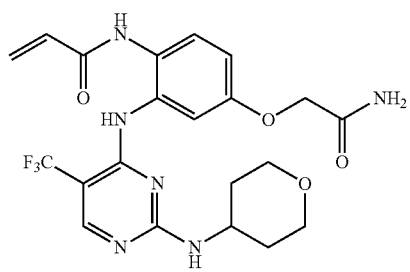 [SMILES: C=CC(=O)Nc1ccc(OCC(N)=O)cc1Nc1nc(NC2CCOCC2)ncc1C(F)(F)F]
I-395
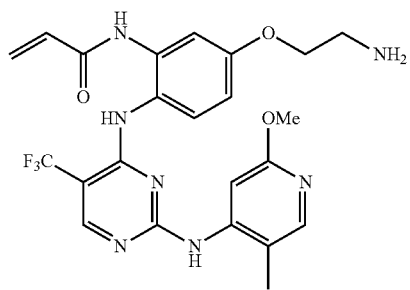 [SMILES: C=CC(=O)Nc1cc(OCCN)ccc1Nc1nc(Nc2cc(OC)ncc2C)ncc1C(F)(F)F]
I-396

TABLE 3-continued
Exemplary Compounds of Formula I
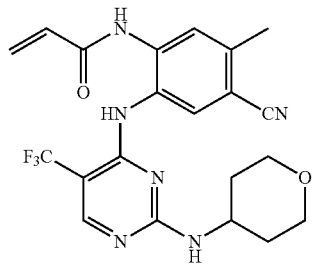 [SMILES: C=CC(=O)Nc1cc(C)c(C#N)cc1Nc1nc(NC2CCOCC2)ncc1C(F)(F)F]
I-397
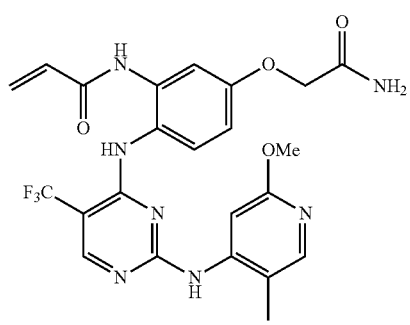 [SMILES: C=CC(=O)Nc1cc(OCC(N)=O)ccc1Nc1nc(Nc2cc(OC)ncc2C)ncc1C(F)(F)F]
I-398
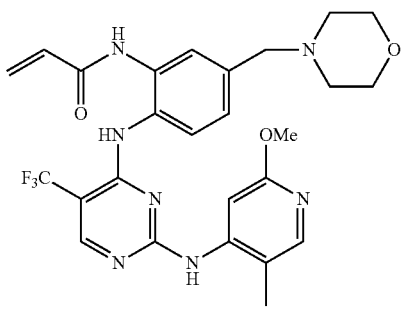 [SMILES: C=CC(=O)Nc1cc(CN2CCOCC2)ccc1Nc1nc(Nc2cc(OC)ncc2C)ncc1C(F)(F)F]
I-399
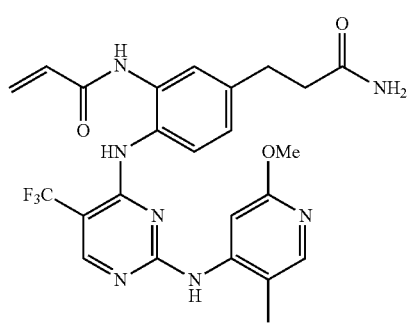 [SMILES: C=CC(=O)Nc1cc(CCC(N)=O)ccc1Nc1nc(Nc2cc(OC)ncc2C)ncc1C(F)(F)F]
I-400
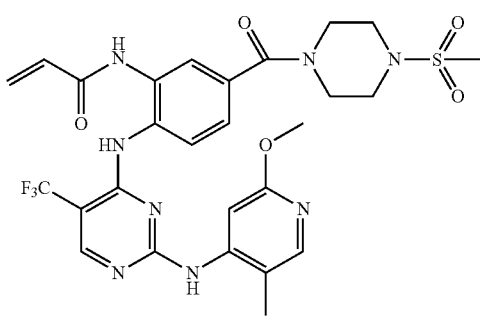 [SMILES: C=CC(=O)Nc1cc(C(=O)N2CCN(S(C)(=O)=O)CC2)ccc1Nc1nc(Nc2cc(OC)ncc2C)ncc1C(F)(F)F]
I-401

TABLE 3-continued
Exemplary Compounds of Formula I
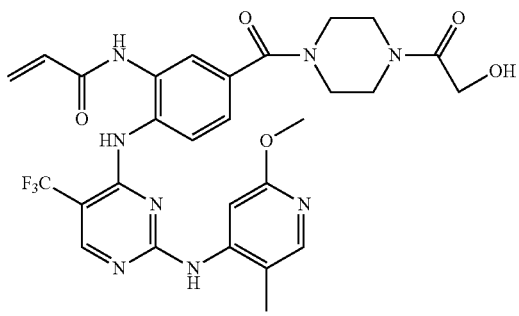 [SMILES: C=CC(=O)Nc1cc(C(=O)N2CCN(C(=O)CO)CC2)ccc1Nc1nc(Nc2cc(OC)ncc2C)ncc1C(F)(F)F]
I-402
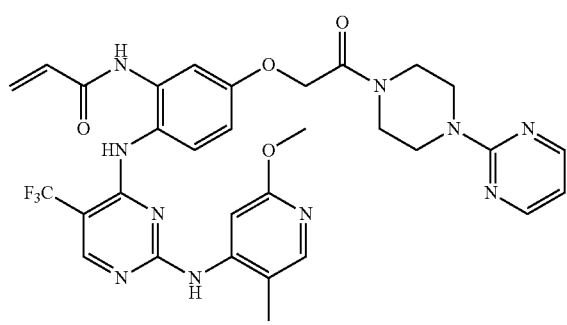 [SMILES: C=CC(=O)Nc1cc(OCC(=O)N2CCN(c3ncccn3)CC2)ccc1Nc1nc(Nc2cc(OC)ncc2C)ncc1C(F)(F)F]
I-403
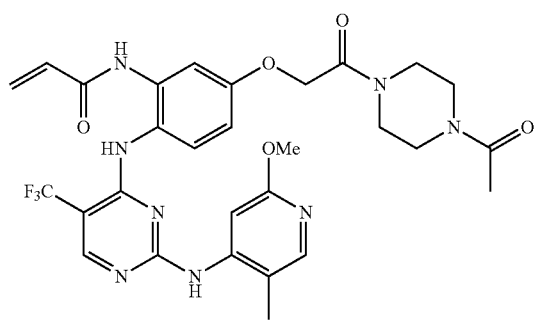 [SMILES: C=CC(=O)Nc1cc(OCC(=O)N2CCN(C(C)=O)CC2)ccc1Nc1nc(Nc2cc(OC)ncc2C)ncc1C(F)(F)F]
I-404
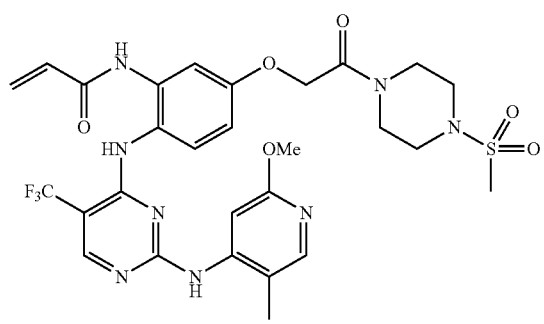 [SMILES: C=CC(=O)Nc1cc(OCC(=O)N2CCN(S(C)(=O)=O)CC2)ccc1Nc1nc(Nc2cc(OC)ncc2C)ncc1C(F)(F)F]
I-405
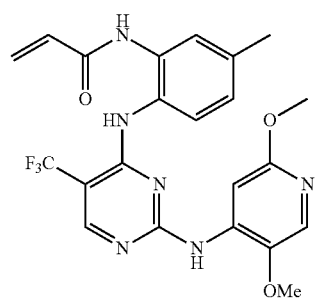 [SMILES: C=CC(=O)Nc1cc(C)ccc1Nc1nc(Nc2cc(OC)ncc2OC)ncc1C(F)(F)F]
I-406

TABLE 3-continued
Exemplary Compounds of Formula I
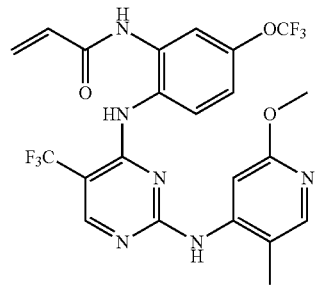 [SMILES: C=CC(=O)Nc1cc(OC(F)(F)F)ccc1Nc1nc(Nc2cc(OC)ncc2C)ncc1C(F)(F)F]
I-407
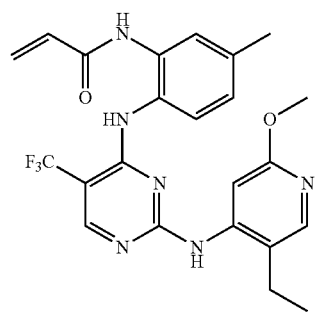 [SMILES: C=CC(=O)Nc1cc(C)ccc1Nc1nc(Nc2cc(OC)ncc2CC)ncc1C(F)(F)F]
I-408
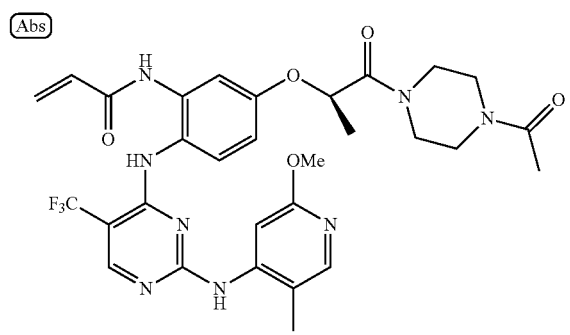 [SMILES: C=CC(=O)Nc1cc(O[C@H](C)C(=O)N2CCN(C(C)=O)CC2)ccc1Nc1nc(Nc2cc(OC)ncc2C)ncc1C(F)(F)F]
I-409
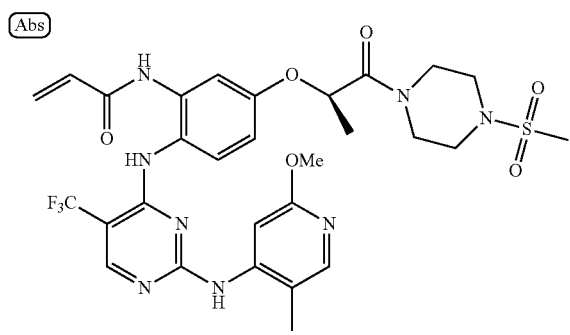 [SMILES: C=CC(=O)Nc1cc(O[C@H](C)C(=O)N2CCN(S(C)(=O)=O)CC2)ccc1Nc1nc(Nc2cc(OC)ncc2C)ncc1C(F)(F)F]
I-410

TABLE 3-continued
Exemplary Compounds of Formula I
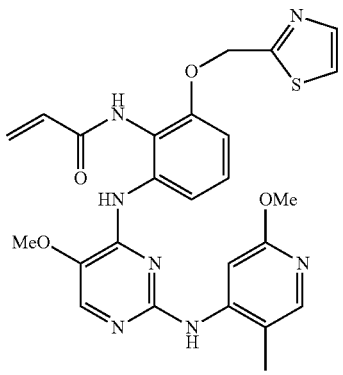 [SMILES: C=CC(=O)Nc1c(Nc2nc(Nc3cc(OC)ncc3C)ncc2OC)cccc1OCc1nccs1]
I-411
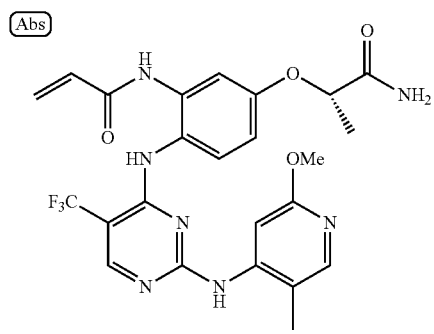 [SMILES: C=CC(=O)Nc1cc(O[C@@H](C)C(N)=O)ccc1Nc1nc(Nc2cc(OC)ncc2C)ncc1C(F)(F)F]
I-412
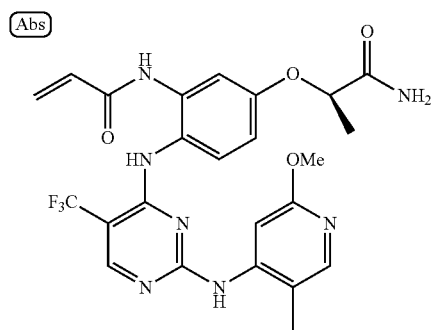 [SMILES: C=CC(=O)Nc1cc(O[C@H](C)C(N)=O)ccc1Nc1nc(Nc2cc(OC)ncc2C)ncc1C(F)(F)F]
I-413
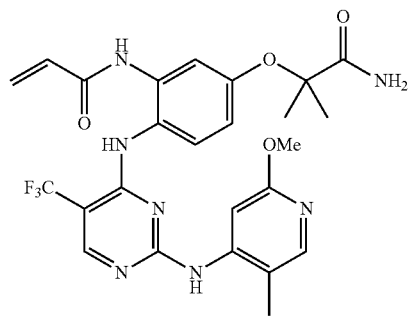 [SMILES: C=CC(=O)Nc1cc(OC(C)(C)C(N)=O)ccc1Nc1nc(Nc2cc(OC)ncc2C)ncc1C(F)(F)F]
I-414

TABLE 3-continued
Exemplary Compounds of Formula I
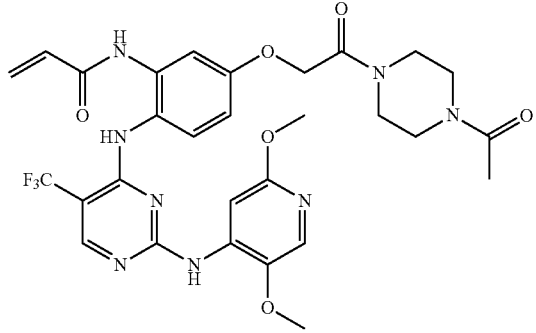 [SMILES: C=CC(=O)Nc1cc(OCC(=O)N2CCN(C(C)=O)CC2)ccc1Nc1nc(Nc2cc(OC)ncc2OC)ncc1C(F)(F)F]
I-415
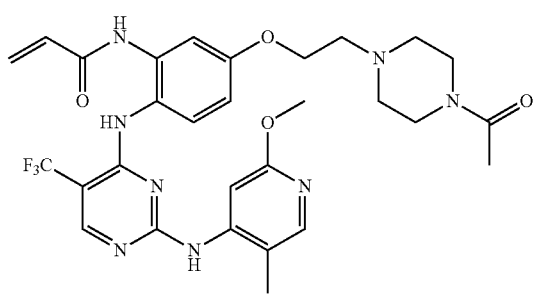 [SMILES: C=CC(=O)Nc1cc(OCCN2CCN(C(C)=O)CC2)ccc1Nc1nc(Nc2cc(OC)ncc2C)ncc1C(F)(F)F]
I-416
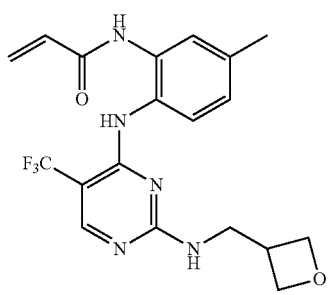 [SMILES: C=CC(=O)Nc1cc(C)ccc1Nc1nc(NCC2COC2)ncc1C(F)(F)F]
I-417
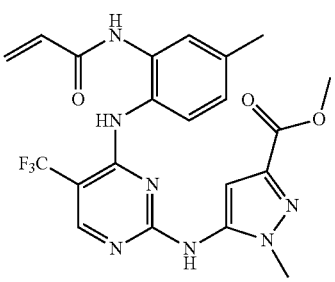 [SMILES: C=CC(=O)Nc1cc(C)ccc1Nc1nc(Nc2cc(C(=O)OC)nn2C)ncc1C(F)(F)F]
I-418
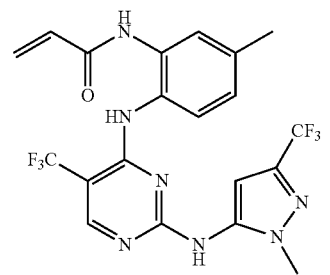 [SMILES: C=CC(=O)Nc1cc(C)ccc1Nc1nc(Nc2cc(C(F)(F)F)nn2C)ncc1C(F)(F)F]
I-419

TABLE 3-continued
Exemplary Compounds of Formula I
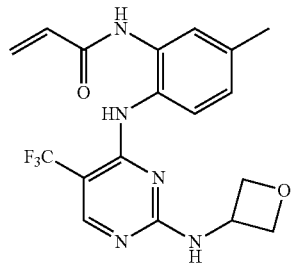 [SMILES: C=CC(=O)Nc1cc(C)ccc1Nc1nc(NC2COC2)ncc1C(F)(F)F]
I-420
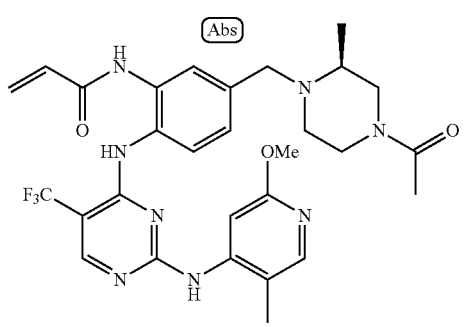 [SMILES: C=CC(=O)Nc1cc(CN2CCN(C(C)=O)C[C@@H]2C)ccc1Nc1nc(Nc2cc(OC)ncc2C)ncc1C(F)(F)F]
I-421
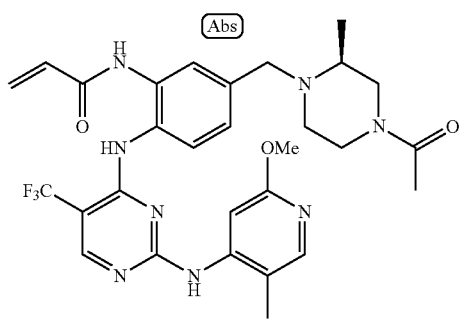 [SMILES: C=CC(=O)Nc1cc(CN2CCN(C(C)=O)C[C@@H]2C)ccc1Nc1nc(Nc2cc(OC)ncc2C)ncc1C(F)(F)F]
I-422
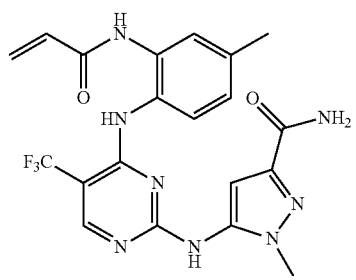 [SMILES: C=CC(=O)Nc1cc(C)ccc1Nc1nc(Nc2cc(C(N)=O)nn2C)ncc1C(F)(F)F]
I-423
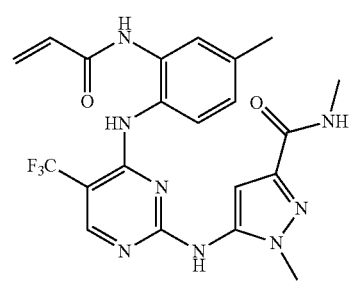 [SMILES: C=CC(=O)Nc1cc(C)ccc1Nc1nc(Nc2cc(C(=O)NC)nn2C)ncc1C(F)(F)F]
I-424

TABLE 3-continued
Exemplary Compounds of Formula I
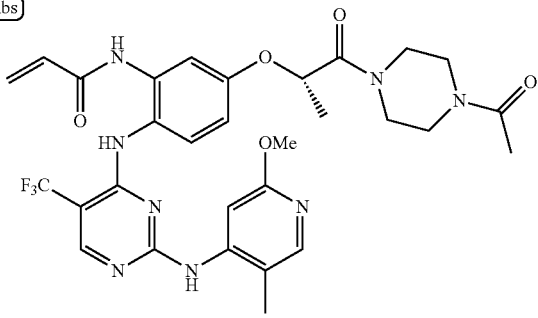
I-425
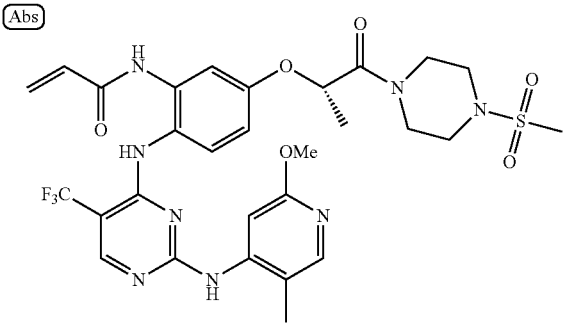 [SMILES: C=CC(=O)Nc1cc(O[C@@H](C)C(=O)N2CCN(S(C)(=O)=O)CC2)ccc1Nc1nc(Nc2cc(OC)ncc2C)ncc1C(F)(F)F]
I-426
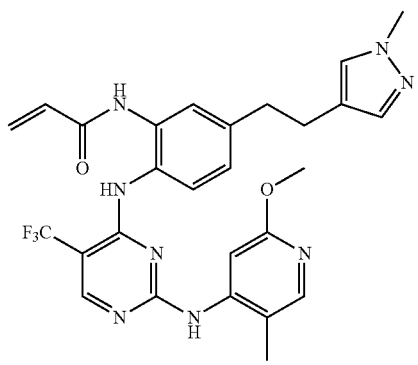 [SMILES: C=CC(=O)Nc1cc(CCc2cnn(C)c2)ccc1Nc1nc(Nc2cc(OC)ncc2C)ncc1C(F)(F)F]
I-427
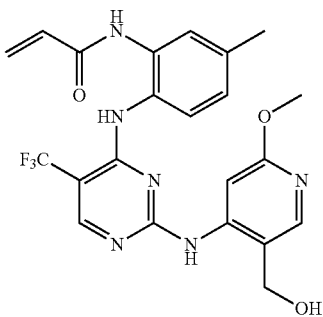 [SMILES: C=CC(=O)Nc1cc(C)ccc1Nc1nc(Nc2cc(OC)ncc2CO)ncc1C(F)(F)F]
I-428

TABLE 3-continued

Exemplary Compounds of Formula I

I-429

I-430

I-431

In some embodiments, the present invention provides a compound set forth in Table 3, above, or a pharmaceutically acceptable salt thereof.

Other compounds contemplated by the invention are selected from those depicted in Table 4, below:

TABLE 4

Additional Exemplary Compounds

I-307

TABLE 4-continued

Additional Exemplary Compounds

I-308

TABLE 4-continued
Additional Exemplary Compounds
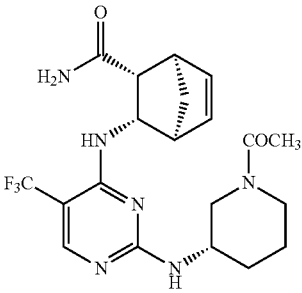 [SMILES: CC(=O)N1CCC[C@H](Nc2ncc(C(F)(F)F)c(N[C@@H]3[C@H](C(N)=O)[C@H]4C=C[C@@H]3C4)n2)C1] I-309
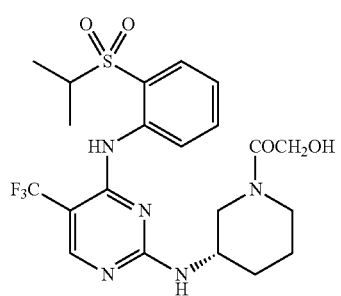 I-310
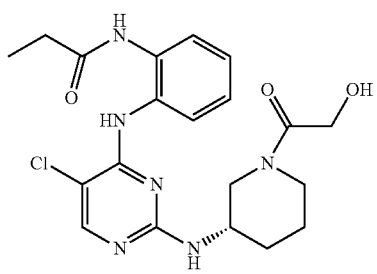 [SMILES: CCC(=O)Nc1ccccc1Nc1nc(N[C@H]2CCCN(C(=O)CO)C2)ncc1Cl] I-311
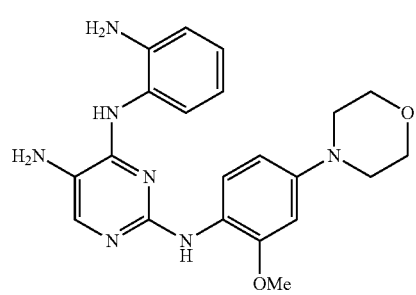 [SMILES: COc1cc(N2CCOCC2)ccc1Nc1ncc(N)c(Nc2ccccc2N)n1] I-312
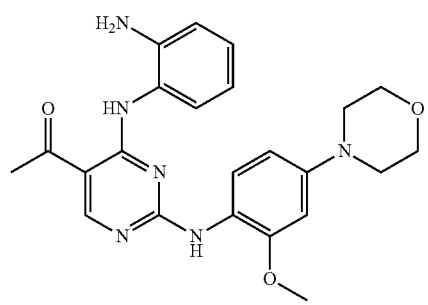 [SMILES: COc1cc(N2CCOCC2)ccc1Nc1ncc(C(C)=O)c(Nc2ccccc2N)n1] I-313
TABLE 4-continued
Additional Exemplary Compounds
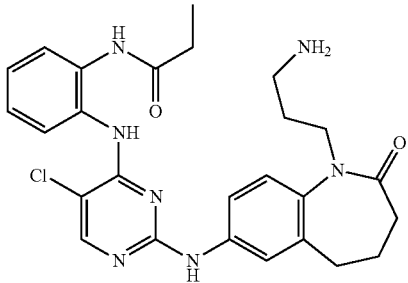 [SMILES: CCC(=O)Nc1ccccc1Nc1nc(Nc2ccc3c(c2)CCCC(=O)N3CCCN)ncc1Cl] I-314
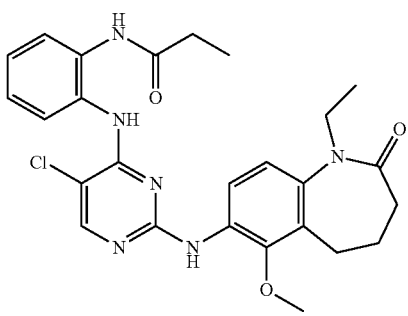 [SMILES: CCC(=O)Nc1ccccc1Nc1nc(Nc2ccc3c(c2OC)CCCC(=O)N3CC)ncc1Cl] I-315
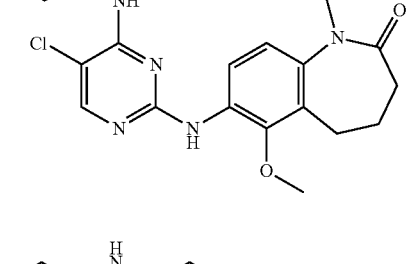 I-316
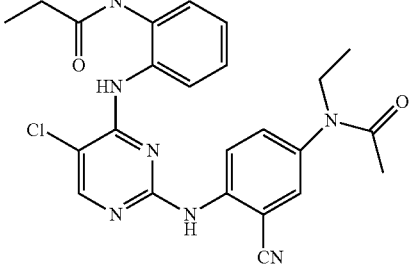 I-317
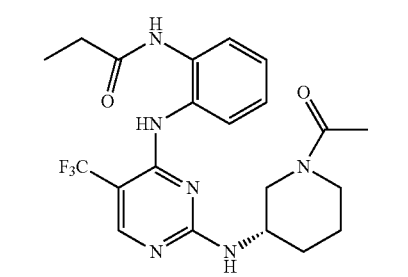 [SMILES: CCC(=O)Nc1ccccc1Nc1nc(N[C@H]2CCCN(C(C)=O)C2)ncc1C(F)(F)F] I-318

TABLE 4-continued

Additional Exemplary Compounds

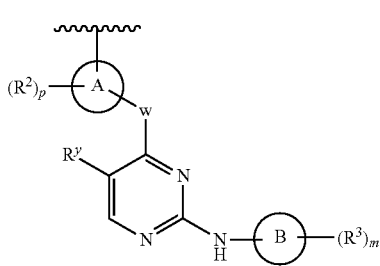

I-352

I-353

Compounds according to the invention can be conjugated to biological molecules, such as antibodies or other biological carriers. In certain embodiments, the present invention provides a conjugate comprising one or both of ERK1 and ERK2 kinase having a cysteine residue, Cys183 (ERK1) and/or Cys166 (ERK2), wherein the Cys183 and/or Cys166 is covalently, and irreversibly, bonded to an inhibitor, such that inhibition of the kinase is maintained. Cys166 of ERK2 is the same positional amino acid as Cys183 of ERK1. Thus, the below discussion regarding Cys183 of ERK1 also applies to Cys166 of ERK2 (and vice versa).

In certain embodiments, the present invention provides a conjugate of the formula A:

Cys183-modifier-inhibitor moiety    A wherein:
the Cys183 is Cys183 of ERK1;
the modifier is a bivalent group resulting from covalent bonding of a warhead group with the Cys183 of ERK1 kinase;
the warhead group is a functional group capable of covalently binding to Cys183; and the inhibitor moiety is a moiety that binds in the ATP binding site of the ERK1 kinase.

In certain embodiments, the inhibitor moiety of conjugate A is of formula I-i:

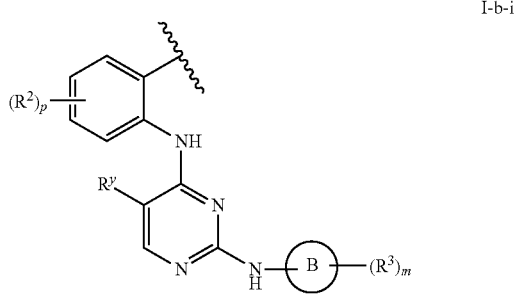

I-i wherein the wavy bond indicates the point of attachment to Cys183 of conjugate A via the modifier, wherein when Ring A is a five or six member ring, then the wavy bond is attached to an atom adjacent to where W is attached; and wherein each of Ring A, Ring B, $R^2$, $R^3$, $R^y$, W, m and p, of formula I-i is as defined for formula I above and as defined and described in embodiments herein. In some embodiments, each of Ring A, Ring B, $R^2$, $R^3$, $R^y$, W, m and p, of formula I-i is as defined for formula I' above and as defined and described in embodiments herein.

In certain embodiments, the inhibitor moiety of conjugate A is of formula I-a-i:

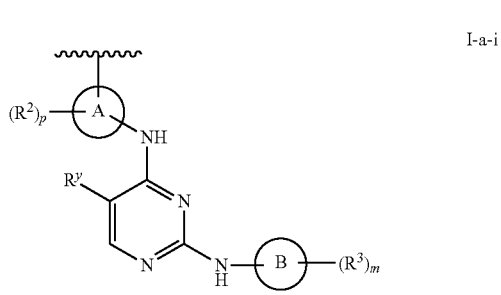

I-a-i wherein the wavy bond indicates the point of attachment to Cys183 of conjugate A via the modifier, wherein when Ring A is a five or six member ring, then the wavy bond is attached to an atom adjacent to where NH is attached; and wherein each of Ring A, Ring B, $R^2$, $R^3$, $R^y$, m and p, of formula I-a-i is as defined for formula I-a above and as defined and described in embodiments herein.

In certain embodiments, the inhibitor moiety of conjugate A is any one of formulae I-b-i, I-c-i, I-d-i, and I-e-i:

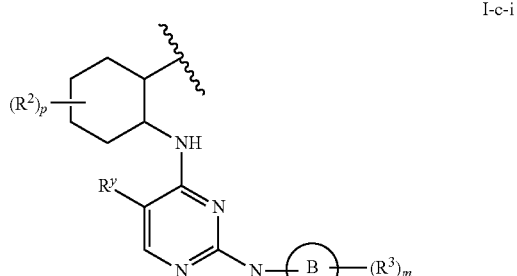

I-b-i

I-c-i

-continued

I-d-i

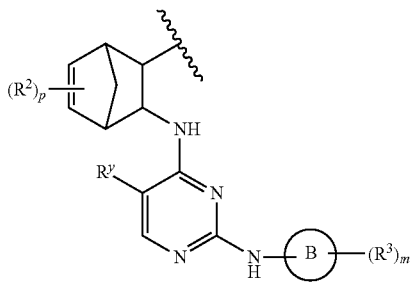

I-e-i

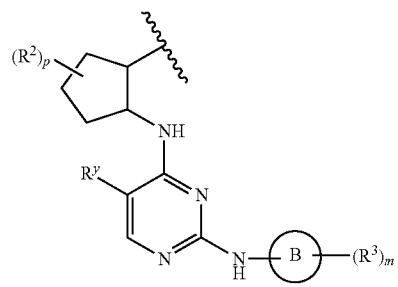

wherein each wavy bond indicates the point of attachment to Cys183 of conjugate A via the modifier, wherein each of Ring B, $R^2$, $R^3$, $R^y$, m and p, of formulae I-b-i, I-c-i, I-d-i, and I-e-i is as defined for formulae I-b, I-c, I-d, and I-e above and as defined and described in embodiments herein.

In certain embodiments, the inhibitor moiety of conjugate A is of formula I-f-i:

I-f-i

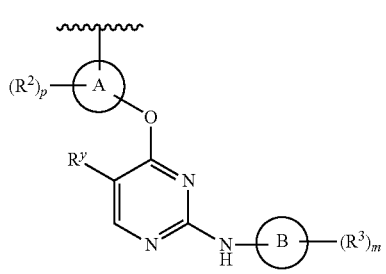

wherein the wavy bond indicates the point of attachment to Cys183 of conjugate A via the modifier, wherein when Ring A is a five or six member ring, then the wavy bond is attached to an atom adjacent to where O is attached; and wherein each of Ring A, Ring B, $R^2$, $R^3$, $R^y$, m and p, of formula I-f-i is as defined for formula I-f above and as defined and described in embodiments herein.

In certain embodiments, the inhibitor moiety of conjugate A is of any one of formulae I-g-i, I-h-i, I-j-i, and I-k-i:

I-g-i

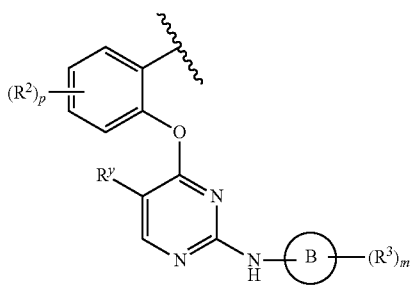

-continued

I-h-i

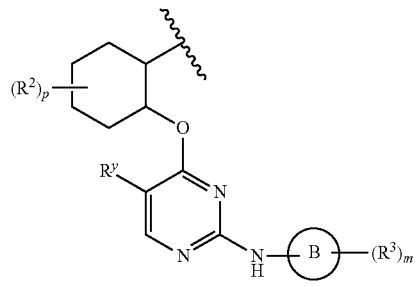

I-j-i

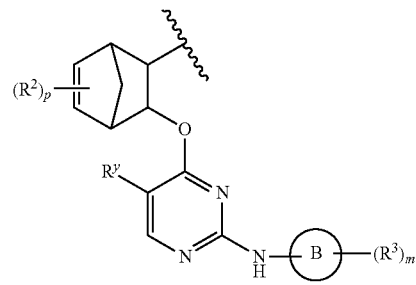

I-k-i

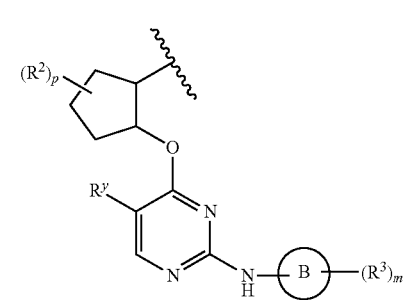

wherein each wavy bond indicates the point of attachment to Cys183 of conjugate A via the modifier, wherein each of Ring B, $R^2$, $R^3$, $R^y$, m and p, of formulae I-g-i, I-h-i, I-j-i, and I-k-i: is as defined for formula I-g, I-h, I-j, and I-k above and as defined and described in embodiments herein.

In certain embodiments, the inhibitor moiety of conjugate A is of formula II-i:

II-i

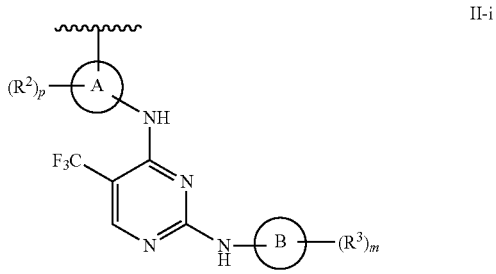

wherein the wavy bond indicates the point of attachment to Cys183 of conjugate A via the modifier, wherein when Ring A is a five or six member ring, then the wavy bond is attached to an atom adjacent to where NH is attached; and wherein each of Ring A, Ring B, $R^2$, $R^3$, m and p, of formula II-i is as defined for formula II above and as defined and described in embodiments herein.

In certain embodiments, the inhibitor moiety of conjugate A is of formula III-i:

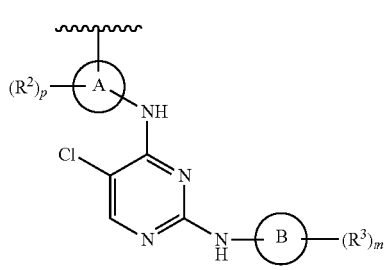

III-i wherein the wavy bond indicates the point of attachment to Cys183 of conjugate A via the modifier, wherein when Ring A is a five or six member ring, then the wavy bond is attached to an atom adjacent to where NH is attached; and wherein each of Ring A, Ring B, $R^2$, $R^3$, m and p, of formula III-i is as defined for formula III above and as defined and described in embodiments herein.

In certain embodiments, the inhibitor moiety of conjugate A is of formula IV-i:

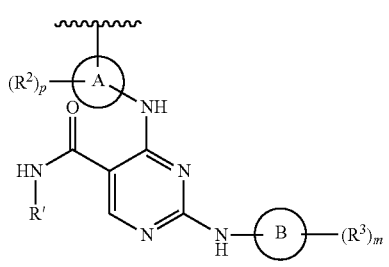

IV-i wherein the wavy bond indicates the point of attachment to Cys183 of conjugate A via the modifier, wherein when Ring A is a five or six member ring, then the wavy bond is attached to an atom adjacent to where NH is attached; and wherein each of Ring A, Ring B, $R^2$, $R^3$, R', m and p, of formula IV-i is as defined for formula IV above and as defined and described in embodiments herein.

In certain embodiments, the inhibitor moiety of conjugate A is of formula V-i:

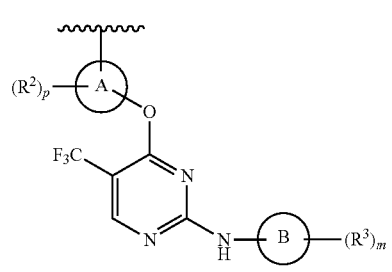

V-i wherein the wavy bond indicates the point of attachment to Cys183 of conjugate A via the modifier, wherein when Ring A is a five or six member ring, then the wavy bond is attached to an atom adjacent to where O is attached; and wherein each of Ring A, Ring B, $R^2$, $R^3$, m and p, of formula V-i is as defined for formula V above and as defined and described in embodiments herein.

In certain embodiments, the inhibitor moiety of conjugate A is of formula VI-i:

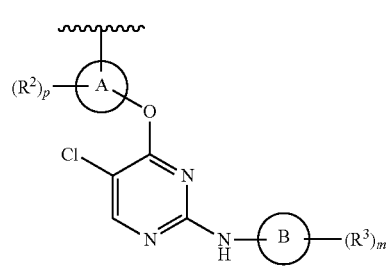

VI-i wherein the wavy bond indicates the point of attachment to Cys183 of conjugate A via the modifier, wherein when Ring A is a five or six member ring, then the wavy bond is attached to an atom adjacent to where O is attached; and wherein each of Ring A, Ring B, $R^2$, $R^3$, m and p, of formula VI-i is as defined for formula VI above and as defined and described in embodiments herein.

In certain embodiments, the inhibitor moiety of conjugate A is of formula VII-i:

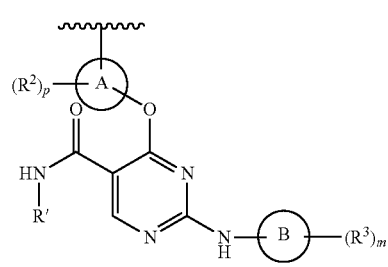

VII-i wherein the wavy bond indicates the point of attachment to Cys183 of conjugate A via the modifier, wherein when Ring A is a five or six member ring, then the wavy bond is attached to an atom adjacent to where O is attached; and wherein each of Ring A, Ring B, $R^2$, $R^3$, R', m and p, of formula VII-i is as defined for formula VII above and as defined and described in embodiments herein.

In certain embodiments, the inhibitor moiety of conjugate A is of formula VIII-i:

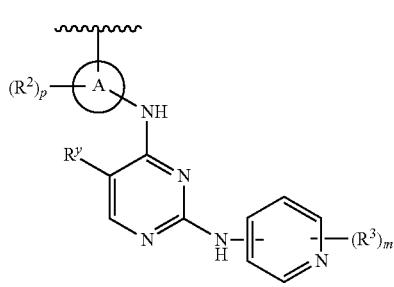

VIII-i wherein the wavy bond indicates the point of attachment to Cys183 of conjugate A via the modifier, wherein when Ring A is a five or six member ring, then the wavy bond is attached to an atom adjacent to where NH is attached; and wherein each of Ring A, Ring B, $R^2$, $R^3$, $R^y$, m and p, of formula VIII-i is as defined for formula VIII above and as defined and described in embodiments herein.

In certain embodiments, the present invention provides a conjugate of the formula B:

Cys166-modifier-inhibitor moiety        B wherein:

the Cys166 is Cys166 of ERK2;

the modifier is a bivalent group resulting from covalent bonding of a warhead group with the Cys166 of ERK2 kinase;

the warhead group is a functional group capable of covalently binding to Cys166; and the inhibitor moiety is a moiety that binds in the ATP binding site of the ERK2 kinase.

In certain embodiments, the inhibitor moiety of conjugate B is of formula I-i:

I-i wherein the wavy bond indicates the point of attachment to Cys166 of conjugate B via the modifier, wherein when Ring A is a five or six member ring, then the wavy bond is attached to an atom adjacent to where W is attached; and wherein each of Ring A, Ring B, $R^2$, $R^3$, $R^y$, W, m and p, of formula I-i is as defined for formula I above and as defined and described in embodiments herein. In some embodiments, each of Ring A, Ring B, $R^2$, $R^3$, $R^y$, W, m and p, of formula I-i is as defined for formula I' above and as defined and described in embodiments herein.

In certain embodiments, the inhibitor moiety of conjugate B is of formula I-a-i:

I-a-i wherein the wavy bond indicates the point of attachment to Cys166 of conjugate B via the modifier, wherein when Ring A is a five or six member ring, then the wavy bond is attached to an atom adjacent to where NH is attached; and wherein each of Ring A, Ring B, $R^2$, $R^3$, $R^y$, m and p, of formula I-a-i is as defined for formula I-a above and as defined and described in embodiments herein.

In certain embodiments, the inhibitor moiety of conjugate B is any one of formulae I-b-i, I-c-i, I-d-i, and I-e-i:

I-b-i

I-c-i

I-d-i

I-e-i wherein each wavy bond indicates the point of attachment to Cys166 of conjugate B via the modifier, wherein each of Ring B, $R^2$, $R^3$, $R^y$, m and p, of formulae I-b-i, I-c-i, I-d-i, and I-e-i is as defined for formula I-b, I-c, I-d, and I-e above and as defined and described in embodiments herein.

In certain embodiments, the inhibitor moiety of conjugate B is of formula I-f-i:

I-f-i

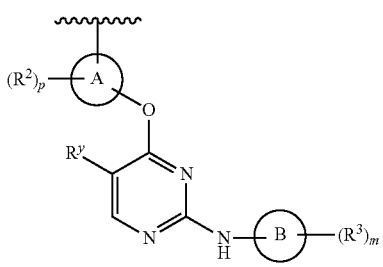

wherein the wavy bond indicates the point of attachment to Cys166 of conjugate B via the modifier, wherein when Ring A is a five or six member ring, then the wavy bond is attached to an atom adjacent to where O is attached; and wherein each of Ring A, Ring B, $R^2$, $R^3$, $R^y$, m and p, of formula I-f-i is as defined for formula I-f above and as defined and described in embodiments herein.

In certain embodiments, the inhibitor moiety of conjugate B is of any one of formulae I-g-i, I-h-i, I-j-i, and I-k-i:

I-g-i

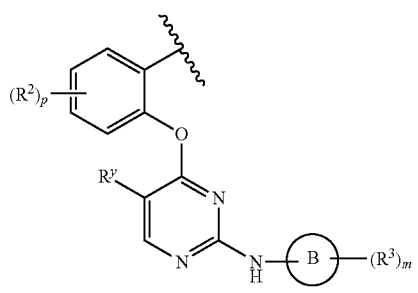

I-h-i

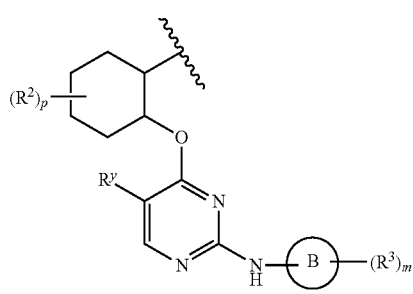

I-j-i

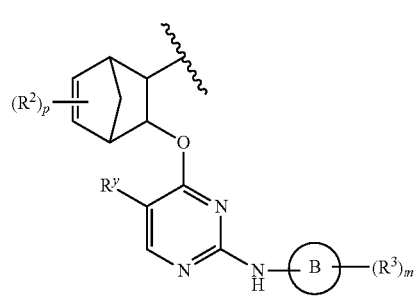

I-k-i

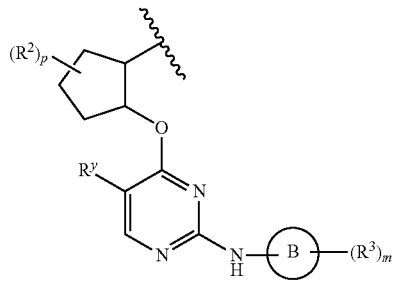

wherein each wavy bond indicates the point of attachment to Cys166 of conjugate B via the modifier, wherein each of Ring B, $R^2$, $R^3$, $R^y$, m and p, of formulae I-g-i, I-h-i, I-j-i, and I-k-i: is as defined for formula I-g, I-h, I-j, and I-k above and as defined and described in embodiments herein.

In certain embodiments, the inhibitor moiety of conjugate B is of formula II-i:

II-i

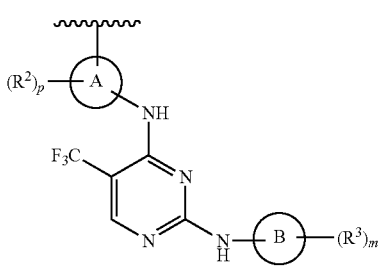

wherein the wavy bond indicates the point of attachment to Cys166 of conjugate B via the modifier, wherein when Ring A is a five or six member ring, then the wavy bond is attached to an atom adjacent to where NH is attached; and wherein each of Ring A, Ring B, $R^2$, $R^3$, m and p, of formula II-i is as defined for formula II above and as defined and described in embodiments herein.

In certain embodiments, the inhibitor moiety of conjugate B is of formula III-i:

III-i

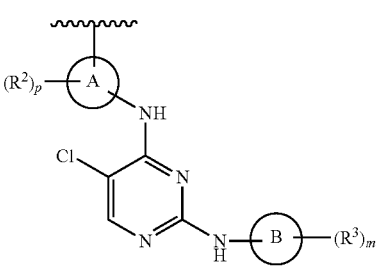

wherein the wavy bond indicates the point of attachment to Cys166 of conjugate B via the modifier, wherein when Ring A is a five or six member ring, then the wavy bond is attached to an atom adjacent to where NH is attached; and wherein each of Ring A, Ring B, $R^2$, $R^3$, m and p, of formula III-i is as defined for formula III above and as defined and described in embodiments herein.

In certain embodiments, the inhibitor moiety of conjugate B is of formula IV-i:

IV-i

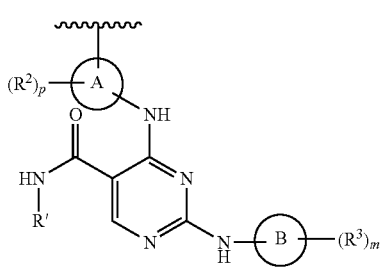

wherein the wavy bond indicates the point of attachment to Cys166 of conjugate B via the modifier, wherein when Ring A is a five or six member ring, then the wavy bond is attached to an atom adjacent to where NH is attached; and wherein each of Ring A, Ring B, $R^2$, $R^3$, R', m and p, of formula IV-i is as defined for formula IV above and as defined and described in embodiments herein.

In certain embodiments, the inhibitor moiety of conjugate B is of formula V-i:

V-i

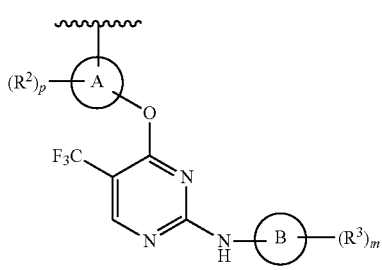

wherein the wavy bond indicates the point of attachment to Cys166 of conjugate B via the modifier, wherein when Ring A is a five or six member ring, then the wavy bond is attached to an atom adjacent to where O is attached; and wherein each of Ring A, Ring B, $R^2$, $R^3$, m and p, of formula V-i is as defined for formula V above and as defined and described in embodiments herein.

In certain embodiments, the inhibitor moiety of conjugate B is of formula VI-i:

VI-i

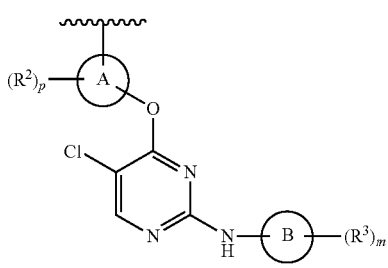

wherein the wavy bond indicates the point of attachment to Cys166 of conjugate B via the modifier, wherein when Ring A is a five or six member ring, then the wavy bond is attached to an atom adjacent to where O is attached; and wherein each of Ring A, Ring B, $R^2$, $R^3$, m and p, of formula VI-i is as defined for formula VI above and as defined and described in embodiments herein.

In certain embodiments, the inhibitor moiety of conjugate B is of formula VII-i:

VII-i

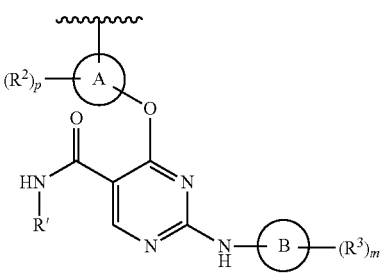

wherein the wavy bond indicates the point of attachment to Cys166 of conjugate B via the modifier, wherein when Ring A is a five or six member ring, then the wavy bond is attached to an atom adjacent to where O is attached; and wherein each of Ring A, Ring B, $R^2$, $R^3$, R', m and p, of formula VII-i is as defined for formula VII above and as defined and described in embodiments herein.

In certain embodiments, the inhibitor moiety of conjugate B is of formula VIII-i:

VIII-i

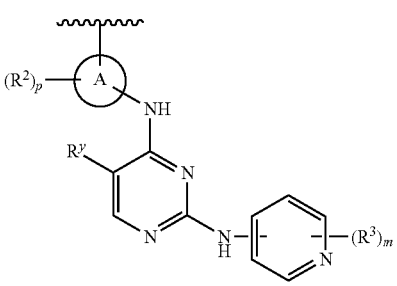

wherein the wavy bond indicates the point of attachment to Cys166 of conjugate B via the modifier, wherein when Ring A is a five or six member ring, then the wavy bond is attached to an atom adjacent to where NH is attached; and wherein each of Ring A, $R^2$, $R^3$, $R^y$, m and p, of formula VIII-i is as defined for formula VIII above and as defined and described in embodiments herein.

In certain embodiments, the present invention provides a conjugate of any of the formulae below:

I-i-m

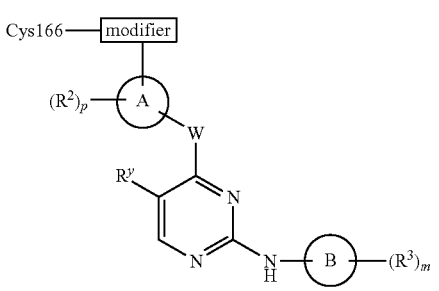

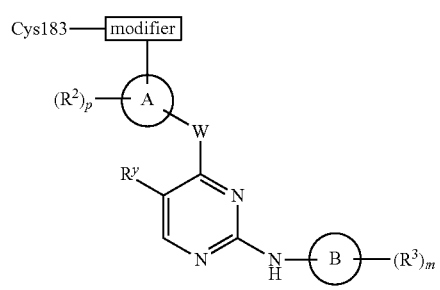
I-i-n
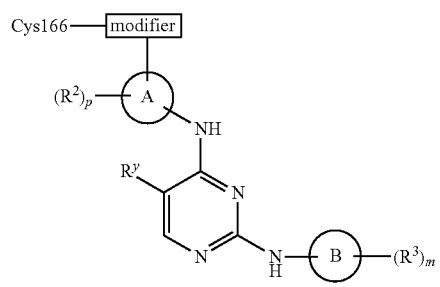
I-a-i-m
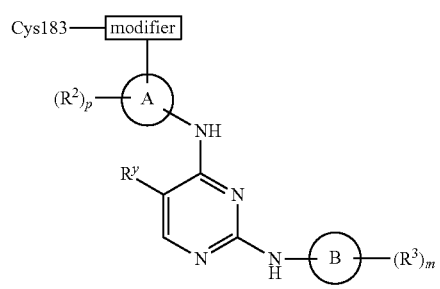
I-a-i-n
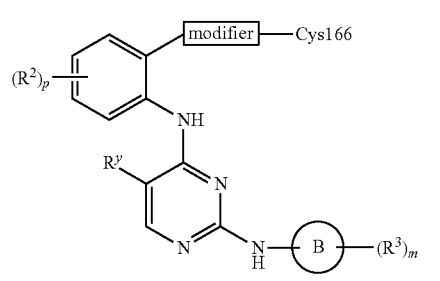
I-b-i-m
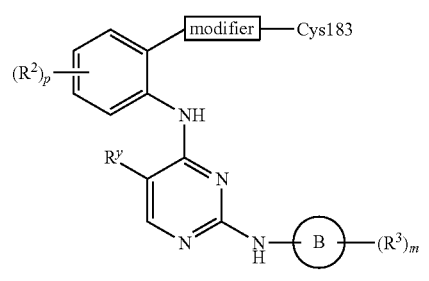
I-b-i-n
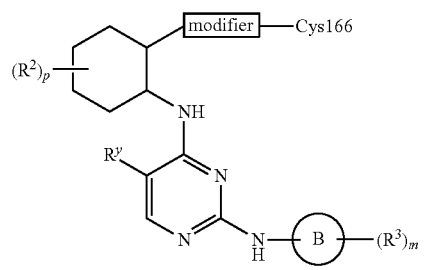
I-c-i-m
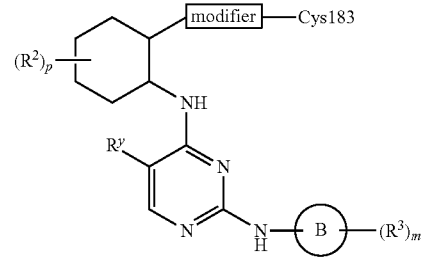
I-c-i-n
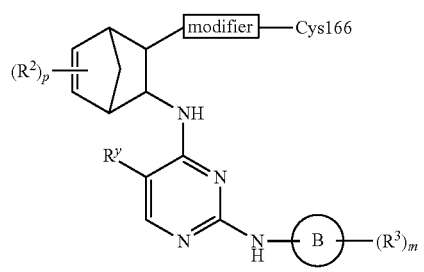
I-d-i-m
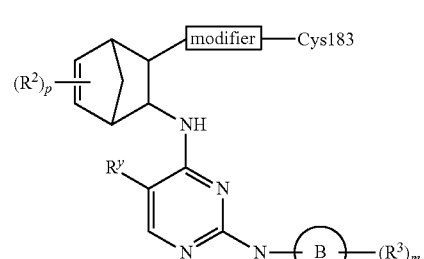
I-d-i-n
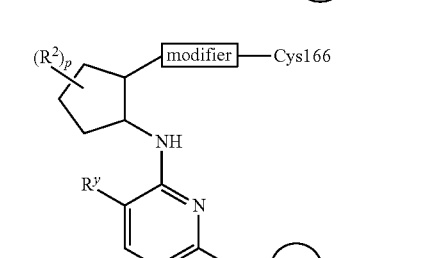
I-e-i-m
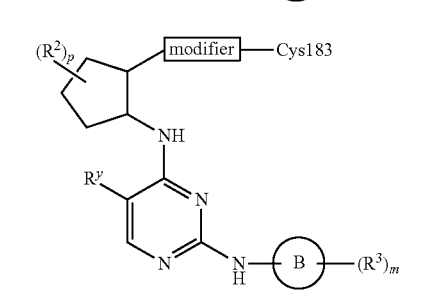
I-e-i-n

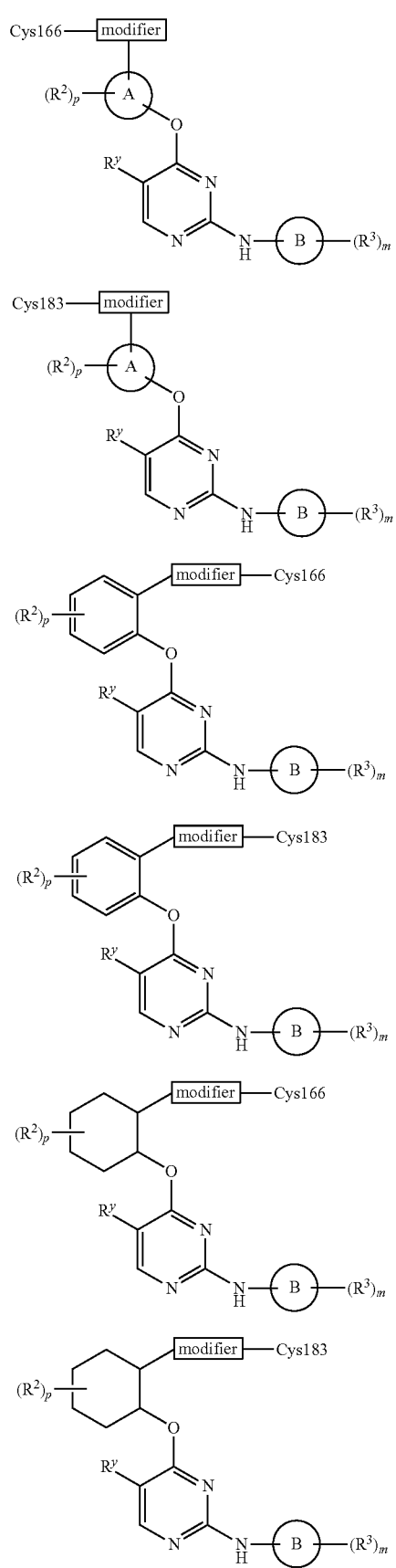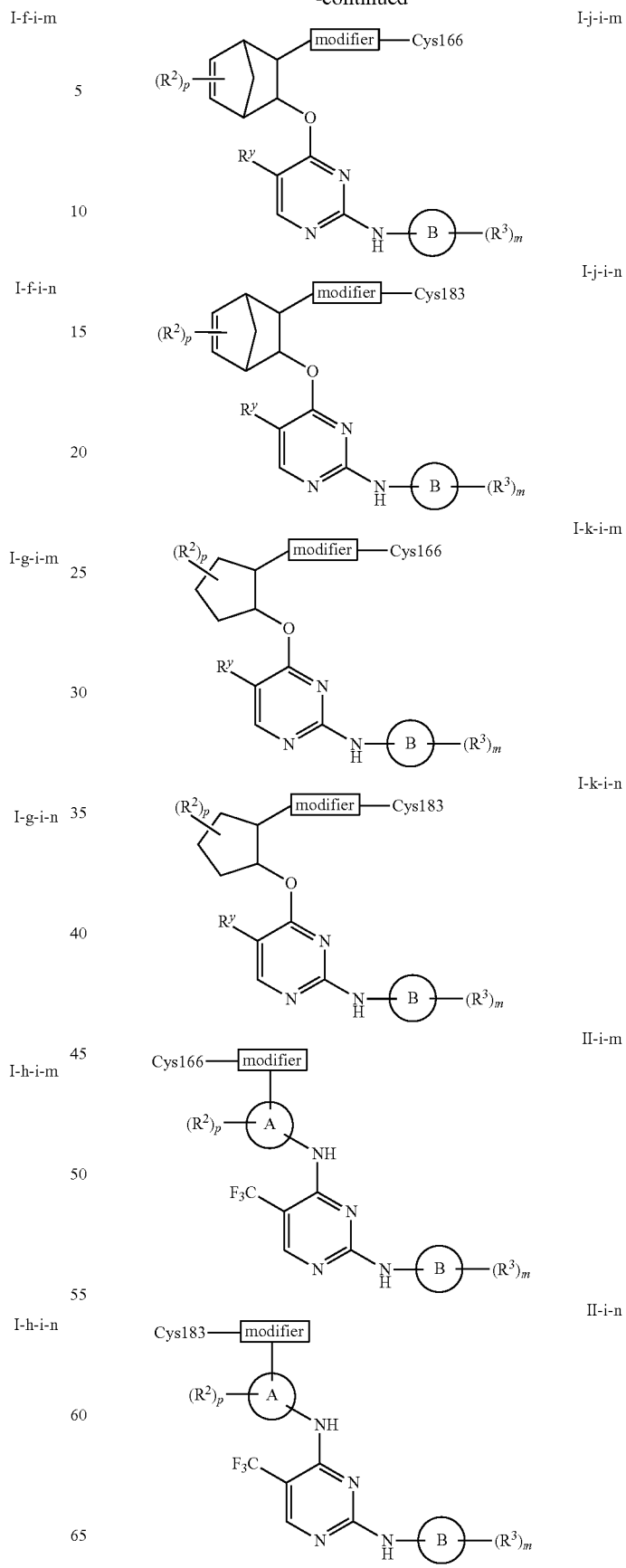

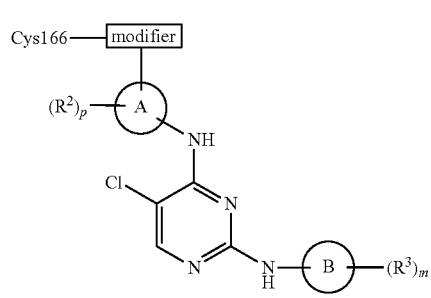

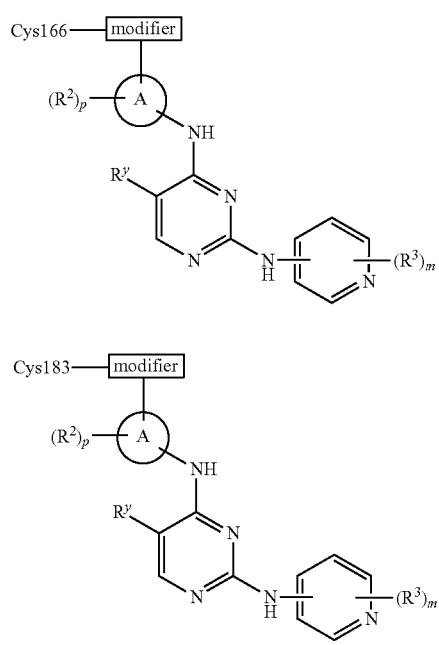

wherein each of Cys183, Cys166, Modifier, Ring A, Ring B, R², R³, Rʸ, W, m and p, with respect to the above formulae is as defined and described in embodiments herein for formulae I, I-a, I-b, I-c, I-d, I-e, I-f, I-g, I-h, I-j, I-l, II, III, IV, V, VI, VII and VIII. In some embodiments, each of Ring A, Ring B, R², R³, Rʸ, W, m and p, with respect to the above formulae is as defined and described in embodiments herein for formula I'. In some embodiments, when Ring A is a five or six member ring, then modifier is attached to an atom adjacent to where W, N, or O is attached.

In other embodiments, the modifier moiety of any of conjugate described above is selected from those set forth in Table 5, below. Exemplary modifiers further include any bivalent group resulting from covalent bonding of a warhead moiety found in Table 1 or Table 2 with a cysteine of the kinases recited herein. It will be understood that the exemplary modifiers below are shown as conjugated to the sulfhydryl of CysX.

TABLE 5

Exemplary Modifiers Conjugated to Cys 183 or Cys 166:

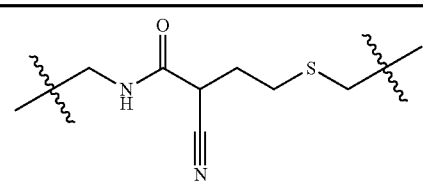 a

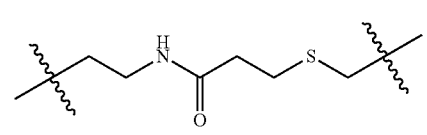 [SMILES: *CCNC(=O)CCSC*] b

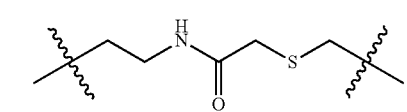 [SMILES: *CCNC(=O)CSC*] c

TABLE 5-continued

Exemplary Modifiers Conjugated to Cys 183 or Cys 166:

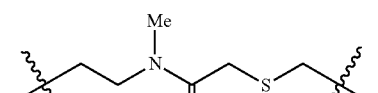 d

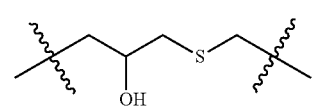 [SMILES: *CSCC(O)C*] e

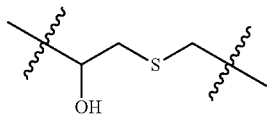 [SMILES: *CSCC(*)O] f

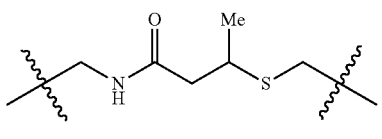 [SMILES: *CNC(=O)CC(C)SC*] g

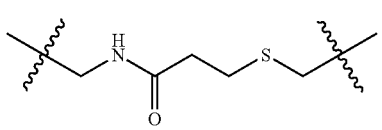 [SMILES: *CNC(=O)CCSC*] h

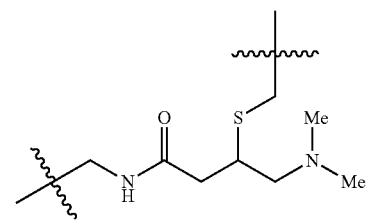 [SMILES: *CNC(=O)CC(CN(C)C)SC*] i

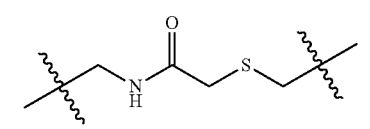 [SMILES: *CNC(=O)CSC*] j

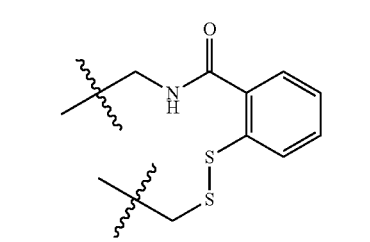 [SMILES: *CNC(=O)c1ccccc1SSC*] k

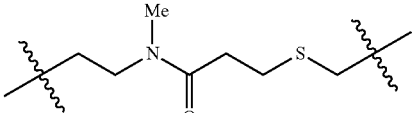 l

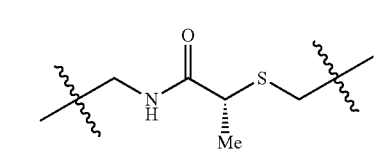 [SMILES: *CNC(=O)C(C)SC*] m

TABLE 5-continued
Exemplary Modifiers Conjugated to Cys 183 or Cys 166:
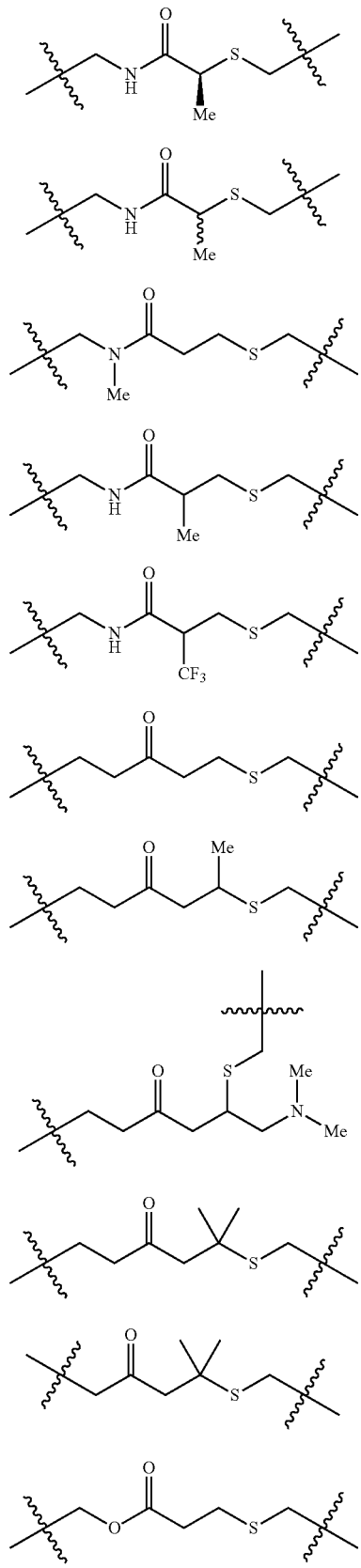
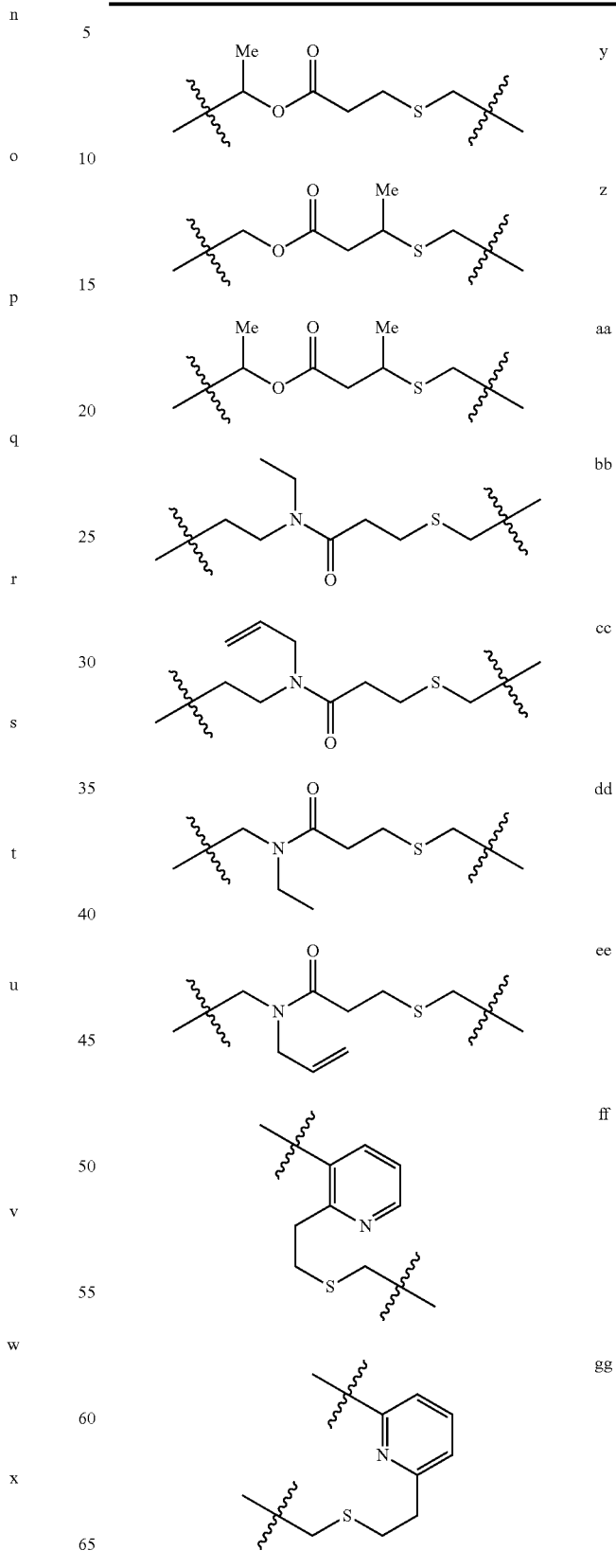

TABLE 5-continued
Exemplary Modifiers Conjugated to Cys 183 or Cys 166:
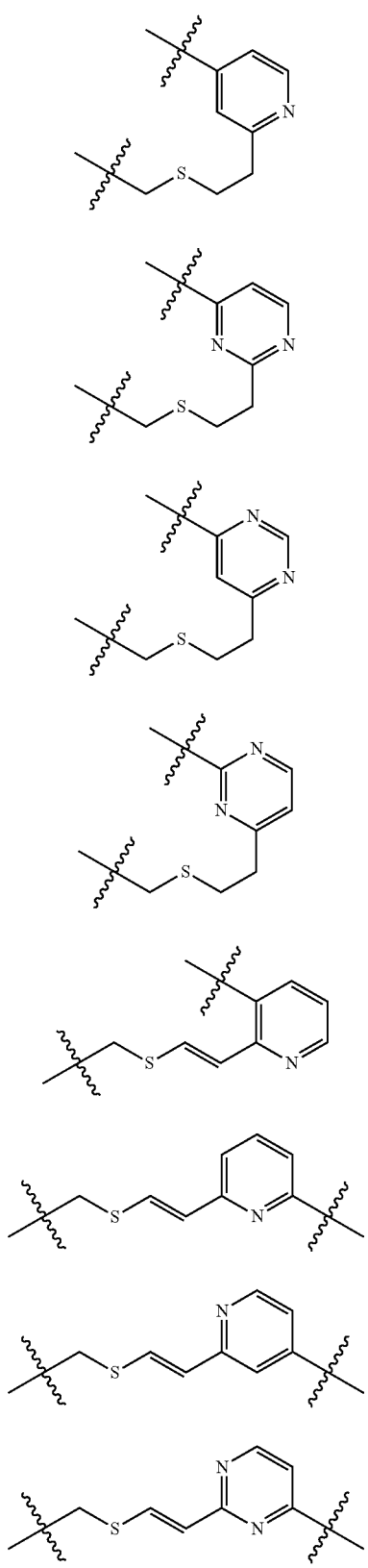
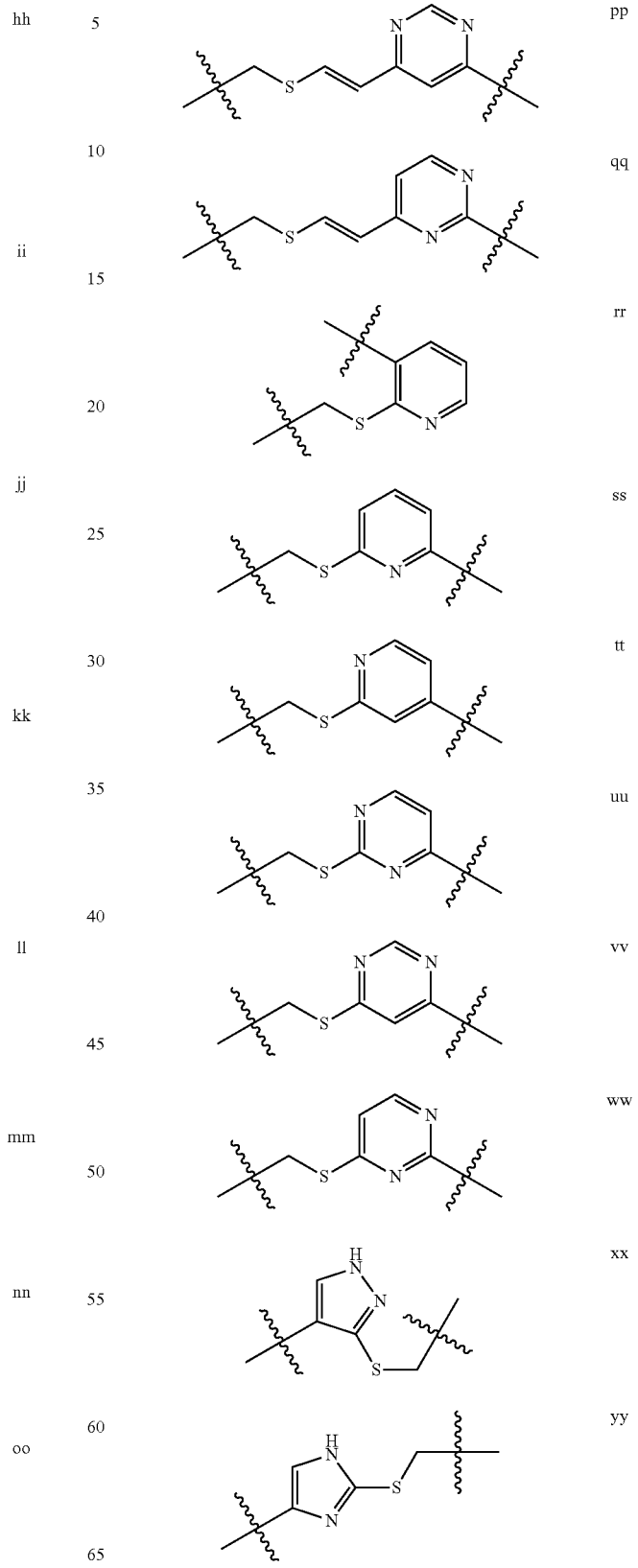

TABLE 5-continued
Exemplary Modifiers Conjugated to Cys 183 or Cys 166:
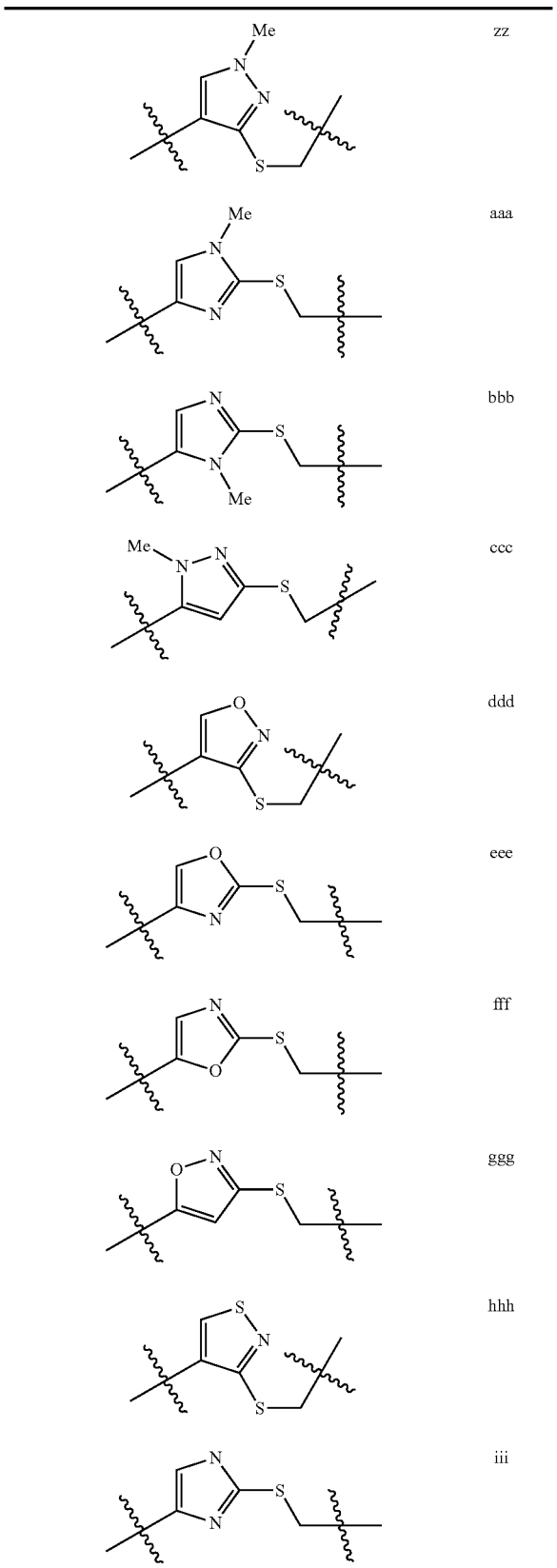
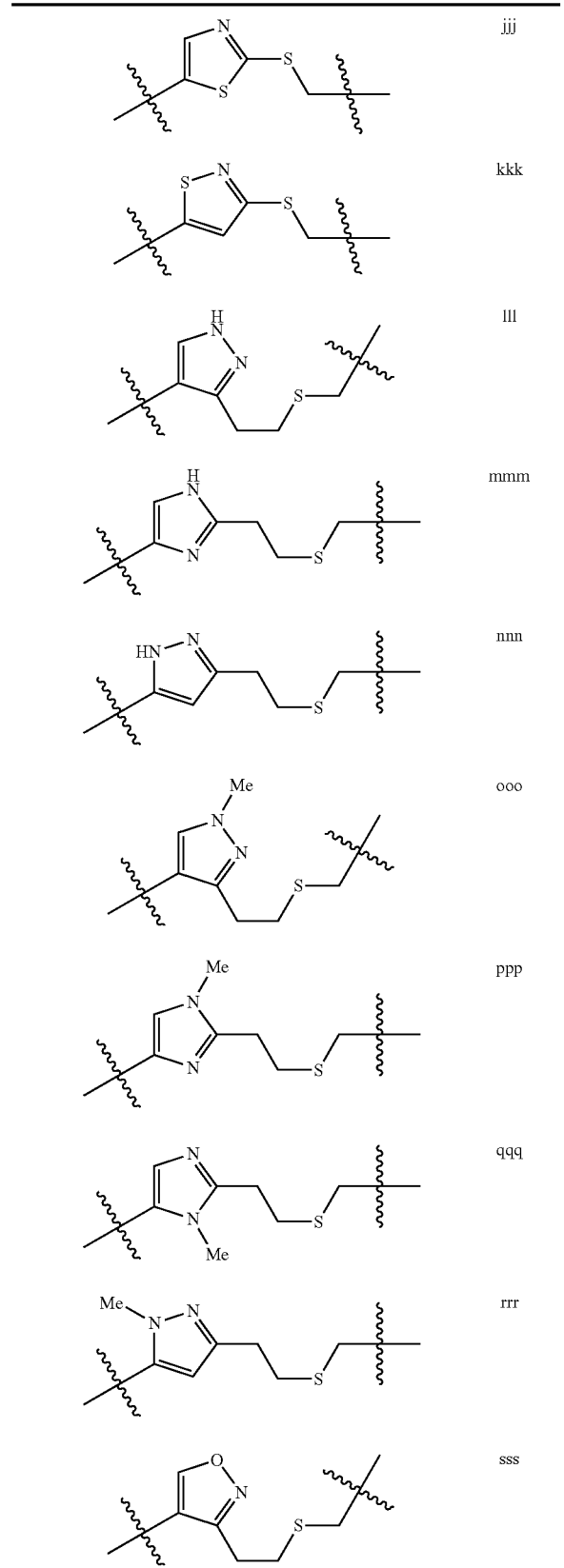

TABLE 5-continued
Exemplary Modifiers Conjugated to Cys 183 or Cys 166:
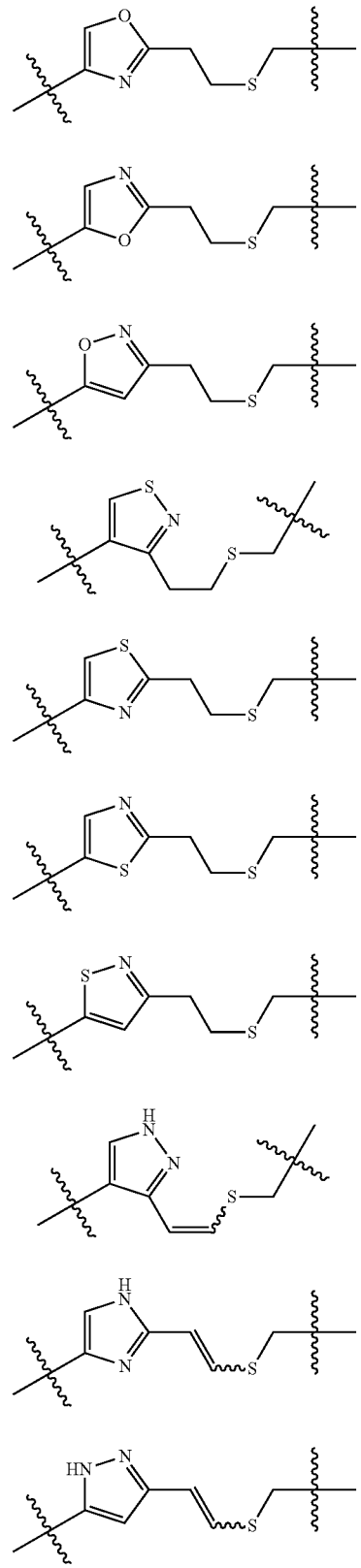
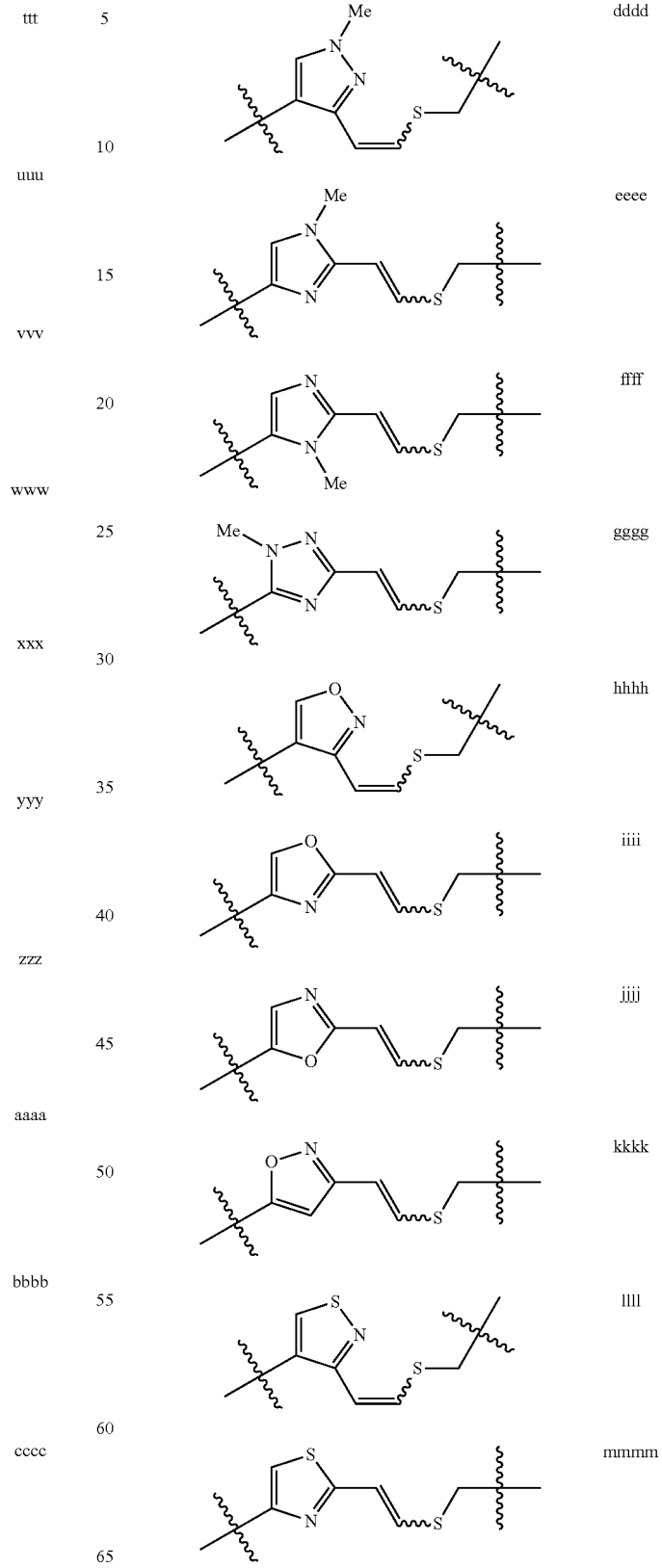

TABLE 5-continued

Exemplary Modifiers Conjugated to Cys 183 or Cys 166:

| Label | 
|---|
| nnnn |
| oooo |
| pppp |
| qqqq |
| rrrr |
| ssss |
| tttt |
| uuuu |
| vvvv |
| wwww |
| xxxx |
| yyyy |
| zzzz |
| aaaaa |
| bbbbb |
| ccccc |
| ddddd |
| eeeee |

TABLE 5-continued

Exemplary Modifiers Conjugated to Cys 183 or Cys 166:

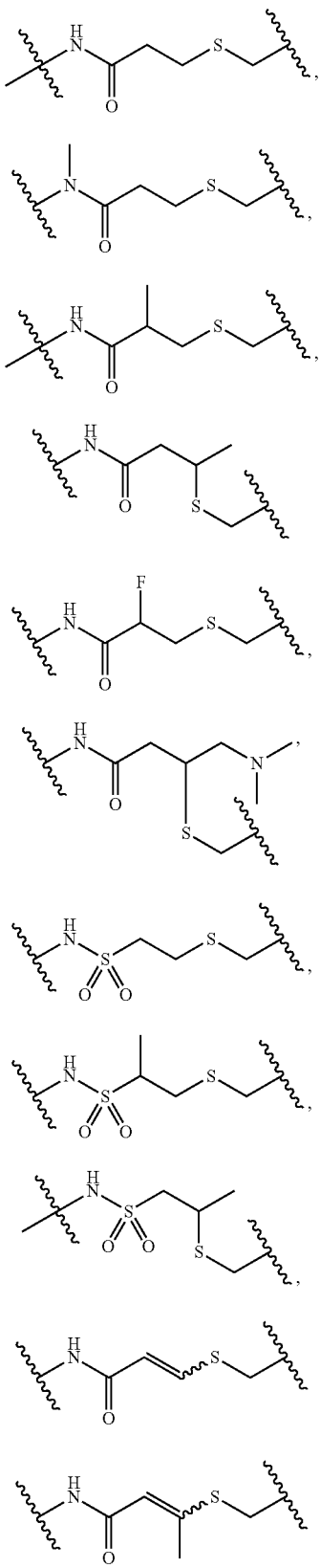

ffff ggggg hhhhh iiiii jjjjj kkkkk lllll mmmmm nnnnn ooooo ppppp

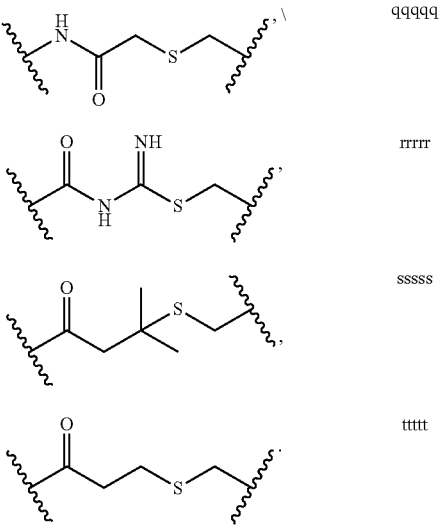

qqqqq rrrrr sssss ttttt

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. In certain embodiments, the amount of compound in compositions of this invention is such that it is effective to measurably inhibit one or both of ERK1 and ERK2, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of one or both of ERK1 and ERK2, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes.

Examples of kinases that are inhibited by the compounds and compositions described herein and against which the methods described herein are useful include one or both of ERK1 and ERK2, or a mutant thereof.

The activity of a compound utilized in this invention as an inhibitor of one or both of an ERK1 and ERK2 kinase, or a mutant thereof, may be assayed in vitro, in vivo or in a cell line. In vitro assays include assays that determine inhibition of either the phosphorylation activity and/or the subsequent functional consequences, or ATPase activity of one or both of activated ERK1 and ERK2 kinase, or a mutant thereof. Alternate in vitro assays quantitate the ability of the test compound to bind to one or both of ERK1 and ERK2. Test compound binding may be measured by radiolabeling the test compound prior to binding, isolating one or both of the compound/ERK1 complex and the compound/ERK2 complex, and determining the amount of radiolabel bound. Alternatively, test compound binding may be determined by running a competition experiment where test compounds are incubated with one or both of ERK1 and ERK2 kinase bound to known radioligands. Detailed conditions for assaying a compound utilized in this invention as an inhibitor of one or both of ERK1 and ERK2, or a mutant thereof, are also set forth in the Examples below.

Without wishing to be bound by any particular theory, it is believed that a provided compound comprising a warhead moiety is more effective at inhibiting one or both of ERK1 and ERK2, or a mutant thereof, as compared to a corresponding compound wherein the $R^1$ moiety of any of the formulae herein is instead a non-warhead group or is completely absent (i.e., is hydrogen). For example, a compound of any of the formulae herein is more effective at inhibition of one or both of ERK1 and ERK2, or a mutant thereof, as compared to a corresponding compound wherein the $R^1$ moiety of any of the formulae herein is instead a non-warhead moiety or is absent.

A provided compound comprising a warhead moiety, as disclosed above, is more potent with respect to an $IC_{50}$ against one or both of ERK1 and ERK2, or a mutant thereof, than a corresponding compound wherein the $R^1$ moiety of any of the formulae herein is instead a non-warhead moiety or is absent. Such comparative potency can be determined by standard time-dependent assay methods, such as those described in detail in the Examples section, infra. In certain embodiments, a compound of any of the formulae herein is measurably more potent than a corresponding compound of any of the formulae herein wherein the $R^1$ moiety is a non-warhead moiety or is absent. In some embodiments, a compound of any of the formulae herein is measurably more potent, wherein such potency is observed after about 1 minute, about 2 minutes, about 5 minutes, about 10 minutes, about 20 minutes, about 30 minutes, about 1 hour, about 2 hours, about 3 hours, about 4 hours, about 8 hours, about 12 hours, about 16 hours, about 24 hours, or about 48 hours, than a corresponding compound of any of the formulae herein wherein the $R^1$ moiety of formula is a non-warhead moiety or is absent. In some embodiments, a compound of any of the formulae herein is any of about 1.5 times, about 2 times, about 5 times, about 10 times, about 20 times, about 25 times, about 50 times, about 100 times, or even about 1000 times more potent than a corresponding compound of any of the formulae herein wherein the $R^1$ moiety is a non-warhead moiety or is absent.

ERK1 and ERK2 Kinase

As described generally above, the compounds of the invention are useful as inhibitors of ERK protein kinases. ERK is one of the key components in the RAS-RAF-MEK-ERK MAPK pathway. As a downstream target, ERK inhibitors are believed to be able to overcome drug resistance from K-RAS and B-RAF mutations, as well as toxicity from RAF and MEK inhibitors. Kinase selectivity was achieved through silencing the selective Cys in a combination of the interactions between the covalent inhibitors of the invention and unique amino acids in the ATP binding pocket. Targeting the selective Cys provides for prolonged pharmacodynamics in silencing ERK activity, as well as potential lower doses in cancer treatment, compared to reversible inhibitors.

In one embodiment, the compounds and compositions of the invention are inhibitors of one or both of ERK1 and ERK2 protein kinases and thus, without wishing to be bound by any particular theory, the compounds and compositions are particularly useful for treating or lessening the severity of a disease, condition, or disorder where activation of one or both of ERK1 and ERK2 protein kinases is implicated in the disease, condition, or disorder. When activation of one or both of ERK1 and ERK2 protein kinases is implicated in a particular disease, condition, or disorder, the disease, condition, or disorder may also be referred to as "a disease, disorder, or condition mediated by one or both of ERK1 and ERK2", or alternatively as an "ERK1- or ERK2-mediated disease", condition, or disease symptom. Accordingly, in another aspect, the present invention provides a method for treating or lessening the severity of a disease, condition, or disorder where activation of one or both of ERK1 and ERK2 protein kinases is implicated in said disease, condition, or disorder.

The activity of a compound utilized in this invention as an inhibitor of one or both of ERK1 and ERK2 protein kinases may be assayed in vitro, in vivo or in a cell line. In vitro assays include assays that determine inhibition of either the phosphorylation activity or ATPase activity of one or both of activated ERK1 and ERK2 protein kinases. Alternate in vitro assays quantitate the ability of the test compound to bind to one or both of ERK1 and ERK2 protein kinases. Test compound binding may be measured by radiolabelling the test compound prior to binding, isolating one or both of the test compound/ERK1 complex and test compound/ERK2 complex, and determining the amount of radiolabel bound. Alternatively, test compound binding may be determined by running a competition experiment where new test compounds are incubated with one or both of ERK1 and ERK2 protein kinases bound to known radioligands. Detailed conditions for assaying a compound utilized in this invention as an inhibitor of one or both of ERK1 and ERK2, or a mutant thereof, are also set forth in the Examples below.

The term "measurably inhibit", as used herein means a measurable change in one or both of ERK1 and ERK2 protein kinase activity between a sample comprising said composition, and one or both of an ERK1 and ERK2 protein kinase and an equivalent sample comprising one or both of ERK1 and ERK2 protein kinase in the absence of said composition. Such measurements of protein kinase activity are known to one of ordinary skill in the art and include those methods set forth herein below.

According to another embodiment, the invention relates to a method of inhibiting one or both of ERK1 and ERK2 protein kinase activity in a patient comprising the step of administering to said patient a compound of the present invention, or a composition comprising said compound.

Diseases, disorders, or conditions treated by the compounds of the invention include cancer, an autoimmune disorder, a neurodegenerative or neurological disorder, liver disease, a cardiac disorder, schizophrenia, or a bone-related disorder, and are referred to herein as an ERK1- and/or ERK2-mediated disease, disorder, or condition.

Specifically, the present invention relates to a method of treating or lessening the severity of a disease, disorder, or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein the method comprises administering to a patient in need thereof a composition according to the present invention. In certain embodiments, the cancer is a MAPK-mediated cancer.

In certain embodiments, the disease, disorder, or condition mediated by one or both of ERK1 and ERK2 includes, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. In some embodiments, the the ERK1- and/or ERK2-mediated disease, disorder, or condition is a cancer selected from breast, ovary, cervix, prostate, testis, genitourinary tract, esophagus, larynx, glioblastoma, neuroblastoma, stomach (gastric), skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. In some embodiments, a leukemia is an acute leukemia. In certain embodiments, a leukemia is acute myeloid leukemia. In some embodiments, a leukemia is an acute leukemia. In certain embodiments, a leukemia is acute lymphoblastic leukemia. According to another embodiment, the present invention relates to a method of treating a cancer selected from breast, ovary, cervix, prostate, testis, genitourinary tract, esophagus, larynx, glioblastoma, neuroblastoma, stomach (gastric), skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. In some embodiments, the present invention relates to a method of treating CNS tumors. In certain embodiments, a CNS tumor is a glioblastoma or glioblastoma multiforme (GBM). In some embodiments, the present invention relates to a method of treating stomach (gastric) and esophageal tumors and cancers.

In some embodiments, the ERK1- and/or ERK2-mediated disease, disorder, or condition is a cancer selected from carcinoma, lymphoma, blastoma, sarcoma, and leukemia. In some embodiments, a sarcoma is a soft tissue sarcoma. In some embodiments, a lymphoma is non-hodgkins lymphoma. More particular examples of such cancers include adenocarcinoma; adenoma; adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophogeal cancer; eye cancer; follicular carcinoma; gallbladder cancer; gastrointestinal cancer; cancer of the genitourinary tract; glioblastoma; hairy cell carcinoma; various types of head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, small-cell lung cancer, squamous carcinoma of the lung, non-small cell lung cancer; melanoma and nonmelanoma skin cancer; lymphoid disorders; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, chronic lymphocytic leukemia (CLL), hypereosinophilic syndrome, systematic mast cell disease, atypical CML, or juvenile myelomonocytic leukemia; multiple myeloma; neuroblastoma; ovarian cancer; papillary carcinoma; pancreatic cancer; cancer of the peritoneum; prostate cancer, including benign prostatic hyperplasia; rectal cancer; salivary gland carcinoma; sarcoma; seminoma; squamous cell cancer; small cell carcinoma; cancer of the small intestine; stomach cancer; testicular cancer; thyroid cancer; undifferentiated carcinoma; and vulval cancer. In particular embodiments, the treated cancer is melanoma, breast cancer, colon cancer, or pancreatic cancer.

In certain embodiments, the cancer is selected from the group consisting of: melanoma, pancreatic cancer, thyroid cancer, colorectal cancer, lung cancer, breast cancer, ovarian cancer, and leukemia. In some embodiments, a leukemia is an acute leukemia. In certain embodiments, a leukemia is acute myeloid leukemia. In some embodiments, a leukemia is an acute leukemia. In certain embodiments, a leukemia is acute lymphoblastic leukemia.

In certain embodiments, the invention provides a method for overcoming drug resistance to Raf and Mek inhibitors, comprising the step of administering to said patient an inhibitor compound of one or both of ERK1 and ERK2.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which changes decrease or abolish the inhibitory effect of the inhibitor on the target protein.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting one or both of ERK 1 and ERK2 kinase, or a mutant thereof, activity in a biological sample comprising the step of contacting said biological sample with a compound of this invention, or a composition comprising said compound. In certain embodiments, the invention relates to a method of irreversibly inhibiting one or both of ERK1 and ERK2 kinase, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or both of ERK1 and ERK2, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or both of ERK1 and ERK2 kinase, or a mutant thereof, activity in a patient comprising the step of administering to said patient a compound of the present invention, or a composition comprising said compound. According to certain embodiments, the invention relates to a method of irreversibly inhibiting one or both of ERK1 and ERK2 kinase, or a mutant thereof, activity in a patient comprising the step of administering to said patient a compound of the present invention, or a composition comprising said compound. In certain embodiments, the activity is inhibited irreversibly by covalently modifying Cys 183 of ERK1. In certain embodiments, the activity is inhibited irreversibly by covalently modifying Cys 166 of ERK2. In certain embodiments, the activity is inhibited irreversibly by covalently modifying Cys 183 of ERK1 and Cys 166 of ERK2. In other embodiments, the present invention provides a method for treating a disease, disorder, or condition mediated by one or both of ERK1 and ERK2 kinase, or a mutant thereof, in a patient in need thereof, comprising the step of administering to said patient a compound according to the present invention or pharmaceutically acceptable composition thereof. Such disorders are described in detail herein.

5. Probe Compounds

In certain aspects, a compound of the present invention is tethered to a detectable moiety to form a probe compound. In one aspect, a probe compound of the invention comprises an irreversible protein kinase inhibitor of any formulae as described herein, a detectable moiety, and a tethering moiety that attaches the inhibitor to the detectable moiety.

In some embodiments, such probe compounds of the present invention comprise a provided compound of any formulae as described herein, tethered to a detectable moiety, $R^P$, by a bivalent tethering moiety, $-T^P-$. In certain embodiments, a provided probe compound is selected from any of following formulae:

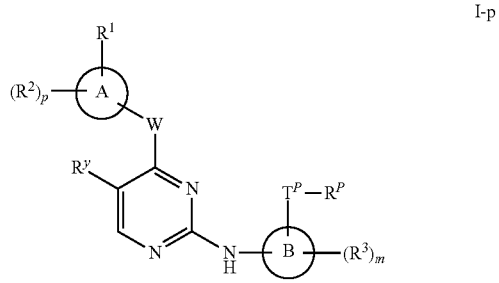

I-a-p
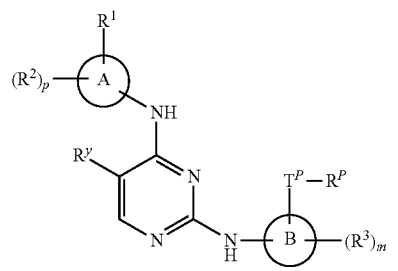
I-b-p
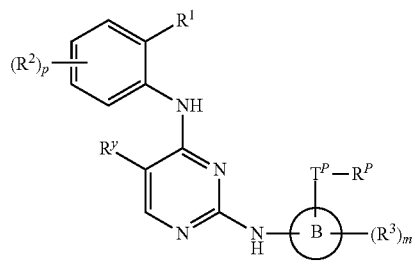
I-c-p
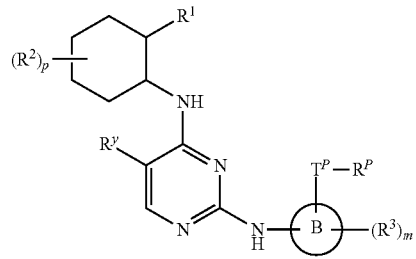
I-d-p
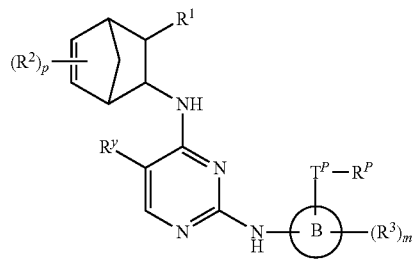
I-e-p
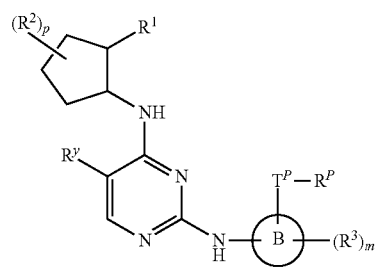
I-f-p
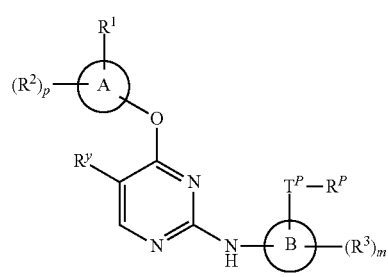
I-g-p
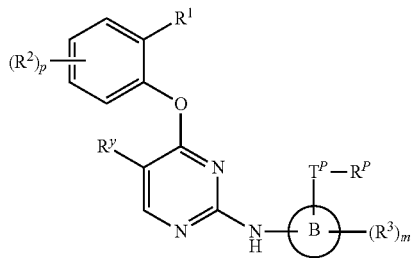
I-h-p
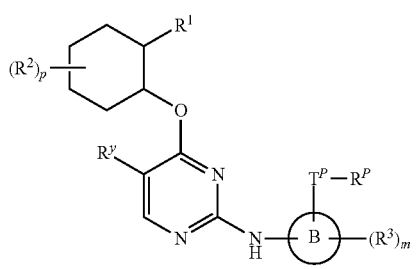
I-j-p
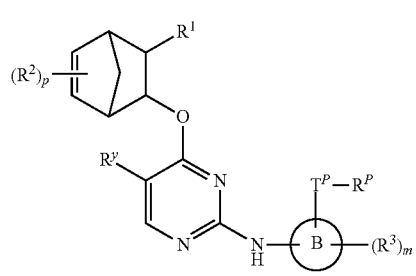
I-k-p
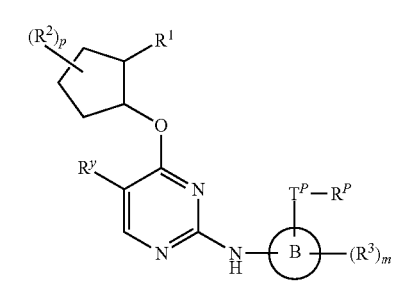
II-p
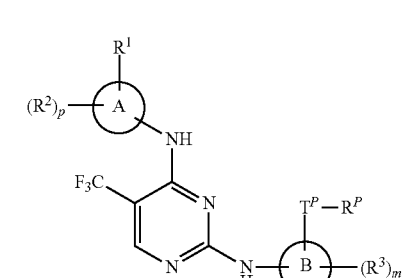
III-p
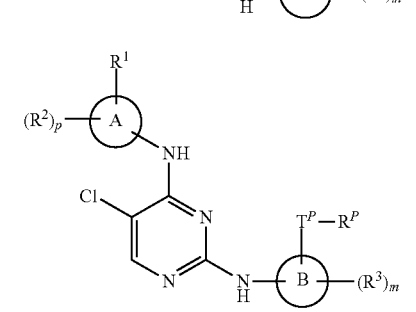

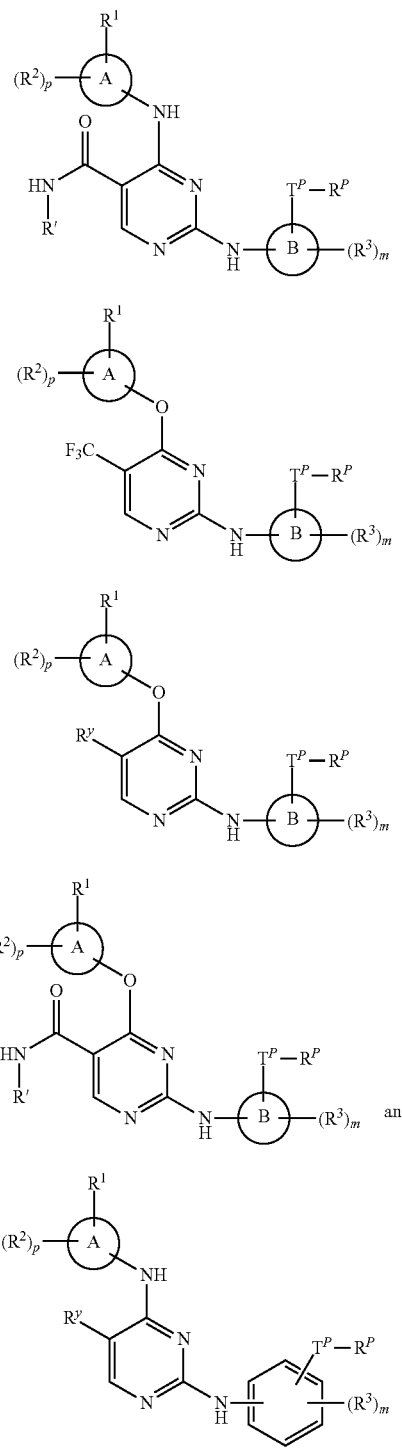

wherein each of Ring A, Ring B, $R^1$, $R^2$, $R^3$, $R^y$, W, m and p, with respect to the formulae above, is as defined and described in embodiments herein, $T^P$ is a bivalent tethering moiety; and $R^P$ is a detectable moiety. In some embodiments, when Ring A is a five or six member ring, then $R^1$ is attached to an atom adjacent to where W, N, or O is attached.

In some embodiments, $R^P$ is a detectable moiety selected from a primary label or a secondary label. In certain embodiments, $R^P$ is a detectable moiety selected from a fluorescent label (e.g., a fluorescent dye or a fluorophore), a mass-tag, a chemiluminescent group, a chromophore, an electron dense group, or an energy transfer agent.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or $^{131}I$), mass-tags are stable isotopes (e.g., $^{13}C$, $^{2}H$, $^{17}O$, $^{18}O$, $^{15}N$, $^{19}F$, and $^{127}I$), positron emitting isotopes (e.g., $^{1}C$, $^{18}F$, $^{13}N$, $^{124}I$, and $^{15}O$), and fluorescent labels, which are signal generating reporter groups which can be detected without further modifications. Detectable moieties are analyzed by methods. Exemplary methods are fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate includes streptavidin-enzyme conjugates. For antigen labels, secondary intermediates include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, —N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) are also used as mass-tags. Stable isotopes (e.g., $^{13}C$, $^{2}H$, $^{17}O$, $^{18}O$, and $^{15}N$) are also used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety is attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties are directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-R$^r$ moiety. As used herein, "click ready" refers to a moiety containing an azide or alkyne for use in a click chemistry reaction. In some embodiments, the click ready inhibitor moiety comprises an azide. In certain embodiments, the click ready -T-R$^r$ moiety comprises a strained cyclooctyne for use in a copper-free click chemistry reaction (for example, using methods described in Baskin et al., Proc. Natl. Acad. Sci. USA 2007, 104, 16793-16797).

In some embodiments, the detectable moiety, R$^P$, is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, R$^P$ is biotin or an analog thereof. In certain embodiments, R$^P$ is biotin. In certain other embodiments, R$^P$ is biotin sulfoxide.

In another embodiment, R$^P$ is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -T$^P$-, that attaches the irreversible inhibitor to the detectable moiety. As used herein, the term "tether" or "tethering moiety" refers to any bivalent chemical spacer. Exemplary tethers are a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -T$^P$-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, —NO$_2$, alkyl, S(O), and S(O)$_2$. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -T$^P$-, such as a water soluble polymer is coupled at one end to a provided irreversible inhibitor and to a detectable moiety, R$^t$, at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -T$^P$-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form. Exemplary forms are linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range. Exemplary ranges are between about 100 Da and about 100,000 Da or more. In yet further embodiments, the molecular weight of the polymer is between about 100 Da and about 100,000 Da, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da. Exemplary ranges are about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

One of ordinary skill in the art will appreciate that when -$T^P$-$R^P$ is attached to a compound of the formulae herein.

In certain embodiments, the tethering moiety, -$T^P$-, has one of the following structures:

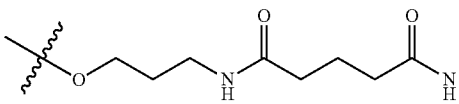

In some embodiments, the tethering moiety, -$T^P$-, has the following structure:

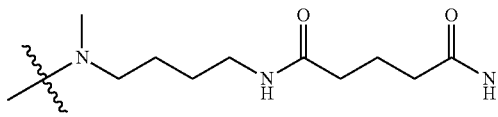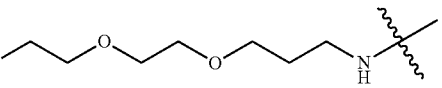

In other embodiments, the tethering moiety, -$T^P$-, has the following structure:

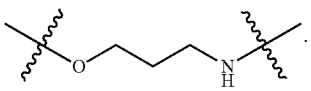 [SMILES: *NCCCO*]

In certain other embodiments, the tethering moiety, -$T^P$-, has the following structure:

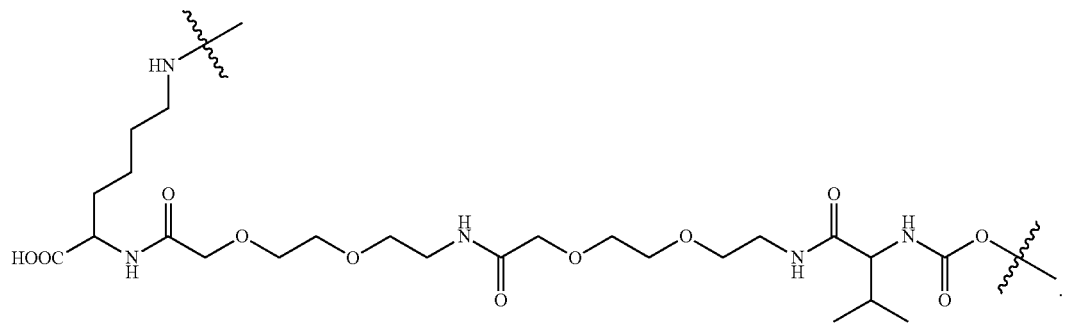 [SMILES: *NCCCCC(NC(=O)COCCOCCNC(=O)COCCOCCNC(=O)C(NC(=O)O*)C(C)C)C(=O)O]
In yet other embodiments, the tethering moiety, -T$^P$-, has the following structure:
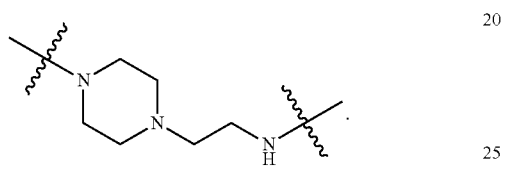
In some embodiments, the tethering moiety, -T$^P$-, has the following structure:
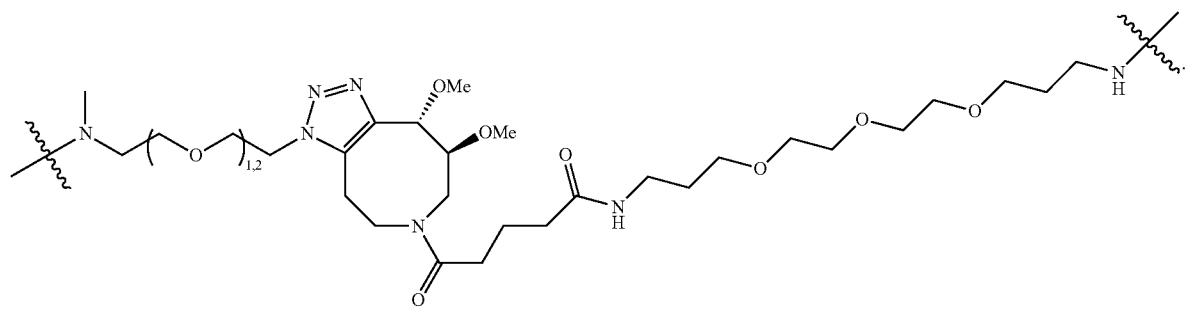
In some embodiments, -T$^P$-R is of the following structure:
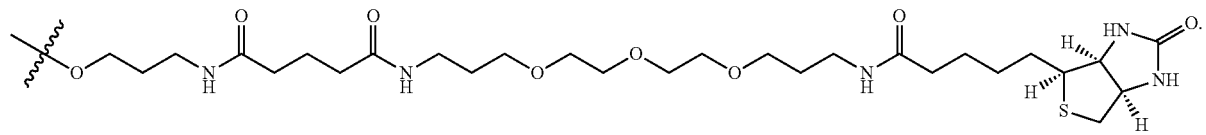 [SMILES: *OCCCNC(=O)CCCC(=O)NCCCOCCOCCOCCCNC(=O)CCCC[C@@H]1SC[C@@H]2NC(=O)N[C@@H]21]
In other embodiments, -T$^P$-R$^P$ is of the following structure:
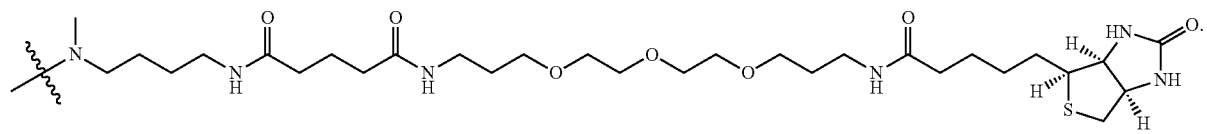 [SMILES: *N(C)CCCCNC(=O)CCCC(=O)NCCCOCCOCCOCCCNC(=O)CCCC[C@@H]1SC[C@@H]2NC(=O)N[C@@H]21]
In certain embodiments, -T$^P$-R$^P$ is of the following structure:

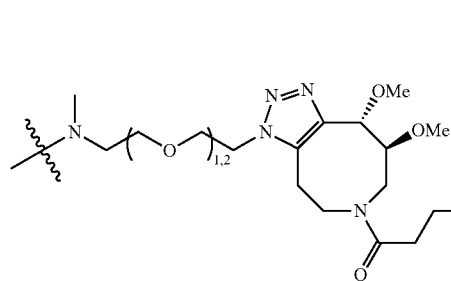
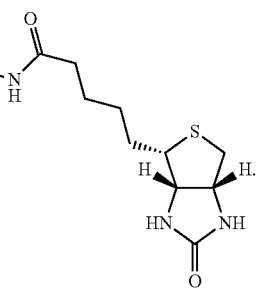
In some embodiments, a probe compound is derived from any compound described herein.
In certain embodiments, the probe compound is one of the following structures:
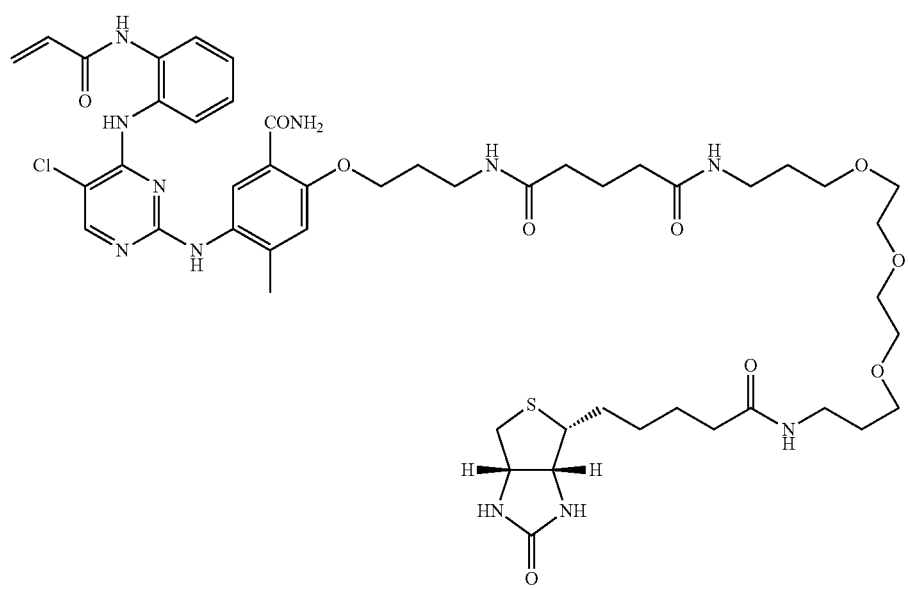
I-299
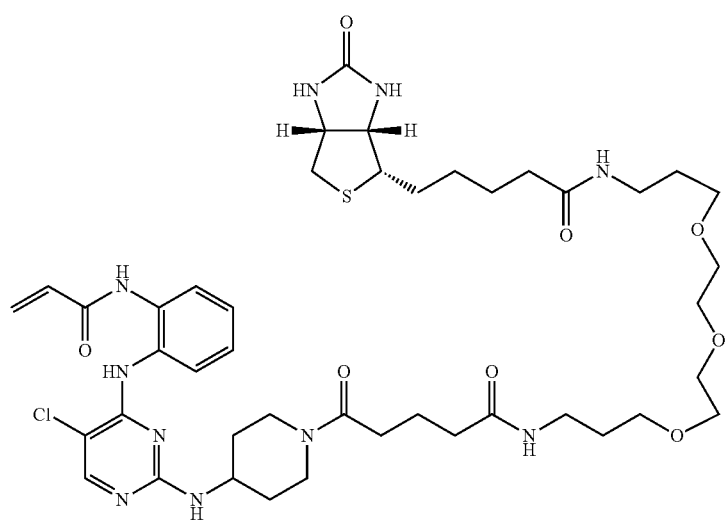
I-300

I-301
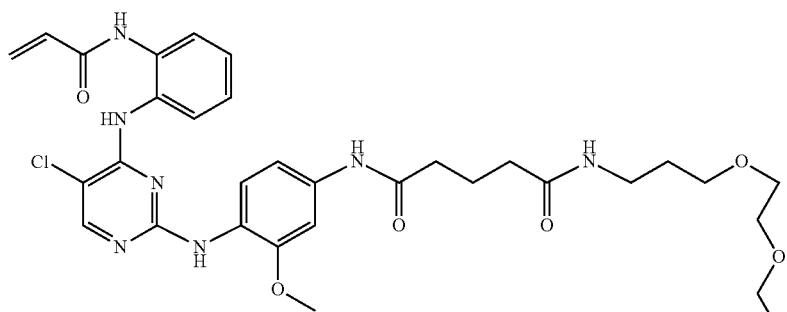
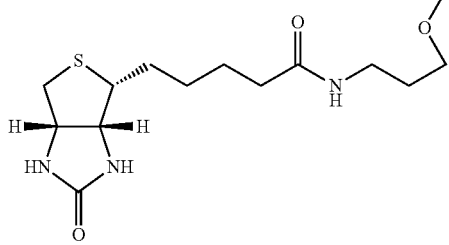
I-302
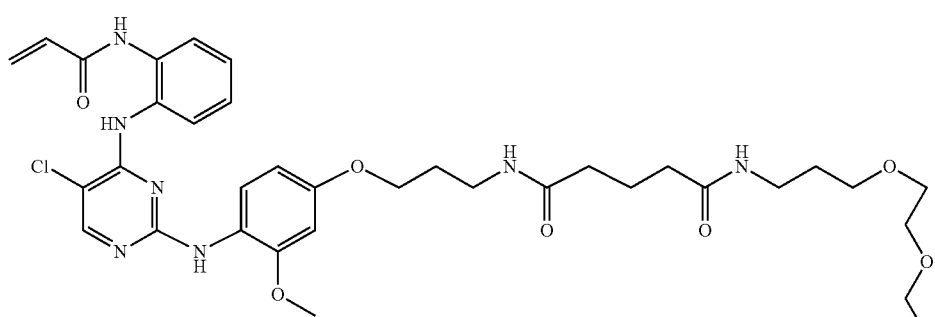
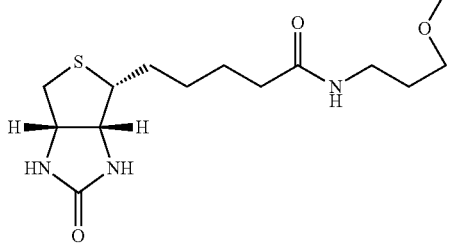
I-303
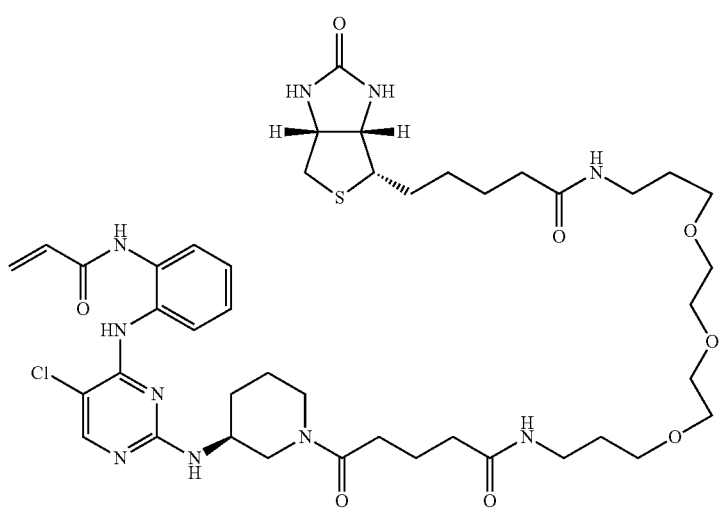

-continued

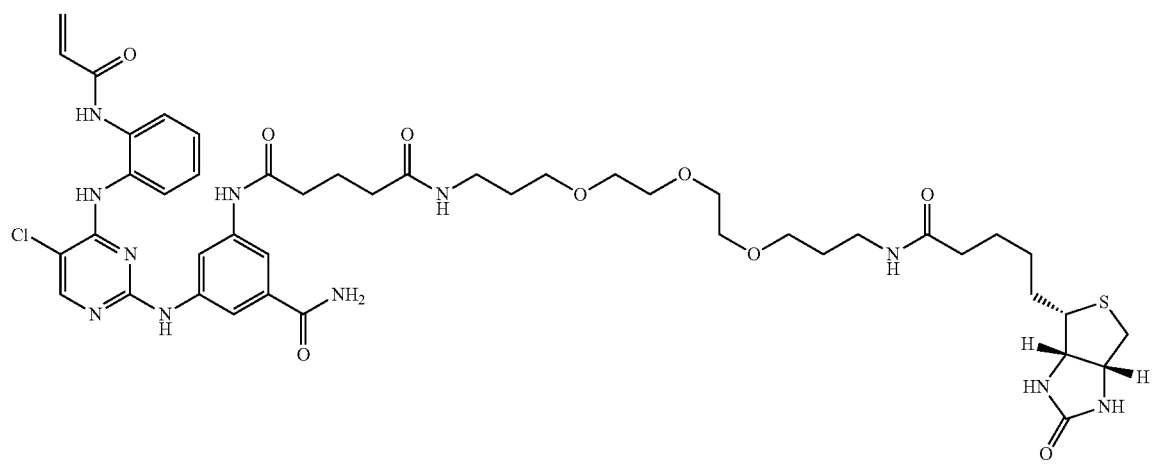
I-304

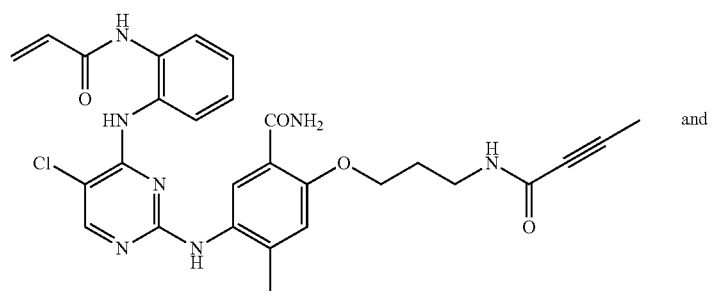
I-305 and

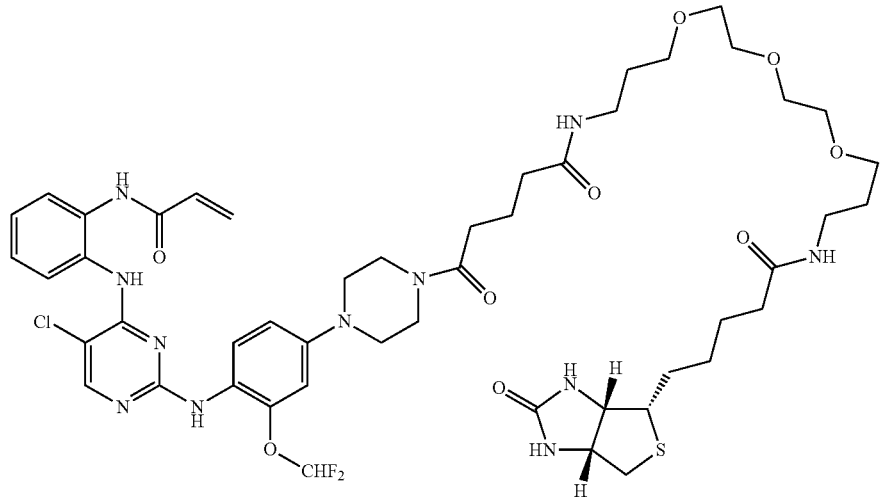
I-306

It will be appreciated that many -T^P-R^P reagents are commercially available. For example, numerous biotinylating reagents are available from, e.g., Thermo Scientific having varying tether lengths. Such reagents include NHS-PEG$_4$-Biotin and NHS-PEG$_{12}$-Biotin.

In some embodiments, analogous probe structures to the ones exemplified above are prepared using click-ready inhibitor moieties and click-ready -T^P-R^P moieties, as described herein.

In some embodiments, a provided probe compound covalently modifies a phosphorylated conformation of a protein kinase. In one aspect, the phosphorylated conformation of the protein kinase is either an active or inactive form of the protein kinase. In certain embodiments, the phosphorylated conformation of the protein kinase is an active form of said kinase. In certain embodiments, the probe compound is cell permeable.

In some embodiments, the present invention provides a method for determining occupancy of a protein kinase by a provided irreversible inhibitor (i.e., a compound of any of the formulae presented herein) in a patient, comprising providing one or more tissues, cell types, or a lysate thereof, obtained from a patient administered at least one dose of a compound of said irreversible inhibitor, contacting said tissue, cell type or lysate thereof with a probe compound to covalent modify at least one protein kinase present in said lysate, and measuring the amount of said protein kinase covalently modified by the probe compound to determine occupancy of said protein kinase by said compound as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is one or both of ERK1 and ERK2.

In some embodiments, the probe compound comprises the irreversible inhibitor for which occupancy is being determined.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In certain embodiments, the probe compound is detected by binding to avidin, streptavidin, neutravidin, or captavidin.

In some embodiments, the probe is detected by Western blot. In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying a one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of any of the formulae presented herein, wherein the assaying step comprises contacting said one or more tissues, cell types, or a lysate thereof, with a provided probe compound and measuring the amount of protein kinase covalently modified by the probe compound.

EXEMPLIFICATION

As depicted in the Examples below, in certain exemplary embodiments, compounds were prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Enantioenriched compounds of the invention were prepared in enantioenriched form using chiral starting materials, or were separated after reaction with a racemic starting material, using chiral chromatography. For compounds prepared as racemic or diastereomeric mixtures, the single isomers can be prepared in optically pure form by either employing chiral starting materials or performing chiral chromatography.

Compound numbers utilized in the Examples below correspond to compound numbers set forth the Tables provided, supra.

General Methods for Preparing Certain Intermediates

Scheme IA, below, depicts a general method for preparing certain intermediates for preparing compounds of formula I, wherein Ring A is phenyl and $R^2$ and p are as defined and described herein. At Step 1, intermediate i can be treated with acryloyl chloride (or other reagent suitable for introducing the acryloyl moiety) to form intermediate ii. As depicted in Step 2, the BOC protecting group can then be removed by treating ii with a suitable acid to form common intermediate iii. One of ordinary skill in the art will recognize that the depicted BOC protecting group can be replaced with other suitable amine protecting groups and then removed via suitable deprotection methods known in the art.

Scheme IA:

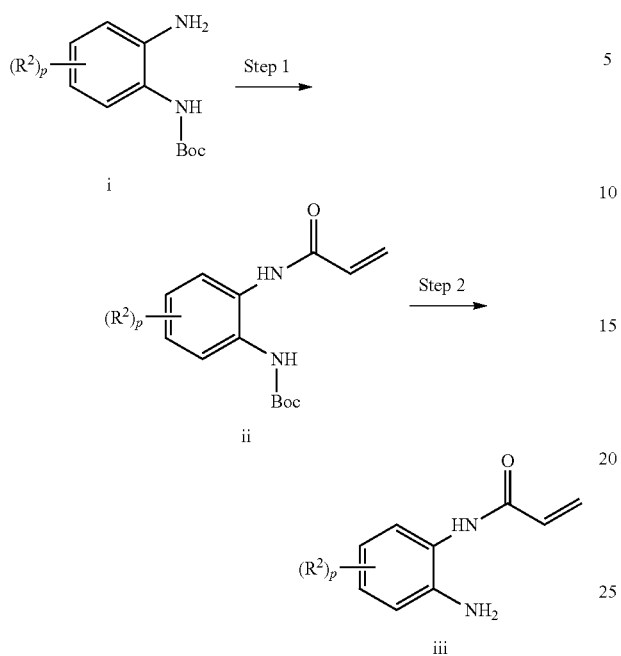

Scheme IB, below, depicts an alternate general method for preparing certain intermediates for preparing compounds of formula I, wherein Ring A is phenyl and $R^2$ and p are as defined and described herein. At Step 1, intermediate iv can be treated with acryloyl chloride (or other reagent suitable for introducing the acryloyl moiety) to form intermediate v. At Step 2, the nitro moiety of intermediate v can then be reduced to an amine to form common intermediate iii. One of ordinary skill in the art will recognize that the reduction step can be achieved in a variety of ways, including treatment of intermediate v with Zn/NH$_4$Cl to form common intermediate iii.

Scheme IB:

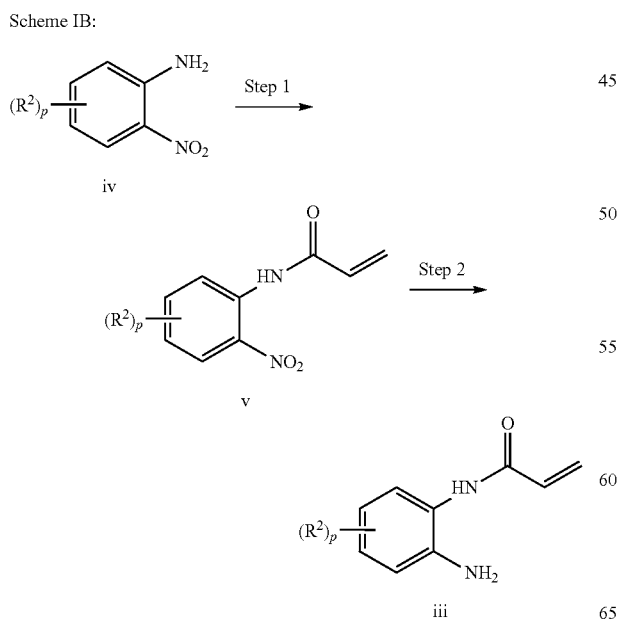

Method A was used to first introduce aliphatic cyclic amine at the C-2 position of 5-CF$_3$-2,4-dichloropyrimidine, followed by introduction of warhead-bearing intermediates at the C-4 position. The general synthetic approach is depicted in Example 1 below.

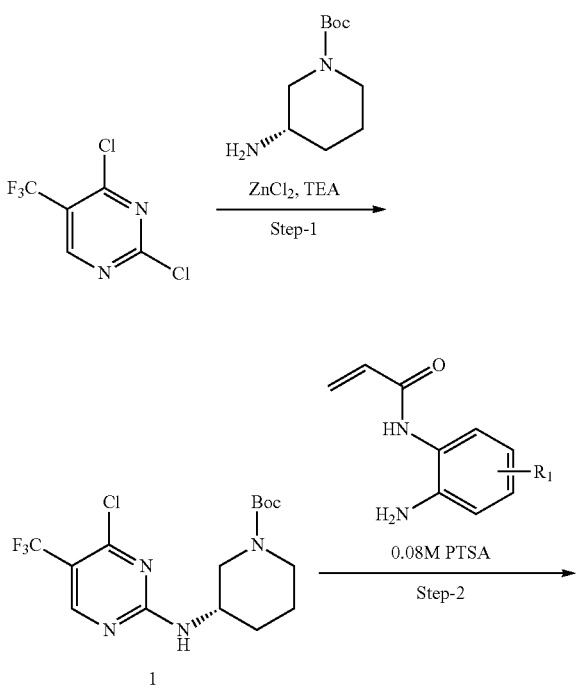

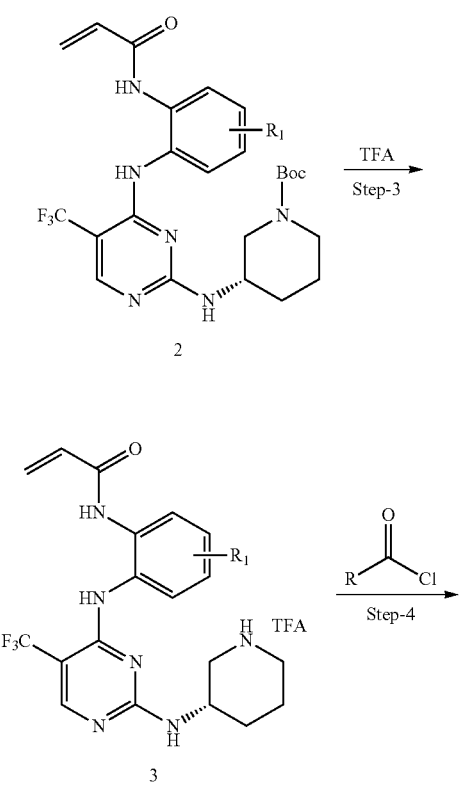

-continued

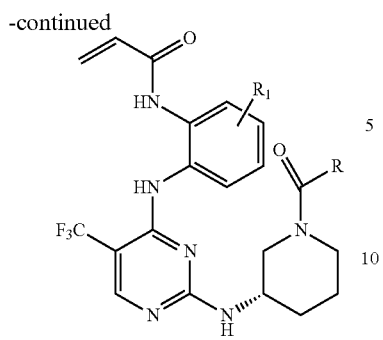

Example 1

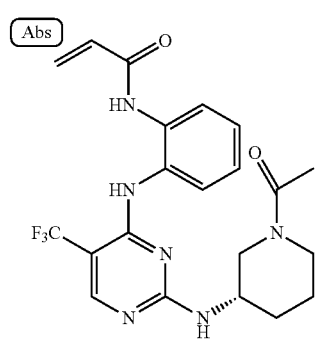

(S)—N-(2-(2-(1-acetylpiperidin-3-ylamino)-5-(trifluoromethyl)pyrimidin-4-ylamino)phenyl)acrylamide The title compound was prepared according to the steps and intermediates as described below.

Step 1: (S)-tert-butyl 3-((4-chloro-5-(trifluoromethyl)pyrimidin-2-yl)amino)piperidine-1-carboxylate (Intermediate 1)

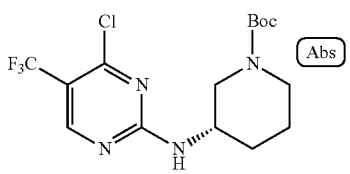 [SMILES: CC(C)(C)OC(=O)N1CCC[C@H](Nc2ncc(C(F)(F)F)c(Cl)n2)C1]

To a solution of 2,4-dichloro-5-(trifluoromethyl)pyrimidine (5 g, 23 mmol) in dichloroethane: t-butanol (50 ml, 1:1) was added dry zinc chloride (3.7 g, 27 mmol) and triethylamine (2.52 g, 25 mmol), and the mixture was stirred at rt for 1 h (pH should not be >7). To this mixture, (S)-tert-butyl 3-aminopiperidine-1-carboxylate (4.9 g, 25 mmol) was added and stirring continued at rt for 16 h. TLC showed formation of the major compound (0.2 Rf) and a minor other isomer (0.25 Rf) and ~10% starting material in 15% EtOAc: hexane solvent system. Solvents were evaporated, and crude was diluted with ice cold water (50 mL) and stirred for 5 min at rt to get a pale yellow gummy mass. The crude pale yellow gummy mass (6 g) was taken in 60 mL hexane and stirred for 10 min at rt to get a solid which was immediately filtered to get the pure desired compound (5 g, 57%). MS m/z: 381.1 (ES+, M+H).

Step 2: (S)-tert-butyl 3-(4-(2-acrylamidophenylamino)-5-(trifluoromethyl)pyrimidin-2-ylamino)piperidine-1-carboxylate (Intermediate 2)

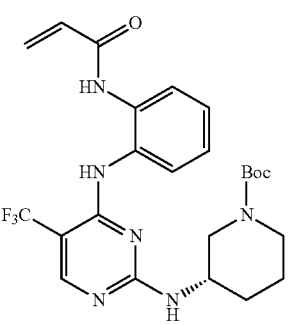 [SMILES: C=CC(=O)Nc1ccccc1Nc1nc(N[C@H]2CCCN(C(=O)OC(C)(C)C)C2)ncc1C(F)(F)F]

To a solution of (S)-tert-butyl 3-((4-chloro-5-(trifluoromethyl)pyrimidin-2-ylamino)piperidine-1-carboxylate (3.5 g, 9.21 mmol) in 0.04 M PTSA in 1,4-dioxane (50 ml) was added N-(2-aminophenyl)acrylamide (2.79 g, 10.13 mmol, TFA salt), and the mixture was stirred at rt for 16 h. TLC showed completion of starting material. (TLC system: 5% methanol in dichloromethane, $R_f$=0.3). 1,4-dioxane was evaporated, and the crude was diluted with water (2×30 mL), extracted with ethyl acetate (50 mL), and washed with saturated sodium bicarbonate solution (2×20 mL). The organic layer was dried over sodium sulfate and concentrated to the crude (4.7 g), which was purified by silica gel column chromatography using 1% MeOH/DCM as eluents to obtain the title compound as a off white solid (3 g, 64%). MS m/z: 507.3 (ES+, M+H).

Step 3: (S)—N-(2-(2-(piperidin-3-ylamino)-5-(trifluoromethyl)pyrimidin-4-ylamino) phenyl)acrylamide (Intermediate 3)

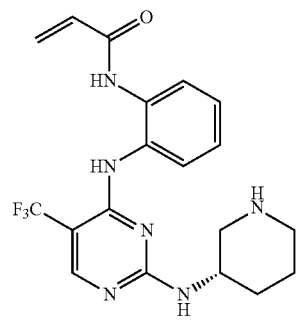 [SMILES: C=CC(=O)Nc1ccccc1Nc1nc(N[C@H]2CCCNC2)ncc1C(F)(F)F]

To a solution of (S)-tert-butyl 3-(4-(2-acrylamidophenylamino)-5-(trifluoromethyl)pyrimidin-2-ylamino)piperidine-1-carboxylate (3 g) in DCM (30 ml) was added trifluoroacetic acid (5 ml) at 0° C. for 10 min and stirred at rt for 2 h. TLC showed completion of starting material. (TLC system: 15% methanol in dichloromethane, $R_f$=0.2). The reaction mixture was concentrated, and the crude was codistilled with DCM (3×20 mL) and washed with diethyl ether (2×10 mL) to obtain (S)—N-(2-(2-(piperidin-3-ylamino)-5-(trifluoromethyl) pyrimidin-4-ylamino)phenyl)acrylamide as an off white solid. (3 g, 97%). MS: m/z=407.1 (ES+, M+H).

Step 4: (S)—N-(2-(2-(1-acetylpiperidin-3-ylamino)-5-(trifluoromethyl)pyrimidin-4-ylamino)phenyl)acrylamide

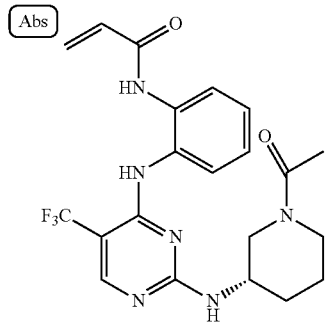 [SMILES: C=CC(=O)Nc1ccccc1Nc1nc(N[C@H]2CCCN(C(C)=O)C2)ncc1C(F)(F)F]

To a solution of intermediate 3 (1.5 g, 2.88 mmol) in DCM (15 ml) was added triethylamine (0.291 g, 8.653 mmol) and acetyl chloride (0.216 g, 2.884 mmol) at 0° C., and the mixture was stirred at rt for 30 min. TLC showed completion of starting material. (TLC System: 5% Methanol in dichloromethane ($R_f$=0.4). [Alternatively, acetic anhydride was used in place of acetyl chloride to provide the title compound.] The reaction mixture was diluted with water (2×30 mL), and extracted with DCM (2×30 mL). The organic layer was dried over sodium sulphate and concentrated to get the crude compound (1.1 g) which was purified by prep-HPLC to obtain the desired compound (430 mg, 35%). MS m/z: 449.6 (ES+, M+1). $^1$H NMR (400 MHz, DMSO-$d_6$) δ 1.21-1.27 (m, 1H), 1.38-1.67 (m, 2H), 1.67-1.70 (t, 1H), 1.83-1.89 (br s, 1H), 1.94-1.96 (d, 1H, J=8.01 Hz), 2.01 (s, 1H), 2.64-2.68 (m, 1H), 2.86-2.96 (m, 1H), 3.49-3.59 (m, 1H), 3.62-3.96 (m, 1H), 3.96-4.14 (m, 1H), 5.78-5.80 (d, 1H, J=10.1 Hz), 6.27-6.31 (d, 1H, J=16.9 Hz), 6.40-6.50 (dd, 1H), 7.18-7.29 (m, 3H), 7.42-7.48 (m, 1H), 7.7-7.8 (m, 1H), 8.14-8.24 (m, 1H), 8.20 (s, 2H), 10.30 (s, 1H).

Example 2

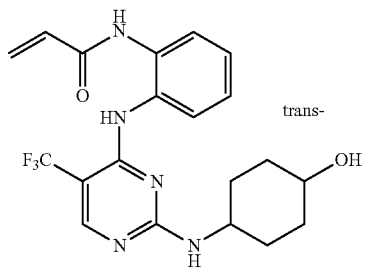

Trans-N-(2-((2-((4-hydroxycyclohexyl)amino)-5-(trifluoromethyl)pyrimidin-4-yl)amino)phenyl)acrylamide Compound I-1 was prepared in a manner similar to Example 1, substituting trans-4-aminocyclohexanol for (S)-tert-butyl 3-aminopiperidine-1-carboxylate. MS m/z: 422.2 (ES+, M+H). $^1$H NMR (DMSO-$d_6$) δ 1.01-1.07 (m, 2H), 1.15-1.22 (m, 4H), 1.74 (br s, 4H), 4.47-4.48 (d, 1H), 5.78-5.81 (d, 1H, J=10.1 Hz), 6.27-6.32 (d, 1H, J=17 Hz), 6.42-6.46 (dd, 1H, J=6.8 Hz and J=17 Hz), 7.20-7.27 (m, 3H), 7.36-7.38 (d, 1H, J=7.1 Hz), 7.74-7.76 (m, 1H), 8.11 (s, 2H), 10.31 (s, 1H).

Example 3

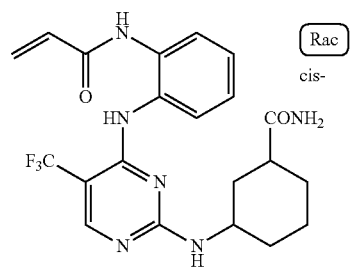

Rac-cis-3-((4-((2-acrylamidophenyl)amino)-5-(trifluoromethyl)pyrimidin-2-yl)amino)cyclohexanecarboxamide Compound I-2 was prepared in a manner similar to Example 1, substituting cis-3-aminocyclohexanecarboxamide for (S)-tert-butyl 3-aminopiperidine-1-carboxylate: MS m/z 449.2 (ES+, M+H). $^1$H NMR (DMSO-$d_6$) δ 1.0-1.3 (m, 5H), 1.50-1.78 (m, 4H), 2.0 (t, 1H), 3.40 (s, 1H), 5.77-5.81 (m, 1H), 6.28-6.32 (m, 1H), 6.42-6.49 (m, 1H), 6.62-6.65 (d, 1H, J=11.8 Hz), 7.13-7.23 (m, 2H), 7.25-7.29 (m, 2H), 7.47-7.49 (d, 1H, J=7.78 Hz), 7.74-7.46 (d, 1H, J=7.82 Hz), 8.12 (s, 1H), 10.3 (s, 1H).

Example 4

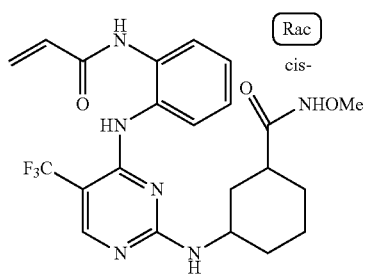

Rac-cis-3-((4-((2-acrylamidophenyl)amino)-5-(trifluoromethyl)pyrimidin-2-yl)amino)-N-methoxycyclohexanecarboxamide Compound I-3 was prepared in a manner similar to Example 1, substituting cis-3-amino-N-methoxycyclohexanecarboxamide for (S)-tert-butyl 3-aminopiperidine-1-carboxylate. MS m/z: 479.4 (ES+, M+H). $^1$H NMR (CD$_3$OD) δ 1.31-1.43 (m, 5H), 1.71-1.74 (d, 1H, J=9 Hz), 1.82-2.05 (m, 4H), 3.38 (m, 1H), 3.63 (s, 3H), 3.86-3.88 (m, 1H), 5.82-5.84 (d, 1H, J=8 Hz), 6.39-6.46 (m, 2H), 7.28-7.39 (m, 3H), 7.73-7.74 (d, 1H, J=6.98 Hz), 8.08 (s, 1H).

Example 5

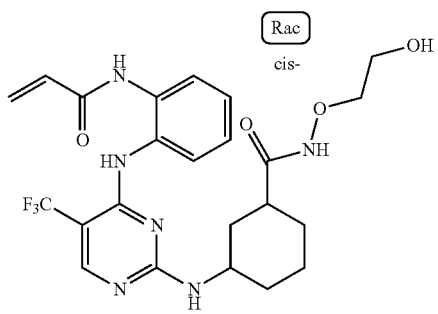

Rac-cis-3-((4-((2-acrylamidophenyl)amino)-5-(trifluoromethyl)pyrimidin-2-yl)amino)-N-(2-hydroxyethoxy)cyclohexanecarboxamide Compound I-4 was prepared in a manner similar to Example 1, substituting cis-3-amino-N-(2-hydroxyethoxy)cyclohexanecarboxamide for (S)-tert-butyl 3-aminopiperidine-1-carboxylate. MS m/z: 509.2 (ES+, M+H). $^1$H NMR (CD$_3$OD) δ 1.20-1.23 (m, 1H), 1.31-1.44 (m, 4H), 1.41-1.44 (m, 1H), 1.73-1.75 (m, 2H), 1.91-1.96 (m, 4H), 1.96-2.0 (m, 1H), 3.79-3.82 (m, 2H), 3.88-3.98 (m, 2H), 5.82-7.83 (d, 1H, J=7.8 Hz), 6.43-6.46 (m, 2H), 7.28-7.39 (m, 3H), 7.73-7.74 (m, 1H), 8.08 (s, 1H).

Example 6

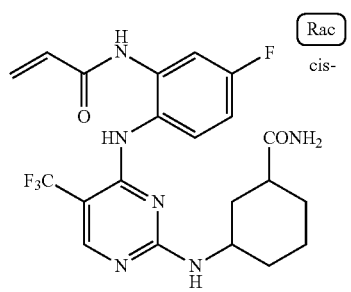

Rac-cis-3-((4-((2-acrylamido-4-fluorophenyl)amino)-5-(trifluoromethyl)pyrimidin-2-yl)amino)cyclohexanecarboxamide Compound I-5 was prepared in a manner similar to Example 1, substituting cis-3-aminocyclohexanecarboxamide for (S)-tert-butyl 3-aminopiperidine-1-carboxylate, and N-(2-amino-5-fluorophenyl)acrylamide for N-(2-aminophenyl)acrylamide. MS m/z: 467.5 (ES+, M+H). $^1$HNMR (DMSO-d$_6$) δ 1.08-1.14 (m, 1H), 1.16-1.23 (m, 2H), 1.23-1.29 (m, 2H), 1.66-1.74 (m, 4H), 1.97-2.01 (m, 1H), 5.78-5.82 (dd, 1H, J=1.6, 11.8 Hz), 6.25-6.31 (d, 1H, J=6.6, 15 Hz), 6.42-6.49 (dd, 1H, J=10, 16.8 Hz), 6.62-6.64 (d, 1H, J=10.3 Hz), 7.08-7.16 (m, 2H), 7.26-7.29 (dd, 1H, J=2.8, 10 Hz), 7.45-7.47 (d, 1H, J=7.7 Hz), 7.61-7.67 (m, 1H), 8.0 (s, 1H), 10.20 (s, 1H).

Example 7

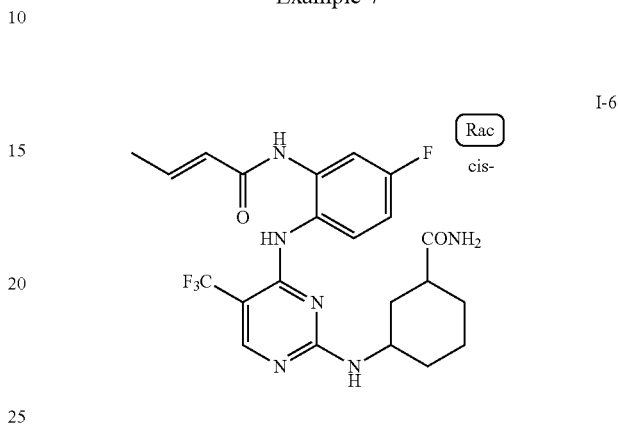

Rac-(E)-3-((4-((2-(but-2-enamido)-4-fluorophenyl)amino)-5-(trifluoromethyl) pyrimidin-2-yl)amino)-cis-cyclohexanecarboxamide Compound I-6 was prepared in a manner similar to Example 1, substituting cis-3-aminocyclohexanecarboxamide for (S)-tert-butyl 3-aminopiperidine-1-carboxylate, and (E)-N-(2-amino-5-fluorophenyl)but-2-enamide for N-(2-aminophenyl)acrylamide. MS m/z: 481.4 (ES+, M+H). $^1$H NMR (DMSO-d$_6$) δ 0.98-1.18 (m, 3H), 1.23-1.32 (m, 2H), 1.65-1.74 (m, 4H), 1.85-1.87 (d, 3H, J=6.6 Hz), 2.01-2.11 (m, 1H), 6.12-6.16 (d, 1H, J=15.4 Hz), 6.62-6.64 (d, 1H, J=11.Hz), 6.83-6.87 (m, 1H), 7.05-7.16 (m, 3H), 7.22-7.24 (m, 1H), 7.44-7.46 (d, 1H, J=7.7 Hz), 7.62-7.65 (m, 1H), 8.11 (s, 1H), 9.99 (s, 1H).

Example 8

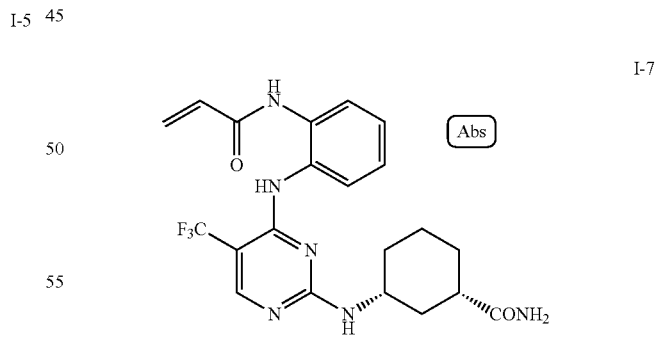

(1S,3R)-3-((4-((2-acrylamidophenyl)amino)-5-(trifluoromethyl)pyrimidin-2-yl) amino)cyclohexanecarboxamide Compound I-7 was prepared in a manner similar to Example 1, substituting (1S,3R)-3-aminocyclohexanecarboxamide for (S)-tert-butyl 3-aminopiperidine-1-carboxylate. MS m/z: 449.2 (ES+, M+H).

Example 9

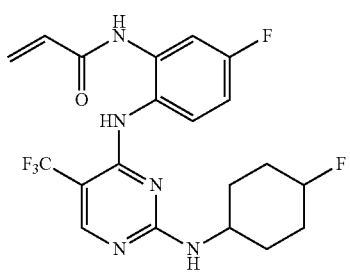

I-8

N-(5-fluoro-2-((2-((cis-4-fluorocyclohexyl)amino)-5-(trifluoromethyl)pyrimidin-4-yl)amino)phenyl)acrylamide Compound I-8 was prepared in a manner similar to Example 1, substituting cis-4-fluorocyclohexanamine for (S)-tert-butyl 3-aminopiperidine-1-carboxylate, and N-(2-amino-5-fluorophenyl)acrylamide for N-(2-aminophenyl)acrylamide. MS m/z: 442.5 (ES+, M+H). $^1$H NMR (DMSO-$d_6$) δ 1.3-1.6 (m, 6H), 1.82-1.85 (br s, 2H), 4.67 (s, 0.5H), 4.79 (s, 0.5H), 5.79-5.81 (dd, J=1.5, 10.2 Hz, 1H), 6.28 (d, J=17.1 Hz, 1H), 6.42-6.49 (dd, J=10.1, 17.0 Hz, 1H), 7.02-7.11 (m, 1H), 7.29-7.31 (dd, J=7.13, 9.75 Hz, 1H), 7.47 (d, J=7.1 Hz, 1H), 7.62-7.65 (m, 1H), 8.08 (s, 1H), 8.12 (s, 1H), 10.15 (br s, 1H).

Example 10

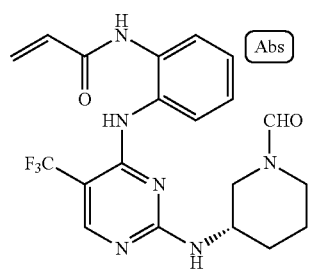

I-9

(S)—N-(2-((2-((1-formylpiperidin-3-yl)amino)-5-(trifluoromethyl)pyrimidin-4-yl)amino)phenyl)acrylamide Compound I-9 was prepared in a manner similar to Example 1, substituting formic acid, HATU, and DIPEA for acetic chloride in amide bond formation. MS m/z: 435.5 (ES+, M+H). $^1$H NMR (DMSO-$d_6$) δ 1.21-1.28 (m, 2H), 1.42-1.54 (m, 1H), 1.60-1.75 (m, 1H), 1.79-1.9 (m, 1H), 2.63-2.66 (m, 1H), 2.71-3 (m, 1H), 3.45-3.62 (m, 1H), 3.81-4 (m, 1H), 5.79 (d, J=11.0 Hz, 1H), 6.29 (d, J=17.0 Hz, 1H), 6.41-6.48 (dd, J=10.1, 16.9 Hz, 1H), 7.18-7.34 (m, 3H), 7.54-7.58 (m, 1H), 7.68-7.7 (m, 1H), 8.01-8.04 (m, 1H), 8.15-8.22 (m, 2H), 10.26-10.32 (m, 1H).

Example 11

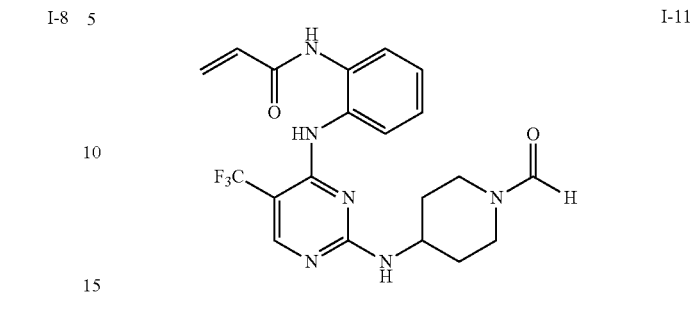

I-11

N-(2-((2-((1-formylpiperidin-4-yl)amino)-5-(trifluoromethyl)pyrimidin-4-yl)amino)phenyl)acrylamide Compound I-11 was prepared in a manner similar to Example 1, substituting tert-butyl-4-aminopiperidine-1-carboxylate for (S)-tert-butyl 3-aminopiperidine-1-carboxylate, and substituting formic acid, HATU, and DIPEA for acetic chloride in final amide bond formation step. MS m/z: 435.4 (ES+, M+H). $^1$H NMR (DMSO-$d_6$) δ 1.14-1.17 (m, 1H), 1.21-1.22 (m, 1H), 1.27-1.34 (m, 1H), 1.73-1.79 (m, 2H), 2.9 (t, J=13.9 Hz, 1H), 3.56 (m, 1H), 3.62-3.65 (d, J=12.8 Hz, 1H), 4.08 (d, J=12.7 Hz, 1H), 5.8 (d, J=10.0 Hz, 1H), 6.3 (d, J=16.9 Hz, 1H), 6.42-6.49 (dd, J=10.0, 16.9 Hz, 1H), 7.22 (d, J=6.8 Hz, 1H), 7.29 (d, J=7.2 Hz, 2H), 7.58 (d, J=6.8 Hz, 1H), 7.67-7.74 (dd, J=7.8, 21.4 Hz, 1H), 7.94 (s, 1H), 8.15-8.21 (m, 2H), 10.27 (d, J=14.5 Hz, 1H).

Example 12

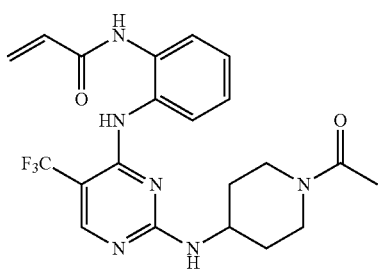

I-12

N-(2-((2-((1-acetylpiperidin-4-yl)amino)-5-(trifluoromethyl)pyrimidin-4-yl)amino)phenyl)acrylamide Compound I-12 was prepared in a manner similar to Example 1, substituting tert-butyl 4-aminopiperidine-1-carboxylate for (S)-tert-butyl 3-aminopiperidine-1-carboxylate. MS m/z: 449.5 (ES+, M+H). $^1$H NMR (DMSO-$d_6$) δ 1.1-1.4 (m, 2H), 1.69-1.77 (m, 2H), 1.95 (s, 3H), 2.40-2.43 (m, 1H), 2.88 (t, J=12.0 Hz, 1H), 3.5 (br s, 1H), 3.75 (d, J=12.8 Hz, 1H), 4.25 (t, J=13.8 Hz, 1H), 5.8 (d, J=10.1 Hz, 1H), 6.3 (d, J=17 Hz, 1H), 6.42-6.49 (dd, J=10.1, 16.9 Hz, 1H), 7.2-7.3 (m, 1H), 7.26-7.29 (m, 2H), 7.53 (d, J=6.7 Hz, 1H), 7.68-7.74 (dd, J=7.7, 19.4 Hz, 1H), 8.14-8.2 (m, 2H), 10.26 (d, J=16.8 Hz, 1H) Mixture of rotamers.

Example 13

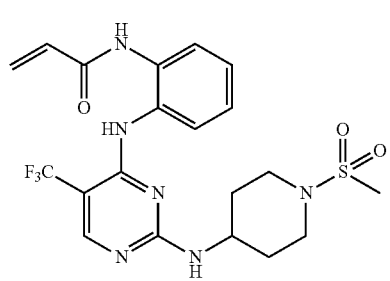

N-(2-((2-((1-(methylsulfonyl)piperidin-4-yl)amino)-5-(trifluoromethyl)pyrimidin-4-yl)amino)phenyl)acrylamide Compound I-13 was prepared in a manner similar to Example 1, substituting tert-butyl 4-aminopiperidine-1-carboxylate for (S)-tert-butyl 3-aminopiperidine-1-carboxylate and substituting MsCl for acetic chloride. MS m/z: 485.5 (ES+, M+H). 1H NMR (DMSO-d6) δ 1.41-1.5 (m, 2H), 1.81-1.89 (m, 2H), 2.59-2.66 (m, 1H), 2.59-2.66 (m, 1H), 2.78-2.83 (m, 1H), 2.85 (s, 3H), 3.5 (d, J=11.5 Hz, 2H), 5.8 (d, J=9.7 Hz, 1H), 6.3 (d, J=16.7 Hz, 1H), 6.42-6.48 (m, 1H), 7.2-7.24 (m, 1H), 7.29-7.33 (m, 2H), 7.54 (d, J=6.5 Hz, 1H), 7.67-7.75 (dd, J=8.2, 20.5 Hz, 1H), 8.15-8.2 (m, 2H), 10.29 (d, J=13 Hz, 1H) Mixture of rotamers.

Example 14

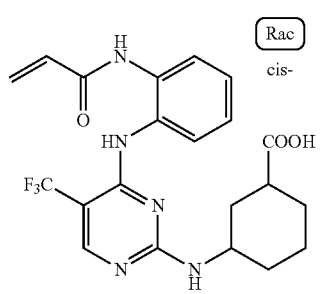

Rac-3-((4-((2-acrylamidophenyl)amino)-5-(trifluoromethyl)pyrimidin-2-yl)amino)-cis-cyclohexanecarboxylic acid Compound I-14 was prepared in a manner similar to Example 1, substituting cis-tert-butyl-3-aminocyclohexanecarboxylate for (S)-tert-butyl 3-aminopiperidine-1-carboxylate, and final deprotection of t-butyl ester with 50% TFA in DCM. MS m/z: 450.2 (ES+, M+H). $^1$H NMR (DMSO-d$_6$) δ 1.10-1.22 (m, 5H), 1.68-1.77 (m, 3H), 1.95-2.00 (m, 2H), 5.78-7.80 (d, 1H, J=10 Hz), 6.26-6.31 (dd, 1H, J=5.9, 16.5 Hz), 6.42-6.49 (dd, 1H, J=9.8, 16.7 Hz), 7.15-7.25 (m, 3H), 7.48-7.50 (d, 1H, J=7 Hz), 7.72-7.75 (m, 1H), 8.11 (s, 1H), 10.28 (s, 1H).

Example 15

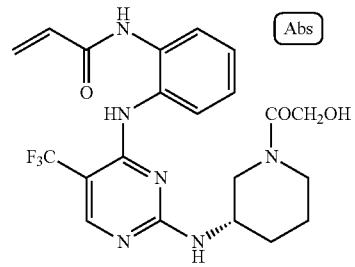

(S)—N-(2-((2-((1-(2-hydroxyacetyl)piperidin-3-yl)amino)-5-(trifluoromethyl) pyrimidin-4-yl)amino)phenyl)acrylamide Compound I-15 was prepared in a manner similar to Example 1, substituting ClCOCH$_2$OAc for acetic chloride followed by hydrolysis with aqueous LiOH. MS m/z: 465.2 (ES+, M+H). $^1$H NMR (DMSO-d$_6$) δ 1.24-1.45 (br s, 1H), 1.45-1.67 (br s, 1H), 1.67-1.70 (d, 1H, J=13.3 Hz), 1.80-1.83 (d, 1H, J=11.45 Hz), 2.78-2.89 (m, 2H), 3.45-3.51 (m, 2H), 3.65-3.75 (m, 1H), 4.04-4.08 (d, 2H, J=10.0 Hz), 4.44-4.48 (d, 1H, J=16.4 Hz), 5.78-5.80 (d, 1H, J=10.2 Hz), 6.27-6.32 (d, 1H, J=16.7 Hz), 6.41-6.48 (dd, 1H, J=10.1, 16.0 Hz), 7.20-7.27 (m, 3H), 7.54 (br s, 1H), 7.68-7.04 (m, 1H), 8.16-8.23 (m, 2H), 10.28 (s, 1H).

Example 16

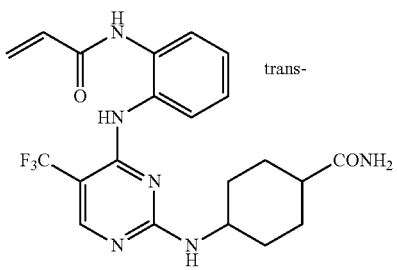

4-((4-((2-acrylamidophenyl)amino)-5-(trifluoromethyl)pyrimidin-2-yl)amino)-trans-cyclohexanecarboxamide Compound I-16 was prepared in a manner similar to Example 1, substituting trans-4-aminocyclohexanecarboxamide for (S)-tert-butyl 3-aminopiperidine-1-carboxylate. MS m/z: 449.2 (ES+, M+H). $^1$H NMR (DMSO-d$_6$) δ 1.13-1.22 (m, 4H), 1.30-1.4 (m, 1H), 1.69-1.71 (d, 2H, J=9.8 Hz), 1.81-1.83 (d, 2H, J=10.4 Hz), 1.94-2.0 (m, 1H), 5.78-7.81 (d, 1H, J=10.1 Hz), 6.26-6.32 (dd, 1H, J=7.2, 16.9 Hz), 6.43-6.49 (dd, 1H, J=10.1, 16.8 Hz), 6.63 (br s, 1H), 7.15 (br s, 1H), 7.21-7.28 (m, 3H), 7.38-7.40 (d, 1H, J=7.6 Hz), 7.74-7.77 (m, 1H), 8.11 (s, 1H), 10.28 (s, 1H).

Example 17

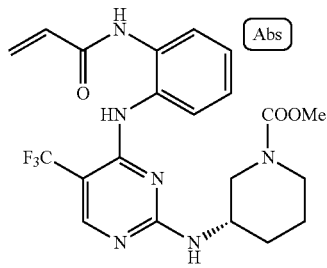

I-17

(S)-Methyl 3-((4-((2-acrylamidophenyl)amino)-5-(trifluoromethyl)pyrimidin-2-yl)amino) piperidine-1-carboxylate Compound I-17 was prepared in a manner similar to Example 1, substituting ClCOOCH$_3$ for acetic chloride. MS m/z: 465.2 (ES+, M+H).

Example 18

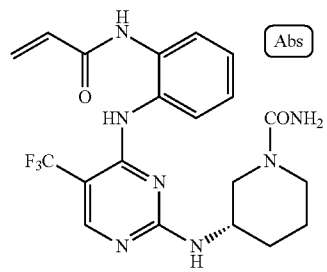

I-18

(S)-3-((4-((2-Acrylamidophenyl)amino)-5-(trifluoromethyl)pyrimidin-2-yl)amino)piperidine-1-carboxamide Compound I-18 was prepared in a manner similar to Example 1, substituting TMSNCO for acetic chloride. MS m/z: 450.2 (ES+, M+H).

Example 19

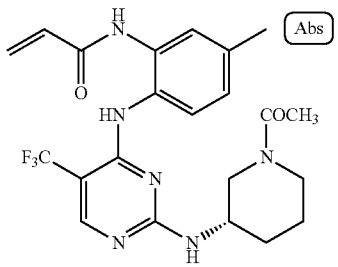

I-19

(S)—N-(2-((2-((1-Acetylpiperidin-3-yl)amino)-5-(trifluoromethyl)pyrimidin-4-yl)amino)-5-methylphenyl)acrylamide Compound I-19 was prepared in a manner similar to Example 1, substituting N-(2-amino-5-methylphenyl)acrylamide for N-(2-aminophenyl)acrylamide. MS m/z: 463.5 (ES+, M+H). $^1$H NMR (DMSO-d$_6$) δ 1.22 (br s, 1H), 1.42 (br s, 2H), 1.67-1.79 (m, 1H), 1.84 (br s, 1H), 1.92-2.01 (m, 1H), 2.31 (s, 3H), 2.5-2.8 (m, 1H), 2.8-3.04 (m, 1H), 3.49 (s, 3H), 3.96-4.13 (m, 1H), 5.76-5.79 (dd, J=1.4, 10.2 Hz, 1H), 6.28 (d, J=16.8 Hz, 1H), 6.4-6.47 (dd, J=10.2, 16.9 Hz, 1H), 6.97-7.08 (m, 2H), 7.40-7.68 (m, 2H), 7.91-8.23 (m, 2H), 10.26 (br s, 1H).

Example 20

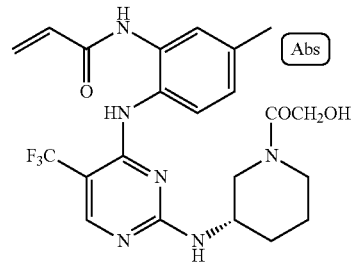

I-20

(S)—N-(2-((2-((1-(2-Hydroxyacetyl)piperidin-3-yl)amino)-5-(trifluoromethyl) pyrimidin-4-yl)amino)-5-methylphenyl)acrylamide Compound I-20 was prepared in a manner similar to Example 1, substituting N-(2-amino-5-methylphenyl)acrylamide for N-(2-aminophenyl)acrylamide, and substituting ClCOCH$_2$OAc for acetic chloride followed by hydrolysis with aqueous LiOH. MS m/z: 479.5 (ES+, M+H). $^1$H NMR (DMSO-d$_6$) δ 1.47 (m, 1H), 1.67 (m, 1H), 1.83-1.86 (m, 2H), 2.31 (s, 3H), 2.81 (m, 1H), 3.42-3.44 (m, 2H), 3.63-3.67 (m, 2H), 4.01-4.08 (m, 2H), 4.24 (br s, 1H), 4.45 (br s, 1H), 5.76-5.79 (d, J=10.0 Hz, 1H), 6.26-6.30 (d, J=16.9 Hz, 1H), 6.40-6.47 (dd, J=10.0, 17.0 Hz, 1H), 7.02 (s, 1H), 7.07-7.09 (d, J=7.0 Hz, 1H), 7.90-8.29 (m, 2H), 8.13-8.22 (m, 2H), 10.27 (s, 1H).

Example 21

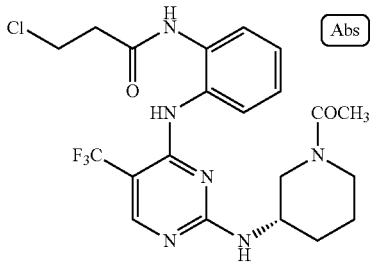

I-21

(S)—N-(2-((2-((1-Acetylpiperidin-3-yl)amino)-5-(trifluoromethyl)pyrimidin-4-yl)amino)phenyl)-3-chloropropanamide Compound I-21 was prepared in a manner similar to Example 1, substituting N-(2-aminophenyl)-3-chloropropanamide for N-(2-aminophenyl)acrylamide. MS m/z: 485.6 (ES+, M+H). $^1$H NMR (CD$_3$OD) δ 1.59 (m, 1H), 1.63-1.64 (m, 2H), 1.77 (m, 1H), 1.97 (m, 1H), 2.13 (s, 2H), 2.80-2.90 (m, 3H), 3.32-3.34 (m, 1H), 3.65 (m, 2H), 3.85-3.88 (m, 3H), 4.88 (br s, 1H), 7.34-7.41 (m, 3H), 7.62-7.66 (t, J=8.4 Hz, 1H), 8.28-8.30 (d, J=6.0 Hz, 1H).

Example 22

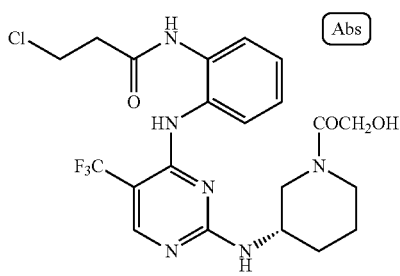

I-22

(S)-3-Chloro-N-(2-((2-((1-(2-hydroxyacetyl)piperidin-3-yl)amino)-5-(trifluoromethyl)pyrimidin-4-yl)amino)phenyl)propanamide Compound I-22 was prepared in a manner similar to Example 1, substituting N-(2-aminophenyl)-3-chloropropanamide for N-(2-aminophenyl)acrylamide, and substituting ClCOCH$_2$OAc for acetic chloride followed by hydrolysis with aqueous LiOH. MS m/z: 501.5 (ES+, M+H). $^1$H NMR (CD$_3$OD) δ 1.47 (m, 1H), 1.60-1.67 (m, 1H), 1.76 (m, 1H), 1.85-2.0 (m, 1H), 2.89 (br s, 2H), 2.95-3.10 (m, 1H), 3.40-3.57 (m, 2H), 3.69 (br s, 1H), 3.87 (t, J=5.2 Hz, 4H), 4.25 (s, 1H), 7.30-7.47 (m, 3H), 7.62 (d, J=5.8 Hz, 1H), 8.29 (s, 1H).

Example 23

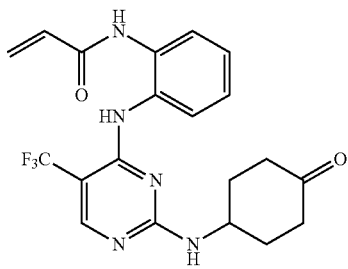

I-23

N-(2-((2-((4-Oxocyclohexyl)amino)-5-(trifluoromethyl)pyrimidin-4-yl)amino) phenyl)acrylamide Compound I-23 was prepared in a manner similar to Example 1, substituting 4-aminocyclohexanone for (S)-tert-butyl 3-aminopiperidine-1-carboxylate. MS m/z 420.2 (ES+, M+H). $^1$H NMR (DMSO-d$_6$) δ 1.62-1.66 (m, 2H), 1.95-2.09 (m, 2H), 2.21-2.32 (m, 3H), 2.48-2.49 (m, 1H), 3.77 (m, 1H), 5.80 (d, J=10.3 Hz, 1H), 6.30 (d, J=16.6 Hz, 1H), 6.42-6.49 (dd, J=10.2, 17.1 Hz, 1H), 7.19-7.29 (m, 4H), 7.60 (d, J=6.5 Hz, 1H), 7.65-7.79 (m, 1H), 8.10-8.25 (m, 2H), 10.28 (d, J=16 Hz, 1H). Mixture of Rotamers.

Example 24

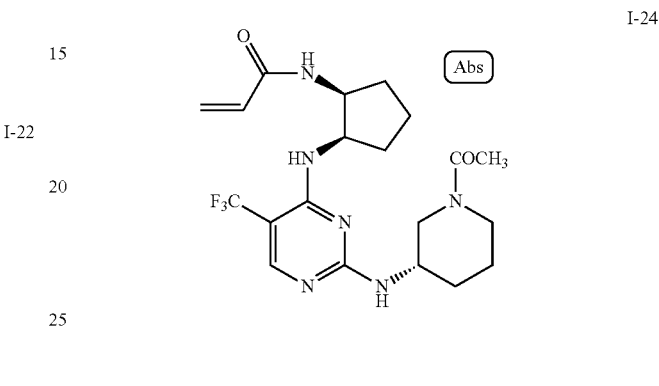

I-24

N-((1S,2S)-2-((2-(((S)-1-Acetylpiperidin-3-yl)amino)-5-(trifluoromethyl) pyrimidin-4-yl)amino)cyclopentyl)acrylamide Compound I-24 was prepared in a manner similar to Example 1, substituting N-((1S,2S)-2-aminocyclopentyl)acrylamide for N-(2-aminophenyl)acrylamide. MS m/z: 441.2 (ES+, M+H).

Example 25

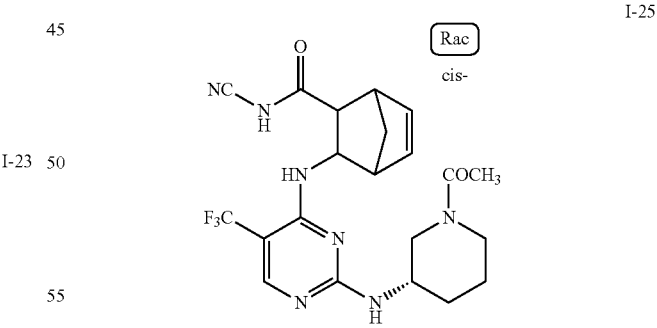

I-25

Rac-3-((2-(((S)-1-acetylpiperidin-3-yl)amino)-5-(trifluoromethyl)pyrimidin-4-yl)-cis-amino)-N-cyanobicyclo[2.2.1]hept-5-ene-2-carboxamide Compound I-25 was prepared in a manner similar to Example 1, substituting cis-3-amino-N-cyanobicyclo[2.2.1]hept-5-ene-2-carboxamide for N-(2-aminophenyl)acrylamide. MS m/z: 464.1 (ES+, M+H).

Example 26

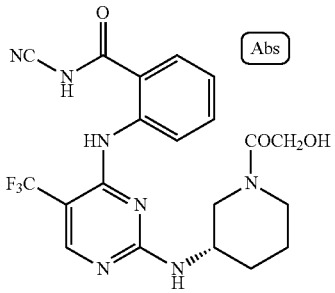

I-26

(S)—N-Cyano-2-((2-((1-(2-hydroxyacetyl)piperidin-3-yl)amino)-5-(trifluoromethyl)pyrimidin-4-yl)amino)benzamide Compound I-26 was prepared in a manner similar to Example 1, substituting 2-amino-N-cyanobenzamide for N-(2-aminophenyl)acrylamide, and substituting ClCOCH$_2$OAc for acetic chloride followed by hydrolysis with aqueous LiOH. MS m/z: 464.5 (ES+, M+H). $^1$H NMR (DMSO-d$_6$) δ 1.42-1.58 (m, 2H), 1.74-176 (m, 1H), 1.89-2.06 (m, 1H), 2.85-2.95 (m, 2H), 3.75-4.08 (m, 3H), 4.08 (s, 2H), 4.47 (br s, 1H), 7.29 (br s, 1H), 7.39 (br s, 1H), 7.60 (d, J=7.5 Hz, 1H), 7.72 (d, J=6 Hz, 1H), 7.88 (br s, 1H), 7.96 (d, J=7.7 Hz, 1H), 8.36 (br s, 1H), 12.38 (br s, 1H).

Example 27

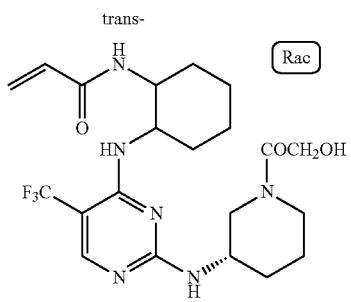

I-27

Rac-N-(2-((2-(((R)-1-(2-hydroxyacetyl)piperidin-3-yl)amino)-5-(trifluoromethyl)pyrimidin-4-yl)amino)-trans-cyclohexyl)acrylamide Compound I-27 was prepared in a manner similar to Example 1, substituting N-trans-2-aminocyclohexylacrylamide for N-(2-aminophenyl)acrylamide, and substituting ClCOCH$_2$OAc for acetic chloride followed by hydrolysis with aqueous LiOH. MS m/z: 471.6 (ES+, M+H). $^1$H NMR (DMSO-d$_6$) δ 1.12-1.37 (m, 4H), 1.40-1.59 (m, 2H), 1.60-1.78 (m, 3H), 1.80-1.89 (m, 1H), 1.91-1.98 (m, 1H), 2.12-2.19 (m, 1H), 2.70-2.82 (m, 1H), 2.83-3.0 (m, 1H), 3.52-3.61 (m, 1H), 3.63-3.72 (m, 1H), 3.75-3.95 (m, 2H), 3.95-4.19 (m, 2H), 4.2-4.6 (m, 2H), 5.52-5.58 (m, 1H), 6.0-6.25 (m, 2H), 6.37 (d, J=32.1 Hz, 1H), 7.11-7.47 (m, 1H), 7.95-8.18 (m, 2H). Mixture of diastereomers.

Example 28

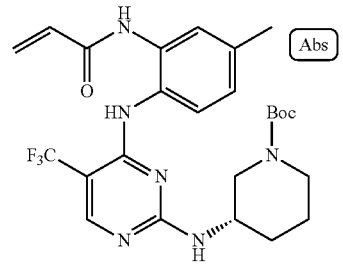

I-28

(S)-tert-Butyl 3-((4-((2-acrylamido-4-methylphenyl)amino)-5-(trifluoromethyl) pyrimidin-2-yl)amino)piperidine-1-carboxylate Compound I-28 was prepared in a manner similar to Example 1, substituting N-(2-amino-5-methylphenyl)acrylamide for N-(2-aminophenyl)acrylamide. MS m/z: 519.5 (ES–, M–H). $^1$H NMR (DMSO-d$_6$) δ 1.22-1.27 (m, 3H), 1.35 (s, 9H), 1.66-1.7 (m, 2H), 2.27 (s, 3H), 2.27-2.29 (m, 1H), 3.36 (br s, 1H), 3.51-3.90 (m, 2H), 5.78 (d, J=10.0 Hz, 1H), 6.26-6.31 (d, J=16.8 Hz, 1H), 6.4-6.47 (dd, J=10.1, 16.8 Hz, 1H), 7.05-7.09 (m, 2H), 7.42-7.52 (m, 1H), 6.63 (d, J=6.3 Hz, 1H), 7.95-8.19 (m, 2H), 10.20 (d, J=33.1 Hz, 1H). Mixture of Rotamers

Example 29

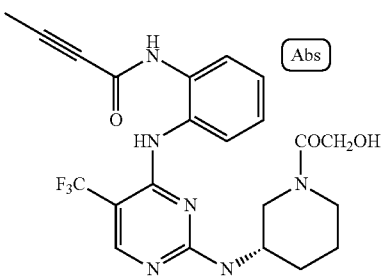

I-29

(S)—N-(2-((2-((1-(2-Hydroxyacetyl)piperidin-3-yl)amino)-5-(trifluoromethyl) pyrimidin-4-yl)amino)phenyl)but-2-ynamide Compound I-29 was prepared in a manner similar to Example 1, substituting N-(2-aminophenyl)but-2-ynamide for N-(2-aminophenyl)acrylamide, and substituting ClCOCH$_2$OAc for acetic chloride followed by hydrolysis with aqueous LiOH. MS m/z: 477.5 (ES+, M+H). $^1$H NMR (DMSO-d$_6$) δ 1.22 (m, 1H), 1.67-1.74 (m, 1H), 1.79-1.85 (m, 1H), 2.03 (s, 3H), 2.70-2.95 (m, 2H), 3.38 (m, 2H), 3.60-3.86 (m, 2H), 4.04-4.11 (m, 2H), 4.45-4.49 (m, 1H), 7.18-7.30 (m, 3H), 7.56 (br s, 1H), 7.67 (m, 1H), 7.76 (d, J=6.7 Hz, 1H), 7.89 (br s, 1H), 8.18 (s, 1H), 8.24 (d, J=13.4 Hz, 1H), 10.66 (br s, 1H).

Example 30

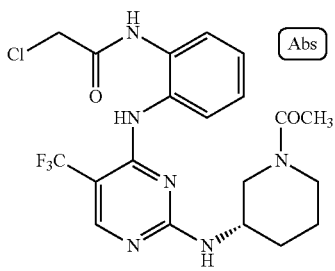

I-30

(S)—N-(2-((2-((1-Acetylpiperidin-3-yl)amino)-5-(trifluoromethyl)pyrimidin-4-yl)amino)phenyl)-2-chloroacetamide Compound I-30 was prepared in a manner similar to Example 1, substituting N-(2-aminophenyl)-2-chloroacetamide for N-(2-aminophenyl) acrylamide. MS m/z: 471.0 (ES+, M+H).

Example 31

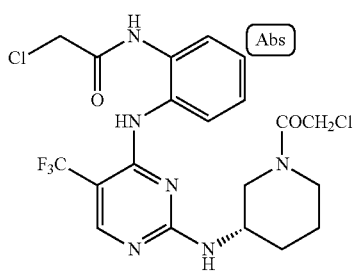

I-31

(S)-2-Chloro-N-(2-((2-((1-(2-chloroacetyl)piperidin-3-yl)amino)-5-(trifluoromethyl)pyrimidin-4-yl)amino)phenyl)acetamide Compound I-31 was prepared in a manner similar to Example 1, substituting N-(2-aminophenyl)-2-chloroacetamide for N-(2-aminophenyl)acrylamide, and substituting ClCOCH₂Cl for acetic chloride. MS m/z: 505.1 (ES+, M+H).

Example 32

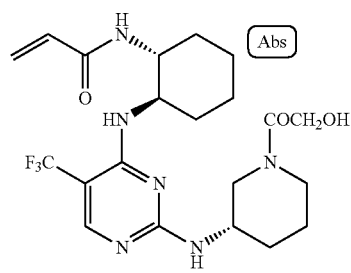

I-32

N-((1R,2R)-2-((2-(((S)-1-(2-hydroxyacetyl)piperidin-3-yl)amino)-5-(trifluoromethyl)pyrimidin-4-yl)amino)cyclohexyl)acrylamide Compound I-32 was prepared in a manner similar to Example 1, substituting N-((1R,2R)-2-aminocyclohexyl)acrylamide for N-(2-aminophenyl)acrylamide, and substituting ClCOCH₂OAc for acetic chloride followed by hydrolysis with aqueous LiOH. MS m/z: 471.6 (ES+, M+H).

Example 33

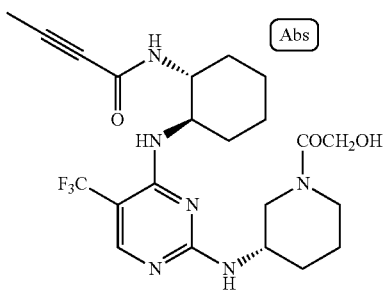

I-33

N-((1R,2R)-2-((2-(((S)-1-(2-Hydroxyacetyl)piperidin-3-yl)amino)-5-(trifluoromethyl)pyrimidin-4-yl)amino)cyclohexyl)but-2-ynamide Compound I-33 was prepared in a manner similar to Example 1, substituting N-((1R,2R)-2-aminocyclohexyl)but-2-ynamide for N-(2-aminophenyl)acrylamide, and substituting ClCOCH₂OAc for acetic chloride followed by hydrolysis with aqueous LiOH. MS m/z: 483.2 (ES+, M+H).

Example 34

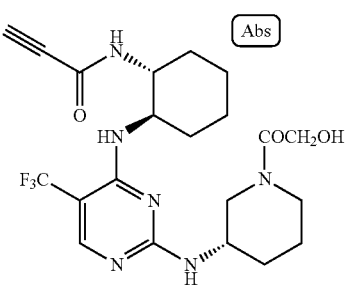

I-34

N-((1R,2R)-2-((2-(((S)-1-(2-Hydroxyacetyl)piperidin-3-yl)amino)-5-(trifluoromethyl)pyrimidin-4-yl)amino)cyclohexyl)propiolamide Compound I-34 was prepared in a manner similar to Example 1, substituting N-((1R,2R)-2-aminocyclohexyl)propiolamide for N-((1R,2R)-2-aminocyclohexyl)but-2-ynamide, and substituting ClCOCH₂OAc for acetic chloride followed by hydrolysis with aqueous LiOH. MS m/z: 469.2 (ES+, M+H).

Example 35

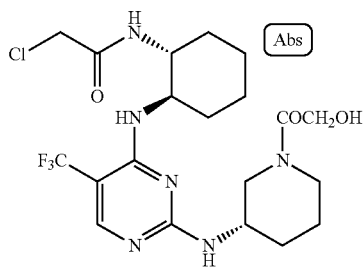

2-Chloro-N-((1R,2R)-2-((2-(((S)-1-(2-hydroxy-acetyl)piperidin-3-yl)amino)-5-(trifluoromethyl) pyrimidin-4-yl)amino)cyclohexyl)acetamide Compound I-35 was prepared in a manner similar to Example 1, substituting N-((1R,2R)-2-aminocyclohexyl)-2-chloroacetamide for N-((1R,2R)-2-aminocyclohexyl)but-2-ynamide, and substituting ClCOCH$_2$OAc for acetic chloride followed by hydrolysis with aqueous LiOH. MS m/z: 493.1 (ES+, M+H).

Example 36

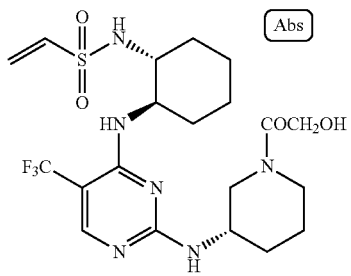

N-((1R,2R)-2-((2-(((S)-1-(2-Hydroxyacetyl)piperidin-3-yl)amino)-5-(trifluoromethyl)pyrimidin-4-yl)amino)cyclohexyl)ethenesulfonamide Compound I-36 was prepared in a manner similar to Example 1, substituting N-((1R,2R)-2-aminocyclohexyl)ethenesulfonamide for N-((1R,2R)-2-aminocyclohexyl)but-2-ynamide, and substituting ClCOCH$_2$OAc for acetic chloride, followed by hydrolysis with aqueous LiOH. MS m/z: 507.2 (ES+, M+H).

Example 37

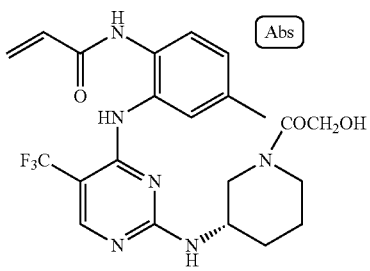

(S)—N-(2-((2-(((1-(2-hydroxyacetyl)piperidin-3-yl)amino)-5-(trifluoromethyl) pyrimidin-4-yl)amino)-4-methylphenyl)acrylamide Compound I-37 was prepared in a manner similar to Example 1, substituting N-(2-amino-4-methylphenyl)acrylamide for N-(2-aminophenyl)acrylamide, and substituting ClCOCH$_2$OAc for acetic chloride, followed by hydrolysis with aqueous LiOH. MS m/z: 478.1 (ES+, M+H). $^1$H NMR (DMSO-d$_6$) δ 1.22 (m, 1H), 1.40-1.55 (m, 1H), 1.70 (m, 1H), 1.84 (m, 1H), 2.26 (s, 3H), 2.72-2.88 (m, 1H), 2.95 (m, 1H), 3.35-3.45 (m, 1H), 3.54 (m, 1H), 3.64-3.70 (m, 1H), 3.83-3.96 (m, 1H), 4.04 (br s, 1H), 4.25-4.39 (m, 1H), 5.75 (d, J=10.1 Hz, 1H), 6.26-6.30 (dd, J=8.4, 16.2 Hz, 1H), 6.39-6.46 (dd, J=10.3, 16.2 Hz, 1H), 6.98-7.04 (m, 1H), 7.09-7.20 (m, 1H), 7.45-7.65 (m, 1H), 8.16-8.23 (m, 2H), 10.27 (d, J=21.4 Hz, 1H). Mixture of Rotamers.

Example 38

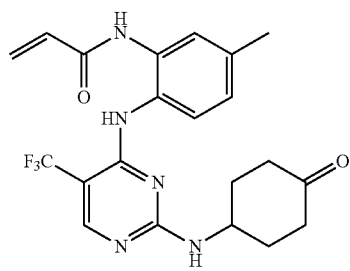

N-(5-Methyl-2-((2-((4-oxocyclohexyl)amino)-5-(trifluoromethyl)pyrimidin-4-yl)amino)phenyl)acrylamide Compound I-38 was prepared in a manner similar to Example 1, substituting 4-aminocyclohexanone for (S)-tert-butyl 3-aminopiperidine-1-carboxylate, and N-(2-amino-5-methylphenyl)acrylamide for N-(2-aminophenyl)acrylamide. MS m/z: 434.5 (ES+, M+H). $^1$H NMR (DMSO-d$_6$) δ 1.64 (br s, 2H) 1.99 (br s, 3H), 2.20 (s, 3H), 2.29 (br s, 3H), 3.77 (s, 1H), 5.78 (d, J=10.1 Hz, 1H), 6.28 (d, J=17 Hz, 1H), 6.41-6.47 (dd, J=10.1, 16.8 Hz, 1H), 7.08 (br s, 2H), 7.53-7.57 (m, 1H), 7.63-7.65 (m, 1H), 8.13 (br s, 1H), 8.20 (br s, 1H), 10.2 (br s, 1H).

Example 39

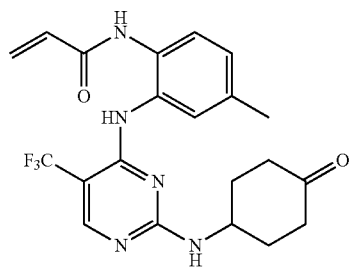

N-(4-Methyl-2-((2-((4-oxocyclohexyl)amino)-5-(trifluoromethyl)pyrimidin-4-yl)amino)phenyl)acrylamide Compound I-39 was prepared in a manner similar to Example 1, substituting 4-aminocyclohexanone for (S)-tert-butyl 3-aminopiperidine-1-carboxylate, and N-(2-amino-4-methylphenyl)acrylamide for N-(2-aminophenyl)acrylamide. MS m/z: 434.6 (ES+, M+H). $^1$H NMR (CD$_3$OD) δ 1.69-1.79 (m, 2H), 2.15 (br s, 2H), 2.33-2.39 (br s, 4H), 2.41 (s, 3H), 3.95 (br s, 1H), 5.79-5.82 (dd, J=2.4, 9.2 Hz, 1H), 6.37-6.44 (m, 2H), 7.09-7.12 (dd, J=1.1, 6.7 Hz, 1H), 7.21-7.27 (dd, J=8, 17 Hz, 1H), 7.54 (s, 1H), 8.12 (s, 1H).

Example 40

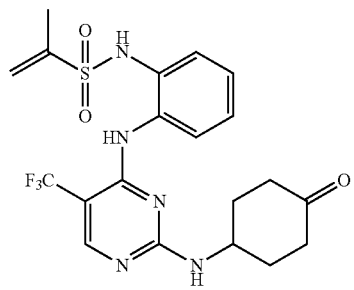

I-40

N-(2-((2-((4-Oxocyclohexyl)amino)-5-(trifluoromethyl)pyrimidin-4-yl)amino)phenyl)prop-1-ene-2-sulfonamide Compound I-40 was prepared in a manner similar to Example 1, substituting 4-aminocyclohexanone for (S)-tert-butyl 3-aminopiperidine-1-carboxylate, and N-(2-aminophenyl)prop-1-ene-2-sulfonamide for N-(2-aminophenyl)acrylamide. MS m/z: 470.5 (ES+, M+H). $^1$H NMR (DMSO-d$_6$) δ 1.66-1.73 (m, 2H), 2.04 (s, 3H), 2.06 (br s, 2H), 2.22-2.32 (br s, 4H), 3.84 (br s, 1H), 5.61 (s, 1H), 5.67 (s, 1H), 7.08-7.13 (m, 2H), 7.29-7.21 (m, 1H), 7.73 (d, J=6 Hz, 1H), 7.98 (d, J=8 Hz, 1H), 8.16-8.24 (m, 1H), 8.31 (s, 1H), 9.48 (d, J=14.0 Hz, 1H). Mixture of Rotamers.

Example 41

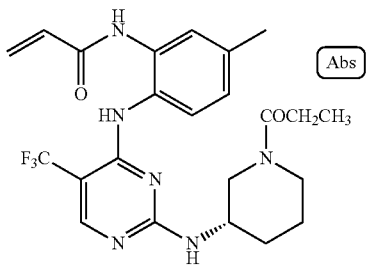

I-41

(S)—N-(5-Methyl-2-((2-((1-propionylpiperidin-3-yl)amino)-5-(trifluoromethyl)pyrimidin-4-yl)amino)phenyl)acrylamide Compound I-41 was prepared in a manner similar to Example 1, substituting N-(2-amino-5-methylphenyl)acrylamide for N-(2-aminophenyl)acrylamide, and substituting CH$_3$CH$_2$CO$_2$H, HATU and DIPEA for acetic chloride in final amide bond formation step. MS m/z: 477.2 (ES+, M+H).

Example 42

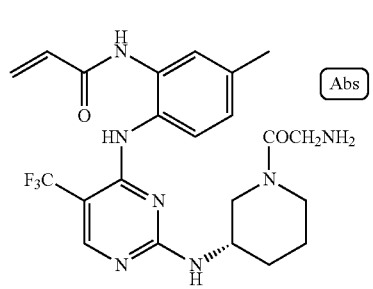

I-42

(S)—N-(2-((2-((1-(2-Aminoacetyl)piperidin-3-yl)amino)-5-(trifluoromethyl) pyrimidin-4-yl)amino)-5-methylphenyl)acrylamide Compound I-42 was prepared in a manner similar to Example 1, substituting N-(2-amino-5-methylphenyl)acrylamide for N-(2-aminophenyl)acrylamide, substituting N-Boc-glycine, HATU and DIPEA for acetic chloride in final amide bond formation step, followed by Boc-deprotection with TFA. MS m/z: 478.3 (ES+, M+H).

Example 43

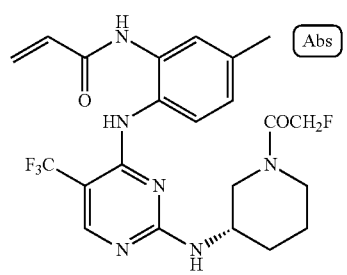

I-43

(S)—N-(2-((2-((1-(2-Fluoroacetyl)piperidin-3-yl)amino)-5-(trifluoromethyl) pyrimidin-4-yl)amino)-5-methylphenyl)acrylamide Compound I-43 was prepared in a manner similar to Example 1, substituting N-(2-amino-5-methylphenyl)acrylamide for N-(2-aminophenyl)acrylamide, and substituting 2-fluoroacetic acid, HATU and DIPEA for acetic chloride in final amide bond formation step. MS m/z: 481.4 (ES+, M+H).

Example 44

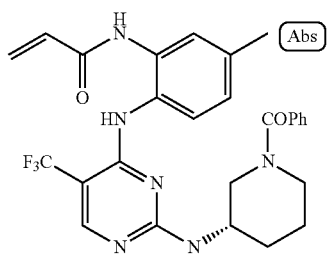

(S)—N-(2-((2-((1-Benzoylpiperidin-3-yl)amino)-5-(trifluoromethyl)pyrimidin-4-yl)amino)-5-methylphenyl)acrylamide Compound I-44 was prepared in a manner similar to Example 1, substituting N-(2-amino-5-methylphenyl)acrylamide for N-(2-aminophenyl)acrylamide, and substituting benzoic acid, HATU and DIPEA for acetic chloride in final amide bond formation step. MS m/z: 525.2 (ES+, M+H).

Example 45

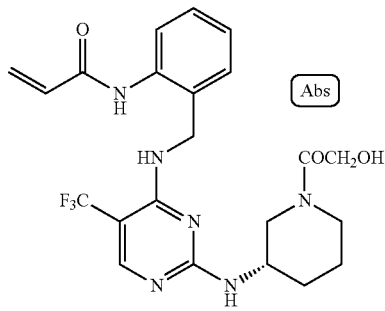

(S)—N-(2-(((2-((1-(2-Hydroxyacetyl)piperidin-3-yl)amino)-5-(trifluoromethyl) pyrimidin-4-yl)amino)methyl)phenyl)acrylamide Compound I-45 was prepared in a manner similar to Example 1, substituting N-(2-(aminomethyl)phenyl)acrylamide for N-(2-aminophenyl)acrylamide, and substituting ClCOCH$_2$OAc for acetic chloride, followed by hydrolysis with aqueous LiOH. MS m/z: 479.3 (ES+, M+H). $^1$H NMR (DMSO-d$_6$) δ 1.22 (m, 1H), 1.32-1.34 (m, 2H), 1.45 (m, 1H), 1.67-1.89 (m, 2H), 2.87 (m, 2H), 3.34-3.39 (m, 1H), 3.63 (m, 1H), 3.99-4.06 (m, 2H), 4.41-4.50 (m, 1H), 4.56-4.59 (m, 1H), 5.74 (d, J=9.2 Hz, 1H), 6.24 (d, J=16.2 Hz, 1H), 6.52-6.59 (m, 1H), 7.08-7.36 (m, 5H), 7.43-7.51 (m, 1H), 8.01-8.12 (m, 1H), 9.55 (d, J=33 Hz, 1H). Mixture of Rotamers

Example 46

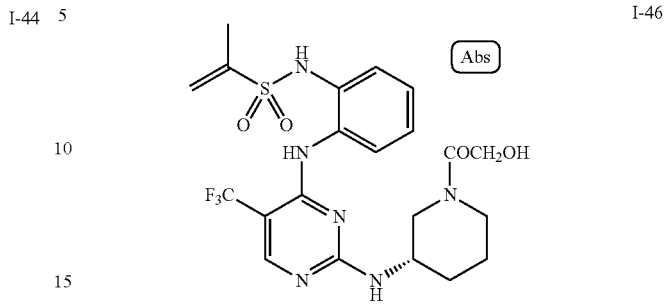

(S)—N-(2-((2-((1-(2-Hydroxyacetyl)piperidin-3-yl)amino)-5-(trifluoromethyl) pyrimidin-4-yl)amino)phenyl)prop-1-ene-2-sulfonamide Compound I-46 was prepared in a manner similar to Example 1, substituting N-(2-aminophenyl)prop-1-ene-2-sulfonamide for N-(2-aminophenyl)acrylamide, and substituting ClCOCH$_2$OAc for acetic chloride, followed by hydrolysis with aqueous LiOH. MS m/z: 515.5 (ES+, M+H). $^1$H NMR (DMSO-d$_6$) δ 1.48 (m, 1H), 1.69 (m, 1H), 1.83-1.89 (m, 1H), 2.04 (s, 3H), 2.87-2.95 (m, 2H), 3.42-3.51 (m, 2H), 3.66-3.77 (m, 2H), 4.07-4.12 (m, 2H), 4.30 (s, 1H), 5.62 (s, 1H), 5.68 (s, 1H), 7.13-7.19 (m, 2H), 7.24-7.30 (m, 1H), 7.81 (s, 1H), 7.90-8.29 (m, 1H), 8.33 (s, 1H), 8.55-8.59 (m, 1H), 9.47 (d, J=8.3 Hz, 1H). Mixture of Rotamers.

Example 47

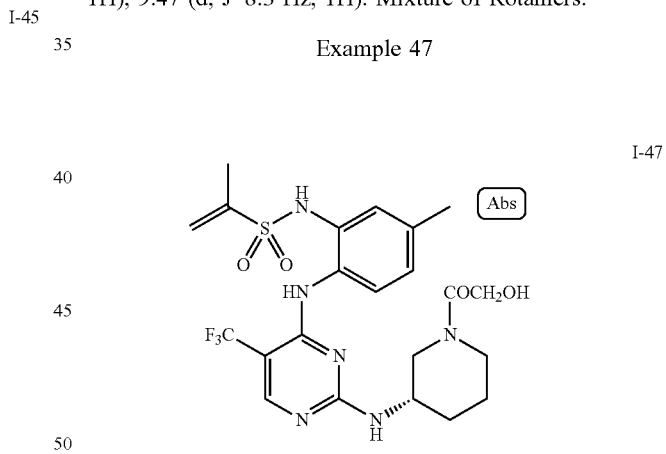

(S)—N-(2-((2-((1-(2-Hydroxyacetyl)piperidin-3-yl)amino)-5-(trifluoromethyl) pyrimidin-4-yl)amino)-5-methylphenyl)prop-1-ene-2-sulfonamide Compound I-47 was prepared in a manner similar to Example 1, substituting N-(2-amino-5-methylphenyl)prop-1-ene-2-sulfonamide for N-(2-aminophenyl)acrylamide, and substituting ClCOCH$_2$OAc for acetic chloride, followed by hydrolysis with aqueous LiOH. MS m/z: 529.5 (ES+, M+H). $^1$H NMR (DMSO-d$_6$) δ 1.47 (m, 1H), 1.69 (m, 1H), 1.86-1.89 (m, 1H), 2.02 (s, 3H), 2.25 (s, 3H), 2.83-2.93 (m, 2H), 3.51 (m, 2H), 3.65-3.77 (m, 2H), 4.05-4.08 (m, 2H), 4.45 (s, 1H), 5.65 (s, 1H), 5.89 (s, 1H), 6.92 (m, 2H), 7.80 (s, 1H), 7.90-8.29 (m, 1H), 8.08-8.29 (m, 2H), 9.38 (d, J=22.0 Hz, 1H). Mixture of Rotamers.

Example 48

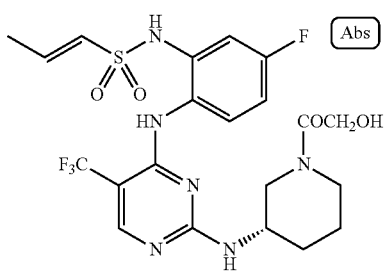

I-48

(S,E)-N-(5-Fluoro-2-((2-((1-(2-hydroxyacetyl)piperidin-3-yl)amino)-5-(trifluoromethyl)pyrimidin-4-yl)amino)phenyl)prop-1-ene-1-sulfonamide Compound I-48 was prepared in a manner similar to Example 1, substituting (E)-N-(2-amino-5-fluorophenyl)prop-1-ene-1-sulfonamide for N-(2-aminophenyl)acrylamide, and substituting ClCOCH$_2$OAc for acetic chloride, followed by hydrolysis with aqueous LiOH. MS m/z: 575.2 (ES+, M+H).

Example 49

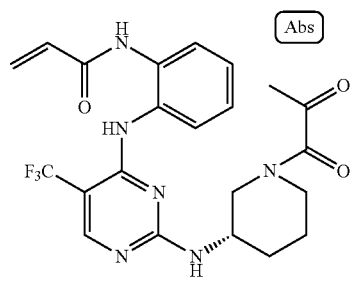

I-49

(S)—N-(2-((2-((1-(2-Oxopropanoyl)piperidin-3-yl)amino)-5-(trifluoromethyl) pyrimidin-4-yl)amino)phenyl)acrylamide Compound I-49 was prepared in a manner similar to Example 1, substituting CH$_3$COCOOH, HATU and DIPEA for acetic chloride in the final amide formation step. MS m/z: 477.1 (ES+, M+H).

Example 50

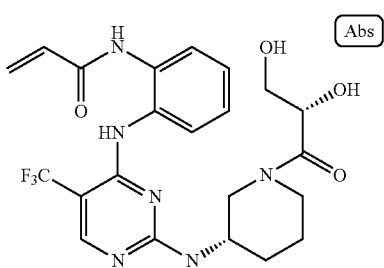

I-50

N-(2-((2-(((S)-1-((S)-2,3-Dihydroxypropanoyl)piperidin-3-yl)amino)-5-(trifluoromethyl)pyrimidin-4-yl)amino)phenyl)acrylamide Compound I-49 was prepared in a manner similar to Example 1, substituting (S)-2,3-dihydroxypropanoic acid, HATU and DIPEA for acetic chloride in the final amide formation step. MS m/z: 495.2 (ES+, M+H).

Example 51

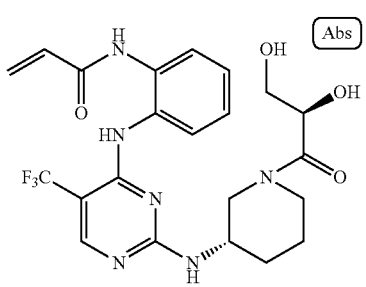

I-51

N-(2-((2-(((S)-1-((R)-2,3-Dihydroxypropanoyl)piperidin-3-yl)amino)-5-(trifluoromethyl)pyrimidin-4-yl)amino)phenyl)acrylamide Compound I-51 was prepared in a manner similar to Example 1, substituting (R)-2,3-dihydroxypropanoic acid, HATU and DIPEA for acetic chloride in the final amide formation step. MS m/z: 495.2 (ES+, M+H).

Example 52

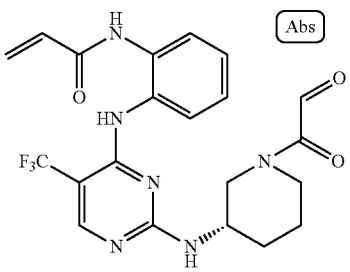

I-52

(S)—N-(2-((2-((1-(2-Oxoacetyl)piperidin-3-yl)amino)-5-(trifluoromethyl) pyrimidin-4-yl)amino)phenyl)acrylamide Compound I-52 was prepared in a manner similar to Example 1, substituting (R)-2,3-dihydroxypropanoic acid for acetic acid, followed by oxidizative-cleavage with NaIO$_4$. MS m/z: 463.1 (ES+, M+H).

Example 53

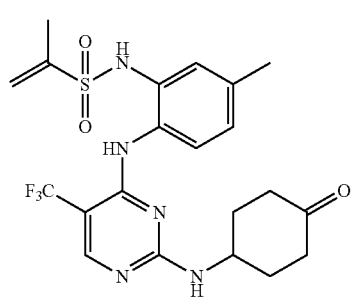

N-(5-Methyl-2-((2-((4-oxocyclohexyl)amino)-5-(trifluoromethyl)pyrimidin-4-yl)amino)phenyl)prop-1-ene-2-sulfonamide Compound I-53 was prepared in a manner similar to Example 1, substituting 4-aminocyclohexanone for (S)-tert-butyl 3-aminopiperidine-1-carboxylate, and N-(2-amino-5-methylphenyl)prop-1-ene-2-sulfonamide for N-(2-aminophenyl)acrylamide. MS m/z: 484.2 (ES+, M+H). $^1$HNMR (DMSO-d$_6$) δ 1.65 (m, 2H), 2.02 (s, 6H), 2.25 (br s, 7H), 3.84 (br s, 1H), 5.62 (s, 1H), 5.66 (s, 1H), 6.92 (s, 1H), 7.11 (d, J=8 Hz, 1H), 7.69 (d, J=6 Hz, 1H), 7.81 (d, J=8 Hz, 1H), 8.22-8.29 (m, 2H), 9.40 (s, 1H).

Example 54

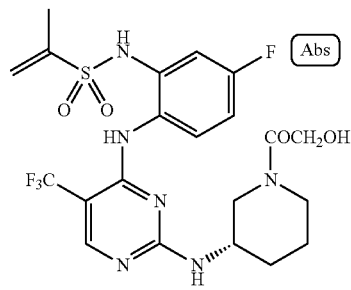

(S)—N-(5-Fluoro-2-((2-((1-(2-hydroxyacetyl)piperidin-3-yl)amino)-5-(trifluoromethyl)pyrimidin-4-yl)amino)phenyl)prop-1-ene-2-sulfonamide Compound I-54 was prepared in a manner similar to Example 1, substituting N-(2-amino-5-fluorophenyl)prop-1-ene-2-sulfonamide for N-(2-aminophenyl)acrylamide, and substituting ClCOCH$_2$OAc and LiOH for acetic chloride, followed by hydrolysis with aqueous LiOH. MS m/z: 533.5 (ES+, M+H). $^1$H NMR: (DMSO-d$_6$) δ 1.46 (m, 1H), 1.68 (m, 1H), 1.89 (m, 1H), 2.03 (s, 3H), 2.88-2.90 (m, 2H), 3.30 (m, 1H), 3.64 (m, 1H), 3.64-3.76 (m, 2H), 4.06-4.09 (m, 2H), 4.46 (s, 1H), 5.65 (s, 1H), 5.69 (s, 1H), 6.94-7.12 (m, 2H), 7.61 (d, J=7.1 Hz, 1H), 7.90-8.29 (br s, 1H), 8.21-8.29 (m, 2H), 9.6 (s, 1H).

Example 55

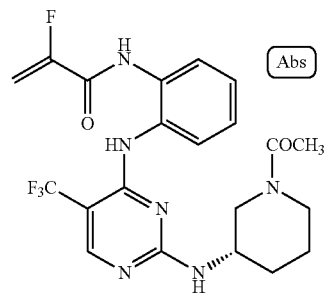

(S)—N-(2-((2-((1-Acetylpiperidin-3-yl)amino)-5-(trifluoromethyl)pyrimidin-4-yl)amino)phenyl)-2-fluoroacrylamide Compound I-55 was prepared in a manner similar to Example 1, substituting N-(2-aminophenyl)-2-fluoroacrylamide for N-(2-aminophenyl) acrylamide. MS m/z: 467.1 (ES+, M+H).

Example 56

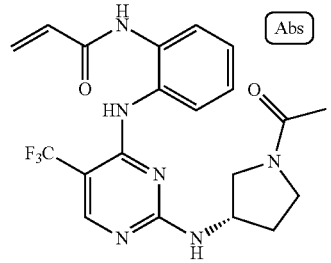

(S)—N-(2-((2-((1-Acetylpyrrolidin-3-yl)amino)-5-(trifluoromethyl)pyrimidin-4-yl)amino)phenyl)acrylamide Compound I-56 was prepared in a manner similar to Example 1, substituting (S)-tert-butyl 3-aminopyrrolidine-1-carboxylate for (S)-tert-butyl 3-aminopiperidine-1-carboxylate. MS m/z: 435.1 (ES+, M+H).

Example 57

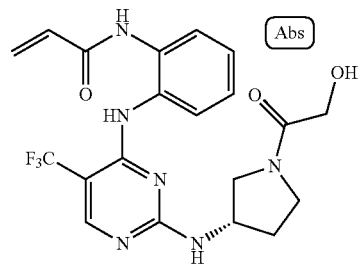

(S)—N-(2-((2-((1-(2-Hydroxyacetyl)pyrrolidin-3-yl)amino)-5-(trifluoromethyl)pyrimidin-4-yl)amino)phenyl)acrylamide Compound I-57 was prepared in a manner similar to Example 1, substituting (S)-tert-butyl 3-aminopyrrolidine-1-carboxylate for (S)-tert-butyl 3-aminopiperidine-1-carboxylate, and substituting ClCOCH₂OAc for acetic chloride, followed by hydrolysis with aqueous LiOH. MS m/z: 451.1 (ES+, M+H).

Example 58

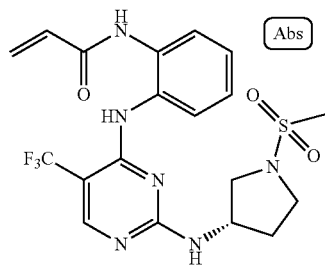
I-58

(S)—N-(2-((2-((1-(Methylsulfonyl)pyrrolidin-3-yl)amino)-5-(trifluoromethyl) pyrimidin-4-yl)amino)phenyl)acrylamide Compound I-58 was prepared in a manner similar to Example 1, substituting (S)-tert-butyl 3-aminopyrrolidine-1-carboxylate for (S)-tert-butyl 3-aminopiperidine-1-carboxylate, and substituting MsCl for acetic chloride. MS m/z: 471.1 (ES+, M+H).

Example 59

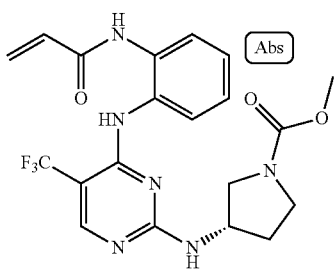
I-59

(S)-methyl 3-((4-((2-Acrylamidophenyl)amino)-5-(trifluoromethyl) pyrimidin-2-yl)amino)pyrrolidine-1-carboxylate Compound I-59 was prepared in a manner similar to Example 1, substituting (S)-tert-butyl 3-aminopyrrolidine-1-carboxylate for (S)-tert-butyl 3-aminopiperidine-1-carboxylate, and substituting ClCOOCH₃ for acetic chloride. MS m/z: 451.1 (ES+, M+H).

Example 60

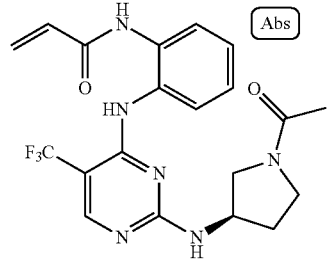
I-60

(R)—N-(2-((2-((1-Acetylpyrrolidin-3-yl)amino)-5-(trifluoromethyl)pyrimidin-4-yl)amino)phenyl)acrylamide Compound I-60 was prepared in a manner similar to Example 1, substituting (R)-tert-butyl 3-aminopyrrolidine-1-carboxylate for (S)-tert-butyl 3-aminopiperidine-1-carboxylate. MS m/z: 435.2 (ES+, M+H).

Example 61

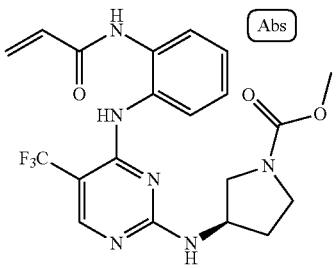
I-61

(R)-Methyl 3-((4-((2-Acrylamidophenyl)amino)-5-(trifluoromethyl)pyrimidin-2-yl)amino)pyrrolidine-1-carboxylate Compound I-61 was prepared in a manner similar to Example 1, substituting (R)-tert-butyl 3-aminopyrrolidine-1-carboxylate for (S)-tert-butyl 3-aminopiperidine-1-carboxylate, and substituting ClCOOCH₃ for acetic chloride. MS m/z: 435.2 (ES+, M+H).

Example 62

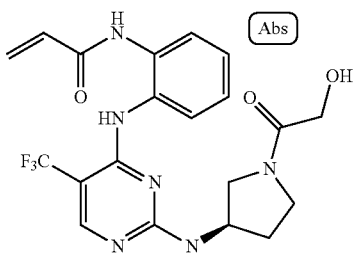
I-62

(R)—N-(2-((2-((1-(2-Hydroxyacetyl)pyrrolidin-3-yl)amino)-5-(trifluoromethyl)pyrimidin-4-yl)amino)phenyl)acrylamide Compound I-62 was prepared in a manner similar to Example 1, substituting (R)-tert-butyl 3-aminopyrrolidine-1-carboxylate for (S)-tert-butyl 3-aminopiperidine-1-carboxylate, and substituting ClCOCH₂OAc for acetic chloride, followed by hydrolysis with aqueous LiOH. MS m/z: 451.1 (ES+, M+H).

Example 63

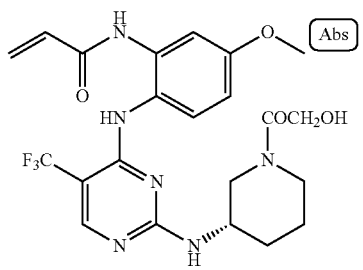

I-64

(S)—N-(2-((2-((1-(2-Hydroxyacetyl)piperidin-3-yl)amino)-5-(trifluoromethyl)pyrimidin-4-yl)amino)-5-methoxyphenyl)acrylamide Compound I-64 was prepared in a manner similar to Example 1, substituting N-(2-amino-5-methoxyphenyl)acrylamide for N-(2-aminophenyl)acrylamide, and substituting ClCOCH₂OAc for acetic chloride, followed by hydrolysis with aqueous LiOH. MS m/z: 495.2 (ES+, M+H).

Example 64

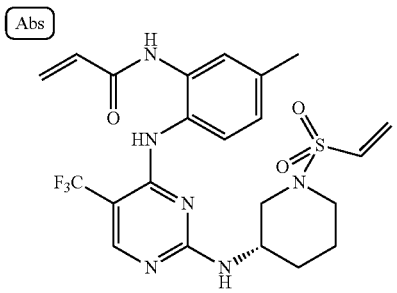

I-277

(S)—N-(5-Methyl-2-((5-(trifluoromethyl)-2-((1-(vinylsulfonyl)piperidin-3-yl)amino)pyrimidin-4-yl)amino)phenyl)acrylamide Compound I-277 was prepared in a manner similar to Example 1, substituting N-(2-amino-5-methylphenyl)acrylamide for N-(2-aminophenyl)acrylamide, and substituting 2-chloroethansulfonyl chloride for acetic chloride. MS m/z: 511.1 (ES+, M+H).

Example 65

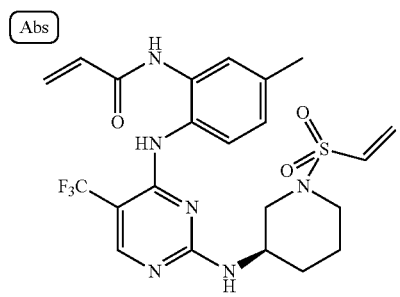

I-278

(R)—N-(5-Methyl-2-((5-(trifluoromethyl)-2-((1-(vinylsulfonyl)piperidin-3-yl)amino)pyrimidin-4-yl)amino)phenyl)acrylamide Compound I-278 was prepared in a manner similar to Example 1, substituting (R)-tert-butyl 3-aminopiperidine-1-carboxylate for (S)-tert-butyl 3-aminopiperidine-1-carboxylate, substituting N-(2-amino-5-methylphenyl)acrylamide for N-(2-aminophenyl)acrylamide, and substituting 2-chloroethansulfonyl chloride for acetic chloride. MS m/z: 511.1 (ES+, M+H).

Example 66

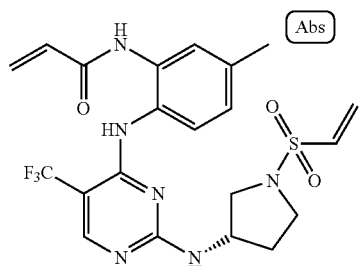

I-279

(S)—N-(5-Methyl-2-((5-(trifluoromethyl)-2-((1-(vinylsulfonyl)pyrrolidin-3-yl)amino)pyrimidin-4-yl)amino)phenyl)acrylamide Compound I-279 was prepared in a manner similar to Example 1, substituting (S)-tert-butyl 3-aminopyrrolidine-1-carboxylate for (S)-tert-butyl 3-aminopiperidine-1-carboxylate, substituting N-(2-amino-5-methylphenyl)acrylamide for N-(2-aminophenyl)acrylamide, and substituting 2-chloroethansulfonyl chloride for acetic chloride. MS m/z: 497.1 (ES+, M+H).

Example 67

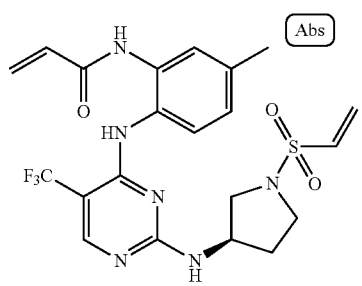

I-280

(R)—N-(5-Methyl-2-((5-(trifluoromethyl)-2-((1-(vinylsulfonyl)pyrrolidin-3-yl)amino)pyrimidin-4-yl)amino)phenyl)acrylamide Compound I-280 was prepared in a manner similar to Example 1, substituting (R)-tert-butyl 3-aminopyrrolidine-1-carboxylate for (S)-tert-butyl 3-aminopiperidine-1-carboxylate, substituting N-(2-amino-5-methylphenyl)acrylamide for N-(2-aminophenyl)acrylamide, and substituting 2-chloroethansulfonyl chloride for acetic chloride. MS m/z: 497.1 (ES+, M+H).

Method B first introduces the aniline at the C-4 position of the pyrimidine system, followed by the coupling of a second aniline or aliphatic amine group at the pyrimidine C-2 position. General reaction sequences are described below.

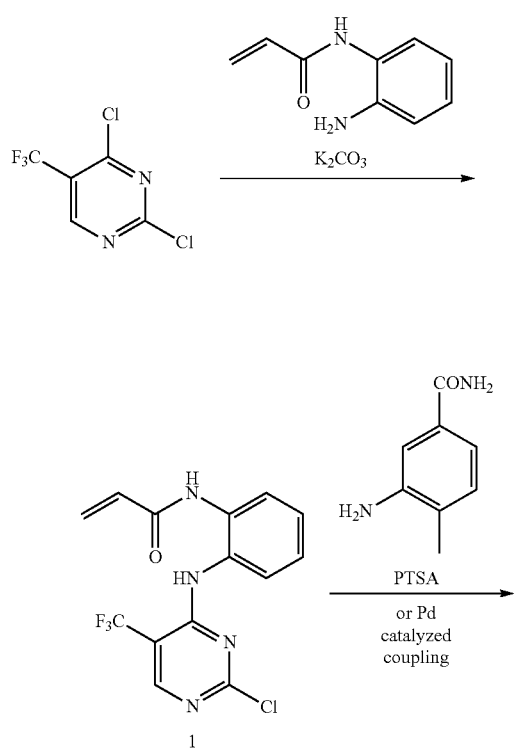

Example 68

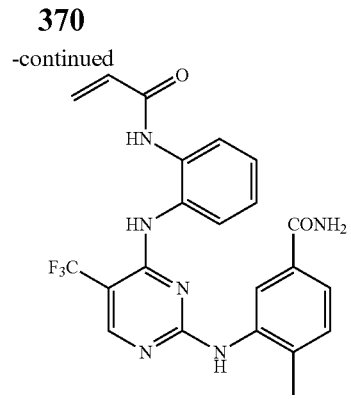

I-68

3-(4-(2-Acrylamidophenylamino)-5-(trifluoromethyl)pyrimidin-2-ylamino)-4-methylbenzamide The title compound was prepared according to the steps and intermediates described below.

Step 1: N-(2-(2-Chloro-5-(trifluoromethyl)pyrimidin-4-ylamino)phenyl)acrylamide (Intermediate 1)

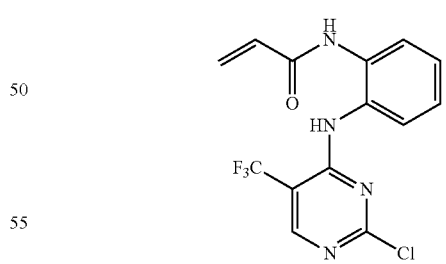

To a stirred solution of N-(2-aminophenyl) acrylamide (3.6 g, 22.2 mmol) in dimethyl acetamide (25 mL) was added potassium carbonate (6.34 g, 46.0 mmol) at rt, and the mixture was stirred for 15 min. To this reaction mixture, 2,4-dichloro-5-trifluoromethylpyrimidine (4.8 g, 22.2 mmol) was added, and the stirring continued at 60° C. for 1 h. TLC showed completion of starting material and formation of two isomers (TLC system: 30% ethyl acetate/hexane). The reaction mixture was diluted with water (2×50 mL) and extracted with EtOAc (2×100 mL). The organic layer was dried over sodium sulfate and concentrated to get the crude (7 g). This crude was purified by silica gel column chromatography using 20% ethyl acetate/hexane and subsequently purified by prep-HPLC to get desired intermediate 1 as a white solid (1.1 g, 14%). MS: m/z 343.1 (ES+, M+H).

Step 2: Acid catalyzed coupling method: 3-(4-(2-Acrylamidophenylamino)-5-(trifluoromethyl)pyrimidin-2-ylamino)-4-methylbenzamide

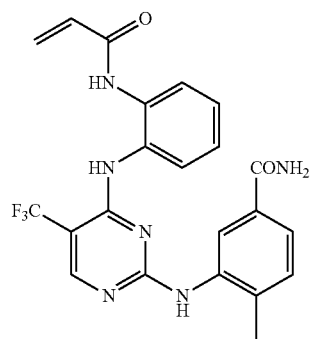 [SMILES: C=CC(=O)Nc1ccccc1Nc1nc(Nc2cc(C(N)=O)ccc2C)ncc1C(F)(F)F]

To a solution of Intermediate 1 (1 g, 2.923 mmol) in 0.04 M PTSA solution in 1,4-Dioxane (20 mL) was added 3-amino-4-methylbenzamide (526 mg, 3.5076 mmol), and the mixture was stirred at 95° C. for 16 h. TLC showed completion of starting material. (TLC system: 10% Methanol/DCM, ($R_f$): 0.6). The reaction mixture was directly absorbed on silica gel and purified by column chromatography using 4% methanol/DCM as eluents. The resulting off-white solid was stirred in a mixture of DCM: EtOAc: Diethyl Ether (10 mL:10 mL:30 mL) for 10 min, then filtered and dried under vacuum to obtain 596 mg of the desired compound (44%). $^1$HNMR (400 MHz, DMSO-$d_6$) δ 2.15 (s, 3H), 5.78-5.81 (dd, 1H, J=1.9, 10.0 Hz), 6.26-6.31 (dd, 1H, J=2.0, 17.0 Hz), 6.40-6.46 (dd, 1H, J=10.0, 16.9 Hz), 7.02-7.09 (m, 2H), 7.13-7.15 (d, 1H, J=7.5 Hz), 7.19-7.21 (dd, 1H, J=7.9 Hz), 7.32 (br s, 1H), 7.57-7.59 (dd, 1H, J=1.6, 7.6 Hz), 7.66-7.68 (d, 1H, J=8 Hz), 7.88-7.91 (d, 2H, J=11.4 Hz), 8.21 (s, 1H), 8.27 (s, 1H), 9.12 (br s, 1H) 10.3 (s, 1H). MS: m/z 457.3 (ES+, M+H).

Step 2: Pd-catalyzed coupling method: 3-(4-(2-Acrylamidophenylamino)-5-(trifluoromethyl)pyrimidin-2-ylamino)-4-methylbenzamide Alternatively, Step 2 was carried out as follows: To a solution of 3-amino-4-methylbenzamide (20 mg, 0.13 mmol), Intermediate 1 (34 mg, 0.10 mmol), and Na$_2$CO$_3$ (44 mg, 0.40 mmol) in 1 mL of degassed tert-amyl alcohol, was added tris-dibenzylamino dipalladium (5.0 mg, 5.5 μmol) and Dave Phos (7.5 mg). The mixture was degassed and purged again with argon, then heated at 100° C. for 1 h. LC-MS confirmed the completion of the reaction. After EtOAc/water workup, the residue was purified by column chromatograph on silica gel, using heptanes/EtOAc gradient system, giving pale white solid 23 mg (50%). MS: m/z 457.3 (ES+, M+H).

Example 69

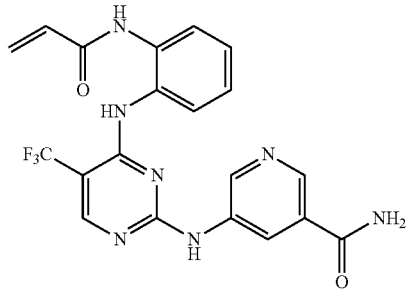

5-((4-((2-Acrylamidophenyl)amino)-5-(trifluoromethyl)pyrimidin-2-yl)amino)nicotinamide Compound I-63 was prepared in a manner similar to Example 68, substituting 5-aminonicotinamide for 3-amino-4-methylbenzamide. MS m/z: 444.1 (ES+, M+H).

Example 70

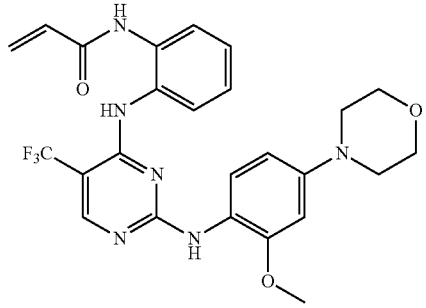

N-(2-((2-((2-Methoxy-4-morpholinophenyl)amino)-5-(trifluoromethyl)pyrimidin-4-yl)amino)phenyl) acrylamide Compound I-65 was prepared in a manner similar to Example 68, substituting 2-methoxy-4-morpholinoaniline for 3-amino-4-methylbenzamide: MS m/z 515.3 (ES+, M+H).

Example 71

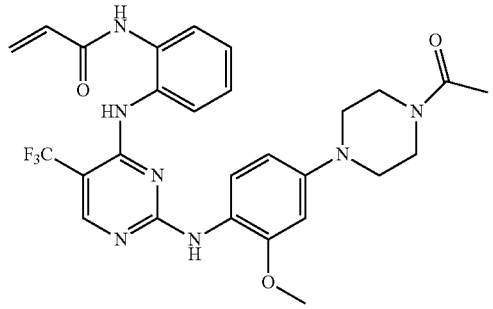

373

N-(2-((2-((4-(4-Acetylpiperazin-1-yl)-2-methoxy-phenyl)amino)-5-(trifluoromethyl)pyrimidin-4-yl)amino)phenyl)acrylamide Compound I-66 was prepared in a manner similar to Example 68, substituting 1-(4-(4-amino-3-methoxyphenyl)piperazin-1-yl)ethanone for 3-amino-4-methylbenzamide: MS m/z 556.2 (ES+, M+H). ¹H NMR (DMSO-d₆) δ 2.04 (s, 3H), 3.03-3.05 (m, 2H), 3.09-3.11 (m, 2H), 3.55-3.58 (m, 4H), 3.75 (s, 3H), 5.77-5.80 (dd, 1H, J=1.8, 10.0 Hz), 6.26-6.31 (m, 2H), 6.41-6.47 (dd, 1H, J=10.0, 16.8 Hz), 6.60 (d, 1H, J=2.4 Hz), 7.21-7.28 (m, 3H), 7.36-7.38 (dd, 1H, J=8.5 Hz), 7.67-7.68 (d, 1H, J=6 Hz), 8.16 (s, 1H), 8.21-8.23 (d, 2H, J=9.7 Hz), 10.28 (s, 1H).

Example 72

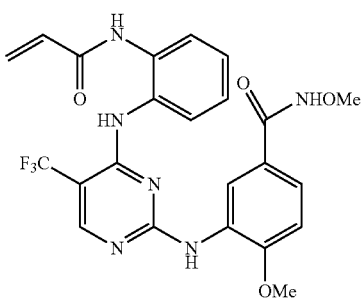

I-67

3-((4-((2-Acrylamidophenyl)amino)-5-(trifluoromethyl)pyrimidin-2-yl)amino)-N,4-dimethoxybenzamide Compound I-67 was prepared in a manner similar to Example 68, substituting 3-amino-N,4-dimethoxybenzamide for 3-amino-4-methylbenzamide: MS m/z 503.2 (ES+, M+H); ¹HNMR (DMSO-d₆) δ 3.69 (s, 3H), 3.79 (s, 3H), 5.77-5.80 (dd, 1H, J=1.9, 10 Hz), 6.26-6.31 (dd, 1H, J=1.9, 17.0 Hz), 6.40-6.47 (dd, 1H, J=2.0, 17.0 Hz), 7.05-7.11 (m, 3H), 7.17-7.19 (d, 1H, J=7.33 Hz), 7.50-7.52 (dd, 1H, J=1.9, 7.5 Hz), 7.65-7.67 (d, 1H, J=7.5 Hz), 7.93 (s, 1H), 8.27-8.30 (d, 2H, J=14.6 Hz), 8.60 (s, 1H), 10.3 (s, 1H), 11.51 (s, 1H).

Example 73

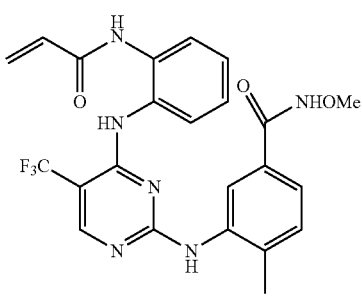

I-69

374

3-((4-((2-Acrylamidophenyl)amino)-5-(trifluoromethyl)pyrimidin-2-yl)amino)-N-methoxy-4-methyl-benzamide Compound I-69 was prepared in a manner similar to Example 68, substituting 3-amino-N-methoxy-4-methylbenzamide for 3-amino-4-methylbenzamide: MS m/z 487.4 (ES+, M+H); 1HNMR (DMSO-d₆) δ 2.16 (s, 3H), 3.70 (s, 3H), 5.78-7.81 (dd, 1H, J=1.9, 10.0 Hz), 6.26-6.31 (dd, 1H, J=1.9, 16.9 Hz), 6.40-6.47 (dd, 1H, J=10, 16.9 Hz), 7.0 (br s, 1H), 7.08-7.10 (d, 1H, J=7.0 Hz), 7.14-7.16 (d, 1H, J=7.0 Hz), 7.22-7.24 (d, 1H, J=8.0 Hz), 7.44-7.47 (dd, 1H, J=1.6, 7.8 Hz), 7.62-7.64 (d, 1H, J=8 Hz), 7.75 (s, 1H), 8.23 (s, 1H), 8.28 (s, 1H), 9.14 (s, 1H) 10.3 (s, 1H), 11.65 (s, 1H).

Example 74

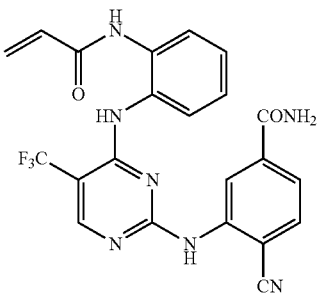

I-70

3-((4-((2-Acrylamidophenyl)amino)-5-(trifluoromethyl)pyrimidin-2-yl)amino)-4-methoxybenzamide Compound I-70 was prepared in a manner similar to Example 68, substituting 3-amino-4-methoxybenzamide for 3-amino-4-methylbenzamide: MS m/z 473.3 (ES+, M+H); ¹HNMR (DMSO-d₆) δ 3.78 (s, 3H), 5.77-5.80 (dd, 1H, J=1.9, 10.0 Hz), 6.26-6.31 (dd, 1H, J=2.0, 17.0 Hz), 6.40-6.47 (dd, 1H, J=10.0 17.0 Hz), 7.03-7.05 (d, 1H, J=8.7 Hz), 7.09-7.12 (m, 2H), 7.16-7.18 (m, 2H), 7.67-7.70 (m, 2H), 7.76 (s, 1H), 8.02 (s, 1H), 8.24 (s, 1H), 8.29 (s, 1H), 8.62 (br s, 1H), 10.29 (s, 1H).

Example 75

I-71

3-((4-((2-Acrylamidophenyl)amino)-5-(trifluoromethyl)pyrimidin-2-yl)amino)-4-cyanobenzamide Compound I-71 was prepared in a manner similar to Example 68, substituting 3-amino-4-cyanobenzamide for 3-amino-4-methylbenzamide: MS m/z 468.1 (ES+, M+H); ¹H NMR (DMSO-d₆) δ 5.78-5.81 (dd, 1H, J=1.9, 10.0 Hz), 6.27-6.32 (dd, 1H, J=2.0, 16.0 Hz), 6.40-6.47 (dd, 1H, J=10.0, 16.9 Hz), 7.07-7.15 (m, 2H), 7.18-7.20 (dd, 1H, J=1.5, 7.8 Hz), 7.62-7.66 (m, 2H), 7.70-7.72 (dd, 1H, J=1.5, 7.8 Hz), 7.81-7.83 (d, 1H, J=8 Hz), 7.96 (s, 1H), 8.14 (br s, 1H), 8.35-8.38 (d, 2H, J=9 Hz), 9.88 (s, 1H), 10.32 (s, 1H).

Example 76

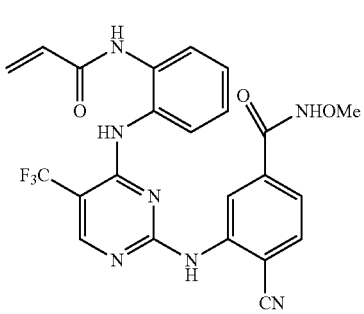

I-72

3-((4-((2-Acrylamidophenyl)amino)-5-(trifluoromethyl)pyrimidin-2-yl)amino)-4-cyano-N-methoxybenzamide Compound I-72 was prepared in a manner similar to Example 68, substituting 3-amino-4-cyano-N-methoxybenzamide for 3-amino-4-methylbenzamide: MS m/z 498.2 (ES+, M+H); ¹HNMR (CD₃OD) δ 3.83 (s, 3H), 5.81-5.84 (dd, 1H, J=3.2, 8.59 Hz), 6.38-6.49 (m, 2H), 7.16-7.29 (m, 3H), 7.55-7.57 (d, 1H, J=8.8 Hz), 7.58-7.60 (d, 1H, J=7.8 Hz), 7.70-7.72 (d, 1H, J=8 Hz), 8.01 (d, 1H, J=1.36 Hz), 8.32 (s, 1H).

Example 77

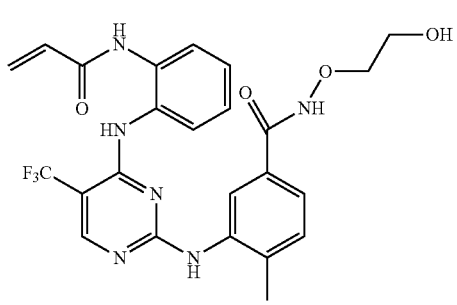

I-73

3-((4-((2-Acrylamidophenyl)amino)-5-(trifluoromethyl)pyrimidin-2-yl)amino)-N-(2-hydroxyethoxy)-4-methylbenzamide Compound I-73 was prepared in a manner similar to Example 68, substituting 3-amino-N-(2-hydroxyethoxy)-4-methylbenzamide for 3-amino-4-methylbenzamide: MS m/z 517.2 (ES+, M+H); ¹HNMR (DMSO-d₆) δ 2.16 (s, 3H), 3.60 (q, 2H, J=10.3, 16.9 Hz), 3.90-3.93 (t, 2H, J=5.6 Hz), 4.75 (t, 1H, J=5.7 Hz), 5.78-5.81 (dd, 1H, J=2.0, 10.0 Hz), 6.26-6.31 (dd, 1H, J=2.0, 17.0 Hz), 6.40-6.50 (dd, 1H, J=10.1, 17.0 Hz), 6.99 (br s, 1H), 7.06-7.10 (t, 1H, J=7.8, 14.5 Hz), 7.14-7.16 (d, 1H, J=7.8 Hz), 7.22-7.24 (d, 1H, J=8 Hz), 7.46-7.49 (dd, 1H, J=1.6, 7.9 Hz), 7.62-7.64 (d, 1H, J=8.2 Hz), 7.77 (s, 1H), 8.23 (s, 1H), 8.28 (s, 1H), 9.15 (s, 1H) 10.3 (s, 1H), 11.68 (s, 1H).

Example 78

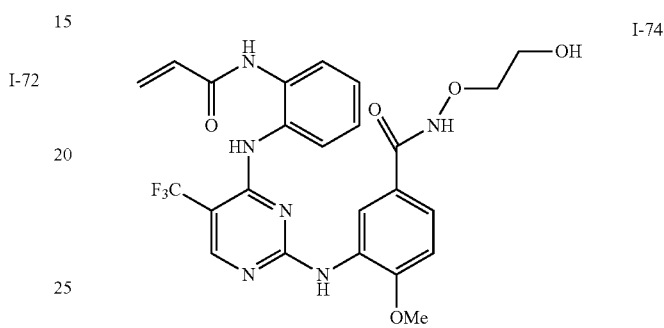

I-74

3-((4-((2-Acrylamidophenyl)amino)-5-(trifluoromethyl)pyrimidin-2-yl)amino)-N-(2-hydroxyethoxy)-4-methoxybenzamide Compound I-74 was prepared in a manner similar to Example 68, substituting 3-amino-N-(2-hydroxyethoxy)-4-methoxybenzamide for 3-amino-4-methylbenzamide: MS m/z 533.2 (ES+, M+H); ¹HNMR (DMSO-d₆) δ 3.58-3.59 (d, 2H, J=4.8 Hz), 3.80 (s, 3H), 3.90-3.91 (m, 2H), 4.75 (m, 1H), 5.77-7.80 (dd, 1H, J=1.9, 10.0 Hz), 6.21-6.31 (dd, 1H, J=1.9, J=17.0 Hz), 6.40-6.47 (dd, 1H, J=10.0, 17.0 Hz), 7.07-7.19 (m, 4H), 7.52-7.55 (d, 1H, J=2.0, 8.5 Hz), 7.65-7.67 (d, 1H, J=8.4 Hz), 7.95 (s, 1H), 8.27 (s, 1H), 8.30 (s, 1H), 8.61 (s, 1H), 10.3 (s, 1H), 11.55 (s, 1H).

Example 79

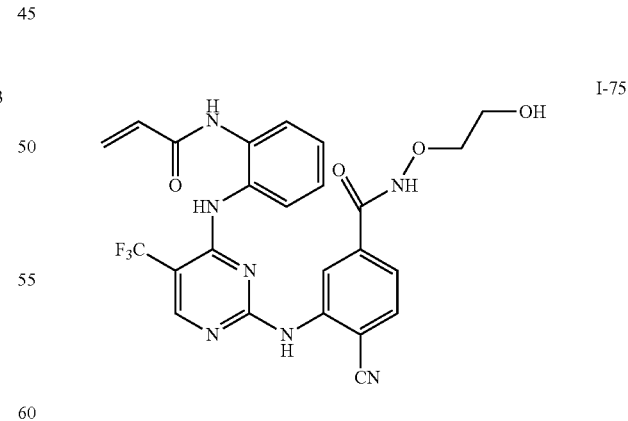

I-75

3-((4-((2-Acrylamidophenyl)amino)-5-(trifluoromethyl)pyrimidin-2-yl)amino)-4-cyano-N-(2-hydroxyethoxy)benzamide Compound I-75 was prepared in a manner similar to Example 68, substituting 3-amino-4-cyano-N-(2-hydroxyethoxy)benzamide for 3-amino-4-methylbenzamide: MS m/z 528.2 (ES+, M+H); 1HNMR (CD₃OD) δ 3.79-3.81 (t, 2H, J=4.7, 9.1 Hz), 4.10 (m, 2H), 5.81-5.84 (dd, 1H, J=3.2, 8.6 Hz), 6.38-6.49 (m, 2H), 7.15-7.25 (m, 2H), 7.28-7.30 (d, 1H, J=6.6 Hz), 7.55-7.60 (m, 2H), 7.70-7.72 (d, 1H, J=8 Hz), 8.0 (s, 1H), 8.32 (s, 1H).

Example 80

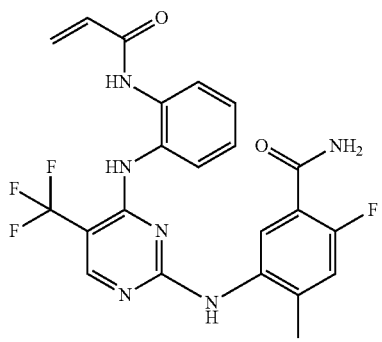

I-76

5-((4-((2-Acrylamidophenyl)amino)-5-(trifluoromethyl)pyrimidin-2-yl)amino)-2-fluoro-4-methylbenzamide Compound I-76 was prepared in a manner similar to Example 68, substituting 5-amino-2-fluoro-4-methylbenzamide for 3-amino-4-methylbenzamide: MS m/z 475.1 (ES+, M+H).

Example 81

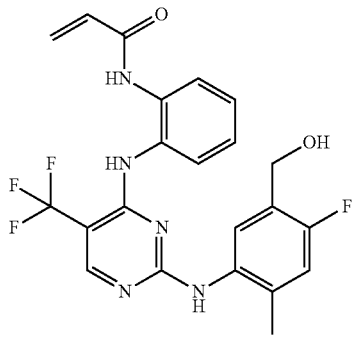

I-77

N-(2-((2-((4-Fluoro-5-(hydroxymethyl)-2-methylphenyl)amino)-5-(trifluoromethyl)pyrimidin-4-yl)amino)phenyl)acrylamide Compound I-77 was prepared in a manner similar to Example 68, substituting (5-amino-2-fluoro-4-methylphenyl)methanol for 3-amino-4-methylbenzamide: MS m/z 462.2 (ES+, M+H).

Example 82

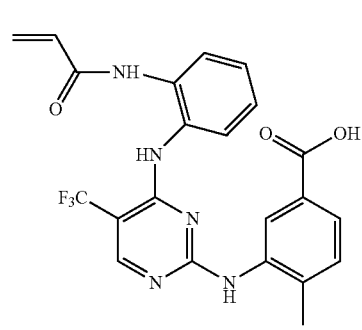

I-78

3-((4-((2-Acrylamidophenyl)amino)-5-(trifluoromethyl)pyrimidin-2-yl)amino)-4-methylbenzoic acid Compound I-78 was prepared in a manner similar to Example 68, substituting 3-amino-4-methylbenzoic acid for 3-amino-4-methylbenzamide: MS m/z 458.4 (ES+, M+H); ¹HNMR (DMSO-d₆) δ 2.16 (s, 3H), 5.77-5.80 (dd, 1H, J=1.9, 10.0 Hz), 6.26-6.31 (dd, 1H, J=1.9, 17 Hz), 6.40-6.47 (dd, 1H, J=10, 17 Hz), 7.08 (br s, 1H), 7.10-7.16 (t, 1H, J=7 Hz), 7.24-7.26 (d, 1H, J=7.9 Hz), 7.60-7.62 (dd, 2H, J=1.5, 7.8 Hz), 7.86 (s, 1H), 8.21 (s, 1H), 8.28 (s, 1H), 9.13 (s, 1H), 10.28 (s, 1H), 12.81 (s, 1H).

Example 83

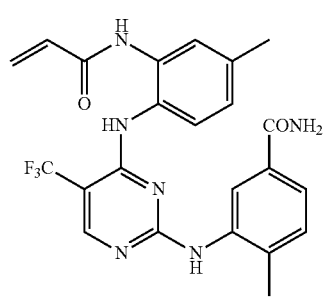

I-79

3-((4-((2-Acrylamido-4-methylphenyl)amino)-5-(trifluoromethyl)pyrimidin-2-yl)amino)-4-methylbenzamide Compound I-79 was prepared in a manner similar to Example 68, substituting N-(2-amino-5-methylphenyl)acrylamide for N-(2-aminophenyl)acrylamide. MS m/z 471.2 (ES+, M+H).

Example 84

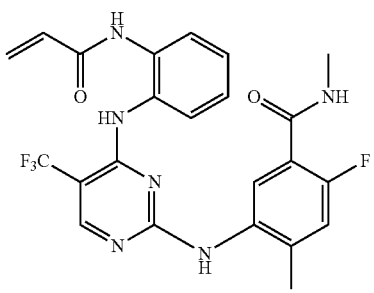

I-80

5-((4-((2-Acrylamidophenyl)amino)-5-(trifluoromethyl)pyrimidin-2-yl)amino)-2-fluoro-N,4-dimethylbenzamide Compound I-80 was prepared in a manner similar to Example 68, substituting 5-amino-2-fluoro-N,4-dimethylbenzamide for 3-amino-4-methylbenzamide. MS m/z 489.2 (ES+, M+H).

Example 85

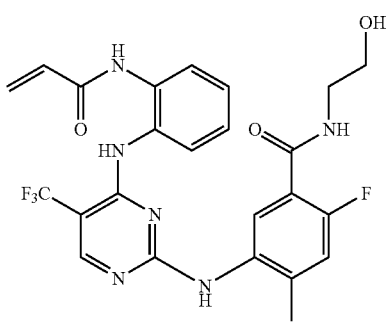

I-81

5-((4-((2-Acrylamidophenyl)amino)-5-(trifluoromethyl)pyrimidin-2-yl)amino)-2-fluoro-N-(2-hydroxyethyl)-4-methylbenzamide Compound I-81 was prepared in a manner similar to Example 68, substituting 5-amino-2-fluoro-N-(2-hydroxyethyl)-4-methylbenzamide for 3-amino-4-methylbenzamide. MS m/z 519.1 (ES+, M+H).

Example 86

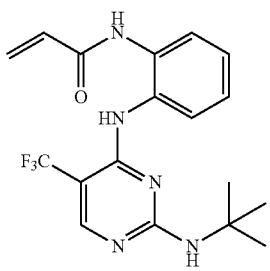

I-82

N-(2-((2-(tert-Butylamino)-5-(trifluoromethyl)pyrimidin-4-yl)amino)phenyl)acrylamide Compound I-82 was prepared in a manner similar to Example 68, substituting 2-methylpropan-2-amine for 3-amino-4-methylbenzamide: MS m/z 380.2 (ES+, M+H); $^1$HNMR (DMSO-$d_6$) δ 1.10-1.31 (s, 9H), 5.77-5.80 (dd, 1H, J=1.9, 10 Hz), 6.26-6.31 (dd, 1H, J=1.8, 16.8 Hz), 6.41-6.48 (dd, 1H, J=10, 17 Hz), 7.02 (br s, 1H), 7.24-7.29 (m, 3H), 7.56 (br s, 1H), 8.02 (br s, 1H), 8.10 (br s, 1H), 10.28 (s, 1H).

Example 87

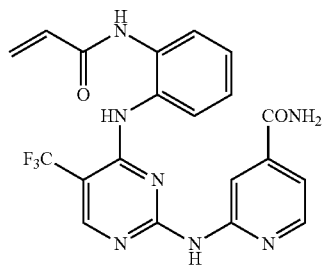

I-83

2-((4-((2-Acrylamidophenyl)amino)-5-(trifluoromethyl)pyrimidin-2-yl)amino)isonicotinamide Compound I-83 was prepared in a manner similar to Example 68, substituting 2-aminoisonicotinamide for 3-amino-4-methylbenzamide. MS m/z 443.3 (ES+, M+H).

Example 88

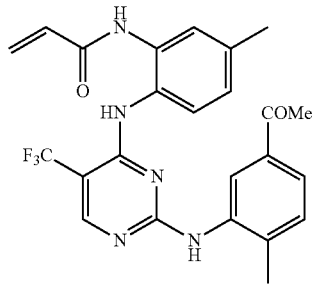

I-84

N-(2-((2-((5-Acetyl-2-methylphenyl)amino)-5-(trifluoromethyl)pyrimidin-4-yl)amino)-5-methylphenyl)acrylamide Compound I-84 was prepared in a manner similar to Example 68, substituting 1-(3-amino-4-methylphenyl)ethanone for 3-amino-4-methylbenzamide: MS m/z 470.5 (ES+, M+H); $^1$HNMR (DMSO-$d_6$) δ 2.21 (s, 6H), 2.38 (m, 3H), 5.76-5.79 (dd, J=1.9, 10.0 Hz, 1H), 6.25-6.30 (dd, J=1.9, 16.9 Hz, 1H), 6.39-6.46 (dd, J=10.0, 16.9 Hz, 1H), 6.71 (br s, 1H), 6.99 (s, 1H), 7.29 (d, J=7.9 Hz, 1H), 7.38 (d, J=7.4 Hz, 1H), 7.61 (d, J=1.6 Hz, 1H), 7.84 (d, J=1.4 Hz, 1H), 8.12 (s, 1H), 8.26 (s, 1H), 9.11 (s, 1H), 10.21 (s, 1H).

Example 89

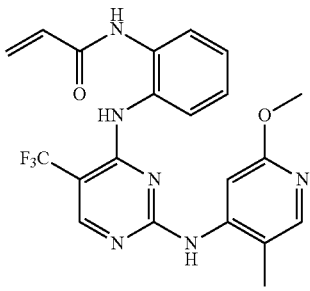

I-85

N-(2-((2-((2-Methoxy-5-methylpyridin-4-yl)amino)-5-(trifluoromethyl) pyrimidin-4-yl)amino)phenyl)acrylamide Compound I-85 was prepared in a manner similar to Example 68, substituting 2-methoxy-5-methylpyridin-4-amine for 3-amino-4-methylbenzamide. MS m/z 443.3 (ES+, M+H).

Example 90

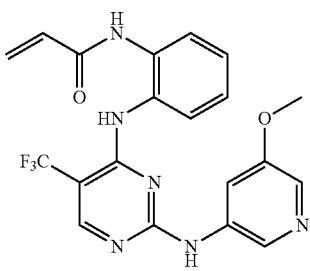

I-86

N-(2-((2-((5-Methoxypyridin-3-yl)amino)-5-(trifluoromethyl)pyrimidin-4-yl)amino)phenyl)acrylamide Compound I-86 was prepared in a manner similar to Example 68, substituting 5-methoxypyridin-3-amine for 3-amino-4-methylbenzamide. MS m/z 431.1 (ES+, M+H).

Example 91

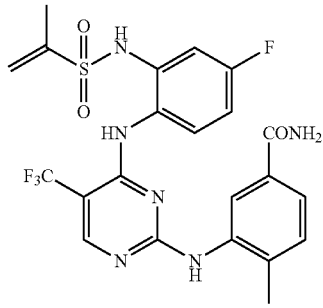

I-87

3-((4-((4-Fluoro-2-(1-methylvinylsulfonamido)phenyl)amino)-5-(trifluoromethyl) pyrimidin-2-yl)amino)-4-methylbenzamide Compound I-87 was prepared in a manner similar to Example 68, substituting N-(2-amino-5-fluorophenyl)prop-1-ene-2-sulfonamide for N-(2-aminophenyl)acrylamide: MS m/z 525.4 (ES+, M+H); $^1$HNMR (DMSO-$d_6$) δ 1.99 (s, 3H), 2.16 (s, 3H), 5.62 (s, 1H), 5.68 (s, 1H), 6.85 (d, J=9.3 Hz, 2H), 7.23 (d, J=7.9 Hz, 1H), 7.31 (s, 1H), 7.61 (d, J=7.7 Hz, 1H), 7.69-7.73 (dd, J=6.5, 8.7 Hz, 1H), 7.81 (s, 1H), 7.89 (s, 1H), 8.20 (s, 1H), 8.34 (s, 1H), 9.24 (s, 1H), 9.59 (s, 1H).

Example 92

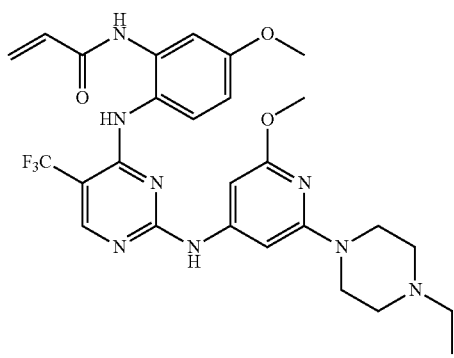

I-88

N-(2-((2-((2-(4-Ethylpiperazin-1-yl)-6-methoxypyridin-4-yl)amino)-5-(trifluoromethyl)pyrimidin-4-yl)amino)-5-methoxyphenyl)acrylamide Compound I-88 was prepared in a manner similar to Example 68, substituting 2-(4-ethylpiperazin-1-yl)-6-methoxypyridin-4-amine for 3-amino-4-methylbenzamide, and substituting N-(2-amino-5-methoxyphenyl)acrylamide for N-(2-aminophenyl)acrylamide. MS m/z 573.1 (ES+, M+H).

Example 93

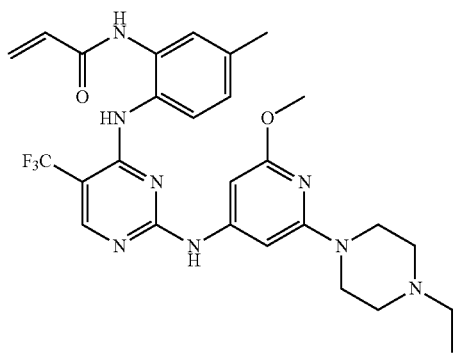

I-89

383

N-(2-((2-((2-(4-Ethylpiperazin-1-yl)-6-methoxypyridin-4-yl)amino)-5-(trifluoromethyl)pyrimidin-4-yl)amino)-5-methylphenyl)acrylamide Compound I-89 was prepared in a manner similar to Example 68, substituting 2-(4-ethylpiperazin-1-yl)-6-methoxypyridin-4-amine for 3-amino-4-methylbenzamide, and substituting N-(2-amino-5-methylphenyl)acrylamide for N-(2-aminophenyl)acrylamide. MS m/z 557.1 (ES+, M+H).

Example 94

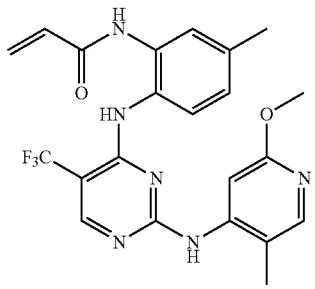

I-90

N-(2-((2-((2-Methoxy-5-methylpyridin-4-yl)amino)-5-(trifluoromethyl)pyrimidin-4-yl)amino)-5-methylphenyl)acrylamide Compound I-90 was prepared in a manner similar to Example 68, substituting 2-methoxy-5-methylpyridin-4-amine for 3-amino-4-methylbenzamide, and substituting N-(2-amino-5-methylphenyl)acrylamide for N-(2-aminophenyl)acrylamide. MS m/z 459.2 (ES+, M+H). $^1$HNMR (DMSO-$d_6$) δ 2.10 (s, 3H), 2.32 (s, 3H), 3.75 (s, 3H), 5.78 (dd, 1H, J=2.0, 10.0 Hz), 6.28 (dd, 1H, J=2.0, 16.8 Hz), 6.45 (dd, 1H, J=10.6, 16.8 Hz), 7.09 (br t, 3H, J=8.0 Hz), 7.50 (d, 1H, J=8.4 Hz), 7.79 (s, 1H), 8.36 (s, 2H), 8.72 (s, 1H), 10.25 (s, 1H).

Example 95

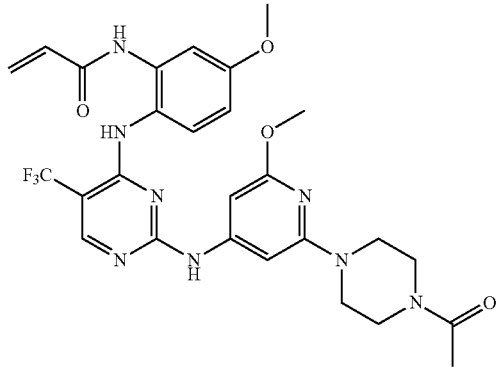

I-91

384

N-(2-((2-((2-(4-Acetylpiperazin-1-yl)-6-methoxypyridin-4-yl)amino)-5-(trifluoromethyl)pyrimidin-4-yl)amino)-5-methoxyphenyl)acrylamide Compound I-91 was prepared in a manner similar to Example 68, substituting 1-(4-(4-amino-6-methoxypyridin-2-yl)piperazin-1-yl)ethanone for 3-amino-4-methylbenzamide, and substituting N-(2-amino-5-methoxyphenyl)acrylamide for N-(2-aminophenyl)acrylamide. MS m/z 587.2 (ES+, M+H).

Example 96

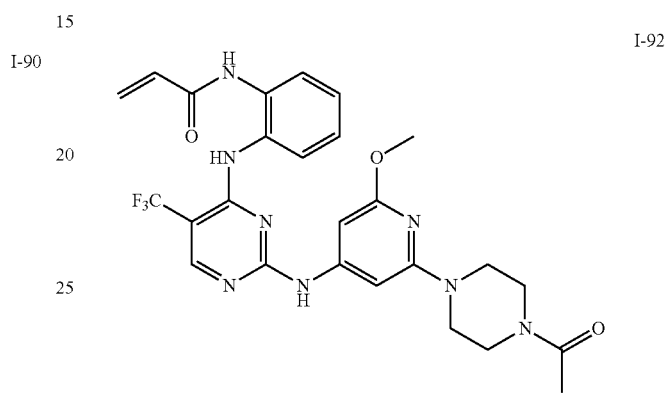

I-92

N-(2-((2-((2-(4-Acetylpiperazin-1-yl)-6-methoxypyridin-4-yl)amino)-5-(trifluoromethyl)pyrimidin-4-yl)amino)-5-methoxyphenyl)acrylamide Compound I-92 was prepared in a manner similar to Example 68, substituting 1-(4-(4-amino-6-methoxypyridin-2-yl)piperazin-1-yl)ethanone for 3-amino-4-methylbenzamide. MS m/z 557.3 (ES+, M+H).

Example 97

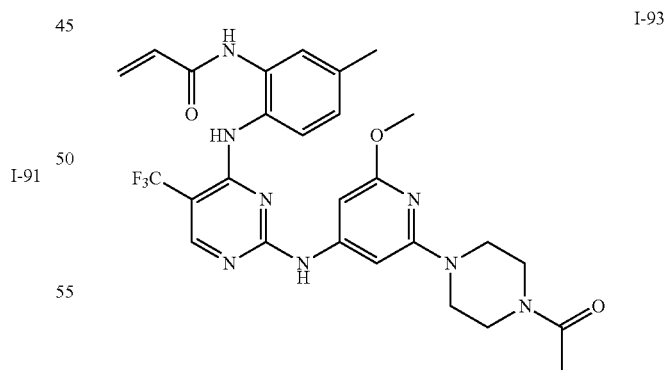

I-93

N-(2-((2-((2-(4-Acetylpiperazin-1-yl)-6-methoxypyridin-4-yl)amino)-5-(trifluoromethyl)pyrimidin-4-yl)amino)-5-methylphenyl)acrylamide Compound I-93 was prepared in a manner similar to Example 68, substituting 1-(4-(4-amino-6-methoxypyridin-2-yl)piperazin-1-yl)ethanone for 3-amino-4-methylbenzamide, and substituting N-(2-amino-5-methylphenyl)acrylamide for N-(2-aminophenyl)acrylamide. MS m/z 571.3 (ES+, M+H); 1HNMR (DMSO-d$_6$) δ 2.02 (s, 3H), 2.33 (s, 3H), 3.12 (br s, 2H), 3.46 (br s, 4H), 3.74 (s, 3H), 5.78 (dd, 1H, J=2.0, 10.0 Hz), 6.28 (30, 1H, J=2.0, 16.8 Hz), 6.45 (m, 3H), 7.10 (d, 1H, J=8.4 Hz), 7.15 (s, 1H), 7.50 (d, 1H, J=8.4 Hz), 8.36 (d, 2H, J=9.6 Hz), 9.70 (s, 1H), 10.30 (s, 1H)

Example 98

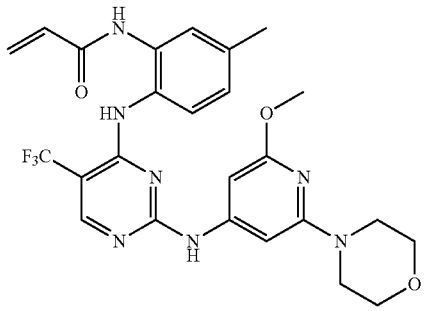

I-94

N-(2-((2-((2-Methoxy-6-morpholinopyridin-4-yl)amino)-5-(trifluoromethyl) pyrimidin-4-yl)amino)-5-methylphenyl)acrylamide Compound I-94 was prepared in a manner similar to Example 68, substituting 2-methoxy-6-morpholinopyridin-4-amine for 3-amino-4-methylbenzamide, and substituting N-(2-amino-5-methylphenyl)acrylamide for N-(2-aminophenyl)acrylamide. MS m/z 530.2 (ES+, M+H).

Example 99

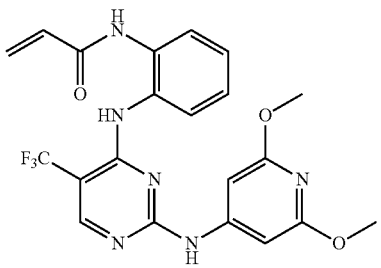

I-95

N-(2-((2-((2,6-Dimethoxypyridin-4-yl)amino)-5-(trifluoromethyl)pyrimidin-4-yl)amino)phenyl)acrylamide Compound I-95 was prepared in a manner similar to Example 68, substituting 2,6-dimethoxypyridin-4-amine for 3-amino-4-methylbenzamide. MS m/z 461.1 (ES+, M+H).

Example 100

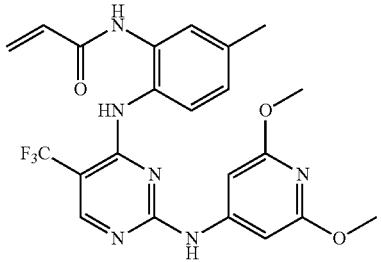

I-96

N-(2-((2-((2,6-Dimethoxypyridin-4-yl)amino)-5-(trifluoromethyl)pyrimidin-4-yl)amino)phenyl)acrylamide Compound I-96 was prepared in a manner similar to Example 68, substituting 2,6-dimethoxypyridin-4-amine for 3-amino-4-methylbenzamide, and substituting N-(2-amino-5-methylphenyl)acrylamide for N-(2-aminophenyl)acrylamide. MS m/z 475.1 (ES+, M+H).

Example 101

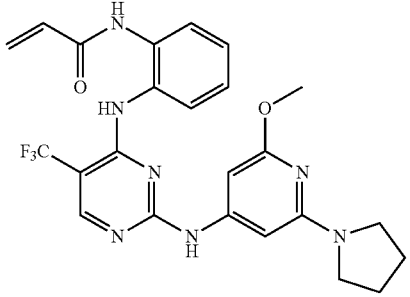

I-281

N-(2-((2-((2-Methoxy-6-(pyrrolidin-1-yl)pyridin-4-yl)amino)-5-(trifluoromethyl) pyrimidin-4-yl)amino)phenyl)acrylamide Compound I-281 was prepared in a manner similar to Example 68, substituting 2-methoxy-6-(pyrrolidin-1-yl)pyridin-4-amine for 3-amino-4-methylbenzamide. MS m/z 500.7 (ES+, M+H).

Example 102

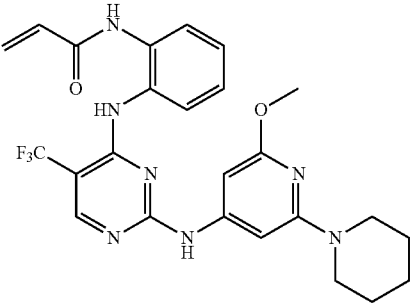

I-282

N-(2-((2-((2-Methoxy-6-(piperidin-1-yl)pyridin-4-yl)amino)-5-(trifluoromethyl) pyrimidin-4-yl)amino) phenyl)acrylamide Compound I-282 was prepared in a manner similar to Example 68, substituting 2-methoxy-6-(piperidin-1-yl)pyridin-4-amine for 3-amino-4-methylbenzamide. MS m/z 514.2 (ES+, M+H).

Example 103

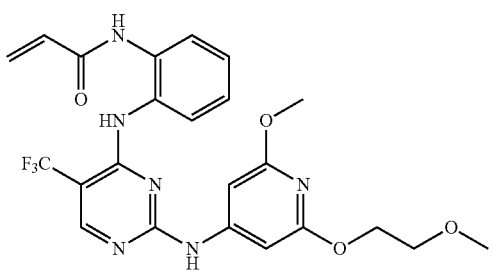

I-283

N-(2-((2-((2-Methoxy-6-(2-methoxyethoxy)pyridin-4-yl)amino)-5-(trifluoromethyl)pyrimidin-4-yl)amino)phenyl)acrylamide Compound I-283 was prepared in a manner similar to Example 68, substituting 2-methoxy-6-(2-methoxyethoxy)pyridin-4-amine for 3-amino-4-methylbenzamide. MS m/z 505.2 (ES+, M+H).

Example 104

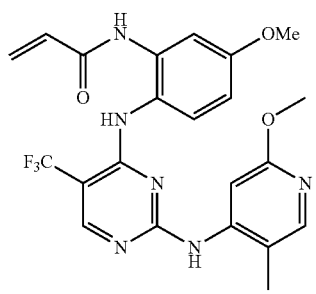

I-284

N-(5-Methoxy-2-((2-((2-methoxy-5-methylpyridin-4-yl)amino)-5-(trifluoromethyl)pyrimidin-4-yl)amino)phenyl)acrylamide Compound I-284 was prepared in a manner similar to Example 68, substituting 2-methoxy-5-methylpyridin-4-amine for 3-amino-4-methylbenzamide, and substituting N-(2-amino-5-methoxyphenyl)acrylamide for N-(2-aminophenyl)acrylamide. MS m/z 475.3 (ES+, M+H).

Example 105

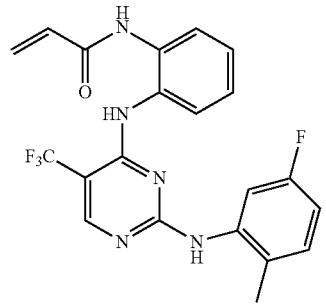

I-285

N-(2-((2-((5-Fluoro-2-methylphenyl)amino)-5-(trifluoromethyl)pyrimidin-4-yl)amino)phenyl)acrylamide Compound I-285 was prepared in a manner similar to Example 68, substituting 5-fluoro-2-methylaniline for 3-amino-4-methylbenzamide. MS m/z 432.2 (ES+, M+H).

Example 106

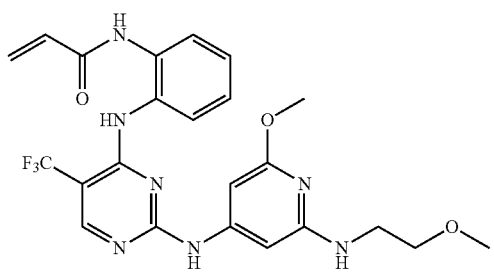

I-286

N-(2-((2-((2-Methoxy-6-((2-methoxyethyl)amino)pyridin-4-yl)amino)-5-(trifluoromethyl)pyrimidin-4-yl)amino)phenyl)acrylamide Compound I-286 was prepared in a manner similar to Example 68, substituting 6-methoxy-$N^2$-(2-methoxyethyl)pyridine-2,4-diamine for 3-amino-4-methylbenzamide. MS m/z 504.2 (ES+, M+H).

Example 107

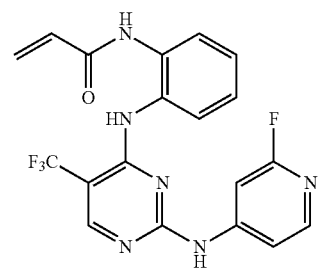

I-287

389

N-(2-((2-((2-Fluoropyridin-4-yl)amino)-5-(trifluoromethyl)pyrimidin-4-yl)amino)phenyl)acrylamide Compound I-287 was prepared in a manner similar to Example 68, substituting 2-fluoropyridin-4-amine for 3-amino-4-methylbenzamide. MS m/z 419.1 (ES+, M+H).

Example 108

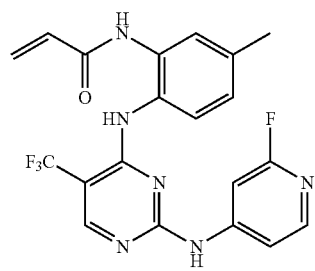

I-288

N-(2-((2-((2-Fluoropyridin-4-yl)amino)-5-(trifluoromethyl)pyrimidin-4-yl)amino)-5-methylphenyl) acrylamide Compound I-288 was prepared in a manner similar to Example 68, substituting 2-fluoropyridin-4-amine for 3-amino-4-methylbenzamide, and substituting N-(2-amino-5-methylphenyl)acrylamide for N-(2-aminophenyl)acrylamide. MS m/z 479.6 (ES+, M+H).

Example 109

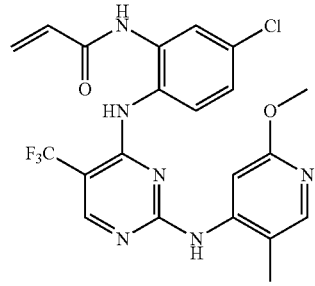

I-289

N-(5-Chloro-2-((2-((2-methoxy-5-methylpyridin-4-yl)amino)-5-(trifluoromethyl)pyrimidin-4-yl)amino) phenyl)acrylamide Compound I-289 was prepared in a manner similar to Example 68, substituting 2-methoxy-5-methylpyridin-4-amine for 3-amino-4-methylbenzamide, and substituting N-(2-amino-5-chlorophenyl)acrylamide for N-(2-aminophenyl)acrylamide. MS m/z 593.2 (ES+, M+H).

390

Example 110

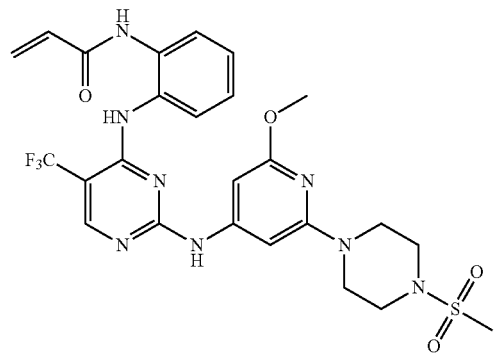

I-290

N-(2-((2-((2-Methoxy-6-(4-(methylsulfonyl)piperazin-1-yl)pyridin-4-yl)amino)-5-(trifluoromethyl) pyrimidin-4-yl)amino)phenyl)acrylamide Compound I-290 was prepared in a manner similar to Example 68, substituting tert-butyl 4-(4-amino-6-methoxypyridin-2-yl)piperazine-1-carboxylate for 3-amino-4-methylbenzamide, followed by deprotection with TFA and reaction with MsCl. MS m/z 514.2 (ES+, M+H).

Example 111

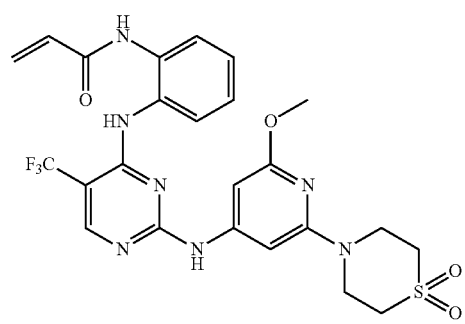

I-291

N-(2-((2-((2-(1,1-Dioxidothiomorpholino)-6-methoxypyridin-4-yl)amino)-5-(trifluoromethyl) pyrimidin-4-yl)amino)phenyl)acrylamide Compound I-291 was prepared in a manner similar to Example 68, substituting 4-(4-amino-6-methoxypyridin-2-yl)thiomorpholine 1,1-dioxide for 3-amino-4-methylbenzamide. MS m/z 595.1 (ES+, M+H).

Example 112

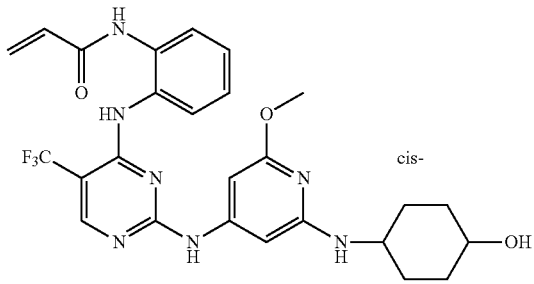

I-292

N-(2-((2-((2-((cis-4-Hydroxycyclohexyl)amino)-6-methoxypyridin-4-yl)amino)-5-(trifluoromethyl)pyrimidin-4-yl)amino)phenyl)acrylimidamide Compound I-292 was prepared in a manner similar to Example 68, substituting Cis-4-((4-amino-6-methoxypyridin-2-yl)amino)cyclohexanol for 3-amino-4-methylbenzamide. MS m/z 544.2 (ES+, M+H).

Example 113

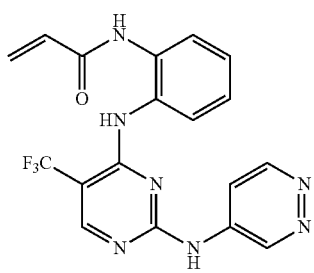

I-293

N-(2-((2-(Pyridazin-4-ylamino)-5-(trifluoromethyl)pyrimidin-4-yl)amino)phenyl) acrylamide Compound I-293 was prepared in a manner similar to Example 68, substituting pyridazin-4-amine for 3-amino-4-methylbenzamide. MS m/z 404.2 (ES+, M+H).

Example 114

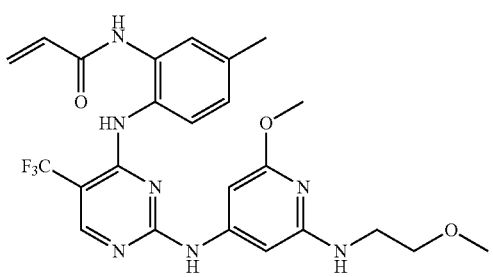

I-294

N-(2-((2-((2-methoxy-6-((2-methoxyethyl)amino)pyridin-4-yl)amino)-5-(trifluoromethyl)pyrimidin-4-yl)amino)-5-methylphenyl)acrylamide Compound I-294 was prepared in a manner similar to Example 68, substituting 6-methoxy-$N^2$-(2-methoxyethyl)pyridine-2,4-diamine for 3-amino-4-methylbenzamide, and substituting N-(2-amino-5-methylphenyl)acrylamide for N-(2-aminophenyl)acrylamide. MS m/z 518.2 (ES+, M+H); $^1$HNMR (DMSO-d$_6$) δ 2.48 (s, 3H), 3.25 (s, 3H), 3.65 (s, 3H), 5.78 (dd, 1H, J=2.0, 10.0 Hz), 5.82 (br s, 1H), 6.10 (br s, 1H), 6.25 (s, 1H), 6.28 (dd, 1H, J=2.0, 16.8 Hz), 6.45 (dd, 1H, J=10.6, 16.8 Hz), 7.14 (s, 1H), 7.50 (d, 1H, J=8.4 Hz), 8.30 (d, 1H, J=8.0 Hz), 8.33 (s, 1H), 9.62 (s, 1H), 10.25 (s, 1H).

Example 115

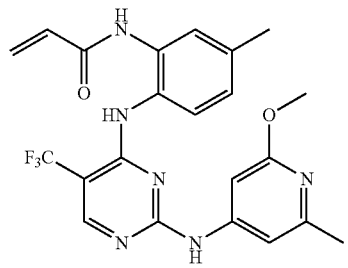

I-295

N-(2-((2-((2-methoxy-6-methylpyridin-4-yl)amino)-5-(trifluoromethyl)pyrimidin-4-yl)amino)-5-methylphenyl)acrylamide Compound I-295 was prepared in a manner similar to Example 68, substituting 2-methoxy-6-methylpyridin-4-amine for 3-amino-4-methylbenzamide, and substituting N-(2-amino-5-methylphenyl)acrylamide for N-(2-aminophenyl)acrylamide. MS m/z 459.2 (ES+, M+H). HCl-salt. 1H NMR (DMSO-d6) δ 2.22 (s, 3H), 2.34 (s, 3H), 3.75 (s, 3H), 5.78 (dd, 1H, J=2.0, 10.0 Hz), 6.28 (dd, 1H, J=2.0, 16.8 Hz), 6.45 (dd, 1H, J=10.6, 16.8 Hz), 7.05 (s, 1H), 7.16 (d, 1H, J=8.4 Hz), 7.26 (s, 1H), 7.47 (d, 1H, J=8.4 Hz), 8.50 (s, 1H), 8.62 (s, 1H), 10.34 (s, 1H), 10.69 (br s, 1H).

Different from Method B, Method C introduces the Boc-protected aniline at the C4-position of CF$_3$-pyrimidine first, followed by the coupling of the second aniline or amine at the C2-position under basic conditions. After Boc-deprotection, final acryloylation was achieved via amide bond formation with acrylic acid or acryloyl chloride. The general synthetic approach is described below.

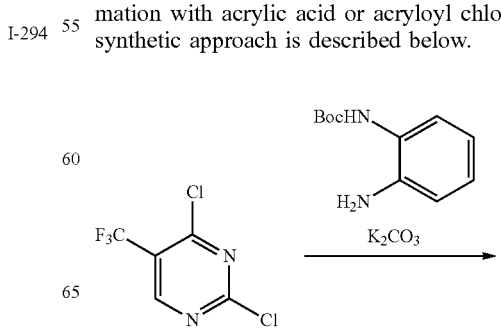

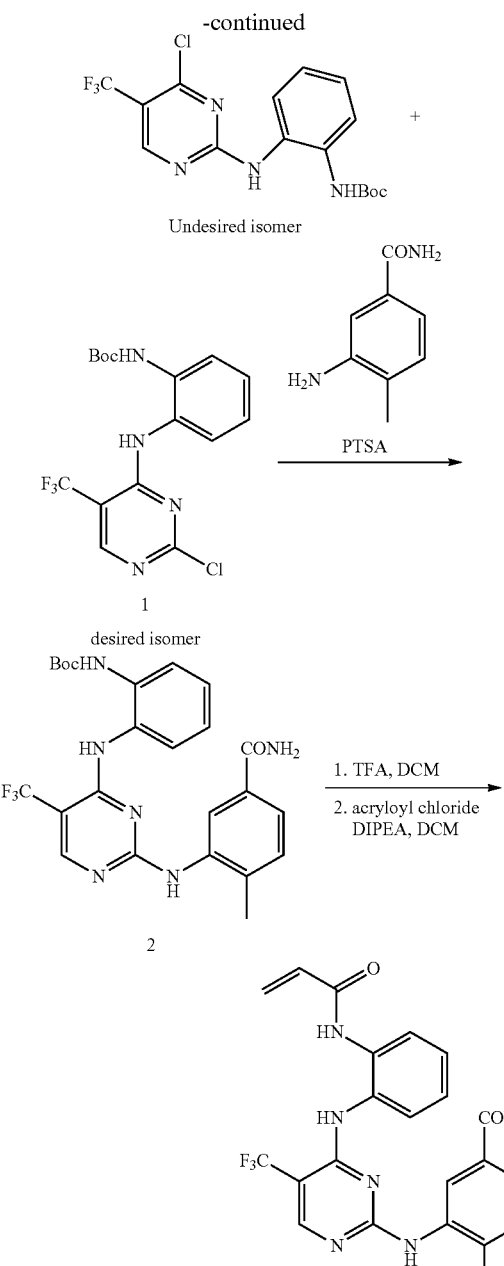

Example 116

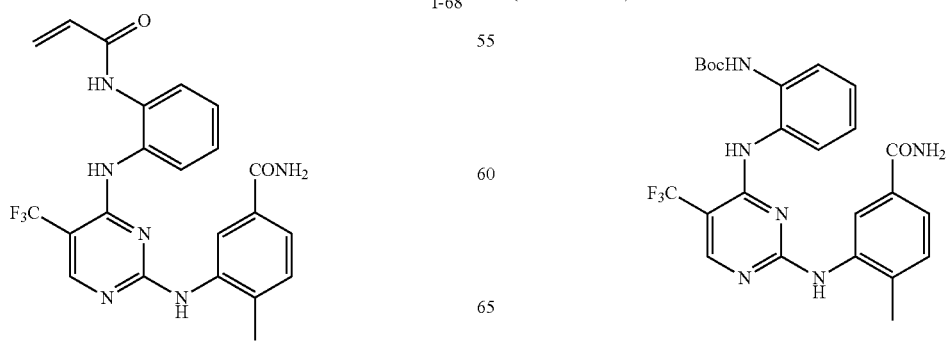

I-68

3-(4-(2-acrylamidophenylamino)-5-(trifluoromethyl) pyrimidin-2-ylamino)-4-methylbenzamide The title compound was prepared according to the steps and intermediates described below.

Step-1. tert-butyl (2-((2-chloro-5-(trifluoromethyl) pyrimidin-4-yl)amino)phenyl)carbamate (Intermediate 1)

This intermediate was synthesized according to step-1 in example 2, using tert-butyl (2-aminophenyl)carbamate to react with 5-CF3-2,4-dichloropyrimidine.

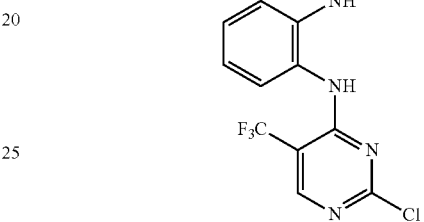

Desired Isomer (Intermediate 1):

$^1$HNMR (400 MHz, DMSO-$d_6$) δ 9.20 (s, 1H), 8.98 (s, 1H), 8.58 (s, 1H), 7.49 (d, 1H, J=7.6 Hz), 7.37 (d, 1H, J=7.6 Hz), 7.18-7.28 (m, 2H), 1.44 (s, 9H). LC-MS: m/z 389.3 (ES+, M+H).

Undesired Isomers:

1HNMR (400 MHz, DMSO-$d_6$) δ 9.80 (s, 1H), 8.68 (s, 1H), 8.52 (s, 1H), 7.60 (d, 1H, J=7.6 Hz), 7.42 (d, 1H, J=7.6 Hz), 7.18 (t, 1H, J=7.2 Hz), 7.10 (t, 1H, J=7.2 Hz), 1.44 (s, 9H). LC-MS: m/z 389.3 (ES+, M+H).

Step-2. tert-butyl (2-((2-((5-carbamoyl-2-methylphenyl)amino)-5-(trifluoromethyl) pyrimidin-4-yl) amino)phenyl)carbamate (Intermediate 2)

This intermediate was synthesized according to step-2 in example 2, using 3-amino-4-methylbenzamide to react with the desired intermediate 1 from Step-1. LC-MS: m/z=503.2 (ES+, M+H)

Step-3. 3-((4-((2-acrylamidophenyl)amino)-5-(trifluoromethyl)pyrimidin-2-yl)amino)-4-methylbenzamide

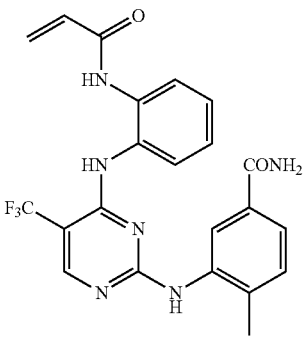 [SMILES: C=CC(=O)Nc1ccccc1Nc1nc(Nc2cc(C(N)=O)ccc2C)ncc1C(F)(F)F]

To a solution of Intermediate 2 (70 mg, 0.133 mmol) in dichloromethane (2 mL) was added trifluoroacetic acid (1 mL) and the reaction mixture was stirred at rt for 2 h. TLC showed completion of starting material. After concentration, the resulting residue is ready to use for the following step. LC-MS: m/z=403.1 (ES+, M+H)

To a solution of de-Boc intermediate obtained above in (1:1) dichloromethane: tetrahydrofuran (5 mL) at −78° C. was added acryloyl chloride (11.9 mg, 0.132 mmol). After stirring for 2 h, TLC showed completion of starting material. The reaction mixture was quenched with ice-cold water (15 mL) and extracted with chloroform (3×10 mL). The organic layer was separated, dried over sodium sulfate and concentrated. The crude compound was purified by preparative TLC to obtain the title compound as a white solid (10 mg, 13%). $^1$HNMR (400 MHz, DMSO-d6) δ 2.15 (s, 3H), 5.78-5.81 (dd, 1H, J=1.9 Hz and J=10.0 Hz), 6.26-6.31 (dd, 1H, J=2.05 Hz and J=16.97 Hz), 6.40-6.46 (dd, 1H, J=10 Hz and J=16.9 Hz), 7.02-7.09 (m, 2H), 7.13-7.15 (d, 1H, J=7.5 Hz), 7.19-7.21 (dd, 1H, J=7.9 Hz), 7.32 (br s, 1H), 7.57-7.59 (dd, 1H, J=1.6 Hz and J=7.6 Hz), 7.66-7.68 (d, 1H, J=8 Hz), 7.88-7.91 (d, 2H, J=11.38 Hz), 8.21 (s, 1H), 8.27 (s, 1H), 9.12 (br s, 1H) 10.3 (s, 1H). MS m/z: m/z 457.3 (ES+).

Example 117

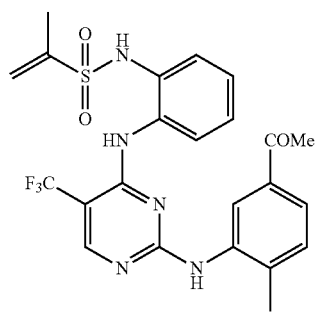

N-(2-((2-((5-acetyl-2-methylphenyl)amino)-5-(trifluoromethyl)pyrimidin-4-yl)amino)phenyl)prop-1-ene-2-sulfonamide Compound I-97 was prepared in a manner similar to Example 116, substituting 1-(3-amino-4-methylphenyl) ethanone for 3-amino-4-methylbenzamide, followed by deprotection with TFA and reaction with prop-1-ene-2-sulfonyl chloride. MS m/z 506.4 (ES+, M+H), 1H NMR (DMSO-d6) δ 2.05 (s, 3H), 2.23 (s, 3H), 2.44 (s, 3H), 5.56 (s, 1H), 5.68 (s, 1H), 6.87 (br s, 1H), 7.01 (d, J=3.6 Hz, 2H), 7.35 (d, J=8.1 Hz, 1H), 7.68 (d, J=1.69 Hz, 1H), 7.8 (br s, 1H), 7.85 (d, J=1.51 Hz, 1H), 8.32 (s, 1H), 8.37 (s, 1H), 9.35 (s, 1H), 9.45 (s, 1H).

Example 118

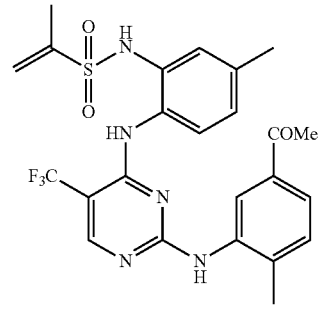

N-(2-((2-((5-acetyl-2-methylphenyl)amino)-5-(trifluoromethyl)pyrimidin-4-yl)amino)-5-methylphenyl) prop-1-ene-2-sulfonamide Compound I-98 was prepared in a manner similar to Example 116, substituting 1-(3-amino-4-methylphenyl) ethanone for 3-amino-4-methylbenzamide, and substituting tert-butyl (2-amino-5-methylphenyl)carbamate for tert-butyl (2-aminophenyl)carbamate, followed by deprotection with TFA and reaction with 2-chloroethylsulfonyl chloride. MS m/z 520.4 (ES+, M+H); $^1$HNMR (DMSO-d$_6$) δ 2.02 (s, 3H), 2.17 (s, 3H), 2.22 (s, 3H), 2.42 (s, 3H), 5.57 (s, 1H), 5.66 (s, 1H), 6.71 (br s, 1H), 6.81 (s, 1H), 7.35 (d, J=7.9 Hz, 1H), 7.55 (br s, 1H), 7.65 (dd, J=1.6, 7.8 Hz, 1H), 7.83 (d, J=1.5 Hz, 1H), 8.24 (s, 1H), 8.34 (s, 1H), 9.27 (s, 1H), 9.35 (s, 1H).

Example 119

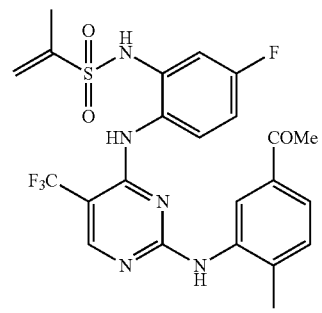

N-(2-((2-((5-acetyl-2-methylphenyl)amino)-5-(trifluoromethyl)pyrimidin-4-yl)amino)-5-fluorophenyl) prop-1-ene-2-sulfonamide Compound I-98 was prepared in a manner similar to Example 116, substituting 1-(3-amino-4-methylphenyl)

ethanone for 3-amino-4-methylbenzamide, and substituting tert-butyl (2-amino-5-fluorophenyl)carbamate for tert-butyl (2-aminophenyl)carbamate, followed by deprotection with TFA and reaction with 2-chloroethylsulfonyl chloride: MS m/z 524.4 (ES+, M+H); $^1$HNMR (DMSO-$d_6$) δ 1.97 (s, 3H), 2.19 (s, 3H), 2.42 (s, 3H), 5.67 (d, J=10.84 Hz, 2H), 6.8 (br s, 1H), 6.89 (d, J=7.7 Hz, 1H), 7.31 (d, J=7.95 Hz, 1H), 7.55 (br s, 1H), 7.66 (dd, J=1.67, 7.87 Hz, 1H), 7.77 (d, J=1.37 Hz, 1H), 8.22 (s, 1H), 8.34 (s, 1H), 9.22 (s, 1H), 9.54 (s, 1H).

Method D was developed for preparation of a 5-chloro-2,4-diamino-pyrimidine analog with an aliphatic amine at the C-2 position of the pyrimidine system. This method uses thio-ether and sulfoxide intermediates, and applies the various acrylamide ring system in the final stage. The general practice of this method is described below.

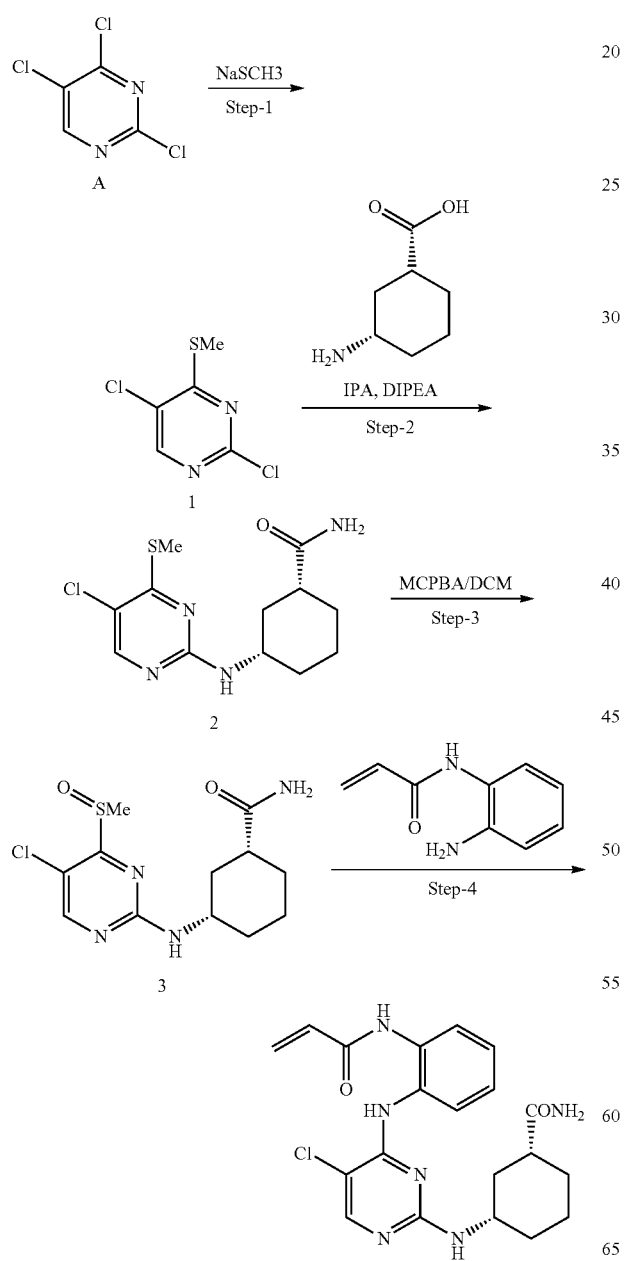

Example 120

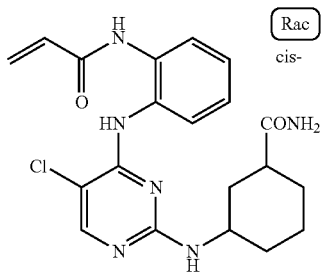

I-102

Rac-cis-3-(4-(2-acrylamidophenylamino)-5-chloro-pyrimidin-2-ylamino)cyclohexane carboxamide The title compound was prepared according to the steps and intermediates as described below.

Step 1: 2,5-dichloro-4-(methylthio)pyrimidine (Intermediate 1)

To a solution of 2,4,5-trichloropyrimidine (5 g, 27.32 mmol) in THF: water (1:1.40 mL), was added sodium thiomethoxide (2.15 g, 30.01 mmol) at 0° C., and the mixture was stirred at rt for 4 h. TLC showed completion of starting material and formation of a slightly polar spot (TLC system: hexane charred in iodine). The reaction mixture was concentrated, water (20 ml) was added, and the product was extracted with ethyl acetate (2×20 ml). The organic layer was dried over sodium sulfate and concentrated to afford the desired compound as a white solid (5 g, 94.8%). MS m/z: 195.2 (ES+, M+H).

Step 2: Rac-Cis-3-(5-chloro-4-(methylthio)pyrimidin-2-ylamino) cyclohexane carboxamide (Intermediate 2)

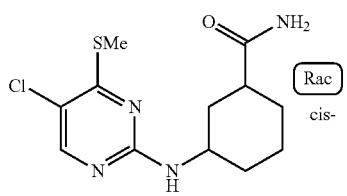 [SMILES: CSc1nc(NC2CCCC(C(N)=O)C2)ncc1Cl]

To a solution of Intermediate 1 (2 g, 10.36 mmol) in isopropyl alcohol (10 mL), was added DIPEA (4.01 g, 31.08 mmol) and Cis-3-aminocyclohexanecarboxamide (2.2 g, 15.45 mmol) at room temperature and heated to 100° C. for 48 h in a sealed tube. TLC showed completion of starting material and formation of a polar spot (TLC System: 10% ethyl acetate/hexane, (R$_f$): 0.1). After cooling down to room temperature, the mixture was concentrated, water (30 ml) was added, and the precipitated product was filtered, washed with pentane (20 ml) and dried to afford Cis-3-(5-chloro-4-(methylthio)pyrimidin-2-ylamino)cyclohexanecarboxamide as a white solid (2.2 g, 70.9%). MS m/z: 301.1 (ES+, M+H).

Step 3: Rac-Cis-3-(5-chloro-4-(methylsulfinyl)pyrimidin-2-ylamino) cyclohexane carboxamide (Intermediate 3

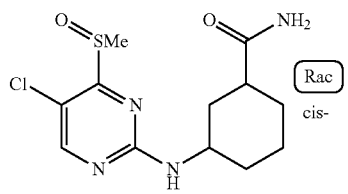

To a stirred solution of Intermediate 2 (1.9 g, 6.33 mmol) in dichloromethane: acetonitrile (700 mL), m-CPBA (1.19 g, 6.96 mmol) was added and stirred at rt for 1 h. TLC showed completion of starting material and formation of a polar spot (TLC System: 10% methanol/chloroform, (R$_f$): 0.4). The reaction mixture was concentrated, diluted with dichloromethane (30 ml), and washed with saturated sodium bicarbonate solution (20 mL) and water (15 mL). The organic layer was dried over sodium sulfate and concentrated under reduced pressure. The crude compound was purified by silica gel column chromatography with 1 to 1.5% methanol in chloroform as eluents to afford Intermediate 3 as colorless gummy solid. (1.4 g, 70%). MS m/z: 317.1 (ES+, M+H).

Step 4: Rac-Cis-3-(4-(2-acrylamidophenylamino)-5-chloropyrimidin-2-ylamino) cyclohexane carboxamide

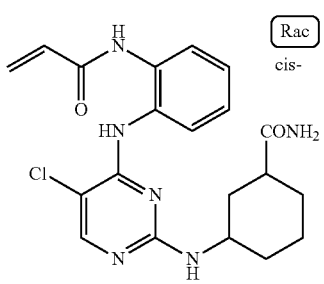 [SMILES: C=CC(=O)Nc1ccccc1Nc1nc(NC2CCCC(C(N)=O)C2)ncc1Cl]

To a solution of Intermediate 3 (1.4 g, 4.43 mmol) in 0.04 M PTSA/1,4-dioxane (12 mL, 0.106 mmol) was added N-(2-aminophenyl)acrylamide (1.72 g, 6.64 mmol), and the reaction mixture was stirred at 70° C. for 1 h. After completion of the reaction (TLC System: 5% methanol/chloroform, (R$_f$): 0.5), the reaction mixture was concentrated and diluted with water (30 mL), and the precipitate was filtered, washed with saturated sodium bicarbonate solution (15 ml) and dried to afford the desired compound as a white solid. (1.1 g, 59.7%). $^1$H NMR (400 MHz, DMSO-d$_6$) δ 1.21-1.26 (m, 3H), 1.26-1.32 (m, 2H), 1.67-1.69 (m, 2H), 1.76-1.79 (m, 2H), 2.05 (m, 1H), 5.79 (d, 1H J=11.4 Hz), 6.28-6.32 (d, 1H J=16.9 Hz), 6.46-6.52 (dd, 1H J=10.2 Hz and 17 Hz), 6.64 (br s, 1H), 7.14 (br s, 1H), 7.22-7.27 (m, 2H), 7.43 (d, 1H J=7.4 Hz), 7.74 (d, 1H J=7.8 Hz), 8.01 (s, 1H), 8.86 (br s, 1H), 10.15 (s, 1H). MS m/z: 415.2 (ES+, M+H).

Example 121

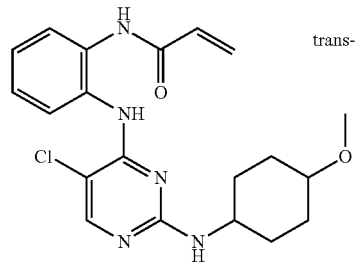

N-(2-((5-chloro-2-((trans-(4-methoxycyclohexyl)amino)pyrimidin-4-yl)amino) phenyl)acrylamide Compound I-100 was prepared in a manner similar to Example 120, substituting trans-4-methoxycyclohexanamine for cis-3-aminocyclohexanecarboxamide: MS m/z 402.2 (ES+, M+H)

Example 122

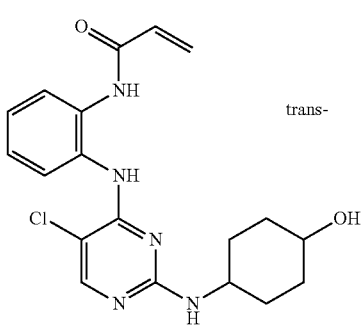

N-(2-((5-chloro-2-((trans-(4-hydroxycyclohexyl)amino)pyrimidin-4-yl)amino) phenyl)acrylamide Compound I-101 was prepared in a manner similar to Example 120, substituting trans-4-hydroxycyclohexanamine for cis-3-aminocyclohexanecarboxamide: MS m/z 388.2 (ES+, M+H) 1H NMR (DMSO-d6) δ 1.12-1.22 (m, 4H), 1.76-1.78 (m, 4H), 2.29 (br s, 1H), 4.46 (br s, 1H), 5.78-5.80 (dd, J=1.6, 10.1 Hz, 1H), 6.30 (d, 1H, J=17.0 Hz), 6.45-6.52 (dd, J=10.1, 16.9 Hz, 1H), 7.15-7.24 (m, 2H), 7.35-7.37 (d, 1H, J=7.7 Hz), 7.81 (s, 1H), 7.91 (s, 1H), 8.27 (s, 1H), 8.30 (s, 1H), 10.16 (s, 1H).

Example 123

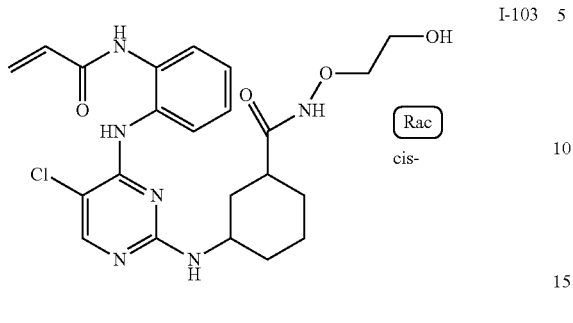

Rac-3-((4-((2-acrylamidophenyl)amino)-5-chloropyrimidin-2-yl)amino)-N-(2-hydroxyethoxy)-cis-cyclohexanecarboxamide Compound I-103 was prepared in a manner similar to Example 120, substituting cis-3-amino-N-(2-hydroxyethoxy)cyclohexanecarboxamide for cis-3-aminocyclohexanecarboxamide: MS m/z 475.1 (ES+, M+H); $^1$HNMR (CD$_3$OD) δ 1.31-1.42 (m, 6H), 1.74 (d, J=9.8 Hz, 2H), 1.85 (d, J=12.0 Hz, 1H), 1.96 (d, J=9.8 Hz, 1H), 3.57 (br s, 1H), 3.65-3.69 (m, 2H), 3.89-3.92 (m, 2H), 5.80-5.83 (dd, J=2.3, 9.7 Hz, 1H), 6.37-6.47 (m, 2H), 7.23-7.27 (dt, J=1.5, 7.6 Hz, 1H), 7.30-7.34 (dt, J=1.5, 7.4 Hz, 1H), 7.45 (d, J=7.1 Hz, 1H), 7.79 (d, J=6.9 Hz, 1H), 7.85 (s, 1H).

Example 124

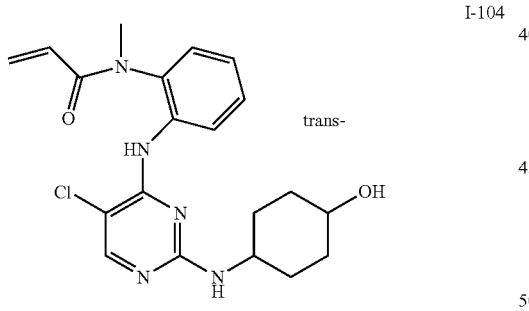

N-(2-((5-chloro-2-(trans-(4-hydroxycyclohexyl)amino)pyrimidin-4-yl)amino)phenyl)-N-methylacrylamide Compound I-104 was prepared in a manner similar to Example 120, substituting trans-4-aminocyclohexanol for cis-3-aminocyclohexanecarboxamide, and substituting N-(2-aminophenyl)-N-methylacrylamide for N-(2-aminophenyl)acrylamide: MS m/z 402.2 (ES+, M+H); $^1$HNMR (CD$_3$OD) δ 1.27-1.35 (m, 4H), 1.94-1.99 (m, 4H), 3.33 (br s, 2H), 3.55 (br s, 2H), 5.53-5.56 (dd, J=2.3 Hz, J=10.1 Hz, 1H), 6.18-6.23 (m, 1H), 6.23-6.28 (dd, J=2.2 Hz, 16.7 Hz, 1H), 7.32 (br s, 2H), 7.47-7.49 (br s, 2H), 7.87 (br s, 1H), 8.05 (br s, 1H).

Example 125

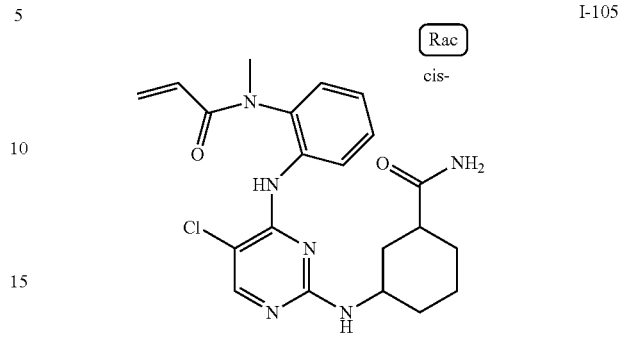

Rac-cis-3-((5-chloro-4-((2-(N-methylacrylamido)phenyl)amino)pyrimidin-2-yl)amino)cyclohexanecarboxamide Compound I-105 was prepared in a manner similar to Example 120, substituting N-(2-aminophenyl)-N-methylacrylamide for N-(2-aminophenyl)acrylamide: MS m/z 429.2 (ES+, M+H); $^1$HNMR (CD$_3$OD) δ 1.35-1.43 (m, 2H), 1.82-1.89 (m, 3H), 1.90-1.98 (m, 1H), 2.03-2.10 (m, 1H), 2.31 (br s, 1H), 3.33 (s, 3H), 3.62-3.74 (m, 1H), 3.75-3.76 (m, 1H), 5.54-5.57 (dd, J=2.9 Hz, 9.4 Hz, 1H), 6.18 (br s, 1H), 6.23-6.27 (dd, J=2.2 Hz, 16.8 Hz, 1H), 7.31 (s, 1H), 7.32 (d, J=1.8 Hz), 7.46-7.49 (m, 1H), 7.87 (s, 1H), 8.0 (br s, 1H).

Example 126

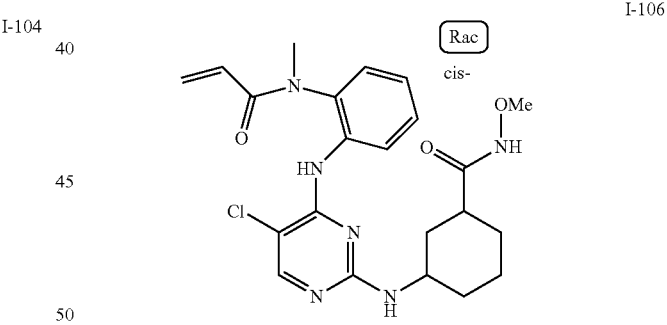

Rac-cis-3-((5-chloro-4-((2-(N-methylacrylamido)phenyl)amino) pyrimidin-2-yl)amino)-N-methoxycyclohexanecarboxamide Compound I-106 was prepared in a manner similar to Example 120, substituting cis-3-amino-N-methoxycyclohexanecarboxamide for cis-3-aminocyclohexanecarboxamide, and substituting N-(2-aminophenyl)-N-methylacrylamide for N-(2-aminophenyl)acrylamide: MS m/z 459.2 (ES+, M+H); $^1$HNMR (CD$_3$OD) δ 1.73-1.85 (m, 1H), 1.83-1.93 (m, 1H), 1.94 (m, 1H), 1.95-1.96 (m, 3H), 1.98-2.04 (m, 2H), 2.08-2.14 (m, 1H), 3.33 (s, 3H), 3.63-3.67 (m, 1H), 3.68 (s, 3H), 5.54-5.57 (dd, J=2.3 Hz, 9.8 Hz, 1H), 6.16-6.27 (m, 2H), 7.30-7.34 (m, 2H), 7.45-7.49 (m, 1H), 7.87 (s, 1H), 7.99 (br s, 1H).

Example 127

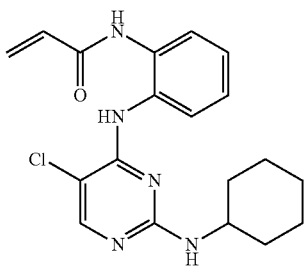

I-107

N-(2-((5-chloro-2-(cyclohexylamino)pyrimidin-4-yl)amino)phenyl)acrylamide

Compound I-107 was prepared in a manner similar to Example 120, substituting cyclohexanamine for cis-3-aminocyclohexanecarboxamide: MS m/z 372.2 (ES+, M+H).

Example 128

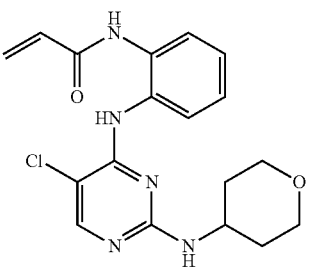

I-108

N-(2-((5-chloro-2-((tetrahydro-2H-pyran-4-yl)amino)pyrimidin-4-yl)amino) phenyl)acrylamide Compound I-108 was prepared in a manner similar to Example 120, substituting tetrahydro-2H-pyran-4-amine for cis-3-aminocyclohexanecarboxamide: MS m/z 374.2 (ES+, M+H).

Example 129

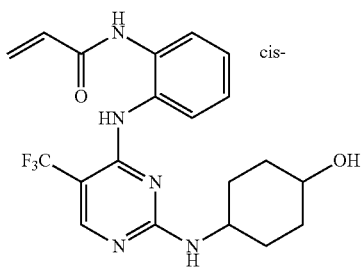

I-109

N-(2-((2-(cis-(4-hydroxycyclohexyl)amino)-5-(trifluoromethyl)pyrimidin-4-yl) amino)phenyl)acrylamide Compound I-109 was prepared in a manner similar to Example 120, substituting cis-4-aminocyclohexanol for cis-3-aminocyclohexanecarboxamide. MS m/z 422.1 (ES+, M+H).

Example 130

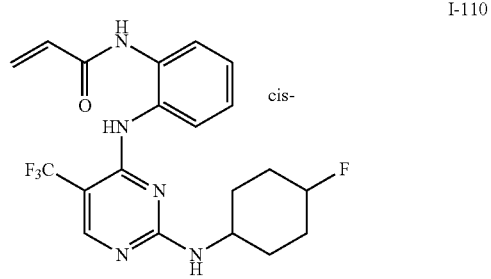 [SMILES: C=CC(=O)Nc1ccccc1Nc1nc(NC2CCC(F)CC2)ncc1C(F)(F)F]

I-110

N-(2-((2-(cis-(4-fluorocyclohexyl)amino)-5-(trifluoromethyl) pyrimidin-4-yl)amino)phenyl)acrylamide Compound I-110 was prepared in a manner similar to Example 120, substituting cis-4-fluorocyclohexanamine for cis-3-aminocyclohexanecarboxamide. MS m/z 424.4 (ES+, M+H).

Example 131

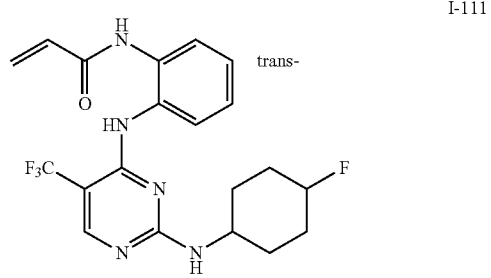 [SMILES: C=CC(=O)Nc1ccccc1Nc1nc(NC2CCC(F)CC2)ncc1C(F)(F)F]

I-111

N-(2-((2-(trans-(4-fluorocyclohexyl)amino)-5-(trifluoromethyl)pyrimidin-4-yl)amino)phenyl)acrylamide Compound I-111 was prepared in a manner similar to Example 120 substituting trans-4-fluorocyclohexanamine for cis-3-aminocyclohexanecarboxamide. MS: m/z 424.1 (ES+, M+H).

Example 132

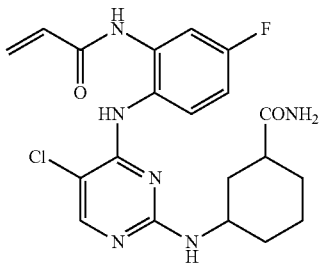

I-112

Rac-cis-3-((4-((2-acrylamido-4-fluorophenyl)amino)-5-chloropyrimidin-2-yl)amino)cyclohexanecarboxamide Compound I-112 was prepared in a manner similar to Example 120, substituting N-(2-amino-5-fluorophenyl)acrylamide for N-(2-aminophenyl)acrylamide. MS m/z 433.2 (ES+, M+H).

Example 133

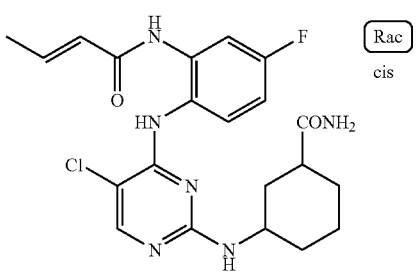

I-113

Rac-cis-(E)-3-((4-((2-(but-2-enamido)-4-fluorophenyl)amino)-5-chloropyrimidin-2-yl)amino)cyclohexanecarboxamide Compound I-113 was prepared in a manner similar to Example 120, substituting (E)-N-(2-amino-5-fluorophenyl)but-2-enamide for N-(2-aminophenyl)acrylamide: MS m/z 447.5 (ES+, M+H); $^1$HNMR (DMSO-d$_6$) δ 1.1-1.27 (m, 4H), 1.6-1.82 (m, 4H), 1.84-1.86 (dd, J=1.5, 6.9 Hz, 3H), 2.09 (br s, 1H), 3.6 (br s, 1H), 6.17-6.21 (dd, J=1.6, 15.3 Hz, 1H), 6.61 (br s, 1H), 6.81-6.88 (m, 2H), 7-7.05 (m, 1H), 7.13 (br s, 1H), 7.42 (d, J=10.4 Hz, 1H), 7.61 (br s, 1H), 7.89 (s, 1H), 8.24 (br s, 1H), 9.8 (br s, 1H).

Example 134

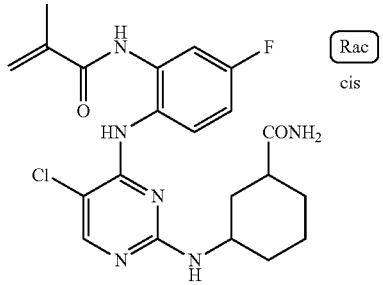

I-114

Rac-cis-3-((5-chloro-4-((4-fluoro-2-methacrylamidophenyl)amino)pyrimidin-2-yl)amino)cyclohexanecarboxamide Compound I-114 was prepared in a manner similar to Example 120, substituting N-(2-amino-5-fluorophenyl)methacrylamide for N-(2-aminophenyl)acrylamide: MS m/z 447.5 (ES+, M+H); $^1$HNMR (DMSO-d$_6$) δ 1.14-1.36 (m, 4H), 1.66-1.78 (m, 4H), 1.9 (s, 3H), 2.1 (br s, 1H), 3.63 (br s, 1H), 5.53 (s, 1H), 5.82 (s, 1H), 6.62 (s, 1H), 6.8-6.9 (m, 1H), 7.08 (t, J=7.6 Hz, 1H), 7.14 (s, 1H), 7.38 (d, J=7.8 Hz, 1H), 7.62-7.71 (m, 1H), 7.92 (br s, 1H), 8.16-8.23 (m, 1H), 9.5-9.7 (m, 1H).

Example 135

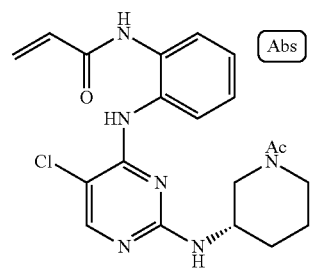

I-115

(S)—N-(2-((2-((1-acetylpiperidin-3-yl)amino)-5-chloropyrimidin-4-yl)amino) phenyl)acrylamide Compound I-115 was prepared in a manner similar to Example 120, substituting (S)-tert-butyl 3-aminopiperidine-1-carboxylate for cis-3-aminocyclohexanecarboxamide, then deprotecting with TFA followed by amide formation with acetic anhydride: MS m/z 415.1 (ES+, M+H); $^1$HNMR (DMSO-d$_6$) δ 1.22-1.27 (m, 2H), 1.32-1.6 (m, 2H), 1.6-1.9 (m, 3H), 1.99 (s, 2H), 2.6 (m, 2H), 2.7-3.0 (m, 1H), 3.6-3.63 (d, 1H, J=13.4 Hz), 3.94-3.98 (d, 1H, J=12.1 Hz), 5.7-5.8 (d, 1H, J=10 Hz), 6.28-6.32 (d, 1H, J=17 Hz), 6.45-6.52 (dd, 1H, J=10.2, 17 Hz), 7.16-7.37 (m, 2H), 7.4 (d, 1H J=8.8 Hz), 7.72-7.74 (d, 1H, J=7.2 Hz), 7.95-7.97 (d, 1H, J=9.7 Hz), 8.30 (br s, 1H), 10.15 (br s, 1H).

Example 136

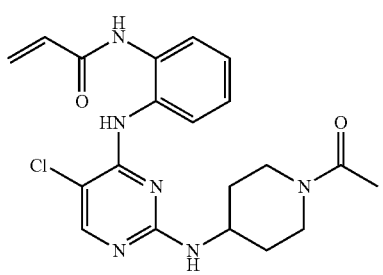

I-116

N-(2-((2-((1-acetylpiperidin-4-yl)amino)-5-chloropyrimidin-4-yl)amino)phenyl) acrylamide Compound I-116 was prepared in a manner similar to Example 120, substituting tert-butyl 4-aminopiperidine-1- carboxylate for cis-3-aminocyclohexanecarboxamide, then deprotecting with TFA followed by amide formation with acetic anhydride. MS m/z 415.2 (ES+, M+H); ¹HNMR (DMSO-d₆) δ 1.12-1.38 (m, 3H), 1.70-1.84 (m, 2H), 1.96 (s, 3H), 2.99 (br s, 1H), 3.58 (br s, 1H), 3.75 (m, 1H), 4.24 (d, J=13.2 Hz, 1H), 5.78-5.81 (dd, J=1.6, 10.2 Hz, 1H), 6.3 (d, J=17.1 Hz, 1H), 6.45-6.52 (dd, J=10.2, 17.2 Hz, 1H), 6.95 (br s, 1H), 7.18 (t, J=7.5 Hz, 1H), 7.25 (t, J=7.5 Hz, 1H), 7.39 (d, J=7.5 Hz, 1H), 7.77 (d, J=7.5 Hz, 1H), 7.93 (s, 1H), 8.28 (br s, 1H), 10.1 (br s, 1H).

Example 137

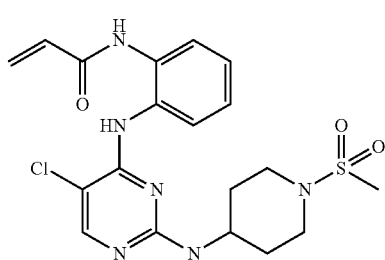

I-117

N-(2-((5-chloro-2-((1-(methylsulfonyl)piperidin-4-yl)amino)pyrimidin-4-yl)amino)phenyl)acrylamide Compound I-117 was prepared in a manner similar to Example 120, substituting tert-butyl 4-aminopiperidine-1-carboxylate for cis-3-aminocyclohexanecarboxamide, then Boc-deprotection with TFA followed by reaction with methylsulfonyl chloride. MS m/z 451.1 (ES+, M+H); ¹HNMR (DMSO-d₆) δ 1.20-1.27 (m, 1H), 1.37-1.50 (m, 2H), 1.84-1.86 (d, J=10.0 Hz, 2H), 2.72 (br s, 2H), 2.84 (s, 3H), 3.49 (d, J=12.1 Hz, 2H), 5.78-5.81 (dd, J=1.9, 10.0 Hz, 1H), 6.27-6.32 (dd, J=1.8, 17.0 Hz, 1H), 6.45-6.52 (dd, J=10.1, 17.0 Hz, 1H), 6.95 (br s, 1H), 7.18 (t, J=7.5 Hz, 1H), 7.27 (t, J=7.6 Hz, 1H), 7.38-7.39 (d, J=6.8 Hz, 1H), 7.75-7.77 (d, J=7.7 Hz, 1H), 7.95 (s, 1H), 8.3 (s, 1H), 10.14 (s, 1H).

Example 138

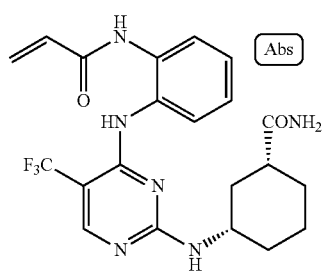

I-118

(1R,3S)-3-((4-((2-acrylamidophenyl)amino-5-trifluoromethyl)pyrimidin-2-yl)amino)cyclohexanecarboxamide Compound I-118 was prepared in a manner similar to Example 1, substituting (1R,3S)-3-aminocyclohexanecarboxamide for cis-3-aminocyclohexanecarboxamide. MS m/z 449.2 (ES+, M+H).

Example 139

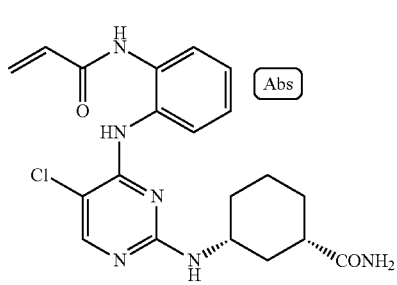

I-119

(1S,3R)-3-((4-((2-acrylamidophenyl)amino)-5-chloropyrimidin-2-yl)amino) cyclohexanecarboxamide Compound I-119 was prepared in a manner similar to Example 120, substituting (1S,3R)-3-aminocyclohexanecarboxamide for cis-3-aminocyclohexanecarboxamide. MS m/z 415.1 (ES+, M+H).

Example 140

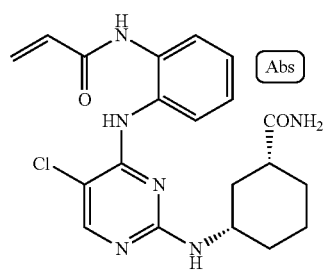

I-120

(1R,3S)-3-((4-((2-acrylamidophenyl)amino)-5-chloropyrimidin-2-yl)amino)cyclohexanecarboxamide Compound I-120 was prepared in a manner similar to Example 120, substituting (1R,3S)-3-aminocyclohexanecarboxamide for cis-3-aminocyclohexanecarboxamide. MS m/z 415.1 (ES+, M+H).

Example 141

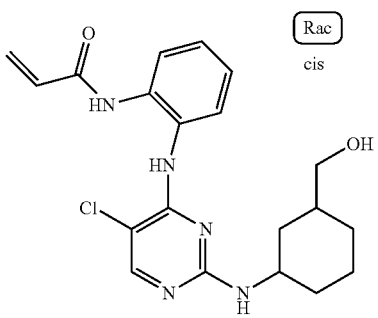

I-121

Rac-cis-N-(2-((5-chloro-2-((3-(hydroxymethyl)cyclohexyl)amino) pyrimidin-4-yl)amino)phenyl)acrylamide Compound I-121 was prepared in a manner similar to Example 120, substituting cis-3-aminocyclohexylmethanol for cis-3-aminocyclohexanecarboxamide: MS m/z 402.5 (ES+, M+H); ¹HNMR (DMSO-d₆) δ 0.72-0.84 (m, 2H), 1.08-1.1 (m, 1H), 1.18-1.28 (m, 3H), 1.62-1.70 (m, 2H), 1.77-1.80 (d, 1H, J=11 Hz), 1.86-1.89 (d, 1H, J=11.9 Hz), 3.19-3.20 (br s, 2H), 4.36 (s, 1H), 5.78-5.81 (d, 1H, J=10.22 Hz), 6.28-6.32 (d, 1H, J=16.8 Hz), 6.45-6.52 (dd, 1H, J=10, 17 Hz), 7.14-7.18 (m, 1H), 7.22-7.26 (m, 1H), 7.33-7.35 (m, 1H), 7.83 (br s, 1H), 7.91 (s, 1H), 8.24 (br s, 1H), 10.18 (s, 1H).

Example 142

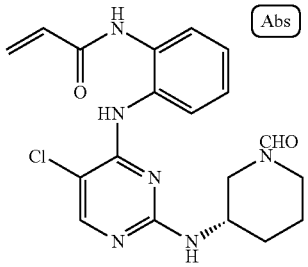

I-122

(S)—N-(2-((5-chloro-2-((1-formylpiperidin-3-yl)amino)pyrimidin-4-yl)amino) phenyl)acrylamide Compound I-122 was prepared in a manner similar to Example 120, substituting (S)-tert-butyl 3-aminopiperidine-1-carboxylate for cis-3-aminocyclohexanecarboxamide, then Boc-deprotection with TFA, followed by reaction with formic acid, HATU and DIPEA in DMA. MS m/z 401.1 (ES+, M+H); ¹HNMR (DMSO-d₆) δ 1.18-1.22 (m, 2H), 1.27-1.3 (m, 1H), 1.47-1.5 (m, 1H), 1.6-1.80 (m, 1H), 1.86-1.89 (m, 1H), 1.90-1.95 (m, 1H), 3.49-3.51 (m, 1H), 3.62 (d, J=13.3 Hz, 1H), 5.78-5.81 (dd, J=1.7, 10.1 Hz, 1H), 6.3 (d, J=16.9 Hz, 1H), 6.45-6.52 (dd, J=10.2, 17.0 Hz, 1H), 7.0 (br s, 1H), 7.15-7.24 (m, 2H), 7.37-7.39 (m, 1H), 7.75-7.77 (m, 1H), 7.97 (d, J=17.3 Hz, 1H), 8.33 (br s, 1H), 10.15 (br s, 1H).

Example 143

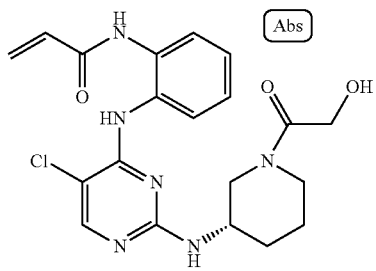

I-123

(S)—N-(2-((5-chloro-2-((1-(2-hydroxyacetyl)piperidin-3-yl)amino)pyrimidin-4-yl)amino)phenyl)acrylamide Compound I-123 was prepared in a manner similar to Example 120, substituting (S)-tert-butyl 3-aminopiperidine-1-carboxylate for cis-3-aminocyclohexanecarboxamide, then Boc-deprotection with TFA, followed by reaction with ClCOCH₂OAc and hydrolysis with aqueous LiOH. MS m/z 461.1 (ES+, M+H); ¹H NMR (400 MHz, CD₃OD) δ 1.49-1.63 (m, 2H), 1.77-1.80 (m, 1H), 1.95-2.05 (m, 2H), 2.94-3.15 (m, 2H), 3.49-3.54 (m, 1H), 3.65-3.72 (m, 1H), 3.91-3.95 (m, 1H), 4.24 (s, 1H), 5.81-5.84 (dd, 1H, J=2.2, 9.6 Hz), 6.38-6.50 (m, 2H), 7.21-7.33 (m, 2H), 7.37-7.44 (dd, 1H, J=7.7, 22.1 Hz), 7.74-7.76 (m, 1H), 7.84-7.91 (m, 1H).

Example 144

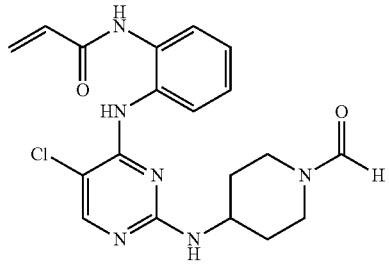

I-124

N-(2-((5-chloro-2-((1-formylpiperidin-4-yl)amino)pyrimidin-4-yl)amino)phenyl) acrylamide Compound I-124 was prepared in a manner similar to Example 120, substituting tert-butyl 4-aminopiperidine-1-carboxylate for cis-3-aminocyclohexanecarboxamide, then Boc-deprotection with TFA, followed by reaction with formic acid, HATU and DIPEA in DMA. MS m/z 401.2 (ES+, M+H); ¹HNMR (DMSO-d₆) δ 1.16-1.32 (m, 3H), 1.80 (t, J=12.3 Hz, 2H), 2.59 (br s, 1H), 2.98 (br s, 1H), 3.63 (d, J=13.6 Hz, 1H), 4.06 (d, J=13.2 Hz, 1H), 5.77-5.80 (dd, J=1.6, 10.1 Hz, 1H), 6.27-6.32 (dd, J=1.3, 16.9 Hz, 1H), 6.45-6.52 (dd, J=10.1, 16.9 Hz, 1H), 6.9 (br s, 1H), 7.17 (t, J=7.0 Hz, 1H), 7.25 (t, J=7.0 Hz, 1H), 7.38 (d, J=7.8 Hz, 1H), 7.76 (d, J=7.6 Hz, 1H), 7.94 (s, 2H), 8.3 (s, 1H), 10.1 (s, 1H).

Example 145

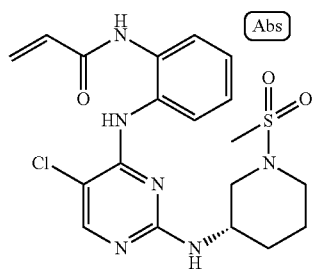

I-125

(S)—N-(2-((5-chloro-2-((1-(methylsulfonyl)piperidin-3-yl)amino)pyrimidin-4-yl)amino)phenyl)acrylamide Compound I-125 was prepared in a manner similar to Example 120, substituting (S)-tert-butyl 3-aminopiperidine-1-carboxylate for cis-3-aminocyclohexanecarboxamide, then Boc-deprotection with TFA, followed by reaction with MsCl. MS m/z 451.1 (ES+, M+H)

Example 146

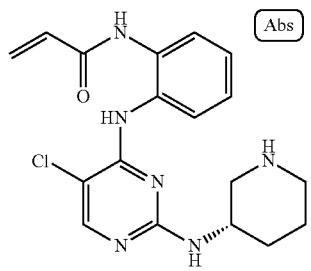

I-126

(S)—N-(2-((5-chloro-2-(piperidin-3-ylamino)pyrimidin-4-yl)amino)phenyl) acrylamide Compound I-126 was prepared in a manner similar to Example 120, substituting (S)-tert-butyl 3-aminopiperidine-1-carboxylate for cis-3-aminocyclohexanecarboxamide, then Boc-deprotection with TFA. MS m/z 373.1 (ES+, M+H)

Example 147

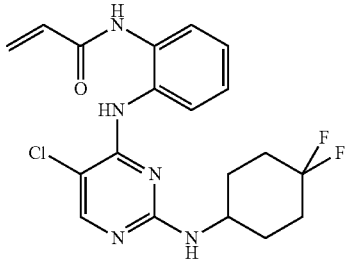

I-127

N-(2-((5-chloro-2-((4,4-difluorocyclohexyl)amino)pyrimidin-4-yl)amino)phenyl) acrylamide Compound I-127 was prepared in a manner similar to Example 120, substituting 4,4-difluorocyclohexanamine for cis-3-aminocyclohexanecarboxamide: MS m/z 408.2 (ES+, M+H); $^1$HNMR(CD$_3$OD) δ 1.31-1.39 (m, 1H), 1.52-1.55 (m, 2H), 1.60-1.75 (m, 2H), 1.93-1.96 (m, 2H), 2.01-2.04 (m, 2H), 5.80-5.83 (dd, 1H, J=2.2, 9.6 Hz), 6.38-6.47 (m, 2H), 7.24-7.33 (m, 2H), 7.45-7.47 (m, 1H), 7.77-7.79 (m, 1H), 7.87 (s, 1H).

Example 148

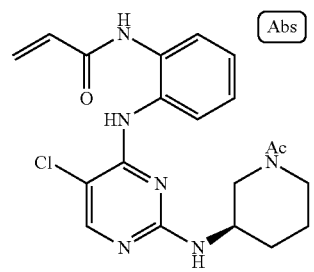

I-128

(R)—N-(2-((2-((1-acetylpiperidin-3-yl)amino)-5-chloropyrimidin-4-yl)amino) phenyl)acrylamide Compound I-128 was prepared in a manner similar to Example 120, substituting (R)-tert-butyl 3-aminopiperidine-1-carboxylate for cis-3-aminocyclohexanecarboxamide, then Boc-deprotection with TFA, followed by reaction with acetic anhydride. MS m/z 415.2 (ES+, M+H); $^1$HNMR (DMSO-d$_6$) δ 1.10-1.18 (m, 1H)), 1.75-1.89 (m, 1H), 1.30-1.52 (m, 2H), 1.60-1.73 (m, 1H), 1.80-1.82 (m, 1H), 1.89-1.99 (m, 1H), 2.72-3.0 (m, 2H), 3.61 (br s 1H), 3.64 (br s 1H), 3.96 (d, J=11.7 Hz, 1H), 5.79 (d, J=10.0 Hz, 1H), 6.29 (d, J=17.0 Hz, 1H), 6.45-6.52 (dd, J=10.1, 17.0 Hz, 1H), 6.8-7.0 (m, 1H), 7.12-7.28 (m, 2H), 7.29-7.40 (m, 1H), 7.70-7.90 (m, 1H), 7.95 (d, J=10.6 Hz, 1H), 8.32 (br s, 1H), 10.25 (br s, 1H).

Example 149

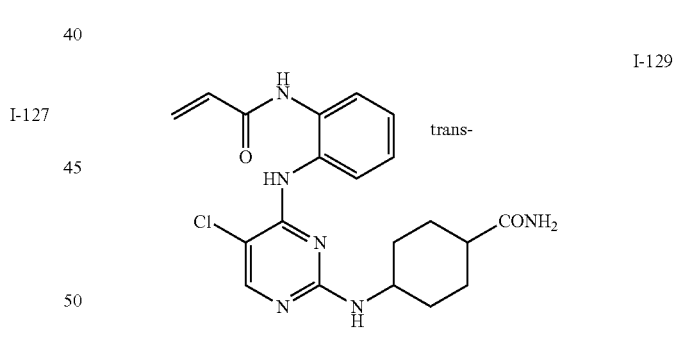

I-129 trans-4-((4-((2-acrylamidophenyl)amino)-5-chloropyrimidin-2-yl)amino)-cyclohexanecarboxamide Compound I-129 was prepared in a manner similar to Example 120, substituting trans-4-aminocyclohexanecarboxamide for cis-3-aminocyclohexanecarboxamide. MS m/z 415.2 (ES+, M+H); $^1$HNMR (DMSO-d$_6$) δ 1.14-1.22 (m, 2H), 1.22-1.26 (m, 2H), 1.26-1.34 (m, 2H), 1.70-1.73 (d, 2H, J=12.3 Hz), 1.84-1.87 (d, 2H, J=9.7 Hz), 1.95-2.01 (m, 1H), 5.78-5.81 (d, 1H, J=10.2 Hz), 6.28-6.32 (d, 1H, J=16.4 Hz), 6.45-6.52 (dd, 1H, J=10.2, J=17 Hz), 6.62 (br s, 1H), 7.15-7.24 (m, 3H), 7.34-7.36 (d, 1H, J=7.4 Hz), 7.8 (br s, 1H), 7.9 (br s, 1H), 8.25 (br s, 1H), 10.2 (br s, 1H).

Example 150

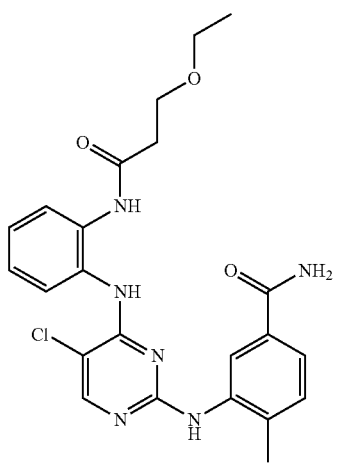

I-130

Compound I-130 was prepared in a manner similar to Example 162, substituting N-(2-aminophenyl)-3-ethoxypropanamide for N-(2-aminophenyl)acrylamide. MS: m/z 469.2 (ES+, M+H); $^1$HNMR (DMSO-d$_6$) δ 1.03 (t, J=7.0 Hz, 3H), 2.15 (s, 3H), 2.56 (t, J=6.3 Hz, 2H), 3.38-3.4 (dd, J=7, 2.2.0 Hz, 2H), 3.62-3.65 (t, J=6.2 Hz, 2H), 7.0-7.07 (m, 2H), 7.14-7.19 (m, 2H), 7.26 (br s, 1H), 7.51-7.54 (dd, J=1.59, 7.7 Hz, 1H), 7.71-7.73 (d, J=9.5 Hz, 1H), 7.86 (br s, 1H), 7.91 (d, J=1.2 Hz, 1H), 8.05 (s, 1H), 8.34 (s, 1H), 8.61 (s, 1H), 9.9 (s, 1H).

Example 151

I-131

(S)—N-(2-((5-chloro-2-((1-propionylpiperidin-3-yl)amino)pyrimidin-4-yl)amino) phenyl)acrylamide Compound I-131 was prepared in a manner similar to Example 120, substituting (S)-tert-butyl 3-aminopiperidine-1-carboxylate for cis-3-aminocyclohexanecarboxamide, followed by Boc-deprotection with TFA and reaction with ClCOCH$_2$CH$_3$: MS m/z 429.5 (ES+, M+H); $^1$HNMR (CD$_3$OD) δ 0.83-1.0 (m, 2H), 1.14 (t, J=7.5 Hz, 1H), 1.38-1.42 (m, 2H), 1.45-1.68 (m, 2H), 1.7-1.84 (m, 1H), 1.93-2.20 (m, 1H), 2.35 (q, J=2.5 Hz, 1H), 2.90-3.03 (m, 1H), 3.62-3.80 (m, 2H), 4.0-4.21 (m, 1H), 5.81-5.84 (dd, J=2.1, 9.7 Hz, 1H), 6.38-6.48 (m, 2H), 7.22-7.31 (m, 2H), 7.42-7.45 (dd, J=1.4, 7.7 Hz, 1H), 7.76-7.78 (dd, J=1.2, 7.7 Hz, 1H), 7.89 (d, J=15.8 Hz, 1H). Mixture of Rotamers.

Example 152

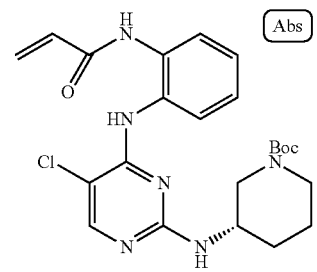

I-132

(S)-tert-butyl 3-((4-((2-acrylamidophenyl)amino)-5-chloropyrimidin-2-yl)amino) piperidine-1-carboxylate Compound I-132 was prepared in a manner similar to Example 120, substituting (S)-tert-butyl 3-aminopiperidine-1-carboxylate for cis-3-aminocyclohexanecarboxamide: MS m/z 507.5 (ES+, M+H) Example 153

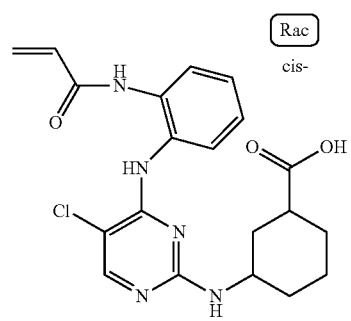

I-133

Rac-3-((4-((2-acrylamidophenyl)amino)-5-chloropyrimidin-2-yl)amino)-cis-cyclohexanecarboxylic acid Compound I-133 was prepared in a manner similar to Example 120, substituting cis-t-butyl 3-aminocyclohexanecarboxylate for cis-3-aminocyclohexanecarboxamide, followed by deprotection with TFA. MS m/z 416.5 (ES+, M+H); $^1$HNMR (DMSO-d$_6$) δ 1.1-1.16 (m, 4H), 1.69-1.89 (m, 4H), 2.02-2.05 (d, 1H, J=11.6 Hz), 2.99 (br s, 1H), 5.78-5.80 (d, 1H, J=20.2 Hz), 6.28-6.32 (d, 1H, J=16.5 Hz), 6.46-6.53 (dd, 1H, J=10.3, 17.1 Hz), 6.7 (br s, 1H), 7.14-7.18 (m, 1H), 7.22-7.25 (t, 1H, J=7.7 Hz), 7.34-7.36 (d, 1H, J=7.4 Hz), 7.79-7.82 (br s, 1H), 7.92 (s, 1H), 8.2 (br s, 1H), 10.2 (br s, 1H), 12.0 (br s, 1H).

Example 154

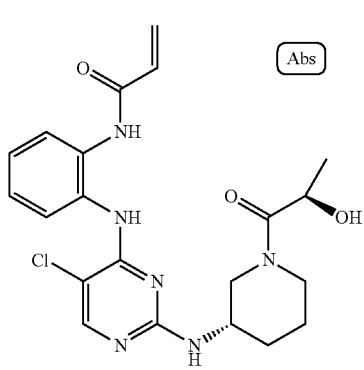

I-134

N-(2-((5-chloro-2-(((S)-1-((R)-2-hydroxypropanoyl)piperidin-3-yl)amino) pyrimidin-4-yl)amino)phenyl)acrylamide Compound I-134 was prepared in a manner similar to Example 120, substituting (S)-tert-butyl 3-aminopiperidine-1-carboxylate for cis-3-aminocyclohexanecarboxamide, followed by Boc-deprotection with TFA and amide formation with (R)-2-hydroxypropanoic acid, HATU and DIPEA in DMA. MS m/z 445.2 (ES+, M+H).

Example 155

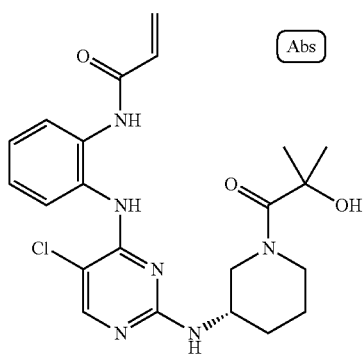

I-135

(S)—N-(2-((5-chloro-2-((1-(2-hydroxy-2-methylpropanoyl)piperidin-3-yl)amino) pyrimidin-4-yl)amino)phenyl)acrylamide Compound I-135 was prepared in a manner similar to Example 120, substituting (S)-tert-butyl 3-aminopiperidine-1-carboxylate for cis-3-aminocyclohexanecarboxamide, followed by Boc-deprotection with TFA and amide formation with 2-hydroxy-2-methylpropanoic acid, HATU and DIPEA in DMA. MS m/z 459.2 (ES+, M+H).

Example 156

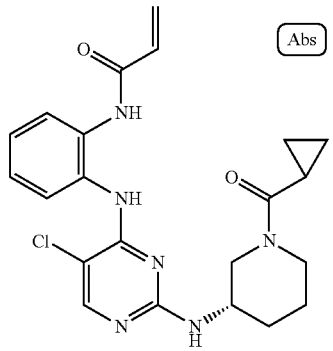

I-136

(S)—N-(2-((5-chloro-2-((1-(cyclopropanecarbonyl)piperidin-3-yl)amino)pyrimidin-4-yl)amino)phenyl)acrylamide Compound I-136 was prepared in a manner similar to Example 120, substituting (S)-tert-butyl 3-aminopiperidine-1-carboxylate for cis-3-aminocyclohexanecarboxamide, followed by Boc-deprotection with TFA and amide formation with cyclopropanecarboxylic acid, HATU and DIPEA in DMA. MS m/z 441.2 (ES+, M+H).

Example 157

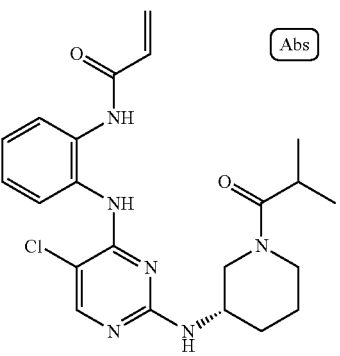

I-137

(S)—N-(2-((5-chloro-2-((1-isobutyrylpiperidin-3-yl)amino)pyrimidin-4-yl)amino)phenyl)acrylamide Compound I-137 was prepared in a manner similar to Example 120, substituting (S)-tert-butyl 3-aminopiperidine-1-carboxylate for cis-3-aminocyclohexanecarboxamide, followed by Boc-deprotection with TFA and amide formation with isobutyric acid, HATU and DIPEA in DMA. MS m/z 443.1 (ES+, M+H).

Example 158

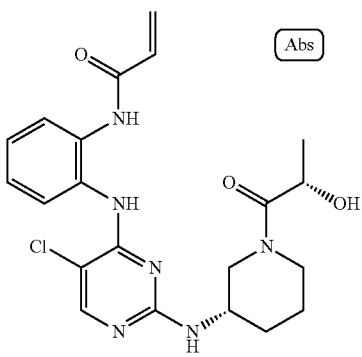

I-138

N-(2-((5-chloro-2-(((S)-1-((S)-2-hydroxypropanoyl)
piperidin-3-yl)amino)pyrimidin-4-yl)amino)phenyl)
acrylamide Compound I-138 was prepared in a manner similar to Example 120, substituting (S)-tert-butyl 3-aminopiperidine-1-carboxylate for cis-3-aminocyclohexanecarboxamide, followed by Boc-deprotection with TFA and amide formation with (S)-2-hydroxypropanoic acid, HATU and DIPEA in DMA. MS m/z 445.1 (ES+, M+H).

Example 159

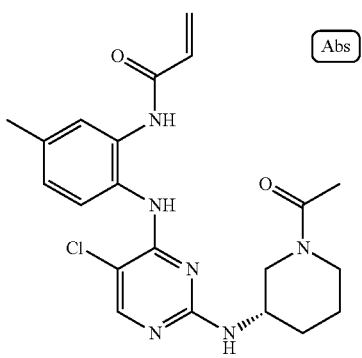

I-139

(S)—N-(2-((2-((1-acetylpiperidin-3-yl)amino)-5-
chloropyrimidin-4-yl)amino)-5-methylphenyl)acryl-
amide Compound I-139 was prepared in a manner similar to Example 120, substituting (S)-tert-butyl 3-aminopiperidine-1-carboxylate for cis-3-aminocyclohexanecarboxamide, and by substituting N-(2-amino-5-methylphenyl)acrylamide for N-(2-aminophenyl)acrylamide, followed by Boc-deprotection with TFA then amide formation with acetic anhydride. MS m/z 429.6 (ES+, M+H) $^1$HNMR (DMSO-d$_6$) δ 1.29 (m, 1H), 1.47-1.50 (m, 2H), 1.61-1.64 (m, 1H), 1.80 (br s, 1H), 1.99 (br s, 1H), 2.30 (s, 3H), 2.75 (br s, 1H), 2.84-2.89 (dd, J=9.2, 13.2 Hz, 1H), 3.12 (br s, 1H), 3.49 (s, 3H), 5.76-5.79 (dd, J=1.8, 10 Hz, 1H), 6.26-6.31 (dd, J=1.8, 16.9 Hz, 1H), 6.44-6.51 (dd, J=10.1, 17 Hz, 1H), 7.03-7.05 (d, J=8.2 Hz, 1H), 7.27-7.37 (d, J=19.3 Hz, 1H), 7.48-7.50 (d, J=8.1 Hz, 1H), 7.82 (br s, 1H), 8.12 (s, 1H), 9.38 (br s, 1H), 10.04 (s, 1H).

Example 160

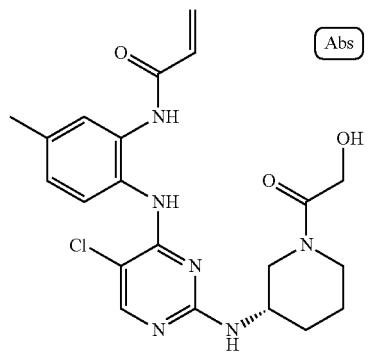

I-140

(S)—N-(2-((5-chloro-2-((1-(2-hydroxyacetyl)piperi-
din-3-yl)amino)pyrimidin-4-yl)amino)-5-methylphe-
nyl)acrylamide Compound I-140 was prepared in a manner similar to Example 120, substituting (S)-tert-butyl 3-aminopiperidine-1-carboxylate for cis-3-aminocyclohexanecarboxamide, and by substituting N-(2-amino-5-methylphenyl)acrylamide for N-(2-aminophenyl)acrylamide, followed by Boc-deprotection with TFA then amide formation with ClCOCH$_2$OAc and final hydrolysis with aqueous LiOH. MS m/z 445.6 (ES+, M+H); $^1$H NMR (DMSO-d$_6$) δ 1.22 (m, 2H), 1.67 (m, 1H), 1.82 (m, 1H), 1.97 (s, 1H), 2.28 (s, 3H), 2.83 (m, 2H), 3.50 (m, 2H), 3.99 (br s, 1H), 4.02-4.06 (m, 1H), 4.45 (br s, 1H), 5.76-5.79 (d, J=10.0 Hz, 1H), 6.26-6.30 (d, J=15.5 Hz, 1H), 6.44-6.50 (dd, J=10.0, 16.8 Hz, 1H), 6.86 (br s, 1H), 7.03 (d, J=7.9 Hz, 1H), 7.18 (s, 1H), 7.58 (d, J=7.3 Hz, 1H), 7.93 (d, J=8.4 Hz, 1H), 8.21 (br s, 1H), 10.07 (s, 1H).

Example 161

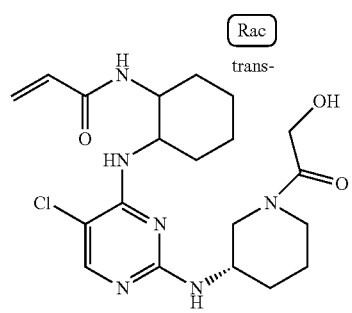

I-141

Rac-N-(2-((5-chloro-2-(((R)-1-(2-hydroxyacetyl)
piperidin-3-yl)amino)pyrimidin-4-yl)amino)-trans-
cyclohexyl)acrylamide Compound I-141 was prepared in a manner similar to Example 120, substituting (S)-tert-butyl 3-aminopiperidine- 1-carboxylate for cis-3-aminocyclohexanecarboxamide, and by substituting N-trans-(2-aminocyclohexyl)acrylamide for N-(2-aminophenyl)acrylamide, followed by Boc-deprotection with TFA then reaction with ClCOCH₂OAc and final hydrolysis with aqueous LiOH. MS m/z 437.1 (ES+, M+H).

Similar to Method B and C, Method E was to introduce an acrylamide-containing or Boc-protected ring system first at the C-4 position of 2,4,5-trichloropyrimidine, followed by the introduction of a second aniline at the C-5 position. General practice of this method is described below.

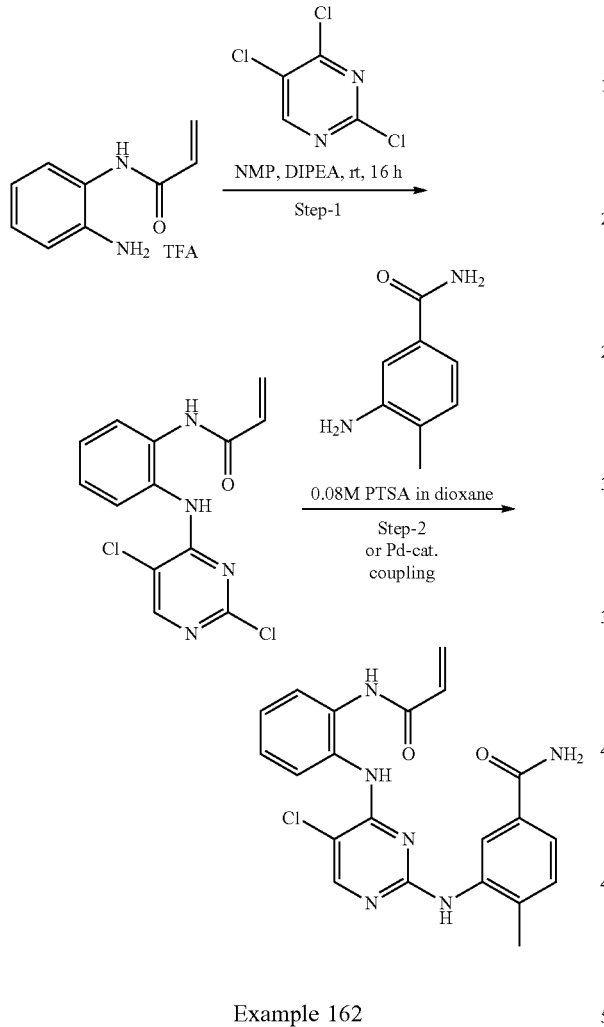

Example 162

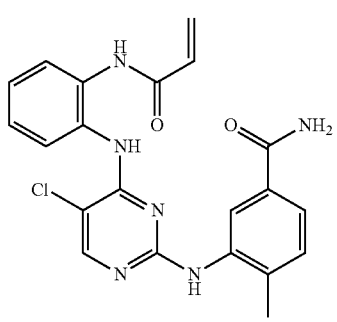

I-319

3-(4-(2-acrylamidophenylamino)-5-chloropyrimidin-2-ylamino)-4-methylbenzamide

The title compound was prepared according to the steps and intermediates as described below.

Step 1: N-(2-(2, 5-dichloropyrimidin-4-ylamino) phenyl) acrylamide (Intermediate 1)

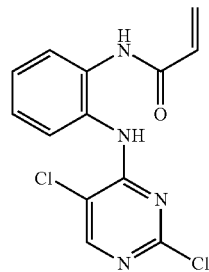 [SMILES: C=CC(=O)Nc1ccccc1Nc1nc(Cl)ncc1Cl]

To a solution of N-(2-aminophenyl) acrylamide (TFA salt) (10 g, 38.6 mmol) in N-methyl pyrrolidinone (30 mL) was added DIPEA (12.6 g, 98.36 mmol), and 2, 4, 5-trichloropyrimidine (9.5 g, 49.18 mmol), and the mixture was stirred at rt for 16 h. TLC showed completion of starting material (TLC system: 50% ethyl acetate/hexane, (R$_f$): 0.5). The reaction mixture was diluted with ethyl acetate (100 mL) and washed with water (3×50 mL). The organic layer was separated, dried over sodium sulfate and concentrated to obtain the crude compound (11 g). MS m/z: 309.1 (ES+, M+1).

Step 2: Acid Catalyzed Coupling Condition

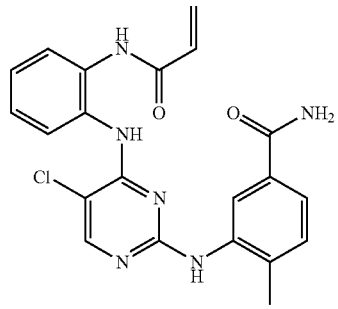 [SMILES: C=CC(=O)Nc1ccccc1Nc1nc(Nc2cc(C(N)=O)ccc2C)ncc1Cl]

3-(4-(2-acrylamidophenylamino)-5-chloropyrimidin-2-ylamino)-4-methylbenzamide

A solution of Intermediate 1 (1 g, 3.24 mmol) and 3-amino-4-methylbenzamide (584 mg, 3.89 mmol) in 0.08 M PTSA in 1,4-dioxane was heated to 90° C. for 48 h. TLC showed the completion of starting material (TLC system: 10% methanol/DCM, (R$_f$): 0.5). The reaction mixture was concentrated, quenched with water, and the precipitated solid was filtered and dried under vacuum. The crude solid was purified by silica gel column chromatography by using 3% methanol/DCM as eluents. The purified solid was further triturated with ether, filtered and dried under vacuum to get the title compound as an off-white solid (430 mg, 31%).

¹HNMR (400 MHz, D₆-DMSO) δ 2.17 (s, 3H), 5.78-5.81 (dd, 1H J=1.8, 10.1 Hz), 6.28-6.32 (dd, 1H J=1.8, 17 Hz), 6.43-6.50 (dd, 1H J=10.1, 17 Hz), 7.04-7.08 (m, 2H), 7.18-7.24 (m, 2H), 7.27 (br s, 1H), 7.52-7.54 (dd, 1H J=1.7, 7.9 Hz), 7.73-7.76 (m, 1H), 7.87 (br s, 1H), 7.92 (d, 1H), 8.03 (s, 1H), 8.39 (s, 1H), 8.62 (s, 1H), 10.19 (s, 1H). MS m/z: 423.5 (ES+, M+H).

Step-2—Palladium Catalyzed Coupling Condition 3-(4-(2-acrylamidophenylamino)-5-chloropyrimidin-2-ylamino)-4-methylbenzamide Alternatively, compound I-319 was also synthesized under a similar Pd-coupling condition substituting N-(2-(2,5-dichloropyrimidin-4-ylamino) phenyl) acrylamide for N-(2-(2-Chloro-5-(trifluoromethyl)pyrimidin-4-ylamino) phenyl)acrylamide. MS m/z: 423.5 (ES+, M+H).

Example 163

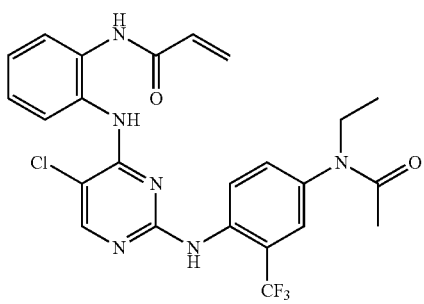

I-320

N-(2-(5-chloro-2-(4-(N-ethylacetamido)-2-(trifluoromethyl)phenylamino) pyrimidin-4-ylamino)phenyl)acrylamide To a stirred solution of Intermediate 1 from Example 162 (100 mg, 0.3246 mmol) in tetrahydrofuran (5 mL), N-(4-amino-3-(trifluoro methyl)phenyl)-N-ethylacetamide (80 mg, 0.3246 mmol) and cesium carbonate (316 mg, 0.9738 mmol) were added and degassed for 10 min. To the reaction mixture palladium acetate (38 mg, 0.1623 mmol) and xanthphos (36.8 mg, 0.0973 mmol) were added and again degassed for another 5 min. The mixture was irradiated by microwave at 80° C. for 20 min. TLC showed completion of starting material (TLC system: 10% methanol/chloroform, (R_f): 0.5). The reaction was quenched with water (15 mL) and extracted with ethyl acetate (3×10 mL). The organic layer was separated, dried over sodium sulfate and concentrated. The crude compound was purified by prep-HPLC to obtain the title compound as yellow solid. (30 mg, 17%). ¹HNMR (DMSO-d₆) δ 0.98 (m, 3H), 1.70 (m, 3H), 1.85 (s, 1H), 3.63 (m, 2H), 5.77-5.80 (dd, 1H J=1.8 Hz and 10.2 Hz), 6.26-6.31 (dd, 1H J=1.8, 17 Hz), 6.44-6.51 (dd, 1H J=10.2, 17 Hz), 7.09-7.17 (m, 2H), 7.32-7.35 (dd, 1H J=1.7, 7.5 Hz), 7.48 (d, 1H J=7.1 Hz), 7.55 (s, 1H), 7.63 (d, 1H J=8.2 Hz), 7.72 (d, 1H J=8.2 Hz), 8.08 (s, 1H), 8.49 (s, 1H), 10.12 (s, 1H). MS m/z: 519.5 (ES+, M+H).

Example 164

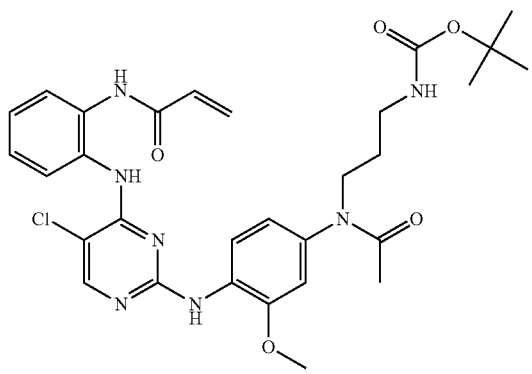

I-173 tert-butyl (3-(N-(4-(((2-acrylamidophenyl)amino)-5-chloropyrimidin-2-yl)amino)-3-methoxyphenyl)acetamido)propyl)carbamate To a stirred solution of tert-butyl-3-(N-(4-amino-3-methoxyphenyl) acetamido) propyl carbamate (109 mg, 0.324 mmol), Intermediate 1 from Example 162 (100 mg, 0.324 mmol), diphenylphosphino-N,N-dimethylamine (56 mg, 0.1428 mmol) in tert-amyl alcohol (5 mL), and sodium carbonate (245 mg, 1.948 mmol) was added, and the mixture was degassed for 20 min. To this mixture, tris-dibenzylamino dipalladium (41 mg, 0.045 mmol) catalyst was added, and the mixture was degassed again for 10 min. The temperature was raised to 90° C., and the mixture was stirred for 2 h. TLC showed completion of starting material (TLC system: 5% methanol/chloroform (R_f): 0.5). The reaction was quenched with water (15 mL) and extracted with ethyl acetate (3×10 mL). The organic layer was separated, dried over sodium sulfate and concentrated. The crude compound was purified by prep-HPLC to obtain the title compound as an off-white solid. (10 mg, 53%). ¹HNMR (400 MHz, DMSO-d₆) δ 1.34 (s, 9H), 1.45-1.51 (m, 2H), 1.71 (s, 3H), 2.90 (q, 2H J=6.4 Hz), 3.56 (t, 2H J=7.3 Hz), 3.82 (s, 3H), 5.76-5.79 (dd, 1H J=1.8, 10.2 Hz), 6.27-6.31 (dd, 1H J=1.8, 17 Hz), 6.45-6.52 (dd, 1H J=10.2, 17 Hz), 6.61 (d, 1H J=7.7 Hz), 6.72 (m, 1H), 6.91 (s, 1H), 7.22-7.31 (m, 2H), 7.44 (d, 1H J=6.8 Hz), 7.68 (d, 1H J=6.8 Hz), 7.79 (s, 1H), 7.88 (s, 1H), 8.11 (s, 1H), 8.58 (s, 1H), 10.13 (s, 1H). MS m/z: 608.1 (ES−, M−H).

Example 165

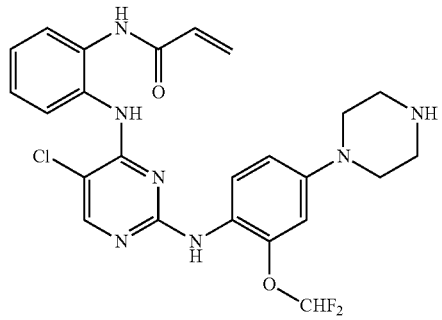

I-142

N-(2-((5-chloro-2-((2-(difluoromethoxy)-4-(piperazin-1-yl)phenyl)amino) pyrimidin-4-yl)amino)phenyl)acrylamide Compound I-142 was prepared in a manner similar to Example 162, substituting tert-butyl 4-(4-amino-3-(difluoromethoxy)phenyl)piperazine-1-carboxylate for 3-amino-4-methylbenzamide, followed by deprotecting with TFA. MS m/z: 516.2 (ES+, M+H).

Example 166

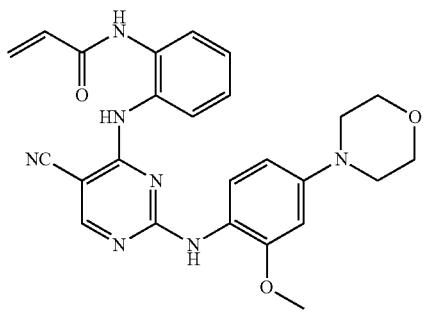

I-143

N-(2-((5-cyano-2-((2-methoxy-4-morpholinophenyl)amino)pyrimidin-4-yl)amino) phenyl)acrylamide Compound I-143 was prepared in a manner similar to Example 162, using 2,4-dichloro-5-cyanopyrimdine as the starting material, and substituting 2-methoxy-4-morpholinoaniline for 3-amino-4-methylbenzamide. MS m/z: 472.2 (ES+, M+H).

Example 167

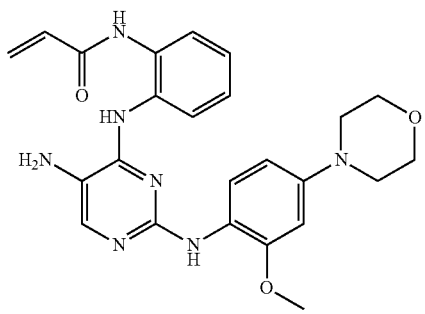

I-144

N-(2-((5-amino-2-((2-methoxy-4-morpholinophenyl)amino)pyrimidin-4-yl)amino)phenyl) acrylamide Compound I-144 was prepared in the similar way as described in Example 162, using 2,4-dichloro-5-aminopyrimidine as the starting material and substituting 2-methoxy-4-morpholinoaniline in for 3-amino-4-methylbenzamide. MS: m/z 462.3 (ES+, M+H); 1HNMR (DMSO-d$_6$) δ 3.00 (t, J=4.6 Hz, 4H), 3.72 (t, J=4.6 Hz, 4H), 3.78 (s, 3H), 4.1 (br s, 2H), 5.70-5.74 (dd, J=1.7, 10.1 Hz, 1H), 6.19-6.24 (dd, J=1.9, 17.0 Hz, 1H), 6.27-6.30 (dd, J=2.5, 8.8 Hz, 1H), 6.43-6.49 (dd, J=10.1, 16.9 Hz, 1H), 6.57 (d, J=2.4 Hz, 1H), 6.91 (s, 1H), 7.12-7.14 (dt, J=1.5, 7.6 Hz, 1H), 7.19-7.24 (dt, J=1.5, 7.6 Hz, 1H), 7.57 (t, J=7.6 Hz, 1H), 7.61 (s, 1H), 7.74 (d, J=6.9 Hz, 1H), 7.88 (d, J=8.7 Hz, 1H), 7.95 (br s, 1H), 9.79 (s, 1H).

Example 168

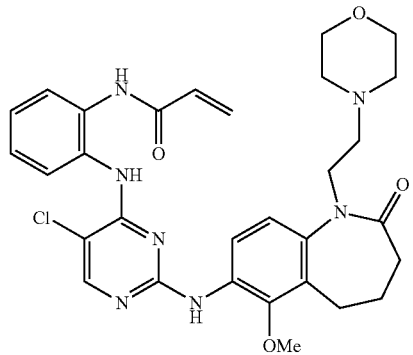

I-145

N-(2-((5-chloro-2-((6-methoxy-1-(2-morpholinoethyl)-2-oxo-2,3,4,5-tetrahydro-1H-benzo[b]azepin-7-yl)amino)pyrimidin-4-yl)amino)phenyl)acrylamide Compound I-145 was prepared in a manner similar to Example 162, substituting 7-amino-6-methoxy-1-(2-morpholinoethyl)-4,5-dihydro-1H-benzo[b]azepin-2(3H)-one for 3-amino-4-methylbenzamide: MS m/z: 590.8 (ES+, M+H); $^1$HNMR (400 MHz, DMSO-d$_6$) δ 2.06 (br s, 3H), 2.29 (br s, 3H), 2.31 (m, 3H), 2.87 (br s, 2H), 3.34 (m, 4H), 3.64 (s, 3H), 4.27 (br s, 1H), 5.76-5.79 (dd, 1H J=1.8 Hz and 10.2 Hz), 6.26-6.31 (dd, 1H J=1.8, 17 Hz), 6.45-6.52 (dd, 1H J=10.2, 17 Hz), 6.94 (d, 1H J=8.9 Hz), 7.20-7.30 (m, 3H), 7.45 (d, 1H J=7.6 Hz), 7.72-7.79 (m, 2H), 7.95 (s, 1H), 8.11 (s, 1H), 8.60 (s, 1H), 10.18 (s, 1H).

Example 169

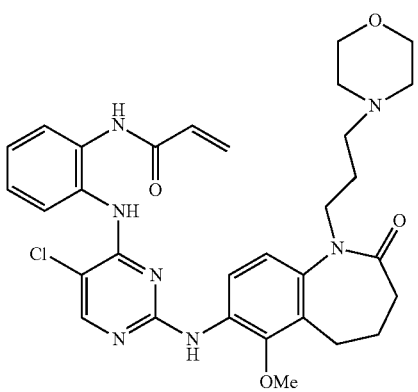

I-146

425

N-(2-((5-chloro-2-((6-methoxy-1-(3-morpholinopropyl)-2-oxo-2,3,4,5-tetrahydro-1H-benzo[b]azepin-7-yl)amino)pyrimidin-4-yl)amino)phenyl)acrylamide Compound I-146 was prepared in a manner similar to Example 162, substituting 7-amino-6-methoxy-1-(3-morpholinopropyl)-4,5-dihydro-1H-benzo[b]azepin-2(3H)-one for 3-amino-4-methylbenzamide: MS m/z: 606.3 (ES+, M+H); 1H NMR (400 MHz, DMSO-d$_6$) δ 1.54 (br s, 2H), 2.09 (br s, 1H), 2.15 (br s, 2H), 2.17-2.21 (t, 3H J=7 Hz), 2.31 (br s, 4H), 2.90 (br s, 1H), 3.50 (t, 4H J=4.6 Hz), 3.64 (s, 1H), 5.76-5.79 (dd, 1H J=1.8, 10.2 Hz), 6.27-6.31 (dd, 1H J=1.9, 17 Hz), 6.45-6.52 (dd, 1H J=10.2, 17 Hz), 6.91 (d, 1H J=8.8 Hz), 7.20-7.32 (m, 3H), 7.42-7.44 (dd, 1H J=1.6, 7.6 Hz), 7.73 (m, 2H), 8.0 (s, 1H), 8.11 (s, 1H), 8.58 (s, 1H), 10.12 (s, 1H).

Example 170

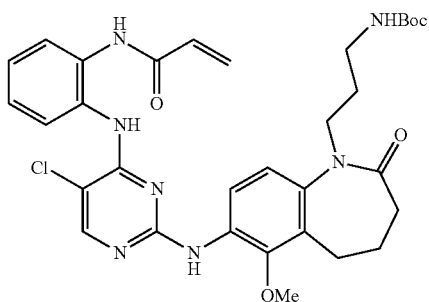

I-147 tert-butyl (3-(7-((4-((2-acrylamidophenyl)amino)-5-chloropyrimidin-2-yl)amino)-6-methoxy-2-oxo-2,3,4,5-tetrahydro-1H-benzo[b]azepin-1-yl)propyl)carbamate Compound I-147 was prepared in a manner similar to Example 162, substituting tert-butyl (3-(7-amino-6-methoxy-2-oxo-2,3,4,5-tetrahydro-1H-benzo[b]azepin-1-yl)propyl)carbamate for 3-amino-4-methylbenzamide: MS m/z: 636.3 (ES+, M+H); $^1$HNMR (400 MHz, DMSO-d$_6$) δ 0.84 (t, 2H J=7.1 Hz), 1.08 (t, 1H), 1.21 (br s, 2H), 1.22 (m, 2H), 1.34 (s, 9H), 1.5 (m, 3H), 1.73 (m, 2H), 2.09 (br s, 3H), 2.76 (s, 1H), 2.84-2.86 (m, 2H), 3.65 (s, 3H), 3.95 (br s, 1H), 5.77-5.79 (d, 1H J=10.2 Hz), 6.27-6.31 (d, 1H J=16.6 Hz), 6.45-6.49 (dd, 1H J=10.2, 16.7 Hz), 6.74 (m, 1H), 6.87 (d, 1H J=8.9 Hz), 7.23-7.27 (m, 2H), 7.43 (d, 1H J=7.4 Hz), 7.71-7.77 (m, 3H), 7.98 (s, 1H), 8.11 (s, 1H), 8.58 (s, 1H), 10.13 (s, 1H).

Example 171

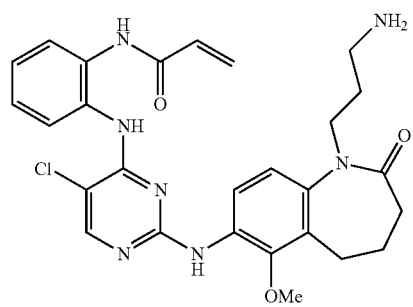

I-148

426

N-(2-((2-((1-(3-aminopropyl)-6-methoxy-2-oxo-2,3,4,5-tetrahydro-1H-benzo[b]azepin-7-yl)amino)-5-chloropyrimidin-4-yl)amino)phenyl)acrylamide Compound I-148 was prepared in a manner similar to Example 162, substituting tert-butyl (3-(7-amino-6-methoxy-2-oxo-2,3,4,5-tetrahydro-1H-benzo[b]azepin-1-yl)propyl)carbamate for 3-amino-4-methylbenzamide, followed by Boc-deprotection with TFA. MS m/z: 536.3 (ES+, M+H).

Example 172

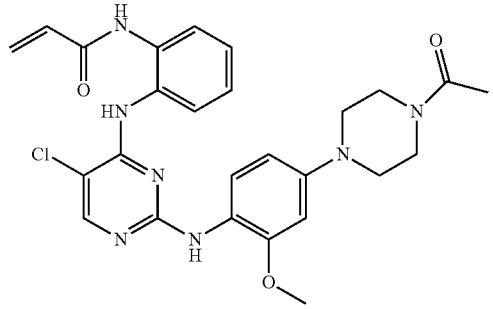

I-149

N-(2-((2-((4-(4-acetylpiperazin-1-yl)-2-methoxyphenyl)amino)-5-chloropyrimidin-4-yl)amino)phenyl)acrylamide Compound I-149 was prepared in a manner similar to Example 162, substituting 1-(4-(4-amino-3-methoxyphenyl)piperazin-1-yl)ethanone for 3-amino-4-methylbenzamide: MS m/z: 522.2 (ES+, M+H); $^1$HNMR (400 MHz, DMSO-d$_6$) δ 1.2 (s, 1H), 2.03 (s, 3H), 3.02-3.03 (m, 2H), 3.07-3.09 (m, 2H), 3.54-3.58 (q, 4H J=4.6 Hz), 3.76 (s, 3H), 5.77-5.80 (dd, 1H J=1.9, 10.2 Hz), 6.27-6.33 (m, 2H), 6.45-6.51 (dd, 1H J=10.2, 17 Hz), 6.60 (d, 1H J=2.5 Hz), 7.19-7.27 (m, 2H), 7.37-7.39 (dd, 1H J=1.8, 7.7 Hz), 7.55 (d, 1H J=8.7 Hz), 7.65 (s, 1H), 7.72-7.24 (dd, 1H J=1.6, 7.8 Hz), 8.03 (s, 1H), 8.44 (s, 1H), 10.16 (s, 1H).

Example 173

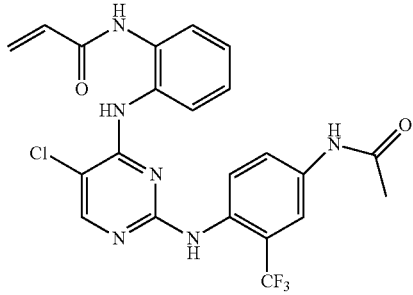

I-150

N-(2-((2-((4-acetamido-2-(trifluoromethyl)phenyl)
amino)-5-chloropyrimidin-4-yl)amino)phenyl)acryl-
amide Compound I-150 was prepared in a manner similar to Example 162, substituting N-(4-amino-3-(trifluoromethyl)phenyl)acetamide for 3-amino-4-methylbenzamide. MS m/z: 491.2 (ES+, M+H).

Example 174

I-151

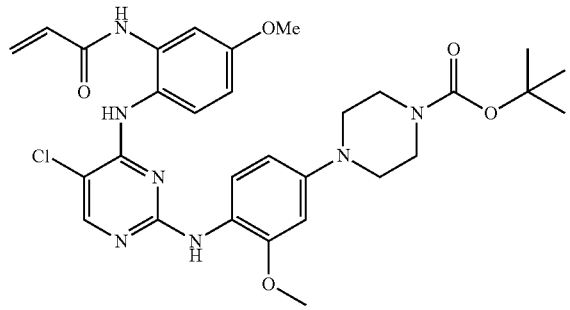

tert-butyl 4-(4-((4-((2-acrylamido-4-methoxyphenyl)
amino)-5-chloropyrimidin-2-yl)amino)-3-methoxy-
phenyl)piperazine-1-carboxylate Compound I-151 was prepared in a manner similar to Example 162, substituting N-(2-amino-5-methoxyphenyl)acrylamide for N-(2-aminophenyl)acrylamide, and substituting tert-butyl 4-(4-amino-3-methoxyphenyl)piperazine-1-carboxylate for 3-amino-4-methylbenzamide. MS: m/z 610.2 (ES+, M+H).

Example 175

I-152

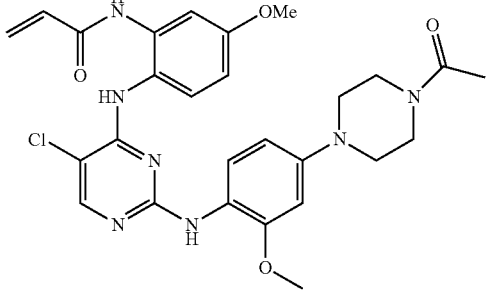

N-(2-((2-((4-(4-acetylpiperazin-1-yl)-2-methoxyphe-
nyl)amino)-5-chloropyrimidin-4-yl)amino)-5-
methoxyphenyl)acrylamide Compound I-152 was prepared in a manner similar to Example 162, substituting N-(2-amino-5-methoxyphenyl)acrylamide for N-(2-aminophenyl)acrylamide, and substituting 1-(4-(4-amino-3-methoxyphenyl)piperazin-1-yl)etha-
none for 3-amino-4-methylbenzamide. MS: m/z 552.2 (ES+, M+H).

Example 176

I-153

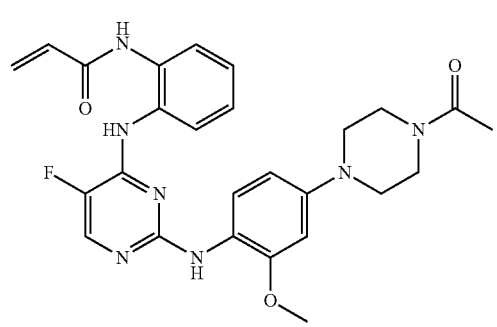

N-(2-((2-((4-(4-acetylpiperazin-1-yl)-2-methoxyphe-
nyl)amino)-5-fluoropyrimidin-4-yl)amino)phenyl)
acrylamide Compound I-153 was prepared in a manner similar to Example 162, using 2,4-dichloro-5-fluoropyrimidine as the starting material and substituting 1-(4-(4-amino-3-methoxyphenyl)piperazin-1-yl)ethanone for 3-amino-4-methylbenzamide. MS: m/z 506.2 (ES+, M+H).

Example 177

I-154

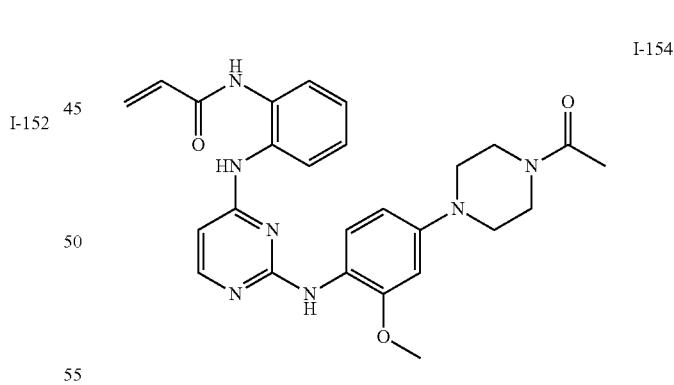

N-(2-((2-((4-(4-acetylpiperazin-1-yl)-2-methoxyphe-
nyl)amino)pyrimidin-4-yl)amino)phenyl)acrylamide Compound I-154 was prepared in a manner similar to Example 162, using 2,4-dichloro-pyrimidine as the starting material, and substituting 1-(4-(4-amino-3-methoxyphenyl)piperazin-1-yl)ethanone for 3-amino-4-methylbenzamide. MS: m/z 488.3 (ES+, M+H).

Example 178

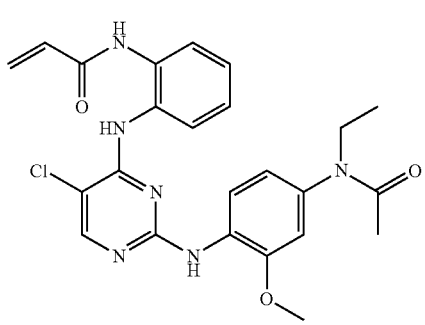

I-155

N-(2-((5-chloro-2-((4-(N-ethylacetamido)-2-methoxyphenyl)amino)pyrimidin-4-yl)amino)phenyl)acrylamide Compound I-155 was prepared in a manner similar to Example 162, substituting N-(4-amino-3-methoxyphenyl)-N-ethylacetamide for 3-amino-4-methylbenzamide. MS m/z: 481.3 (ES+, M+H); $^1$HNMR (400 MHz, DMSO-d$_6$) δ 0.98 (t, 3H J=7.1 Hz), 1.71 (s, 3H), 3.58 (q, 2H J=7.1 Hz), 3.81 (s, 3H), 5.76-5.79 (dd, 1H J=1.9, 10.2 Hz), 6.26-6.31 (dd, 1H J=1.9, 17 Hz), 6.45-6.51 (dd, 1H J=10.2, 17 Hz), 6.59-6.62 (dd, 1H J=1.7, 8.4 Hz), 6.89 (d, 1H J=1.9 Hz), 7.21-7.30 (m, 2H), 7.43-7.45 (dd, 1H J=1.6, 7.8 Hz), 7.67-7.69 (dd, 1H J=1.4, 7.8 Hz), 7.80 (s, 1H), 7.86 (d, 1H), 8.11 (s, 1H), 8.58 (s, 1H), 10.13 (s, 1H).

Example 179

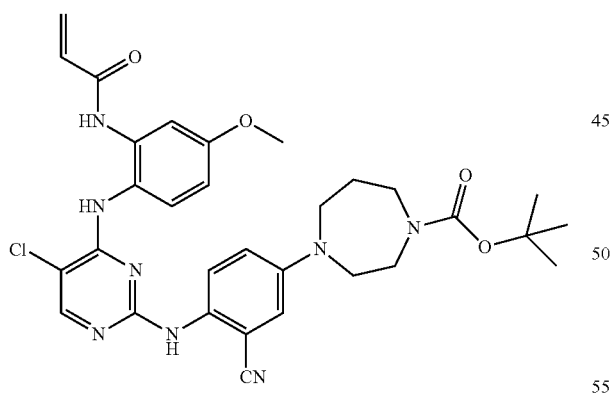

I-156 tert-butyl 4-(4-((4-((2-acrylamido-4-methoxyphenyl)amino)-5-chloropyrimidin-2-yl)amino)-3-cyanophenyl)-1,4-diazepane-1-carboxylate Compound I-155 was prepared in a manner similar to Example 162, substituting N-(2-amino-5-methoxyphenyl)acrylamide for N-(2-aminophenyl)acrylamide, and substituting tert-butyl 4-(4-amino-3-cyanophenyl)-1,4-diazepane-1-carboxylate for 3-amino-4-methylbenzamide. MS m/z: 619.2 (ES+, M+H).

Example 180

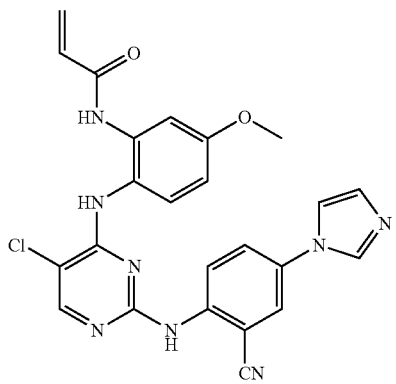

I-157

N-(2-((5-chloro-2-((2-cyano-4-(1H-imidazol-1-yl)phenyl)amino)pyrimidin-4-yl)amino)-5-methoxyphenyl)acrylamide Compound I-157 was prepared in a manner similar to Example 162, substituting N-(2-amino-5-methoxyphenyl)acrylamide for N-(2-aminophenyl)acrylamide, and substituting 2-amino-5-(1H-imidazol-1-yl)benzonitrile for 3-amino-4-methylbenzamide. MS m/z: 487.1 (ES+, M+H).

Example 181

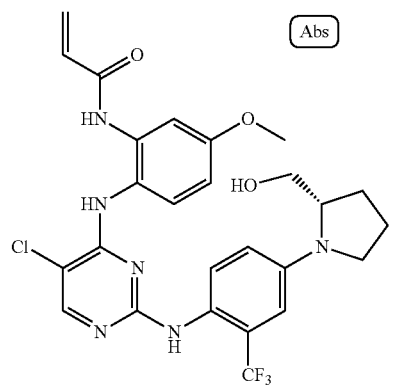

I-158

(S)—N-(2-((5-chloro-2-((4-(2-(hydroxymethyl)pyrrolidin-1-yl)-2-(trifluoromethyl) phenyl)amino)pyrimidin-4-yl)amino)-5-methoxyphenyl)acrylamide Compound I-158 was prepared in a manner similar to Example 162, substituting N-(2-amino-5-methoxyphenyl)acrylamide for N-(2-aminophenyl)acrylamide, and substituting (S)-(1-(4-amino-3-(trifluoromethyl)phenyl)pyrrolidin-2-yl)methanol for 3-amino-4-methylbenzamide. MS m/z: 563.2 (ES+, M+H).

Example 182

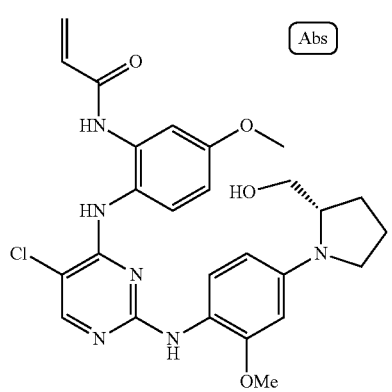

I-159

(S)—N-(2-((5-chloro-2-((4-(2-(hydroxymethyl)pyrrolidin-1-yl)-2-methoxyphenyl) amino)pyrimidin-4-yl)amino)-5-methoxyphenyl)acrylamide Compound I-159 was prepared in a manner similar to Example 162, substituting N-(2-amino-5-methoxyphenyl)acrylamide for N-(2-aminophenyl)acrylamide, and substituting (S)-(1-(4-amino-3-methoxyphenyl)pyrrolidin-2-yl)methanol for 3-amino-4-methylbenzamide. MS m/z: 525.2 (ES+, M+H).

Example 183

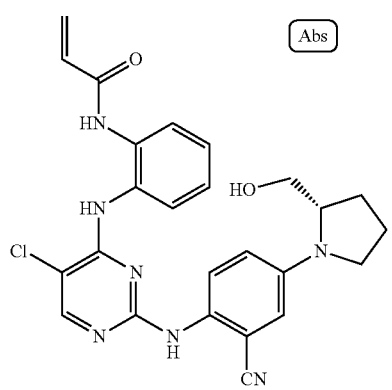

I-160

(S)—N-(2-((5-chloro-2-((2-cyano-4-(2-(hydroxymethyl)pyrrolidin-1-yl)phenyl) amino)pyrimidin-4-yl)amino)phenyl)acrylamide Compound I-160 was prepared in a manner similar to Example 162, substituting (S)-2-amino-5-(2-(hydroxymethyl)pyrrolidin-1-yl)benzonitrile for 3-amino-4-methylbenzamide. MS m/z: 491.1 (ES+, M+H).

Example 184

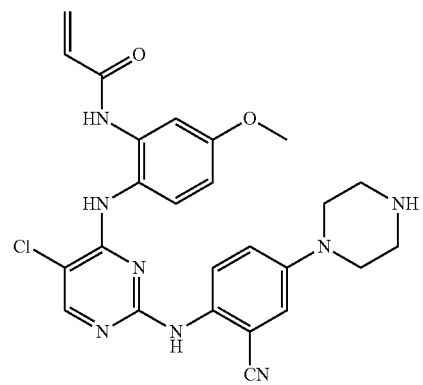

I-161

N-(2-((5-chloro-2-((2-cyano-4-(piperazin-1-yl)phenyl)amino)pyrimidin-4-yl)amino)-5-methoxyphenyl)acrylamide Compound I-161 was prepared in a manner similar to Example 162, substituting N-(2-amino-5-methoxyphenyl)acrylamide for N-(2-aminophenyl)acrylamide, and substituting tert-butyl 4-(4-amino-3-cyanophenyl)piperazine-1-carboxylate for 3-amino-4-methylbenzamide, followed by Boc-deprotection with TFA. MS m/z: 506.1 (ES+, M+H).

Example 185

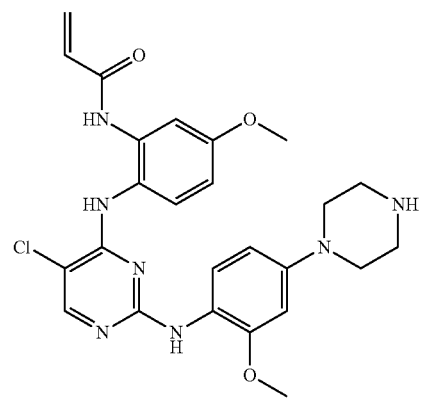

I-162

N-(2-((5-chloro-2-((2-methoxy-4-(piperazin-1-yl)phenyl)amino)pyrimidin-4-yl)amino)-5-methoxyphenyl)acrylamide Compound I-162 was prepared in a manner similar to Example 162, substituting N-(2-amino-5-methoxyphenyl)acrylamide for N-(2-aminophenyl)acrylamide, and substituting tert-butyl 4-(4-amino-3-methoxyphenyl)piperazine-1-carboxylate for 3-amino-4-methylbenzamide, followed by Boc-deprotection with TFA. MS m/z: 510.2 (ES+, M+H).

Example 186

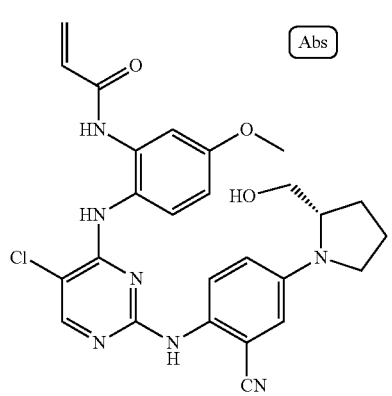

I-163

(S)—N-(2-((5-chloro-2-((2-cyano-4-(2-(hydroxymethyl)pyrrolidin-1-yl)phenyl) amino)pyrimidin-4-yl) amino)-5-methoxyphenyl)acrylamide Compound I-163 was prepared in a manner similar to Example 162, substituting N-(2-amino-5-methoxyphenyl)acrylamide for N-(2-aminophenyl)acrylamide, and substituting (S)-2-amino-5-(2-(hydroxymethyl)pyrrolidin-1-yl)benzonitrile for 3-amino-4-methylbenzamide. MS m/z: 520.2 (ES+, M+H).

Example 187

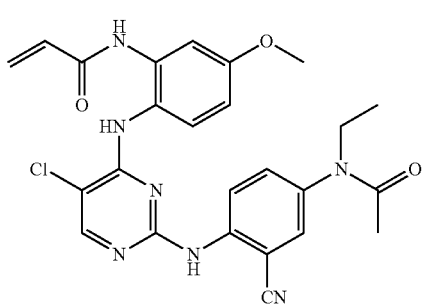

I-164

N-(2-((5-chloro-2-((2-cyano-4-(N-ethylacetamido)phenyl)amino)pyrimidin-4-yl)amino)-5-methoxyphenyl)acrylamide Compound I-164 was prepared in a manner similar to Example 162, substituting N-(2-amino-5-methoxyphenyl)acrylamide for N-(2-aminophenyl)acrylamide, and substituting N-(4-amino-3-cyanophenyl)-N-ethylacetamide for 3-amino-4-methylbenzamide. MS m/z: 506.1 (ES+, M+H).

Example 188

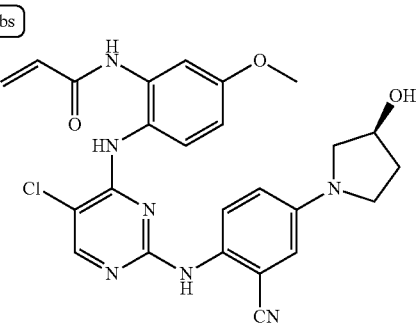

I-165

(S)—N-(2-((5-chloro-2-((2-cyano-4-(3-hydroxypyrrolidin-1-yl)phenyl)amino) pyrimidin-4-yl)amino)-5-methoxyphenyl)acrylamide Compound I-165 was prepared in a manner similar to Example 162, substituting N-(2-amino-5-methoxyphenyl)acrylamide for N-(2-aminophenyl)acrylamide, and substituting (S)-2-amino-5-(3-hydroxypyrrolidin-1-yl)benzonitrile for 3-amino-4-methylbenzamide. MS m/z: 506.1 (ES+, M+H).

Example 189

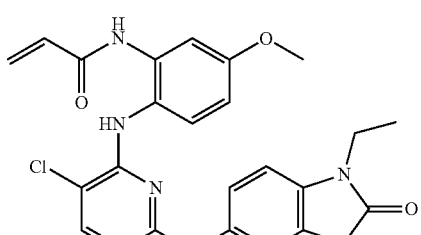

I-166

N-(2-((5-chloro-2-((1-ethyl-2-oxoindolin-5-yl)amino)pyrimidin-4-yl)amino)-5-methoxyphenyl)acrylamide Compound I-166 was prepared in a manner similar to Example 162, substituting N-(2-amino-5-methoxyphenyl)acrylamide for N-(2-aminophenyl)acrylamide, and substituting 5-amino-1-ethylindolin-2-one for 3-amino-4-methylbenzamide. MS m/z: 479.1 (ES+, M+H).

Example 190

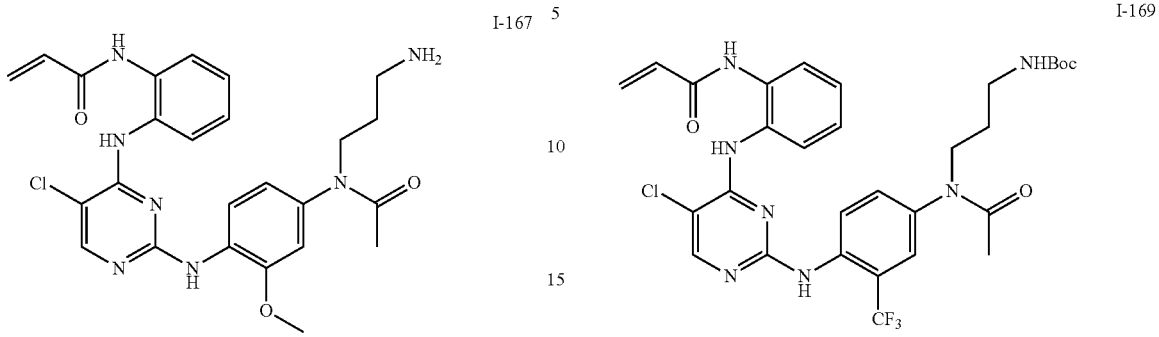

I-167

N-(2-((2-((4-(N-(3-aminopropyl)acetamido)-2-methoxyphenyl)amino)-5-chloropyrimidin-4-yl)amino)phenyl)acrylamide Compound I-167 was prepared in a manner similar to Example 162, substituting tert-butyl (3-(N-(4-amino-3-methoxyphenyl)acetamido)propyl)carbamate for 3-amino-4-methylbenzamide, followed by Boc-deprotection with TFA. MS m/z: 510.2 (ES+, M+H).

Example 191

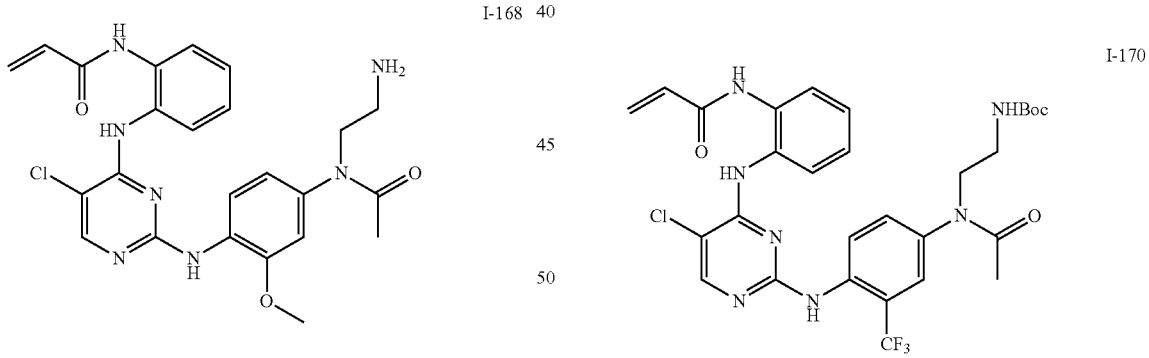

I-168

N-(2-((2-((4-(N-(2-aminoethyl)acetamido)-2-methoxyphenyl)amino)-5-chloropyrimidin-4-yl)amino)phenyl)acrylamide Compound I-168 was prepared in a manner similar to Example 162, substituting tert-butyl (2-(N-(4-amino-3-methoxyphenyl)acetamido)ethyl)carbamate for 3-amino-4-methylbenzamide, followed by Boc deprotection with TFA. MS m/z: 496.2 (ES+, M+H).

Example 192

I-169 tert-butyl (3-(N-(4-((4-((2-acrylamidophenyl)amino)-5-chloropyrimidin-2-yl)amino)-3-(trifluoromethyl)phenyl)acetamido)propyl)carbamate Compound I-169 was prepared in a manner similar to Example 162, substituting tert-butyl (3-(N-(4-amino-3-(trifluoromethyl)phenyl)acetamido)propyl)carbamate for 3-amino-4-methylbenzamide. MS m/z: 648.4 (ES+, M+H); ¹HNMR (400 MHz, DMSO-d₆) δ 1.35 (s, 9H), 1.47 (m, 2H), 1.69 (m, 3H), 2.88-2.93 (q, 2H, J=6.3 Hz), 3.59 (t, 2H, J=7.1 Hz), 5.77-5.78 (dd, 1H, J=1.8, 10.2 Hz), 6.27-6.31 (dd, 1H, J=1.8, 17 Hz), 6.44-6.51 (dd, 1H, J=10.2, 17 Hz), 6.75 (br s, 1H), 7.107-7.18 (m, 2H), 7.33 (d, 1H, J=6.3 Hz), 7.49 (d, 1H, J=6.7 Hz), 7.57 (s, 1H), 7.63 (d, 1H, J=7.1 Hz), 7.74 (d, 1H, J=7.8 Hz), 8.08 (s, 1H), 8.43 (s, 1H), 8.53 (s, 1H), 10.13 (s, 1H).

Example 193

I-170 tert-butyl (2-(N-(4-((4-((2-acrylamidophenyl)amino)-5-chloropyrimidin-2-yl)amino)-3-(trifluoromethyl)phenyl)acetamido)ethyl)carbamate Compound I-170 was prepared in a manner similar to Example 162, substituting tert-butyl (2-(N-(4-amino-3-(trifluoromethyl)phenyl)acetamido)ethyl)carbamate for 3-amino-4-methylbenzamide. MS m/z: 634.2 (ES+, M+H); 1HNMR (400 MHz, DMSO-d₆) δ 1.32 (s, 9H), 1.67 (br s, 3H), 302 (m, 2H), 3.61 (s, 2H), 5.79 (dd, 1H, J=1.7, 10.1 Hz), 6.27-6.31 (dd, 1H, J=1.7, 16.9 Hz), 6.44-6.51 (dd, 1H, J=10.1, 16.9 Hz), 6.88 (br s, 1H), 7.10-7.19 (m, 2H), 7.33 (d, 1H, J=7.2 Hz), 7.54 (d, 1H, J=7.8 Hz), 7.65 (d, 1H, J=7.9 Hz), 7.74 (d, 1H, J=7.6 Hz), 8.08 (s, 1H), 8.40 (s, 1H), 8.53 (s, 1H), 10.13 (s, 1H).

Example 194

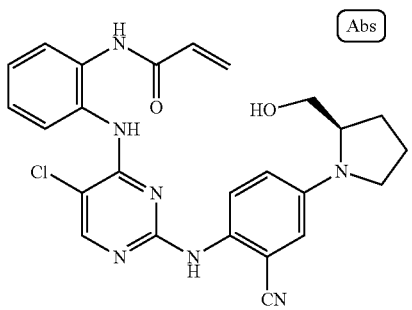

(R)—N-(2-((5-chloro-2-((2-cyano-4-(2-(hydroxymethyl)pyrrolidin-1-yl)phenyl) amino)pyrimidin-4-yl) amino)phenyl)acrylamide Compound I-171 was prepared in a manner similar to Example 162, substituting (R)-2-amino-5-(2-(hydroxymethyl)pyrrolidin-1-yl)benzonitrile for 3-amino-4-methylbenzamide. MS m/z: 490.2 (ES+, M+H); $^1$H NMR (400 MHz, DMSO-d$_6$) δ 1.88-2.03 (m, 4H), 3.10-3.16 (m, 1H), 3.25-3.30 (m, 1H), 3.43-3.48 (m, 2H), 3.85-3.86 (m, 1H), 5.78-5.81 (dd, 1H, J=1.6, 10.2 Hz), 6.29-6.34 (dd, 1H, J=1.8, 17 Hz), 6.49-6.56 (dd, 1H, J=10.2, 17 Hz), 7.22 (d, 1H, J=9.1 Hz), 7.34-7.43 (m, 4H), 7.61-7.64 (dd, 1H, J=1.5 Hz and 7.7 Hz), 7.72-7.74 (dd, 1H, J=1.3, 7.9 Hz), 9.33 (s, 1H) for TFA salt.

Example 195

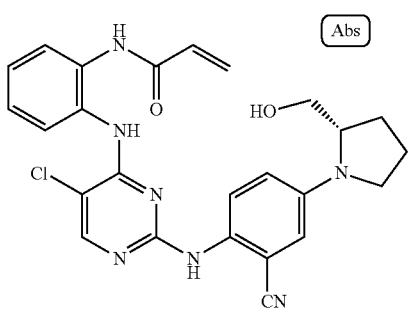

(S)—N-(2-((5-chloro-2-((2-cyano-4-(2-(hydroxymethyl)pyrrolidin-1-yl)phenyl) amino)pyrimidin-4-yl) amino)phenyl)acrylamide Compound I-172 was prepared in a manner similar to Example 162, substituting (S)-2-amino-5-(2-(hydroxymethyl)pyrrolidin-1-yl)benzonitrile for 3-amino-4-methylbenzamide. MS m/z: 490.2 (ES+, M+H).

Example 196

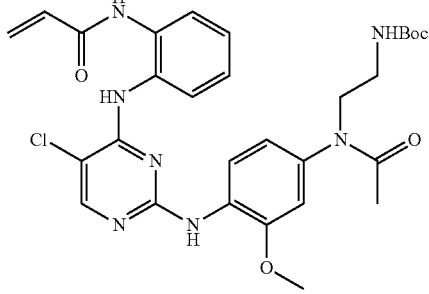

tert-butyl (2-(N-(4-((4-((2-acrylamidophenyl) amino)-5-chloropyrimidin-2-yl)amino)-3-methoxyphenyl)acetamido)ethyl)carbamate Compound I-174 was prepared in a manner similar to Example 162, substituting tert-butyl (2-(N-(4-amino-3-methoxyphenyl)acetamido)ethyl)carbamate for 3-amino-4-methylbenzamide. MS m/z: 596.3 (ES+, M+H); $^1$HNMR (400 MHz, DMSO-d$_6$) δ 1.32 (s, 9H), 1.71 (s, 3H), 3.02 (m, 2H), 3.58 (t, 2H J=6.4 Hz), 3.82 (s, 3H), 5.76-5.79 (dd, 1H, J=1.9, 10.2 Hz), 6.27-6.32 (dd, 1H, J=1.9, 17 Hz), 6.45-6.52 (dd, 1H, J=10.2, 17 Hz), 6.67 (d, 1H J=8.5 Hz), 6.80 (m, 1H), 6.99 (s, 1H), 7.22-7.32 (m, 2H), 7.43 (d, 1H, J=7.9 Hz), 7.69 (d, 1H, J=6.7 Hz), 7.76 (s, 1H), 7.87 (d, 1H, J=8.3 Hz), 8.11 (s, 1H), 8.58 (s, 1H), 10.16 (s, 1H).

Example 197

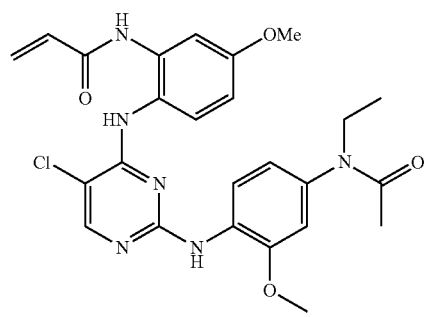

N-(2-((5-chloro-2-((4-(N-ethylacetamido)-2-methoxyphenyl)amino)pyrimidin-4-yl)amino)-5-methoxyphenyl)acrylamide Compound I-175 was prepared in a manner similar to Example 162, substituting N-(4-amino-3-methoxyphenyl)-N-ethylacetamide for 3-amino-4-methylbenzamide and substituting N-(2-amino-5-methoxyphenyl)acrylamide for N-(2-aminophenyl)acrylamide. MS m/z: 511.2 (ES+, M+H); $^1$H NMR (400 MHz, DMSO-d$_6$) δ 0.84 (t, 2H), 0.98 (t, 3H, J=7.19 Hz), 1.22-1.26 (m, 3H), 1.70 (s, 3H), 3.57 (q, 2H, J=7.2 Hz), 3.75 (s, 3H), 3.81 (s, 3H), 5.74-5.77 (dd, 1H, J=1.8, 10.2 Hz), 6.24-6.29 (dd, 1H, J=1.8, 17.0 Hz), 6.44-

6.51 (dd, 1H, J=10.2, 17.0 Hz), 6.57 (d, 1H, J=8.7 Hz), 6.85-6.87 (m, 2H), 7.17 (d, 1H, J=2.8 Hz), 7.46 (d, 1H, J=8.8 Hz), 7.69 (s, 1H), 7.85 (d, 1H, J=8.3 Hz), 8.05 (s, 1H), 8.43 (s, 1H), 9.95 (s, 1H).

Example 198

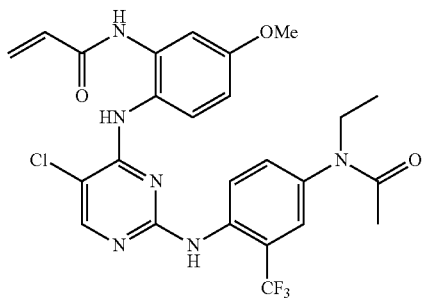

I-176

N-(2-((5-chloro-2-((4-(N-ethylacetamido)-2-(trifluoromethyl)phenyl)amino) pyrimidin-4-yl)amino)-5-methoxyphenyl)acrylamide Compound I-176 was prepared in a manner similar to Example 162, substituting N-(4-amino-3-(trifluoromethyl)phenyl)-N-ethylacetamide for 3-amino-4-methylbenzamide and substituting N-(2-amino-5-methoxyphenyl)acrylamide for N-(2-aminophenyl)acrylamide. MS m/z: 549.2 (ES+, M+H); $^1$H NMR (400 MHz, DMSO-$d_6$) δ 0.97 (br s, 3H), 1.68 (br s, 3H), 3.63 (m, 2H), 3.71 (s, 3H), 5.75-5.78 (dd, 1H J=1.8, 10.2 Hz), 6.24-6.29 (dd, 1H J=1.8, 17 Hz), 6.44-6.50 (dd, 1H J=10.2, 17 Hz), 6.74-6.77 (dd, 1H J=2.9, 9 Hz), 7.04 (d, 1H, J=2.7 Hz), 7.42-7.46 (m, 2H), 7.53 (br s, 1H), 7.73 (d, 1H, J=8 Hz), 8.04 (s, 1H), 8.29 (s, 1H), 8.38 (s, 1H), 9.95 (s, 1H).

Example 199

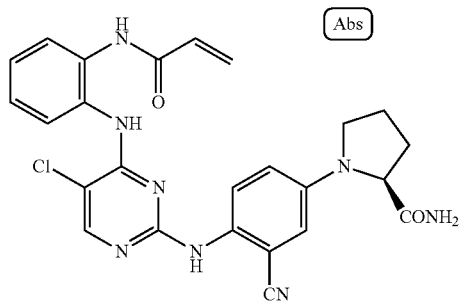

I-177

(S)-1-(4-((4-((2-acrylamidophenyl)amino)-5-chloropyrimidin-2-yl)amino)-3-cyanophenyl)pyrrolidine-2-carboxamide Compound I-177 was prepared in a manner similar to Example 162, substituting (S)-1-(4-amino-3-cyanophenyl)pyrrolidine-2-carboxamide for 3-amino-4-methylbenzamide. MS m/z: 503.2 (ES+, M+H); $^1$H NMR (400 MHz, DMSO-$d_6$) δ 1.93-2.0 (m, 3H), 2.19-2.24 (m, 1H), 3.19-3.24 (m, 1H), 3.51-3.55 (m, 1H), 3.92-3.95 (m, 1H), 5.77-5.80 (dd, 1H, J=1.9, 10.1 Hz), 6.28-6.32 (dd, 1H, J=1.9, 17 Hz), 6.45-6.52 (dd, 1H, J=10.2, 17.1 Hz), 6.66-6.68 (m, 2H), 7.09 (br s, 1H), 7.14-7.17 (m, 2H), 7.23 (d, 1H, J=9.4 Hz), 7.31-7.33 (m, 1H), 7.43 (br s, 1H), 7.72-7.75 (m, 1H), 8.01 (s, 1H), 8.40 (s, 1H), 8.88 (s, 1H), 10.16 (s, 1H).

Example 200

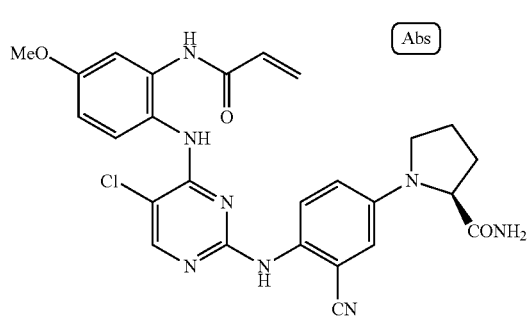

I-178

(S)-1-(4-((4-((2-acrylamido-4-methoxyphenyl)amino)-5-chloropyrimidin-2-yl)amino)-3-cyanophenyl)pyrrolidine-2-carboxamide Compound I-178 was prepared in a manner similar to Example 162, substituting (S)-1-(4-amino-3-cyanophenyl)pyrrolidine-2-carboxamide for 3-amino-4-methylbenzamide, and substituting N-(2-amino-5-methoxyphenyl)acrylamide for N-(2-aminophenyl)acrylamide. MS m/z: 533.2 (ES+, M+H); $^1$H NMR (400 MHz, DMSO-$d_6$) δ 1.96 (q, 3H, J=5.75 Hz), 2.18-2.20 (m, 1H), 3.20 (m, 1H), 3.52 (m, 1H), 3.74 (s, 3H), 3.93 (d, 1H J=7.7 Hz), 3.76-3.79 (dd, 1H, J=1.7, 10.1 Hz), 6.26-6.31 (dd, 1H, J=1.8, 16.9 Hz), 6.45-6.51 (dd, 1H, J=10.1, 16.9 Hz), 6.65 (m, 2H), 6.76-6.78 (dd, 1H J=2.7, 8.9 Hz), 7.03 (br s, 1H), 7.19-7.23 (m, 1H), 7.42 (br s, 1H), 7.51 (d, 1H J=9.0 Hz), 7.96 (s, 1H), 8.26 (s, 1H), 8.78 (s, 1H), 10.01 (s, 1H).

Example 201

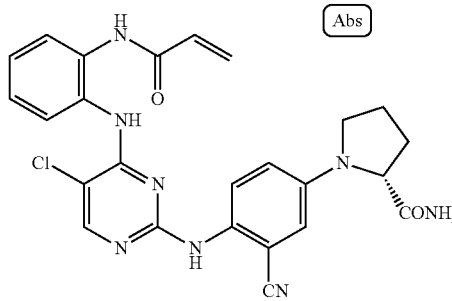

I-179

441

(R)-1-(4-((4-((2-acrylamidophenyl)amino)-5-chloro-pyrimidin-2-yl)amino)-3-cyanophenyl)pyrrolidine-2-carboxamide Compound I-179 was prepared in a manner similar to Example 162, substituting (R)-1-(4-amino-3-cyanophenyl)pyrrolidine-2-carboxamide for 3-amino-4-methylbenzamide. MS m/z: 503.2 (ES+, M+H); $^1$HNMR (400 MHz, DMSO-d$_6$) δ 1.94-2.0 (m, 3H), 2.19-2.24 (m, 1H), 3.51-3.55 (m, 1H), 3.92-3.95 (m, 1H), 5.77-5.80 (dd, 1H, J=1.9, 10.2 Hz), 6.28-6.32 (dd, 1H J=1.9, 17 Hz), 6.45-6.52 (dd, 1H, J=10.2, 17.1 Hz), 6.66-6.68 (m, 2H), 7.09 (br s, 1H), 7.14-7.17 (m, 2H), 7.23 (d, 1H, J=9.4 Hz), 7.31-7.33 (m, 1H), 7.42 (br s, 1H), 7.72-7.75 (m, 1H), 8.01 (s, 1H), 8.4 (s, 1H), 8.88 (s, 1H), 9.14 (s, 1H), 10.16 (s, 1H).

Example 202

I-180

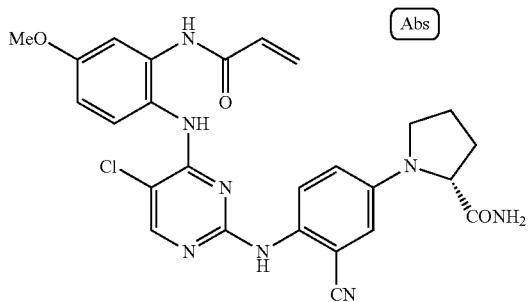

(R)-1-(4-((4-((2-acrylamido-4-methoxyphenyl)amino)-5-chloropyrimidin-2-yl)amino)-3-cyanophenyl)pyrrolidine-2-carboxamide Compound I-180 was prepared in a manner similar to Example 162, substituting (R)-1-(4-amino-3-cyanophenyl)pyrrolidine-2-carboxamide for 3-amino-4-methylbenzamide and substituting N-(2-amino-5-methoxyphenyl)acrylamide for N-(2-aminophenyl)acrylamide. MS m/z: 520.2 (ES+, M+H); $^1$H NMR (400 MHz, DMSO-d$_6$) δ 1.89-2.02 (m, 3H), 2.22 (m, 1H), 3.29 (q, 1H, J=7.5 Hz), 3.60-3.64 (m, 1H), 3.80 (s, 3H), 4.12 (d, 1H, J=8.4 Hz), 5.78-0.581 (dd, 1H, J=1.8, 10.1 Hz), 6.28-6.33 (dd, 1H, J=1.9, 17 Hz), 6.49-6.56 (dd, 1H J=10.2, 17 Hz), 6.90-6.94 (m, 2H), 7.33-7.36 (m, 2H), 7.41-7.46 (m, 2H), 9.30 (s, 1H), 9.9 (s, 1H) for TFA salt.

Example 203

I-181

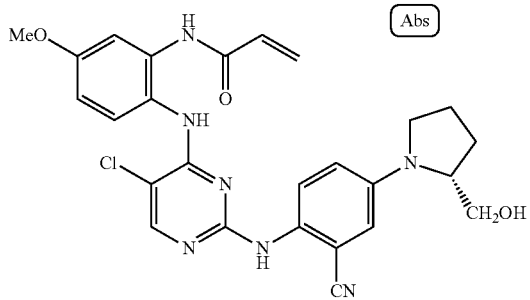

442

(R)—N-(2-((5-chloro-2-((2-cyano-4-(2-(hydroxymethyl)pyrrolidin-1-yl)phenyl) amino)pyrimidin-4-yl)amino)-5-methoxyphenyl)acrylamide Compound I-181 was prepared in a manner similar to Example 162, substituting (R)-2-amino-5-(2-(hydroxymethyl)pyrrolidin-1-yl)benzonitrile for 3-amino-4-methylbenzamide and substituting N-(2-amino-5-methoxyphenyl)acrylamide for N-(2-aminophenyl)acrylamide. MS m/z: 520.2 (ES+, M+H); $^1$HNMR (400 MHz, DMSO-d$_6$) δ 1.83-1.98 (m, 5H), 2.97-3.03 (m, 1H), 3.15-3.21 (m, 1H), 3.34-3.38 (m, 1H), 3.41-3.46 (m, 1H), 3.62-3.67 (m, 1H), 3.73 (s, 3H), 4.76 (t, 1H, J=6.1 Hz), 5.76-5.79 (dd, 1H, J=1.9, 10.2 Hz), 6.26-6.30 (dd, 1H, J=1.9, 17 Hz), 6.44-6.51 (dd, 1H, J=10.1, 17 Hz), 6.73-6.83 (m, 3H), 7.0 (d, 1H, J=2.7 Hz), 7.18 (d, 1H, J=8.8 Hz), 7.52 (d, 1H, J=8.9 Hz), 7.96 (s, 1H), 8.25 (s, 1H), 8.77 (s, 1H), 10.01 (s, 1H).

Example 204

I-182

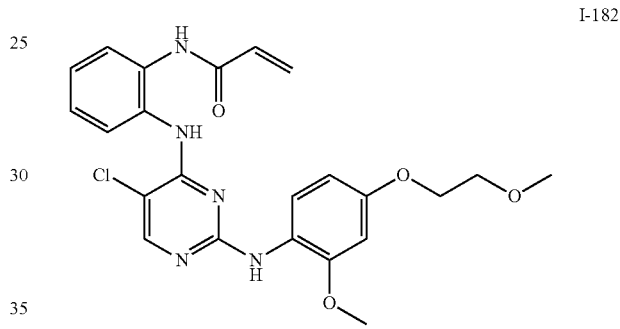

N-(2-((5-chloro-2-((2-methoxy-4-(2-methoxyethoxy)phenyl)amino)pyrimidin-4-yl)amino)phenyl)acrylamide Compound I-182 was prepared in a manner similar to Example 162, substituting 2-methoxy-4-(2-methoxyethoxy)aniline for 3-amino-4-methylbenzamide. MS m/z: 470.2 (ES+, M+H).

Example 205

I-183

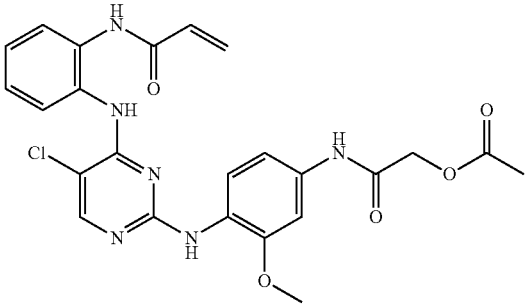

443

2-((4-((4-((2-acrylamidophenyl)amino)-5-chloropyrimidin-2-yl)amino)-3-methoxyphenyl)amino)-2-oxoethyl acetate Compound I-183 was prepared in a manner similar to Example 162, substituting tert-butyl (4-amino-3-methoxyphenyl)carbamate for 3-amino-4-methylbenzamide, followed by Boc-deprotection with TFA and reaction with ClCOCH₂OAc. MS m/z: 511.1 (ES+, M+H).

Example 206

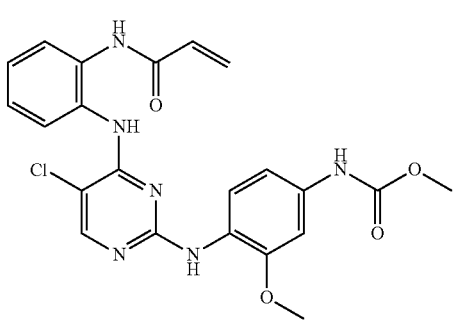

I-184 methyl (4-((4-((2-acrylamidophenyl)amino)-5-chloropyrimidin-2-yl)amino)-3-methoxyphenyl)carbamate Compound I-184 was prepared in a manner similar to Example 162, substituting tert-butyl (4-amino-3-methoxyphenyl)carbamate for 3-amino-4-methylbenzamide, followed by Boc-deprotection with TFA and reaction with methyl chloroformate. MS m/z: 469.0 (ES+, M+H).

Example 207

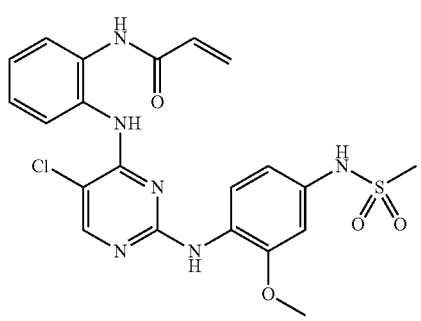

I-185

N-(2-((5-chloro-2-((2-methoxy-4-(methylsulfonamido)phenyl)amino)pyrimidin-4-yl)amino)phenyl)acrylamide Compound I-185 was prepared in a manner similar to Example 162, substituting tert-butyl (4-amino-3-methoxyphenyl)carbamate for 3-amino-4-methylbenzamide, followed by Boc-deprotection with TFA and reaction with MsCl. MS m/z: 489.1 (ES+, M+H).

444

Example 208

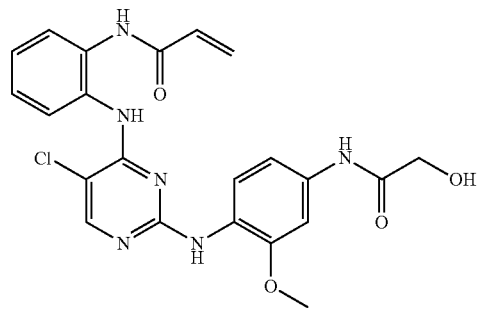

I-186

N-(2-((5-chloro-2-((4-(2-hydroxyacetamido)-2-methoxyphenyl)amino)pyrimidin-4-yl)amino)phenyl)acrylamide Compound I-186 was prepared in a manner similar to Example 162, substituting tert-butyl (4-amino-3-methoxyphenyl)carbamate for 3-amino-4-methylbenzamide, followed by Boc-deprotection with TFA and reaction with ClCOCH₂OAc and hydrolysis with aqueous LiOH. MS m/z: 469.0 (ES+, M+H).

Example 209

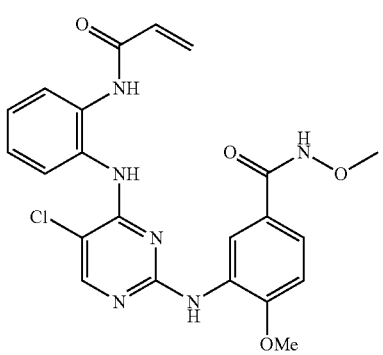

I-187

3-((4-((2-acrylamidophenyl)amino)-5-chloropyrimidin-2-yl)amino)-N,4-dimethoxybenzamide Compound I-187 was prepared in a manner similar to Example 162, substituting 3-amino-N,4-dimethoxybenzamide for 3-amino-4-methylbenzamide. MS m/z: 469.1 (ES+, M+H); ¹HNMR (DMSO-d₆) δ 3.68 (s, 3H), 3.81 (s, 3H), 5.77-5.80 (dd, J=1.8, 10.1 Hz, 1H), 6.27-6.32 (dd, J=1.8, 17 Hz, 1H), 6.44-6.50 (dd, J=10.1, 16.9 Hz, 1H), 7.04 (d, J=8.6 Hz, 1H), 7.11-7.18 (m, 2H), 7.29 (d, J=2.2 Hz, 1H), 7.40-7.42 (dd, J=2.1, 8.5 Hz, 1H), 7.73-7.75 (dd, J=2.2, 7.7 Hz, 1H), 7.96 (s, 1H), 8.16 (d, J=1.6 Hz, 1H), 8.52 (s, 1H), 10.18 (s, 1H), 11.47 (s, 1H).

Example 210

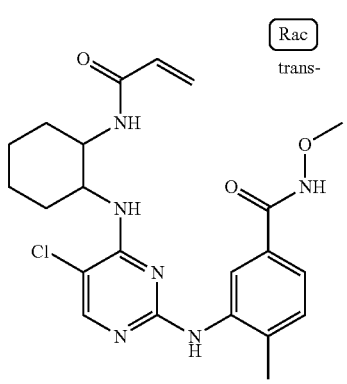

I-188

Rac-trans-3-((4-((2-acrylamidocyclohexyl)amino)-5-chloropyrimidin-2-yl)amino)-N-methoxy-4-methyl-benzamide Compound I-188 was prepared in a manner similar to Example 162, substituting 3-amino-N-methoxy-4-methylbenzamide for 3-amino-4-methylbenzamide and substituting trans-N-(2-aminocyclohexyl)acrylamide for N-(2-aminophenyl)acrylamide. MS m/z: 459.2 (ES+, M+H); ¹HNMR (DMSO-d₆) δ 1.04-1.28 (m, 4H), 1.54-1.63 (m, 2H), 1.81 (m, 1H), 2.04 (m, 1H), 2.25 (s, 3H), 3.58-3.68 (m, 1H), 3.67 (s, 3H), 3.80-3.85 (m, 1H), 5.51-5.54 (dd, J=2.6, 9.6 Hz, 1H), 6.01-6.14 (m, 2H), 6.64 (d, J=6.8 Hz, 1H), 7.23 (d, J=7.9 Hz, 2H), 7.35-7.38 (dd, J=1.6, 7.8 Hz, 1H), 7.84 (s, 1H), 7.99 (d, J=1.4 Hz, 1H), 8.0 (d, J=8.1 Hz, 1H), 8.42 (s, 1H), 11.60 (s, 1H).

Example 211

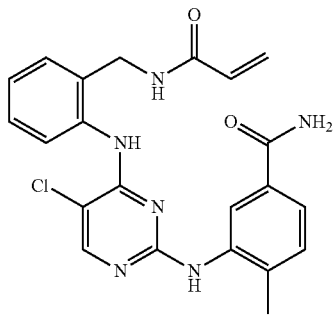

I-189

3-((4-((2-(acrylamidomethyl)phenyl)amino)-5-chloropyrimidin-2-yl)amino)-4-methylbenzamide Compound I-189 was prepared in a manner similar to Example 162, substituting N-(2-aminobenzyl)acrylamide for N-(2-aminophenyl)acrylamide. MS: m/z: 437.1 (ES+, M+H).

Example 212

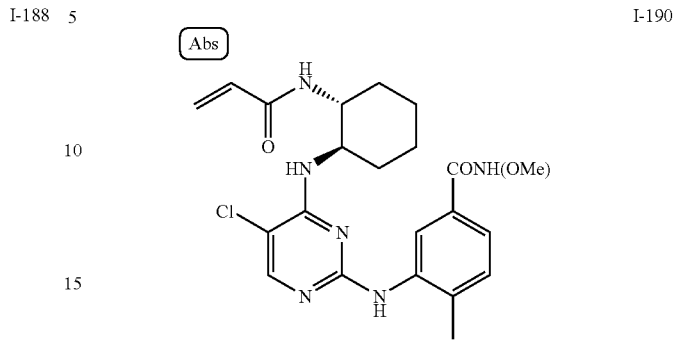

I-190

3-((4-(((1R,2R)-2-acrylamidocyclohexyl)amino)-5-chloropyrimidin-2-yl)amino)-N-methoxy-4-methyl-benzamide Compound I-190 was prepared in a manner similar to Example 162, substituting 3-amino-N-methoxy-4-methylbenzamide for 3-amino-4-methylbenzamide and substituting N-((1R,2R)-2-aminocyclohexyl)acrylamide for N-(2-aminophenyl)acrylamide. MS m/z: 459.2 (ES+, M+H); ¹HNMR (DMSO-d₆) δ 1.04-1.1 (m, 1H), 1.20-1.28 (m, 6H), 1.54-1.63 (m, 2H), 1.82 (d, 1H J=9.2 Hz), 2.24 (s, 3H), 3.58-3.63 (m, 1H), 3.67 (s, 3H), 3.77-3.85 (m, 1H), 5.51-5.54 (dd, 1H J=2.6, 9.6 Hz), 6.0-6.05 (dd, 1H J=2.6, 17.1 Hz), 6.08-6.14 (dd, 1H J=10.7, 17.1 Hz), 6.64 (d, 1H J=7.8 Hz), 7.23 (d, 1H J=7.9 Hz), 7.35-7.38 (dd, 1.7, 7.8 Hz), 7.84 (s, 1H), 7.99 (d, 1H J=7.9 Hz), 8.03 (s, 1H), 8.42 (s, 1H), 11.6 (s, 1H).

Example 213

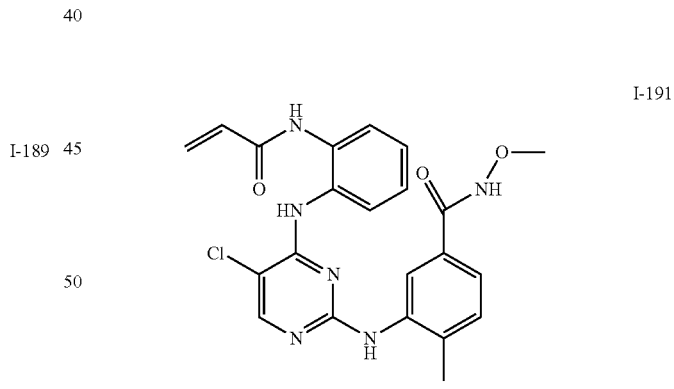

I-191

3-((4-((2-acrylamidophenyl)amino)-5-chloropyrimidin-2-yl)amino)-N-methoxy-4-methylbenzamide Compound I-191 was prepared in a manner similar to Example 162, substituting 3-amino-N-methoxy-4-methylbenzamide for 3-amino-4-methylbenzamide. MS m/z: 453.2 (ES+, M+H); ¹HNMR (DMSO-d₆) δ 2.17 (s, 3H), 3.69 (s, 3H), 5.78-5.81 (dd, J=1.8, 10.0 Hz, 1H), 6.27-6.32 (dd, J=1.9, 17.0 Hz, 1H), 6.43-6.50 (dd, J=10.1, 17.0 Hz, 1H), 7.01-7.10 (m, 2H), 7.20-7.25 (dt, J=1.4, 7.8 Hz, 1H), 7.39-7.41 (dd, J=1.6, 7.8 Hz, 1H), 7.70-7.72 (dd, J=1.4, 7.8 Hz, 1H), 7.81 (d, J=1.5 Hz, 1H), 8.06 (s, 1H), 8.43 (s, 1H), 8.65 (s, 1H), 10.20 (s, 1H), 11.63 (s, 1H).

Example 214

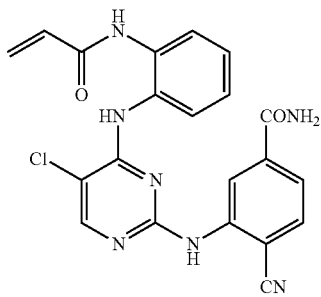

3-((4-((2-acrylamidophenyl)amino)-5-chloropyrimidin-2-yl)amino)-4-cyanobenzamide Compound I-192 was prepared in a manner similar to Example 162, substituting 3-amino-4-cyanobenzamide for 3-amino-4-methylbenzamide. MS m/z: 434.1 (ES+, M+H); $^1$HNMR (DMSO-$d_6$) δ 5.78-5.81 (dd, 1H, J=1.9, 10.2 Hz), 6.28-6.33 (dd, 1H, J=1.9, 17 Hz), 6.44-6.51 (dd, 1H, J=10.2, 17 Hz), 7.10-7.13 (m, 2H), 7.27-7.31 (m, 1H), 7.63-7.66 (m, 2H), 7.69-7.01 (m, 1H), 7.79 (d, 1H, J=8.1 Hz), 8.0 (d, 1H, J=1.4 Hz), 8.11-8.13 (m, 2H), 8.57 (s, 1H), 10.2 (s, 1H).

Example 215

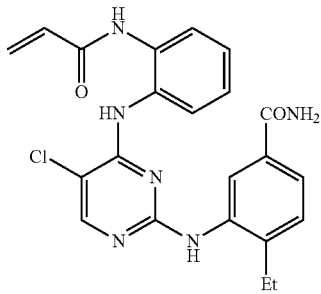

3-((4-((2-acrylamidophenyl)amino)-5-chloropyrimidin-2-yl)amino)-4-ethylbenzamide Compound I-193 was prepared in a manner similar to Example 162, substituting 3-amino-4-ethylbenzamide for 3-amino-4-methylbenzamide. MS m/z: 437.1 (ES+, M+H).

Example 216

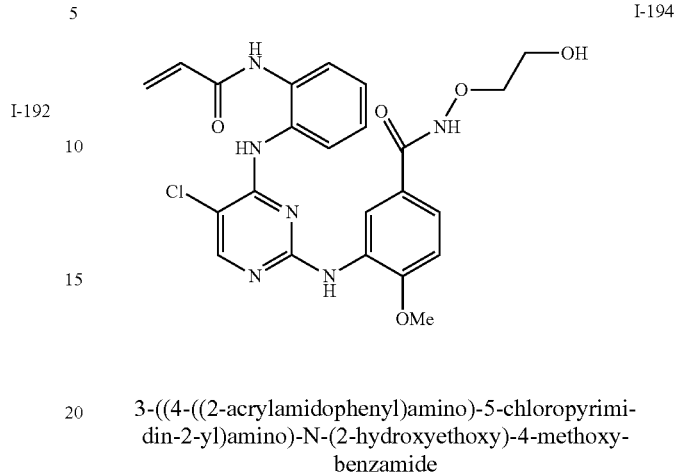

3-((4-((2-acrylamidophenyl)amino)-5-chloropyrimidin-2-yl)amino)-N-(2-hydroxyethoxy)-4-methoxybenzamide Compound I-194 was prepared in a manner similar to Example 162, substituting 3-amino-N-(2-hydroxyethoxy)-4-methoxybenzamide for 3-amino-4-methylbenzamide. MS m/z: 499.4 (ES+, M+H); $^1$HNMR (DMSO-$d_6$) δ 3.58 (q, J=5.3 Hz, 2H), 3.89 (t, J=5.1 Hz, 2H), 4.76 (t, J=5.7 Hz, 1H), 5.77-5.80 (dd, J=1.8, 10.0 Hz, 1H), 6.27-6.32 (dd, J=1.8, 16.9 Hz, 1H), 6.44-6.50 (dd, J=10.0, 16.9 Hz, 1H), 7.04 (d, J=8.6 Hz, 1H), 7.13-7.17 (m, 2H), 7.29-7.31 (dd, J=1.9, 6.7 Hz, 1H), 7.42-7.45 (dd, J=2.2, 8.8 Hz, 1H), 7.72-7.75 (dd, J=2.6, 7.7 Hz, 1H), 7.97 (s, 1H), 8.12 (s, 1H), 8.17 (d, J=1.7 Hz, 1H), 8.53 (s, 1H), 10.19 (s, 1H), 11.51 (s, 1H).

Example 217

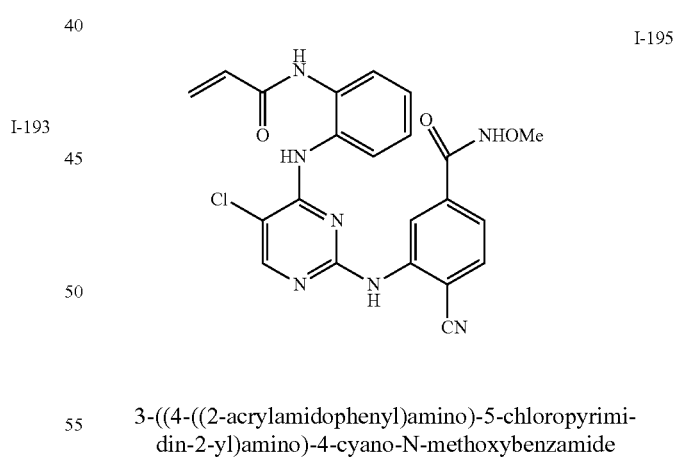

3-((4-((2-acrylamidophenyl)amino)-5-chloropyrimidin-2-yl)amino)-4-cyano-N-methoxybenzamide Compound I-195 was prepared in a manner similar to Example 162, substituting 3-amino-4-cyano-N-methoxybenzamide for 3-amino-4-methylbenzamide: MS m/z: 464.1 (ES+, M+H); $^1$HNMR (DMSO-$d_6$) δ 3.70 (s, 3H), 5.78-5.81 (dd, 1H, J=1.8, 10 Hz), 6.28-6.33 (dd, 1H, J=1.8, 16.97 Hz), 6.45-6.51 (dd, 1H, J=10, J=17 Hz), 7.08-7.15 (m, 2H), 7.30-7.32 (dd, 1H, J=1.9, J=7.7 Hz), 7.50-7.52 (dd, 1H, J=1.3, 8 Hz), 7.67-7.69 (dd, 1H, J=1.68, 7 Hz), 7.80-7.82 (d, 1H, J=8 Hz), 7.88 (s, 1H), 8.14 (s, 1H), 8.60 (s, 1H), 9.48 (s, 1H), 10.21 (s, 1H), 11.91 (s, 1H).

Example 218

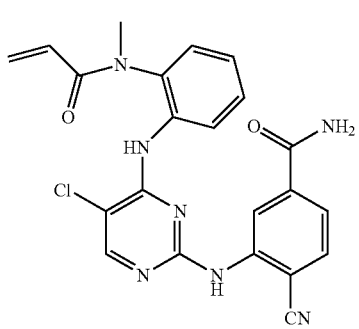

3-((5-chloro-4-((2-(N-methylacrylamidophenyl)amino)pyrimidin-2-yl)amino)-4-cyano-N-cyanobenzamide Compound I-196 was prepared in a manner similar to Example 162, substituting N-(2-aminophenyl)-N-methylacrylamide for N-(2-aminophenyl)acrylamide. MS m/z: 448.1 (ES+, M+H); HNMR (DMSO-$d_6$) δ.3.07 (s, 3H), 5.31-5.36 (dd, J=2.4, 10.0 Hz, 1H), 5.80-5.87 (dd, J=10.0, 16.7 Hz, 1H), 5.98-6.02 (dd, J=2.4, 16.7 Hz, 1H), 7.20 (d, J=1.4 Hz, 1H), 7.23-7.27 (m, 1H), 7.41-7.16 (m, 1H), 7.58-7.63 (m, 3H), 7.73 (d, J=8.0 Hz, 1H), 7.91 (d, J=1.0 Hz, J=8 Hz), 8.07 (s, 1H), 8.10 (s, 1H), 8.51 (s, 1H), 9.34 (s, 1H).

Example 219

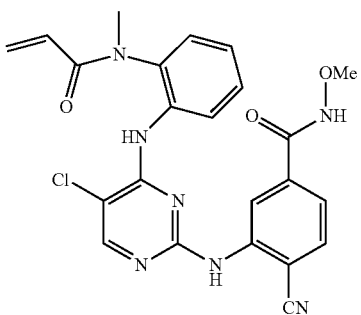

3-((5-chloro-4-((2-(N-methylacrylamido)phenyl)amino)pyrimidin-2-yl)amino)-4-cyano-N-methoxybenzamide Compound I-197 was prepared in a manner similar to Example 162, substituting 3-amino-4-cyano-N-methoxybenzamide for 3-amino-4-methylbenzamide, and substituting N-(2-aminophenyl)-N-methylacrylamide for N-(2-aminophenyl)acrylamide. MS m/z: 479.2 (ES+, M+H); $^1$HNMR (CD$_3$OD) δ.3.21 (s, 3H), 3.83 (s, 3H), 5.42-5.45 (dd, J=1.9, 10.3 Hz, 1H), 5.97-6.04 (dd, J=10.2, 16.8 Hz, 1H), 6.15-6.20 (dd, J=1.8, 16.8 Hz, 1H), 7.24 (d, J=7.8 Hz, 1H), 7.34 (t, J=7.4 Hz, 1H), 7.41-7.16 (dd, J=6.6, 13.4 Hz, 2H), 7.68-7.71 (dd, J=2.5, 7.8 Hz, 2H), 8.09 (s, 1H), 8.13 (s, 1H).

Example 220

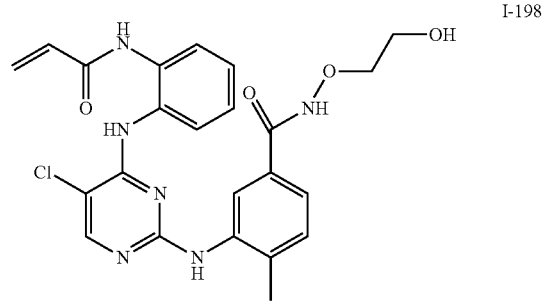 [SMILES: C=CC(=O)Nc1ccccc1Nc1nc(Nc2cc(C(=O)NOCCO)ccc2C)ncc1Cl]

3-((4-((2-acrylamidophenyl)amino)-5-chloropyrimidin-2-yl)amino)-N-(2-hydroxyethoxy)-4-methylbenzamide Compound I-198 was prepared in a manner similar to Example 162, substituting 3-amino-N-(2-hydroxyethoxy)-4-methylbenzamide for 3-amino-4-methylbenzamide. MS m/z: 483.2 (ES+, M+H); $^1$HNMR (DMSO-$d_6$) δ 2.31 (s, 3H), 3.58 (t, J=5.0 Hz, 2H), 3.90 (t, J=5.0 Hz, 2H), 4.80 (br s, 1H), 5.78-5.81 (dd, J=1.8, 10.0 Hz, 1H), 6.27-6.32 (dd, J=1.8, 16.9 Hz, 1H), 6.43-6.50 (dd, J=10.0, 17.0 Hz, 1H), 7.00-7.09 (m, 2H), 7.20-7.25 (m, 2H), 7.41-7.43 (dd, J=1.5, 7.8 Hz, 1H), 7.70-7.72 (dd, J=1.4, 7.8 Hz, 1H), 7.82 (d, J=1.4 Hz, 1H), 8.05 (s, 1H), 8.43 (s, 1H), 8.66 (s, 1H), 10.22 (s, 1H).

Example 221

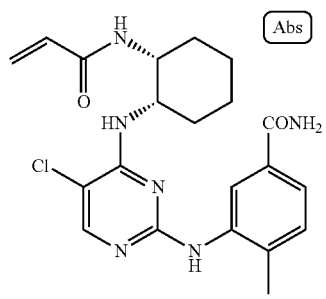

3-((4-(((1 S,2R)-2-acrylamidocyclohexyl)amino)-5-chloropyrimidin-2-yl)amino)-4-methylbenzamide Compound I-199 was prepared in a manner similar to Example 162, substituting N-((1R,2S)-2-aminocyclohexyl)acrylamide for N-(2-aminophenyl)acrylamide. MS m/z: 429.2 (ES+, M+H).

Example 222

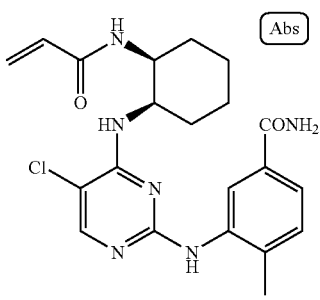

I-200

3-((4-(((1R,2S)-2-acrylamidocyclohexyl)amino)-5-chloropyrimidin-2-yl)amino)-4-methylbenzamide Compound I-200 was prepared in a manner similar to Example 162, substituting N-((1S,2R)-2-aminocyclohexyl)acrylamide for N-(2-aminophenyl)acrylamide. MS m/z: 429.2 (ES+, M+H).

Example 223

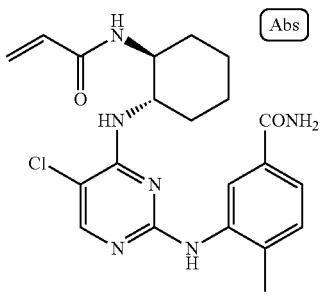

I-201

3-((4-(((1S,2S)-2-acrylamidocyclohexyl)amino)-5-chloropyrimidin-2-yl)amino)-4-methylbenzamide Compound I-201 was prepared in a manner similar to Example 162, substituting N-((1S,2S)-2-aminocyclohexyl)acrylamide for N-(2-aminophenyl)acrylamide. MS m/z: 429.2 (ES+, M+H).

Example 224

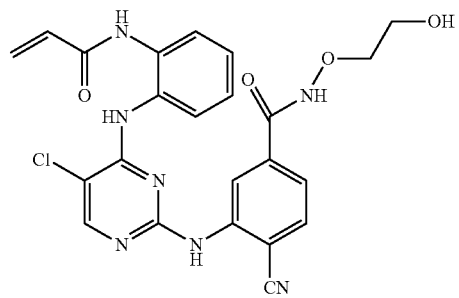

I-202

3-((4-((2-acrylamidophenyl)amino)-5-chloropyrimidin-2-yl)amino)-4-cyano-N-(2-hydroxyethoxy)benzamide Compound I-202 was prepared in a manner similar to Example 162, substituting 3-amino-4-cyano-N-(2-hydroxyethoxy)benzamide for 3-amino-4-methylbenzamide. MS m/z: 492.1 (ES+, M+H); $^1$HNMR (DMSO-$d_6$) δ 3.6 (m, 2H), 3.91-3.92 (m, 2H), 4.72 (br s, 1H), 5.78-5.81 (dd, J=1.7, 10.2 Hz, 1H), 6.28-6.33 (dd, J=1.8, 16.9 Hz, 1H), 6.45-6.51 (dd, J=10.2, 17.0 Hz, 1H), 7.08-7.15 (m, 2H), 7.30-7.32 (dd, J=1.9, 7.3 Hz, 1H), 7.52-7.54 (dd, J=1.4, 8.1 Hz, 1H), 7.67-7.70 (dd, J=1.8, 7.3 Hz, 1H), 7.80 (d, J=8.0 Hz, 1H), 8.14 (s, 1H), 8.59 (s, 1H), 9.47 (s, 1H), 10.20 (s, 1H), 10.94 (s, 1H).

Example 225

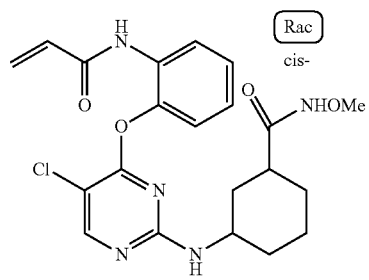

I-203

Rac-cis-3-((4-((2-acrylamidophenyl)amino)-5-chloropyrimidin-2-yl)amino)-N-methoxy-cyclohexanecarboxamide Compound I-203 was prepared in a manner similar to Example 120, substituting racemic cis-3-amino-N-methoxy-cyclohexanecarboxamide for 3 cis-3-aminocyclohexanecarboxamide. MS m/z: 445.2 (ES+, M+H); $^1$HNMR (DMSO-$d_6$) δ 0.8-1.11 (m, 2H), 1.19-1.27 (m, 2H), 1.27-1.31 (m, 1H), 1.57 (m, 1H), 1.71-1.89 (m, 3H), 1.95 (br s, 1H), 3.52 (s, 3H), 5.79 (d, J=10.6 Hz, 1H), 6.30 (d, J=16.3 Hz, 1H), 6.45-6.51 (dd, J=10.1, 16.5 Hz, 1H), 7.17 (t, J=6.4 Hz, 1H), 7.25 (t, J=7.4 Hz, 1H), 7.36 (d, J=7.7 Hz, 1H), 7.79 (br s, 1H), 7.91 (s, 1H), 8.25 (br s, 1H), 10.16 (s, 1H), 10.91 (s, 1H).

Example 226

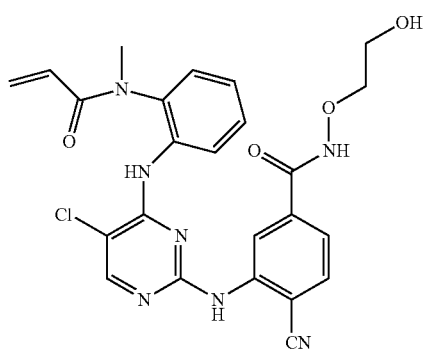

I-204

3-((5-chloro-4-((2-(N-methylacrylamido)phenyl)amino)pyrimidin-2-yl)amino)-4-cyano-N-(2-hydroxyethoxy)benzamide Compound I-204 was prepared in a manner similar to Example 162, substituting 3-amino-4-cyano-N-(2-hydroxyethoxy)benzamide for 3-amino-4-methylbenzamide, and substituting N-(2-aminophenyl)-N-methylacrylamide for N-(2-aminophenyl)acrylamide. MS m/z: 506.2 (ES+, M+H); $^1$HNMR (DMSO-$d_6$) δ 3.03 (s, 3H), 3.58-3.60 (m, 2H), 3.89-3.91 (t, J=4.25 Hz, 2H), 4.71-4.74 (t, J=5.58 Hz, 1H), 5.32-5.35 (dd, J=2.7 Hz, 10.2 Hz, 1H), 5.81-5.87 (dd, J=10.2 Hz, 1H), 5.98-6.02 (dd, J=2.3 Hz, 10.3 Hz, 1H), 7.19-7.23 (m, 2H), 7.30-7.34 (m, 1H), 7.48-7.50 (m, 1H), 7.59-7.61 (d, J=7.6 Hz, 1H), 7.73-7.75 (d, J=8 Hz, 1H), 7.83 (s, 1H), 8.10 (s, 1H), 8.57 (s, 1H), 9.37 (s, 1H), 11.89 (s, 1H).

Example 227

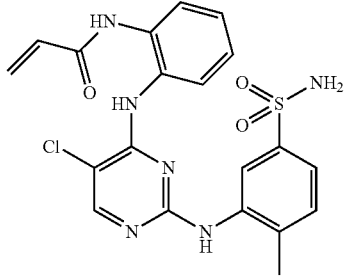

I-205

N-(2-((5-chloro-2-((2-methyl-5-sulfamoylphenyl)amino)pyrimidin-4-yl)amino) phenyl)acrylamide Compound I-202 was prepared in a manner similar to Example 162, substituting 3-amino-4-methylbenzenesulfonamide for 3-amino-4-methylbenzamide. MS m/z: 459.1 (ES+, M+H); $^1$HNMR (DMSO-$d_6$) δ 2.18 (s, 3H), 5.78-7.81 (dd, 1H, J=1.8, 10 Hz), 6.27-6.31 (dd, 1H, J=1.9, 17 Hz), 6.44-6.51 (dd, 1H, J=10, 17 Hz), 7.09-7.14 (m, 1H), 7.16-7.18 (m, 1H), 7.20 (s, 2H), 7.24-34 (m, 2H), 7.46-7.48 (dd, 1H, J=1.9. 7.9 Hz), 7.70 (d, 1H, J=1.3 Hz), 7.72 (d, 1H, J=1.3 Hz), 7.79 (d, 1H, J=1.8 Hz), 8.04 (s, 1H), 8.44 (s, 1H), 8.70 (s, 1H), 10.18 (s, 1H).

Example 228

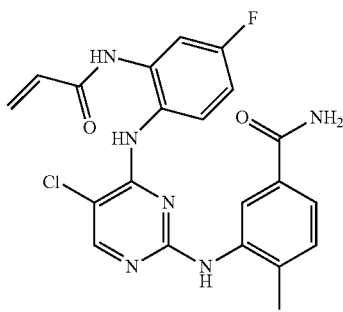

I-206

3-((4-((2-acrylamido-4-fluorophenyl)amino)-5-chloropyrimidin-2-yl)amino)-4-methylbenzamide Compound I-206 was prepared in a manner similar to Example 162, substituting N-(2-amino-5-fluorophenyl)acrylamide for N-(2-aminophenyl)acrylamide. MS m/z: 441.1 (ES+, M+H); $^1$HNMR (DMSO-$d_6$) δ 2.15 (s, 3H), 5.78-5.81 (dd, 1H, J=1.6, 10 Hz), 6.26-6.31 (dd, 1H, J=1.7, 17 Hz), 6.44-6.50 (dd, 1H, J=10, 17 Hz), 6.82-6.87 (m, 1H), 7.14-7.19 (d, 1H, J=7.9 Hz), 7.27-7.29 (d, 2H, J=7.3 Hz), 7.50-7.52 (d, 1H, J=7.8 Hz), 7.62-7.64 (m, 1H), 7.87-7.89 (d, 2H, J=7 Hz), 8.03 (s, 1H), 8.32 (s, 1H), 8.58 (s, 1H), 10.08 (s, 1H).

Example 229

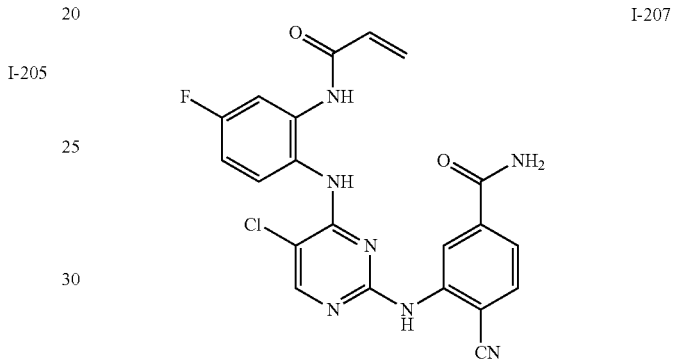

I-207

3-(4-(2-acrylamido-4-fluorophenylamino)-5-chloropyrimidin-2-ylamino)-4-cyanobenzamide Compound I-207 was prepared according to the step described below. To a stirred solution of N-(2-((2,5-dichloropyrimidin-4-yl)amino)-5-fluorophenyl)acrylamide (200 mg, 0.613 mmol), which was prepared using N-(2-amino-5-fluorophenyl)acrylamide and 2,4,5-trichloropyrimidine in a method similar to step 1 of Example 162, in tert-amyl alcohol (5 mL) was added aqueous sodium carbonate (96 mg, 0.905 mmol), 3-amino-4-cyanobenzamide (100 mg, 0.324 mmol) and diphenylphosphino-N,N-dimethylamine (125 mg, 0.919 mmol). The mixture was degassed for 20 min. To this mixture, $Pd_2(dba)_3$ (625 mg, 0.733 mmol) and Davephos (96 mg, 0.244 mmol) were added and again degassed for 10 min. The reaction mixture was heated to 90° C. for 2 h. TLC showed completion of starting material. The crude mixture was purified by silica gel column chromatography followed by preparative HPLC to yield 30 mg of the title compound. MS m/z: 452.1 (ES+, M+H); $^1$HNMR (DMSO-$d_6$) δ 5.77-5.80 (dd, 1H J=2.0 Hz and 10.2 Hz), 6.26-6.31 (dd, 1H J=1.9 Hz and 17 Hz), 6.46-6.52 (dd, 1H J=10.2, 17 Hz), 6.90-6.95 (dt, 3.0, 8.4 Hz), 7.38-7.41 (dd, 1H J=3.0, 10.4 Hz), 7.56-7.64 (m, 3H), 7.78 (d, 1H J=8.1 Hz), 7.96 (d, 1H J=1.2 Hz), 8.10-8.12 (m, 2H), 8.5 (s, 1H), 9.4 (s, 1H), 10.02 (s, 1H). MS m/z: 452.1 (ES+, M+H).

Example 230

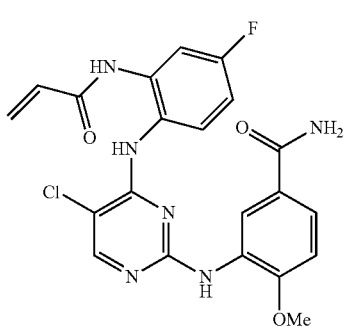

I-208

3-((4-((2-acrylamido-4-fluorophenyl)amino)-5-chloropyrimidin-2-yl)amino)-4-methoxybenzamide Compound I-208 was prepared in a manner similar to Example 162, substituting 3-amino-4-methoxybenzamide for 3-amino-4-methylbenzamide, and substituting N-(2-amino-5-fluorophenyl)acrylamide for N-(2-aminophenyl)acrylamide. MS m/z: 457.3 (ES+, M+H); $^1$HNMR (DMSO-$d_6$) δ 3.8 (s, 3H), 5.77-5.80 (dd, 1H, J=1.9, J=10 Hz), 6.26-6.31 (dd, 1H, J=2, 18 Hz), 6.44-6.51 (dd, 1H, J=10, 17 Hz), 6.93-7.02 (m, 2H), 7.18 (s, 1H), 7.32-7.36 (dd, 1H, J=2, 10 Hz), 7.53-7.56 (dd, 1H, J=2.2, 18 Hz), 7.63-7.67 (m, 1H), 7.84 (s, 1H), 7.89 (s, 1H), 8.20 (d, 1H, J=1.8 Hz), 8.42 (s, 1H), 10.07 (s, 1H).

Example 231

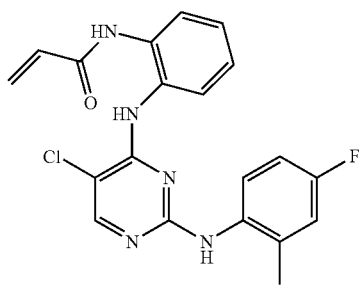

I-209

N-(2-((5-chloro-2-((4-fluoro-2-methylphenyl)amino)pyrimidin-4-yl)amino) phenyl)acrylamide Compound I-209 was prepared in a manner similar to Example 162, substituting 4-fluoro-2-methylaniline for 3-amino-4-methylbenzamide. MS m/z: 398.4 (ES+, M+H); $^1$HNMR (DMSO-$d_6$) δ 2.13 (s, 3H), 5.77-5.80 (dd, 1H, J=1.8, 10.1 Hz), 6.27-6.33 (dd, 1H, J=1.8, 14 Hz), 6.44-6.51 (dd, 1H, J=10, 16.9 Hz), 6.86-6.91 (dt, 1H, J=10, 16.9 Hz), 6.96-7.00 (dd, 1H, J=2.9, 9.7 Hz), 7.12-7.18 (m, 2H), 7.31-7.36 (m, 2H), 7.67-7.69 (m, 1H), 8.01 (s, 1H), 8.38 (s, 1H), 8.45 (s, 1H), 10.15 (s, 1H).

Example 232

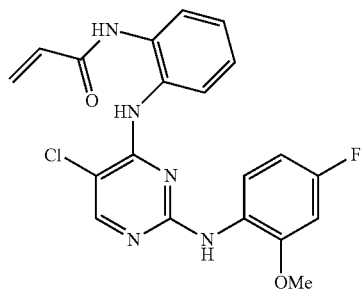

I-210

N-(2-((5-chloro-2-((4-fluoro-2-methoxyphenyl)amino)pyrimidin-4-yl)amino) phenyl)acrylamide Compound I-210 was prepared in a manner similar to Example 162, substituting 4-fluoro-2-methoxyaniline for 3-amino-4-methylbenzamide. MS m/z: 414.1 (ES+, M+H); $^1$HNMR (DMSO-$d_6$) δ 3.78 (s, 3H), 5.76-5.79 (dd, 1H, J=1.9, 10 Hz), 6.27-6.31 (dd, 1H, J=1.8, 17 Hz), 6.44-6.56 (m, 2H), 6.88-6.91 (dd, 1H, J=2.7, 10.8 Hz), 7.20-7.28 (m, 2H), 7.40-7.42 (dd, 1H, J=1.6, 7.3 Hz), 7.66-7.68 (dd, 1H, J=1.8, 7.6 Hz), 7.78 (s, 1H), 8.07 (s, 1H), 8.52 (s, 1H), 10.15 (s, 1H).

Example 233

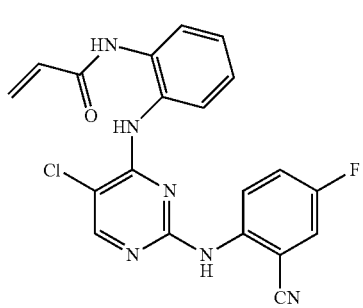

I-211

N-(2-((5-chloro-2-((2-cyano-4-fluorophenyl)amino)pyrimidin-4-yl)amino)phenyl) acrylamide Compound I-211 was prepared in a manner similar to Example 162, substituting 2-amino-5-fluorobenzonitrile for 3-amino-4-methylbenzamide. MS m/z: 409.1 (ES+, M+H); $^1$HNMR (DMSO-$d_6$) δ 5.77-5.80 (dd, 1H, J=1.8, 10.1 Hz)), 6.28-6.32 (dd, 1H, J=1.8, 17 Hz), 6.45-6.52 (dd, 1H, J=10, 17 Hz), 7.15-7.23 (m, 2H), 7.36-7.48 (dd, 1H, J=1.2, 7 Hz), 7.42-7.47 (m, 1H), 7.52-7.55 (m, 1H), 7.65-7.71 (m, 1H), 8.09 (s, 1H), 8.55 (s, 1H), 9.24 (s, 1H), 10.15 (s, 1H).

Example 234

I-212

N-(2-((5-chloro-2-((4-fluoro-2-methylphenyl)amino)pyrimidin-4-yl)amino)-5-fluorophenyl)acrylamide Compound I-212 was prepared in a manner similar to Example 162, substituting 3-amino-4-methoxybenzamide for 3-amino-4-methylbenzamide, and substituting N-(2-amino-5-fluorophenyl)acrylamide for N-(2-aminophenyl)acrylamide. MS m/z: 416.4 (ES+, M+H); $^1$HNMR (DMSO-d$_6$) δ 2.11 (s, 3H), 5.77-5.80 (dd, 1H, J=1.4, 10.2 Hz), 6.26-6.30 (dd, 1H, J=1.8, 17 Hz), 6.47-6.53 (dd, 1H, J=10, 17 Hz), 6.83-6.88 (m, 1H), 6.94-7.02 (m, 2H), 7.28-7.32 (m, 1H), 7.43-7.47 (dd, 1H, J=2.9, 10.5 Hz), 7.52-7.56 (m, 1H), 8.0 (s, 1H), 8.33 (s, 1H), 8.39 (s, 1H), 9.97 (s, 1H).

Example 235

I-213

N-(2-((5-chloro-2-((4-fluoro-2-methoxyphenyl)amino)pyrimidin-4-yl)amino)-5-fluorophenyl)acrylamide Compound I-213 was prepared in a manner similar to Example 162, substituting 4-fluoro-2-methoxyaniline for 3-amino-4-methylbenzamide, and substituting N-(2-amino-5-fluorophenyl)acrylamide for N-(2-aminophenyl)acrylamide. MS m/z: 432.4 (ES+, M+H); $^1$HNMR (DMSO-d$_6$) δ 3.78 (s, 3H), 5.75-5.78 (dd, 1H, J=1.9, 10.2 Hz), 6.24-6.29 (dd, 1H, J=1.9, 17 Hz), 6.47-6.54 (m, 2H), 6.87-6.90 (dd, 1H, J=2.8, 10.8 Hz), 7.05-7.09 (m, 1H), 7.53-7.58 (m, 2H), 7.64-7.69 (m, 2H), 8.05 (s, 1H), 8.49 (s, 1H), 9.96 (s, 1H).

Example 236

I-214

5-((4-((2-acrylamidophenyl)amino)-5-chloropyrimidin-2-yl)amino)-2-fluoro-4-methylbenzamide Compound I-214 was prepared in a manner similar to Example 162, substituting 5-amino-2-fluoro-4-methylbenzamide for 3-amino-4-methylbenzamide. MS m/z: 441.0 (ES+, M+H).

Example 237

I-215

3-((4-(((1S,2S)-2-acrylamidocyclopentyl)amino)-5-chloropyrimidin-2-yl)amino)-4-methylbenzamide Compound I-215 was prepared in a manner similar to Example 162, substituting N-((1S,2S)-2-aminocyclopentyl)acrylamide for N-(2-aminophenyl)acrylamide. MS m/z: 415.1 (ES+, M+H).

Example 238

I-216

3-((5-chloro-4-((2-(3-methylbut-2-enoyl)phenyl)amino)pyrimidin-2-yl)amino)-4-methylbenzamide Compound I-216 was prepared in a manner similar to Example 162, substituting 1-(2-aminophenyl)-3-methylbut-2-en-1-one for N-(2-aminophenyl)acrylamide. MS m/z: 436.1 (ES+, M+H).

Example 239

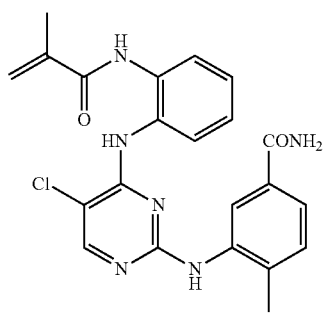

I-217

3-((5-chloro-4-((2-methacrylamidophenyl)amino)pyrimidin-2-yl)amino)-4-methylbenzamide Compound I-217 was prepared in a manner similar to Example 162, substituting N-(2-aminophenyl)methacrylamide for N-(2-aminophenyl)acrylamide. MS m/z: 437.1 (ES+, M+H).

Example 240

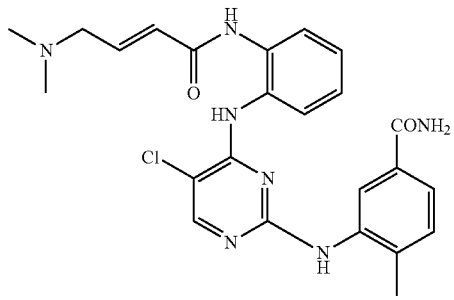

I-218

(E)-3-((5-chloro-4-((2-(4-(dimethylamino)but-2-enamido)phenyl)amino) pyrimidin-2-yl)amino)-4-methylbenzamide Compound I-218 was prepared in a manner similar to Example 162, substituting (E)-N-(2-aminophenyl)-4-(dimethylamino)but-2-enamide for N-(2-aminophenyl)acrylamide. MS m/z: 480.2 (ES+, M+H).

Example 241

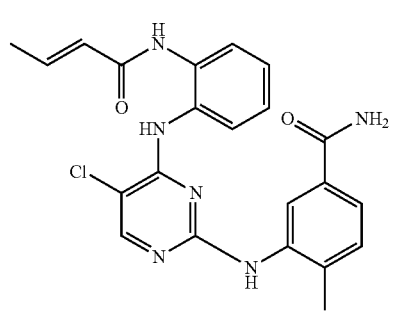

I-219

(E)-3-((4-((2-(but-2-enamido)phenyl)amino)-5-chloropyrimidin-2-yl)amino)-4-methylbenzamide Compound I-219 was prepared in a manner similar to Example 162, substituting (E)-N-(2-aminophenyl)but-2-enamide for N-(2-aminophenyl)acrylamide. MS m/z: 437.1 (ES+, M+H).

Example 242

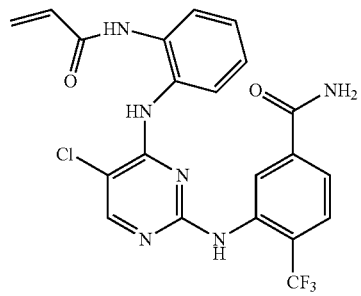

I-220

3-((4-((2-acrylamidophenyl)amino)-5-chloropyrimidin-2-yl)amino)-4-(trifluoromethyl)benzamide Compound I-220 was prepared in a manner similar to Example 162, substituting 3-amino-4-(trifluoromethyl)benzamide for 3-amino-4-methylbenzamide. MS m/z: 477.4 (ES+, M+H); $^1$HNMR (DMSO-$d_6$) δ 5.78-5.81 (dd, J=1.9, 10.1 Hz, 1H), 6.27-6.32 (dd, J=1.9, 17.0 Hz, 1H), 6.43-6.50 (dd, J=10.1, 17.0 Hz, 1H), 6.79-7.01 (dd, J=1.4, 8.0 Hz, 1H), 7.04-7.08 (dt, J=1.4, 7.5 Hz, 1H), 7.23-7.25 (dd, J=1.2, 7.8 Hz, 1H), 7.64 (t, J=7.9 Hz, 2H), 7.71-7.73 (d, J=8.3 Hz, 1H), 7.81-7.83 (d, J=8.4 Hz, 1H), 8.08 (s, 1H), 8.13 (s, 1H), 8.16 (s, 1H), 8.47 (s, 1H), 8.67 (s, 1H), 10.19 (s, 1H).

Example 243

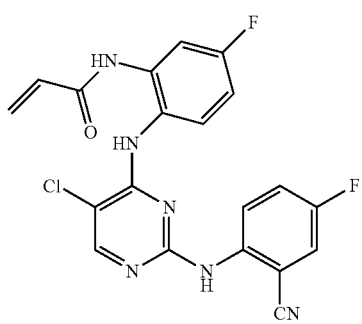

I-221

N-(2-((5-chloro-2-((2-cyano-4-fluorophenyl)amino)pyrimidin-4-yl)amino)-5-fluorophenyl)acrylamide Compound I-221 was prepared in a manner similar to Example 162, substituting 2-amino-5-fluorobenzonitrile for 3-amino-4-methylbenzamide, and substituting N-(2-amino-5-fluorophenyl)acrylamide for N-(2-aminophenyl)acrylamide. MS m/z: 427.4 (ES+, M+H); $^1$HNMR (DMSO-$d_6$) δ 5.78-5.84 (dd, 1H J=2.2, 9.6 Hz), 6.35-6.45 (m, 2H), 6.98-7.03 (dt, 1H J=3.0, 7.9 Hz), 7.22-7.27 (dt, 1H J=3.0, 8.1 Hz), 7.39-7.42 (dd, 1H J=3.0, 8.0 Hz), 7.46-7.50 (dd, 1H J=2.9, 10.1 Hz), 7.52-7.56 (dd, 1H J=5.9, 9.0 Hz), 7.66-7.70 (dd, 1H J=4.9, 9.2 Hz), 8.03 (s, 1H).

Example 244

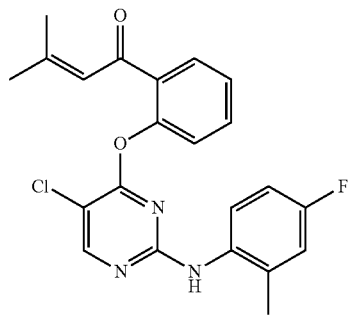

I-222

1-(2-((5-chloro-2-((4-fluoro-2-methylphenyl)amino)pyrimidin-4-yl)oxy)phenyl)-3-methylbut-2-en-1-one Compound I-222 was prepared in a manner similar to Example 162, substituting 4-fluoro-2-methylaniline for 3-amino-4-methylbenzamide, and substituting 1-(2-hydroxyphenyl)-3-methylbut-2-en-1-one for N-(2-aminophenyl)acrylamide. MS m/z: 412.1 (ES+, M+H); $^1$HNMR (DMSO-$d_6$) δ 1.81 (s, 3H), 1.89 (s, 3H), 2.04 (s, 3H), 6.37 (s, 1H), 6.77 (br t, 1H), 6.92-6.95 (dd, 1H, J=2.7, 9.7 Hz), 7.06-7.09 (m, 1H), 7.30-7.32 (d, 1H, J=8 Hz), 7.36-7.39 (m, 1H), 7.57-7.59 (m, 1H), 7.61-7.66 (m, 1H), 8.29 (s, 1H), 8.84 (s, 1H).

Example 245

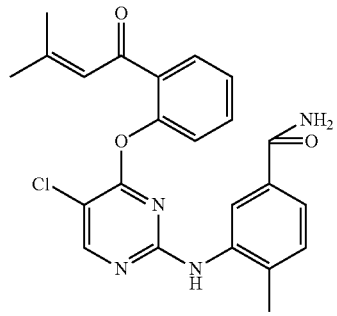

I-223

3-((5-chloro-4-(2-(3-methylbut-2-enoyl)phenoxy)pyrimidin-2-yl)amino)-4-methylbenzamide Compound I-223 was prepared in a manner similar to Example 162, substituting 1-(2-hydroxyphenyl)-3-methylbut-2-en-1-one for N-(2-aminophenyl)acrylamide. MS m/z: 437.4 (ES+, M+H); $^1$HNMR (DMSO-$d_6$) δ 1.81 (s, 3H), 1.92 (s, 3H), 2.08 (s, 3H), 6.35 (br s, 1H), 7.15-7.17 (d, 1H, J=8.0 Hz), 7.22 (br s, 1H), 7.31-7.35 (m, 2H), 7.51-7.60 (m, 3H), 7.65 (d, 1H, J=1.5 Hz), 7.76 (br s, 1H), 8.30 (s, 1H), 8.98 (s, 1H).

Example 246

I-224

3-(4-(2-acrylamidophenylamino)-5-methylpyrimidin-2-ylamino)-4-methyl benzamide

Compound I-224 was prepared in the similar way as described in Method E of Example 162 using 2,4-dichloro-5-methylpyrimidine as the starting material. m/z 403.5 (ES+, M+H); $^1$HNMR (DMSO-$d_6$) δ 1.97 (s, 3H, Me), 2.17 (s, 3H), 5.78-5.81 (dd, 1H J=1.8, 10.1 Hz), 6.28-6.32 (dd, 1H J=1.8, 17 Hz), 6.43-6.50 (dd, 1H J=10.1, 17 Hz), 7.04-7.08 (m, 2H), 7.16 (d, 1H J=8.0 Hz), 7.27 (br s, 1H), 7.29 (m, 1H), 7.48 (dd, 1H J=1.7, 7.9 Hz), 7.80 (m, 2H), 7.83 (br s, 1H), 7.92 (s, 1H), 7.97 (s, 1H), 8.62 (s, 1H), 10.11 (s, 1H), 10.94 (s, 1H).

Example 247

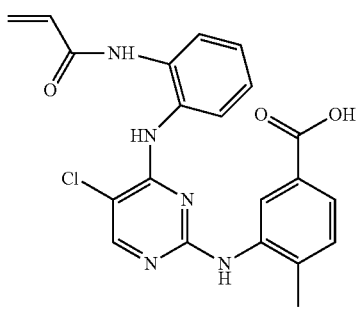

I-225

3-((4-((2-acrylamidophenyl)amino)-5-chloropyrimidin-2-yl)amino)-4-methylbenzoic acid Compound I-225 was prepared in a manner similar to Example 162, substituting tert-butyl 3-amino-4-methylbenzoate for 3-amino-4-methylbenzamide, and final t-butyl ester cleavage by TFA. MS m/z: 424.4 (ES+, M+H); $^1$HNMR (DMSO-$d_6$) δ 2.2 (s, 3H), 5.77-5.8 (dd, J=1.9, 10 Hz, 1H), 6.27-6.32 (dd, J=1.9, 17 Hz, 1H), 6.44-6.5 (dd, J=10.1, 17 Hz, 1H), 7.01-7.11 (m, 2H), 7.25 (t, J=7.6 Hz, 2H), 7.56-7.58 (dd, J=1.7, 7.9 Hz, 1H), 7.69-7.71 (dd, J=1.2, 8 Hz, 1H), 7.93 (d, J=1.5 Hz, 1H), 8.05 (s, 1H), 8.42 (s, 1H), 8.64 (s, 1H), 10.2 (s, 1H), 12.8 (s, 1H).

Example 248

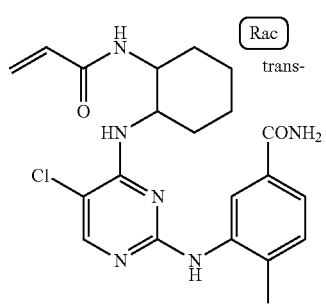

I-226

Rac-trans-3-((4-((2-acrylamidocyclohexyl)amino)-5-chloropyrimidin-2-yl)amino)-4-methylbenzamide Compound I-226 was prepared in a manner similar to Example 162, substituting trans-N-(2-aminocyclohexyl)acrylamide for N-(2-aminophenyl)acrylamide. MS m/z: 429.2 (ES+, M+H).

Example 249

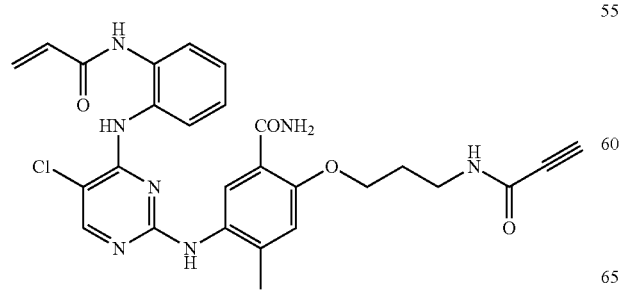

I-227

5-((4-((2-acrylamidophenyl)amino)-5-chloropyrimidin-2-yl)amino)-4-methyl-2-(3-propiolamidopropoxy)benzamide Compound I-227 was prepared in a manner similar to Example 162, substituting tert-butyl (3-(4-amino-2-carbamoyl-5-methylphenoxy)propyl)carbamate for 3-amino-4-methylbenzamide, followed by Boc-deprotection with TFA and amide formation with propiolic acid, HATU, DIPEA in DMA. MS m/z: 548.2 (ES+, M+H).

Example 250

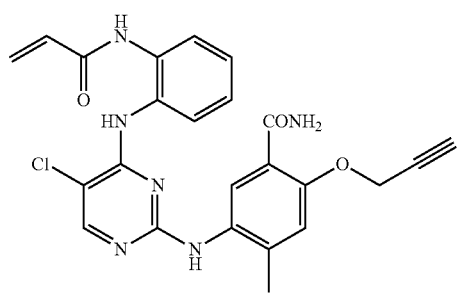

I-228

5-((4-((2-acrylamidophenyl)amino)-5-chloropyrimidin-2-yl)amino)-4-methyl-2-(prop-2-yn-1-yloxy)benzamide Compound I-228 was prepared in a manner similar to Example 162, substituting 5-amino-4-methyl-2-(prop-2-yn-1-yloxy)benzamide for 3-amino-4-methylbenzamide. MS m/z: 477.1 (ES+, M+H).

Example 251

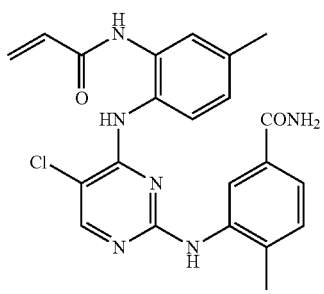

I-229

3-((4-((2-acrylamido-4-methylphenyl)amino)-5-chloropyrimidin-2-yl)amino)-4-methylbenzamide Compound I-229 was prepared in a manner similar to Example 162, substituting N-(2-amino-5-methylphenyl)acrylamide for N-(2-aminophenyl)acrylamide. MS m/z: 437.1 (ES+, M+H).

Example 252

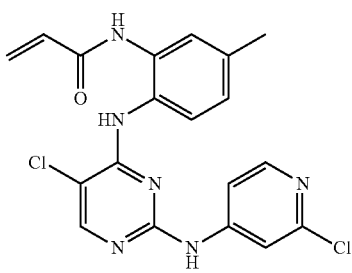

I-230

N-(2-((5-chloro-2-((2-chloropyridin-4-yl)amino)pyrimidin-4-yl)amino)-5-methylphenyl)acrylamide Compound I-230 was prepared in a manner similar to Example 162, substituting 2-chloropyridin-4-amine for 3-amino-4-methylbenzamide, and substituting N-(2-amino-5-methylphenyl)acrylamide for N-(2-aminophenyl)acrylamide. MS m/z: 415.1 (ES+, M+H).

Example 253

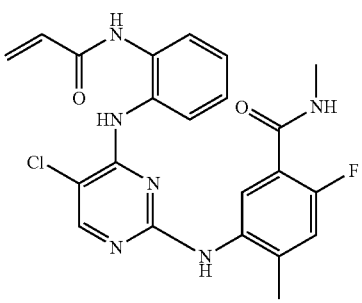

I-231

5-((4-((2-acrylamidophenyl)amino)-5-chloropyrimidin-2-yl)amino)-2-fluoro-N,4-dimethylbenzamide Compound I-231 was prepared in a manner similar to Example 162, substituting tert-butyl 5-amino-2-fluoro-4-methylbenzoate for 3-amino-4-methylbenzamide, followed by t-Bu ester deprotection with TFA, then coupling with methylamine in the presence of HATU and DIPEA. MS m/z: 455.1 (ES+, M+H).

Example 254

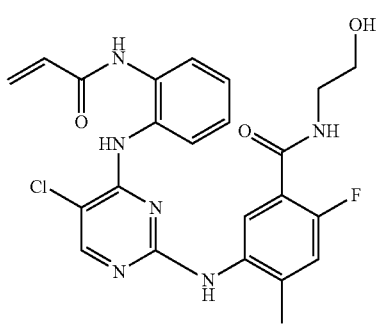

I-232

5-((4-((2-acrylamidophenyl)amino)-5-chloropyrimidin-2-yl)amino)-2-fluoro-N-(2-hydroxyethyl)-4-methylbenzamide Compound I-232 was prepared in a manner similar to Example 162, substituting tert-butyl 5-amino-2-fluoro-4-methylbenzoate for 3-amino-4-methylbenzamide, followed by t-Bu ester deprotection with TFA, then coupling with 2-aminoethanol in the presence of HATU and DIPEA. MS m/z: 485.1 (ES+, M+H).

Example 255

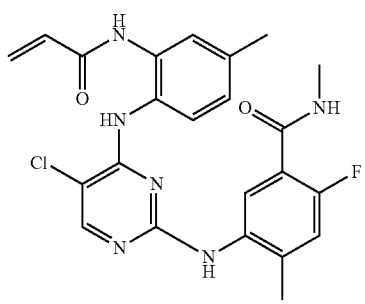

I-233

5-((4-((2-acrylamido-4-methylphenyl)amino)-5-chloropyrimidin-2-yl)amino)-2-fluoro-N,4-dimethylbenzamide Compound I-233 was prepared in a manner similar to Example 162, substituting tert-butyl 5-amino-2-fluoro-4-methylbenzoate for 3-amino-4-methylbenzamide, and substituting N-(2-amino-5-methylphenyl)acrylamide for N-(2-aminophenyl)acrylamide, followed by t-Bu ester deprotection with TFA, then coupling with methylamine in the presence of HATU and DIPEA. MS m/z: 469.1 (ES+, M+H).

Example 256

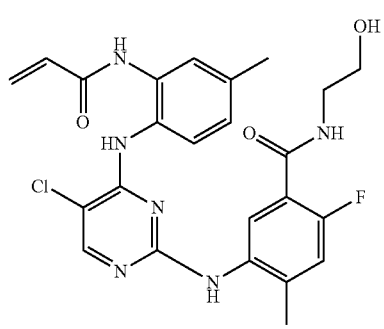

I-234

5-((4-((2-acrylamido-4-methylphenyl)amino)-5-chloropyrimidin-2-yl)amino)-2-fluoro-N-(2-hydroxyethyl)-4-methylbenzamide Compound I-234 was prepared in a manner similar to Example 162, substituting tert-butyl 5-amino-2-fluoro-4- methylbenzoate for 3-amino-4-methylbenzamide, and substituting N-(2-amino-5-methylphenyl)acrylamide for N-(2-aminophenyl)acrylamide, followed by t-Bu ester deprotection with TFA, then coupling with 2-aminoethanol in the presence of HATU and DIPEA. MS m/z: 499.1 (ES+, M+H).

Example 257

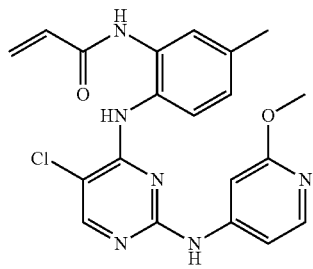

I-235

N-(2-((5-chloro-2-((2-methoxypyridin-4-yl)amino)pyrimidin-4-yl)amino)-5-methylphenyl)acrylamide Compound I-235 was prepared in a manner similar to Example 162, substituting 2-methoxypyridin-4-amine for 3-amino-4-methylbenzamide and substituting N-(2-amino-5-methylphenyl)acrylamide for N-(2-aminophenyl)acrylamide. MS m/z: 411.0 (ES+, M+H).

Example 258

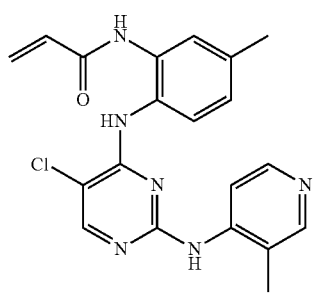

I-236

N-(2-((5-chloro-2-((3-methylpyridin-4-yl)amino)pyrimidin-4-yl)amino)-5-methylphenyl)acrylamide Compound I-236 was prepared in a manner similar to Example 162, substituting 3-methylpyridin-4-amine for 3-amino-4-methylbenzamide and substituting N-(2-amino-5-methylphenyl)acrylamide for N-(2-aminophenyl)acrylamide. MS m/z: 395.1 (ES+, M+H).

Example 259

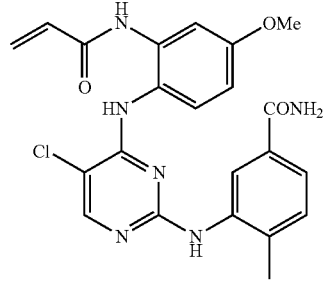

I-237

3-((4-((2-acrylamido-4-methoxyphenyl)amino)-5-chloropyrimidin-2-yl)amino)-4-methylbenzamide Compound I-237 was prepared in a manner similar to Example 162, substituting N-(2-amino-5-methoxyphenyl)acrylamide for N-(2-aminophenyl)acrylamide. MS m/z: 444.4 (ES+, M+H).

Example 260

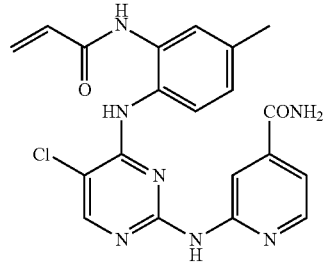

I-238

2-((4-((2-acrylamido-4-methylphenyl)amino)-5-chloropyrimidin-2-yl)amino)isonicotinamide Compound I-238 was prepared in a manner similar to Example 162, substituting 2-aminoisonicotinamide for 3-amino-4-methylbenzamide and substituting N-(2-amino-5-methylphenyl)acrylamide for N-(2-aminophenyl)acrylamide. MS m/z: 424.1 (ES+, M+H).

Example 261

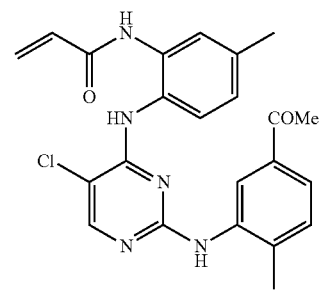

I-239

N-(2-((2-((5-acetyl-2-methylphenyl)amino)-5-chloropyrimidin-4-yl)amino)-5-methylphenyl)acrylamide Compound I-239 was prepared in a manner similar to Example 162, substituting 1-(3-amino-4-methylphenyl)ethanone for 3-amino-4-methylbenzamide, and substituting N-(2-amino-5-methylphenyl)acrylamide for N-(2-aminophenyl)acrylamide. MS m/z: 436.2 (ES+, M+H); $^1$HNMR (DMSO-d$_6$) δ 2.22 (s, 6H), 2.38 (m, 3H), 5.76-5.79 (dd, J=1.7, 10.1 Hz, 1H), 6.25-6.30 (dd, J=1.7, 17 Hz, 1H), 6.42-6.48 (dd, J=10.2, 17.0 Hz, 1H), 7.12 (t, J=8.1 Hz, 2H), 7.45 (d, J=8.2 Hz, 1H), 7.47 (d, J=8.2 Hz, 1H), 7.56-7.59 (dd, J=1.7, 7.9 Hz, 1H), 7.92 (d, J=1.4 Hz, 1H), 8.04 (s, 1H), 8.38 (s, 1H), 8.61 (s, 1H), 10.11 (s, 1H).

Example 262

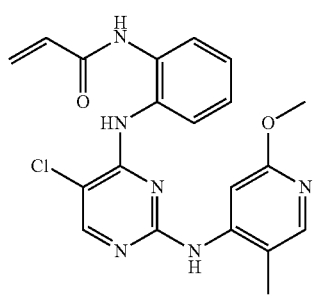

I-240

N-(2-((5-chloro-2-((2-methoxy-5-methylpyridin-4-yl)amino)pyrimidin-4-yl)amino)phenyl)acrylamide Compound I-240 was prepared in a manner similar to Example 162, 2-methoxy-5-methylpyridin-4-amine for 3-amino-4-methylbenzamide. MS m/z: 411.0 (ES+, M+H).

Example 263

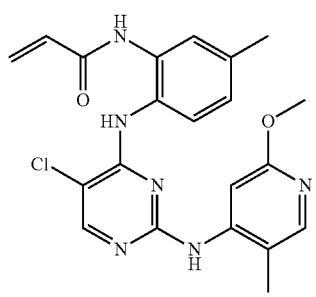

I-241

N-(2-((5-chloro-2-((2-methoxy-5-methylpyridin-4-yl)amino)pyrimidin-4-yl)amino)-5-methylphenyl)acrylamide Compound I-241 was prepared in a manner similar to Example 162, substituting 2-methoxy-5-methylpyridin-4-amine for 3-amino-4-methylbenzamide and substituting N-(2-amino-5-methylphenyl)acrylamide for N-(2-aminophenyl)acrylamide. MS m/z: 425.1 (ES+, M+H).

Example 264

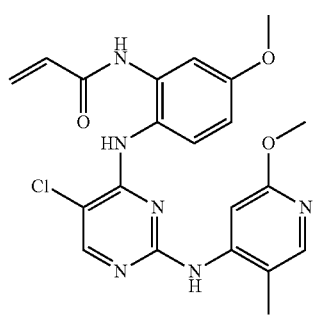

I-242

N-(2-((5-chloro-2-((2-methoxy-5-methylpyridin-4-yl)amino)pyrimidin-4-yl)amino)-5-methoxyphenyl)acrylamide Compound I-242 was prepared in a manner similar to Example 162, substituting 2-methoxy-5-methylpyridin-4-amine for 3-amino-4-methylbenzamide and substituting N-(2-amino-5-methoxyphenyl)acrylamide for N-(2-aminophenyl)acrylamide. MS m/z: 441.0 (ES+, M+H).

Example 265

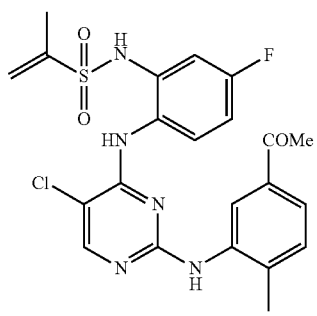

I-243

N-(2-((2-((5-acetyl-2-methylphenyl)amino)-5-chloropyrimidin-4-yl)amino)-5-fluorophenyl)prop-1-ene-2-sulfonamide Compound I-243 was prepared in a manner similar to Example 162, substituting 1-(3-amino-4-methylphenyl)ethanone for 3-amino-4-cyanobenzamide, and substituting N-(2-amino-5-fluorophenyl)prop-1-ene-2-sulfonamide for N-(2-aminophenyl)acrylamide. MS m/z: 490.1 (ES+, M+H); $^1$HNMR (DMSO-d$_6$) δ 1.96 (s, 3H), 2.20 (s, 3H), 2.38 (m, 3H), 5.65 (s, 1H), 5.68 (s, 1H), 6.80 (t, J=2.9 Hz, 1H), 6.94-6.97 (dd, J=3.6, 9.8 Hz, 1H), 7.29 (d, J=7.9 Hz, 1H), 7.59-7.61 (m, 2H), 7.83 (d, J=1.6 Hz, 1H), 8.10 (s, 1H), 8.30 (s, 1H), 8.71 (s, 1H), 9.68 (s, 1H).

Example 266

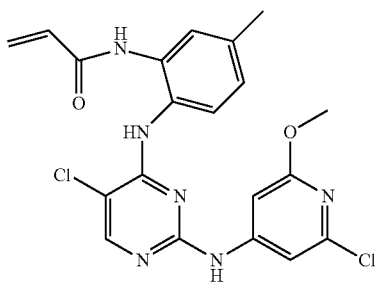

I-244

N-(2-((5-chloro-2-((2-chloro-6-methoxypyridin-4-yl)amino)pyrimidin-4-yl)amino)-5-methylphenyl)acrylamide Compound I-244 was prepared in a manner similar to Example 162, substituting 2-chloro-6-methoxypyridin-4-amine for 3-amino-4-methylbenzamide and substituting N-(2-amino-5-methylphenyl)acrylamide for N-(2-aminophenyl)acrylamide. MS m/z: 446.1 (ES+, M+H).

Example 267

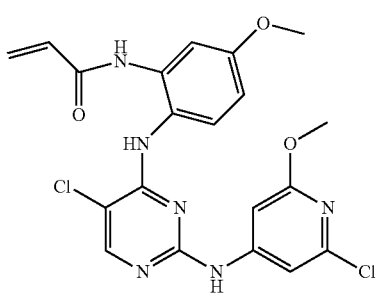

I-245

N-(2-((5-chloro-2-((2-chloro-6-methoxypyridin-4-yl)amino)pyrimidin-4-yl)amino)-5-methoxyphenyl)acrylamide Compound I-245 was prepared in a manner similar to Example 162, substituting 2-chloro-6-methoxypyridin-4-amine for 3-amino-4-methylbenzamide and substituting N-(2-amino-5-methoxyphenyl)acrylamide for N-(2-aminophenyl)acrylamide. MS m/z: 462.1 (ES+, M+H).

Example 268

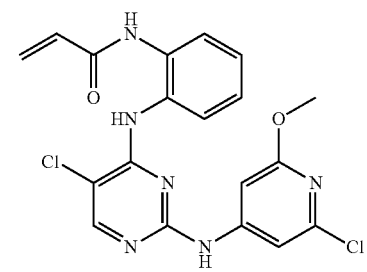

I-246

N-(2-((5-chloro-2-((2-chloro-6-methoxypyridin-4-yl)amino)pyrimidin-4-yl)amino)phenyl)acrylamide Compound I-246 was prepared in a manner similar to Example 162, substituting 2-chloro-6-methoxypyridin-4-amine for 3-amino-4-methylbenzamide. MS m/z: 431.0 (ES+, M+H).

Example 269

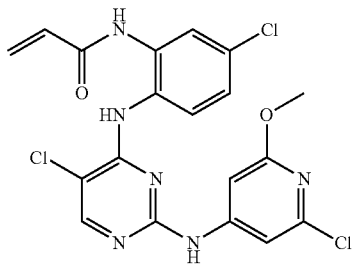

I-247

N-(5-chloro-2-((5-chloro-2-((2-chloro-6-methoxypyridin-4-yl)amino)pyrimidin-4-yl)amino)phenyl)acrylamide Compound I-247 was prepared in a manner similar to Example 162, substituting 2-chloro-6-methoxypyridin-4-amine for 3-amino-4-methylbenzamide and substituting N-(2-amino-5-chlorophenyl)acrylamide for N-(2-aminophenyl)acrylamide. MS m/z: 465.0 (ES+, M+H).

Example 270

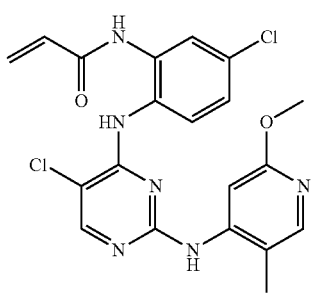

I-248

N-(5-chloro-2-((5-chloro-2-((2-methoxy-5-methylpyridin-4-yl)amino)pyrimidin-4-yl)amino)phenyl)acrylamide Compound I-248 was prepared in a manner similar to Example 162, substituting 2-methoxy-5-methylpyridin-4-amine for 3-amino-4-methylbenzamide and substituting N-(2-amino-5-chlorophenyl)acrylamide for N-(2-aminophenyl)acrylamide. MS m/z: 445.1 (ES+, M+H).

Example 271

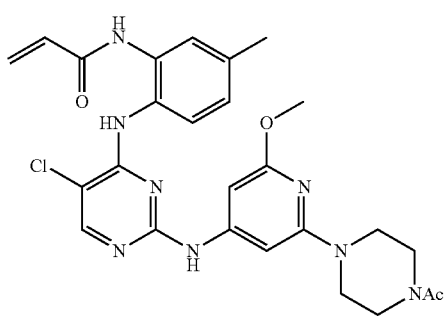

I-296

N-(2-((2-((2-(4-acetylpiperazin-1-yl)-6-methoxy-pyridin-4-yl)amino)-5-chloropyrimidin-4-yl)amino)-5-methylphenyl)acrylamide Compound I-296 was prepared in a manner similar to Example 162, substituting 1-(4-(4-amino-6-methoxypyridin-2-yl)piperazin-1-yl)ethanone for 3-amino-4-methylbenzamide, and substituting N-(2-amino-5-methylphenyl)acrylamide for N-(2-aminophenyl)acrylamide. MS m/z=537.2 (ES+, M+H).

Example 272

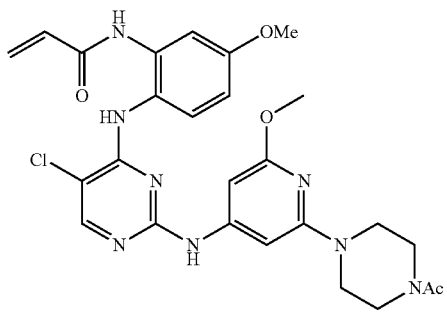

I-297

N-(2-((2-((2-(4-acetylpiperazin-1-yl)-6-methoxy-pyridin-4-yl)amino)-5-chloropyrimidin-4-yl)amino)-5-methoxyphenyl)acrylamide Compound I-297 was prepared in a manner similar to Example 162, substituting 1-(4-(4-amino-6-methoxypyridin-2-yl)piperazin-1-yl)ethanone for 3-amino-4-methylbenzamide, and substituting N-(2-amino-5-methoxyphenyl)acrylamide for N-(2-aminophenyl)acrylamide. MS m/z=553.8 (ES+, M+H).

Example 273

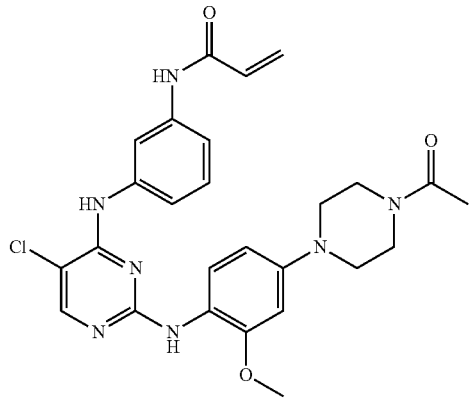

I-298

N-(3-((2-((4-(4-acetylpiperazin-1-yl)-2-methoxyphenyl)amino)-5-chloropyrimidin-4-yl)amino)phenyl)acrylamide Compound I-298 was prepared in a manner similar to Example 162, substituting 1-(4-(4-amino-3-methoxyphenyl)piperazin-1-yl)ethanone for 3-amino-4-methylbenzamide, and substituting N-(3-aminophenyl)acrylamide for N-(2-aminophenyl)acrylamide. MS m/z=523.2 (ES+, M+H).

Method F starts with 2,4-dichloropyrimidine-5-carbonyl chloride reacting with various amines to construct the C5-substitution, then follows the chemistry in Method E to finish all the final targets.

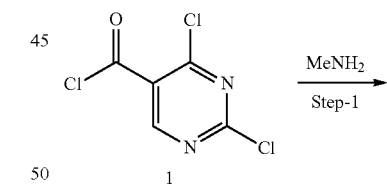

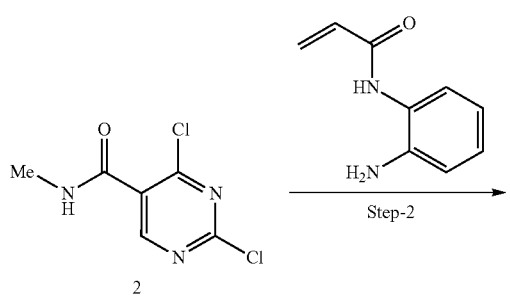

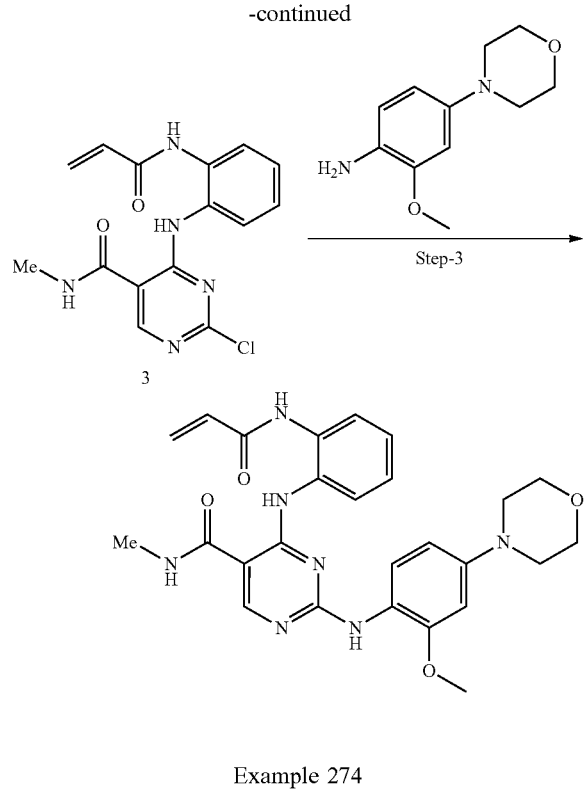

Example 274

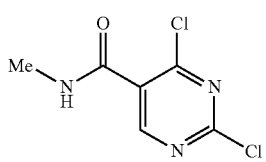 [SMILES: CNC(=O)c1cnc(Cl)nc1Cl]

4-((2-acrylamidophenyl)amino)-2-((2-methoxy-4-morpholinophenyl)amino) pyrimidine-5-carboxamide The title compound was prepared according to the steps and intermediates described below.

Step-1. Preparation of 2,4-dichloro-N-methylpyrimidine-5-carboxamide (2)

To a solution of methyl amine (2M) in THF (2.4 mL, 4.70 mmol) in DCM (50 ml), TEA (963 mg, 9.50 mmol) and 2,4-dichloropyrimidine-5-carbonyl chloride (1 g, 4.70 mmol) were added slowly at −78° C. for 1 h. TLC showed completion of starting material (TLC system: 10% ethyl acetate in hexane ($R_f$: 0.3). The reaction mixture was diluted with DCM (50 ml), washed with water (2×30 ml) and a saturated solution of NaHCO$_3$. The organic layer was separated, dried over sodium sulphate, and concentrated. Crude compound was purified by column chromatography using silica gel (100-200 mesh) with 5% ethyl acetate in hexane to obtain 2, 4-dichloro-N-methylpyrimidine-5-carboxamide as white solid. Yield: (400 mg, 33%). $^1$HNMR (400 MHz, CDCl$_3$) δ 8.98 (s, 1H), 6.50 (br s, 1H), 3.07 (d, 3H, J=4.8 Hz).

Step-2. Preparation of 4-(2-acrylamidophenylamino)-2-chloro-N-methylpyrimidine-5-carboxamide

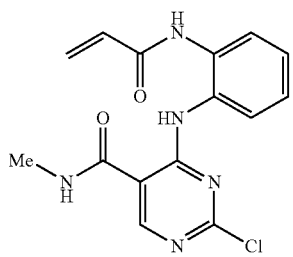 [SMILES: C=CC(=O)Nc1ccccc1Nc1nc(Cl)ncc1C(=O)NC]

To a solution of 2,4-dichloro-N-methylpyrimidine-5-carboxamide (400 mg, 1.95 mmol) in NMP (1 ml), N-(2-aminophenyl)acrylamide (316 mg, 1.951 mmol) and DIPEA (503 mg, 3.902 mmol) were added and heated at 120° C. for 1 h. TLC showed completion of starting material (TLC system: 5% methanol in DCM ($R_f$: 0.3). The reaction mixture was diluted with water (30 ml) and extracted with ethyl acetate (3×15 ml). The organic layer was separated, dried over sodium sulphate, and concentrated. Crude compound was purified by column chromatography using silica gel (100-200 mesh) with 2% methanol in DCM to obtain 4-(2-acrylamidophenylamino)-2-chloro-N-methylpyrimidine-5-carboxamide as an off white solid. Yield: (180 mg, 28%). MS: m/z 332.1 (ES+, M+H).

Step 3. Preparation of 4-(2-acrylamidophenylamino)-2-(2-methoxy-4-morpholino phenylamino)-N-methylpyrimidine-5-carboxamide

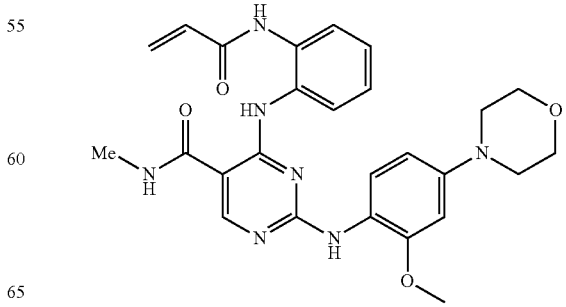

To a solution of 4-(2-acrylamidophenylamino)-2-chloro-N-methylpyrimidine-5-carboxamide (40 mg, 0.12 mmol) in 0.08M p-TSA/1,4-dioxane (5 mL), 2-methoxy-4-morpholinoaniline (25.13 mg, 0.12 mmol) was added and heated at 100° C. for 1 h. TLC showed completion of starting material (TLC system: 5% methanol in DCM ($R_f$): 0.3). 1,4 dioxane was evaporated, and the residue was diluted with ethyl acetate (15 mL) and washed with water (2×5 mL). The organic layer was separated, dried over sodium sulphate, and concentrated. Crude compound was purified by column chromatography using silica gel (100-200 mesh) with 2% methanol in DCM to obtain 4-(2-acrylamidophenylamino)-2-(2-methoxy-4-morpholino phenylamino)-N-methylpyrimidine-5-carboxamide as off white solid. Yield: (8 mg, 13%). MS: m/z 504.3 (ES+, M+H).

Example 275

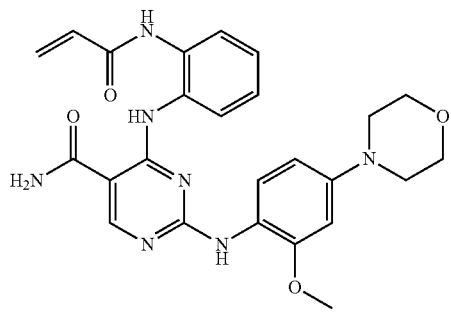

I-249

4-((2-acrylamidophenyl)amino)-2-((2-methoxy-4-morpholinophenyl)amino) pyrimidine-5-carboxamide Compound I-249 was made in a manner similar to Example 274, substituting ammonia hydroxide for methyl amine in step-1. MS: m/z 490.4 (ES+).

Example 276

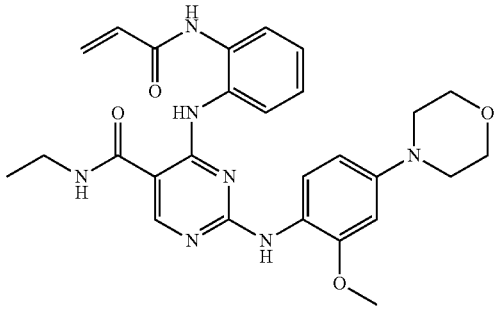

I-251

4-((2-acrylamidophenyl)amino)-N-ethyl-2-((2-methoxy-4-morpholinophenyl) amino)pyrimidine-5-carboxamide Compound I-251 was prepared in a manner similar to Example 274, substituting ethyl amine for methyl amine in step-1: MS m/z 518.3 (ES+, M+H).

Example 277

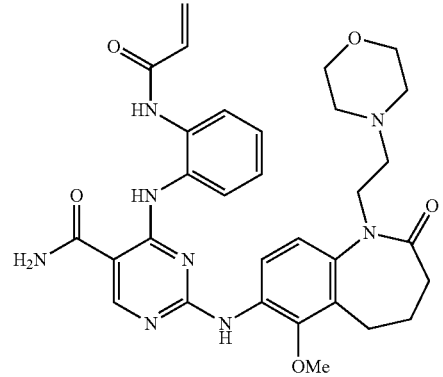

I-252

4-((2-acrylamidophenyl)amino)-2-((6-methoxy-1-(2-morpholinoethyl)-2-oxo-2,3,4,5-tetrahydro-1H-benzo[b]azepin-7-yl)amino)pyrimidine-5-carboxamide Compound I-252 was prepared in a manner similar to Example 274, substituting ammonia hydroxide for methyl amine, and substituting 7-amino-6-methoxy-1-(2-morpholinoethyl)-4,5-dihydro-1H-benzo[b]azepin-2(3H)-one for 2-methoxy-4-morpholinoaniline. MS m/z 601.3 (ES+, M+H); $^1$HNMR (DMSO-$d_6$) δ 1.46 (m, 1H), 1.68 (m, 1H), 1.89 (m, 1H), 2.03 (s, 3H), 2.88-2.90 (m, 2H), 3.30 (m, 1H), 3.64 (m, 1H), 3.64-3.76 (m, 2H), 4.06-4.09 (m, 2H), 4.46 (s, 1H), 5.65 (s, 1H), 5.69 (s, 1H), 6.94-7.12 (m, 2H), 7.61 (d, J=7.1 Hz, 1H), 7.90-8.29 (br s, 1H), 8.21-8.29 (m, 2H), 9.6 (s, 1H).

Example 278

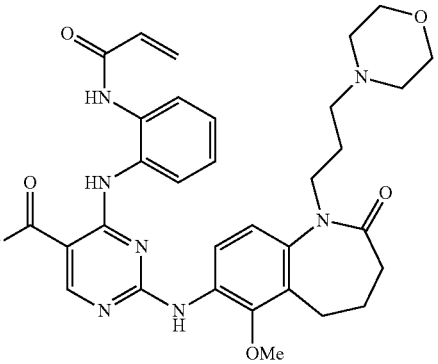

I-253

4-((2-acrylamidophenyl)amino)-2-((6-methoxy-1-(3-morpholinopropyl)-2-oxo-2,3,4,5-tetrahydro-1H-benzo[b]azepin-7-yl)amino)pyrimidine-5-carboxamide Compound I-253 was prepared in a manner similar to Example 274, substituting ammonia hydroxide for methyl amine, and substituting 7-amino-6-methoxy-1-(3-morpholinopropyl)-4,5-dihydro-1H-benzo[b]azepin-2(3H)-one for 2-methoxy-4-morpholinoaniline. MS m/z 615.4 (ES+, M+H); $^1$HNMR (DMSO-d$_6$) δ 1.22-1.26 (m, 3H), 1.59 (br s, 3H), 2.2 (m, 10H), 3.49 (br s, 4H), 3.67 (s, 3H), 5.68-5.71 (dd, J=2.0, 10.0 Hz, 1H), 6.16-6.21 (dd, J=2.0, 17.1 Hz, 1H), 6.39-6.46 (dd, J=10.3, 17.1 Hz, 1H), 7.03 (t, J=6.2 Hz, 1H), 7.07 (m, 2H), 7.30 (d, J=7.6 Hz, 1H), 7.41 (br s, 1H), 7.68 (d, J=8.8 Hz, 1H), 7.93 (br s, 1H), 8.17 (d, J=8.0 Hz, 1H), 8.65 (d, J=5.0 Hz, 1H), 8.68 (s, 1H), 9.68 (s, 1H), 11.44 (s, 1H).

Example 279

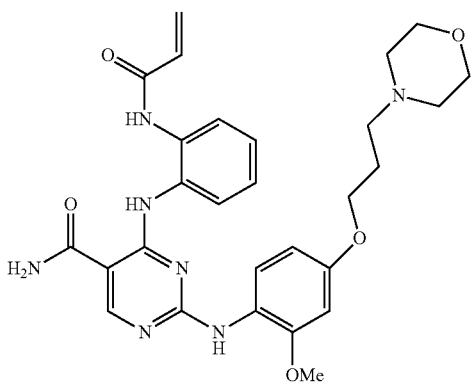

4-((2-acrylamidophenyl)amino)-2-((2-methoxy-4-(3-morpholinopropoxy)phenyl) amino)pyrimidine-5-carboxamide Compound I-254 was prepared in a manner similar to Example 274, substituting ammonia hydroxide for methyl amine, and substituting 2-methoxy-4-(3-morpholinopropoxy)aniline for 2-methoxy-4-morpholinoaniline. MS m/z 546.3 (ES+, M+H); $^1$HNMR (DMSO-d$_6$)) δ 1.88 (m, 2H), 2.37 (br s, 4H), 2.44 (d, J=7.2 Hz, 2H), 3.57 (t, J=4.5 Hz, 4H), 3.74 (s, 3H), 4.03 (t, 6.2 Hz, 2H), 5.68-5.71 (dd, J=1.6, 10.3 Hz, 1H), 6.16-6.21 (dd, J=1.9, 17.0 Hz, 1H), 6.39-6.47 (m, 2H), 6.62 (d, J=2.6 Hz, 1H), 6.97-7.04 (m, 2H), 7.25 (d, J=7.69 Hz, 1H), 7.45 (d, J=8.3 Hz, 1H), 7.80 (br s, 1H), 8.19 (br s, 1H), 8.35 (s, 1H), 8.59 (s, 1H), 9.67 (s, 1H), 11.45 (s, 1H).

Example 280

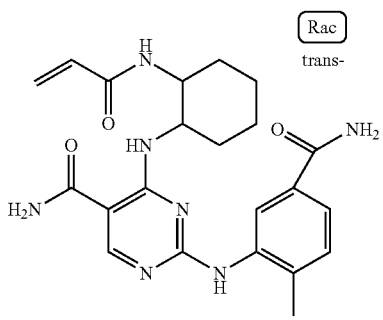

Rac-trans-4-((2-acrylamidocyclohexyl)amino)-2-((5-carbamoyl-2-methylphenyl) amino)pyrimidine-5-carboxamide Compound I-255 was prepared in a manner similar to Example 274, substituting ammonia hydroxide for methyl amine, substituting 3-amino-4-methylbenzamide for 2-methoxy-4-morpholinoaniline, and substituting trans-N-(2-aminocyclohexyl)acrylamide for N-(2-aminophenyl) acrylamide. MS m/z 438.2 (ES+, M+H); $^1$HNMR (DMSO-d$_6$) δ 1.23 (m, 4H), 1.16 (m, 2H), 1.58 (d, J=10.2 Hz, 2H), 1.80 (d, J=12.3 Hz, 1H), 2.01 (d, J=9.8 Hz, 1H), 2.28 (s, 3H), 5.43-5.46 (dd, J=3.3, 8.9 Hz, 1H), 5.94 (m, 2H), 6.90 (br s, 1H), 7.24 (d, J=8.1 Hz, 1H), 7.33 (s, 1H), 7.53-7.56 (dd, J=1.7, 7.8 Hz, 1H), 7.87 (t, J=8.3 Hz, 2H), 8.18 (s, 1H), 8.43 (s, 1H), 8.72 (s, 1H), 9.02 (d, J=7.5 Hz, 1H).

Example 281

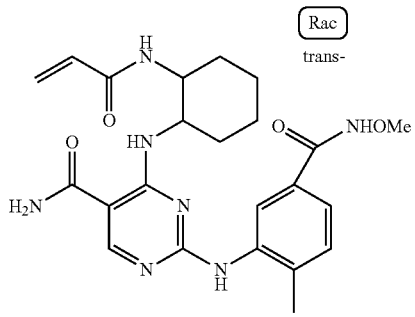

Rac-trans-4-((2-acrylamidocyclohexyl)amino)-2-((5-(methoxycarbamoyl)-2-methylphenyl)amino)pyrimidine-5-carboxamide Compound I-256 was prepared in a manner similar to Example 274, substituting ammonia hydroxide for methyl amine, substituting 3-amino-N-methoxy-4-methylbenzamide for 2-methoxy-4-morpholinoaniline, and substituting trans-N-(2-aminocyclohexyl)acrylamide for N-(2-aminophenyl)acrylamide. MS m/z 468.2 (ES+, M+H); $^1$HNMR (DMSO-d$_6$) δ 1.08-1.14 (m, 4H), 1.22 (m, 2H), 1.57 (d, J=10.0 Hz, 2H), 1.81 (d, J=11.5 Hz, 1H), 2.04 (d, J=10.0 Hz, 1H), 2.28 (s, 3H), 3.64 (s, 3H), 5.44-5.47 (dd, J=3.6, 8.6 Hz, 1H), 5.94 (m, 2H), 6.90 (br s, 1H), 7.26 (d, J=7.9 Hz, 1H), 7.39-7.42 (dd, J=1.4, 7.8 Hz, 1H), 7.68 (br s, 1H), 7.81 (d, J=7.7 Hz, 1H), 8.05 (s, 1H), 8.43 (s, 1H), 8.76 (s, 1H), 9.02-9.04 (d, J=6.7 Hz, 1H), 11.63 (s, 1H).

Example 282

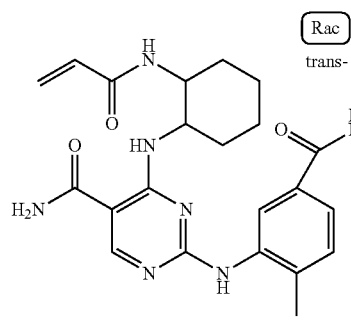

481

Rac-trans-4-((2-acrylamidocyclohexyl)amino)-2-((5-((2-hydroxyethoxy) carbamoyl)-2-methylphenyl)amino)pyrimidine-5-carboxamide Compound I-257 was prepared in a manner similar to Example 274, substituting ammonia hydroxide for methyl amine, substituting 3-amino-N-(2-hydroxyethoxy)-4-methoxybenzamide for 2-methoxy-4-morpholinoaniline, and substituting trans-N-2-(aminocyclohexyl)acrylamide for N-(2-aminophenyl)acrylamide. MS m/z 498.2 (ES+, M+H); $^1$HNMR (DMSO-$d_6$) δ 1.08-1.25 (m, 4H), 1.57 (d, J=8.8 Hz, 2H), 1.80 (br s, 1H), 1.86 (br s, 2H), 2.05 (d, J=12.0 Hz, 2H), 2.31 (s, 3H), 3.57 (t, J=5.0 Hz, 2H), 3.59 (m, 3H), 3.88 (t, J=5.0 Hz, 2H), 5.44-5.47 (dd, J=3.5, 8.9 Hz, 1H), 5.95 (m, 2H), 6.90 (br s, 1H), 7.26 (d, J=7.9 Hz, 1H), 7.42-7.44 (dd, J=1.6, 7.7 Hz, 1H), 7.68 (br s, 1H), 7.82 (d, J=7.5 Hz, 1H), 8.04 (s, 1H), 8.43 (s, 1H), 8.76 (s, 1H), 9.02 (d, J=6.9 Hz, 1H).

Method G describes the synthesis of final targets with an ether linkage between the aromatic ring substituted with a warhead group and the pyrimidine core. The chemistry sequence and conditions are demonstrated below.

482

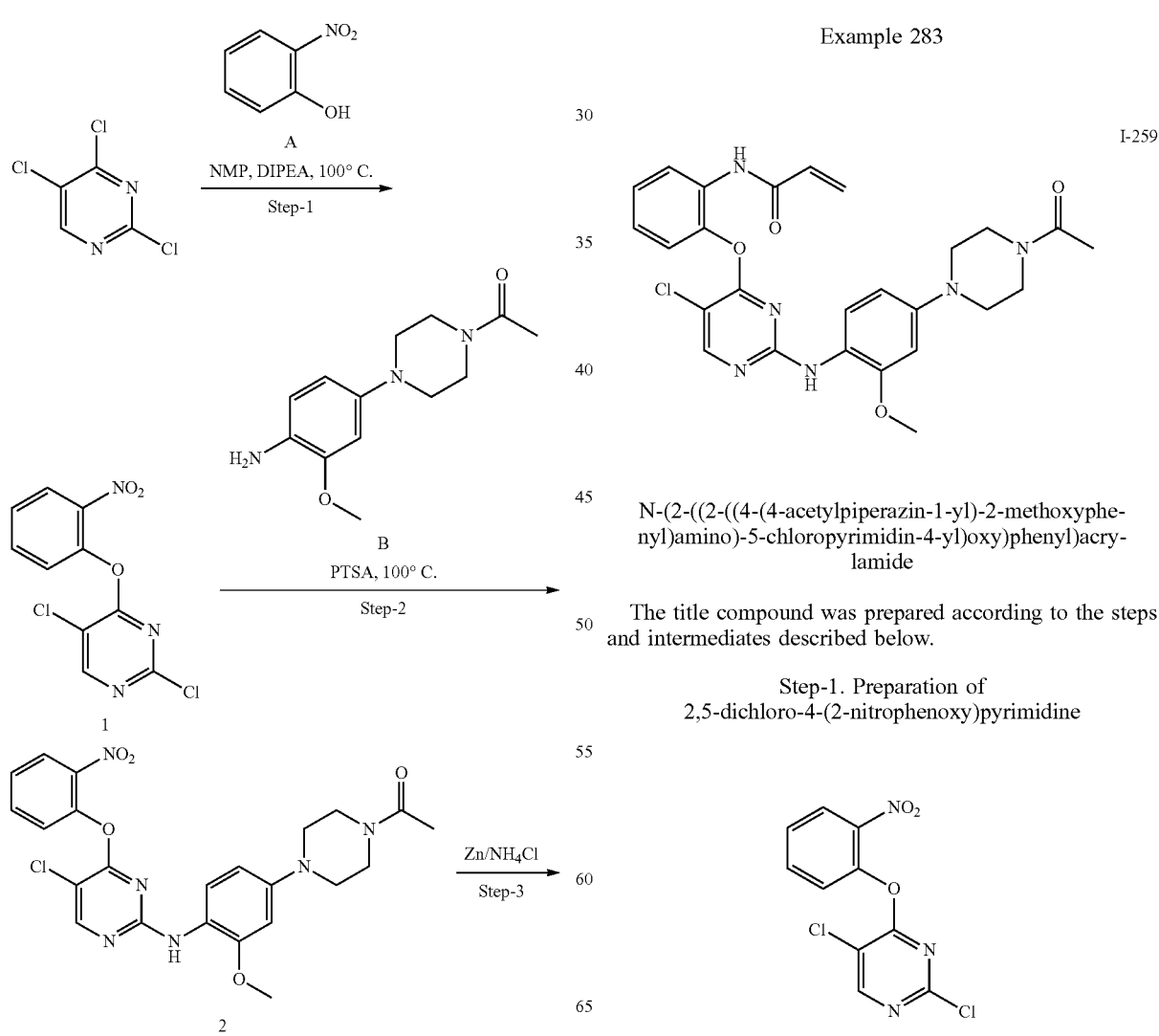

Example 283

I-259

N-(2-((2-((4-(4-acetylpiperazin-1-yl)-2-methoxyphenyl)amino)-5-chloropyrimidin-4-yl)oxy)phenyl)acrylamide The title compound was prepared according to the steps and intermediates described below.

Step-1. Preparation of 2,5-dichloro-4-(2-nitrophenoxy)pyrimidine

To a stirred solution of 2, 4, 5-trichloropyrimidine (1.3 g, 7.19 mmol) in NMP (3 mL), DIPEA (1.85 g, 14.3 mmol) and 2-nitrophenol (1 g, 7.19 mmol) were added and heated to 100° C. for 1 h. TLC showed completion of starting material (TLC system: 20% ethyl acetate in hexane ($R_f$): 0.3). The reaction mixture was poured into crushed ice (50 mL). The obtained solid was filtered, washed with water (50 mL) and dried to obtain 2,5-dichloro-4-(2-nitrophenoxy)pyrimidine as an off-white solid. (Yield: 1.7 g, 85%). $^1$H NMR (400 MHz, $D_6$-DMSO) δ 8.98 (s, 1H), 8.25 (d, 1H), 7.92 (t, 1H), 7.70 (m, 2H).

Step-2. Preparation of 1-(4-(4-(5-chloro-4-(2-nitrophenoxy)pyrimidin-2-ylamino)-3-methoxyphenyl)piperazin-1-yl)ethanone

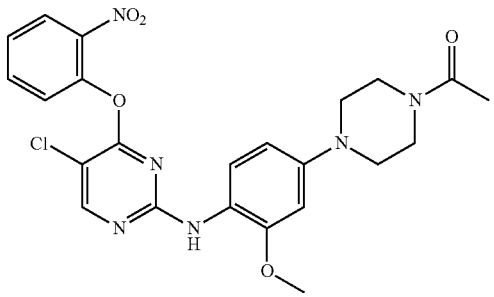

To a stirred solution of 2,5-dichloro-4-(2-nitrophenoxy)pyrimidine (300 mg, 1.052 mmol) in 0.08M p-PTSA/1,4-dioxane (10 mL) was added 1-(4-(4-amino-3-methoxy phenyl)piperazin-1-yl)ethanone (262 mg, 1.052 mmol), and the mixture was heated to 100° C. for 16 h. TLC showed completion of starting material (TLC system: 5% methanol in chloroform ($R_f$): 0.4). 1,4-dioxane was evaporated under reduced pressure, and the remainder was diluted with ethyl acetate (35 mL) and the remainder was washed with water (10 mL) followed by saturated $NaHCO_3$ solution (10 mL). The organic layer was separated, dried over sodium sulphate, and concentrated. Crude compound was purified by column chromatography using silica gel (100-200 mesh) with 3% methanol in chloroform to obtain 1-(4-(4-(5-chloro-4-(2-nitrophenoxy)pyrimidin-2-ylamino)-3-methoxyphenyl) piperazin-1-yl)ethanone as a grey solid. (Yield: 140 mg, 26.6%). MS: m/z 308.4 (ES+, M+H).

Step-3. Preparation of 1-(4-(4-(4-(2-aminophenoxy)-5-chloropyrimidin-2-ylamino)-3-methoxy phenyl)piperazin-1-yl)ethanone

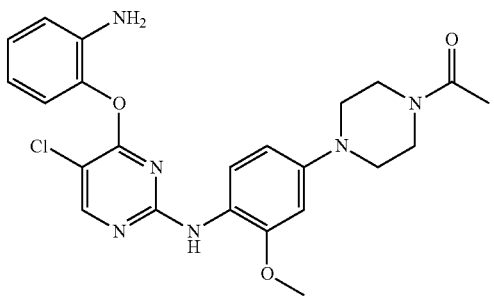 [SMILES: COc1cc(N2CCN(C(C)=O)CC2)ccc1Nc1ncc(Cl)c(Oc2ccccc2[N+](=O)[O-])n1]

To a stirred solution of 1-(4-(4-(5-chloro-4-(2-nitrophenoxy)pyrimidin-2-ylamino)-3-methoxyphenyl)piperazin-1-yl)ethanone (140 mg, 0.28 mmol) in 1,4-dioxane:water (10 mL:4 mL), Zinc dust (81 mg, 1.4 mmol) and ammonium chloride (74 mg, 1.4 mmol) were added, and the mixture was stirred at rt for 30 min. TLC showed completion of starting material (TLC system: 5% methanol in chloroform ($R_f$): 0.3). The reaction mixture was filtered, concentrated, diluted with water (20 mL) and extracted with ethyl acetate (3×10 mL). The organic layer was separated, dried over sodium sulphate, and concentrated. Crude compound was washed with n-pentane to obtain 1-(4-(4-(4-(2-aminophenoxy)-5-chloropyrimidin-2-ylamino)-3-methoxy phenyl)piperazin-1-yl)ethanone as a pale yellow solid. (Yield: 90 mg, 68.7%). $^1$HNMR (DMSO-$d_6$) δ 8.30 (s, 1H), 7.90 (s, 1H), 7.35 (d, 1H), 7.00 (m, 2H), 6.80 (d, 1H), 6.58 (m, 2H), 6.20 (br s, 1H), 4.90 (br s, 2H), 3.75 (s, 3H), 3.55 (m, 4H), 3.05 (m, 2H), 2.95 (m, 2H), 2.02 (s, 3H).

Step-4. Preparation of N-(2-(2-(4-(4-acetylpiperazin-1-yl)-2-methoxyphenylamino)-5-chloro pyrimidin-4-yloxy)phenyl)acrylamide

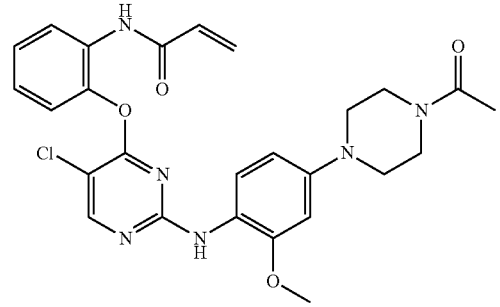 [SMILES: C=CC(=O)Nc1ccccc1Oc1nc(Nc2ccc(N3CCN(C(C)=O)CC3)cc2OC)ncc1Cl]

To a stirred solution of 1-(4-(4-(4-(2-aminophenoxy)-5-chloropyrimidin-2-ylamino)-3-methoxy phenyl)piperazin-1-yl)ethanone (75 mg, 0.16 mmol) in DCM (5 mL), DIPEA (42 mg, 0.33 mmol) and acryloyl chloride (15 mg, 0.165 mmol) were added at −78° C., and the mixture was stirred for 15 min. TLC showed completion of starting material (TLC system: 10% methanol in chloroform ($R_f$): 0.2). The reaction mixture was quenched with water (15 mL) and extracted with DCM (2×10 mL). The organic layer was separated, dried over sodium sulphate, and concentrated. Crude compound was purified by prep-HPLC to obtain N-(2-(2-(4-(4-acetylpiperazin-1-yl)-2-methoxyphenylamino)-5-chloropyrimidin-4-yloxy)phenyl) acrylamide as a yellow solid. (Yield: 28 mg, 33.7%). MS: m/z 523.2 (ES+, M+H). $^1$HNMR (DMSO-$d_6$) δ 9.54 (s, 1H), 8.33 (s, 1H), 8.01 (s, 1H), 7.99 (br s, 1H), 7.25 (m, 4H), 6.56 (s, 1H), 6.50 (d, 1H, J=10.4 Hz), 6.22 (br s, 1H), 6.127 (s, 1H), 5.70 (dd, 1H, J=2.0, 10.4 Hz), 3.73 (s, 3H), 3.57 (m, 4H), 3.06 (br t, 2), 3.00 (br t, 2H), 2.03 (s, 3H).

Example 284

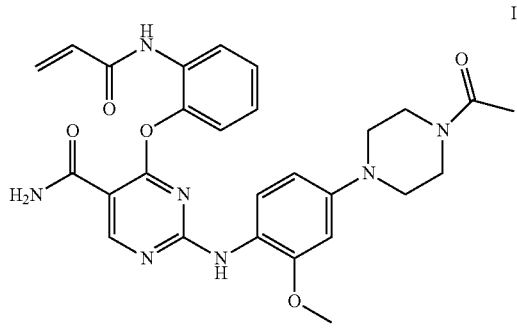

I-258

2-((4-(4-acetylpiperazin-1-yl)-2-methoxyphenyl)amino)-4-(2-acrylamidophenoxy) pyrimidine-5-carboxamide Compound I-258 was prepared in a manner similar to Example 283, using 2,4-dichloropyrimidine-5-carboxamide as the pyrimidine: MS m/z 532.2 (ES+, M+H); $^1$HNMR (DMSO-$d_6$) δ 2.05 (s, 3H), 3.12 (t, J=4.9 Hz, 2H), 3.18 (t, J=4.9 Hz, 2H), 3.60 (d, J=4.9 Hz, 4H), 3.75 (s, 3H), 6.14 (dd, J=1.4, 10.2 Hz, 1H), 6.41-6.48 (dd, J=10.2, 17.3 Hz, 1H), 6.50-6.58 (m, 2H), 6.68 (d, J=2.2 Hz, 1H), 7.01 (d, J=5.8 Hz, 1H), 7.15 (d, J=9.3 Hz, 1H), 7.38 (d, J=8.0 Hz, 1H), 7.93 (br s, 1H), 8.52 (br s, 1H), 8.60 (s, 1H), 11.75 (s, 1H).

Example 285

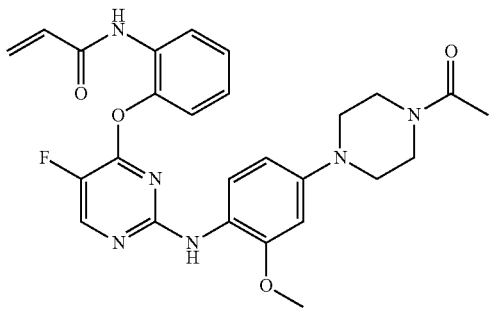

I-260

N-(2-((2-((4-(4-acetylpiperazin-1-yl)-2-methoxyphenyl)amino)-5-fluoropyrimidin-4-yl)oxy)phenyl)acrylamide Compound I-260 was prepared in a manner similar to Example 283, using 2,4-dichloro-5-fluoropyrimidine as the pyrimidine: MS m/z 507.3 (ES+, M+H).

Example 286

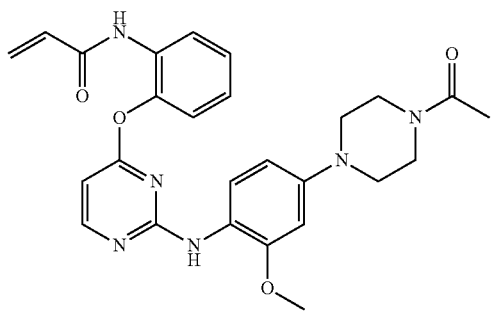

I-261

N-(2-((2-((4-(4-acetylpiperazin-1-yl)-2-methoxyphenyl)amino)pyrimidin-4-yl)oxy)phenyl)acrylamide Compound I-261 was prepared in a manner similar to Example 283, using 2,4-dichloropyrimidine as the pyrimidine. MS m/z 489.3 (ES+, M+H); $^1$HNMR (DMSO-$d_6$) δ 2.02 (s, 3H), 3.00 (t, J=4.8 Hz, 2H), 3.06 (t, J=4.8 Hz, 2H), 3.55 (d, J=4.8 Hz, 4H), 3.76 (s, 3H), 5.65-5.68 (dd, J=1.8, 10.2 Hz, 1H), 6.15-6.20 (dd, J=1.9, 17.0 Hz, 1H), 6.26-6.31 (m, 2H), 6.50-6.56 (dd, J=10.1, 17.0 Hz, 1H), 6.59 (d, J=2.4 Hz, 1H), 7.19-7.22 (m, 2H), 7.25 (m, 1H), 7.44 (d, J=8.6 Hz, 1H), 7.81 (s, 1H), 8.03 (d, J=7.9 Hz, 1H), 8.24 (d, J=5.5 Hz, 1H), 9.60 (s, 1H).

Example 287

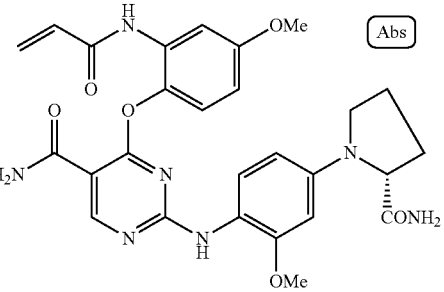

I-262

(R)-4-(2-acrylamido-4-methoxyphenoxy)-2-((4-(2-carbamoylpyrrolidin-1-yl)-2-methoxyphenyl)amino)pyrimidine-5-carboxamide Compound I-262 was prepared in a manner similar to Example 283, using 2,4-dichloropyrimidine-5-carboxamide as the pyrimidine, substituting 4-methoxy-2-nitrophenol for 2-nitrophenol, and substituting (R)-1-(4-amino-3-methoxyphenyl)pyrrolidine-2-carboxamide for 1-(4-(4-amino-3-methoxyphenyl)piperazin-1-yl)ethanone. MS m/z 548.2 (ES+, M+H).

Example 288

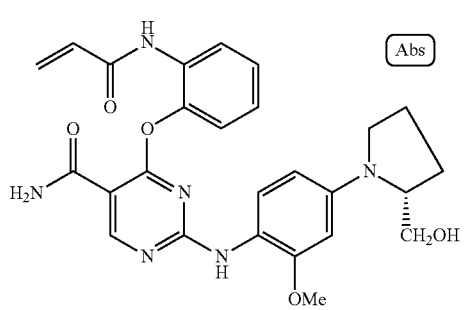

I-263

(R)-4-(2-acrylamidophenoxy)-2-((4-(2-(hydroxymethyl)pyrrolidin-1-yl)-2-methoxyphenyl)amino)pyrimidine-5-carboxamide Compound I-263 was prepared in a manner similar to Example 283, substituting (R)-(1-(4-amino-3-methoxyphenyl)pyrrolidin-2-yl)methanol for 1-(4-(4-amino-3-methoxyphenyl)piperazin-1-yl)ethanone. MS m/z 505.2 (ES+, M+H).

Example 289

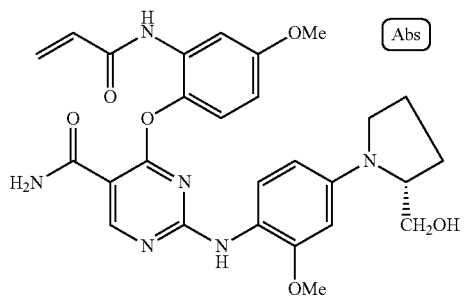

I-264

(R)-4-(2-acrylamido-4-methoxyphenoxy)-2-((4-(2-(hydroxymethyl)pyrrolidin-1-yl)-2-methoxyphenyl)amino)pyrimidine-5-carboxamide Compound I-264 was prepared in a manner similar to Example 283, using 2,4-dichloropyrimidine-5-carboxamide as the pyrimidine, substituting 4-methoxy-2-nitrophenol for 2-nitrophenol, and substituting (R)-(1-(4-amino-3-methoxyphenyl)pyrrolidin-2-yl)methanol for 1-(4-(4-amino-3-methoxyphenyl)piperazin-1-yl)ethanone. MS m/z 535.2 (ES+, M+H); $^1$HNMR (DMSO-$d_6$) δ 1.85-2.05 (m, 3H), 3.05 (q, J=8.2 Hz, 1H), 3.15-3.21 (m, 1H), 3.15-3.21 (m, 1H), 3.39 (t, J=8.0 Hz, 1H), 3.51-3.58 (m, 1H), 3.65-3.69 (m, 1H), 3.73 (s, 3H), 4.75 (t, J=5.3 Hz, 1H), 6.11-6.16 (m, 2H), 6.24 (d, J=2.3 Hz, 1H), 6.39-6.46 (dd, J=10.2, 17.3 Hz, 1H), 6.52-6.56 (m, 2H), 7.05 (d, J=8.8 Hz, 1H), 7.24 (d, J=8.6 Hz, 1H), 7.33 (br s, 1H), 7.88 (br s, 1H), 8.03 (br s, 1H), 8.39 (s, 1H), 8.58 (s, 1H), 11.8 (s, 1H).

Example 290

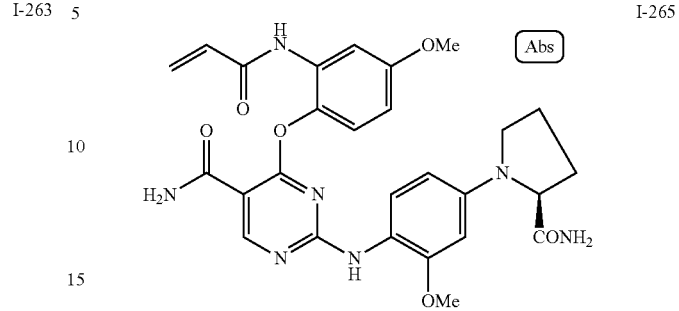

I-265

(S)-4-(2-acrylamido-4-methoxyphenoxy)-2-((4-(2-carbamoylpyrrolidin-1-yl)-2-methoxyphenyl)amino)pyrimidine-5-carboxamide Compound I-265 was prepared in a manner similar to Example 283, using 2,4-dichloropyrimidine-5-carboxamide as the pyrimidine, substituting 4-methoxy-2-nitrophenol for 2-nitrophenol, and substituting (S)-1-(4-amino-3-methoxyphenyl)pyrrolidine-2-carboxamide for 1-(4-(4-amino-3-methoxyphenyl)piperazin-1-yl)ethanone: MS m/z 548.4 (ES+, M+H); $^1$HNMR (DMSO-$d_6$) δ 2.01-2.03 (m, 1H), 2.18-2.23 (m, 1H), 3.21-3.24 (m, 1H), 3.50-3.53 (m, 1H), 3.56-3.60 (m, 2H), 3.72 (s, 3H), 3.89-3.91 (m, 1H), 6.02-6.05 (dd, J=2.4, 8.6 Hz, 1H), 6.11-6.14 (dd, J=1.5, 10.1 Hz, 1H), 6.17 (d, J=2.4 Hz, 1H), 6.39-6.46 (dd, J=10.1, 17.3 Hz, 1H), 6.51-6.56 (m, 2H), 7.03-7.06 (m, 2H), 7.28 (d, J=8.6 Hz, 1H), 7.32 (br s, 2H), 7.88 (br s, 1H), 8.06 (br s, 1H), 8.39 (s, 1H), 8.57 (br s, 1H), 11.79 (s, 1H).

Example 291

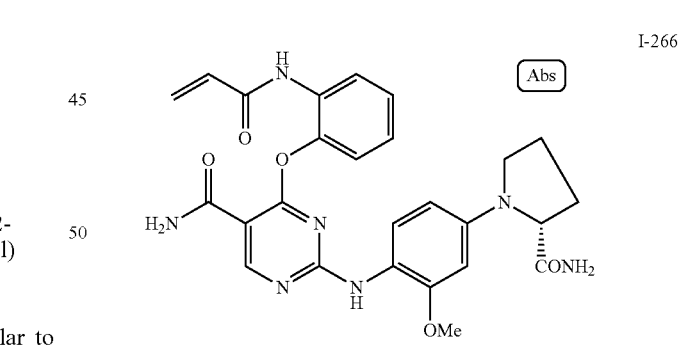

I-266

(R)-4-(2-acrylamidophenoxy)-2-((4-(2-carbamoylpyrrolidin-1-yl)-2-methoxyphenyl)amino)pyrimidine-5-carboxamide Compound I-266 was prepared in a manner similar to Example 283, using 2,4-dichloropyrimidine-5-carboxamide as the pyrimidine, and substituting (R)-1-(4-amino-3-methoxyphenyl)pyrrolidine-2-carboxamide for 1-(4-(4-amino-3-methoxyphenyl)piperazin-1-yl)ethanone. MS m/z 518.2 (ES+, M+H); $^1$HNMR (CDCl$_3$) δ 2.03-2.08 (m, 2H), 2.27-2.33 (m, 2H), 3.22-3.29 (m, 1H), 3.63-3.68 (m, 1H), 3.84 (s, 3H), 4.00 (m, 1H), 5.39 (br s, 1H), 5.60 (br s, 2H), 6.01-6.03 (dd, J=1.0, 10.4 Hz, 1H), 6.19 (d, J=2.4 Hz, 1H), 6.22-6.25 (dd, J=2.4, 8.8 Hz, 1H), 6.39-6.48 (m, 2H), 6.63-6.68 (m, 2H), 7.12 (d, J=8.8 Hz, 1H), 7.38 (br s, 1H), 8.05 (br s, 2H), 8.07 (br s, 1H), 8.34 (s, 1H), 11.14 (br s, 1H).

Example 292

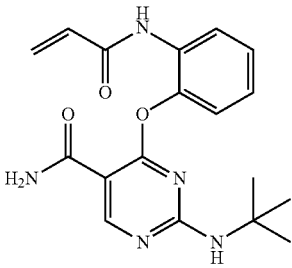

I-267

4-(2-acrylamidophenoxy)-2-(tert-butylamino)pyrimidine-5-carboxamide

Compound I-267 was prepared in a manner similar to Example 283, using 2,4-dichloropyrimidine-5-carboxamide as the pyrimidine, and substituting t-Butyl amine for 1-(4-(4-amino-3-methoxyphenyl)piperazin-1-yl)ethanone. MS m/z 356.2 (ES+, M+H); ¹HNMR (DMSO-d₆) δ 1.38 (s, 9H), 6.13-6.16 (dd, J=1.1, 10.3 Hz, 1H), 6.40-6.58 (m, 2H), 7.05 (br s, 2H), 7.17-7.25 (m, 2H), 7.81 (br s, 1H), 8.56 (br s, 1H), 11.68 (s, 1H).

Example 293

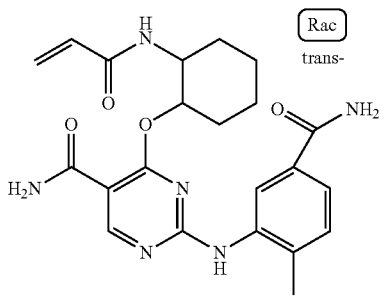

I-268

Rac-trans-4-((2-acrylamidocyclohexyl)oxy)-2-((5-carbamoyl-2-methylphenyl) amino)pyrimidine-5-carboxamide Compound I-267 was prepared in a manner similar to Example 283, using 2,4-dichloropyrimidine-5-carboxamide as the pyrimidine, substituting tert-butyl trans-2-(hydroxycyclohexyl)carbamate for 2-nitrophenol, and substituting 3-amino-4-methylbenzamide for 1-(4-(4-amino-3-methoxyphenyl)piperazin-1-yl)ethanone: MS m/z 439.3 (ES+, M+H).

Example 294

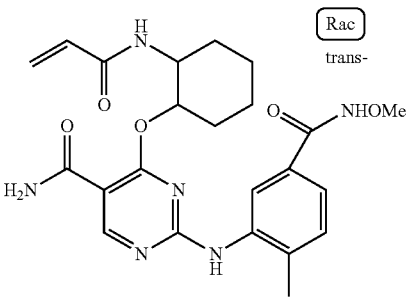

I-269

Rac-trans-4-((2-acrylamidocyclohexyl)oxy)-2-((5-(methoxycarbamoyl)-2-methylphenyl)amino)pyrimidine-5-carboxamide Compound I-269 was prepared in a manner similar to Example 283, using 2,4-(dichloropyrimidine-5-carboxamide as the pyrimidine, substituting tert-butyl trans-2-hydroxycyclohexyl)carbamate for 2-nitrophenol, and substituting 3-amino-N-methoxy-4-methylbenzamide for 1-(4-(4-amino-3-methoxyphenyl)piperazin-1-yl)ethanone, followed by Boc-deprotection using TFA and amide formation with acryloyl chloride. MS m/z 469.2 (ES+, M+H); ¹HNMR (DMSO-d₆) δ 1.04-1.28 (m, 4H), 1.60 (d, J=8.6 Hz, 2H), 1.81 (br s, 1H), 1.86 (br s, 2H), 2.10-2.20 (br s, 1H), 2.26 (s, 3H), 3.68 (s, 3H), 4.01-4.07 (m, 1H), 4.70 (br s, 1H), 5.52-5.55 (dd, J=3.2, 9.1 Hz, 1H), 6.01-6.14 (m, 2H), 7.08 (s, 1H), 7.31 (d, J=8.0 Hz, 2H), 7.47-7.50 (dd, J=1.6, 7.8 Hz, 1H), 7.90 (s, 1H), 8.11 (d, J=8.8 Hz, 1H), 8.63 (s, 1H), 9.38 (s, 1H), 11.64 (s, 1H).

Example 295

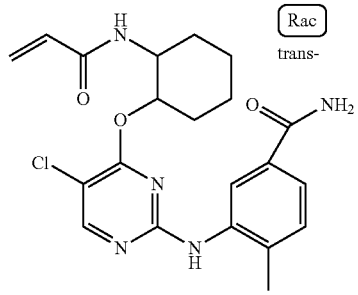

I-270

Rac-trans-3-((4-((2-acrylamidocyclohexyl)oxy)-5-chloropyrimidin-2-yl)amino)-4-methylbenzamide Compound I-270 was prepared in a manner similar to Example 283, substituting tert-butyl trans-2-(hydroxycyclohexyl)carbamate for 2-nitrophenol, and substituting 3-amino-4-methylbenzamide for 1-(4-(4-amino-3-methoxyphenyl)piperazin-1-yl)ethanone, followed by Boc-deprotection using TFA and amide formation with acryloyl chloride. MS m/z 430.1 (ES+, M+H).

Example 296

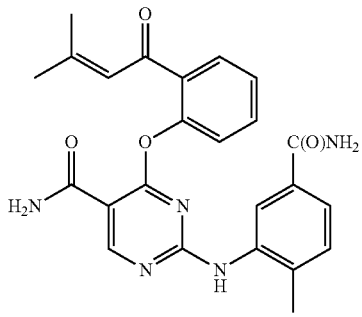

I-271

2-((5-carbamoyl-2-methylphenyl)amino)-4-(2-(3-methylbut-2-enoyl)phenoxy) pyrimidine-5-carboxamide Compound I-271 was prepared in a manner similar to Example 283, using 2,4-dichloropyrimidine-5-carboxamide as the pyrimidine, substituting 2-hydroxy-N-methoxy-N-methylbenzamide for 2-nitrophenol, and substituting 3-amino-4-methylbenzamide for 1-(4-(4-amino-3-methoxyphenyl)piperazin-1-yl)ethanone, followed by reaction with (2-methylprop-1-en-1-yl)magnesium chloride. MS m/z 446.2 (ES+, M+H); $^1$HNMR (DMSO-d$_6$) δ 1.78 (s, 3H), 1.88 (s, 3H), 2.06 (s, 3H), 6.4 (br s, 1H), 7.16 (d, J=7.5 Hz, 1H), 7.2 (s, 1H), 7.3-7.32 (m, 1H), 7.36 (d, J=7.6 Hz, 2H), 7.53 (d, J=8.5 Hz, 3H), 7.59 (d, J=8.4 Hz, 1H), 7.62 (s, 1H), 7.77 (s, 1H), 8.68 (s, 1H), 9.28 (s, 1H).

Example 297

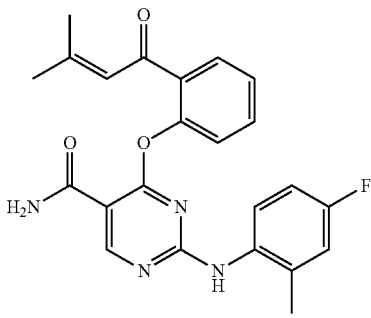

I-272

2-((4-fluoro-2-methylphenyl)amino)-4-(2-(3-methylbut-2-enoyl)phenoxy) pyrimidine-5-carboxamide Compound I-272 was prepared in a manner similar to Example 283, using 2,4-dichloropyrimidine-5-carboxamide as the pyrimidine, substituting 2-hydroxy-N-methoxy-N-methylbenzamide for 2-nitrophenol, and substituting 4-fluoro-2-methylaniline for 1-(4-(4-amino-3-methoxyphenyl)piperazin-1-yl)ethanone, followed by reaction with (2-methylprop-1-en-1-yl)magnesium chloride. MS m/z 421.4 (ES+, M+H); $^1$HNMR (DMSO-d$_6$) δ 1.78 (s, 3H), 1.85 (s, 3H), 2.05 (s, 3H), 6.44 (s, 1H), 6.75 (br s, 1H), 6.93 (d, J=7.6 Hz, 1H), 7.05-7.09 (m, 1H), 7.36-7.38 (m, 3H), 7.55-7.60 (m, 2H), 7.65-7.67 (dd, J=1.5 Hz, 7.6 Hz, 1H), 8.69 (s, 1H), 9.14 (s, 1H).

Example 298

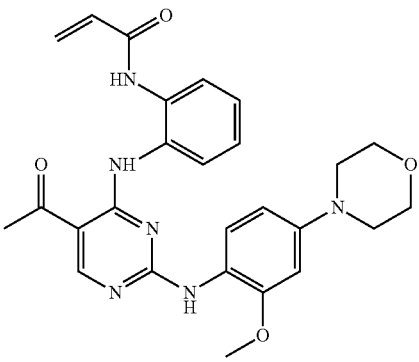 [SMILES: C=CC(=O)Nc1ccccc1Nc1nc(Nc2ccc(N3CCOCC3)cc2OC)ncc1C(C)=O]

I-273

N-(2-(5-acetyl-2-(2-methoxy-4-morpholinophenylamino)pyrimidin-4-yl amino)phenyl) acrylamide The title compound was prepared according to the steps and intermediates described below.

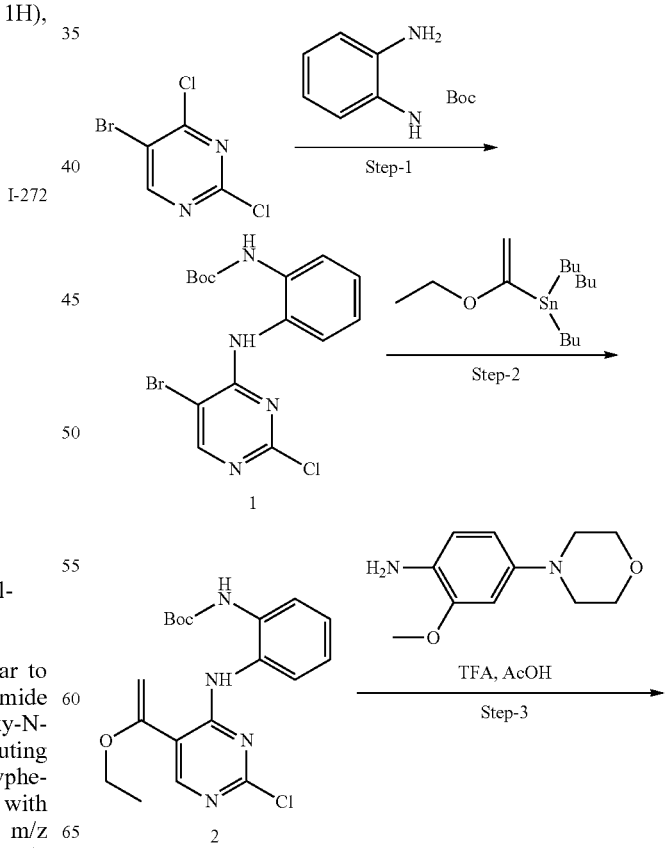

-continued

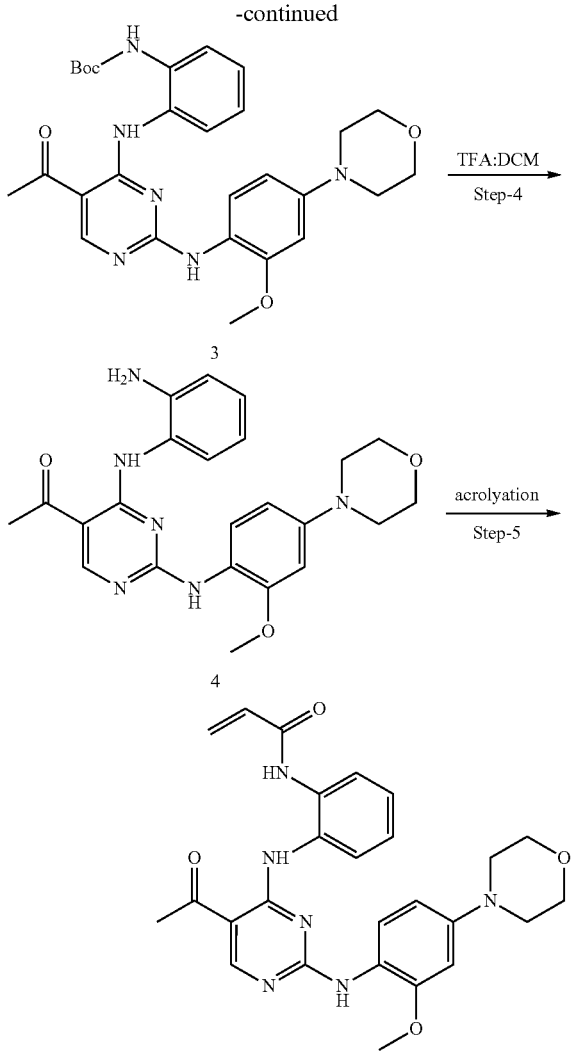

Step-1. Preparation of tert-butyl 2-(5-bromo-2-chloropyrimidin-4-ylamino) phenylcarbamate

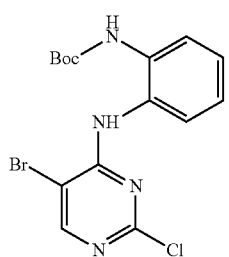 [SMILES: CC(C)(C)OC(=O)Nc1ccccc1Nc1nc(Cl)ncc1Br]

To a solution of tert-butyl 2-aminophenylcarbamate (2 g, 9.6 mol) in NMP (15 mL), DIPEA (3.1 g, 24 mmol) and 5-bromo-2,4-dichloropyrimidine (2.78 g, 14.4 mmol) were added and heated to 120° C. for 1 h. TLC showed completion of starting material (TLC system: 5% methanol in DCM ($R_f$: 0.6). The reaction mixture was diluted with water (50 mL). The obtained solid was filtered, washed with water (35 mL) and dried to obtain tert-butyl 2-(5-bromo-2-chloropyrimidin-4-ylamino) phenylcarbamate as a pale yellow solid. Yield: (2.2 g, 62%). MS: m/z 399.1 (ES+, M+H).

Step-2. Preparation of tert-butyl 2-(2-chloro-5-(1-ethoxyvinyl)pyrimidin-4-ylamino)phenyl carbamate

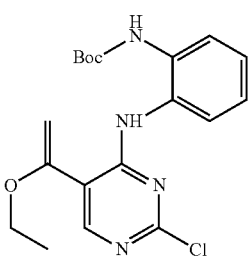 [SMILES: C=C(OCC)c1cnc(Cl)nc1Nc1ccccc1NC(=O)OC(C)(C)C]

To a solution of tert-butyl 2-(5-bromo-2-chloropyrimidin-4-ylamino) phenylcarbamate (1.4 g, 3.5 mmol) in dry DMF (15 mL), tributyl(1-ethoxyvinyl)stannane (2.5 g, 7 mmol) was added and degassed for 20 min. To the reaction mixture PdCl$_2$ (PPh$_3$)$_2$(122 mg, 0.1 mmol) was added and again degassed for another 5 min. The temperature was raised to 100° C., and the mixture was stirred for 4 h. TLC showed completion of starting material (TLC system: 30% ethyl acetate in hexane ($R_f$): 0.4). The reaction mixture was quenched with water (60 mL) and extracted with ethyl acetate (3×35 mL). The organic layer was separated, dried over sodium sulphate, and concentrated. Crude compound was purified by column chromatography using silica gel (100-200 mesh) with 10% ethyl acetate in hexane to obtain tert-butyl 2-(2-chloro-5-(1-ethoxyvinyl)pyrimidin-4-ylamino)phenyl carbamate as a pale yellow solid. Yield: (500 mg, 38%). MS: m/z 391.1 (ES+, M+H).

Step-3. Preparation of tert-butyl 2-(5-acetyl-2-(2-methoxy-4-morpholinophenylamino) pyrimidin-4-ylamino)phenylcarbamate

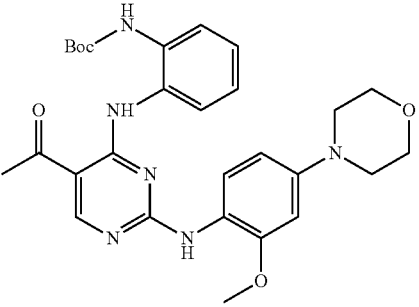 [SMILES: COc1cc(N2CCOCC2)ccc1Nc1ncc(C(C)=O)c(Nc2ccccc2NC(=O)OC(C)(C)C)n1]

To a solution of tert-butyl 2-(2-chloro-5-(1-ethoxyvinyl) pyrimidin-4-ylamino) phenyl carbamate (350 mg, 0.897 mmol) in 1, 4 dioxane (10 mL), acetic acid (54 mg, 0.897 mmol) and TFA (9 mg, 0.0897 mmol) were added and heated to 80° C. for 1 h. The reaction mixture was cooled; 2-methoxy-4-morpholinoaniline (186 mg, 0.897 mmol) was added and stirred at 100° C. for 4 h. TLC showed completion of starting material (TLC system: 30% ethyl acetate in hexane ($R_f$): 0.3). The reaction mixture was evaporated under reduced pressure. Crude compound was purified by column chromatography using silica gel (100-200 mesh)

with 20% ethyl acetate in hexane to obtain tert-butyl 2-(5-acetyl-2-(2-methoxy-4-morpholino phenylamino)pyrimidin-4-ylamino)phenyl carbamate as a yellow solid. Yield: (250 mg, 52%). MS: m/z 535.3 (ES+, M+H).

Step-4. Preparation of 1-(4-(2-aminophenylamino)-2-(2-methoxy-4-morpholinophenylamino) pyrimidin-5-yl) ethanone (4)

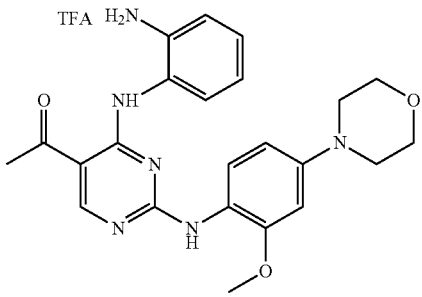 [SMILES: COc1cc(N2CCOCC2)ccc1Nc1ncc(C(C)=O)c(Nc2ccccc2N)n1]

To a solution of tert-butyl 2-(5-acetyl-2-(2-methoxy-4-morpholinophenyl amino)pyrimidin-4-ylamino)phenylcarbamate (100 mg) in DCM (5 ml), TFA (1 ml) was added at 0° C., and the mixture was stirred for 1 h at rt. TLC showed completion of starting material (TLC system: 5% methanol in DCM (R$_f$: 0.5). After removal of TFA under reduced pressure, the residue was triturated with diethyl ether to give the desired compound as a yellow solid 85 mg (Yield: 98%). MS: m/z 435.2 (ES+).

Step-5. Preparation of N-(2-(5-acetyl-2-(2-methoxy-4-morpholinophenylamino)pyrimidin-4-yl amino) phenyl)acrylamide

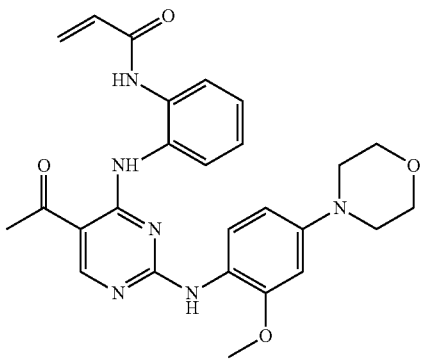 [SMILES: C=CC(=O)Nc1ccccc1Nc1nc(Nc2ccc(N3CCOCC3)cc2OC)ncc1C(C)=O]

To a solution of 1-(4-(2-aminophenylamino)-2-(2-methoxy-4-morpholinophenylamino) pyrimidin-5-yl)ethanone (100 mg, 0.23 mmol) in DCM (10 ml), DIPEA (55 mg, 0.46 mmol) and acrolyl chloride (20.7 mg, 0.23 mmol) were added at −20° C., and the mixture was stirred for 30 min. TLC showed completion of starting material (TLC system: 5% methanol in DCM. (R$_f$): 0.5). The reaction mixture was diluted with DCM (20 mL) and washed with water (2×10 mL). The organic layer was separated, dried over sodium sulphate, and concentrated. Crude compound was purified by column chromatography using silica gel (100-200 mesh) with 3% methanol in DCM to obtain N-(2-(5-acetyl-2-(2-methoxy-4-morpholinophenylamino) pyrimidin-4-yl amino) phenyl) acrylamide as a pale yellow solid. Yield: (30 mg, 26%). MS: m/z 489.2 (ES+); $^1$HNMR (DMSO-d$_6$) δ 11.25 (s, 1H), 9.76 (s, 1H), 8.77 (s, 1H), 8.73 (s, 1H), 8.10 (br s, 1H), 7.35 (d, 1H, J=8.4 Hz), 7.25 (br s, 1H), 0.06 (br t, 2H), 6.65 (s, 1H), 6.45 (m, 2H), 6.20 (dd, 1H, J=2.0, 17.2 Hz), 5.74 (dd, 1H, J=8.0 Hz), 3.72 (m, 7H), 3.12 (m, 4H), 3.24 (br s, 3H).

Example 299

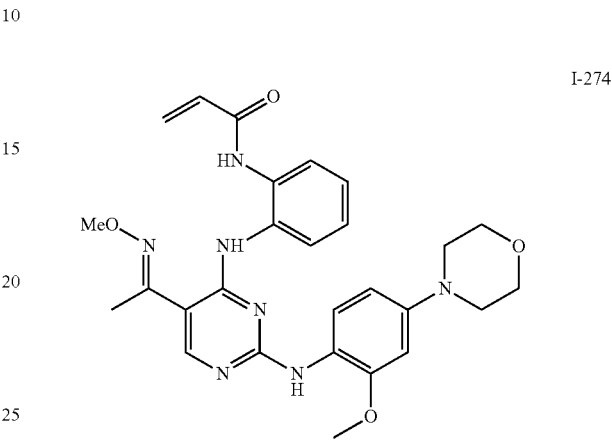

I-274

(E)-N-(2-((2-((2-methoxy-4-morpholinophenyl) amino)-5-(1-(methoxyimino)ethyl) pyrimidin-4-yl) amino)phenyl)acrylamide This compound was synthesized through the following intermediates:

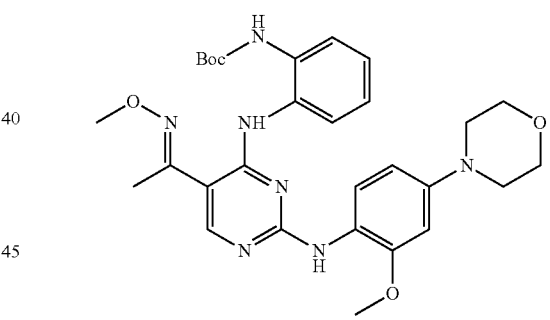

(E)-tert-butyl 2-(2-(2-methoxy-4-morpholinophenylamino)-5-(1-(methoxy imino)ethyl) pyrimidin-4-ylamino)phenylcarbamate To a solution of tert-butyl 2-(5-acetyl-2-(2-methoxy-4-morpholino phenylamino)pyrimidin-4-ylamino)phenylcarbamate (Intermediate 3 in Example 298) (100 mg, 0.18 mmol) in ethanol (5 mL), methoxylamine hydrochloride (55 mg, 0.79 mmol), DIPEA (46 mg, 0.36 mmol) and pyridine (0.5 mL) were added and heated to 100° C. for 16 h. TLC showed completion of starting material (TLC system: 5% methanol in DCM (R$_f$): 0.3). The ethanol was evaporated under reduced pressure, and the remainder was diluted with water (10 mL), filtered and dried to obtain (E)-tert-butyl 2-(2-(2-methoxy-4-morpholinophenylamino)-5-(1-(methoxyimino)ethyl)pyrimidin-4-ylamino) phenyl carbamate as white solid. Yield: (70 mg, 66%). MS: m/z 564.3 (S+, M+H).

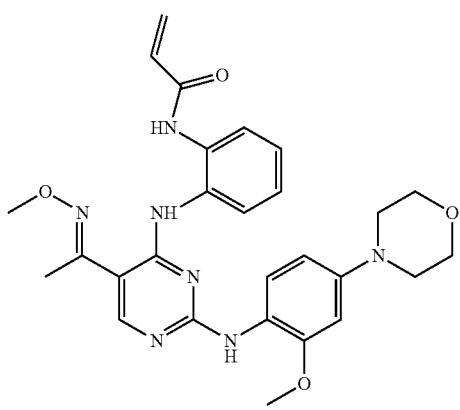 [SMILES: C=CC(=O)Nc1ccccc1Nc1nc(Nc2ccc(N3CCOCC3)cc2OC)ncc1/C(C)=N/OC]

(E)-N-(2-(2-(2-methoxy-4-morpholinophenylamino)-5-(1-(methoxyimino) ethyl) pyrimidin-4-ylamino) phenyl) acrylamide The title compound was prepared in the same manner as described in Step 4 of Example 283 with Boc-deprotection using TFA followed by reaction with acryloyl chloride. MS: m/z 518.4 (ES+, M+H).

Example 300

I-275

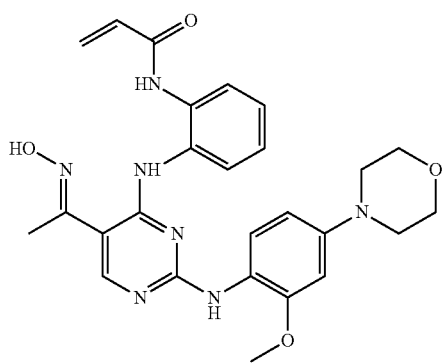

(E)-N-(2-((5-(1-(hydroxyimino)ethyl)-2-((2-methoxy-4-morpholinophenyl) amino)pyrimidin-4-yl)amino)phenyl)acrylamide This compound was synthesized through the following intermediates:

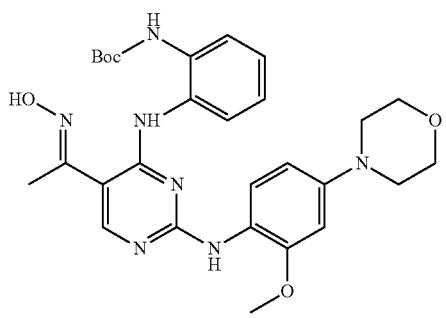 [SMILES: COc1cc(N2CCOCC2)ccc1Nc1ncc(/C(C)=N/O)c(Nc2ccccc2NC(=O)OC(C)(C)C)n1]

(E)-tert-butyl 2-(5-(1-(hydroxyimino)ethyl)-2-(2-methoxy-4-morpholino phenylamino)pyrimidin-4-ylamino)phenylcarbamate This intermediate was prepared in the same way as for Intermediate 3 in Example 298 in Example 299, using hydroxylamine hydrochloride instead of methoxylamine hydrochloride. MS: m/z 550.4 (ES+).

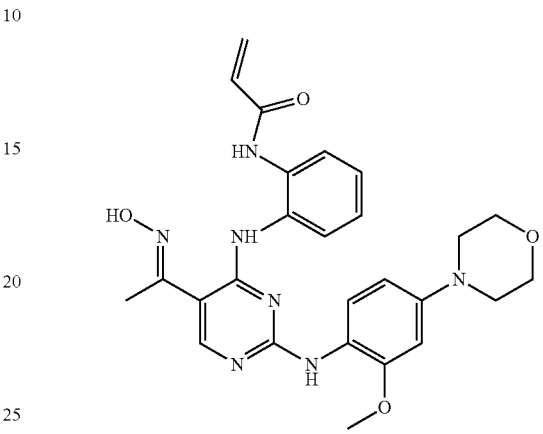

(E)-N-(2-((5-(1-(hydroxyimino)ethyl)-2-((2-methoxy-4-morpholinophenyl) amino)pyrimidin-4-yl)amino)phenyl)acrylamide The title compound was prepared in same manner as described in Step 4 of Example 283 with Boc-deprotection using TFA followed by reaction with acryloyl chloride. MS: m/z 504.3 (ES+, M+H).

Example 301

I-276

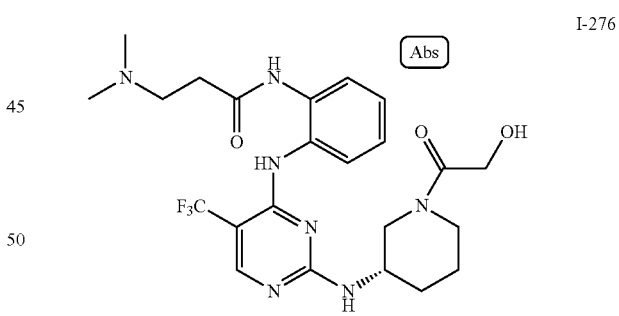

(S)-3-(dimethylamino)-N-(2-((2-((1-(2-hydroxy-acetyl)piperidin-3-yl)amino)-5-(trifluoromethyl) pyrimidin-4-yl)amino)phenyl)propanamide Compound I-276 was prepared in a manner similar to Example 1, substituting N-(2-aminophenyl)-3-(dimethyl-amino)propanamide for N-(2-aminophenyl)acrylamide. MS: m/z 510.2 (ES+, M+H); $^1$HNMR (CD$_3$OD) δ 1.47 (br s, 1H), 1.62-2.0 (m, 4H), 2.96 (s, 6H), 3.04 (br s, 2H), 3.14 (br s, 1H), 3.51 (t, J=7.0 Hz, 4H), 3.65-3.80 (m, 2H), 3.90 (br s, 1H), 7.27-7.43 (m, 2H), 7.50-7.65 (m, 2H), 8.38 (s, 1H).

Example 302-Covalent Probes
I-299
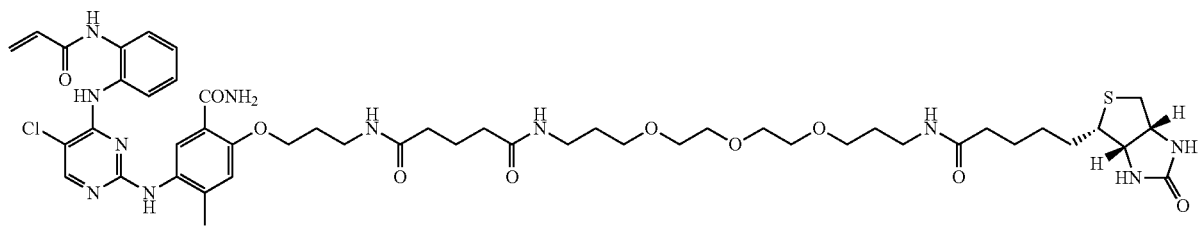
N[1]-(3-(4-((4-((2-acrylamidophenyl)amino)-5-chloro-pyrimidin-2-yl)amino)-2-carbamoyl-5-methylphenoxy)propyl)-N-(15-oxo-19-((3aS,4S,6aR)-2-oxo-hexahydro-1H-thieno[3,4-d]imidazol-4-yl)-4,7,10-trioxa-14-azanonadecyl)glutaramide
The title compound was prepared according to the steps and intermediates as described below.

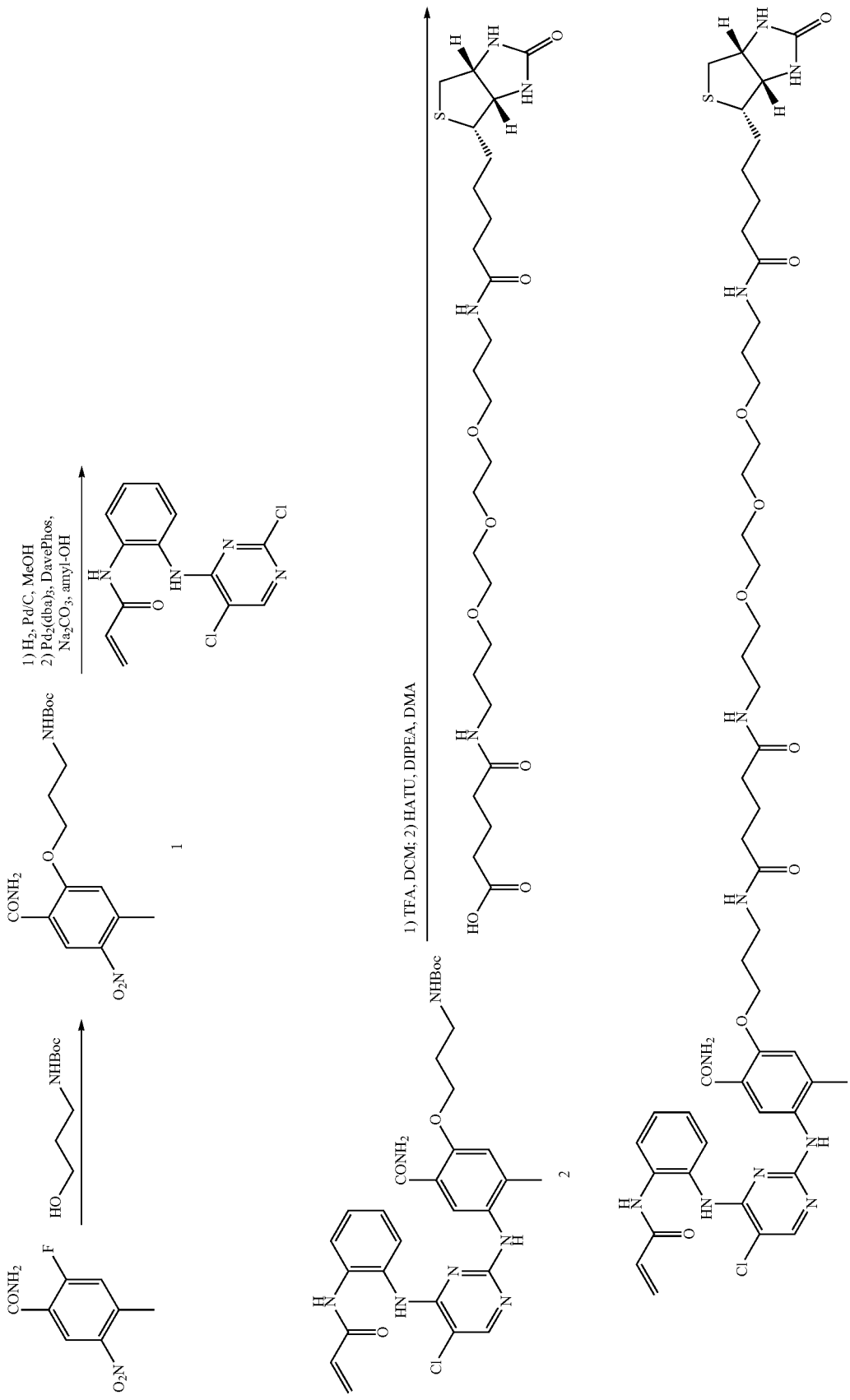

Step-1: tert-butyl (3-(2-carbamoyl-5-methyl-4-nitrophenoxy)propyl)carbamate

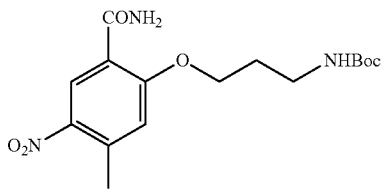 [SMILES: Cc1cc(OCCCNC(=O)OC(C)(C)C)c(C(N)=O)cc1[N+](=O)[O-]]

To a suspension of sodium hydride (200 mg, 60% in mineral oil, 5 mmol) in 4 mL of anhydrous THF, was added tert-butyl (3-hydroxypropyl)carbamate (100 mg, 0.57 mmol) in 1 mL of anhydrous THF. After stirring at rt for 5 min, 2-fluoro-4-methyl-5-nitrobenzamide (100 mg, 0.50 mmol) was added in one portion. The resulting mixture was stirred for an additional 30 min; and LC-MS showed completion of the reaction. The reaction was quenched with ice-water, and the final product was extracted with EtOAc, washed with aqueous NH$_4$Cl, and dried over anhydrous sodium sulfate. After concentration, 133 mg of white solid was obtained as the desired product in 75% yield. $^1$HNMR (400 MHz, CDCl$_3$) δ 8.88 (s, 1H), 6.83 (s, 1H), 4.25 (t, 2H, J=6.8 Hz), 3.33 (br t, 2H), 2.65 (s, 3H, Me), 2.05 (m, 2H), 1.39 (s, 9H). MS: m/z 254.1 (ES+, M+H-Boc).

tert-butyl (3-(4-amino-2-carbamoyl-5-methylphenoxy)propyl)carbamate

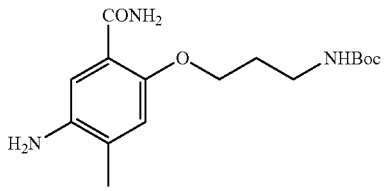

The nitro-intermediate obtained above was dissolved in MeOH, and stirred with 30 mg of 10% Pd/C under hydrogen at rt for 1 hr. After filtration, the desired aniline was obtained in quantitative yield as a red solid. MS: m/z 224.1 (ES+, M+H-Boc).

Step 2. tert-butyl (3-(4-((4-((2-acrylamidophenyl)amino)-5-chloropyrimidin-2-yl)amino)-2-carbamoyl-5-methylphenoxy)propyl)carbamate

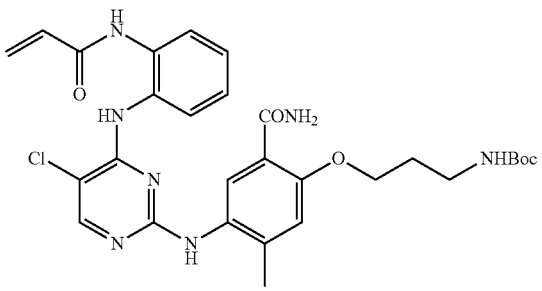 [SMILES: C=CC(=O)Nc1ccccc1Nc1nc(Nc2cc(C(N)=O)c(OCCCNC(=O)OC(C)(C)C)cc2C)ncc1Cl]

To a mixture of N-(2-((2,5-dichloropyrimidin-4-yl)amino)phenyl)acrylamide (15 mg, 49 umol), tert-butyl (3-(4-amino-2-carbamoyl-5-methylphenoxy)propyl)carbamate (22 mg, 68 umol), and sodium carbonate (25 mg, 23 umol) in 1 mL of amyl alcohol under Ar, was added Pd$_2$(dba)$_3$ (9.6 mg) and DavePhos (15 mg). The resulting mixture was heated at 100° C. for 2 hr. After filtration, the product was purified by prep-HPLC, giving 18 mg of white powder (62%). MS: m/z 596.2 (ES+, M+H).

Step 3. N$^1$-(3-(4-((4-((2-acrylamidophenyl)amino)-5-chloropyrimidin-2-yl)amino)-2-carbamoyl-5-methylphenoxy)propyl)-N-(15-oxo-19-((3aS,4S,6aR)-2-oxohexahydro-1H-thieno[3,4-d]imidazol-4-yl)-4,7,10-trioxa-14-azanonadecyl)glutaramide

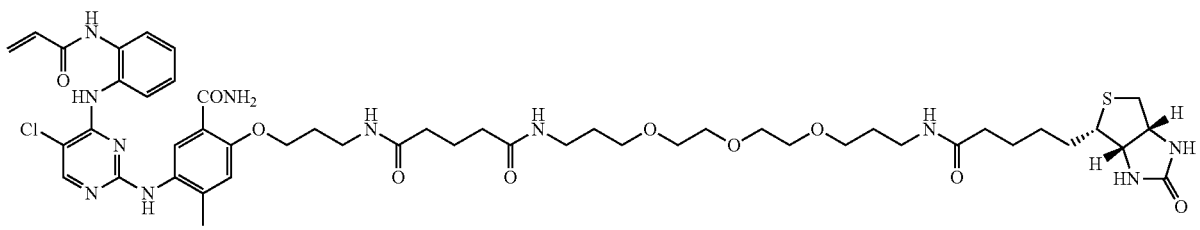 [SMILES: C=CC(=O)Nc1ccccc1Nc1nc(Nc2cc(C(N)=O)c(OCCCNC(=O)CCCC(=O)NCCCOCCOCCOCCCNC(=O)CCCC[C@@H]3SC[C@@H]4NC(=O)N[C@@H]43)cc2C)ncc1Cl]

To the NBoc intermediate (18 mg) obtained from the previous step in 1 mL of dichloromethane, was added 1 mL of trifluoroacetic acid. After stirring for 15 min, the solvent was removed completely under reduced pressure, giving de-Boc intermediate. MS: m/z 496.3 (M+H).

The de-Boc intermediate was re-dissolved in 1 mL of acetonitrile and 1 mL of DMA, followed by addition of 100 uL of N,N-diisopropyl ethylamine, 30 mg of 20-atom biotin acid, and 40 mg of HATU. After 10 min stirring at rt, LC-MS showed completion of the reaction. The reaction mixture was subject to prep-HPLC purification, giving desired biotin-linked compound 17.4 mg as white powder. MS: m/z 1038.3 (ES+, M+H).

Compound I-300

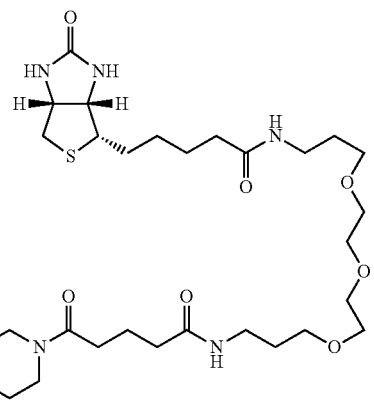

5-(4-((4-((2-acrylamidophenyl)amino)-5-chloropyrimidin-2-yl)amino)piperidin-1-yl)-5-oxo-N-(15-oxo-19-((3aS,4S,6aR)-2-oxohexahydro-1H-thieno[3,4-d]imidazol-4-yl)-4,7,10-trioxa-14-azanonadecyl)pentanamide Compound I-300 was prepared in a manner similar to Compound I-299, using I-116 for the starting material, then coupled to the acid to provide the titled compound. MS m/z 915.3 (ES+, M+H).

Compound I-301

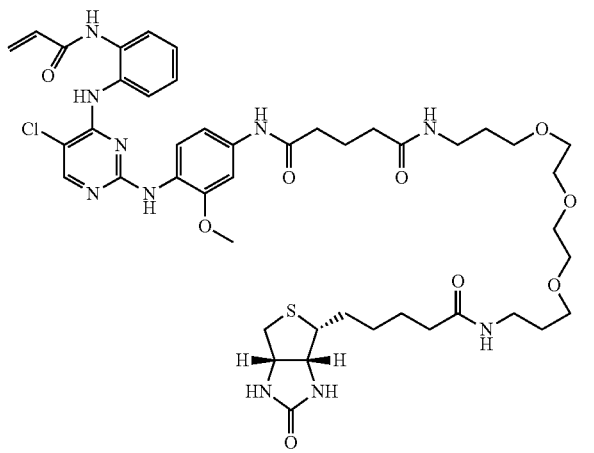 [SMILES: C=CC(=O)Nc1ccccc1Nc1nc(Nc2ccc(NC(=O)CCCC(=O)NCCCOCCOCCOCCCNC(=O)CCCC[C@H]3SC[C@H]4NC(=O)N[C@H]43)cc2OC)ncc1Cl]

$N^1$-(4-((4-((2-acrylamidophenyl)amino)-5-chloropyrimidin-2-yl)amino)-3-methoxyphenyl)-$N^5$-(15-oxo-19-((3aR,4R,6aS)-2-oxohexahydro-1H-thieno[3,4-d]imidazol-4-yl)-4,7,10-trioxa-14-azanonadecyl)glutaramide Compound I-301 was prepared in a manner similar to Compound I-299, using I-183 intermediate as the starting material, followed by coupling with the acid to provide the title compound. MS m/z 953.3 (ES+, M+H).

Compound I-302

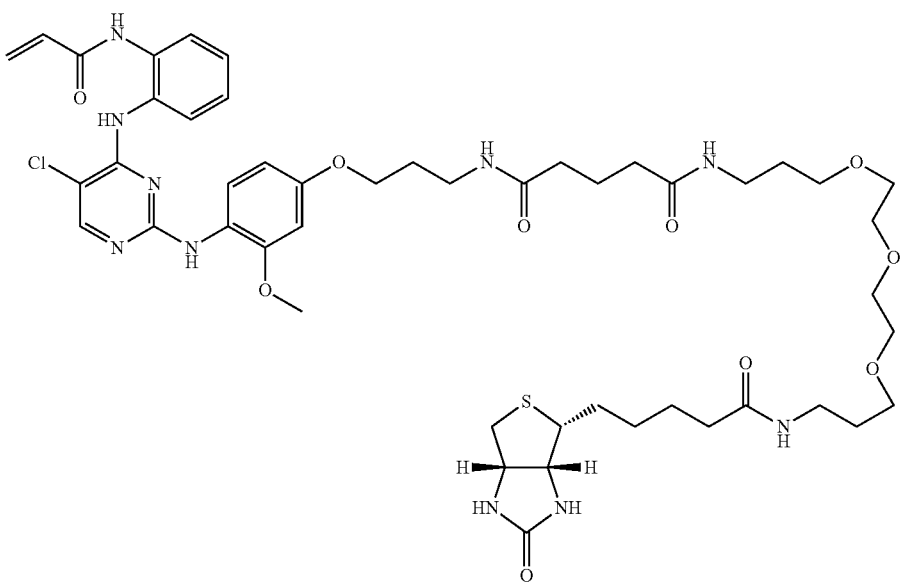 [SMILES: C=CC(=O)Nc1ccccc1Nc1nc(Nc2ccc(OCCCNC(=O)CCCC(=O)NCCCOCCOCCOCCCNC(=O)CCCC[C@H]3SC[C@H]4NC(=O)N[C@H]43)cc2OC)ncc1Cl]

$N^1$-(3-(4-((4-((2-acrylamidophenyl)amino)-5-chloropyrimidin-2-yl)amino)-3-methoxyphenoxy)propyl)-$N^5$-(15-oxo-19-((3aR,4R,6aS)-2-oxohexahydro-1H-thieno[3,4-d]imidazol-4-yl)-4,7,10-trioxa-14-azanonadecyl)glutaramide Compound I-302 was prepared in a manner similar to Compound I-299, substituting 4-fluoro-2-methoxy-1-nitrobenzene for 2-fluoro-4-methyl-5-nitrobenzamide. MS m/z 1011.3 (ES+, M+H).

Compound I-303

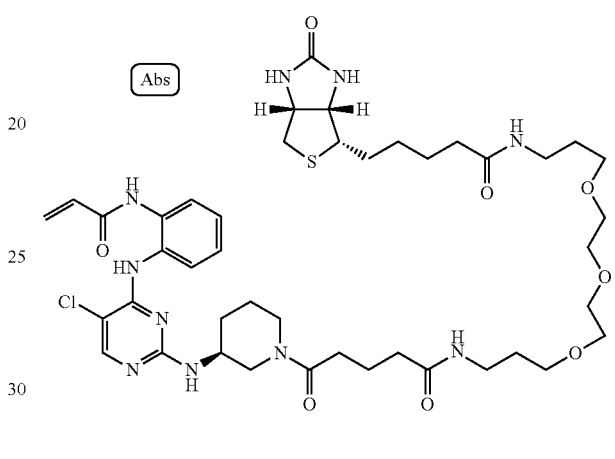

5-((S)-3-((4-((2-acrylamidophenyl)amino)-5-chloropyrimidin-2-yl)amino)piperidin-1-yl)-5-oxo-N-(15-oxo-19-((3aS,4S,6aR)-2-oxohexahydro-1H-thieno[3,4-d]imidazol-4-yl)-4,7,10-trioxa-14-azanonadecyl)pentanamide Compound I-303 was prepared similar to Compound I-299 via amide formation between I-126 and commercially available 20-atom biotin acid in the presence of HATU, DIPEA in DMA. MS m/z 915.3 (ES+, M+H).

Compound I-304

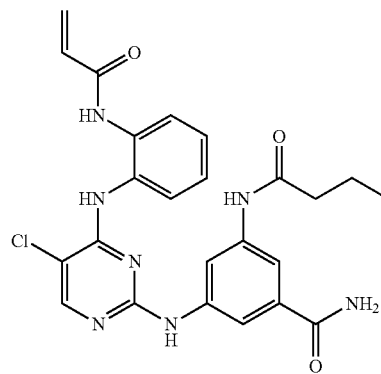

N[1]-(3-((4-((2-acrylamidophenyl)amino)-5-chloropyrimidin-2-yl)amino)-5-carbamoylphenyl)-N[5]-(15-oxo-19-((3aS,4S,6aR)-2-oxohexahydro-1H-thieno[3,4-d]imidazol-4-yl)-4,7,10-trioxa-14-azanonadecyl)glutaramide Compound I-304 was prepared in a manner similar to Compound I-299 via amide formation between 3-((4-((2-acrylamidophenyl)amino)-5-chloropyrimidin-2-yl)amino)-5-aminobenzamide and commercially available 20-atom biotin acid in the presence of HATU, DIPEA in DMA. MS m/z 967.1 (ES+, M+H).

Compound I-305

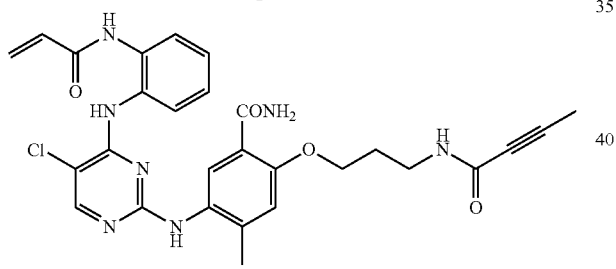

5-((4-((2-acrylamidophenyl)amino)-5-chloropyrimidin-2-yl)amino)-2-(3-(but-2-ynamido)propoxy)-4-methylbenzamide Compound I-305 was prepared in a manner similar to Example 162, substituting tert-butyl (3-(4-amino-2-carbamoyl-5-methylphenoxy)propyl) carbamate for 3-amino-4-methylbenzamide, followed by Boc-deprotection with TFA and amide formation with but-2-ynoic acid, HATU, DIPEA in DMA. MS m/z 562.2 (ES+, M+H).

Compound I-306

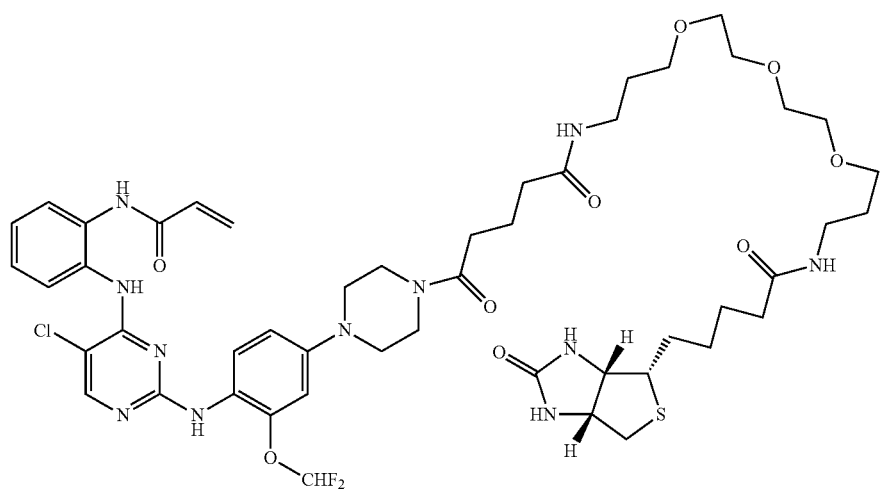 [SMILES: C=CC(=O)Nc1ccccc1Nc1nc(Nc2ccc(N3CCN(C(=O)CCCC(=O)NCCCOCCOCCOCCCNC(=O)CCCC[C@@H]4SC[C@@H]5NC(=O)N[C@@H]54)CC3)cc2OC(F)F)ncc1Cl]

5-(4-(4-((4-((2-acrylamidophenyl)amino)-5-chloro-pyrimidin-2-yl)amino)-3-(difluoromethoxy)phenyl)piperazin-1-yl)-5-oxo-N-(15-oxo-19-((3aS,4S,6aR)-2-oxohexahydro-1H-thieno[3,4-d]imidazol-4-yl)-4,7,10-trioxa-14-azanonadecyl)pentanamide Compound I-306 was prepared in a manner similar to Compound I-299, using I-142 for the starting material, then coupled with commercially available 20-atom biotin acid in the presence of HATU, DIPEA in DMA. MS m/z 1170.3 (ES+, M+H).

Example 303

Compound I-307

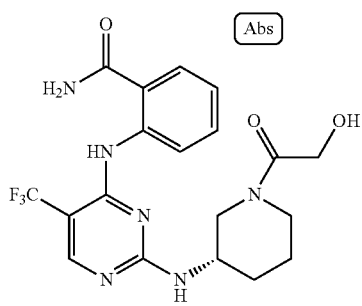 [SMILES: NC(=O)c1ccccc1Nc1nc(N[C@H]2CCCN(C(=O)CO)C2)ncc1C(F)(F)F]

(S)-2-((2-((1-(2-hydroxyacetyl)piperidin-3-yl)amino)-5-(trifluoromethyl) pyrimidin-4-yl)amino)benzamide The title compound was prepared in a manner similar to Compound I-15, using 2-amino aniline as the starting material. MS: m/z 439.2 (ES+, M+H); (CD$_3$OD) δ 1.42 (m, 1H), 1.50-170 (m, 2H), 1.84-1.88 (m, 1H), 2.0-2.09 (m, 1H), 2.98-3.13 (m, 2H), 3.59-3.69 (m, 1H), 3.88-4.09 (m, 1H), 4.11-4.12 (m, 1H), 4.27 (s, 2H), 7.13 (t, J=7.8 Hz, 1H), 7.51 (t, J=7.4 Hz, 1H), 7.73-7.75 (m, 1H), 8.26 (br s, 1H), 8.69 (m, 1H).

Compound I-308

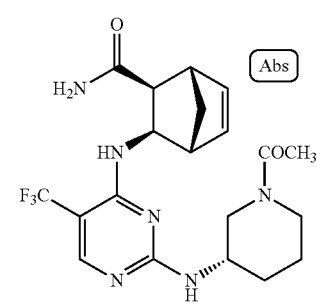 [SMILES: CC(=O)N1CCC[C@H](Nc2ncc(C(F)(F)F)c(N[C@H]3[C@@H](C(N)=O)[C@@H]4C=C[C@H]3C4)n2)C1]

(1S,2S,3R,4R)-3-((2-(((S)-1-acetylpiperidin-3-yl)amino)-5-(trifluoromethyl) pyrimidin-4-yl)amino)bicyclo[2.2.1]hept-5-ene-2-carboxamide The title compound was prepared as described in Example 1, by substituting (1S,2S,3R,4R)-3-aminobicyclo[2.2.1]hept-5-ene-2-carboxamide for N-(2-aminophenyl)acrylamide. MS m/z: 439.1 (ES+, M+H).

Compound I-309

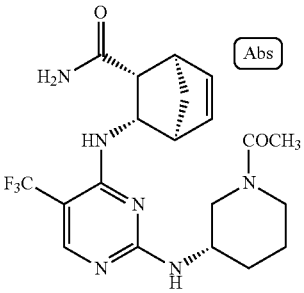 [SMILES: CC(=O)N1CCC[C@H](Nc2ncc(C(F)(F)F)c(N[C@@H]3[C@H](C(N)=O)[C@H]4C=C[C@@H]3C4)n2)C1]

(1R,2R,3S,4S)-3-((2-(((S)-1-acetylpiperidin-3-yl)amino)-5-(trifluoromethyl) pyrimidin-4-yl)amino)bicyclo[2.2.1]hept-5-ene-2-carboxamide The title compound was prepared as described in Example 1, by substituting (1R,2R,3 S,4S)-3-aminobicyclo[2.2.1]hept-5-ene-2-carboxamide for N-(2-aminophenyl)acrylamide. MS m/z: 439.1 (ES+, M+H).

Compound I-310

(S)-2-hydroxy-1-(3-((4-((2-(isopropylsulfonyl)phenyl)amino)-5-(trifluoromethyl) pyrimidin-2-yl)amino)piperidin-1-yl)ethanone The title compound was prepared as described in Example 1, by substituting 2-(isopropylsulfonyl)aniline for N-(2-aminophenyl)acrylamide. MS m/z: 502.1 (ES+, M+H).

Compound I-311

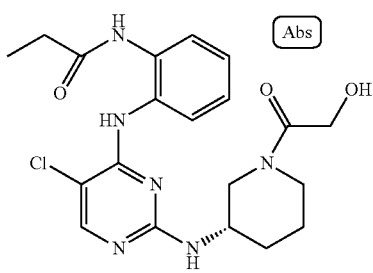 [SMILES: CCC(=O)Nc1ccccc1Nc1nc(N[C@H]2CCCN(C(=O)CO)C2)ncc1Cl]

(S)—N-(2-((5-chloro-2-((1-(2-hydroxyacetyl)piperidin-3-yl)amino)pyrimidin-4-yl)amino)phenyl)propionamide The title compound was made by the palladium mediated hydrogenation over I-123. MS m/z: 433.2 (ES+, M+H); ¹HNMR (DMSO-$d_6$) δ 2.16 (s, 3H), 5.77-5.80 (dd, 1H, J=1.9 Hz and J=10 Hz), 6.26-6.31 (dd, 1H, J=1.9, 17 Hz), 6.40-6.47 (dd, 1H, J=10, 17 Hz), 7.08 (br s, 1H), 7.10-7.1615 (t, 1H, J=7, 16 Hz), 7.24-7.26 (d, 1H, J=7.9 Hz), 7.60-7.62 (dd, 2H, J=1.5, 7.8 Hz), 7.86 (s, 1H), 8.21 (s, 1H), 8.28 (s, 1H), 9.13 (s, 1H), 10.28 (s, 1H), 12.81 (s, 1H)

Compound I-312

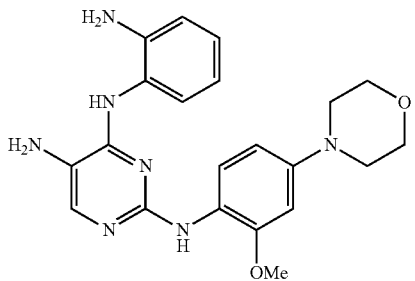 [SMILES: COc1cc(N2CCOCC2)ccc1Nc1ncc(N)c(Nc2ccccc2N)n1]

$N^4$-(2-aminophenyl)-$N^2$-(2-methoxy-4-morpholinophenyl)pyrimidine-2,4,5-triamine The title compound was prepared in a manner similar to Example 162, using tert-butyl (2-aminophenyl)carbamate as the starting material, and substituting 2-methoxy-4-morpholinoaniline for 3-amino-4-methylbenzamide, and finally Boc deprotection with TFA. MS m/z: 408.2 (ES+, M+H); ¹HNMR (DMSO-$d_6$) δ 3.01 (t, J=4.5 Hz, 4H), 3.72 (t, J=4.5 Hz, 4H), 3.77 (s, 3H), 4.50 (br s, 2H), 4.92 (br s, 2H), 6.24-6.27 (dd, J=2.3, 8.8 Hz, 1H), 6.57-6.60 (m, 2H), 6.62 (d, J=1.2 Hz, 1H), 6.78 (dd, J=1.1, 7.9 Hz, 1H), 6.98 (t, J=7.5 Hz, 1H), 7.20 (d, J=7.8 Hz, 1H), 7.39 (s, 1H), 7.70 (s, 1H), 8.15 (s, 1H).

Compound I-313

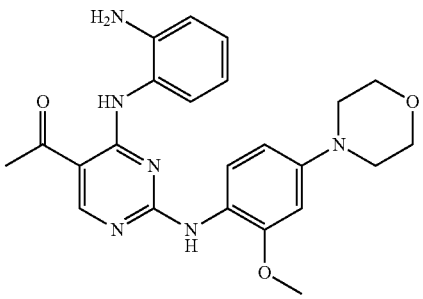 [SMILES: COc1cc(N2CCOCC2)ccc1Nc1ncc(C(C)=O)c(Nc2ccccc2N)n1]

1-(4-((2-aminophenyl)amino)-2-((2-methoxy-4-morpholinophenyl)amino) pyrimidin-5-yl)ethanone Compound I-313 was prepared in a manner similar to I-273, substituting tert-butyl (2-aminophenyl)carbamate for the starting material, and finally Boc deprotection with TFA. MS m/z: 435.3 (ES+, M+H); ¹HNMR (CDCl₃) δ 2.54 (s, 3H), 3.08 (t, J=4.5 Hz, 4H), 3.85 (br s, 2H), 3.86-3.87 (m, 7H), 6.19 (br s, 1H), 6.45 (d, J=2.0 Hz, 1H), 6.82 (d, J=1.2 Hz, 1H), 6.85 (d, J=7.6 Hz, 1H), 7.14 (t, J=7.4 Hz, 1H), 7.39 (d, J=7.6 Hz, 1H), 7.78 (br s, 1H), 8.01 (br s, 1H), 8.67 (s, 1H), 10.77 (s, 1H).

Compound I-314

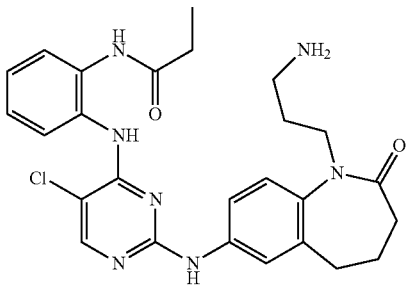 [SMILES: CCC(=O)Nc1ccccc1Nc1nc(Nc2ccc3c(c2)CCCC(=O)N3CCCN)ncc1Cl]

N-(2-((2-((1-(3-aminopropyl)-2-oxo-2,3,4,5-tetrahydro-1H-benzo[b]azepin-7-yl)amino)-5-chloropyrimidin-4-yl)amino)phenyl)propionamide Compound I-148 (20 mg) was hydrogenated in 4 mL of methanol with 5 mg of 10% palladium on charcoal under hydrogen. After stirring 30 min at rt, the catalyst was filtered out, and the desired product was obtained after solvent removal. MS m/z: 508.2 (ES+, M+H).

Compound I-315

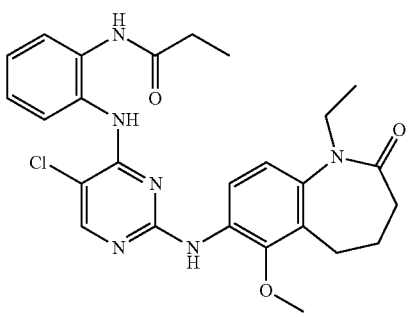 [SMILES: CCC(=O)Nc1ccccc1Nc1nc(Nc2ccc3c(c2OC)CCCC(=O)N3CC)ncc1Cl]

N-(2-((5-chloro-2-((1-ethyl-6-methoxy-2-oxo-2,3,4,5-tetrahydro-1H-benzo[b]azepin-7-yl)amino)pyrimidin-4-yl)amino)phenyl)propionamide Compound I-315 was prepared in a manner similar to Example 162, substituting 7-amino-6-methoxy-1-(ethyl)-4,5-dihydro-1H-benzo[b]azepin-2(3H)-one for 3-amino-4-methylbenzamide, which was then hydrogenated in 4 mL of methanol with 5 mg of 10% palladium on charcoal under hydrogen. After stirring 30 min at rt, the catalyst was filtered out, and the desired product was obtained after solvent removal. MS m/z: 509.1 (ES+, M+H).

Compound I-316

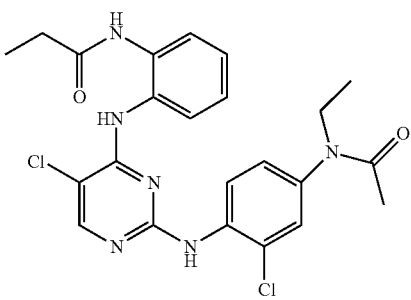

N-(2-((5-chloro-2-((2-cyano-4-(N-ethylacetamido)
phenyl)amino)pyrimidin-4-yl)amino)phenyl)propio-
namide Compound I-316 was prepared in a manner similar to Example 162, substituting N-(4-amino-3-cyanophenyl)-N-ethylacetamide for 3-amino-4-methylbenzamide, which was hydrogenated in 4 mL of methanol with 5 mg of 10% palladium on charcoal under hydrogen. After stirring 30 min at rt, the catalyst was filtered out, and the desired product was obtained after solvent removal. MS m/z: 478.3 (ES+, M+H).

Compound I-317

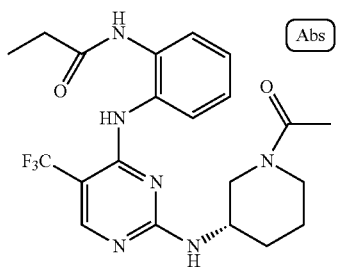 [SMILES: CCC(=O)Nc1ccccc1Nc1nc(N[C@H]2CCCN(C(C)=O)C2)ncc1C(F)(F)F]

(S)—N-(2-((2-((1-acetylpiperidin-3-yl)amino)-5-
(trifluoromethyl)pyrimidin-4-yl)amino)phenyl)pro-
pionamide Compound I-317 was prepared by Pd-catalyzed hydrogenation of compound I-10. MS m/z: 451.1 (ES+, M+H).

Compound I-318

I-318

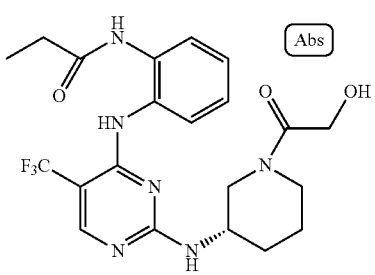

(S)—N-(2-((2-((1-(2-hydroxyacetyl)piperidin-3-yl)
amino)-5-(trifluoromethyl) pyrimidin-4-yl)amino)
phenyl)propionamide Compound I-318 was prepared by Pd-catalyzed hydrogenation of compound I-15. MS: m/z 467.1 (ES+, M+H).

Example 304

I-321

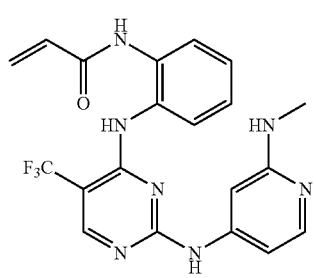

N-(2-((2-((2-(methylamino)pyridin-4-yl)amino)-5-
(trifluoromethyl)pyrimidin-4-yl)amino)phenyl)acryl-
amide Compound I-321 was prepared in a manner similar to Example 68, substituting $N^2$-methylpyridine-2,4-diamine for 3-amino-4-methylbenzamide. MS m/z 430.1 (ES+, M+H).

Example 305

I-322

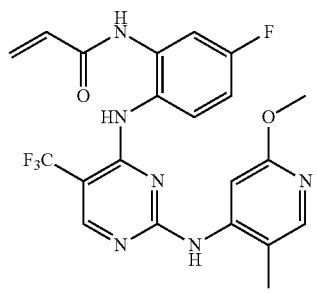

N-(5-fluoro-2-((2-((2-methoxy-5-methylpyridin-4-
yl)amino)-5-(trifluoromethyl) pyrimidin-4-yl)amino)
phenyl)acrylamide Compound I-322 was prepared in a manner similar to Example 68, substituting N-(2-amino-5-fluorophenyl)acrylamide for N-(2-aminophenyl)acrylamide, and substituting 2-methoxy-5-methylpyridin-4-amine for 3-amino-4-methylbenzamide. MS m/z 463.5 (ES+, M+H).

Example 306

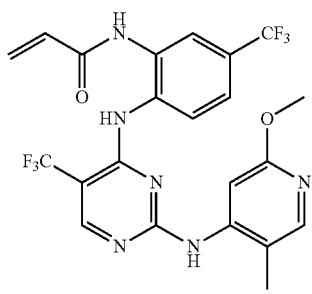

I-323

N-(2-((2-((2-methoxy-5-methylpyridin-4-yl)amino)-5-(trifluoromethyl)pyrimidin-4-yl)amino)-5-(trifluoromethyl)phenyl)acrylamide Compound I-323 was prepared in a manner similar to Example 68, substituting N-(2-amino-5-(trifluoromethyl)phenyl)acrylamide for N-(2-aminophenyl)acrylamide, and substituting 2-methoxy-5-methylpyridin-4-amine for 3-amino-4-methylbenzamide. MS m/z 513.2 (ES+, M+H).

Example 307

I-324

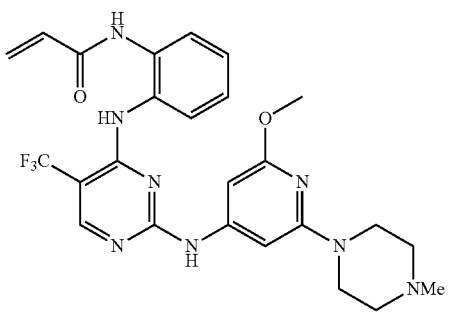

N-(2-((2-((2-methoxy-6-(4-methylpiperazin-1-yl)pyridin-4-yl)amino)-5-(trifluoromethyl)pyrimidin-4-yl)amino)phenyl)acrylamide Compound I-324 was prepared in a manner similar to Example 68, substituting 2-methoxy-6-(4-methylpiperazin-1-yl)pyridin-4-amine for 3-amino-4-methylbenzamide. MS m/z 529.6 (ES+, M+H).

Example 308

I-325

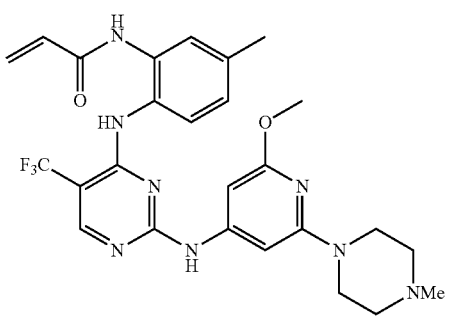

N-(2-((2-((2-methoxy-6-(4-methylpiperazin-1-yl)pyridin-4-yl)amino)-5-(trifluoromethyl)pyrimidin-4-yl)amino)-5-methylphenyl)acrylamide Compound I-325 was prepared in a manner similar to Example 68, substituting N-(2-amino-5-methylphenyl)acrylamide for N-(2-aminophenyl)acrylamide, and substituting 2-methoxy-6-(4-methylpiperazin-1-yl)pyridin-4-amine for 3-amino-4-methylbenzamide. MS m/z 543.2 (ES+, M+H).

Example 309

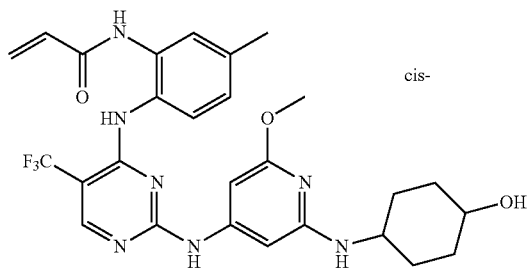

I-326 cis-

N-(2-((2-((2-((cis-4-hydroxycyclohexyl)amino)-6-methoxypyridin-4-yl)amino)-5-(trifluoromethyl)pyrimidin-4-yl)amino)-5-methylphenyl)acrylamide Compound I-326 was prepared in a manner similar to Example 68, substituting N-(2-amino-5-methylphenyl)acrylamide for N-(2-aminophenyl)acrylamide, and substituting cis-4-((4-amino-6-methoxypyridin-2-yl)amino)cyclohexanol for 3-amino-4-methylbenzamide. MS m/z 558.2 (ES+, M+H).

Example 310

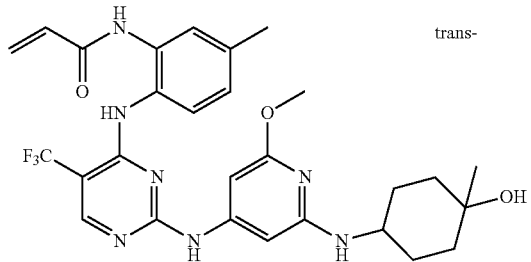

I-327 trans-

N-(2-((2-((2-((trans-4-hydroxy-4-methylcyclohexyl)amino)-6-methoxypyridin-4-yl)amino)-5-(trifluoromethyl)pyrimidin-4-yl)amino)-5-methylphenyl)acrylamide Compound I-327 was prepared in a manner similar to Example 68, substituting N-(2-amino-5-methylphenyl)acrylamide for N-(2-aminophenyl)acrylamide, and substituting trans-4-((4-amino-6-methoxypyridin-2-yl)amino)-1-methylcyclohexanol for 3-amino-4-methylbenzamide. MS m/z 572.3 (ES+, M+H).

Example 311

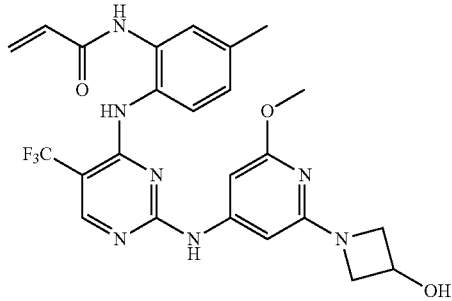

I-328

N-(2-((2-((2-(3-hydroxyazetidin-1-yl)-6-methoxypyridin-4-yl)amino)-5-(trifluoromethyl)pyrimidin-4-yl)amino)-5-methylphenyl)acrylamide Compound I-328 was prepared in a manner similar to Example 68, substituting N-(2-amino-5-methylphenyl)acrylamide for N-(2-aminophenyl)acrylamide, and substituting 1-(4-amino-6-methoxypyridin-2-yl)azetidin-3-ol for 3-amino-4-methylbenzamide. MS m/z 516.2 (ES+, M+H).

Example 312

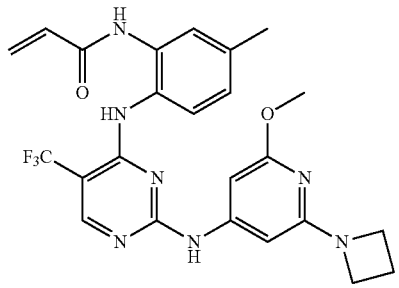

I-329

N-(2-((2-((2-(azetidin-1-yl)-6-methoxypyridin-4-yl)amino)-5-(trifluoromethyl)pyrimidin-4-yl)amino)-5-methylphenyl)acrylamide Compound I-329 was prepared in a manner similar to Example 68, substituting N-(2-amino-5-methylphenyl)acrylamide for N-(2-aminophenyl)acrylamide, and substituting 2-(azetidin-1-yl)-6-methoxypyridin-4-amine for 3-amino-4-methylbenzamide. MS m/z 500.1 (ES+, M+H).

Example 313

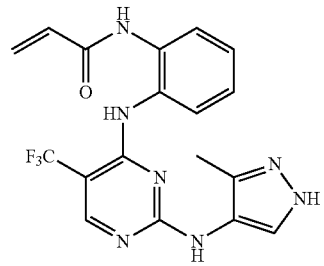

I-330

N-(2-((2-((3-methyl-1H-pyrazol-4-yl)amino)-5-(trifluoromethyl)pyrimidin-4-yl)amino)phenyl)acrylamide Compound I-330 was prepared in a manner similar to Example 68, substituting 3-methyl-1H-pyrazol-4-amine for 3-amino-4-methylbenzamide. MS m/z 404.1 (ES+, M+H).

Example 314

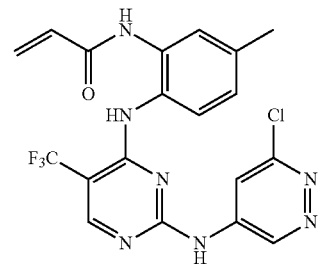

I-331

N-(2-((2-((6-chloropyridazin-4-yl)amino)-5-(trifluoromethyl)pyrimidin-4-yl)amino)-5-methylphenyl)acrylamide Compound I-331 was prepared in a manner similar to Example 68, substituting N-(2-amino-5-methylphenyl)acrylamide for N-(2-aminophenyl)acrylamide, and substituting 6-chloropyridazin-4-amine for 3-amino-4-methylbenzamide. MS m/z 450.1 (ES+, M+H).

Example 315

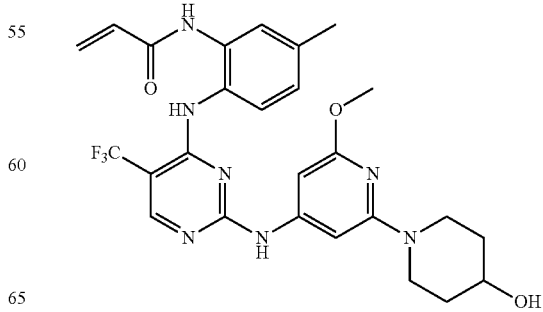

I-332

N-(2-((2-((2-(4-hydroxypiperidin-1-yl)-6-methoxy-pyridin-4-yl)amino)-5-(trifluoromethyl)pyrimidin-4-yl)amino)-5-methylphenyl)acrylamide Compound I-332 was prepared in a manner similar to Example 68, substituting N-(2-amino-5-methylphenyl)acrylamide for N-(2-aminophenyl)acrylamide, and substituting 1-(4-amino-6-methoxypyridin-2-yl)piperidin-4-ol for 3-amino-4-methylbenzamide. MS m/z 544.3 (ES+, M+H).

Example 316

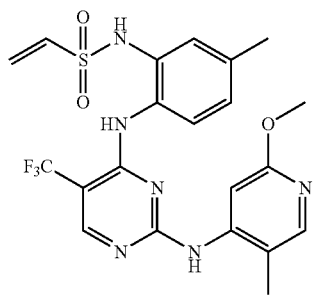

I-333

N-(2-((2-((2-methoxy-5-methylpyridin-4-yl)amino)-5-(trifluoromethyl)pyrimidin-4-yl)amino)-5-methylphenyl)ethenesulfonamide Compound I-333 was prepared in a manner similar to Example 116, substituting 2-methoxy-5-methylpyridin-4-amine for 3-amino-4-methylbenzamide, and substituting tert-butyl (2-aminophenyl)carbamate for N-(2-aminophenyl)acrylamide, followed by deprotection with TFA and reaction with 2-chloroethylsulfonyl chloride. MS m/z 495.5 (ES+, M+H).

Example 317

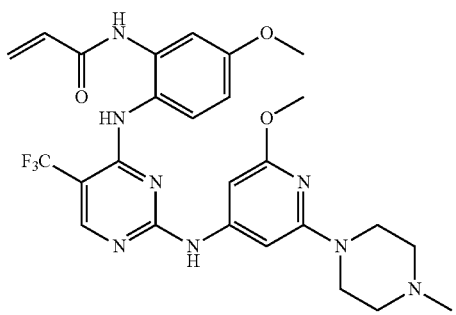

I-334

N-(5-methoxy-2-((2-((2-methoxy-6-(4-methylpiperazin-1-yl)pyridin-4-yl)amino)-5-(trifluoromethyl)pyrimidin-4-yl)amino)phenyl)acrylamide Compound I-334 was prepared in a manner similar to Example 68, substituting N-(2-amino-5-methoxyphenyl)acrylamide for N-(2-aminophenyl)acrylamide, and substituting 2-methoxy-6-(4-methylpiperazin-1-yl)pyridin-4-amine for 3-amino-4-methylbenzamide. MS m/z 557.4 (ES+, M+H).

Example 318

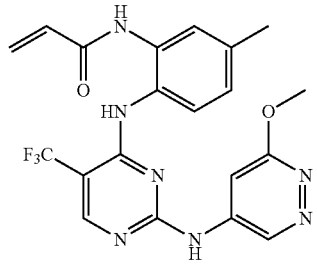

I-335

N-(2-((2-((6-methoxypyridazin-4-yl)amino)-5-(trifluoromethyl)pyrimidin-4-yl)amino)-5-methylphenyl)acrylamide Compound I-335 was prepared in a manner similar to Example 68, substituting N-(2-amino-5-methylphenyl)acrylamide for N-(2-aminophenyl)acrylamide, and substituting 6-methoxypyridazin-4-amine for 3-amino-4-methylbenzamide. MS m/z 446.1 (ES+, M+H).

Example 319

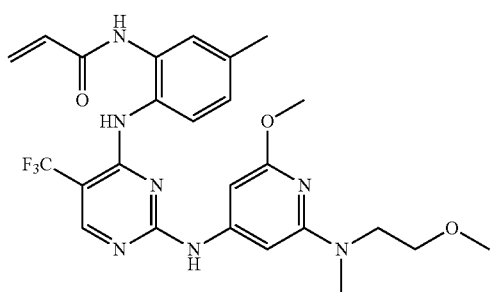

I-336

N-(2-((2-((2-methoxy-6-((2-methoxyethyl)(methyl)amino)pyridin-4-yl)amino)-5-(trifluoromethyl)pyrimidin-4-yl)amino)-5-methylphenyl)acrylamide Compound I-336 was prepared in a manner similar to Example 68, substituting N-(2-amino-5-methylphenyl)acrylamide for N-(2-aminophenyl)acrylamide, and substituting 6-methoxy-$N^2$-(2-methoxyethyl)-$N^2$-methylpyridine-2,4-diamine for 3-amino-4-methylbenzamide. MS m/z 532.3 (ES+, M+H).

Example 320

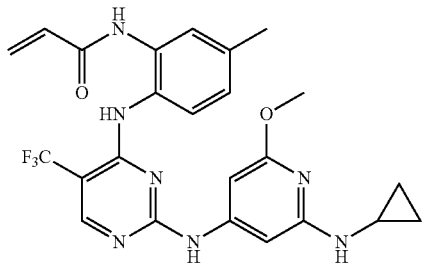

I-337

N-(2-((2-((2-(cyclopropylamino)-6-methoxypyridin-4-yl)amino)-5-(trifluoromethyl)pyrimidin-4-yl)amino)-5-methylphenyl)acrylamide Compound I-337 was prepared in a manner similar to Example 68, substituting N-(2-amino-5-methylphenyl)acrylamide for N-(2-aminophenyl)acrylamide, and substituting $N^2$-cyclopropyl-6-methoxypyridine-2,4-diamine for 3-amino-4-methylbenzamide. MS m/z 500.2 (ES+, M+H).

Example 321

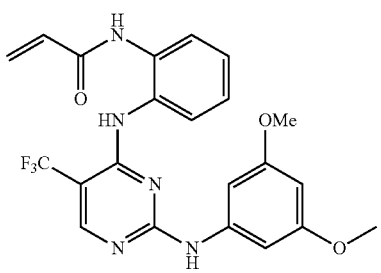

I-338

N-(2-((2-((3,5-dimethoxyphenyl)amino)-5-(trifluoromethyl)pyrimidin-4-yl)amino)phenyl)acrylamide Compound I-338 was prepared in a manner similar to Example 68, substituting 3,5-dimethoxyaniline for 3-amino-4-methylbenzamide. MS m/z 460.5 (ES+, M+H).

Example 322

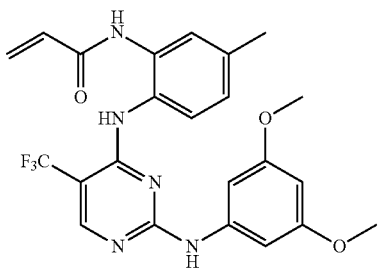

I-339

N-(2-((2-((3,5-dimethoxyphenyl)amino)-5-(trifluoromethyl)pyrimidin-4-yl)amino)-5-methylphenyl)acrylamide Compound I-339 was prepared in a manner similar to Example 68, substituting N-(2-amino-5-methylphenyl)acrylamide for N-(2-aminophenyl)acrylamide, and substituting 3,5-dimethoxyaniline for 3-amino-4-methylbenzamide. MS m/z 474.2 (ES+, M+H).

Example 323

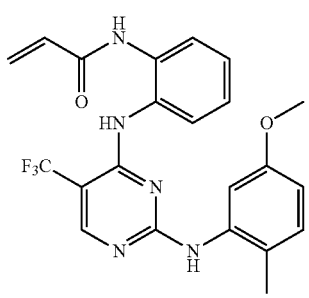

I-340

N-(2-((2-((5-methoxy-2-methylphenyl)amino)-5-(trifluoromethyl)pyrimidin-4-yl)amino)phenyl)acrylamide Compound I-338 was prepared in a manner similar to Example 68, substituting 5-methoxy-2-methylaniline for 3-amino-4-methylbenzamide. MS m/z 444.2 (ES+, M+H).

Example 324

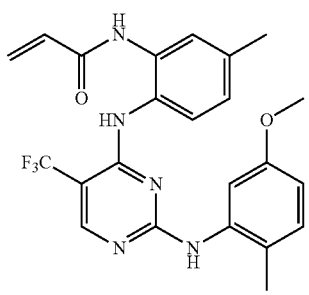

I-341

N-(2-((2-((5-methoxy-2-methylphenyl)amino)-5-(trifluoromethyl)pyrimidin-4-yl)amino)-5-methylphenyl)acrylamide Compound I-341 was prepared in a manner similar to Example 68, substituting N-(2-amino-5-methylphenyl)acrylamide for N-(2-aminophenyl)acrylamide, and substituting 5-methoxy-2-methylaniline for 3-amino-4-methylbenzamide. MS m/z 458.2 (ES+, M+H).

Example 325

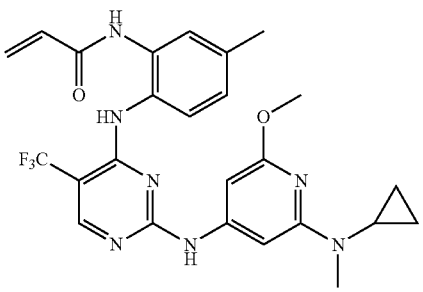

I-342

N-(2-((2-((2-(cyclopropyl(methyl)amino)-6-methoxypyridin-4-yl)amino)-5-(trifluoromethyl)pyrimidin-4-yl)amino)-5-methylphenyl)acrylamide Compound I-342 was prepared in a manner similar to Example 68, substituting N-(2-amino-5-methylphenyl)acrylamide for N-(2-aminophenyl)acrylamide, and substituting $N^2$-cyclopropyl-6-methoxy-$N^2$-methylpyridine-2,4-diamine for 3-amino-4-methylbenzamide. MS m/z 514.3 (ES+, M+H).

Example 326

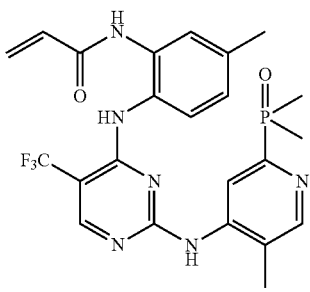

I-343

N-(2-((2-((2-(dimethylphosphoryl)-5-methylpyridin-4-yl)amino)-5-(trifluoromethyl)pyrimidin-4-yl)amino)-5-methylphenyl)acrylamide Compound I-343 was prepared in a manner similar to Example 68, substituting N-(2-amino-5-methylphenyl)acrylamide for N-(2-aminophenyl)acrylamide, and substituting (4-amino-5-methylpyridin-2-yl)dimethylphosphine oxide for 3-amino-4-methylbenzamide. MS m/z 505.3 (ES+, M+H).

Example 327

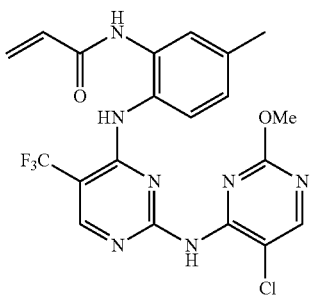

I-344

N-(2-((2-((5-chloro-2-methoxypyrimidin-4-yl)amino)-5-(trifluoromethyl) pyrimidin-4-yl)amino)-5-methylphenyl)acrylamide Compound I-344 was prepared in a manner similar to Example 68, substituting N-(2-amino-5-methylphenyl)acrylamide for N-(2-aminophenyl)acrylamide, and substituting 5-chloro-2-methoxypyrimidin-4-amine for 3-amino-4-methylbenzamide. MS m/z 480.2 (ES+, M+H).

Example 328

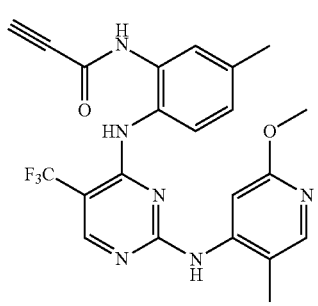

I-345

N-(2-((2-((2-methoxy-5-methylpyridin-4-yl)amino)-5-(trifluoromethyl)pyrimidin-4-yl)amino)-5-methylphenyl)propiolamide Compound I-345 was prepared in a manner similar to Example 116, substituting 2-methoxy-5-methylpyridin-4-amine for 3-amino-4-methylbenzamide, and substituting tert-butyl (2-aminophenyl)carbamate for N-(2-aminophenyl)acrylamide, followed by deprotection with TFA and amide coupling with propiolic acid in the presence of HATU and DIPEA. MS m/z 457.2 (ES+, M+H).

Example 329

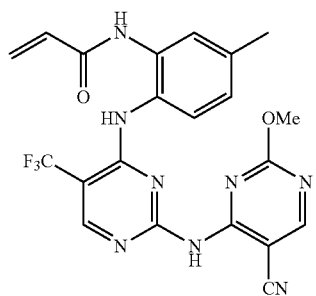

I-346

N-(2-((2-((5-cyano-2-methoxypyrimidin-4-yl)amino)-5-(trifluoromethyl) pyrimidin-4-yl)amino)-5-methylphenyl)acrylamide Compound I-346 was prepared in a manner similar to Example 68, substituting N-(2-amino-5-methylphenyl)acrylamide for N-(2-aminophenyl)acrylamide, and substituting 4-amino-2-methoxypyrimidine-5-carbonitrile for 3-amino-4-methylbenzamide. MS m/z 471.2 (ES+, M+H).

Example 330

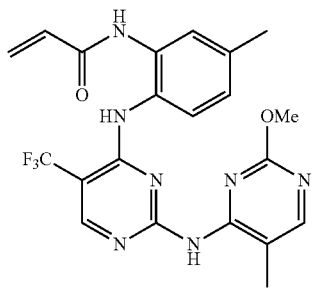

I-347

N-(2-((2-((2-methoxy-5-methylpyrimidin-4-yl)amino)-5-(trifluoromethyl) pyrimidin-4-yl)amino)-5-methylphenyl)acrylamide Compound I-347 was prepared in a manner similar to Example 68, substituting N-(2-amino-5-methylphenyl)acrylamide for N-(2-aminophenyl)acrylamide, and substituting 2-methoxy-5-methylpyrimidin-4-amine for 3-amino-4-methylbenzamide. MS m/z 460.3 (ES+, M+H).

Example 331

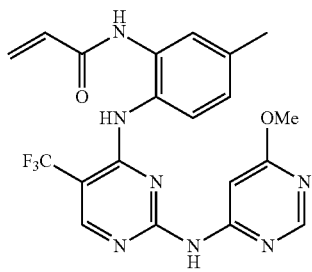

I-348

N-(2-((2-((6-methoxypyrimidin-4-yl)amino)-5-(trifluoromethyl)pyrimidin-4-yl)amino)-5-methylphenyl)acrylamide Compound I-348 was prepared in a manner similar to Example 68, substituting N-(2-amino-5-methylphenyl)acrylamide for N-(2-aminophenyl)acrylamide, and substituting 6-methoxypyrimidin-4-amine for 3-amino-4-methylbenzamide. MS m/z 446.1 (ES+, M+H).

Example 332

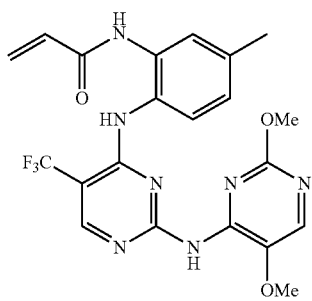

I-349

N-(2-((2-((2,5-dimethoxypyrimidin-4-yl)amino)-5-(trifluoromethyl)pyrimidin-4-yl)amino)-5-methylphenyl)acrylamide Compound I-349 was prepared in a manner similar to Example 68, substituting N-(2-amino-5-methylphenyl)acrylamide for N-(2-aminophenyl)acrylamide, and substituting 2,5-dimethoxypyrimidin-4-amine for 3-amino-4-methylbenzamide. MS m/z 476.1 (ES+, M+H).

Example 333

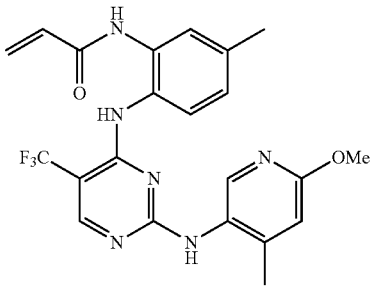

I-350

N-(2-((2-((6-methoxy-4-methylpyridin-3-yl)amino)-5-(trifluoromethyl)pyrimidin-4-yl)amino)-5-methylphenyl)acrylamide Compound I-350 was prepared in a manner similar to Example 68, substituting N-(2-amino-5-methylphenyl)acrylamide for N-(2-aminophenyl)acrylamide, and substituting 6-methoxy-4-methylpyridin-3-amine for 3-amino-4-methylbenzamide. MS m/z 459.2 (ES+, M+H).

Example 334

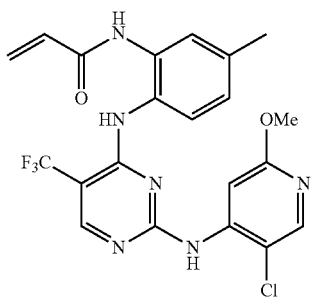

I-351

N-(2-((2-((5-chloro-2-methoxypyridin-4-yl)amino)-5-(trifluoromethyl)pyrimidin-4-yl)amino)-5-methylphenyl)acrylamide Compound I-351 was prepared in a manner similar to Example 68, substituting N-(2-amino-5-methylphenyl)acrylamide for N-(2-aminophenyl)acrylamide, and substituting 5-chloro-2-methoxypyridin-4-amine for 3-amino-4-methylbenzamide. MS m/z 479.1 (ES+, M+H).

Example 335

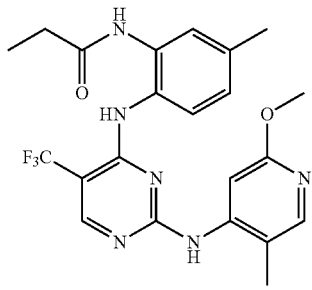

I-352

N-(2-((2-((2-methoxy-5-methylpyridin-4-yl)amino)-5-(trifluoromethyl)pyrimidin-4-yl)amino)-5-methylphenyl)propionamide Compound I-352 was prepared by Pd-catalyzed hydrogenation of compound I-90. MS: m/z 469.1 (ES+, M+H).

Example 336

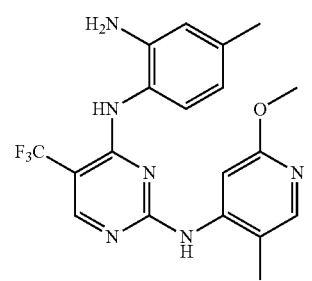

I-353

$N^4$-(2-amino-4-methylphenyl)-$N^2$-(2-methoxy-5-methylpyridin-4-yl)-5-(trifluoromethyl)pyrimidine-2,4-diamine The title compound was prepared in a manner similar to Example 116, substituting tert-butyl (2-amino-5-methylphenyl)carbamate for tert-butyl (2-amino-5-methylphenyl)carbamate, substituting 2-methoxy-5-methylpyridin-4-amine for 3-amino-4-methylbenzamide, and followed by Boc deprotection with TFA. MS m/z: 405.2 (ES+, M+H); $^1$HNMR (DMSO-$d_6$) δ 8.45 (s, 1H), 8.32 (br s, 2H), 7.74 (s, 1H), 7.12 (s, 1H), 6.86 (d, 1H, J=8.0 Hz), 6.39 (d, 1H, J=8.0 Hz), 4.60 (s, 2H), 3.70 (s, 3H), 2.70 (s, 3H), 2.59 (s, 3H).

Example 337

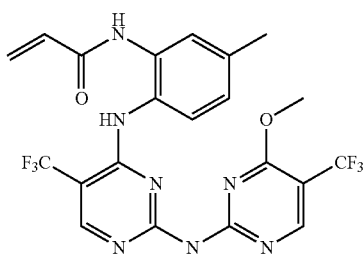

I-354

N-(2-((2-((4-methoxy-5-(trifluoromethyl)pyrimidin-2-yl)amino)-5-(trifluoro methyl)pyrimidin-4-yl)amino)-5-methylphenyl)acrylamide Compound I-354 was prepared in a manner similar to Example 68, substituting N-(2-amino-5-methylphenyl)acrylamide for N-(2-aminophenyl)acrylamide, and substituting 4-methoxy-5-(trifluoromethyl)pyrimidin-2-amine for 3-amino-4-methylbenzamide. MS m/z 514.1 (ES+, M+H).

Example 338

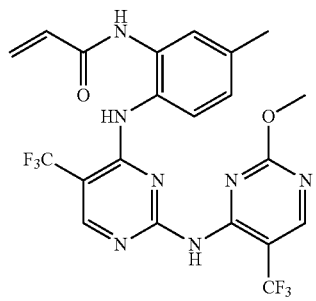

I-355

N-(2-((2-((2-methoxy-5-(trifluoromethyl)pyrimidin-4-yl)amino)-5-(trifluoromethyl)pyrimidin-4-yl)amino)-5-methylphenyl)acrylamide Compound I-355 was prepared in a manner similar to Example 68, substituting N-(2-amino-5-methylphenyl)acrylamide for N-(2-aminophenyl)acrylamide, and substituting 2-methoxy-5-(trifluoromethyl)pyrimidin-4-amine for 3-amino-4-methylbenzamide. MS m/z 514.1 (ES+, M+H).

Example 339

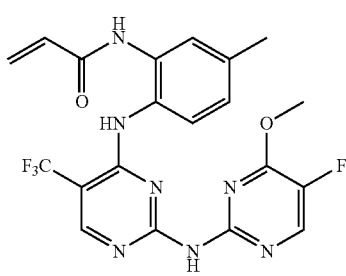

I-356

N-(2-((2-((5-fluoro-4-methoxypyrimidin-2-yl)amino)-5-(trifluoromethyl) pyrimidin-4-yl)amino)-5-methylphenyl)acrylamide Compound I-356 was prepared in a manner similar to Example 68, substituting N-(2-amino-5-methylphenyl)acrylamide for N-(2-aminophenyl)acrylamide, and substituting 5-fluoro-4-methoxypyrimidin-2-amine for 3-amino-4-methylbenzamide. MS m/z 464.1 (ES+, M+H).

Example 340

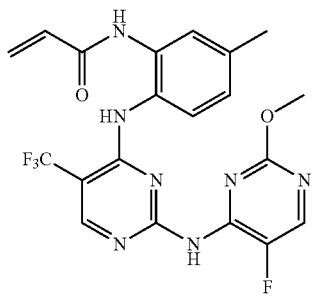

I-357

N-(2-((2-((5-fluoro-2-methoxypyrimidin-4-yl)amino)-5-(trifluoromethyl) pyrimidin-4-yl)amino)-5-methylphenyl)acrylamide Compound I-357 was prepared in a manner similar to Example 68, substituting N-(2-amino-5-methylphenyl)acrylamide for N-(2-aminophenyl)acrylamide, and substituting 5-fluoro-2-methoxypyrimidin-4-amine for 3-amino-4-methylbenzamide. MS m/z 464.1 (ES+, M+H).

Example 341

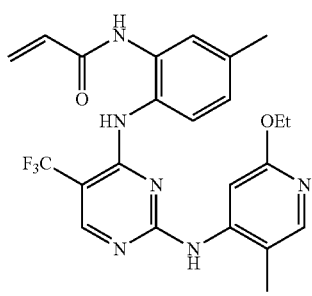

I-358

N-(2-((2-((2-ethoxy-5-methylpyridin-4-yl)amino)-5-(trifluoromethyl)pyrimidin-4-yl)amino)-5-methylphenyl)acrylamide Compound I-358 was prepared in a manner similar to Example 68, substituting N-(2-amino-5-methylphenyl)acrylamide for N-(2-aminophenyl)acrylamide, and substituting 2-ethoxy-5-methylpyridin-4-amine for 3-amino-4-methylbenzamide. MS m/z 473.5 (ES+, M+H).

Example 342

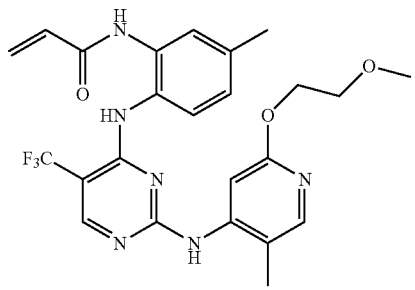

I-359

N-(2-((2-((2-(2-methoxyethoxy)-5-methylpyridin-4-yl)amino)-5-(trifluoromethyl) pyrimidin-4-yl)amino)-5-methylphenyl)acrylamide Compound I-359 was prepared in a manner similar to Example 68, substituting N-(2-amino-5-methylphenyl)acrylamide for N-(2-aminophenyl)acrylamide, and substituting 2-(2-methoxyethoxy)-5-methylpyridin-4-amine for 3-amino-4-methylbenzamide. MS m/z 503.2 (ES+, M+H).

Example 343

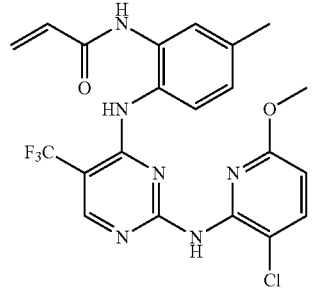

I-360

N-(2-((2-((3-chloro-6-methoxypyridin-2-yl)amino)-5-(trifluoromethyl)pyrimidin-4-yl)amino)-5-methylphenyl)acrylamide Compound I-360 was prepared in a manner similar to Example 68, substituting N-(2-amino-5-methylphenyl)acrylamide for N-(2-aminophenyl)acrylamide, and substituting 3-chloro-6-methoxypyridin-2-amine for 3-amino-4-methylbenzamide. MS m/z 479.2 (ES+, M+H).

Example 344

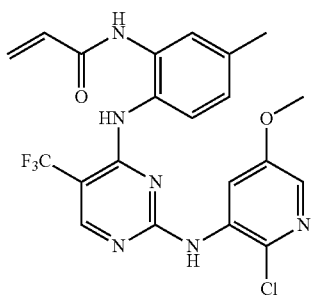

I-361

N-(2-((2-((2-chloro-5-methoxypyridin-3-yl)amino)-5-(trifluoromethyl)pyrimidin-4-yl)amino)-5-methylphenyl)acrylamide Compound I-361 was prepared in a manner similar to Example 68, substituting N-(2-amino-5-methylphenyl)acrylamide for N-(2-aminophenyl)acrylamide, and substituting 2-chloro-5-methoxypyridin-3-amine for 3-amino-4-methylbenzamide. MS m/z 479.1 (ES+, M+H).

Example 345

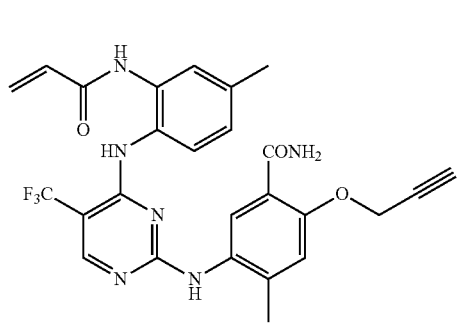

I-362

5-((4-((2-acrylamido-4-methylphenyl)amino)-5-(trifluoromethyl)pyrimidin-2-yl)amino)-4-methyl-2-(prop-2-yn-1-yloxy)benzamide Compound I-362 was prepared in a manner similar to Example 68, substituting N-(2-amino-5-methylphenyl)acrylamide for N-(2-aminophenyl)acrylamide, and substituting 5-amino-4-methyl-2-(prop-2-yn-1-yloxy)benzamide for 3-amino-4-methylbenzamide. MS m/z 491.1 (ES+, M+H).

Example 346

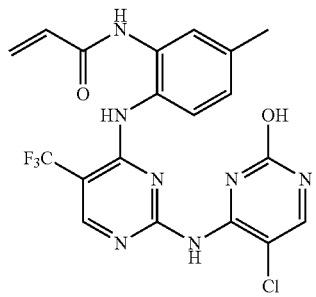

I-363

N-(2-((2-((5-chloro-2-hydroxypyrimidin-4-yl)amino)-5-(trifluoromethyl) pyrimidin-4-yl)amino)-5-methylphenyl)acrylamide 50 mg of I-344 was treated with 1M solution of BBr$_3$ in dichloromethane (4 equiv.) at 40° C. for 16 hr. After evaporation of solvent, the residue was treated with DBU (10 equiv.) in dichlorometane for 3 hr. The reaction mixture was subject to a aqueous work up and the extracted product was purified by prep-HPLC, giving 10 mg of white powder as I-363. MS m/z 466.1 (ES+, M+H).

Example 347

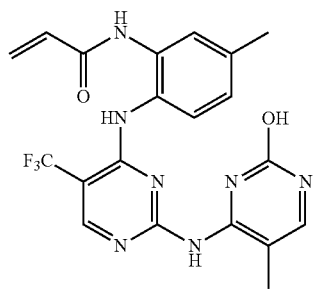

I-364

N-(2-((2-((2-hydroxy-5-methylpyrimidin-4-yl)amino)-5-(trifluoromethyl) pyrimidin-4-yl)amino)-5-methylphenyl)acrylamide Compound I-364 was prepared in a manner similar to Example 346, substituting starting material I-347 for I-344. MS m/z 446.1 (ES+, M+H).

Example 348

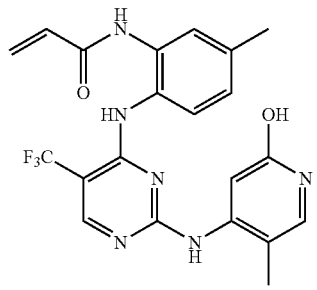

I-365

N-(2-((2-((2-hydroxy-5-methylpyridin-4-yl)amino)-5-(trifluoromethyl)pyrimidin-4-yl)amino)-5-methylphenyl)acrylamide Compound I-365 was prepared in a manner similar to Example 346, substituting starting material I-90 for I-344. MS m/z 445.2 (ES+, M+H).

Example 349

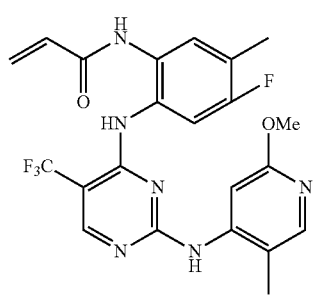

I-366

533

N-(4-fluoro-2-((2-((2-methoxy-5-methylpyridin-4-yl)amino)-5-(trifluoromethyl) pyrimidin-4-yl)amino)-5-methylphenyl)acrylamide Compound I-366 was prepared in a manner similar to Example 68, substituting N-(2-amino-4-fluoro-5-methylphenyl)acrylamide for N-(2-aminophenyl)acrylamide, and substituting 2-methoxy-5-methylpyridin-4-amine for 3-amino-4-methylbenzamide. MS m/z 477.2 (ES+, M+H).

Example 350

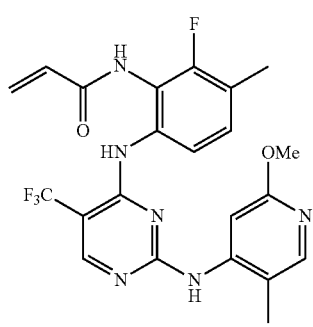

I-367

N-(2-fluoro-6-((2-((2-methoxy-5-methylpyridin-4-yl)amino)-5-(trifluoromethyl) pyrimidin-4-yl)amino)-3-methylphenyl)acrylamide Compound I-367 was prepared in a manner similar to Example 68, substituting N-(6-amino-2-fluoro-3-methylphenyl)acrylamide for N-(2-aminophenyl)acrylamide, and substituting 2-methoxy-5-methylpyridin-4-amine for 3-amino-4-methylbenzamide. MS m/z 477.1 (ES+, M+H).

Example 351

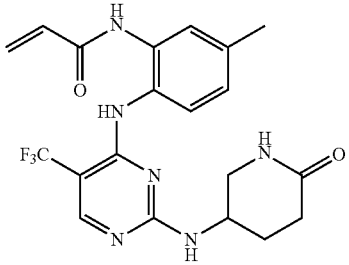

I-368

Rac-N-(5-methyl-2-((2-((6-oxopiperidin-3-yl)amino)-5-(trifluoromethyl)pyrimidin-4-yl)amino)phenyl)acrylamide Compound I-368 was prepared in a manner similar to Example 1, substituting rac-5-aminopiperidin-2-one for (S)-tert-butyl 3-aminopiperidine-1-carboxylate, and N-(2-amino-5-methylphenyl)acrylamide for N-(2-aminophenyl)acrylamide. MS m/z: 435.2 (ES+, M+H).

534
Example 352

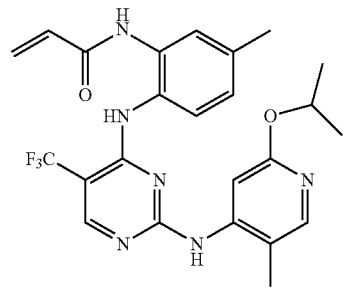

I-369

N-(2-((2-((2-isopropoxy-5-methylpyridin-4-yl)amino)-5-(trifluoromethyl)pyrimidin-4-yl)amino)-5-methylphenyl)acrylamide Compound I-369 was prepared in a manner similar to Example 68, substituting 2-isopropoxy-5-methylpyridin-4-amine for 3-amino-4-methylbenzamide, and substituting N-(2-amino-5-methylphenyl)acrylamide for N-(2-aminophenyl)acrylamide. MS: m/z 487.1 (ES+, M+H). $^1$HNMR (DMSO-$d_6$) δ 1.27 (d, J=6.1 Hz, 6H), 2.27 (s, 3H), 5.15 (br s, 1H), 6.54 (br s, 1H), 6.84 (br s, 3H), 7.11 (br s, 2H), 7.74 (br s, 2H), 8.19 (br s, 2H), 8.30 (br s, 1H), 9.58 (s, 1H).

Example 353

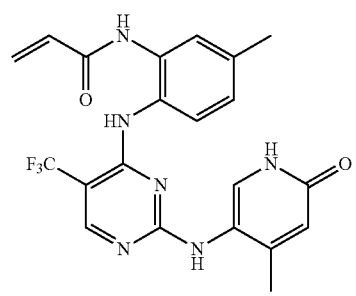

I-370

N-(5-methyl-2-((2-((4-methyl-6-oxo-1,6-dihydropyridin-3-yl)amino)-5-(trifluoromethyl) pyrimidin-4-yl)amino)phenyl)acrylamide Compound I-370 was prepared in a manner similar to Example 68, substituting 5-amino-4-methylpyridin-2(1H)-one for 3-amino-4-methylbenzamide, and N-(2-amino-5-methylphenyl)acrylamide for N-(2-aminophenyl)acrylamide. MS: m/z 445.2 (ES+, M+H). $^1$HNMR (DMSO-$d_6$) δ 1.92 (s, 3H), 2.26 (s, 3H), 5.78 (d, J=9.9 Hz, 1H), 6.14 (s, 1H), 6.28 (d, J=17.2 Hz, 1H), 6.39-6.46 (dd, J=10.1, 16.6 Hz, 1H), 6.96-7.08 (m, 2H), 7.19 (s, 1H), 7.45-7.54 (m, 1H), 8.11 (s, 1H), 8.20 (s, 1H), 8.69-8.71 (m, 1H), 10.21 (s, 1H), 11.29 (s, 1H).

Example 354

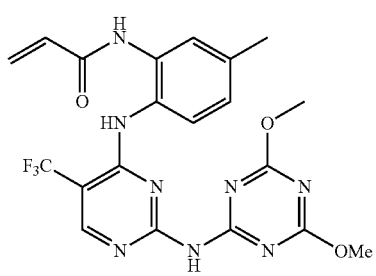

I-371

N-(2-((2-((4,6-dimethoxy-1,3,5-triazin-2-yl)amino)-5-(trifluoromethyl)pyrimidin-4-yl)amino)-5-methyl-phenyl)acrylamide Compound I-371 was prepared in a manner similar to Example 68, substituting 4,6-dimethoxy-1,3,5-triazin-2-amine for 3-amino-4-methylbenzamide, and N-(2-amino-5-methylphenyl)acrylamide for N-(2-aminophenyl)acrylamide. MS: m/z 477.2 (ES+, M+H). $^1$HNMR (DMSO-d$_6$) δ 2.29 (s, 3H), 3.84 (s, 6H), 5.78 (d, J=10.2 Hz, 1H), 6.28 (d, J=16.0 Hz, 1H), 6.39-6.46 (dd, J=9.7, 16.5 Hz, 1H), 7.04 (s, 2H), 7.94 (d, J=8.6 Hz, 1H), 8.48 (s, 1H), 8.55 (s, 1H), 10.24 (s, 1H), 10.65 (s, 1H).

Example 355

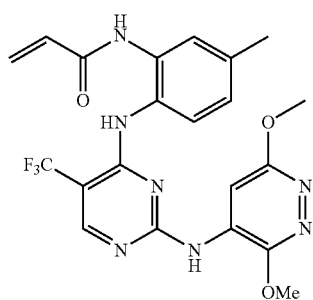

I-372

N-(2-((2-((3,6-dimethoxypyridazin-4-yl)amino)-5-(trifluoromethyl)pyrimidin-4-yl)amino)-5-methyl-phenyl)acrylamide Compound I-372 was prepared in a manner similar to Example 68, substituting 3,6-dimethoxypyridazin-4-amine for 3-amino-4-methylbenzamide, and N-(2-amino-5-methylphenyl)acrylamide for N-(2-aminophenyl)acrylamide. MS: m/z 476.2 (ES+, M+H). $^1$HNMR (DMSO-d$_6$) δ 2.38 (s, 3H), 3.86 (s, 3H), 3.97 (s, 3H), 5.76-5.79 (dd, J=1.8, 10.0 Hz, 1H), 6.25-6.30 (dd, J=1.9, 17.0 Hz, 1H), 6.39-6.46 (dd, J=10.0, 17.0 Hz, 1H), 7.15 (d, J=8.2 Hz, 1H), 7.19 (s, 1H), 7.32 (s, 1H), 7.46 (d, J=8.1 Hz, 1H), 8.33 (s, 1H), 8.45 (s, 1H), 8.55 (s, 1H), 10.22 (s, 1H).

Example 356

I-373

N-(5-methyl-2-((2-((2-methyl-5-(1H-1,2,4-triazol-3-yl)phenyl)amino)-5-(trifluoromethyl) pyrimidin-4-yl)amino)phenyl)acrylamide Compound I-373 was prepared in a manner similar to Example 68, substituting 2-methyl-5-(1H-1,2,4-triazol-3-yl)aniline for 3-amino-4-methylbenzamide, and N-(2-amino-5-methylphenyl)acrylamide for N-(2-aminophenyl)acrylamide. MS: m/z 495.2 (ES+, M+H). $^1$HNMR (DMSO-d$_6$) δ 2.09 (s, 3H), 2.16 (s, 3H), 5.76-5.79 (dd, J=1.8, 10.0 Hz, 1H), 6.24-6.29 (dd, J=1.9, 17.0 Hz, 1H), 6.38-6.45 (dd, J=10.0, 16.9 Hz, 1H), 6.91 (s, 1H), 7.23-7.25 (m, 1H), 7.47 (br s, 1H), 7.68 (br s, 1H), 7.95 (br s, 1H), 8.03 (br s, 1H), 8.12 (br s, 1H), 8.26 (s, 1H), 8.61 (br s, 1H), 9.07-9.13 (m, 1H), 10.19 (s, 1H), 14.05 (s, 0.50H), 14.25 (s, 0.35H).

Example 357

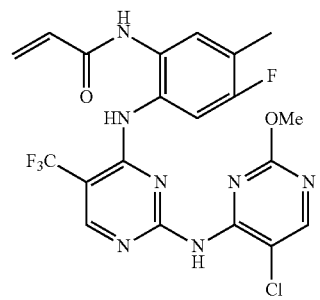

I-374

N-(2-((2-((5-chloro-2-methoxypyrimidin-4-yl)amino)-5-(trifluoromethyl)pyrimidin-4-yl)amino)-4-fluoro-5-methylphenyl)acrylamide Compound I-374 was prepared in a manner similar to Example 68, substituting 5-chloro-2-methoxypyrimidin-4-amine for 3-amino-4-methylbenzamide, and N-(2-amino-4-fluoro-5-methylphenyl)acrylamide for N-(2-aminophenyl)acrylamide. MS: m/z 498.1 (ES+, M+H). $^1$HNMR (DMSO-d$_6$) δ 2.19 (s, 3H), 3.81 (s, 3H), 5.80 (d, J=10.3 Hz, 1H), 6.29 (d, J=17.0 Hz, 1H), 6.38-6.45 (dd, J=10.0, 17.0 Hz, 1H), 7.11 (d, J=7.8 Hz, 1H), 7.56 (d, J=11.4 Hz, 1H), 8.47 (s, 1H), 8.49 (s, 2H), 10.24 (d, J=4.0 Hz, 2H).

Example 358

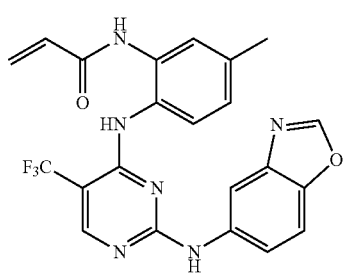

I-375

N-(2-((2-(benzo[d]oxazol-5-ylamino)-5-(trifluoromethyl)pyrimidin-4-yl)amino)-5-methylphenyl)acrylamide Compound I-375 was prepared in a manner similar to Example 68, substituting benzo[d]oxazol-5-amine for 3-amino-4-methylbenzamide, and N-(2-amino-5-methylphenyl)acrylamide for N-(2-aminophenyl)acrylamide. MS: m/z 455.1 (ES+, M+H).

Example 359

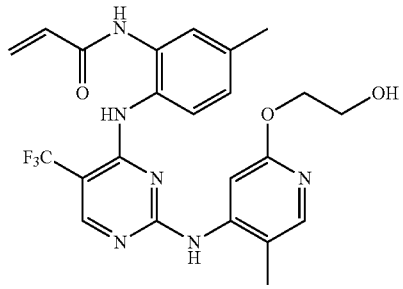

I-376

N-(2-((2-((2-(2-hydroxyethoxy)-5-methylpyridin-4-yl)amino)-5-(trifluoromethyl)pyrimidin-4-yl)amino)-5-methylphenyl)acrylamide Compound I-376 was prepared in a manner similar to Example 68, substituting 2-((4-amino-5-methylpyridin-2-yl)oxy)ethanol for 3-amino-4-methylbenzamide, and N-(2-amino-5-methylphenyl)acrylamide for N-(2-aminophenyl)acrylamide. MS: m/z 489.2 (ES+, M+H). $^1$HNMR (DMSO-$d_6$) δ 2.10 (s, 3H), 2.31 (s, 3H), 3.71 (t, J=5.2 Hz, 2H), 4.17 (t, J=5.3 Hz, 2H), 4.80 (br s, 1H), 5.77-5.80 (dd, J=1.8, 10.0 Hz, 1H), 6.26-6.31 (dd, J=1.8, 16.9 Hz, 1H), 6.40-6.47 (dd, J=10.1, 17.0 Hz, 1H), 7.06 (s, 1H), 7.18 (d, J=10.3 Hz, 2H), 7.56 (d, J=8.2 Hz, 1H), 7.78 (s, 1H), 8.37 (s, 2H), 8.70 (s, 1H), 10.26 (s, 1H). 9.07-9.13 (m, 1H), 10.19 (s, 1H), 14.05 (s, 0.50H), 14.25 (s, 0.35H).

Example 360

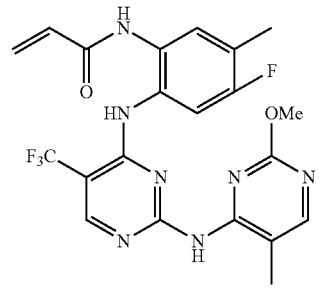

I-377

N-(4-fluoro-2-((2-((2-methoxy-5-methylpyrimidin-4-yl)amino)-5-(trifluoromethyl) pyrimidin-4-yl)amino)-5-methylphenyl)acrylamide Compound I-377 was prepared in a manner similar to Example 68, substituting 2-methoxy-5-methylpyrimidin-4-amine for 3-amino-4-methylbenzamide, and N-(2-amino-4-fluoro-5-methylphenyl)acrylamide for N-(2-aminophenyl)acrylamide. MS: m/z 478.2 (ES+, M+H). $^1$HNMR (DMSO-$d_6$) δ 2.00 (s, 3H), 2.18 (s, 3H), 3.78 (s, 3H), 5.79 (d, J=10.0 Hz, 1H), 6.28 (dd, J=1.8, 17.2 Hz, 1H), 6.41 (dd, J=10.1, 17.0 Hz, 1H), 7.10 (d, J=8.0 Hz, 1H), 7.59 (d, J=11.3 Hz, 1H), 8.22 (s, 1H), 8.38 (s, 1H), 8.43 (s, 1H), 9.88 (s, 1H), 10.21 (s, 1H).

Example 361

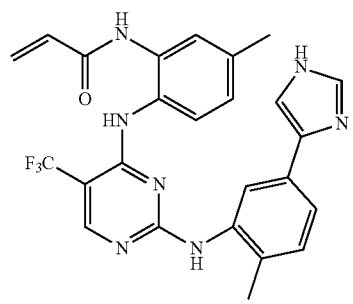

I-378

N-(2-((2-((5-(1H-imidazol-4-yl)-2-methylphenyl)amino)-5-(trifluoromethyl)pyrimidin-4-yl)amino)-5-methylphenyl)acrylamide Compound I-378 was prepared in a manner similar to Example 68, substituting 5-(1H-imidazol-4-yl)-2-methylaniline for 3-amino-4-methylbenzamide, and N-(2-amino-5-methylphenyl)acrylamide for N-(2-aminophenyl)acrylamide. MS: m/z 494.2 (ES+, M+H). $^1$HNMR (DMSO-$d_6$) δ 2.10 (s, 6H), 5.75-5.78 (dd, J=1.9, 12.0 Hz, 1H), 6.24-6.29 (dd, J=1.7, 16.9 Hz, 1H), 6.38-6.45 (dd, J=10.0, 17.0 Hz, 1H), 6.90 (br s, 1H), 7.10 (d, J=7.8 Hz, 1H), 7.13-7.15 (m, 0.27H), 7.29-7.33 (m, 0.46H), 7.47 (d, J=7.8 Hz, 1H), 7.54-7.55 (m, 2H), 7.70 (d, J=9.5 Hz, 2H), 8.08 (s, 1H), 8.23 (s, 1H), 8.97 (br s, 1H), 10.19 (s, 1H), 12.10 (s, 0.62H), 12.42 (s, 0.17H).

Example 362

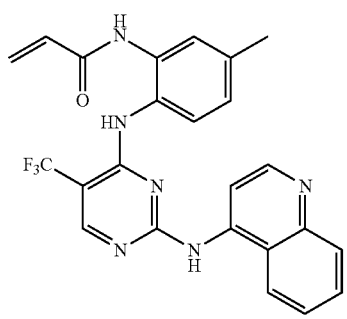

I-379

N-(5-methyl-2-((2-(quinolin-4-ylamino)-5-(trifluoromethyl)pyrimidin-4-yl)amino)phenyl) acrylamide Compound I-379 was prepared in a manner similar to Example 68, substituting quinolin-4-amine for 3-amino-4-methylbenzamide, and N-(2-amino-5-methylphenyl)acrylamide for N-(2-aminophenyl)acrylamide. MS: m/z 465.1 (ES+, M+H).

Example 363

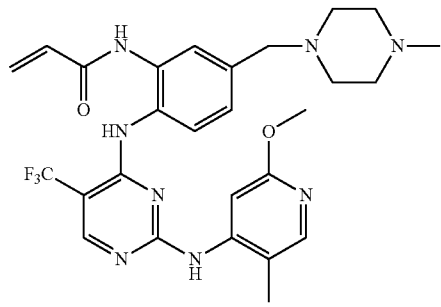

I-380

N-(2-((2-((2-methoxy-5-methylpyridin-4-yl)amino)-5-(trifluoromethyl)pyrimidin-4-yl)amino)-5-((4-methylpiperazin-1-yl)methyl)phenyl)acrylamide Compound I-380 was prepared in a manner similar to Example 68, substituting 2-methoxy-5-methylpyridin-4-amine for 3-amino-4-methylbenzamide, and N-(2-amino-5-((4-methylpiperazin-1-yl)methyl)phenyl) acrylamide for N-(2-aminophenyl)acrylamide. MS: m/z 555.3 (ES−, M−H). $^1$HNMR (DMSO-d$_6$) δ 2.08 (s, 3H), 2.16 (s, 3H), 2.37 (m, 8H), 3.44 (s, 2H), 3.76 (s, 3H), 5.79 (d, J=8.5 Hz, 1H), 6.29 (d, J=15.5 Hz, 1H), 6.41 (d, J=9.6 Hz, 1H), 7.07-7.19 (m, 3H), 7.61 (d, J=6.9 Hz, 1H), 7.79 (br s, 1H), 8.37 (s, 1H), 8.41 (s, 1H), 8.79 (br s, 1H), 10.32 (br s, 1H).

Example 364

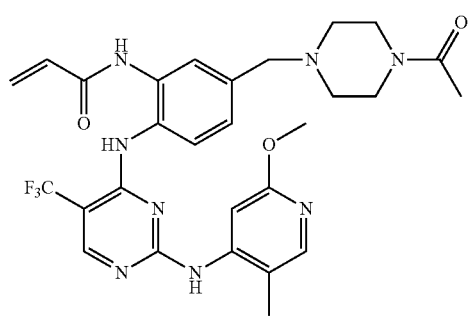

I-381

N-(5-((4-acetylpiperazin-1-yl)methyl)-2-((2-((2-methoxy-5-methylpyridin-4-yl)amino)-5-(trifluoromethyl)pyrimidin-4-yl)amino)phenyl)acrylamide Compound I-381 was prepared in a manner similar to Example 68, substituting 2-methoxy-5-methylpyridin-4-amine for 3-amino-4-methylbenzamide, and tert-butyl 4-(3-acrylamido-4-aminobenzyl)piperazine-1-carboxylate for N-(2-aminophenyl)acrylamide. After Boc-deprotection with TFA, the resulting amine was acylated with acetyl chloride to yield desired compound I-381. MS: m/z 585.2 (ES+, M+H). $^1$HNMR (DMSO-d$_6$) δ 1.97 (s, 3H), 2.09 (s, 3H), 2.31 (m, 2H), 2.37 (m, 2H), 3.41 (m, 4H), 3.49 (m, 2H), 3.77 (s, 3H), 5.79 (d, J=10.4 Hz, 1H), 6.29 (d, J=16.6 Hz, 1H), 6.42 (dd, J=10.0, 17.7 Hz, 1H), 7.10 (s, 1H), 7.19 (d, J=8.8 Hz, 1H), 7.22 (s, 1H), 7.62 (d, J=8.1 Hz, 1H), 7.79 (s, 1H), 8.37 (s, 1H), 8.42 (s, 1H), 8.81 (s, 1H), 10.33 (s, 1H).

Example 365

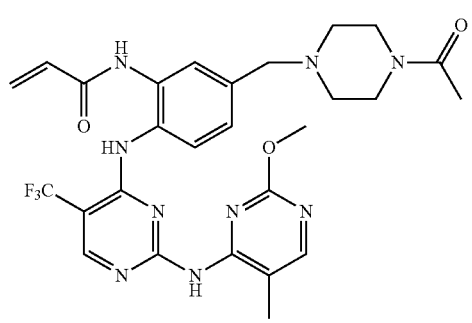

I-382

N-(5-((4-acetylpiperazin-1-yl)methyl)-2-((2-((2-methoxy-5-methylpyrimidin-4-yl)amino)-5-(trifluoromethyl)pyrimidin-4-yl)amino)phenyl)acrylamide Compound I-382 was prepared in a manner similar to Example 68, substituting 2-methoxy-5-methylpyrimidin-4-amine for 3-amino-4-methylbenzamide, and tert-butyl 4-(3-acrylamido-4-aminobenzyl)piperazine-1-carboxylate for N-(2-aminophenyl)acrylamide. After Boc-deprotection with TFA, the resulting amine was acylated with acetyl chloride to yield desired compound I-382. MS: m/z 586.3 (ES+, M+H). ¹HNMR (DMSO-d₆) δ 1.97 (s, 3H), 1.98 (s, 3H), 2.27 (m, 2H), 2.35 (m, 2H), 3.40-3.44 (m, 6H), 3.83 (s, 3H), 5.80 (d, J=11.4 Hz, 1H), 6.27-6.31 (dd, J=1.7, 17.0 Hz, 1H), 6.40-6.46 (dd, J=10.2, 17.0 Hz, 1H), 7.04 (d, J=8.1 Hz, 1H), 7.14 (s, 1H), 7.76 (d, J=8.3 Hz, 1H), 8.19 (s, 1H), 8.41 (s, 1H), 8.48 (s, 1H), 9.81 (s, 1H), 10.32 (s, 1H).

Example 366

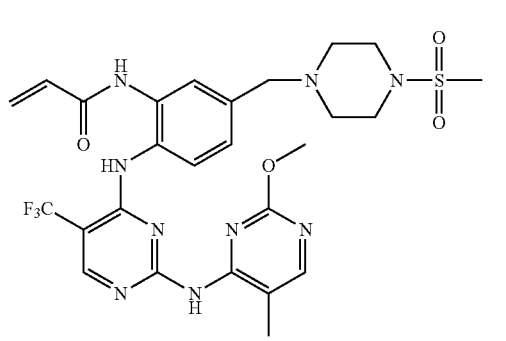

I-383

N-(2-((2-((2-methoxy-5-methylpyrimidin-4-yl)amino)-5-(trifluoromethyl)pyrimidin-4-yl)amino)-5-((4-(methylsulfonyl)piperazin-1-yl)methyl)phenyl)acrylamide Compound I-383 was prepared in a manner similar to Example 365, substituting methanesulfonyl chloride for acetyl chloride in the final step. MS: m/z 622.2 (ES+, M+H). ¹HNMR (DMSO-d₆) δ 1.98 (s, 3H), 2.49 (m, 4H), 2.87 (s, 3H), 3.10 (m, 4H), 3.48 (s, 2H), 3.83 (s, 3H), 5.78-5.81 (dd, J=1.6, 10.0 Hz, 1H), 6.27-6.31 (dd, J=1.8, 17.0 Hz, 1H), 6.40-6.47 (dd, J=10.2, 17.2 Hz, 1H), 7.03-7.05 (dd, J=1.4, 8.2 Hz, 1H), 7.15 (s, 1H), 7.76 (d, J=8.3 Hz, 1H), 8.19 (s, 1H), 8.41 (s, 1H), 8.48 (s, 1H), 9.81 (s, 1H), 10.35 (s, 1H).

Example 367

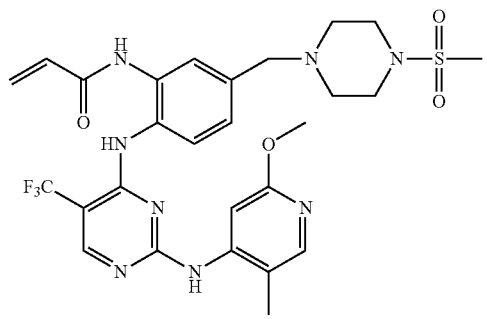

I-384

N-(2-((2-((2-methoxy-5-methylpyridin-4-yl)amino)-5-(trifluoromethyl)pyrimidin-4-yl)amino)-5-((4-(methylsulfonyl)piperazin-1-yl)methyl)phenyl)acrylamide Compound I-384 was prepared in a manner similar to Example 364, substituting methanesulfonyl chloride for acetyl chloride in the final step. MS: m/z 621.3 (ES+, M+H). ¹HNMR (DMSO-d₆) δ 2.09 (s, 3H), 2.49 (m, 4H), 2.86 (s, 3H), 3.10 (m, 4H), 3.52 (s, 2H), 3.77 (s, 3H), 5.79 (d, J=9.7 Hz, 1H), 6.27-6.31 (dd, J=1.6, 16.9 Hz, 1H), 6.40-6.47 (dd, J=10.0, 17.2 Hz, 1H), 7.10 (s, 1H), 7.19-7.22 (m, 2H), 7.62 (d, J=8.0 Hz, 1H), 7.79 (s, 1H), 8.37 (s, 1H), 8.41 (s, 1H), 8.80 (s, 1H), 10.32 (s, 1H).

Example 368

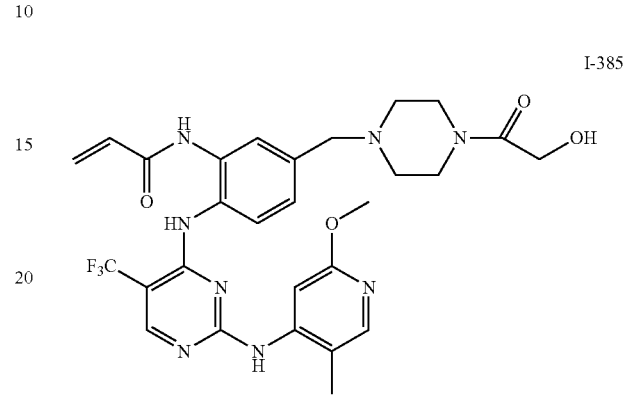

I-385

N-(5-((4-(2-hydroxyacetyl)piperazin-1-yl)methyl)-2-((2-((2-methoxy-5-methylpyridin-4-yl)amino)-5-(trifluoromethyl)pyrimidin-4-yl)amino)phenyl)acrylamide Compound I-385 was prepared in a manner similar to Example 364, substituting 2-chloro-2-oxoethyl acetate for acetyl chloride followed by basic hydrolysis with aqueous LiOH in the final step. MS: m/z 601.2 (ES+, M+H). ¹HNMR (DMSO-d₆) δ 2.09 (s, 3H), 2.34-2.36 (m, 4H), 3.34 (m, 2H), 3.48 (m, 4H), 3.77 (s, 3H), 4.06 (d, J=5.4 Hz, 2H), 4.52 (t, J=5.5 Hz, 1H), 5.79 (d, J=9.8 Hz, 1H), 6.31 (d, J=16.9 Hz, 1H), 6.41 (d, J=9.6 Hz, 1H), 7.11 (s, 1H), 7.20 (m, 2H), 7.62 (br s, 1H), 7.79 (s, 1H), 8.36 (br s, 1H), 8.42 (br s, 1H), 8.81 (br s, 1H), 10.33 (s, 1H).

Example 369

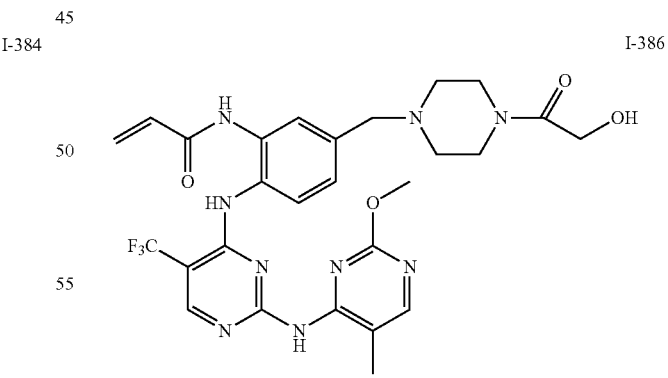

I-386

N-(5-((4-(2-hydroxyacetyl)piperazin-1-yl)methyl)-2-((2-((2-methoxy-5-methylpyrimidin-4-yl)amino)-5-(trifluoromethyl)pyrimidin-4-yl)amino)phenyl)acrylamide Compound I-386 was prepared in a manner similar to Example 365, substituting 2-chloro-2-oxoethyl acetate for acetyl chloride followed by basic hydrolysis with aqueous LiOH in the final step. MS: m/z 602.2 (ES+, M+H). ¹HNMR (DMSO-d₆) δ 1.98 (s, 3H), 2.31-2.34 (m, 4H), 3.45 (m, 6H), 3.83 (s, 3H), 4.06 (d, J=5.3 Hz, 2H), 4.51 (t, J=5.5 Hz, 1H), 5.80 (d, J=10.7 Hz, 1H), 6.29 (d, J=16.7 Hz, 1H), 6.39-6.46 (dd, J=9.9, 16.8 Hz, 1H), 7.04 (d, J=7.8 Hz, 1H), 7.14 (s, 1H), 7.76 (d, J=8.3 Hz, 1H), 8.19 (s, 1H), 8.41 (s, 1H), 8.48 (s, 1H), 9.81 (s, 1H), 10.32 (s, 1H).

Example 370

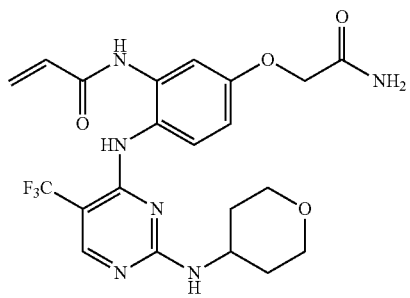

I-387

N-(5-(2-amino-2-oxoethoxy)-2-((2-((tetrahydro-2H-pyran-4-yl)amino)-5-(trifluoromethyl) pyrimidin-4-yl)amino)phenyl)acrylamide Compound I-387 was prepared in a manner similar to Example 1, substituting tetrahydro-2H-pyran-4-amine for (S)-tert-butyl 3-aminopiperidine-1-carboxylate, and N-(2-amino-5-(2-amino-2-oxoethoxy)phenyl)acrylamide for N-(2-aminophenyl)acrylamide. MS: m/z 481.2 (ES+, M+H). ¹HNMR (DMSO-d₆) δ 1.32-1.47 (m, 2H), 1.65-1.67 (m, 2H), 3.15-3.20 (m, 2H), 3.27 (m, 1H), 3.80 (d, J=10.6 Hz, 2H), 4.43 (s, 2H), 5.79 (d, J=9.6 Hz, 1H), 6.26-6.31 (dd, J=10.2, 16.9 Hz, 1H), 6.41-6.48 (dd, J=9.9, 16.9 Hz, 1H), 6.85-6.88 (dd, J=2.7, 8.9 Hz, 1H), 6.93 (d, J=2.6 Hz, 1H), 7.38 (s, 1H), 7.46-7.57 (m, 2H), 7.63 (m, 1H), 8.15-8.25 (m, 2H), 10.17-10.24 (m, 1H).

Example 371

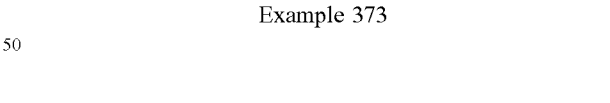

I-388

N-(2-((2-((2-methoxy-5-methylpyridin-4-yl)amino)-5-(trifluoromethyl)pyrimidin-4-yl)amino)-5-((4-picolinoylpiperazin-1-yl)methyl)phenyl)acrylamide Compound I-388 was prepared in a manner similar to Example 364, substituting picolinic acid/HATU/DIPEA for acetyl chloride in the final step. MS: m/z 646.5 (ES−, M−H). ¹HNMR (DMSO-d₆) δ 2.27 (s, 3H), 3.32-3.33 (m, 8H), 3.82 (s, 3H), 4.43 (s, 2H), 5.81-5.84 (dd, J=2.6, 9.2 Hz, 1H), 6.36-6.41 (dd, J=2.6, 17.0 Hz, 1H), 6.41-6.48 (dd, J=9.2, 17.0 Hz, 1H), 7.48-7.50 (dd, J=2.0, 8.3 Hz, 1H), 7.55-7.57 (m, 1H), 7.67 (d, J=1.9 Hz, 1H), 7.74-7.78 (m, 2H), 7.89 (s, 1H), 7.91 (br s, 1H), 7.99-8.03 (dt, J=1.6, 7.8 Hz, 1H), 8.53 (s, 1H), 8.64 (d, J=4.6 Hz, 1H).

Example 372

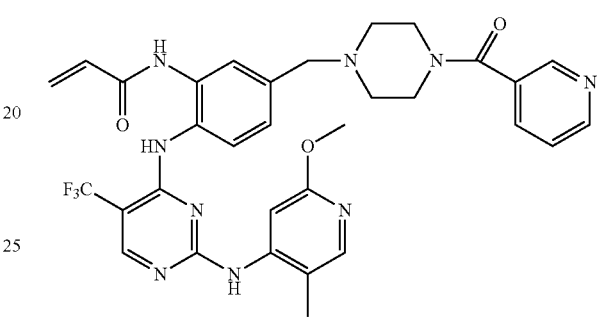

I-389

N-(2-((2-((2-methoxy-5-methylpyridin-4-yl)amino)-5-(trifluoromethyl)pyrimidin-4-yl)amino)-5-((4-nicotinoylpiperazin-1-yl)methyl)phenyl)acrylamide Compound I-389 was prepared in a manner similar to Example 364, substituting nicotinic acid/HATU/DIPEA for acetyl chloride in the final step. MS: m/z 646.4 (ES−, M−H). ¹HNMR (DMSO-d₆) δ 2.08 (s, 3H), 2.44 (m, 4H), 3.49 (m, 2H), 3.51 (s, 2H), 3.64-3.65 (m, 2H), 3.75 (s, 3H), 5.78-5.81 (dd, J=1.7, 10.0 Hz, 1H), 6.27-6.31 (dd, J=1.8, 16.9 Hz, 1H), 6.40-6.46 (dd, J=9.9, 17.0 Hz, 1H), 7.09 (s, 1H), 7.19 (d, J=8.3 Hz, 1H), 7.22 (s, 1H), 7.45-7.48 (dd, J=4.9, 7.8 Hz, 1H), 7.62 (d, J=8.2 Hz, 1H), 7.76 (s, 1H), 7.80-7.83 (m, 1H), 8.37 (s, 1H), 8.42 (s, 1H), 8.59 (d, J=2.0 Hz, 1H), 8.63-8.64 (dd, J=1.5, 4.8 Hz, 1H), 8.82 (s, 1H), 10.34 (s, 1H).

Example 373

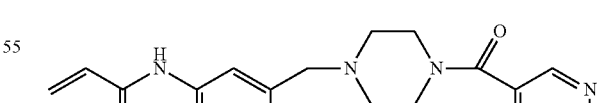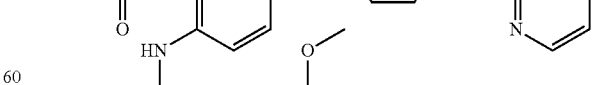

I-390

545

N-(2-((2-((2-methoxy-5-methylpyridin-4-yl)amino)-5-(trifluoromethyl)pyrimidin-4-yl)amino)-5-((4-(pyrazine-2-carbonyl)piperazin-1-yl)methyl)phenyl)acrylamide Compound I-390 was prepared in a manner similar to Example 364, substituting pyrazine-2-carboxylic acid/HATU/DIPEA for acetyl chloride in the final step. MS: m/z 649.2 (ES+, M+H). $^1$HNMR (DMSO-$d_6$) δ 2.08 (s, 3H), 2.42 (br s, 2H), 2.49 (s, 2H), 3.42 (br s, 2H), 3.52 (s, 2H), 3.67 (br s, 2H), 3.76 (s, 3H), 5.80 (d, J=10.0 Hz, 1H), 6.30 (d, J=17.0 Hz, 1H), 6.40-6.47 (dd, J=10.1, 16.9 Hz, 1H), 7.10 (s, 1H), 7.20 (d, J=8.2 Hz, 1H), 7.23 (s, 1H), 7.62 (d, J=8.1 Hz, 1H), 7.77 (s, 1H), 8.37 (s, 1H), 8.42 (s, 1H), 8.66 (br s, 1H), 8.73 (d, J=2.4 Hz, 1H), 8.81 (s, 1H), 8.83 (s, 1H), 10.34 (s, 1H).

Example 374

I-391

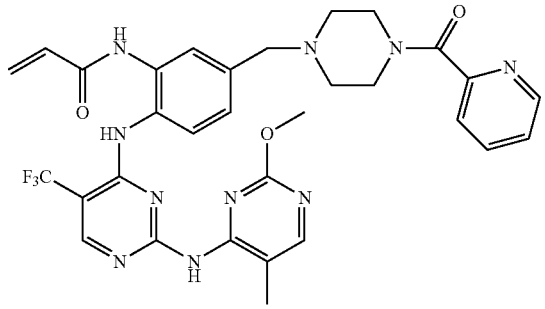

N-(2-((2-((2-methoxy-5-methylpyrimidin-4-yl)amino)-5-(trifluoromethyl)pyrimidin-4-yl)amino)-5-((4-picolinoylpiperazin-1-yl)methyl)phenyl)acrylamide Compound I-391 was prepared in a manner similar to Example 365, substituting picolinic acid/HATU/DIPEA for acetyl chloride in the final step. MS: m/z 647.2 (ES−, M−H). $^1$HNMR (DMSO-$d_6$) δ 1.97 (s, 3H), 2.34 (m, 2H), 2.42 (m, 2H), 3.39 (m, 2H), 3.46 (s, 2H), 3.65 (m, 2H), 3.81 (s, 3H), 5.77-5.80 (dd, J=1.6, 10.0 Hz, 1H), 6.26-6.30 (dd, J=1.8, 17.0 Hz, 1H), 6.38-6.45 (dd, J=10.0, 16.9 Hz, 1H), 7.02 (d, J=8.3 Hz, 1H), 7.20 (br s, 1H), 7.44-7.47 (m, 1H), 7.55 (d, J=7.8 Hz, 1H), 7.78 (d, J=8.3 Hz, 1H), 7.88-7.93 (m, 1H), 8.16 (s, 1H), 8.37 (s, 1H), 8.57 (d, J=4.4 Hz, 1H), 10.32 (br s, 1H).

Example 375

I-392

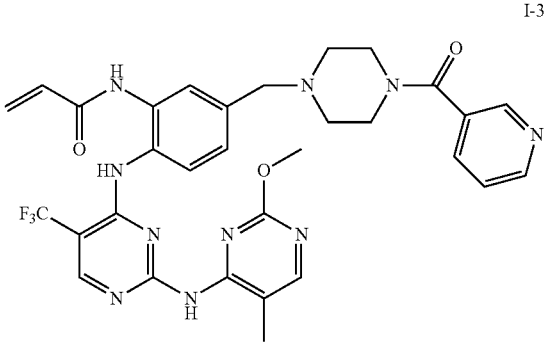

546

N-(2-((2-((2-methoxy-5-methylpyrimidin-4-yl)amino)-5-(trifluoromethyl)pyrimidin-4-yl)amino)-5-((4-nicotinoylpiperazin-1-yl)methyl)phenyl)acrylamide Compound I-392 was prepared in a manner similar to Example 365, substituting nicotinic acid/HATU/DIPEA for acetyl chloride in the final step. MS: m/z 649.2 (ES+, M+H). $^1$HNMR (DMSO-$d_6$) δ 1.97 (s, 3H), 2.36-2.41 (m, 4H), 3.30 (m, 2H), 3.47 (s, 2H), 3.64 (br s, 2H), 3.81 (s, 3H), 5.78-5.80 (d, J=9.5 Hz, 1H), 6.27-6.31 (d, J=17.2 Hz, 1H), 6.39-6.46 (dd, J=10.0, 17.0 Hz, 1H), 7.04 (d, J=8.7 Hz, 1H), 7.15 (s, 1H), 7.45-7.48 (dd, J=4.8, 7.6 Hz, 1H), 7.76 (d, J=8.3 Hz, 1H), 7.82 (d, J=7.8 Hz, 1H), 8.16 (s, 1H), 8.41 (s, 1H), 8.48 (s, 1H), 8.59 (s, 1H), 8.64 (d, J=3.7 Hz, 1H), 9.81 (s, 1H), 10.32 (s, 1H).

Example 376

I-393

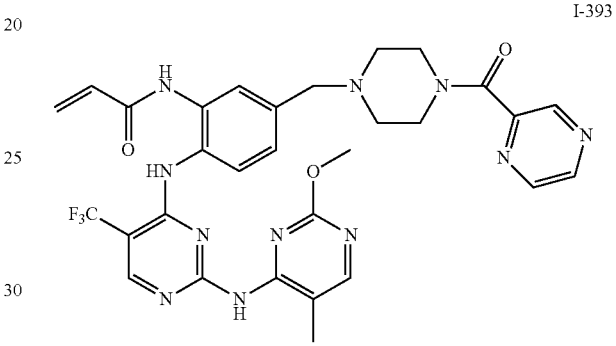

N-(2-((2-((2-methoxy-5-methylpyrimidin-4-yl)amino)-5-(trifluoromethyl)pyrimidin-4-yl)amino)-5-((4-(pyrazine-2-carbonyl)piperazin-1-yl)methyl)phenyl)acrylamide Compound I-393 was prepared in a manner similar to Example 365, substituting pyrazine-2-carboxylic acid/HATU/DIPEA for acetyl chloride in the final step. MS: m/z 648.5 (ES−, M−H). $^1$HNMR (DMSO-$d_6$) δ 2.00 (s, 3H), 3.18 (m, 4H), 3.34-3.39 (m, 2H), 3.84 (s, 3H), 4.33 (s, 2H), 5.83 (d, J=9.1 Hz, 1H), 6.31 (d, J=16.5 Hz, 1H), 6.44-6.48 (dd, J=10.2, 16.4 Hz, 1H), 7.21 (d, J=8.9 Hz, 1H), 7.40 (s, 1H), 7.98 (d, J=8.4 Hz, 1H), 8.20 (s, 1H), 8.47 (s, 1H), 8.53 (s, 1H), 8.69 (s, 1H), 8.78 (s, 1H), 8.89 (s, 1H), 9.90 (br s, 1H), 10.42 (s, 1H).

Example 377

I-394

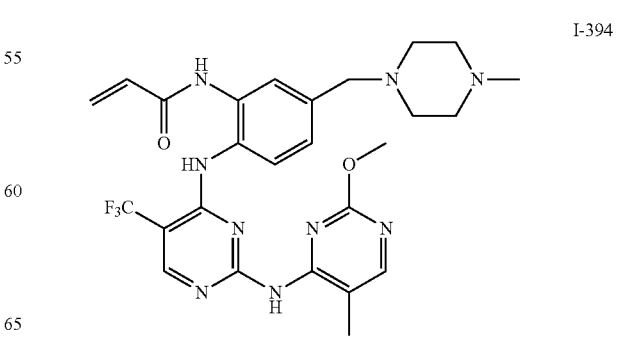

N-(2-((2-((2-methoxy-5-methylpyrimidin-4-yl)amino)-5-(trifluoromethyl)pyrimidin-4-yl)amino)-5-((4-methylpiperazin-1-yl)methyl)phenyl)acrylamide Compound I-394 was prepared in a manner similar to Example 68, substituting 2-methoxy-5-methylpyrimidin-4-amine for 3-amino-4-methylbenzamide, and N-(2-amino-5-((4-methylpiperazin-1-yl)methyl)phenyl) acrylamide for N-(2-aminophenyl)acrylamide. MS: m/z 558.2 (ES+, M+H). ¹HNMR (DMSO-d₆) δ 1.97 (s, 3H), 2.16 (s, 3H), 2.35 (m, 8H), 3.40 (s, 2H), 3.83 (s, 3H), 5.79 (d, J=9.2 Hz, 1H), 6.29 (d, J=16.6 Hz, 1H), 6.40-6.46 (m, 1H), 7.02 (d, J=7.6 Hz, 1H), 7.12 (s, 1H), 7.75 (d, J=8.3 Hz, 1H), 8.18 (s, 1H), 8.40 (s, 1H), 8.48 (s, 1H), 9.80 (s, 1H), 10.33 (s, 1H).

Example 378

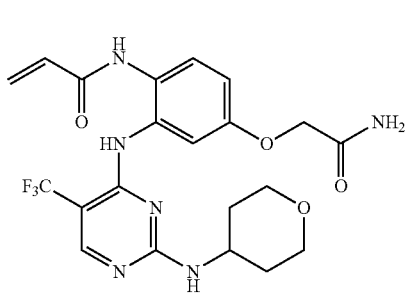

I-395

N-(4-(2-amino-2-oxoethoxy)-2-((2-((tetrahydro-2H-pyran-4-yl)amino)-5-(trifluoromethyl) pyrimidin-4-yl)amino)phenyl)acrylamide Compound I-395 was prepared in a manner similar to Example 1, substituting tetrahydro-2H-pyran-4-amine for (S)-tert-butyl 3-aminopiperidine-1-carboxylate, and N-(2-amino-4-(2-amino-2-oxoethoxy)phenyl)acrylamide for N-(2-aminophenyl)acrylamide. MS: m/z 481.2 (ES+, M+H). ¹HNMR (DMSO-d₆) δ 1.38-1.50 (m, 2H), 1.69-1.72 (m, 2H), 3.17 (t, J=11.4 Hz, 2H), 3.61-3.83 (m, 3H), 3.75-3.83 (m, 2H), 4.43 (d, J=16.0 Hz, 2H), 5.77 (d, J=10.0 Hz, 1H), 6.27 (d, J=16.9 Hz, 1H), 6.38-6.45 (dd, J=10.1, 16.9 Hz, 1H), 6.82 (d, J=8.6 Hz, 1H), 7.16 (d, J=8.7 Hz, 1H), 7.38 (s, 1H), 7.41 (s, 1H), 7.49 (br s, 1H), 7.57 (d, J=7.0 Hz, 1H), 8.15 (s, 1H), 8.21 (s, 1H), 10.18 (s, 1H).

Example 379

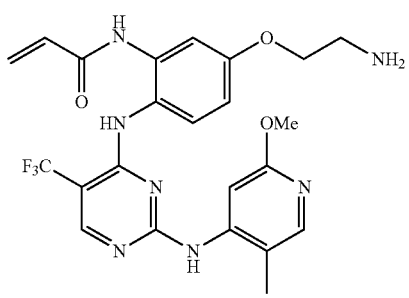

I-396

N-(5-(2-aminoethoxy)-2-((2-((2-methoxy-5-methylpyridin-4-yl)amino)-5-(trifluoromethyl) pyrimidin-4-yl)amino)phenyl)acrylamide Compound I-396 was prepared in a manner similar to Example 68, substituting 2-methoxy-5-methylpyridin-4-amine for 3-amino-4-methylbenzamide, tert-butyl (2-(3-acrylamido-4-aminophenoxy)ethyl)carbamate for N-(2-aminophenyl)acrylamide, and final Boc-deprotection with TFA in the last step. MS: m/z 504.2 (ES+, M+H). ¹HNMR (DMSO-d₆) δ 2.10 (s, 3H), 3.21 (t, J=5.1 Hz, 2H), 3.75 (s, 3H), 4.12 (t, J=4.9 Hz, 2H), 5.77-5.80 (dd, J=1.8, 10.0 Hz, 1H), 6.25-6.30 (dd, J=1.9, 17.0 Hz, 1H), 6.40-6.47 (dd, J=10.0, 16.9 Hz, 1H), 6.85-6.88 (dd, J=2.8, 8.8 Hz, 1H), 6.99 (d, J=2.8 Hz, 1H), 7.11 (s, 1H), 7.52 (d, J=8.8 Hz, 1H), 7.78 (s, 1H), 8.28 (br s, 1H), 8.36 (s, 1H), 8.71 (s, 1H), 10.15 (s, 1H).

Example 380

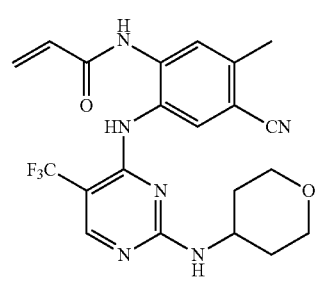

I-397

N-(4-cyano-5-methyl-2-((2-((tetrahydro-2H-pyran-4-yl)amino)-5-(trifluoromethyl) pyrimidin-4-yl)amino) phenyl)acrylamide Compound I-397 was prepared in a manner similar to Example 1, substituting tetrahydro-2H-pyran-4-amine for (S)-tert-butyl 3-aminopiperidine-1-carboxylate, and N-(2-amino-4-cyano-5-methylphenyl)acrylamide for N-(2-aminophenyl)acrylamide. MS: m/z 447.2 (ES+, M+H). ¹HNMR (DMSO-d₆, with D₂O exchange) δ 1.38-1.43 (m, 2H), 1.62-0.165 (m, 2H), 2.43 (s, 3H), 3.17-3.23 (m, 2H), 3.49 (m, 1H), 3.77-3.82 (m, 2H), 5.84 (d, J=9.6 Hz, 1H), 6.29 (d, J=17.0 Hz, 1H), 6.38-6.45 (dd, J=10.1, 17.1 Hz, 1H), 7.38 (s, 1H), 8.09 (s, 1H), 8.12 (s, 1H). (Based on D₂O values updated)

Example 381

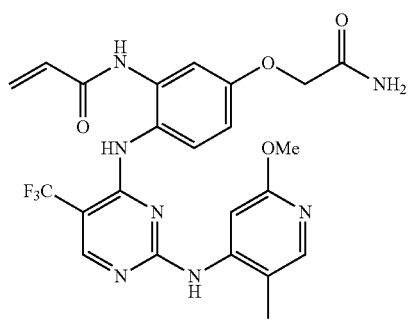

I-398

N-(5-(2-amino-2-oxoethoxy)-2-((2-((2-methoxy-5-methylpyridin-4-yl)amino)-5-(trifluoromethyl)pyrimidin-4-yl)amino)phenyl)acrylamide Compound I-398 was prepared in a manner similar to Example 68, substituting 2-methoxy-5-methylpyridin-4-amine for 3-amino-4-methylbenzamide, and N-(2-amino-5-(2-amino-2-oxoethoxy)phenyl)acrylamide for N-(2-aminophenyl)acrylamide. MS: m/z 518.2 (ES+, M+H). $^1$HNMR (DMSO-d$_6$) δ 2.10 (s, 3H), 3.74 (s, 3H), 4.42 (s, 2H), 5.78 (d, J=10.3 Hz, 1H), 6.28 (d, J=17.5 Hz, 1H), 6.44 (dd, J=10.0, 16.9 Hz, 1H), 6.85 (d, J=7.1 Hz, 1H), 6.92 (br s, 1H), 7.09 (s, 1H), 7.41 (br s, 1H), 7.50 (d, J=8.7 Hz, 1H), 7.54 (br s, 1H), 7.78 (s, 1H), 8.26 (s, 1H), 8.35 (s, 1H), 8.69 (s, 1H), 10.26 (s, 1H).

Example 382

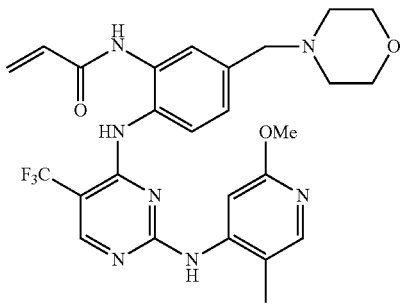

I-399

N-(2-((2-((2-methoxy-5-methylpyridin-4-yl)amino)-5-(trifluoromethyl)pyrimidin-4-yl)amino)-5-(morpholinomethyl)phenyl)acrylamide Compound I-399 was prepared in a manner similar to Example 68, substituting 2-methoxy-5-methylpyridin-4-amine for 3-amino-4-methylbenzamide, and N-(2-amino-5-(morpholinomethyl)phenyl)acrylamide for N-(2-aminophenyl)acrylamide. MS: m/z 544.2 (ES+, M+H).

Example 383

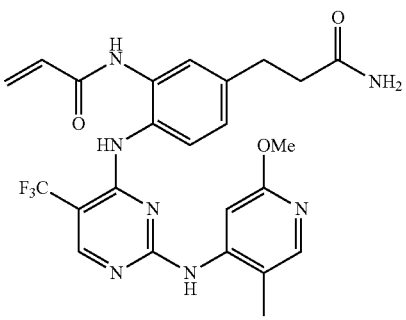

I-400

N-(5-(3-amino-3-oxopropyl)-2-((2-((2-methoxy-5-methylpyridin-4-yl)amino)-5-(trifluoromethyl)pyrimidin-4-yl)amino)phenyl)acrylamide Compound I-400 was prepared in a manner similar to Example 68, substituting 2-methoxy-5-methylpyridin-4-amine for 3-amino-4-methylbenzamide, and N-(2-amino-5-(3-amino-3-oxopropyl)phenyl)acrylamide for N-(2-aminophenyl)acrylamide. MS: m/z 516.2 (ES+, M+H). $^1$HNMR (DMSO-d$_6$) δ 2.10 (s, 3H), 2.36 (t, J=7.8 Hz, 2H), 2.81 (t, J=7.5 Hz, 2H), 3.76 (s, 3H), 5.79 (d, J=10.0 Hz, 1H), 6.29 (d, J=17.0 Hz, 1H), 6.40-6.47 (dd, J=10.3, 16.8 Hz, 1H), 6.76 (br s, 1H), 7.11 (m, 3H), 7.30 (br s, 1H), 7.56 (d, J=7.6 Hz, 1H), 7.80 (s, 1H), 8.36 (s, 2H), 8.74 (s, 1H), 10.31 (s, 1H).

Example 384

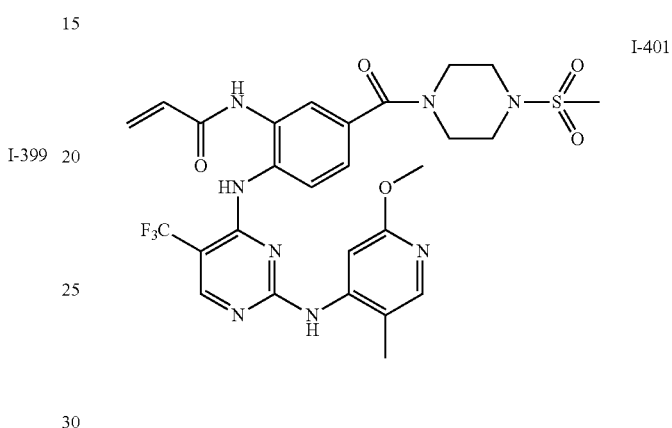

I-401

N-(2-((2-((2-methoxy-5-methylpyridin-4-yl)amino)-5-(trifluoromethyl)pyrimidin-4-yl)amino)-5-(4-(methylsulfonyl)piperazine-1-carbonyl)phenyl)acrylamide Compound I-401 was prepared in a manner similar to Example 68, substituting 2-methoxy-5-methylpyridin-4-amine for 3-amino-4-methylbenzamide, and N-(2-amino-5-(4-(methylsulfonyl)piperazine-1-carbonyl)phenyl) acrylamide for N-(2-aminophenyl)acrylamide. MS: m/z 635.1 (ES+, M+H). $^1$HNMR (DMSO-d$_6$) δ 2.09 (s, 3H), 2.91 (s, 3H), 3.17 (m, 4H), 3.58 (m, 4H), 3.72 (s, 3H), 5.82 (dd, J=1.9, 11.9 Hz, 1H), 6.31 (dd, J=1.8, 17.0 Hz, 1H), 6.45 (dd, J=10.2, 17.0 Hz, 1H), 7.09 (s, 1H), 7.30 (d, J=8.2 Hz, 1H), 7.39 (d, J=1.7 Hz, 1H), 7.76 (d, J=8.3 Hz, 1H), 7.81 (s, 1H), 8.41 (s, 1H), 8.50 (s, 1H), 8.90 (s, 1H), 10.37 (s, 1H).

Example 385

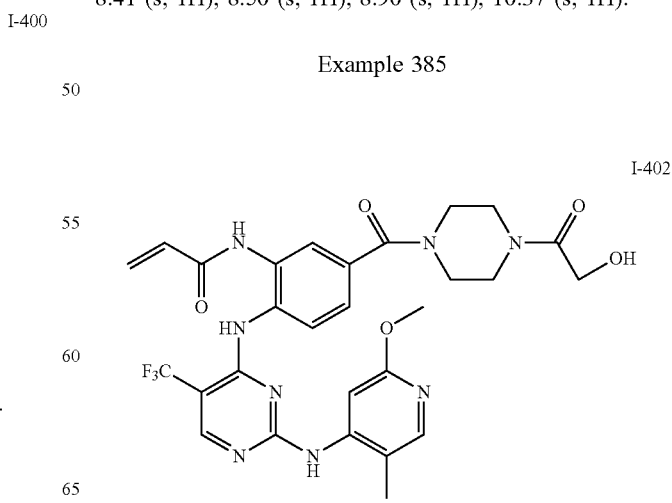

I-402

N-(5-(4-(2-hydroxyacetyl)piperazine-1-carbonyl)-2-((2-((2-methoxy-5-methylpyridin-4-yl)amino)-5-(trifluoromethyl)pyrimidin-4-yl)amino)phenyl)acrylamide Compound I-402 was prepared in a manner similar to Example 68, substituting 2-methoxy-5-methylpyridin-4-amine for 3-amino-4-methylbenzamide, and N-(2-amino-5-(4-(2-hydroxyacetyl)piperazine-1-carbonyl)phenyl)acrylamide for N-(2-aminophenyl)acrylamide. MS: m/z 615.3 (ES+, M+H).

Example 386

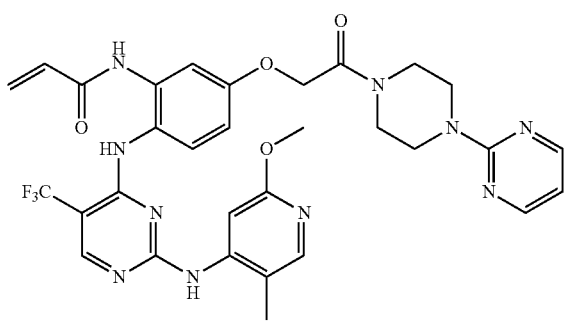

I-403

N-(2-((2-((2-methoxy-5-methylpyridin-4-yl)amino)-5-(trifluoromethyl)pyrimidin-4-yl)amino)-5-(2-oxo-2-(4-(pyrimidin-2-yl)piperazin-1-yl)ethoxy)phenyl)acrylamide Compound I-403 was prepared in a manner similar to Example 68, substituting 2-methoxy-5-methylpyridin-4-amine for 3-amino-4-methylbenzamide, and N-(2-amino-5-(2-oxo-2-(4-(pyrimidin-2-yl)piperazin-1-yl)ethoxy)phenyl)acrylamide for N-(2-aminophenyl)acrylamide. MS: m/z 664.8 (ES+, M+H).

Example 387

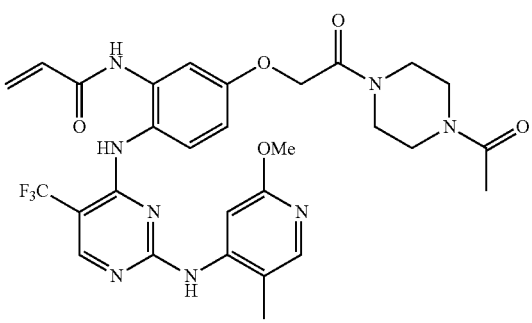

I-404

N-(5-(2-(4-acetylpiperazin-1-yl)-2-oxoethoxy)-2-((2-((2-methoxy-5-methylpyridin-4-yl)amino)-5-(trifluoromethyl)pyrimidin-4-yl)amino)phenyl)acrylamide Compound I-404 was prepared in a manner similar to Example 68, substituting 2-methoxy-5-methylpyridin-4-amine for 3-amino-4-methylbenzamide, and N-(5-(2-(4-acetylpiperazin-1-yl)-2-oxoethoxy)-2-aminophenyl)acrylamide for N-(2-aminophenyl)acrylamide. MS: m/z 628.7 (ES+, M+H).

Example 388

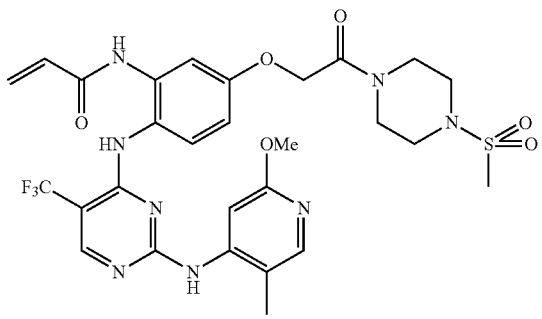

I-405

N-(2-((2-((2-methoxy-5-methylpyridin-4-yl)amino)-5-(trifluoromethyl)pyrimidin-4-yl)amino)-5-(2-(4-(methylsulfonyl)piperazin-1-yl)-2-oxoethoxy)phenyl)acrylamide Compound I-405 was prepared in a manner similar to Example 68, substituting 2-methoxy-5-methylpyridin-4-amine for 3-amino-4-methylbenzamide, and N-(2-amino-5-(2-(4-(methylsulfonyl)piperazin-1-yl)-2-oxoethoxy)phenyl) acrylamide for N-(2-aminophenyl) acrylamide. MS: m/z 664.5 (ES+, M+H).

Example 389

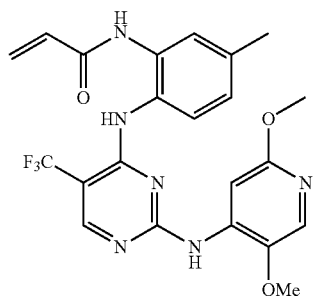

I-406

N-(2-((2-((2,5-dimethoxypyridin-4-yl)amino)-5-(trifluoromethyl)pyrimidin-4-yl)amino)-5-methylphenyl)acrylamide Compound I-406 was prepared in a manner similar to Example 68, substituting 2,5-dimethoxy pyridin-4-amine for 3-amino-4-methylbenzamide, and N-(2-amino-5-methylphenyl) acrylamide for N-(2-aminophenyl)acrylamide. MS: m/z 475.2 (ES+, M+H). $^1$HNMR (DMSO-$d_6$) δ 2.36 (s, 3H), 3.72 (s, 3H), 3.83 (s, 3H), 5.76-5.79 (dd, J=1.9, 10.0 Hz, 1H), 6.26-6.31 (dd, J=2.0, 17.0 Hz, 1H), 6.40-6.47 (dd, J=10.1, 17.0 Hz, 1H), 7.14-7.16 (m, 2H), 7.29 (s, 1H), 7.49 (d, J=8.0 Hz, 1H), 7.70 (s, 1H), 8.02 (s, 1H), 8.40 (s, 1H), 8.47 (s, 1H), 10.25 (s, 1H).

Example 390

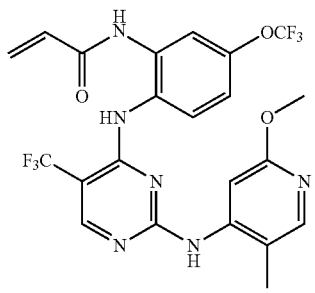

I-407

N-(2-((2-((2-methoxy-5-methylpyridin-4-yl)amino)-5-(trifluoromethyl)pyrimidin-4-yl)amino)-5-(trifluoromethoxy)phenyl)acrylamide Compound I-407 was prepared in a manner similar to Example 68, substituting 2-methoxy-5-methylpyridin-4-amine for 3-amino-4-methylbenzamide, and N-(2-amino-5-(trifluoromethoxy)phenyl)acrylamide for N-(2-aminophenyl)acrylamide. MS: m/z 528.7 (ES+, M+H).

Example 391

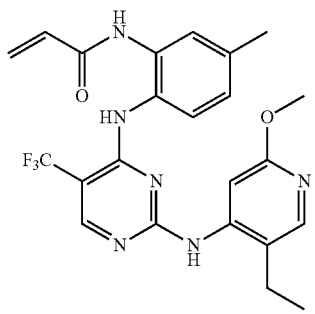

I-408

N-(2-((2-((5-ethyl-2-methoxypyridin-4-yl)amino)-5-(trifluoromethyl)pyrimidin-4-yl)amino)-5-methylphenyl)acrylamide Compound I-408 was prepared in a manner similar to Example 68, substituting 5-ethyl-2-methoxypyridin-4-amine for 3-amino-4-methylbenzamide, and N-(2-amino-5-methylphenyl) acrylamide for N-(2-aminophenyl)acrylamide. MS: m/z 473.2 (ES+, M+H). $^1$HNMR (DMSO-$d_6$) δ 1.04 (t, J=7.5 Hz, 3H), 2.32 (s, 3H), 2.57-2.69 (m, 2H), 3.76 (s, 3H), 5.76-5.79 (dd, J=1.9, 10.0 Hz, 1H), 6.26-6.30 (dd, J=1.8, 17.0 Hz, 1H), 6.39-6.46 (dd, J=10.2, 17.1 Hz, 1H), 7.07-7.08 (m, 3H), 7.51 (d, J=8.6 Hz, 1H), 7.80 (s, 1H), 8.35 (s, 2H), 8.75 (s, 1H), 10.24 (br s, 1H).

Example 392

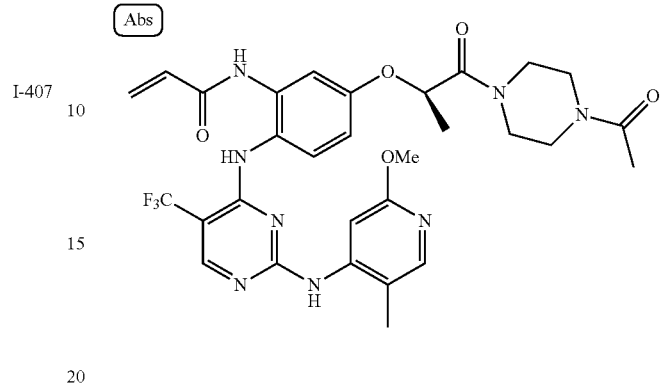

I-409

(R)—N-(5-((1-(4-acetylpiperazin-1-yl)-1-oxopropan-2-yl)oxy)-2-((2-((2-methoxy-5-methylpyridin-4-yl)amino)-5-(trifluoromethyl)pyrimidin-4-yl)amino) phenyl)acrylamide Compound I-409 was prepared in a manner similar to Example 68, substituting 2-methoxy-5-methylpyridin-4-amine for 3-amino-4-methylbenzamide, and (R)-tert-butyl 4-(2-(3-acryl amido-4-aminophenoxy)propanoyl)piperazine-1-carboxylate for N-(2-aminophenyl)acrylamide. After Boc-deprotection with TFA, the resulting amine was acylated with acetyl chloride to yield desired compound I-409. MS: m/z 643.3 (ES+, M+H). $^1$HNMR (DMSO-$d_6$) δ 1.45 (d, J=6.4 Hz, 3H), 1.99 (s, 3H), 2.08 (s, 3H), 3.45-3.59 (m, 8H), 3.75 (s, 3H), 5.18-5.21 (m, 1H), 5.76-5.79 (dd, J=1.5, 10.1 Hz, 1H), 6.24-6.28 (dd, J=1.6, 16.9 Hz, 1H), 6.39-6.46 (dd, J=10.0, 17.0 Hz, 1H), 6.78-6.79 (m, 1H), 6.89 (s, 1H), 7.10 (s, 1H), 7.48 (d, J=9.0 Hz, 1H), 7.79 (s, 1H), 8.24 (s, 1H), 8.35 (s, 1H), 8.72 (s, 1H), 10.13 (br s, 1H).

Example 393

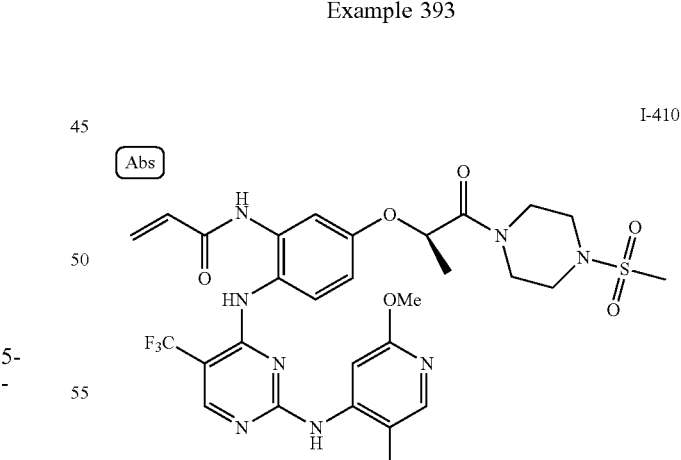

I-410

(R)—N-(2-((2-((2-methoxy-5-methylpyridin-4-yl) amino)-5-(trifluoromethyl)pyrimidin-4-yl)amino)-5-((1-(4-(methylsulfonyl)piperazin-1-yl)-1-oxopropan-2-yl)oxy)phenyl) acrylamide Compound I-410 was prepared in a manner similar to Example 68, substituting 2-methoxy-5-methylpyridin-4- amine for 3-amino-4-methylbenzamide, and (R)-tert-butyl 4-(2-(3-acryl amido-4-aminophenoxy)propanoyl)piperazine-1-carboxylate for N-(2-aminophenyl) acrylamide. After Boc-deprotection with TFA, the resulting amine reacted with methanesulfonyl chloride to yield desired compound I-410. MS: m/z 679.2 (ES+, M+H). ¹HNMR (DMSO-d₆) δ 1.46 (d, J=6.5 Hz, 3H), 2.08 (s, 3H), 2.85 (s, 3H), 3.08 (m, 4H), 3.54-3.64 (m, 4H), 3.75 (s, 3H), 5.17-5.22 (m, 1H), 5.75-5.78 (dd, J=1.9, 10.0 Hz, 1H), 6.26 (d, J=15.4 Hz, 1H), 6.40-6.46 (dd, J=9.9, 16.9 Hz, 1H), 6.77-6.80 (dd, J=2.2, 8.9 Hz, 1H), 6.90 (s, 1H), 7.09 (s, 1H), 7.48 (d, J=8.7 Hz, 1H), 7.79 (s, 1H), 8.24 (s, 1H), 8.35 (s, 1H), 8.73 (s, 1H), 10.13 (s, 1H).

Example 394

I-411

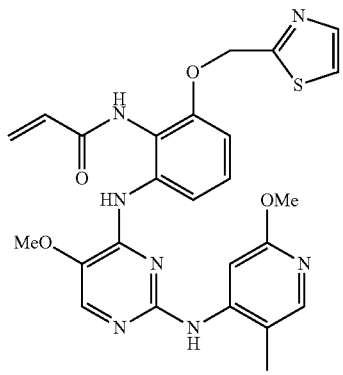

N-(2-((5-methoxy-2-((2-methoxy-5-methylpyridin-4-yl)amino)pyrimidin-4-yl)amino)-6-(thiazol-2-yl-methoxy)phenyl)acrylamide Compound I-411 was prepared in a manner similar to Example 68, substituting 2-methoxy-5-methylpyridin-4-amine for 3-amino-4-methyl benzamide, and N-(2-amino-6-(thiazol-2-ylmethoxy)phenyl)acrylamide for N-(2-aminophenyl) acrylamide. MS: m/z 520.2 (ES+, M+H). ¹HNMR (DMSO-d₆) δ 2.14 (s, 3H), 3.79 (s, 3H), 3.88 (s, 3H), 5.42 (s, 2H), 5.79 (d, J=10.8 Hz, 1H), 6.29 (d, J=17.1 Hz, 1H), 6.52-6.56 (dd, J=10.1, 17.2 Hz, 1H), 6.88 (d, J=8.3 Hz, 1H), 7.16 (t, J=8.3 Hz, 1H), 7.54 (br s, 1H), 7.67 (d, J=8.3 Hz, 1H), 7.71 (s, 1H), 7.76 (t, J=1.7 Hz, 1H), 7.81-7.82 (m, 1H), 7.86 (br s, 1H), 7.90 (s, 1H), 7.92 (s, 1H), 9.61 (s, 1H).

Example 395

I-412

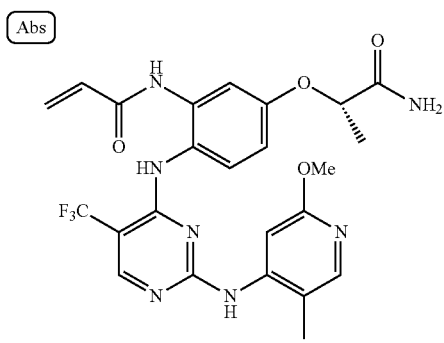

(S)—N-(5-((1-amino-1-oxopropan-2-yl)oxy)-2-((2-((2-methoxy-5-methylpyridin-4-yl)amino)-5-(trifluoromethyl)pyrimidin-4-yl)amino)phenyl)acrylamide Compound I-412 was prepared in a manner similar to Example 68, substituting 2-methoxy-5-methylpyridin-4-amine for 3-amino-4-methylbenzamide, and (S)—N-(2-amino-5-((1-amino-1-oxopropan-2-yl)oxy)phenyl) acrylamide for N-(2-aminophenyl) acrylamide. MS: m/z 532.2 (ES+, M+H). ¹HNMR (DMSO-d₆) δ 1.46 (d, J=6.6 Hz, 3H), 2.09 (s, 3H), 3.76 (s, 3H), 4.54-4.59 (m, 1H), 5.76-5.79 (dd, J=1.9, 10.1 Hz, 1H), 6.25-6.30 (dd, J=1.9, 17.0 Hz, 1H), 6.39-6.46 (dd, J=10.0, 16.9 Hz, 1H), 6.80-6.83 (dd, J=2.9, 8.9 Hz, 1H), 6.86 (d, J=2.8 Hz, 1H), 7.11 (s, 1H), 7.26 (br s, 1H), 7.48 (br s, 1H), 7.51 (d, J=8.8 Hz, 1H), 7.79 (s, 1H), 8.24 (s, 1H), 8.35 (s, 1H), 8.71 (s, 1H), 10.23 (s, 1H).

Example 396

I-413

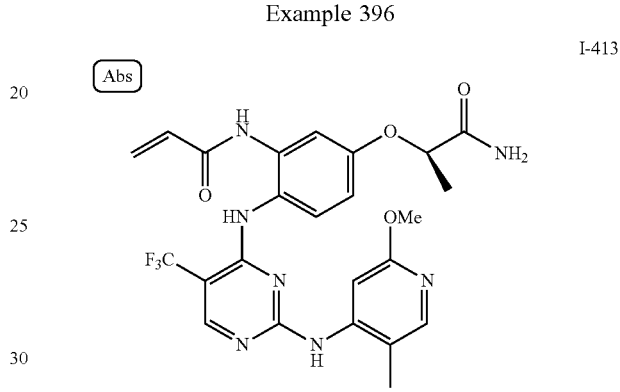

(R)—N-(5-((1-amino-1-oxopropan-2-yl)oxy)-2-((2-((2-methoxy-5-methylpyridin-4-yl)amino)-5-(trifluoromethyl)pyrimidin-4-yl)amino)phenyl)acrylamide Compound I-413 was prepared in a manner similar to Example 68, substituting 2-methoxy-5-methylpyridin-4-amine for 3-amino-4-methylbenzamide, and (R)—N-(2-amino-5-((1-amino-1-oxopropan-2-yl)oxy)phenyl) acrylamide for N-(2-aminophenyl) acrylamide. MS: m/z 530.2 (ES-, M-H). ¹HNMR (DMSO-d₆) δ 1.46 (d, J=6.7 Hz, 3H), 2.09 (s, 3H), 3.76 (s, 3H), 4.54-4.59 (m, 1H), 5.76-5.79 (dd, J=1.8, 10.2 Hz, 1H), 6.25-6.30 (dd, J=1.9, 16.9 Hz, 1H), 6.39-6.46 (dd, J=10.0, 17.0 Hz, 1H), 6.80-6.83 (dd, J=2.8, 8.9 Hz, 1H), 6.86 (d, J=2.9 Hz, 1H), 7.11 (s, 1H), 7.26 (br s, 1H), 7.48 (br s, 1H), 7.51 (d, J=8.8 Hz, 1H), 7.79 (s, 1H), 8.24 (s, 1H), 8.35 (s, 1H), 8.70 (s, 1H), 10.22 (s, 1H).

Example 397

I-414

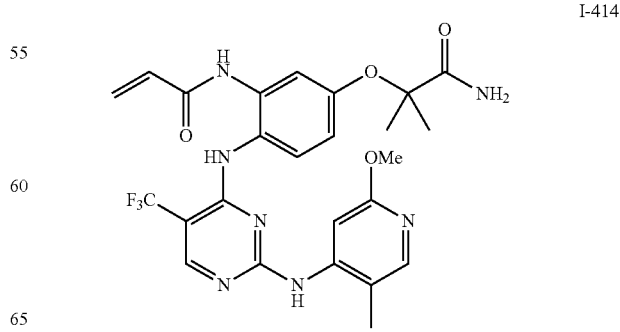

N-(5-((1-amino-2-methyl-1-oxopropan-2-yl)oxy)-2-((2-((2-methoxy-5-methylpyridin-4-yl)amino)-5-(trifluoromethyl)pyrimidin-4-yl)amino)phenyl)acrylamide Compound I-414 was prepared in a manner similar to Example 68, substituting 2-methoxy-5-methylpyridin-4-amine for 3-amino-4-methylbenzamide, and N-(2-amino-5-((1-amino-2-methyl-1-oxopropan-2-yl)oxy)phenyl) acrylamide for N-(2-aminophenyl) acrylamide. MS: m/z 546.2 (ES+, M+H). $^1$HNMR (DMSO-d$_6$) δ 1.43 (s, 6H), 2.09 (s, 3H), 3.77 (s, 3H), 5.77-5.80 (dd, J=1.3, 11.8 Hz, 1H), 6.26-6.30 (dd, J=1.9, 16.9 Hz, 1H), 6.38-6.45 (dd, J=9.9, 17.2 Hz, 1H), 6.80-6.83 (m, 2H), 7.12 (s, 1H), 7.25 (s, 1H), 7.47 (s, 1H), 7.54 (d, J=8.5 Hz, 1H), 7.80 (s, 1H), 8.28 (s, 1H), 8.35 (s, 1H), 8.75 (s, 1H), 10.25 (s, 1H).

Example 398

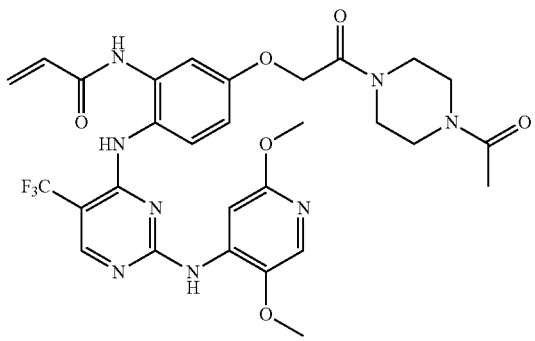

I-415

N-(5-(2-(4-acetylpiperazin-1-yl)-2-oxoethoxy)-2-((2-((2,5-dimethoxypyridin-4-yl)amino)-5-(trifluoromethyl)pyrimidin-4-yl)amino)phenyl)acrylamide Compound I-415 was prepared in a manner similar to Example 68, substituting 2,5-dimethoxypyridin-4-amine for 3-amino-4-methylbenzamide, and N-(5-(2-(4-acetylpiperazin-1-yl)-2-oxoethoxy)-2-aminophenyl) acrylamide for N-(2-aminophenyl) acrylamide. MS: m/z 644.6 (ES+, M+H).

Example 399

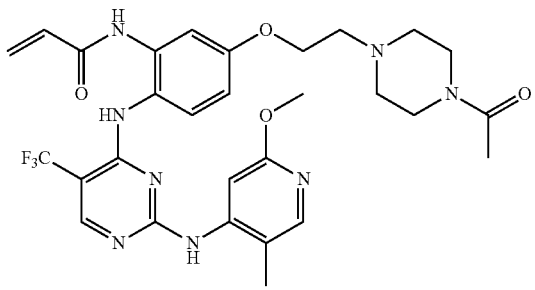

I-416

N-(5-(2-(4-acetylpiperazin-1-yl)ethoxy)-2-((2-((2-methoxy-5-methylpyridin-4-yl)amino)-5-(trifluoromethyl)pyrimidin-4-yl)amino)phenyl)acrylamide Compound I-416 was prepared in a manner similar to Example 68, substituting 2-methoxy-5-methylpyridin-4-amine for 3-amino-4-methylbenzamide, and N-(5-(2-(4-acetylpiperazin-1-yl)ethoxy)-2-aminophenyl)acrylamide for N-(2-aminophenyl) acrylamide. MS: m/z 614.8 (ES+, M+H).

Example 400

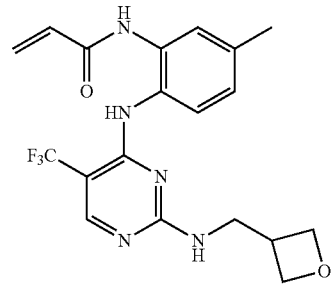

I-417

N-(5-methyl-2-((2-((oxetan-3-ylmethyl)amino)-5-(trifluoromethyl)pyrimidin-4-yl)amino) phenyl)acrylamide Compound I-417 was prepared in a manner similar to Example 1, substituting oxetan-3-ylmethanamine for (S)-tert-butyl 3-aminopiperidine-1-carboxylate, and N-(2-amino-5-methylphenyl)acrylamide for N-(2-aminophenyl) acrylamide. MS: m/z 407.8 (ES+, M+H).

Example 401

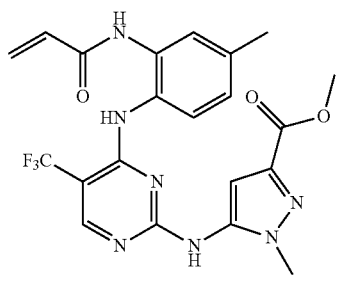

I-418

Methyl 5-((4-((2-acrylamido-4-methylphenyl)amino)-5-(trifluoromethyl)pyrimidin-2-yl)amino)-1-methyl-1H-pyrazole-3-carboxylate Compound I-418 was prepared in a manner similar to Example 68, substituting methyl 5-amino-1-methyl-1H-pyrazole-3-carboxylate for 3-amino-4-methylbenzamide, and N-(2-amino-5-methylphenyl)acrylamide for N-(2-aminophenyl) acrylamide. MS: m/z 475.7 (ES+, M+H).

Example 402

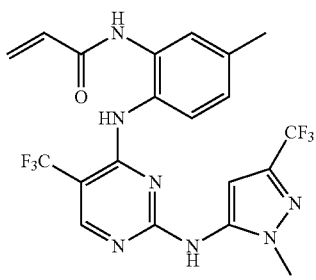

I-419

N-(5-methyl-2-((2-((1-methyl-3-(trifluoromethyl)-1H-pyrazol-5-yl)amino)-5-(trifluoromethyl)pyrimidin-4-yl)amino)phenyl)acrylamide Compound I-419 was prepared in a manner similar to Example 68, substituting methyl 1-methyl-3-(trifluoromethyl)-1H-pyrazol-5-amine for 3-amino-4-methylbenzamide, and N-(2-amino-5-methylphenyl)acrylamide for N-(2-aminophenyl) acrylamide. MS: m/z 485.8 (ES+, M+H).

Example 403

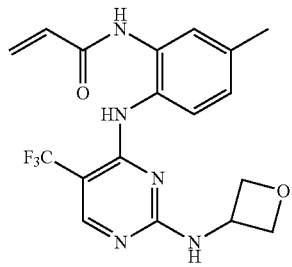

I-420

N-(5-methyl-2-((2-(oxetan-3-ylamino)-5-(trifluoromethyl)pyrimidin-4-yl)amino)phenyl) acrylamide Compound I-420 was prepared in a manner similar to Example 1, substituting oxetan-3-amine for (S)-tert-butyl 3-aminopiperidine-1-carboxylate, and N-(2-amino-5-methylphenyl)acrylamide for N-(2-aminophenyl)acrylamide. MS: m/z 394.2 (ES+, M+H).

Example 404

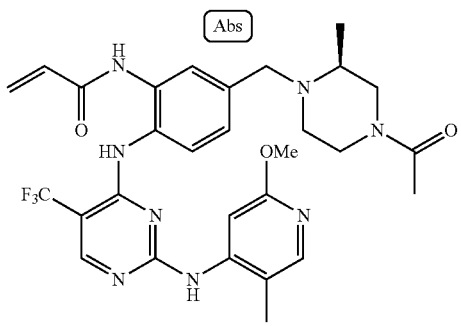

I-421

(S)—N-(5-((4-acetyl-2-methylpiperazin-1-yl)methyl)-2-((2-((2-methoxy-5-methylpyridin-4-yl)amino)-5-(trifluoromethyl)pyrimidin-4-yl)amino)phenyl)acrylamide Compound I-421 was prepared in a manner similar to Example 68, substituting 2-methoxy-5-methylpyridin-4-amine for 3-amino-4-methylbenzamide, and (S)—N-(5-((4-acetyl-2-methylpiperazin-1-yl)methyl)-2-aminophenyl)acrylamide for N-(2-aminophenyl) acrylamide. MS: m/z 598.7 (ES+, M+H).

Example 405

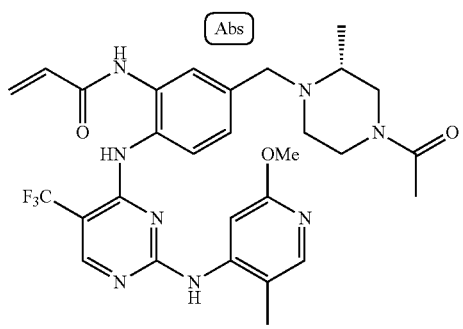

I-422

(R)—N-(5-((4-acetyl-2-methylpiperazin-1-yl)methyl)-2-((2-((2-methoxy-5-methylpyridin-4-yl)amino)-5-(trifluoromethyl)pyrimidin-4-yl)amino)phenyl)acrylamide Compound I-422 was prepared in a manner similar to Example 68, substituting 2-methoxy-5-methylpyridin-4-amine for 3-amino-4-methylbenzamide, and (R)—N-(5-((4-acetyl-2-methylpiperazin-1-yl)methyl)-2-aminophenyl)acrylamide for N-(2-aminophenyl) acrylamide. MS: m/z 598.7 (ES+, M+H).

Example 406

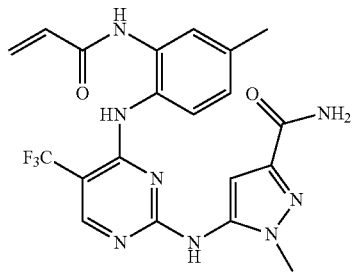

I-423

5-((4-((2-acrylamido-4-methylphenyl)amino)-5-(trifluoromethyl)pyrimidin-2-yl)amino)-1-methyl-1H-pyrazole-3-carboxamide Compound I-423 was prepared in a manner similar to Example 68, substituting 5-amino-1-methyl-1H-pyrazole-3- carboxamide for 3-amino-4-methylbenzamide, and N-(2-amino-5-methylphenyl)acrylamide for N-(2-aminophenyl) acrylamide. MS: m/z 461.7 (ES+, M+H).

Example 407

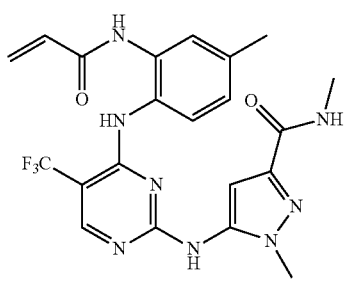

I-424

5-((4-((2-acrylamido-4-methylphenyl)amino)-5-(trifluoromethyl)pyrimidin-2-yl)amino)-N,1-dimethyl-1H-pyrazole-3-carboxamide Compound I-424 was prepared in a manner similar to Example 68, substituting 5-amino-N, 1-dimethyl-1H-pyrazole-3-carboxamide for 3-amino-4-methylbenzamide, and N-(2-amino-5-methylphenyl)acrylamide for N-(2-aminophenyl) acrylamide. MS: m/z 461.7 (ES+, M+H).

Example 408

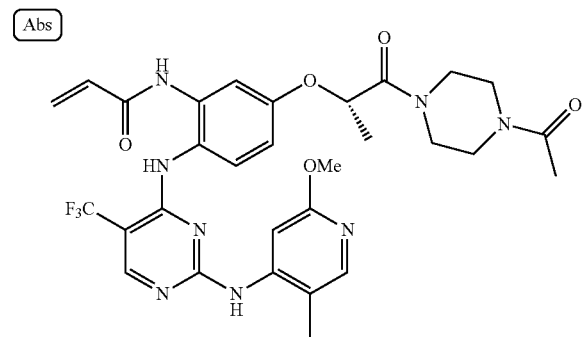

I-425

(S)—N-(5-(((1-(4-acetylpiperazin-1-yl)-1-oxopropan-2-yl)oxy)-2-((2-((2-methoxy-5-methylpyridin-4-yl)amino)-5-(trifluoromethyl)pyrimidin-4-yl)amino)phenyl)acrylamide Compound I-425 was prepared in a manner similar to Example 68, substituting 2-methoxy-5-methylpyridin-4-amine for 3-amino-4-methylbenzamide, and (S)-tert-butyl 4-(2-(3-acryl amido-4-aminophenoxy)propanoyl)piperazine-1-carboxylate for N-(2-aminophenyl)acrylamide. After Boc-deprotection with TFA, the resulting amine was acylated with acetyl chloride to yield desired compound I-425. MS: m/z 643.4 (ES+, M+H). $^1$HNMR (DMSO-d$_6$) δ 1.45 (d, J=6.5 Hz, 3H), 1.99 (s, 3H), 2.08 (s, 3H), 3.41 (m, 8H), 3.75 (s, 3H), 5.19 (m, 1H), 5.76-5.79 (dd, J=1.5, 10.0 Hz, 1H), 6.24-6.28 (dd, J=1.5, 16.9 Hz, 1H), 6.39-6.46 (dd, J=10.0, 16.8 Hz, 1H), 6.79 (m, 1H), 6.89 (s, 1H), 7.10 (s, 1H), 7.46-7.48 (m, 1H), 7.79 (s, 1H), 8.24 (s, 1H), 8.35 (s, 1H), 8.72 (s, 1H), 10.12 (br s, 1H).

Example 409

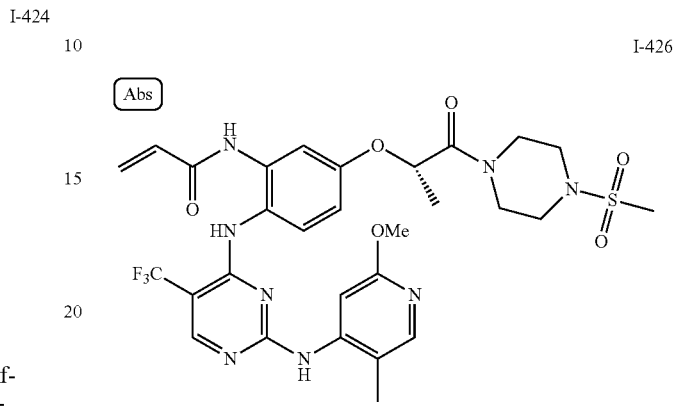

I-426

(S)—N-(2-((2-((2-methoxy-5-methylpyridin-4-yl)amino)-5-(trifluoromethyl)pyrimidin-4-yl)amino)-5-((1-(4-(methylsulfonyl)piperazin-1-yl)-1-oxopropan-2-yl)oxy)phenyl) acrylamide Compound I-426 was prepared in a manner similar to Example 68, substituting 2-methoxy-5-methylpyridin-4-amine for 3-amino-4-methylbenzamide, and (S)-tert-butyl 4-(2-(3-acryl amido-4-aminophenoxy)propanoyl)piperazine-1-carboxylate for N-(2-aminophenyl) acrylamide. After Boc-deprotection with TFA, the resulting amine reacted with methanesulfonyl chloride to yield desired compound I-426. MS: m/z 677.2 (ES−, M−H). $^1$HNMR (DMSO-d$_6$) δ 1.46 (d, J=6.4 Hz, 3H), 2.08 (s, 3H), 2.85 (s, 3H), 3.07 (m, 4H), 3.59-3.64 (m, 4H), 3.75 (s, 3H), 5.20 (m, 1H), 5.75-5.78 (dd, J=1.7, 10.0 Hz, 1H), 6.24-6.28 (dd, J=1.6, 16.9 Hz, 1H), 6.39-6.46 (dd, J=10.1, 17.0 Hz, 1H), 6.77-6.80 (dd, J=2.8, 8.8 Hz, 1H), 6.90 (d, J=2.6 Hz, 1H), 7.09 (s, 1H), 7.48 (d, J=8.9 Hz, 1H), 7.79 (s, 1H), 8.24 (s, 1H), 8.35 (s, 1H), 8.73 (s, 1H), 10.11 (s, 1H).

Example 410

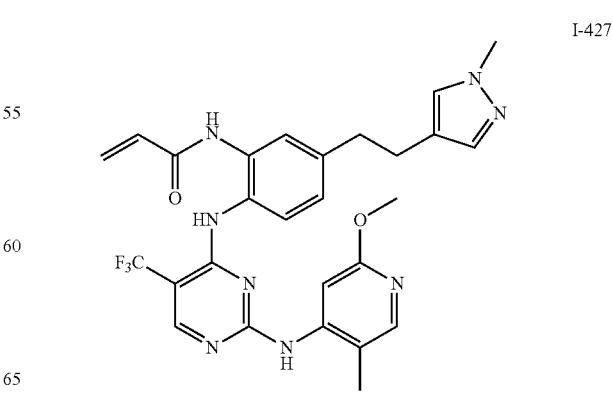

I-427

N-(2-((2-((2-methoxy-5-methylpyridin-4-yl)amino)-5-(trifluoromethyl)pyrimidin-4-yl) amino)-5-(2-(1-methyl-1H-pyrazol-4-yl)ethyl)phenyl)acrylamide Compound I-427 was prepared in a manner similar to Example 68, substituting 2-methoxy-5-methylpyridin-4-amine for 3-amino-4-methylbenzamide, and N-(2-amino-5-(2-(1-methyl-1H-pyrazol-4-yl)ethyl)phenyl) acrylamide for N-(2-aminophenyl) acrylamide. MS: m/z 553.2 (ES+, M+H). ¹HNMR (DMSO-d$_6$) δ 2.12 (s, 3H), 2.71 (d, J=7.7 Hz, 2H), 2.81 (d, J=7.2 Hz, 2H), 3.71 (s, 3H), 3.73 (s, 3H), 5.78 (d, J=9.4 Hz, 1H), 6.28 (d, J=16.4 Hz, 1H), 6.40-6.46 (m, 1H), 7.12-7.23 (m, 4H), 7.43 (s, 1H), 7.56 (d, J=7.8 Hz, 1H), 7.82 (s, 1H), 8.39 (s, 1H), 8.43 (s, 1H), 8.85 (s, 1H), 10.29 (s, 1H).

Example 411

N-(2-((2-((5-(fluoromethyl)-2-methoxypyridin-4-yl)amino)-5-(trifluoromethyl)pyrimidin-4-yl)amino)-5-methylphenyl)acrylamide Compound I-429 was prepared by fluorination of I-428 with DAST in dichloromethane. MS: m/z 477.2 (ES+, M+H). ¹HNMR (DMSO-d$_6$) δ 2.34 (s, 3H), 3.80 (s, 3H), 5.45 (s, 1H), 5.57 (s, 1H), 5.76-5.79 (dd, J=1.7, 10.1 Hz, 1H), 6.26-6.31 (dd, J=1.9, 16.9 Hz, 1H), 6.40-6.46 (dd, J=10.0, 16.9 Hz, 1H), 7.09 (s, 1H), 7.12 (s, 1H), 7.24 (s, 1H), 7.49 (d, J=8.0 Hz, 1H), 8.02 (d, J=3.3 Hz, 1H), 8.40 (s, 1H), 8.43 (s, 1H), 8.84 (s, 1H), 10.25 (s, 1H).

Example 413

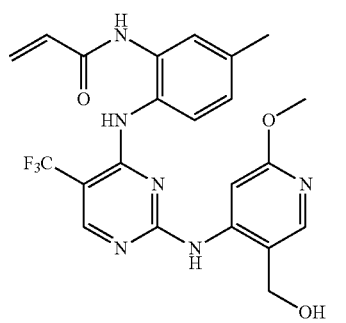

I-428

N-(2-((2-((5-(hydroxymethyl)-2-methoxypyridin-4-yl)amino)-5-(trifluoromethyl)pyrimidin-4-yl)amino)-5-methylphenyl)acrylamide Compound I-428 was prepared in a manner similar to Example 68, substituting (4-amino-6-methoxypyridin-3-yl)methanol for 3-amino-4-methyl benzamide, and N-(2-amino-5-methylphenyl)acrylamide for N-(2-aminophenyl) acrylamide. MS: m/z 473.1 (ES−, M−H). ¹HNMR (DMSO-d$_6$) δ 2.35 (s, 3H), 3.76 (s, 3H), 4.51 (d, J=4.8 Hz, 2H), 5.70 (t, J=4.9 Hz, 1H), 5.77-5.80 (dd, J=9.9, 1.7 Hz, 1H), 6.27-6.31 (dd, J=1.7, 16.9 Hz, 1H), 6.40-6.47 (dd, J=9.9, 16.8 Hz, 1H), 7.13-7.14 (m, 2H), 7.29 (s, 1H), 7.50 (d, J=8.7 Hz, 1H), 7.82 (s, 1H), 8.38 (s, 1H), 8.44 (s, 1H), 9.06 (s, 1H), 10.27 (s, 1H).

Example 412

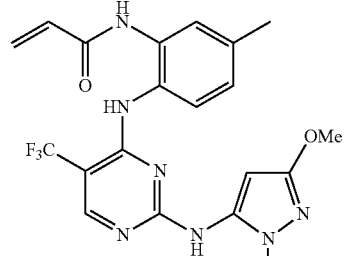

I-430

N-(2-((2-((3-methoxy-1-methyl-1H-pyrazol-5-yl)amino)-5-(trifluoromethyl)pyrimidin-4-yl)amino)-5-methylphenyl)acrylamide Compound I-430 was prepared in a manner similar to Example 68, substituting 3-methoxy-1-methyl-1H-pyrazol-5-amine for 3-amino-4-methyl benzamide, and N-(2-amino-5-methylphenyl)acrylamide for N-(2-aminophenyl) acrylamide. MS: m/z 448.2 (ES+, M+H). ¹HNMR (DMSO-d$_6$) δ 2.30 (s, 3H), 3.42 (s, 3H), 3.64 (s, 3H), 4.51 (d, J=4.8 Hz, 2H), 5.41 (s, 1H), 5.77-5.80 (dd, J=10, 2.0 Hz, 1H), 6.27-6.31 (dd, J=2.0, 16.8 Hz, 1H), 6.40-6.47 (dd, J=10, 16.8 Hz, 1H), 7.05 (d, J=7.8 Hz, 1H), 7.11 (s, 1H), 7.47 (d, J=8.0 Hz, 1H), 8.25 (s, 1H), 8.30 (s, 1H), 9.5 (br s, 1H), 10.2 (br s, 1H).

Example 414

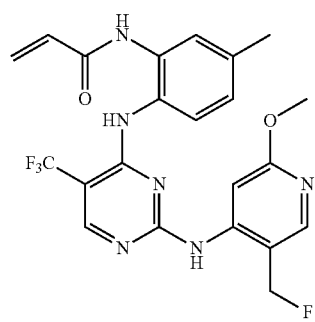

I-429

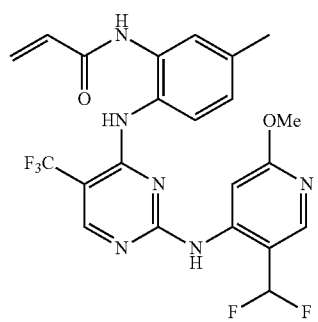

I-431

N-(2-((2-((5-(difluoromethyl)-2-methoxypyridin-4-yl)amino)-5-(trifluoromethyl)pyrimidin-4-yl)amino)-5-methylphenyl)acrylamide Compound I-431 was prepared in a manner similar to Example 68, substituting 5-(difluoromethyl)-2-methoxypyridin-4-amine for 3-amino-4-methyl benzamide, and N-(2-amino-5-methylphenyl)acrylamide for N-(2-aminophenyl) acrylamide. MS: m/z 494.8 (ES+, M+H).

Example 415

Described below are in vitro assays used to measure the biological activity of provided compounds as selective inhibitors of one or both of ERK 1 and ERK 2.

Protein Mass Modification Assay

Intact protein: Erk1 from Millipore (Cat. No. 14-439) was incubated for 60 min. at room temperature with a 10-fold excess of test compound to protein. 4 µL aliquots of the resulting mixture were diluted with 15 µL of 0.2% TFA prior to micro C4 ZipTipping directly onto the MALDI target using sinapinic acid as the desorption matrix (10 mg/ml in 0.1% TFA:Acetonitrile 50:50, v/v). The centroid mass of the target protein in the control sample was compared with the centroid mass of the target protein incubated with compound. A shift in the centroid mass of the treated protein compared to the untreated protein was divided by the molecular weight of the compound. This number corresponds to the percentage of modified protein after one hour incubation. Results from this assay are reported in Table A under the column "ERK1 Mass Mod (%)."

Omnia Assay Protocol for Potency Assessment Against MEK1 Activated ERK1:

The protocol below describes continuous-read kinase assays to measure potency of compounds against activated ERK1 enzyme. The mechanics of the assay platform are best described by the vendor (Invitrogen, Carlsbad, Calif.) on their website at the following URL: invitrogen.com/site/us/en/home.html.

Briefly, a 1.25× stock of ERK1 enzyme (14-439-K) from Millipore (Billerica, Mass.), 5×ATP (AS001A) and ST17-Sox conjugated peptide substrate (KNZ1171C) were prepared in 1× kinase reaction buffer consisting of 20 mM Tris, pH 7.5, 5 mM MgCl$_2$, 1 mM EGTA, 5 mM β-glycerophosphate, 5% glycerol (10× stock, KB002A) and 0.2 mM DTT. 10 µL of ATP/ST17-sox peptide substrate mix was combined with 0.5 µL volume of 100% DMSO and serially diluted compounds were prepared in 100% DMSO in a Corning (#3574) 384-well, white, non-binding surface microtiter plate (Corning, N.Y.). Kinase reactions were started with the addition of 40 µL of ERK1 solution and monitored every 71 seconds for 30-240 minutes at $\lambda_{ex}$360/$\lambda_{em}$485 in a Synergy plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~30+ minutes) from each reaction was determined from the slope of a plot of relative fluorescence units vs time (minutes or seconds) and then plotted against inhibitor concentration to estimate $^{App}IC_{50}$ from log [Inhibitor] vs Response, Variable Slope model in GraphPad Prism from GraphPad Software (San Diego, Calif.).

[Reagent] used in optimized protocol:
[ERK1]=4 nM, [ATP]=50 µM, [ST17-Sox]=10 µM (ATP $^{app}$KM 48 µM)

The results of this assay show the degree of inhibition of ERK activity, which is a direct measurement of inhibition of ERK activity. Results from this assay are reported in Table A under the column "ERK1 Omnia WT ATP KM IC$_{50}$ (nM)."

pRSK MSD Assay

The protocol below describes an assay to measure the kinase activity of ERK1/2 to phosphorylate a substrate, p90RSK, in the presence or absence of a test compound. This experiment was conducted using a Mesoscale Discovery plate. The day before the assay, HT29 cells were split and plated at 50,000 cells/well in complete growth media. After allowing cells to adhere, the media was removed and replaced with media containing 0.1% FBS and incubated overnight. Blank MSD plates (Mesoscale Discovery, Cat # L15XA3) were coated with 25 µl/well RSK capture antibody (BD Biosciences, Cat. #610226) and incubated at 4° C. overnight, then blocked with 150 µl of 3% BSA solution. The next day, the media from the cell culture plate was removed and replaced with 100 µl of media containing a test compound and incubated for 120 minutes at 37° C. The media was removed and replaced with 55 µl per well of lysis buffer with protease inhibitors (Roche Biosciences, Cat. #11836170001) and phosphatase inhibitors (Sigma-Aldrich, Cat. # P-0044 and P-5726), followed by incubation at 4° C. for 30 minutes. 50 µl of lysate was transferred to a blocked MSD plate, followed by incubation at room temperature for 2 hours under constant shaking. The plate was washed 3 times with MSD wash buffer (Mesoscale Discovery, Cat. # R617TX), and 25 µl/well phospho-RSK (pRSK) detection antibody (Cell Signaling Technology, Cat. #9335) was added with Sulfo-tagged detection antibody (Mesoscale Discovery, Cat. # R32AB-1) diluted in 1% BSA in MSD wash buffer. This mixture was incubated for 1 hour at room temperature under constant shaking. The plate was washed 3 times, and 150 µl 1×MSD read buffer was added, followed by signal detection in an MSD plate reader. Curve fitting analysis was done with variable slope in GraphPad software to generate EC$_{50}$ based on DMSO control (untreated) being 100% pRSK signal and maximum inhibition with a reference compound provided by the manufacturer as a positive control. Results from this assay, showing EC$_{50}$ (i.e., the concentration at which a test compound inhibits phosphorylation of RSK by 50%) are reported in Table A under the column "ERK1/ERK2 PRSK MSD HT29 EC$_{50}$ (nM)."

Measurement of Erk Occupancy with Biotinylated Covalent Probe

This experiment measured occupancy of the ERK1/ERK2 target by compounds according to the invention. This experiment was conducted using the Mesoscale Discovery test kit (Cat. # N45107B). One day before the assay, cells were split and added at 50,000 cells per well to a flat-bottom 96 well plate in 200 µl of growth medium. The next day, the medium was discarded, 100 µl medium containing test compound was added, and the plate was incubated at 37° C. for 120 minutes. The plate was rinsed once with PBS, and 50 µl lysis buffer with test compound was added. The plate was incubated at 4° C. for 30 min, and 30 µl of lysate was transferred to a plate to capture total and phosphor-Erk. Biotinylated probe I-299 was diluted in lysis buffer and added to each well to a final concentration of 0.2 µM. The plate was incubated for 2 hr under constant shaking at room temperature. The plate was washed 3 times with MSD wash buffer. To detect the biotinylated probe bonding, tagged streptavidin was added (Mesoscale Discovery, Cat. # R32AD-1) at 1 µg/ml, 25 µl/well, followed by a 60 min incubation under shaking. The plate was washed 3 times, 150 µl MSD Read Buffer (Mesoscale Discovery, Cat. R61TX) was added and the plate was read in a plate reader manufactured by MSD. Percent occupancy by test compound at Erk was calculated by comparing the chemiluminescence readings from treated cells as compared to the chemiluminescence readings in untreated controls (which are defined as 100% probe bonding or 0% test compound occupancy). The amount of covalent probe signal divided by the amount of ERK signal for samples with no test compound treatment represents the maximum probe signal (MPS). In samples treated with test compound prior to covalent probe, the ratio of probe signal to ERK signal (the test probe signal, TPS) was reduced by the degree of target occupancy by the test compound which blocks covalent probe binding. The difference between the MPS and the TPS, divided by the MPS gave the target occupancy by the test compound. This ratio was then expressed as a percent occupancy. Results from this assay are provided in Table A below under the column "Occupancy $EC_{50}$ (nM) HT-29."

Measurement of Duration of Action of Test Compounds

This example shows the extended activity of compounds according to the invention. One day before the assay, the cells were split and added at 50,000 cells per well in flat-bottom 96 well plate in 200 μl of growth media. The next day, the medium was discarded, 100 μl medium containing test compounds was added, and the plate was incubated at 37° C. for 120 minutes. The medium was discarded, and the cells were rinsed 3 times with PBS followed by addition of 200 μl of fresh grow medium. The plate was returned to a 37° C. incubator, and separate cell lysates were made using MSD lysis buffer after 0.25, 0.5, 1, 2, 4, 6, 8 and 18 or 24 hours. Thereafter, pRSK was measured as described above in the section entitled pRSK MSD Assay. The data is presented in Table A under the column titled "p-RSK inhibition at 6 hr (%)."

Measurement of Inhibition of Cancer Cell Proliferation (HT-29/Colorectal Adenocarcinoma)

The following protocol used an HT-29 cell line, which cell line is a model for colorectal adenocarcinoma. HT-29 cells were split and 3000 cells in 100 μl of growth medium were added per well of a flat-bottom 96-well plate. A two-fold test compound solution in serum-free RPM1640 was made, starting at 5,000 nM. Then, 3-fold serial dilutions were made across the plate from well 1 to well 11. Well 12, the last well in a row on the plate, was left as untreated control. 100 μl compound solutions were then transferred to the wells, so the total volume of media was 200 μl per well. Plates were returned to a 37° C. incubator, and the cells were cultured for 72 hours. To measure cell proliferation after 72 hours, media was discarded from the plates, 50 μl/well of fresh medium was added, and 50 μl CellTiterGlo solution was added (Promega Cat#G7573). The plate was covered with a dark lid and incubated for 10 min. A white sealing tape was applied to the bottom of the plate, and the plate was read in a luminescence plate reader. In order to calculate $GI_{50}$ (the proliferation of HT29 was inhibited by 50%) a standard curve was established to measure luminescence readings at certain cell densities by the following method. A 2-fold serial dilution was used to generate 8 cell densities from 50,000–390 cells per well in 50 μl media. 50 μl CellTiterGlo was added per well, and the plate was read in a luminescence plate reader after 10 min. The reading was plotted vs. cell number to generate a standard curve and the equation of the curve fit. The compound-treated sample luminescence readings were converted to cell numbers using the curve-fit equation. The percent of inhibition, using untreated control as 100% growth, was then calculated. $GI_{50}$ was then calculated by GraphPad Prism. Accordingly, this assay provides the dose at which 50% inhibition of cell growth was achieved and this data is shown in Table A, in the column entitled "HT-29 $GI_{50}$ (nM)."

Measurement of Inhibition of Cancer Cell Proliferation (HCT116/Colorectal Carcinoma)

The following protocol used a HCT116 cell line, which cell line is a model for colorectal carcinoma. HCT116 cells were split and 3000 cells in 100 μl of growth medium were added per well of a flat-bottom 96-well plate. A two-fold test compound solution in serum-free RPM1640 was made, starting at 5,000 nM. Then, 3-fold serial dilutions were made across the plate from well 1 to well 11. Well 12, the last well in a row on the plate, was left as untreated control. 100 μl compound solutions were then transferred to the wells, so the total volume of media was 200 μl per well. Plates were returned to a 37° C. incubator, and the cells were cultured for 72 hours. To measure cell proliferation after 72 hours, media was discarded from the plates, 50 μl/well of fresh medium was added, and 50 μl CellTiterGlo solution was added (Promega Cat#G7573). The plate was covered with a dark lid and incubated for 10 min. A white sealing tape was applied to the bottom of the plate, and the plate was read in a luminescence plate reader. In order to calculate $GI_{50}$ (the concentration at which 50% of growth is inhibited) a standard curve was established to measure luminescence readings at specific cell densities by the following method: a 2-fold serial dilution was used to generate 8 cell densities from 50,000–390 cells per well in 50 μl media. 50 μl CellTiterGlo was added per well, and the plate was read in a luminescence plate reader after 10 min. The reading was plotted vs. cell number to generate a standard curve and the equation of the curve fit. The compound-treated sample luminescence readings were converted to cell numbers using the curve-fit equation. The percent of inhibition, using untreated control as 100% growth, was then calculated. $GI_{50}$ was then calculated by GraphPad Prism. Accordingly, this assay provides the dose at which 50% inhibition of cell growth was achieved and this data is shown in Table A, in the column entitled "HCT116 $GI_{50}$ (nM)."

Measurement of Inhibition of Cancer Cell Proliferation (A375/Malignant Melanoma)

The following protocol used an A375 cell line, which cell line is a model for malignant melanoma. A375 cells were split and 3000 cells in 100 μl of growth medium were added per well of a flat-bottom 96-well plate. A two-fold test compound solution in serum-free DMEM was made, starting at 5,000 nM. Then, 3-fold serial dilutions were made across the plate from well 1 to well 11. Well 12, the last well in a row on the plate, was left as untreated control. 100 μl compound solutions were then transferred to the wells, so the total volume of media was 200 μl per well. Plates were returned to a 37° C. incubator, and the cells were cultured for 72 hours. To measure cell proliferation after 72 hours, media was discarded from the plates, 50 μl/well of fresh medium was added, and 50 μl CellTiterGlo solution was added (Promega Cat#G7573). The plate was covered with a dark lid and incubated for 10 min. A white sealing tape was applied to the bottom of the plate, and the plate was read in a luminescence plate reader. In order to calculate $GI_{50}$ (the concentration at which 50% of growth is inhibited) a standard curve was established to measure luminescence readings at specific cell densities by the following method: a 2-fold serial dilution was used to generate 8 cell densities from 50,000–390 cells per well in 50 μl media. 50 μl CellTiterGlo was added per well, and the plate was read in a luminescence plate reader after 10 min. The reading was plotted vs. cell number to generate a standard curve and the equation of the curve fit. The compound-treated sample luminescence readings were converted to cell numbers using the curve-fit equation. The percent of inhibition, using untreated control as 100% growth, was then calculated. $GI_{50}$ was then calculated by GraphPad Prism. Accordingly, this assay provides the dose at which 50% inhibition of cell growth was achieved and this data is shown in Table A, in the column entitled "A375 $GI_{50}$ (nM)."

Example 416

Detection of Total and Phosphor-RSK by MSD ELISA (A375)

The protocol below describes an assay to measure the kinase activity of ERK1/2 to phosphorylate a substrate, p90RSK, in the presence or absence of a test compound.
Cell Treatment A375 cells were grown in DMEM/10% FBS. Twenty four hours prior to the assay, 50,000 cells per well were plated in a 96 well flat bottom plate. Once cells attached to the plate, the medium was replaced with 100 ul of DMEM/0.1% FBS. Cells were cultured overnight in an incubator at 37° C.
Compound Dilution Compound stock solutions of 10 mM in DMSO were prepared. 1000× dilutions were then prepared in DMSO. 1 uL of DMSO solution was then transferred to 1 ml DMEM/ 0.1% FBS in a deep well plate. Cell plate media was discarded, followed by addition of 100 uL of the compound-containing media. The preparation was incubated at 37° C. for 2 hrs.

Cell lysates were prepared as described below.
pRSK or Total RSK MSD Assay
Day 1

MSD plates: Blank MSD plates were coated with 30 uL capture antibody (BD 610226) at a final concentration of 1 ug/mL in PBS. Both pRSK and total RSK MSD assays used the same capture antibody at the same concentration. Antibody stock concentration was 250 ug/mL. Once antibody solution was added to the MSD plate, the sides were tapped to be certain it was coated completely (visual inspection). It was then covered and placed at 4° C. overnight on a level surface.
Day 2

Block MSD Plate: The coating antibody was removed and the plate was washed on a plate washer in MSD wash buffer. The last bit of wash solution was tapped out and 150 uL/well of 3% BSA in MSD wash buffer was added in. The preparation was placed on a shaker at room temperature for at least an hour.

Add samples: Media was removed from compound-treated cells and replaced with 55 uL/well MSD cell lysis buffer containing protease and phosphotase I & II inhibitors. The preparation was incubated on a shaker in a cold room for 30-45 min. The blocked MSD plate was washed a on plate washer, tapping out the last bit of wash solution, followed by addition of 50 uL (of the 55 ul) cell lysate in a well-well transfer. The preparation was covered and incubated on a shaker at room temp for 2 hours. The lysate was removed, washed on a plate washer 3 times, and the last bit of wash buffer was tapped out and replace with 25 uL/well detection antibody (described below).
Detection Antibody:

For pRSK detection, a pRSK antibody stock of 21 ug/mL was prepared as follows: 1 ug/mL pRSK Ser380 antibody (Cell Signaling Technology, Cat. #9335)+1:750 anti-rabbit SulfoTag (Mesoscale Discovery, Cat. # R32AB-1) in 1% BSA in MSD wash buffer.

For total RSK detection, a total RSK antibody stock of 200 ug/mL was prepared as follows: 1 ug/mL total RSK (Santa Cruz sc-231G) antibody+1:750 anti-goat SulfoTag (from MSD, R32AG-1) in 1% BSA in MSD wash buffer.

The plate was incubated for 1 hr at room temperature on a shaker, followed by three washings. The last bit of wash buffer was tapped out. 150 uL/well 1×MSD Read buffer was added and the plate was then analyzed. Curve fitting analysis was done with variable slope in Graph Pad software to generate $EC_{50}$ based on DMSO control (untreated) being 100% pRSK signal and maximum inhibition with a reference compound provided by the manufacturer as a positive control. Results from this assay, showing $EC_{50}$ (i.e., the concentration at which a test compound inhibits phosphorylation of RSK by 50%) are reported in Table A under the column "ERK1/ERK2 PRSK MSD A375 $EC_{50}$ (nM)."

Example 417

Detection of Total and Phospho-RSK by MSD ELISA (HCT116)

The protocol below describes an assay to measure the kinase activity of ERK1/2 to phosphorylate a substrate, p90RSK, in the presence or absence of a test compound.
Cell Treatment HCT116 cells were grown in RPMI/10% FBS. Prior to the assay, 50,000 cells per well were plated in a 96 well flat bottom plate. Cells were cultured overnight in an incubator at 37° C.
Compound Dilution Compound stocks were 10 mM in DMSO. A 1000× dilution was made in DMSO. 1 uL of the DMSO solution was transferred to 1 ml RPMI/10% FBS in a deep well plate. Media in the cell plate was discarded, and 100 uL of the compound-containing media was added. The preparation was ncubated at 37° C. for 2 hrs.
Preparation of cell lysates are described below.
pRSK or Total RSK MSD Assay
Day 1

MSD plates: Blank MSD plates were coated with 30 uL capture antibody (BD 610226) at a final concentration of 1 ug/mL in PBS. Both pRSK and total RSK MSD assays used the same capture antibody at the same concentration. Antibody stock concentration was 250 ug/mL. Once antibody solution was added to MSD plate, the sides were tapped to be certain it was coated completely (visual inspection). It was then covered and placed at 4° C. overnight on a level surface.
Day 2

Block MSD Plate: The coating antibody was removed and the plate was washed on a plate washer in MSD wash buffer. The last bit of wash solution was tapped out and 150 uL/well 3% BSA (MSD Blocker A) in MSD wash buffer was added. The preparation was placed on a shaker at room temperature for at least an hour.

Add samples: Media was removed from compound-treated cells and replaced with 55 uL/well MSD cell lysis buffer containing protease and phosphotase I & II inhibitors. The preparations was incubate on a shaker in a cold room for 30-45 min. The blocked MSD plate was washed on a plate washer, and the last bit of wash solution was tapped out. Next was added 50 uL (of the 55 uL) cell lysate in a well-well transfer. The preparation was covered and incubated on shaker at room temp for 2 hours. The lysate was then removed and washed on plate washer 3 times. The last bit of wash buffer was then tapped out and replaced with 25 uL/well detection antibody (described below).

Detection Antibody:

For pRSK detection, a pRSK antibody stock of 21 ug/mL was prepared as follows: 1 ug/mL pRSK Ser380 antibody (Cell Signaling Technology, Cat. #9335)+1:750 anti-rabbit SulfoTag (from MSD, R32AB-1) in 1% BSA in MSD wash buffer.

For total RSK detection, a total RSK antibody stock of 200 ug/mL was prepared as follows: 1 ug/mL total RSK (Santa Cruz sc-231G) antibody+1:750 anti-goat SulfoTag (from MSD, R32AG-1) in 1% BSA in MSD wash buffer.

The plate was incubated for 1 hr at room temperature on a shaker, followed by three washes. The last bit of wash buffer was tapped out. Next, 150 uL/well 1×MSD Read buffer was added and the plate was analyzed by the MSD reader. Curve fitting analysis was done with variable slope in Graph Pad software to generate $EC_{50}$ based on DMSO control (untreated) being 100% pRSK signal and maximum inhibition with a reference compound provided by the manufacturer as a positive control. Results from this assay, showing $EC_{50}$ (i.e., the concentration at which a test compound inhibits phosphorylation of RSK by 50%) are reported in Table A under the column "ERK1/ERK2 PRSK MSD HCT116 $EC_{50}$ (nM)."

Example 418

Table A shows data for selected compounds in various assays. Compound numbers in Table A correspond to Compound numbers in Table 3, above. Compounds having an activity designated as "A" provided an $EC_{50}/IC_{50}/GI_{50} \leq 100$ nM; compounds having an activity designated as "B" provided an $EC_{50}/IC_{50}/GI_{50}$ of 101-500 nM; compounds having an activity designated as "C" provided an $EC_{50}/IC_{50}/GI_{50}$ of 501-999 nM; compounds having an activity designated as "D" provided an $EC_{50}/IC_{50}/GI_{50}$ of $\geq 1000$ nM.

Compounds having an activity designated as "E" provided a mass modification of $\geq 70\%$; compounds having an activity designated as "F" provided a mass modification of 31-69%; compounds having an activity designated as "G" provided a mass modification $\leq 30\%$.

With regard to p-RSK inhibition at 6 hours, compounds having an activity designated as "E" provided a p-RSK inhibition percent of $\geq 70\%$; compounds having an activity designated as "F" provided a p-RSK inhibition percent of 31-69%; compounds having an activity designated as "G" provided a p-RSK inhibition percent of $\leq 30\%$.

TABLE A

| Cmpd # | ERK1 Omnia WT ATP KM $IC_{50}$ (nM) | ERK1/ERK2 PRSK MSD HT29 $EC_{50}$ (nM) | ERK1 Mass Mod (%) | HT-29 $GI_{50}$ (nM) | HT-29 Occupancy $EC_{50}$ (nM) | p-RSK inhibition at 6 hr (%) | ERK1/ERK2 PRSK A375 $EC_{50}$ (nM) | ERK1/ERK2 PRSK HCT116 $EC_{50}$ (nM) | A375 $GI_{50}$ (nM) | HCT116 $GI_{50}$ (nM) |
|---|---|---|---|---|---|---|---|---|---|---|
| I-1 | B | B | G | | | | | | | |
| I-2 | A | A | E | B | A | | | | | |
| I-3 | B | | E | | | | | | | |
| I-4 | B | | F | | | | | | | |
| I-5 | A | B | E | B | | | | | | |
| I-6 | D | D | E | | | | | | | |
| I-7 | A | C | E | C | | | | | | |
| I-8 | B | A | E | C | | | | | | |
| I-9 | A | A | E | B | | | | | | |
| I-10 | A | A | E | A | | | | | A | A |
| I-11 | B | B | E | B | | | | | | |
| I-12 | B | B | E | B | | | | | | |
| I-13 | A | B | E | B | | | | | | |
| I-14 | B | D | E | | | | | | | |
| I-15 | A | A | E | A | | E | A | | A | A |
| I-16 | B | C | E | | | | | | | |
| I-17 | A | B | F | | | | | | | |
| I-18 | A | B | E | B | | | | B | | |
| I-19 | A | A | E | A | | | | | A | A |
| I-20 | A | A | E | A | | | | | A | A |
| I-21 | B | D | G | | | | | | | |
| I-22 | B | D | G | C | | | | B | | |
| I-23 | A | B | E | A | | | | B | | |
| I-24 | D | D | G | | | | | | | |
| I-25 | D | D | G | | | | | | | |
| I-26 | D | | G | | | | | | | |
| I-27 | | C | F | | | | | | | |
| I-28 | | | | | | | | | | |
| I-29 | D | D | G | | | | | | | |
| I-30 | B | D | G | | | | | | | |
| I-31 | C | D | G | | | | | | | |
| I-32 | B | D | F | | | | | | | |
| I-33 | D | D | F | | | | | | | |
| I-34 | B | D | F | | | | | | | |
| I-35 | B | D | G | | | | | | | |
| I-36 | A | C | E | | | | | | | |
| I-37 | A | A | E | A | | | | A | | |
| I-38 | A | D | E | C | | | | B | | |
| I-39 | B | C | E | | | | | | | |
| I-40 | A | D | F | | | | | | | |
| I-41 | A | B | E | A | | | | A | | |
| I-42 | A | B | E | D | | | | D | | |
| I-43 | A | B | E | A | | | | A | | |
| I-44 | D | D | E | | | | | | | |
| I-45 | D | D | G | | | | | | | |

TABLE A-continued

| Cmpd # | ERK1 Omnia WT ATP KM IC$_{50}$ (nM) | ERK1/ERK2 PRSK MSD HT29 EC$_{50}$ (nM) | ERK1 Mass Mod (%) | HT-29 GI$_{50}$ (nM) | HT-29 Occupancy EC$_{50}$ (nM) | p-RSK inhibition at 6 hr (%) | ERK1/ERK2 PRSK A375 EC$_{50}$ (nM) | ERK1/ERK2 PRSK HCT116 EC$_{50}$ (nM) | A375 GI$_{50}$ (nM) | HCT116 GI$_{50}$ (nM) |
|---|---|---|---|---|---|---|---|---|---|---|
| I-46 | A | C | G | C | | | | | C | |
| I-47 | A | B | G | B | | | | | A | |
| I-48 | A | D | G | D | | | | | D | |
| I-49 | C | | E | | | | | | | |
| I-50 | B | | E | | | | | | | |
| I-51 | B | | E | | | | | | | |
| I-52 | B | | E | B | | | | | B | D |
| I-53 | A | D | G | | | | | | | |
| I-54 | A | D | G | | | | | | | |
| I-55 | A | B | E | A | | | | | A | B |
| I-56 | B | B | F | B | | | | | B | B |
| I-57 | B | B | F | B | | | | | B | B |
| I-58 | B | B | E | B | | | | | B | B |
| I-59 | C | D | E | B | | | | | B | C |
| I-60 | C | D | E | B | | | | | D | C |
| I-61 | D | D | E | | | | | | | |
| I-62 | D | D | F | | | | | | | |
| I-63 | B | D | E | | | | | | | |
| I-64 | A | A | E | A | | | B | | A | A |
| I-65 | | | E | | | | | | | |
| I-66 | C | | E | | | | | | | |
| I-67 | B | C | E | | | | | | | |
| I-68 | A | A | E | A | A | E | B | | A | A |
| I-69 | A | B | E | A | | | | | | |
| I-70 | A | A | E | A | | | | | A | |
| I-71 | A | A | E | B | | | | | | |
| I-72 | B | | E | D | | | | | | |
| I-73 | B | B | E | B | | | | | | |
| I-74 | B | C | E | B | | | | | | |
| I-75 | B | D | E | | | | | | | |
| I-76 | A | C | E | A | A | | | | B | |
| I-77 | A | B | E | A | A | | | | B | B |
| I-78 | C | | E | | | | | | | |
| I-79 | B | A | E | A | | E | | | A | |
| I-80 | B | B | E | A | | | | | B | |
| I-81 | B | B | E | A | | | | | A | |
| I-82 | C | D | E | | | | | | | |
| I-83 | B | B | E | | | | | | | |
| I-84 | B | A | E | B | | | | | B | C |
| I-85 | A | A | E | A | | E | A | A | A | B |
| I-86 | A | A | E | A | | E | | | A | A |
| I-87 | B | D | G | | | | | | | |
| I-88 | A | B | E | A | | | B | | A | A |
| I-89 | B | B | F | A | | | B | | A | A |
| I-90 | A | A | E | B | | | A | B | B | C |
| I-91 | A | B | E | A | | | A | A | A | A |
| I-92 | A | A | E | A | | | A | A | A | A |
| I-93 | B | A | E | A | | | A | A | A | A |
| I-94 | B | A | F | A | | | B | | A | A |
| I-95 | A | A | E | A | | | A | | A | A |
| I-96 | B | A | E | A | | | B | | B | A |
| I-97 | C | | G | | | | | | | |
| I-98 | B | D | G | | | | | | | |
| I-99 | C | D | G | | | | | | | |
| I-100 | B | C | F | D | | | | | | |
| I-101 | B | B | E | | | | | | | |
| I-102 | A | A | E | B | A | | | | | |
| I-103 | A | B | E | A | | | | | | |
| I-104 | C | C | E | C | | | | | | |
| I-105 | C | D | F | C | | | | | | |
| I-106 | D | D | F | | | | | | | |
| I-107 | B | B | E | | | | | | | |
| I-108 | A | A | E | A | | | | | B | |
| I-109 | C | D | E | | | | | | | |
| I-110 | B | B | E | | | | | | | |
| I-111 | B | B | E | | | | | | | |
| I-112 | A | A | E | B | | | | | | |
| I-113 | D | D | F | | | | | | | |
| I-114 | D | D | F | | | | | | | |
| I-115 | A | A | E | A | | | | | A | B |
| I-116 | B | B | E | B | | | | | | |
| I-117 | B | B | E | B | | | | | | |
| I-118 | A | A | E | B | | | | | B | |
| I-119 | A | C | E | B | | | | | | |
| I-120 | A | A | E | A | | | | | B | |

TABLE A-continued

| Cmpd # | ERK1 Omnia WT ATP KM IC$_{50}$ (nM) | ERK1/ERK2 PRSK MSD HT29 EC$_{50}$ (nM) | ERK1 Mass Mod (%) | HT-29 GI$_{50}$ (nM) | HT-29 Occupancy EC$_{50}$ (nM) | p-RSK inhibition at 6 hr (%) | ERK1/ERK2 PRSK A375 EC$_{50}$ (nM) | ERK1/ERK2 PRSK HCT116 EC$_{50}$ (nM) | A375 GI$_{50}$ (nM) | HCT116 GI$_{50}$ (nM) |
|---|---|---|---|---|---|---|---|---|---|---|
| I-121 | A | A | E | A | | | | | | |
| I-122 | A | A | E | B | | | | | | |
| I-123 | A | A | E | A | | | | | A | A |
| I-124 | A | A | E | B | | | | | | |
| I-125 | A | B | E | B | | | | | | |
| I-126 | B | C | E | C | | | | | | |
| I-127 | B | B | E | B | | | | | | |
| I-128 | B | | E | | | | | | | |
| I-129 | B | | E | | | | | | | |
| I-130 | D | | G | D | | | | | | |
| I-131 | A | A | E | A | | | | | A | |
| I-132 | D | | E | | | | | | | |
| I-133 | B | D | E | | | | | | | |
| I-134 | A | B | E | A | | | | | A | |
| I-135 | B | D | E | | | | | | | |
| I-136 | A | C | E | | | | | | | |
| I-137 | A | C | E | | | | | | | |
| I-138 | C | D | E | | | | | | | |
| I-139 | A | A | E | A | | | | | A | A |
| I-140 | A | A | E | A | | F | A | | A | A |
| I-141 | B | C | E | | | | | | | |
| I-142 | B | | E | | | | | | | |
| I-143 | | | F | | | | | | | |
| I-144 | | | F | | | | | | | |
| I-145 | | | E | | | | | | | |
| I-146 | | | E | | | | | | | |
| I-147 | | | E | | | | | | | |
| I-148 | | | E | | | | | | | |
| I-149 | B | | E | | | | | | | |
| I-150 | D | | E | | | | | | | |
| I-151 | D | | F | | | | | | | |
| I-152 | C | | E | | | | | | | |
| I-153 | D | | F | | | | | | | |
| I-154 | D | | G | | | | | | | |
| I-155 | B | D | E | D | | | | | | |
| I-156 | B | C | E | D | | | | | | |
| I-157 | D | | F | | | | | | | |
| I-158 | D | | F | | | | | | | |
| I-159 | D | | F | | | | | | | |
| I-160 | D | | G | | | | | | | |
| I-161 | D | | G | | | | | | | |
| I-162 | D | | E | | | | | | | |
| I-163 | C | | E | | | | | | | |
| I-164 | B | D | E | D | | | | | | |
| I-165 | D | | F | | | | | | | |
| I-166 | B | B | E | B | | | | | | |
| I-167 | B | D | E | D | | | | | | |
| I-168 | B | D | E | D | | | | | | |
| I-169 | C | | E | | | | | | | |
| I-170 | D | | E | | | | | | | |
| I-171 | D | | E | | | | | | | |
| I-172 | D | | F | | | | | | | |
| I-173 | C | | E | | | | | | | |
| I-174 | C | | E | | | | | | | |
| I-175 | B | | E | | | | | | | |
| I-176 | C | | E | | | | | | | |
| I-177 | B | | E | | | | | | | |
| I-178 | B | | E | | | | | | | |
| I-179 | B | C | E | D | | | | | | |
| I-180 | C | C | E | D | | | | | | |
| I-181 | C | | E | | | | | | | |
| I-182 | D | | E | | | | | | | |
| I-183 | B | C | E | D | | | | | | |
| I-184 | D | | E | | | | | | | |
| I-185 | B | B | E | C | | | | | | |
| I-186 | B | C | E | D | | | | | | |
| I-187 | B | B | | | | | | | | |
| I-188 | D | D | F | | | | | | | |
| I-189 | D | | G | | | | | | | |
| I-190 | D | | F | D | | | | | | |
| I-191 | A | B | E | A | | | | | A | |
| I-192 | A | A | E | A | | | | | | |
| I-193 | A | B | E | B | | | | | | |
| I-194 | B | C | E | | | | | | | |
| I-195 | B | D | E | | | | | | | |

TABLE A-continued

| Cmpd # | ERK1 Omnia WT ATP KM IC$_{50}$ (nM) | ERK1/ERK2 PRSK MSD HT29 EC$_{50}$ (nM) | ERK1 Mass Mod (%) | HT-29 GI$_{50}$ (nM) | HT-29 Occupancy EC$_{50}$ (nM) | p-RSK inhibition at 6 hr (%) | ERK1/ERK2 PRSK A375 EC$_{50}$ (nM) | ERK1/ERK2 PRSK HCT116 EC$_{50}$ (nM) | A375 GI$_{50}$ (nM) | HCT116 GI$_{50}$ (nM) |
|---|---|---|---|---|---|---|---|---|---|---|
| I-196 | C | D | E | | | | | | | |
| I-197 | D | D | E | | | | | | | |
| I-198 | B | B | E | | | | | | | |
| I-199 | D | | G | | | | | | | |
| I-200 | D | | G | | | | | | | |
| I-201 | D | | G | | | | | | | |
| I-202 | B | | F | | | | | | | |
| I-203 | B | | E | | | | | | | |
| I-204 | D | | F | | | | | | | |
| I-205 | A | A | E | A | A | | | | | |
| I-206 | A | B | E | A | A | | | | | |
| I-207 | B | D | E | | | | | | | |
| I-208 | A | A | E | B | | | | | | |
| I-209 | B | B | F | C | | | | | | |
| I-210 | B | B | F | | | | | | | |
| I-211 | A | A | F | B | A | | | | | |
| I-212 | A | A | F | B | A | | | | | |
| I-213 | B | B | E | | | | | | | |
| I-214 | A | A | F | A | A | | | | | |
| I-215 | D | | G | | | | | | | |
| I-216 | D | | G | | | | | | | |
| I-217 | D | D | G | | | | | | | |
| I-218 | D | D | G | | | | | | | |
| I-219 | D | D | G | | | | | | | |
| I-220 | B | C | E | | | | | | | |
| I-221 | A | A | E | C | | | | | | |
| I-222 | D | D | G | | | | | | | |
| I-223 | D | D | E | | | | | | | |
| I-224 | B | B | E | B | | | | | | |
| I-225 | B | D | F | | | | | | | |
| I-226 | C | C | E | | | | | | | |
| I-227 | B | D | E | | | | | | | |
| I-228 | B | B | E | | | | | | | |
| I-229 | A | B | E | A | E | | | | A | |
| I-230 | C | B | E | | | | | | | |
| I-231 | B | B | E | A | | | | | A | |
| I-232 | B | B | E | A | | | | | B | |
| I-233 | B | B | E | B | | | | | B | |
| I-234 | B | B | F | B | | | | | B | |
| I-235 | B | A | E | A | | | | | A | |
| I-236 | B | B | E | B | | | | | A | |
| I-237 | A | B | E | A | | | | | A | C |
| I-238 | B | A | E | B | | | | | B | D |
| I-239 | B | | E | B | | | | | B | C |
| I-240 | A | A | E | A | E | | | | A | B |
| I-241 | A | A | E | A | E | | | | B | B |
| I-242 | A | A | E | A | E | A | | D | A | B |
| I-243 | D | D | G | | | | | | | |
| I-244 | D | B | E | | | | | | | |
| I-245 | B | A | F | B | | | | | B | B |
| I-246 | B | A | E | A | | | | | A | B |
| I-247 | D | B | F | | | | | | | |
| I-248 | A | B | E | C | | | | | C | D |
| I-249 | | | F | | | | | | | |
| I-250 | | | G | | | | | | | |
| I-251 | | | G | | | | | | | |
| I-252 | | | F | | | | | | | |
| I-253 | | | F | | | | | | | |
| I-254 | | | E | | | | | | | |
| I-255 | D | | F | D | | | | | | |
| I-256 | D | | G | D | | | | | | |
| I-257 | D | | G | | | | | | | |
| I-258 | A | | E | D | | | | | | |
| I-259 | D | | F | | | | | | | |
| I-260 | D | | G | | | | | | | |
| I-261 | D | | G | | | | | | | |
| I-262 | D | | F | | | | | | | |
| I-263 | B | D | E | D | | | | | | |
| I-264 | D | | F | | | | | | | |
| I-265 | D | | F | | | | | | | |
| I-266 | B | | E | D | | | | | | |
| I-267 | B | D | E | D | | | | | | |
| I-268 | D | | G | | | | | | | |
| I-269 | D | | G | | | | | | | |
| I-270 | D | | G | | | | | | | |

TABLE A-continued

| Cmpd # | ERK1 Omnia WT ATP KM IC$_{50}$ (nM) | ERK1/ERK2 PRSK MSD HT29 EC$_{50}$ (nM) | ERK1 Mass Mod (%) | HT-29 GI$_{50}$ (nM) | HT-29 Occupancy EC$_{50}$ (nM) | p-RSK inhibition at 6 hr (%) | ERK1/ERK2 PRSK A375 EC$_{50}$ (nM) | ERK1/ERK2 PRSK HCT116 EC$_{50}$ (nM) | A375 GI$_{50}$ (nM) | HCT116 GI$_{50}$ (nM) |
|---|---|---|---|---|---|---|---|---|---|---|
| I-271 | D | D | G | | | | | | | |
| I-272 | D | D | G | | | | | | | |
| I-273 | | | G | | | | | | | |
| I-274 | | | G | | | | | | | |
| I-275 | | | G | | | | | | | |
| I-276 | D | D | G | B | | | | | D | |
| I-277 | D | D | E | | | | D | D | | |
| I-278 | D | D | F | | | | D | D | | |
| I-279 | C | D | E | | | | D | D | | |
| I-280 | D | D | E | | | | D | D | | |
| I-281 | A | A | E | A | | | A | A | A | A |
| I-282 | B | B | E | A | | | A | A | A | A |
| I-283 | A | A | E | A | | | A | A | A | A |
| I-284 | A | A | E | C | | | A | A | A | B |
| I-285 | C | B | E | | | | D | D | | |
| I-286 | A | A | E | A | | | A | A | A | A |
| I-287 | B | A | E | | | | A | B | | |
| I-288 | C | B | E | | | | B | B | | |
| I-289 | A | A | E | | | | A | B | | |
| I-290 | D | D | E | | | | D | C | | |
| I-291 | A | A | E | A | | | A | A | A | A |
| I-292 | A | A | E | A | | | A | A | A | A |
| I-293 | B | B | E | A | | | C | A | A | B |
| I-294 | B | A | E | A | | | A | A | A | A |
| I-295 | B | A | E | | | | A | A | | |
| I-296 | A | A | E | A | | | A | A | A | A |
| I-297 | A | A | E | | | | D | A | | |
| I-298 | D | | G | | | | | | | |
| I-299 | B | D | E | D | | | | | | |
| I-300 | B | D | E | D | | | | | | |
| I-301 | C | D | E | D | | | | | | |
| I-302 | D | D | E | D | | | | | | |
| I-303 | D | D | G | D | | | | | | |
| I-304 | B | D | D | | | | | | | |
| I-305 | B | D | E | | | | | | | |
| I-306 | B | | E | | | | | | | |
| I-307 | A | D | | B | | | | | A | |
| I-308 | B | D | G | B | | | | | B | |
| I-309 | D | D | G | | | | | | | |
| I-310 | A | C | G | A | | | | | A | |
| I-311 | A | C | | C | | | | | D | D |
| I-312 | D | | G | | | | | | | |
| I-313 | | | G | | | | | | | |
| I-314 | A | | G | | | | | | | |
| I-315 | D | | G | | | | | | | |
| I-316 | D | D | | | | | | | | |
| I-317 | A | D | G | A | | | | | A | |
| I-318 | A | C | G | B | | | | | A | |
| I-319 | A | A | E | B | A | | | | | |
| I-320 | C | | F | | | | | | | |
| I-321 | D | D | E | | | | D | D | | |
| I-322 | A | A | E | B | | | A | B | A | B |
| I-323 | B | A | E | B | | | A | B | B | C |
| I-324 | A | B | E | A | | | B | A | A | A |
| I-325 | B | B | E | A | | | B | A | A | A |
| I-326 | B | A | E | A | | | A | A | A | A |
| I-327 | B | A | E | A | | | A | A | A | A |
| I-328 | A | A | E | A | | | A | A | A | A |
| I-329 | D | B | E | | | | D | B | | |
| I-330 | D | D | E | | | | B | D | | |
| I-331 | D | B | E | | | | C | D | | |
| I-332 | D | A | E | | | | B | B | | |
| I-333 | B | B | E | D | | | B | D | D | D |
| I-334 | A | A | E | A | | | A | A | A | A |
| I-335 | D | C | E | | | | C | C | | |
| I-336 | C | A | E | A | | | B | B | A | B |
| I-337 | C | A | E | A | | | A | A | A | A |
| I-338 | B | A | E | A | | | A | A | A | A |
| I-339 | D | B | E | A | | | C | B | A | A |
| I-340 | B | A | E | B | | | A | B | B | C |
| I-341 | C | B | E | | | | D | D | | |
| I-342 | C | B | E | A | | | B | B | B | B |
| I-343 | B | B | F | | | | B | B | | |
| I-344 | A | A | E | B | | | B | B | B | C |
| I-345 | B | D | E | | | | D | D | | |

TABLE A-continued

| Cmpd # | ERK1 Omnia WT ATP KM IC$_{50}$ (nM) | ERK1/ERK2 PRSK MSD HT29 EC$_{50}$ (nM) | ERK1 Mass Mod (%) | HT-29 GI$_{50}$ (nM) | HT-29 Occupancy EC$_{50}$ (nM) | p-RSK inhibition at 6 hr (%) | ERK1/ERK2 PRSK A375 EC$_{50}$ (nM) | ERK1/ERK2 PRSK HCT116 EC$_{50}$ (nM) | A375 GI$_{50}$ (nM) | HCT116 GI$_{50}$ (nM) |
|---|---|---|---|---|---|---|---|---|---|---|
| I-346 | C | B | E | B | | | B | B | B | C |
| I-347 | A | A | E | B | | | B | B | A | C |
| I-348 | D | B | G | | | | C | C | | |
| I-349 | B | B | E | B | | | B | B | B | D |
| I-350 | C | D | F | | | | D | D | | |
| I-351 | B | B | F | | | | B | C | | |
| I-352 | D | D | G | | | | D | D | | |
| I-353 | D | D | G | | | | D | D | | |
| I-354 | B | B | E | B | | | B | B | C | C |
| I-355 | B | B | E | C | | | B | B | B | D |
| I-356 | C | B | E | C | | | B | C | C | D |
| I-357 | B | B | E | A | | | B | B | B | C |
| I-358 | B | B | E | | | | B | C | | |
| I-359 | B | B | E | C | | | B | C | B | D |
| I-360 | D | B | E | D | | | B | C | B | D |
| I-361 | A | A | E | B | | | B | B | B | C |
| I-362 | D | C | E | | | | C | D | | |
| I-363 | D | D | E | | | | D | D | | |
| I-364 | A | A | E | B | | | A | B | A | B |
| I-365 | D | D | E | | | | D | D | | |
| I-366 | D | D | E | | | | D | D | | |
| I-367 | B | B | E | | | | B | C | | |
| I-368 | B | C | E | | | | D | B | | |
| I-369 | D | D | F | | | | D | D | | |
| I-370 | B | C | E | | | | D | C | | |
| I-371 | B | B | F | | | | B | D | | |
| I-372 | C | A | F | | | | B | B | | |
| I-373 | D | B | F | | | | C | C | | |
| I-374 | A | A | E | B | | | A | A | A | B |
| I-375 | D | D | E | | | | B | D | | |
| I-376 | B | A | E | B | | | A | A | B | C |
| I-377 | A | A | E | A | | | A | A | B | D |
| I-378 | C | B | E | | | | C | D | | |
| I-379 | B | A | E | B | | | A | C | B | B |
| I-380 | D | C | E | | | | D | | | |
| I-381 | A | A | E | B | | | A | A | B | B |
| I-382 | B | B | E | | | | D | C | | |
| I-383 | B | A | E | | | | D | B | | |
| I-384 | A | A | E | A | | | A | A | A | B |
| I-385 | A | A | E | | | | A | A | | |
| I-386 | C | C | E | | | | D | C | | |
| I-387 | B | B | E | | | | B | B | | |
| I-388 | B | A | E | | | | A | A | | |
| I-389 | A | A | E | A | | | A | A | A | B |
| I-390 | A | A | E | A | | | A | A | A | B |
| I-391 | B | B | E | | | | D | B | | |
| I-392 | B | C | E | | | | D | D | | |
| I-393 | C | C | E | | | | D | C | | |
| I-394 | B | C | E | | | | D | C | | |
| I-395 | D | D | E | | | | D | D | | |
| I-396 | A | B | E | | | | B | B | | |
| I-397 | D | C | F | | | | C | D | | |
| I-398 | A | A | E | A | | | A | A | A | B |
| I-399 | B | C | E | | | | C | B | | |
| I-400 | A | A | E | B | | | A | A | B | C |
| I-401 | B | B | E | | | | B | B | | |
| I-402 | | C | E | | | | C | B | | |
| I-403 | | A | E | | | | B | B | | |
| I-404 | | B | | | | | B | B | | |
| I-405 | | A | | | | | B | A | | |
| I-406 | | B | | | | | B | B | | |
| I-407 | B | A | | | | | B | B | | |
| I-408 | B | B | | | | | B | C | | |
| I-409 | A | C | | | | | D | C | | |
| I-410 | A | B | | | | | B | B | | |
| I-411 | D | D | | | | | D | D | | |
| I-412 | A | D | | | | | A | B | | |
| I-413 | A | A | | | | | A | A | | |
| I-414 | A | A | | | | | A | | | |
| I-415 | A | C | | | | | C | B | | |
| I-416 | A | B | | | | | B | B | | |
| I-417 | D | D | | | | | D | D | | |
| I-418 | B | C | | | | | C | B | | |
| I-419 | D | D | | | | | D | D | | |
| I-420 | D | D | | | | | D | D | | |

TABLE A-continued

| Cmpd # | ERK1 Omnia WT ATP KM IC$_{50}$ (nM) | ERK1/ERK2 PRSK MSD HT29 EC$_{50}$ (nM) | ERK1 Mass Mod (%) | HT-29 GI$_{50}$ (nM) | HT-29 Occupancy EC$_{50}$ (nM) | p-RSK inhibition at 6 hr (%) | ERK1/ERK2 PRSK A375 EC$_{50}$ (nM) | ERK1/ERK2 PRSK HCT116 EC$_{50}$ (nM) | A375 GI$_{50}$ (nM) | HCT116 GI$_{50}$ (nM) |
|---|---|---|---|---|---|---|---|---|---|---|
| I-421 | A | B |   |   |   |   | B | B |   |   |
| I-422 | A | B |   |   |   |   | B | A |   |   |
| I-423 | D | D |   |   |   |   | D | D |   |   |
| I-424 | D | B |   |   |   |   | C | B |   |   |
| I-425 | B | B |   |   |   |   | C | C |   |   |
| I-426 | C | A |   |   |   |   | B | B |   |   |
| I-427 | B | B |   |   |   |   | B | C |   |   |
| I-428 | D |   |   |   |   |   | B | B |   |   |
| I-429 | D |   |   |   |   |   | B | C |   |   |
| I-430 | C |   |   |   |   |   | C | C |   |   |
| I-431 | C | B | E |   |   |   | B | C |   |   |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

SEQUENCE LISTING

<160> NUMBER OF SEQ ID NOS: 4

<210> SEQ ID NO 1
<211> LENGTH: 379
<212> TYPE: PRT
<213> ORGANISM: Homo sapiens

<400> SEQUENCE: 1

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
              20                  25                  30

Gly Gln Pro Phe Asp Val Gly Pro Arg Tyr Thr Gln Leu Gln Tyr Ile
              35                  40                  45

Gly Glu Gly Ala Tyr Gly Met Val Ser Ser Ala Tyr Asp His Val Arg
          50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
              85                  90                  95

His Glu Asn Val Ile Gly Ile Arg Asp Ile Leu Arg Ala Ser Thr Leu
              100                 105                 110

Glu Ala Met Arg Asp Val Tyr Ile Val Gln Asp Leu Met Glu Thr Asp
          115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
              165                 170                 175

Thr Cys Asp Leu Lys Ile Cys Asp Phe Gly Leu Ala Arg Ile Ala Asp
              180                 185                 190

Pro Glu His Asp His Thr Gly Phe Leu Thr Glu Tyr Val Ala Thr Arg
          195                 200                 205

```
Trp Tyr Arg Ala Pro Glu Ile Met Leu Asn Ser Lys Gly Tyr Thr Lys
            210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
            275                 280                 285

Lys Val Ala Trp Ala Lys Leu Phe Pro Lys Ser Asp Ser Lys Ala Leu
            290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
            340                 345                 350

Asp Asp Leu Pro Lys Glu Arg Leu Lys Glu Leu Ile Phe Gln Glu Thr
            355                 360                 365

Ala Arg Phe Gln Pro Gly Val Leu Glu Ala Pro
            370                 375

<210> SEQ ID NO 2
<211> LENGTH: 20
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Represents Cys 183 of ERK1

<400> SEQUENCE: 2

Asn Leu Leu Ile Asn Thr Thr Cys Asp Leu Lys Ile Cys Asp Phe Gly
1               5                   10                  15

Leu Ala Arg Ile
            20

<210> SEQ ID NO 3
<211> LENGTH: 360
<212> TYPE: PRT
<213> ORGANISM: Homo sapiens

<400> SEQUENCE: 3

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
        50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
```

```
                100             105             110
Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
        130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
                180                 185                 190

Tyr Arg Ala Pro Glu Ile Met Leu Asn Ser Lys Gly Tyr Thr Lys Ser
                195                 200                 205

Ile Asp Ile Trp Ser Val Gly Cys Ile Leu Ala Glu Met Leu Ser Asn
                210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
                260                 265                 270

Val Pro Trp Asn Arg Leu Phe Pro Asn Ala Asp Ser Lys Ala Leu Asp
                275                 280                 285

Leu Leu Asp Lys Met Leu Thr Phe Asn Pro His Lys Arg Ile Glu Val
                290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
                340                 345                 350

Arg Phe Gln Pro Gly Tyr Arg Ser
                355                 360

<210> SEQ ID NO 4
<211> LENGTH: 20
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Represents Cys 166 of ERK2

<400> SEQUENCE: 4

Lys Pro Ser Asn Leu Leu Leu Asn Thr Thr Cys Asp Leu Lys Ile Cys
1               5                   10                  15

Asp Phe Gly Leu
            20
```

25. A composition comprising a compound according to claim 1, and a pharmaceutically acceptable adjuvant, carrier, or vehicle.
26. The compound according to claim 2, wherein said compound is of formula VIII-a:
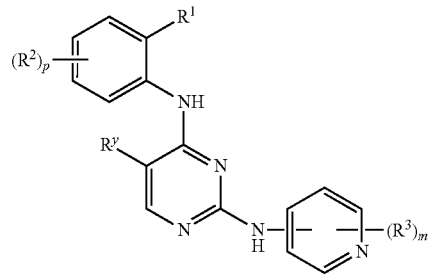
VIII-a
or a pharmaceutically acceptable salt thereof.
27. The compound according to claim 26, wherein $R^1$ is
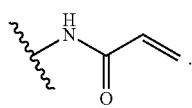
28. The compound according to claim 23, wherein $R^1$ is
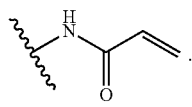

We claim:
1. A compound of formula VIII:

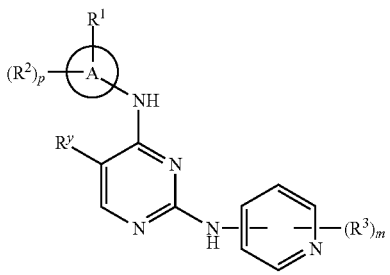

or a pharmaceutically acceptable salt thereof, wherein:
Ring A is an optionally substituted group selected from phenyl, a 3-8 membered saturated or partially unsaturated monocyclic carbocyclic ring, a 4-7 membered monocyclic heterocylic ring having 1-2 heteroatoms independently selected from nitrogen, oxygen, or sulfur, a 5-6 membered monocyclic heteroaryl ring having 1-4 heteroatoms independently selected from nitrogen, oxygen, or sulfur, or
Ring A is selected from

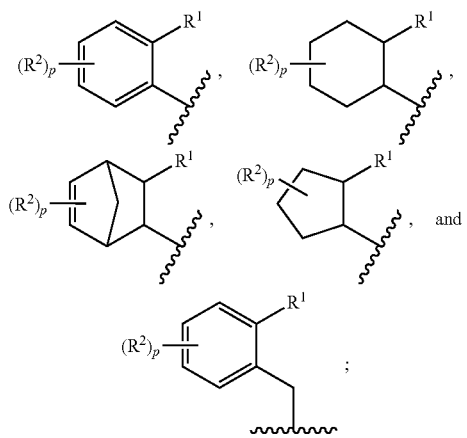

$R^1$ is a warhead group -L-Y, wherein $R^1$ is attached to an atom adjacent to where NH is attached, wherein:
L is a bivalent $C_{2-8}$ straight or branched, hydrocarbon chain wherein L has at least one double bond and one or two methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; or
L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one additional methylene unit of L is optionally replaced by cyclopropylene, —O—, —N(R)—, or —C(O)—; or
L is a bivalent $C_{2-8}$ straight or branched, hydrocarbon chain wherein L has at least one triple bond and one or two methylene units of L are optionally and independently replaced by —NRC(O)—, —C(O) NR—, —N(R)SO$_2$—, —SO$_2$N(R)—, —S—, —S(O)—, —SO$_2$—, —OC(O)—, or —C(O)O—; and Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; or L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, or —SO$_2$NH—, and Y is selected from:
(i) $C_{1-6}$ alkyl substituted with oxo, halogen, NO$_2$, or CN; or
(ii) $C_{2-6}$ alkenyl substituted with oxo, halogen, NO$_2$, or CN; or
(iii) $C_{2-6}$ alkynyl optionally substituted with oxo, halogen, NO$_2$, or CN; or
(iv) a saturated 3-4 membered heterocyclic ring having 1 heteroatom selected from oxygen or nitrogen wherein said ring is substituted with 1-2 $R^e$ groups; or
(v) a saturated 5-6 membered heterocyclic ring having 1-2 heteroatom selected from oxygen or nitrogen wherein said ring is substituted with 1-4 $R^e$ groups; or (vi)

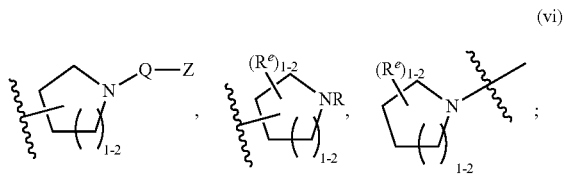

or
(vii) a saturated 3-6 membered carbocyclic ring, wherein said ring is substituted with 1-4 $R^e$ groups; or
(viii) a partially unsaturated 3-6 membered monocyclic ring having 0-3 heteroatoms independently selected from nitrogen, oxygen, or sulfur, wherein said ring is substituted with 1-4 $R^e$ groups; or
(ix) a partially unsaturated 3-6 membered carbocyclic ring, wherein said ring is substituted with 1-4 $R^e$ groups; or (x)

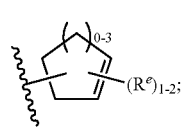

or
(xi) a partially unsaturated 4-6 membered heterocyclic ring having 1-2 heteroatoms independently selected from nitrogen, oxygen, or sulfur, wherein said ring is substituted with 1-4 $R^e$ groups; or

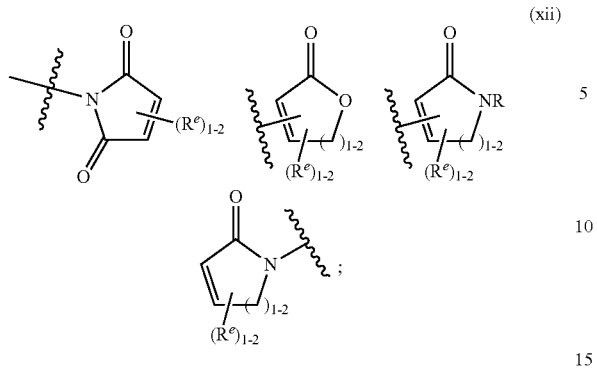

(xii)

or (xiii) a 6-membered aromatic ring having 0-2 nitrogens wherein said ring is substituted with 1-4 $R^e$ groups; or

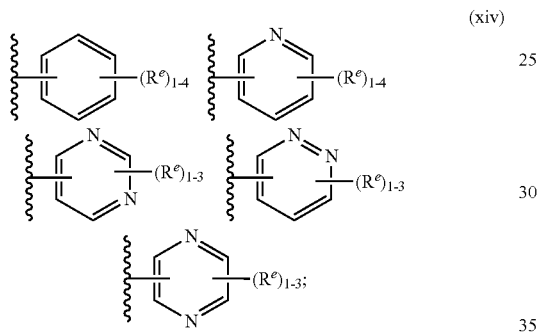

(xiv)

or (xv) a 5-membered heteroaryl ring having 1-3 heteroatoms independently selected from nitrogen, oxygen, or sulfur, wherein said ring is substituted with 1-3 $R^e$ groups; or

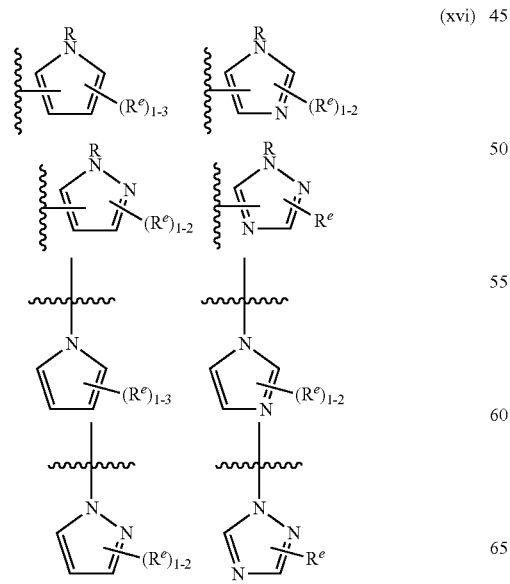

(xvi)

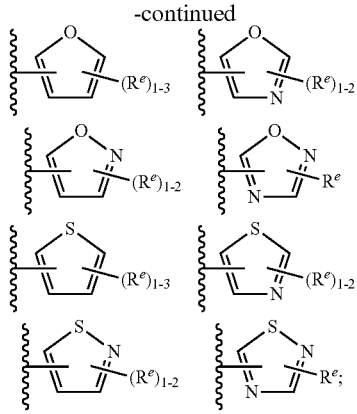

-continued or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups; or L is a covalent bond, —C(O)—, —N(R)C(O)—, or a bivalent $C_{1-8}$ saturated or unsaturated, straight or branched, hydrocarbon chain; and Y is selected from the following (i) through (xvii):

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups; or (v) a saturated 5-6 membered heterocyclic ring having 1-2 heteroatom selected from oxygen or nitrogen wherein said ring is substituted with 1-4 $R^e$ groups; or

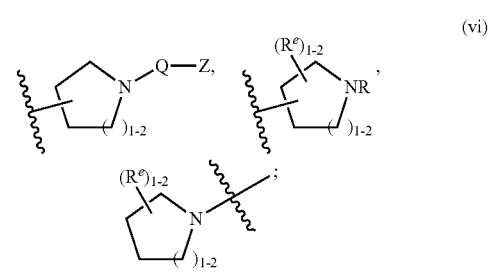

(vi)

or (vii) a saturated 3-6 membered carbocyclic ring, wherein said ring is substituted with 1-4 $R^e$ groups; or (viii) a partially unsaturated 3-6 membered monocyclic ring having 0-3 heteroatoms independently selected from nitrogen, oxygen, or sulfur, wherein said ring is substituted with 1-4 $R^e$ groups; or (ix) a partially unsaturated 3-6 membered carbocyclic ring, wherein said ring is substituted with 1-4 $R^e$ groups; or (x)

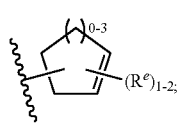

or (xi) a partially unsaturated 4-6 membered heterocyclic ring having 1-2 heteroatoms independently selected from nitrogen, oxygen, or sulfur, wherein said ring is substituted with 1-4 $R^e$ groups; or (xii)

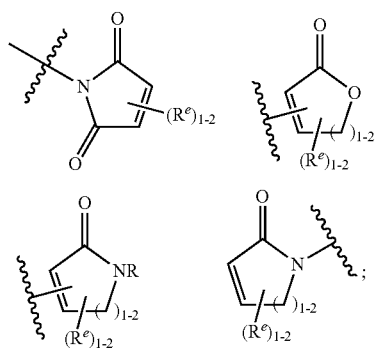

or (xiii) a 6-membered aromatic ring having 0-2 nitrogens wherein said ring is substituted with 1-4 $R^e$ groups; or (xiv)

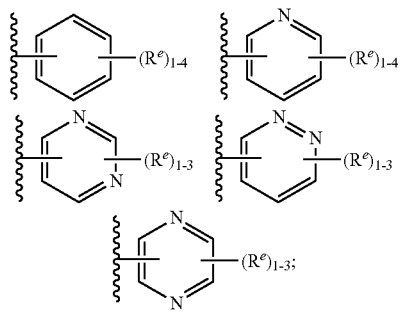

or (xv) a 5-membered heteroaryl ring having 1-3 heteroatoms independently selected from nitrogen, oxygen, or sulfur, wherein said ring is substituted with 1-3 $R^e$ groups; or (xvi)

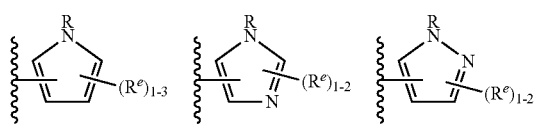

-continued

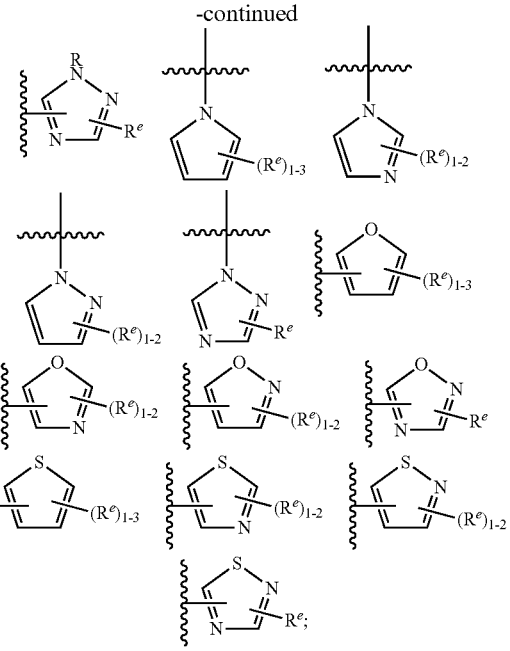

or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups;

each $R^e$ is independently selected from Q-Z, oxo, $NO_2$, halogen, CN, $C_{1-6}$ aliphatic optionally substituted with oxo, halogen, $NO_2$, or CN, or a suitable leaving group selected from alkoxy, sulphonyloxy, optionally substituted alkylsulphonyloxy, optionally substituted alkenylsulfonyloxy, optionally substituted arylsulfonyloxy, acyloxy, or diazonium, wherein:

Q is a bivalent $C_{1-6}$ saturated or unsaturated, straight or branched, hydrocarbon chain, wherein one or two methylene units of Q are optionally and independently replaced by N(R)—, —S—, —O—, —C(O)—, —OC(O)—, —C(O)O—, —SO—, —$SO_2$—, —N(R)C(O)—, —C(O)N(R)—, —N(R)$SO_2$—, or —$SO_2$N(R)—; and each Z is independently hydrogen or $C_{1-6}$ aliphatic substituted with oxo, halogen, $NO_2$, or CN;

each $R^2$ is independently hydrogen, an optionally substituted $C_{1-6}$ aliphatic, —CN, halogen, —OR, or -$L^1$-$R^x$;

each $L^1$ is a $C_{1-6}$ saturated straight or branched hydrocarbon chain wherein one or two methylene units of $L^1$ is optionally and independently replaced by -Hy-, —N($R^z$)—, —S—, —O—, —C(O)—, —OC(O)—, —C(O)O—, —SO—, or —$SO_2$—, —N($R^z$)C(O)—, —C(O)N($R^z$)—, —N($R^z$)$SO_2$—, or —$SO_2$N($R^z$)—;

each -Hy- is independently a bivalent saturated 6-membered heterocyclic ring having 1-2 nitrogens;

each $R^z$ is independently hydrogen or $C_{1-6}$ alkyl;

each $R^x$ is a 4-8 membered saturated, partially unsaturated, or heteroaromatic ring having 1-4 heteroatoms independently selected from nitrogen, oxygen, or sulfur, wherein $R^x$ is optionally substituted with 1-3 groups selected from $C_{1-6}$ alkyl, —C(O)$R^z$, —C(O)$CH_2OR^z$, —C(O)$OR^z$, —OC(O)$C_{1-6}$ alkyl, —C(O)

N(R$^z$)$_2$, —OR$^z$, —SR$^z$, —SO$_2$R$^z$, —N(R$^z$)$_2$, —N(R$^z$)C(O)R$^z$, —N(R$^z$)S(O)$_2$C$_{1-6}$ alkyl, or —SO$_2$N(R$^z$)$_2$;

each R$^3$ is independently selected from —R, —Cy, halogen, —OR, —SR, —CN, —NO$_2$, —SO$_2$NR, —SO$_2$R, —SOR, —C(O)R, —C(O)OR, —OC(O)R, —OC(O)N(R)$_2$, —C(O)N(R)$_2$, —C(O)N(R)—OR —C(O)C(O)R, —P(O)(R)$_2$, —NRC(O)OR, —NRC(O)R, —NRC(O)N(R)$_2$, —NRSO$_2$R, or —N(R)$_2$; or two R$^3$ groups on the same carbon atom together form —C(O)—, —C(S)—, or —C(N—R)—;

each R is independently hydrogen or an optionally substituted group selected from C$_{1-6}$ aliphatic, phenyl, a 3-8 membered saturated or partially unsaturated carbocyclic ring, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur; or two R groups on the same nitrogen are taken together with the nitrogen atom to which they are attached to form a 4-7 membered heterocyclic ring having 0-2 additional heteroatoms independently selected from nitrogen, oxygen, or sulfur, or a 4-7 membered heteroaryl ring having 0-4 additional heteroatoms independently selected from nitrogen, oxygen, or sulfur;

Cy is an optionally substituted 5-6 membered monocyclic heteroaryl ring having 1-4 heteroatoms independently selected from nitrogen, oxygen, or sulfur, or an optionally substituted 4-7 membered saturated or partially unsaturated heterocyclic ring having 1-3 heteroatoms independently selected from nitrogen, oxygen, or sulfur;

R$^y$ is hydrogen, optionally substituted C$_{1-6}$ aliphatic, halogen, haloalkyl, —CN, —OR, —C(O)R', —C(O)N(R')$_2$, —C(=N—R'')R' or —N(R')$_2$;

each R' is independently hydrogen or an optionally substituted C$_{1-6}$ aliphatic;

R'' is hydrogen or —OR; and m and p are each independently 0-4.

2. The compound according to claim 1, wherein said compound is any of formula VIII-a, VIII-b, VIII-c, or VIII-d:

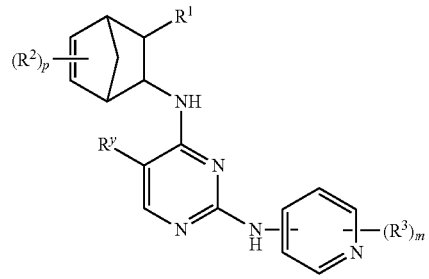

VIII-a

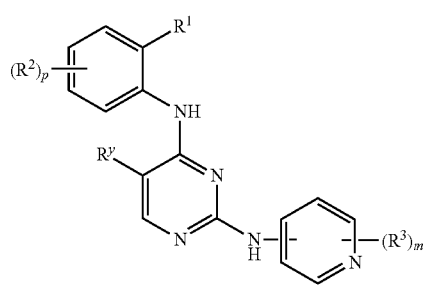

VIII-b

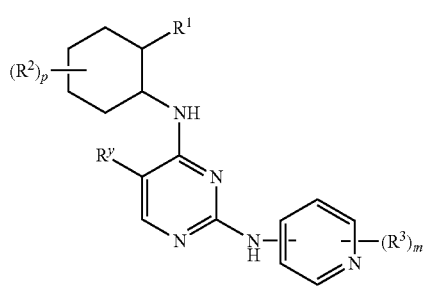

VIII-c

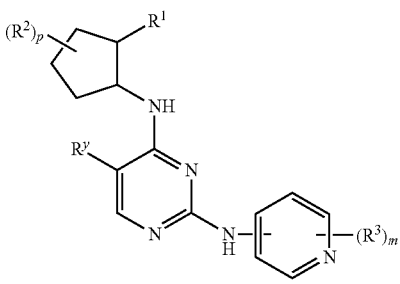

VIII-d or a pharmaceutically acceptable salt thereof.

3. The compound according to claim 1, wherein R$^y$ is haloalkyl.

4. The compound according to claim 3, wherein R$^y$ is —CF$_3$.

5. The compound according to claim 1, wherein R$^y$ is halogen.

6. The compound according to claim 5, wherein R$^y$ is —Cl.

7. The compound according claim 1, wherein at least one R$^3$ is —OMe.

8. The compound according to claim 1, wherein:

L is a bivalent C$_{2-8}$ straight or branched, hydrocarbon chain wherein L has at least one double bond and one or two methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—.

9. The compound according to claim 8, wherein:

L is a bivalent C$_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one additional methylene unit of L is optionally replaced by cyclopropylene, —O—, —N(R)—, or —C(O)—; and Y is hydrogen or C$_{1-6}$ aliphatic optionally substituted with oxo, halogen, NO$_2$, or CN.

10. The compound according to claim 9, wherein L is a bivalent C$_{2-8}$ straight or branched, hydrocarbon chain wherein L has at least one double bond and at least one methylene unit of L is replaced by —C(O)—, and one additional methylene unit of L is optionally replaced by cyclopropylene, —O—, —N(R)—, or —C(O)—.

11. The compound according to claim 1 wherein L is a bivalent C$_{2-8}$ straight or branched, hydrocarbon chain wherein L has at least one double bond and at least one methylene unit of L is replaced by —OC(O)—.

12. The compound according to claim 9, wherein L is —NRC(O)CH=CH—, —NRC(O)CH=CHCH$_2$N (CH₃)—, —NRC(O)CH=CHCH₂O—, —CH₂NRC(O)CH=CH—, —NRSO₂CH=CH—, —NRSO₂CH=CHCH₂—, or —NRC(O)C(=CH₂)CH₂—; wherein the R group of L is H or optionally substituted $C_{1-6}$ aliphatic; and wherein Y is hydrogen or $C_{1-6}$ aliphatic optionally substituted with oxo, halogen, $NO_2$, or CN.

13. The compound according to claim 12, wherein L is —NHC(O)CH=CH—, —NHC(O)CH=CHCH₂N(CH₃)—, —NHC(O)CH=CHCH₂O—, —CH₂NHC(O)CH=CH—, —NHSO₂CH=CH—, —NHSO₂CH=CHCH₂—, or —NHC(O)C(=CH₂)CH₂—.

14. The compound according to claim 1, wherein L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)SO₂—, —SO₂N(R)—, —S—, —S(O)—, —SO₂—, —OC(O)—, or —C(O)O—, and one additional methylene unit of L is optionally replaced by cyclopropylene, —O—, —N(R)—, or —C(O)—.

15. The compound according to claim 1, wherein:
L is a bivalent $C_{2-8}$ straight or branched, hydrocarbon chain wherein L has at least one triple bond and one or two methylene units of L are optionally and independently replaced by —NRC(O)—, —C(O)NR—, —N(R)SO₂—, —SO₂N(R)—, —S—, —S(O)—, —SO₂—, —OC(O)—, or —C(O)O—.

16. The compound according to claim 15, wherein Y is hydrogen or $C_{1-6}$ aliphatic optionally substituted with oxo, halogen, $NO_2$, or CN.

17. The compound according to claim 16, wherein L is —C≡C—, —CH₂—C≡C—CH₂—, or —CH₂OC(=O)C≡C—.

18. The compound according to claim 1, wherein:
L is a covalent bond, —C(O)—, —N(R)C(O)—, or a bivalent $C_{1-8}$ saturated or unsaturated, straight or branched, hydrocarbon chain.

19. The compound according to claim 1, wherein L is a covalent bond, —CH₂—, —NH—, —C(O)—, —CH₂NH—, —NHCH₂—, —NHC(O)—, —NHC(O)CH₂OC(O)—, —CH₂NHC(O)—, —NHSO₂—, —NHSO₂CH₂—, or —SO₂NH—.

20. The compound according to claim 19, wherein L is a covalent bond.

21. The compound according to claim 1, wherein Y is selected from:

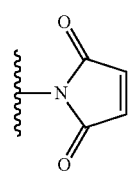
a

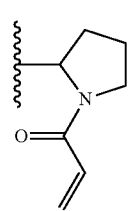
b

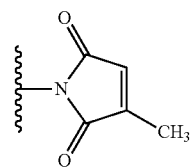
c

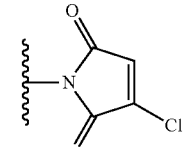
d

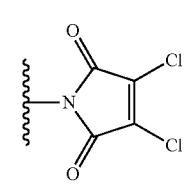
e

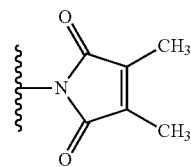
f

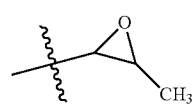
h

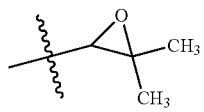
i

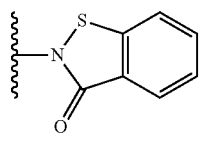
j

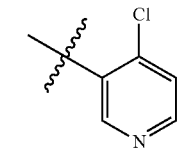
k

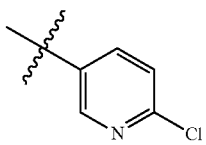
l

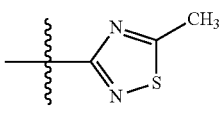
m

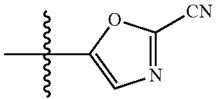
n

| 599 -continued | | 600 -continued | |
|---|---|---|---|
| 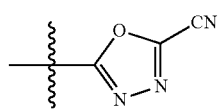 | | 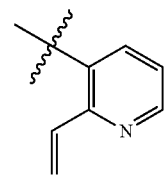 | o |
| 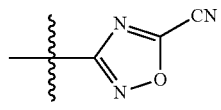 | | 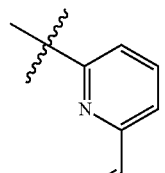 | p |
| 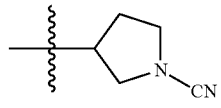 | | | q |
| 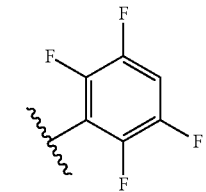 | | 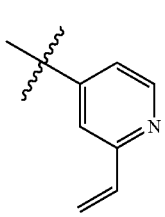 | s |
| 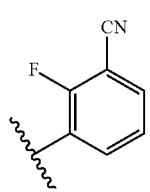 | | 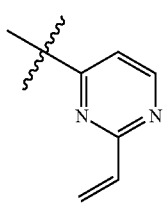 | bb |
| 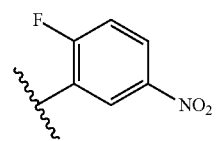 | | 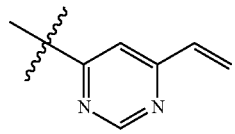 | cc |
| 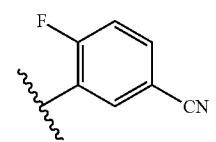 | | | t |
|  | | 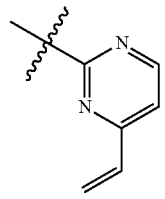 | dd |
| 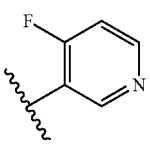 | | 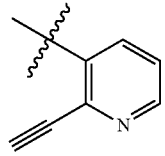 | ee |
| 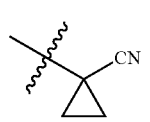 | | 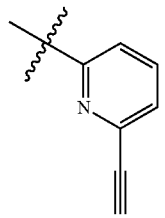 | ff |

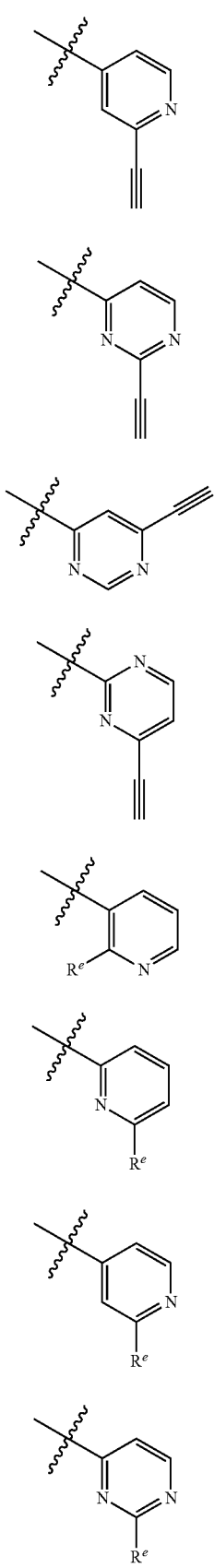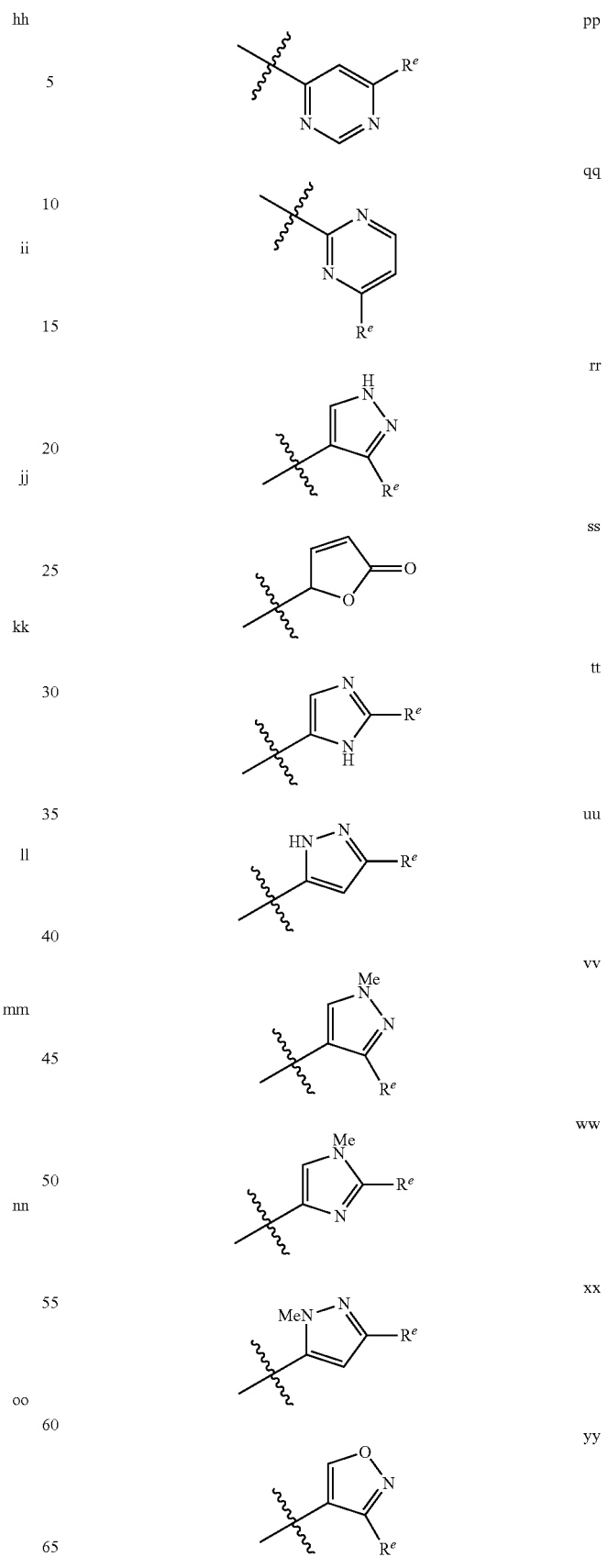

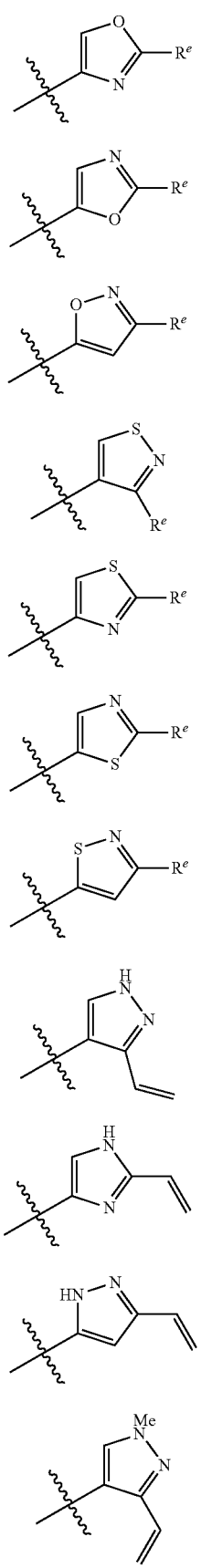
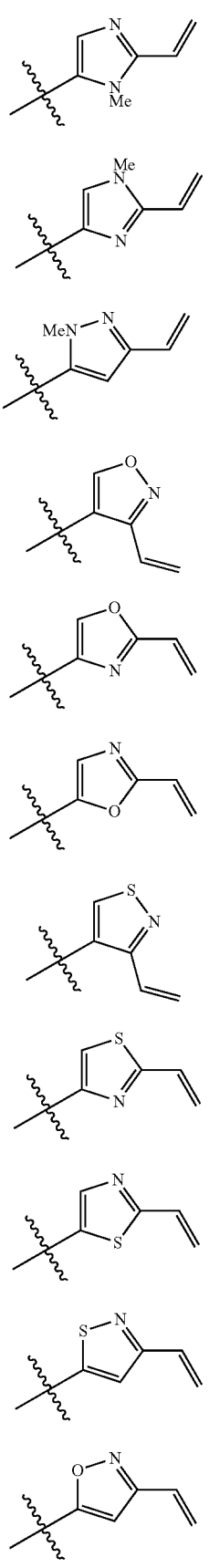

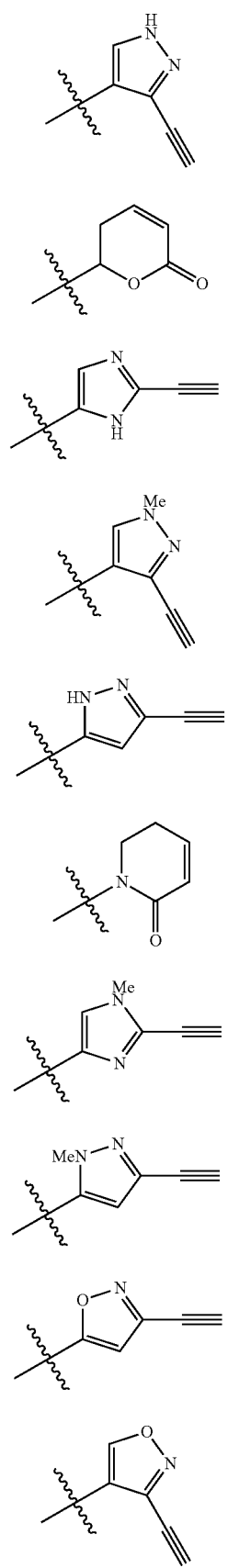
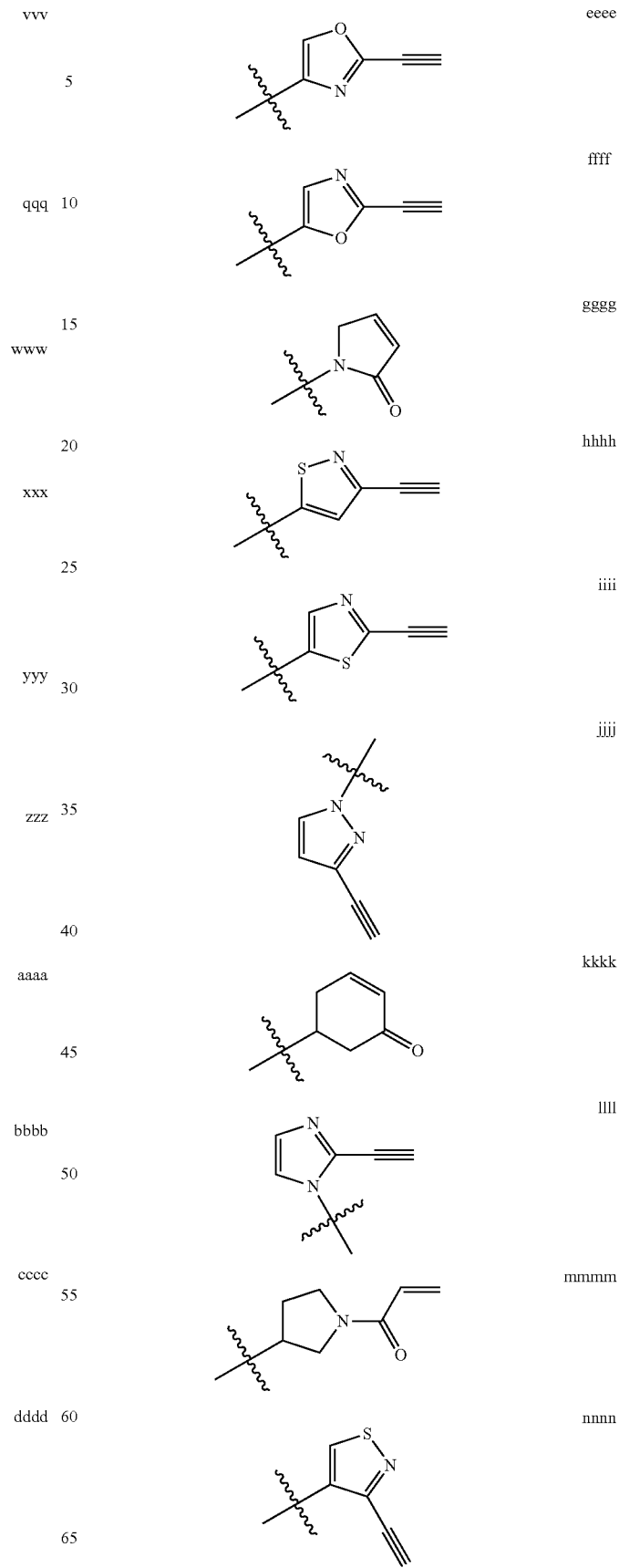

607
-continued
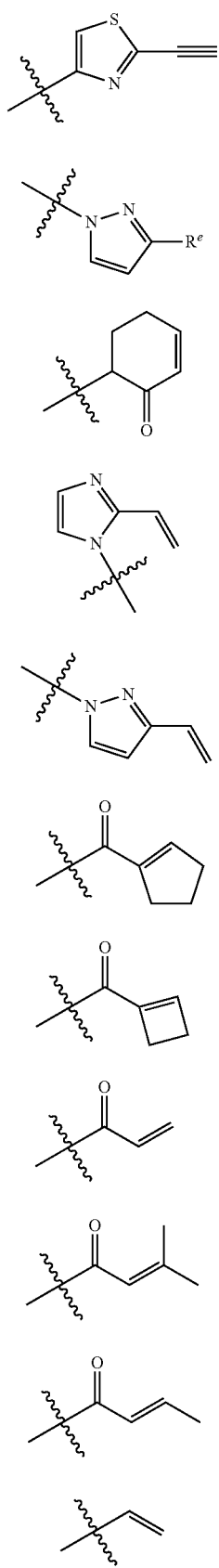
608
-continued
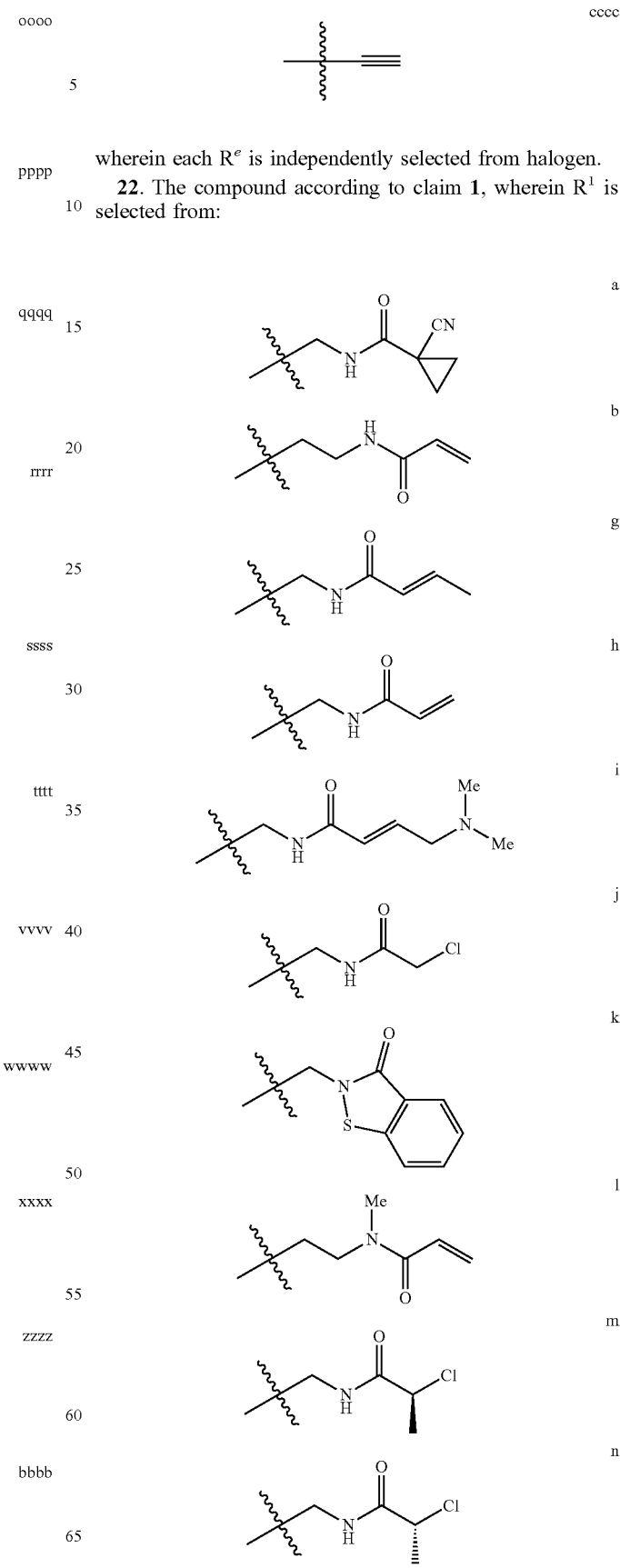
wherein each $R^e$ is independently selected from halogen.
22. The compound according to claim 1, wherein $R^1$ is selected from:

609
-continued
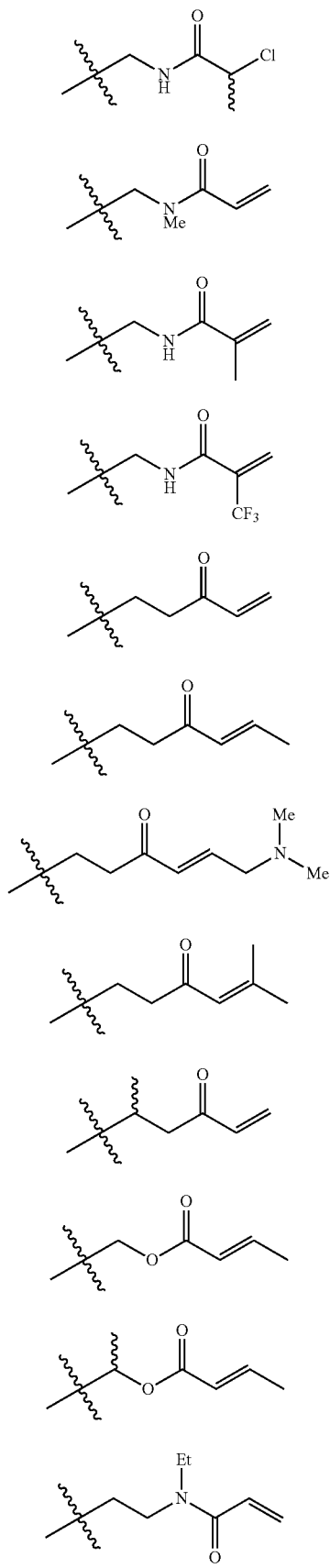
o
p
q
r
s
t
u
v
y
z
aa
bb
610
-continued
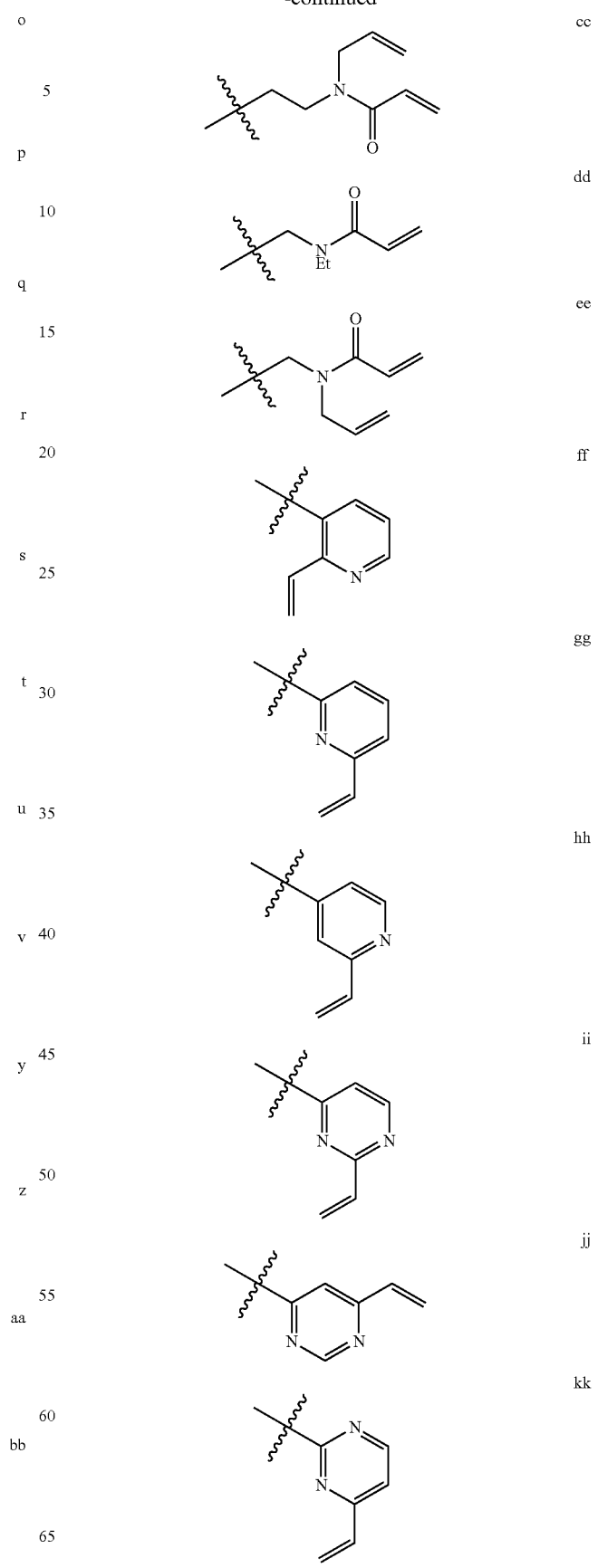
cc
dd
ee
ff
gg
hh
ii
jj
kk

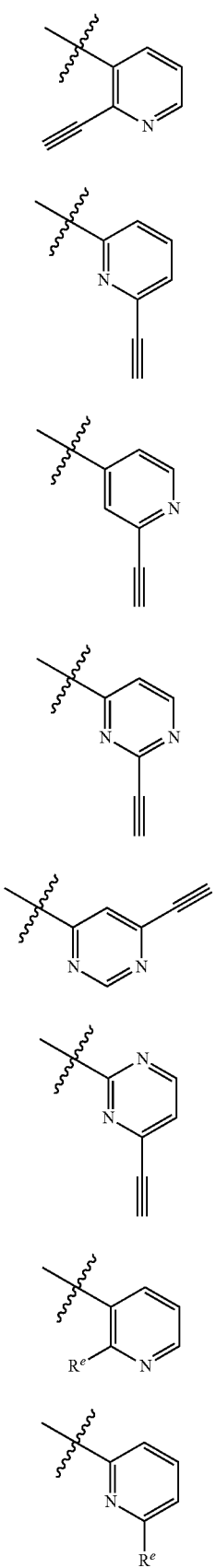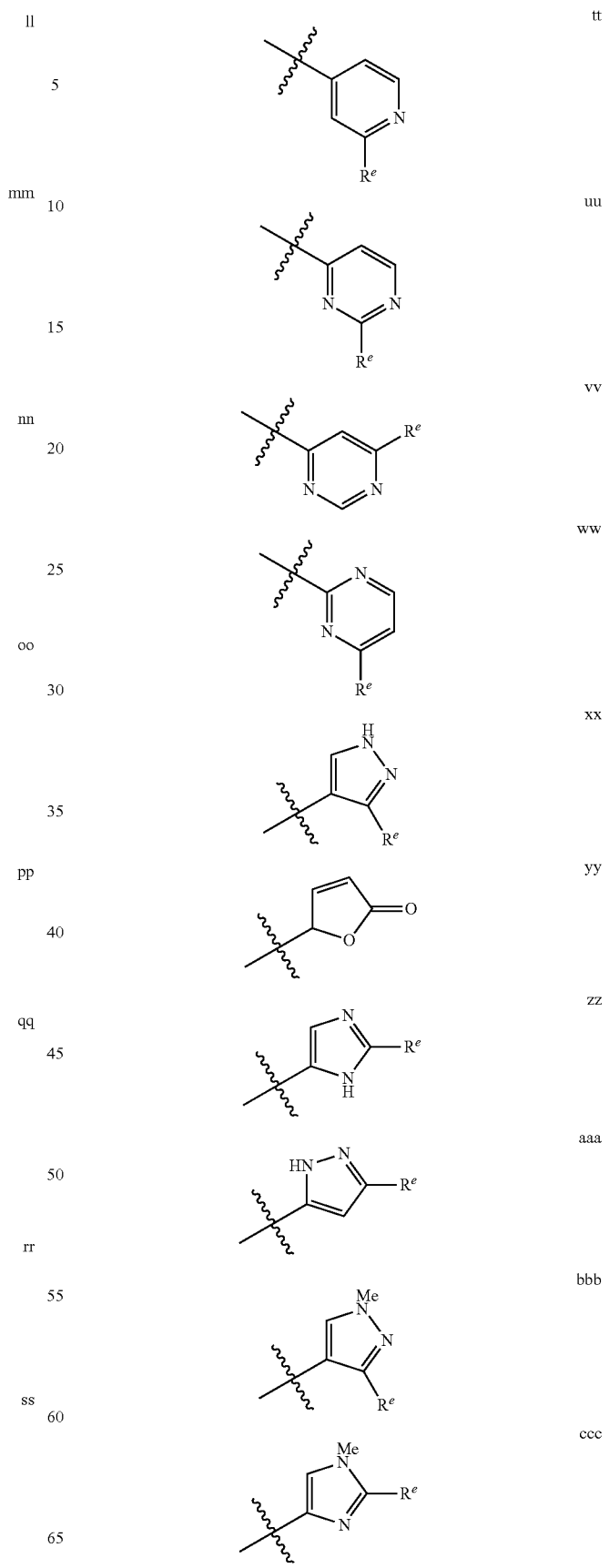

| 613 -continued | | | 614 -continued | |
|---|---|---|---|---|
| 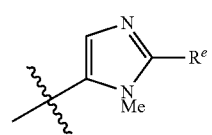 | ddd | 5 | 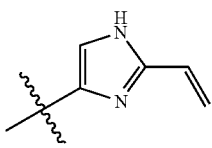 | ooo |
| 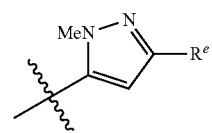 | eee | 10 | 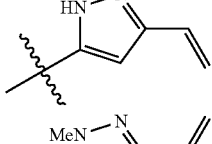 | ppp |
| 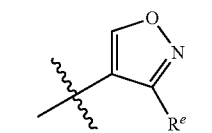 | fff | 15 | | qqq |
| 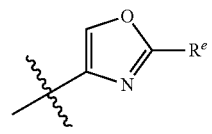 | ggg | 20 | 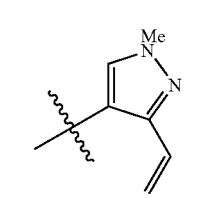 | |
| 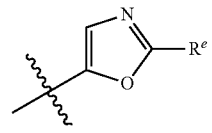 | hhh | 25 | 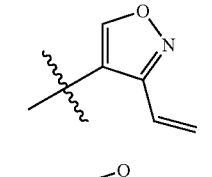 | rrr |
| 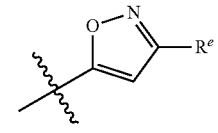 | iii | 30 35 | 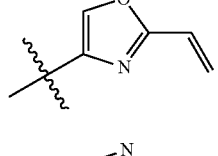 | sss |
| 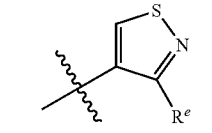 | jjj | 40 | 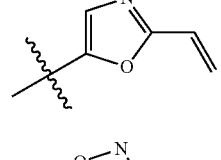 | ttt |
| 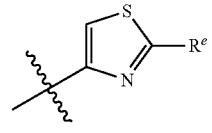 | kkk | 45 | 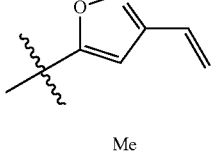 | uuu |
| 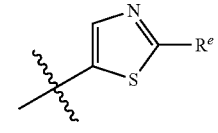 | lll | 50 | 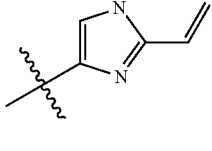 | vvv |
| 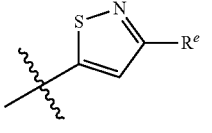 | mmm | 55 | 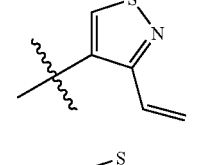 | www |
| 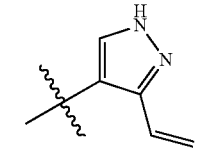 | nnn | 60 65 | | xxx |

| | | | |
|---|---|---|---|
| yyy | 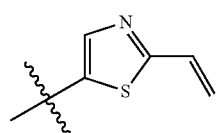 | iiii | 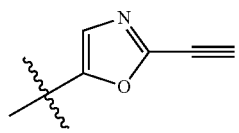 |
| zzz | 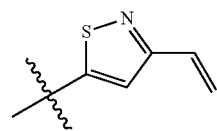 | jjjj | 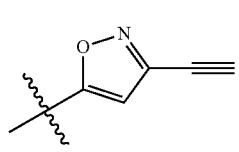 |
| aaaa | 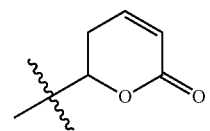 | kkkk | 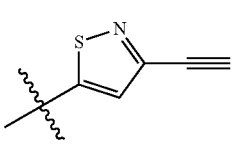 |
| bbbb | 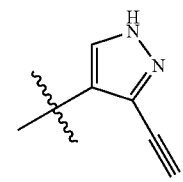 | llll | 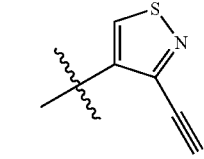 |
| cccc | 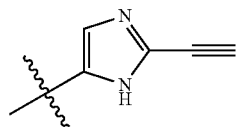 | mmmm | 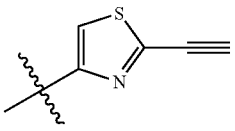 |
| dddd | 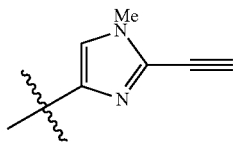 | nnnn | 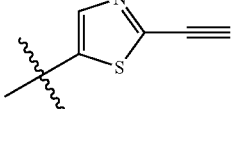 |
| eeee | 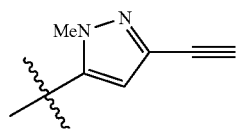 | oooo | 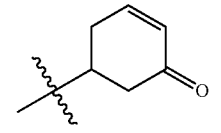 |
| ffff | 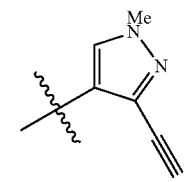 | pppp | 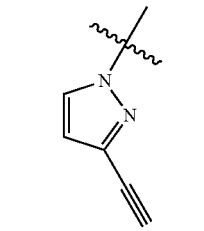 |
| gggg | 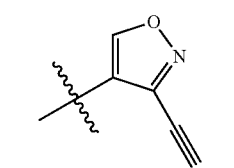 | qqqq | 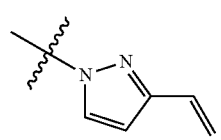 |
| hhhh | 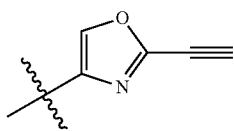 | rrrr | 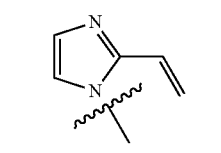 |

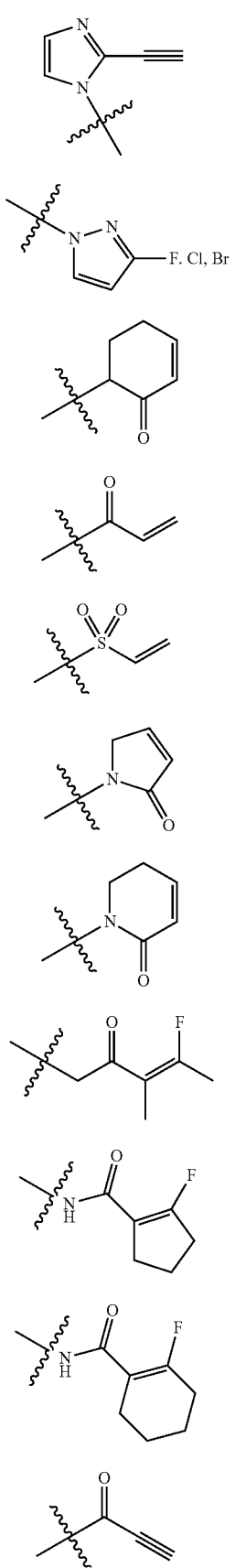
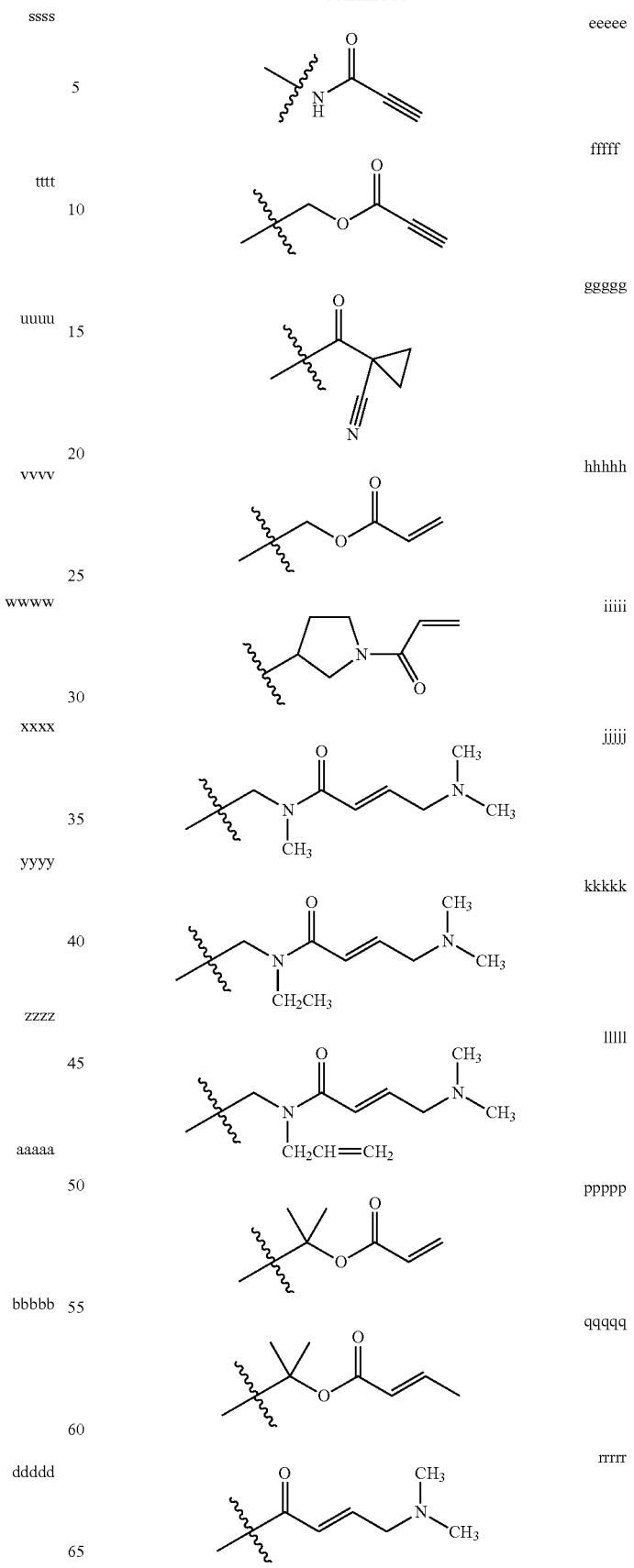

-continued
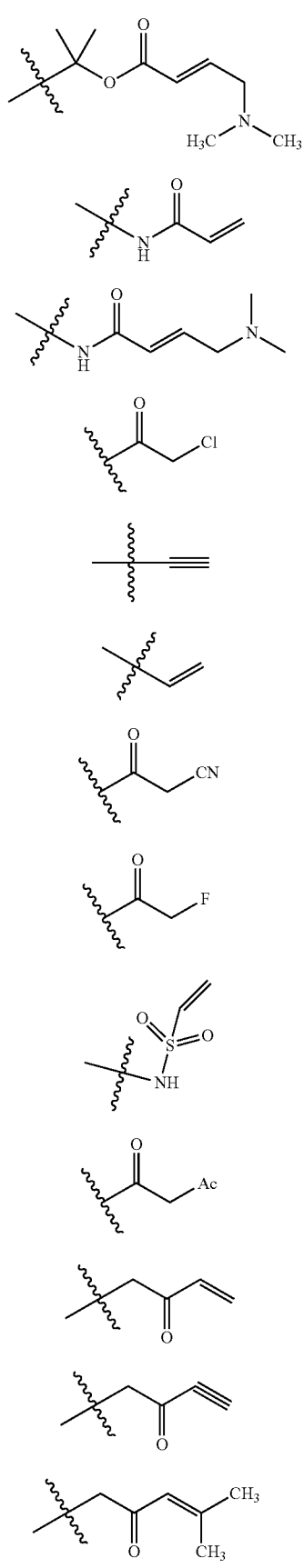
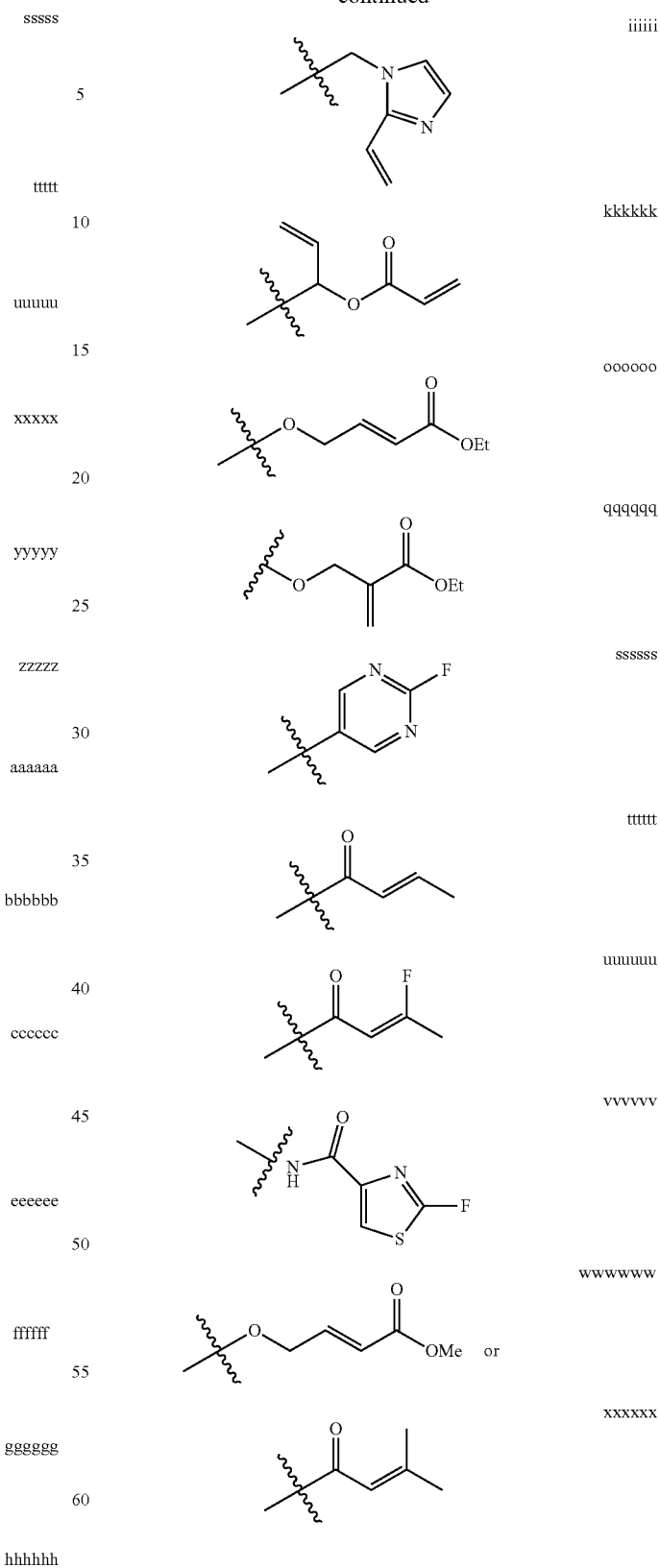
wherein each $R^e$ is independently a suitable leaving group, $NO_2$, CN, or oxo.
23. The compound according to claim 22, wherein $R^1$ is selected from:

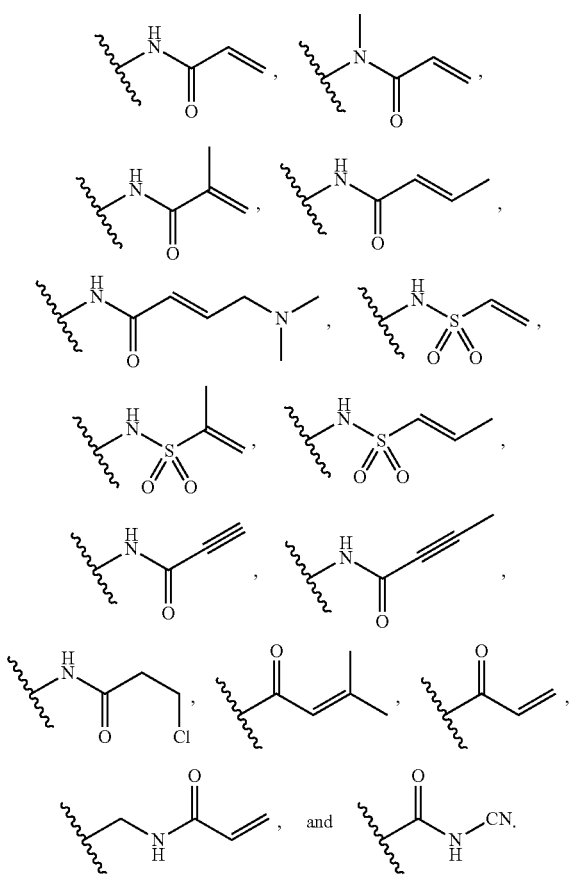
24. A compound selected from:
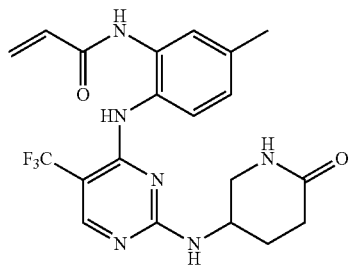
I-368
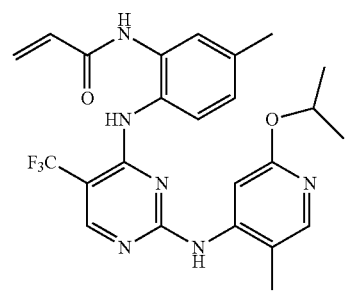
I-369
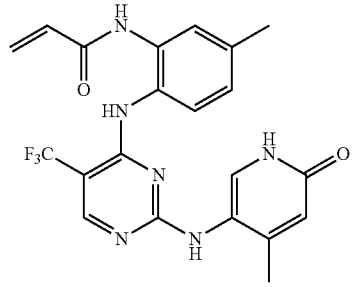
I-370
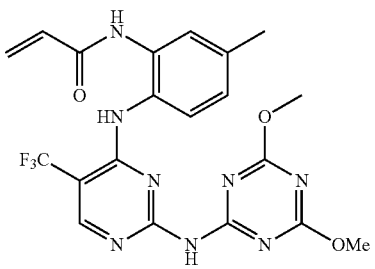
I-371
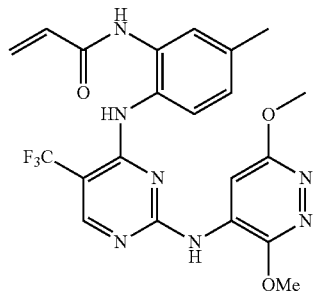
I-372
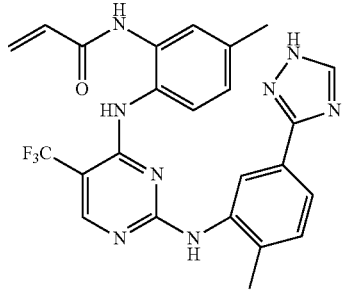
I-373
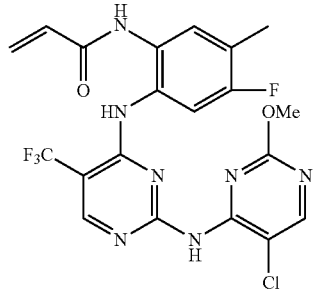
I-374

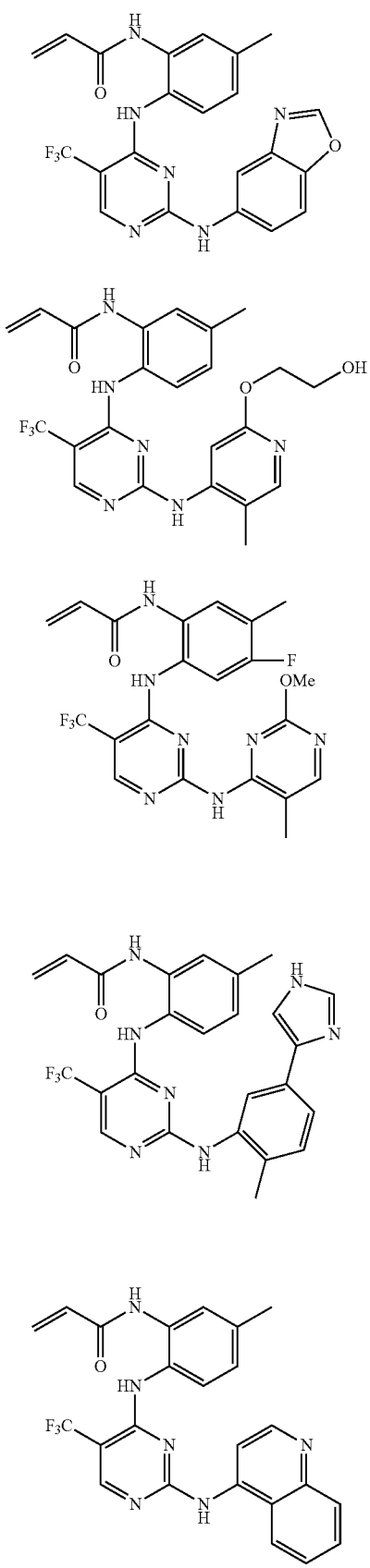
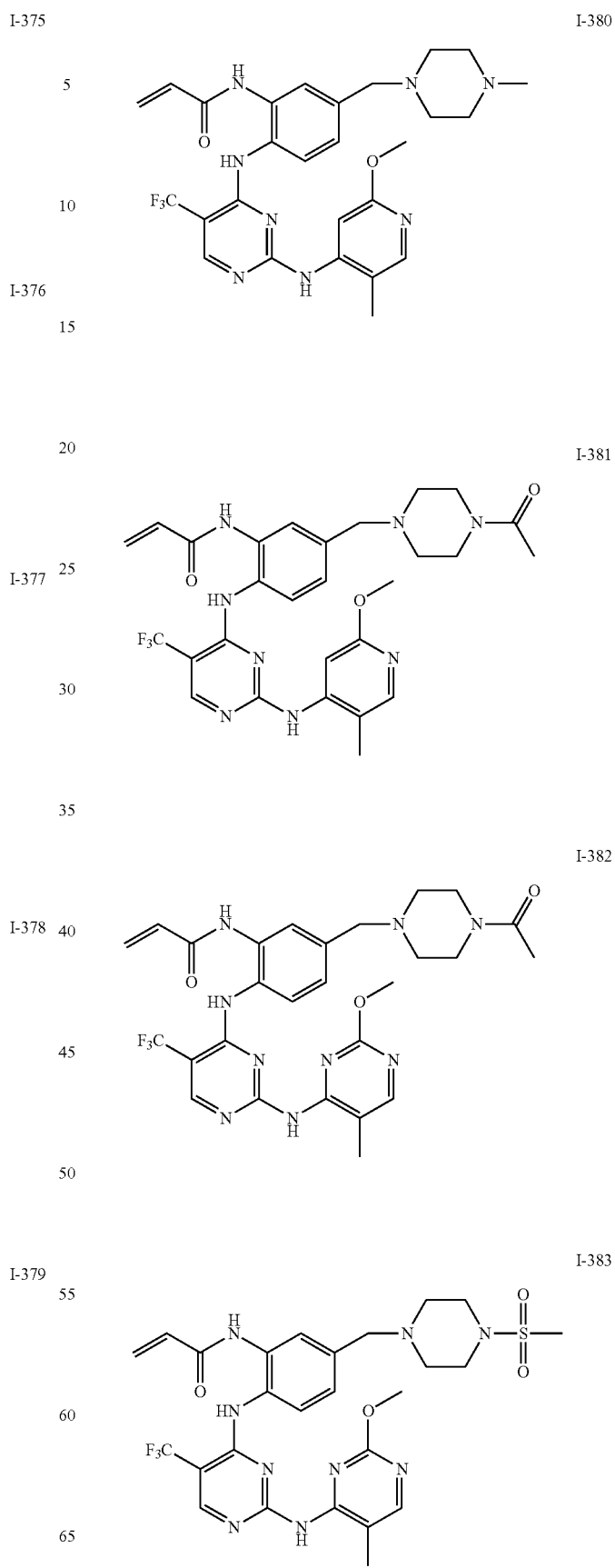

I-384
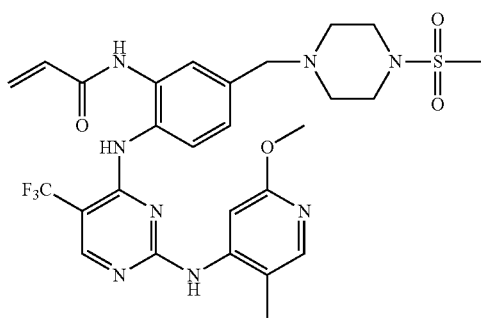
I-385
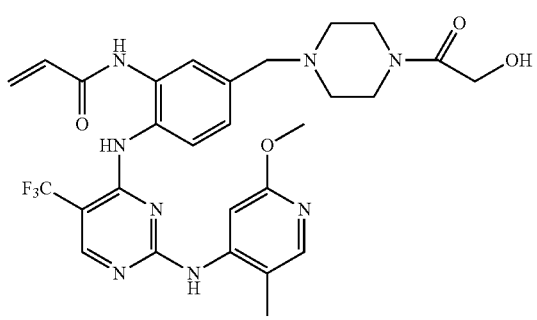
I-386
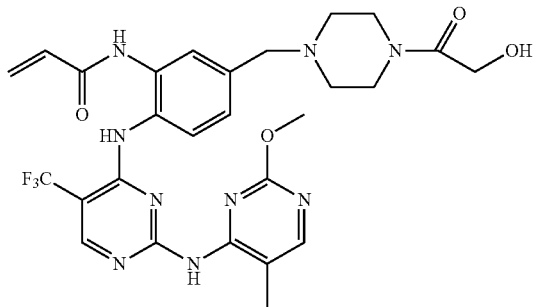
I-387
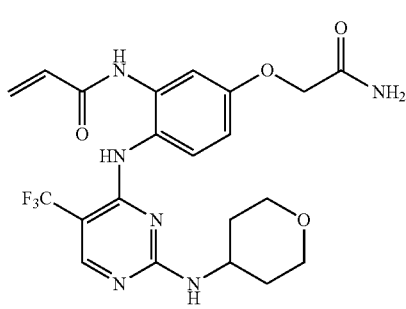
I-388
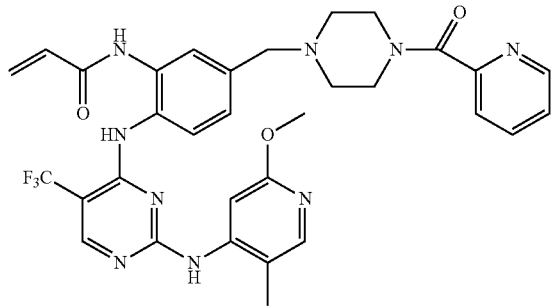
I-389
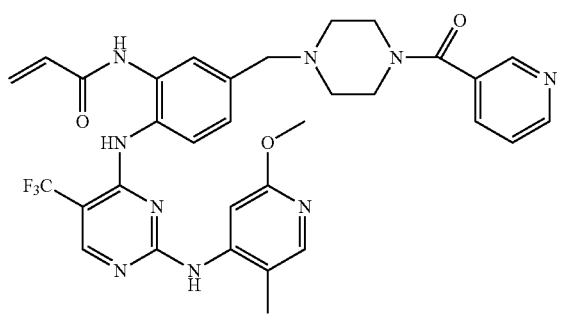
I-390
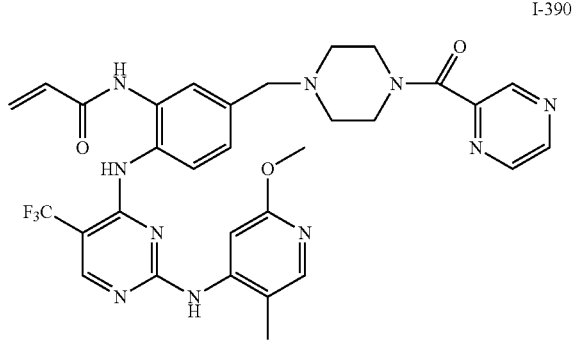 [SMILES: C=CC(=O)Nc1cc(CN2CCN(C(=O)c3cnccn3)CC2)ccc1Nc1nc(Nc2cc(OC)ncc2C)ncc1C(F)(F)F]
I-391
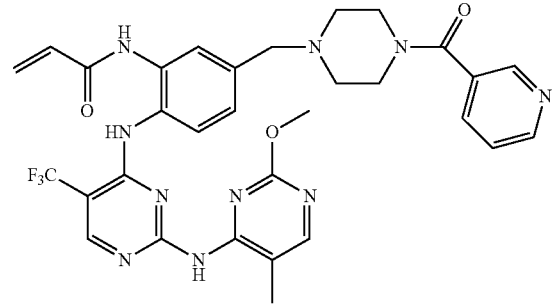
I-392

-continued
I-393
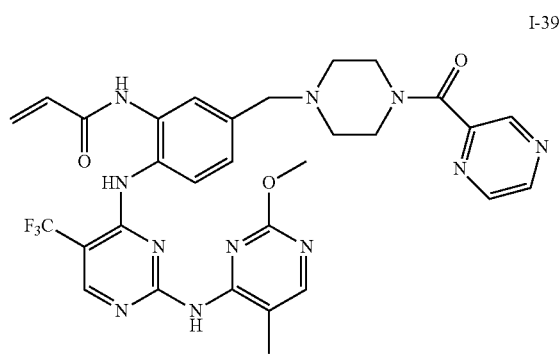 [SMILES: C=CC(=O)Nc1cc(CN2CCN(C(=O)c3ccccn3)CC2)ccc1Nc1nc(Nc2nc(OC)ncc2C)ncc1C(F)(F)F]
I-394
I-395
I-396
I-397
-continued
I-398
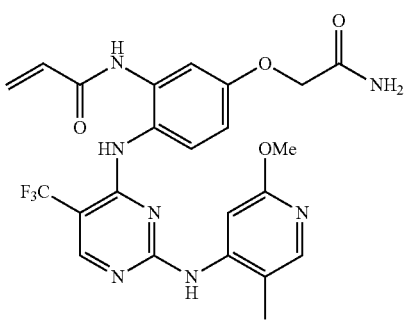
I-399
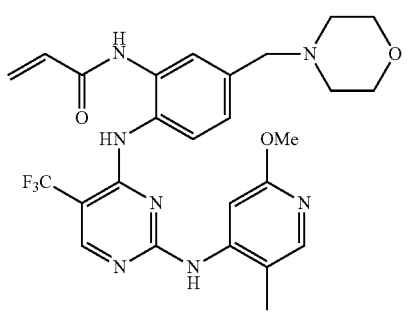
I-400
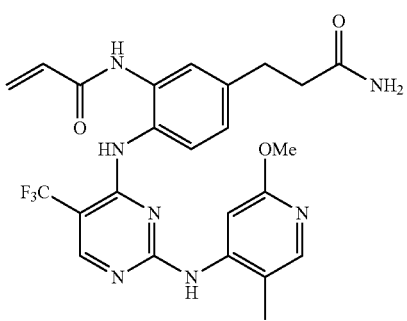
I-401
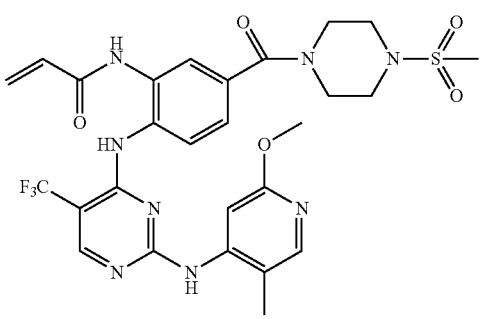
I-402
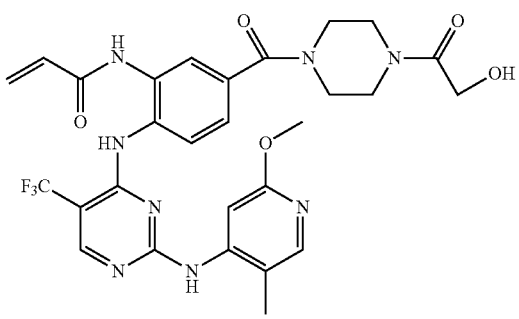

-continued
I-403
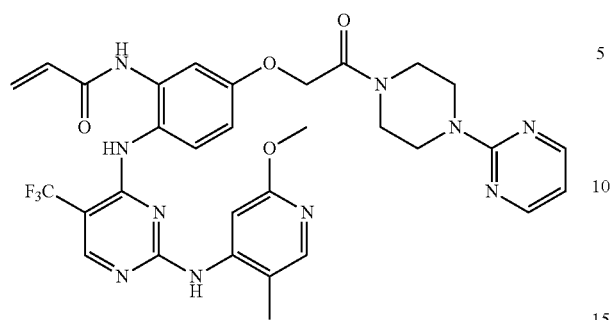
I-404
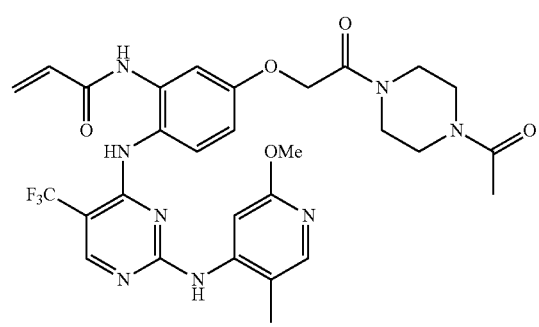
I-405
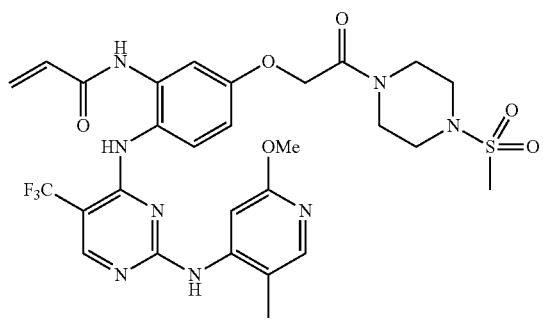
I-406
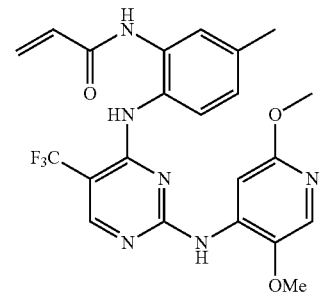
I-407
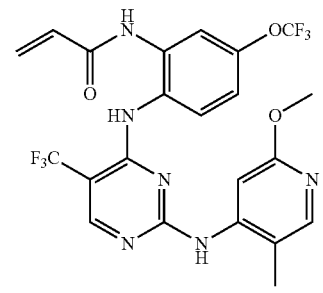
-continued
I-408
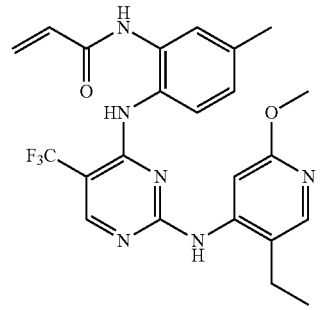
I-409
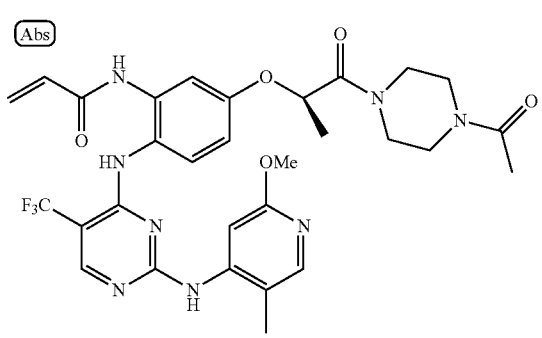
I-410
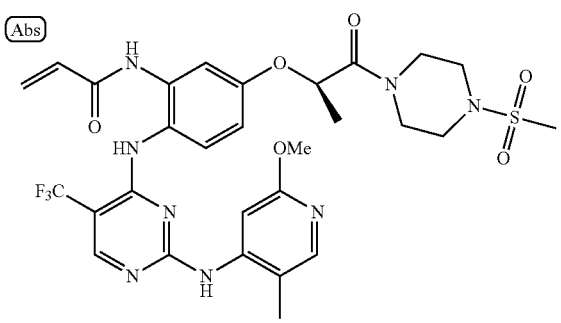
I-411
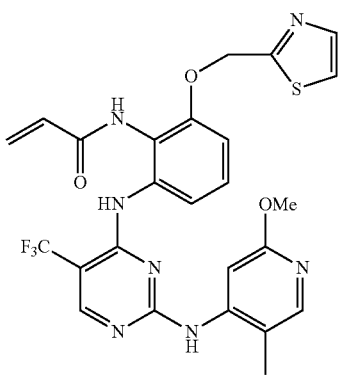

I-412
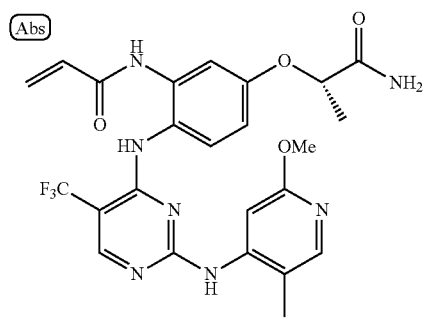
I-413
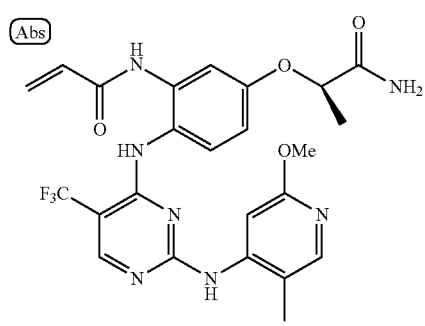
I-414
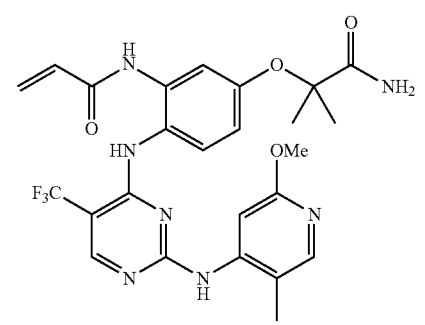
I-415
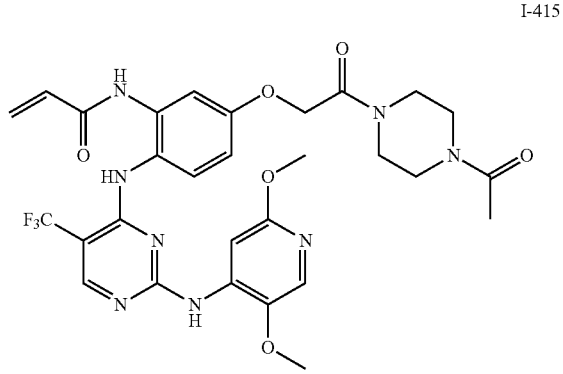 [SMILES: C=CC(=O)Nc1cc(OCC(=O)N2CCN(C(C)=O)CC2)ccc1Nc1nc(Nc2cc(OC)ncc2OC)ncc1C(F)(F)F]
I-416
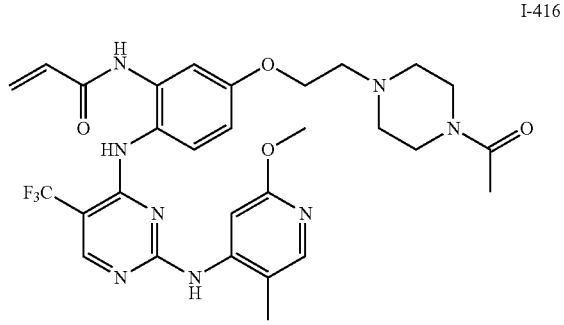 [SMILES: C=CC(=O)Nc1cc(OCCN2CCN(C(C)=O)CC2)ccc1Nc1nc(Nc2cc(OC)ncc2C)ncc1C(F)(F)F]
I-417
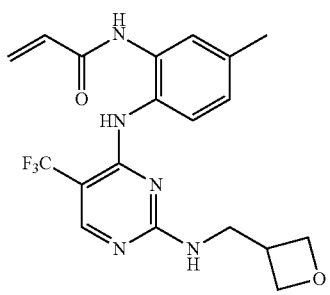
I-418
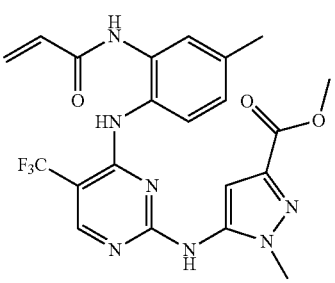
I-419
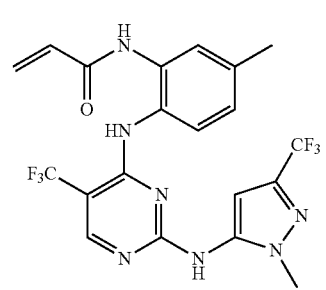
I-420
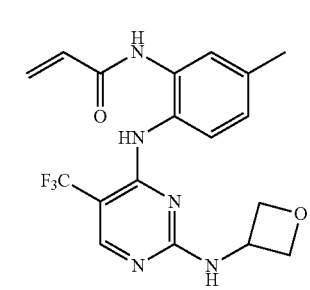
I-421
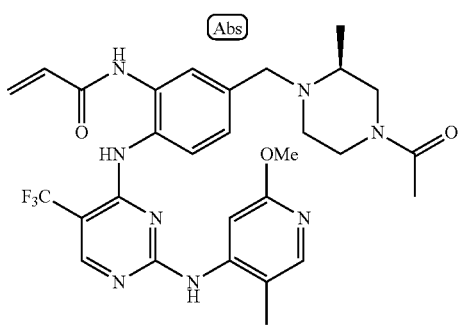

I-422
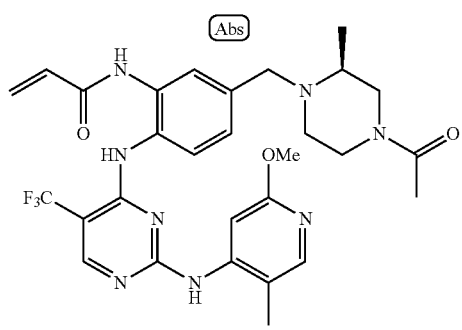
I-423
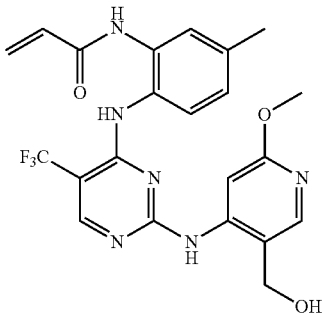
I-424
I-425
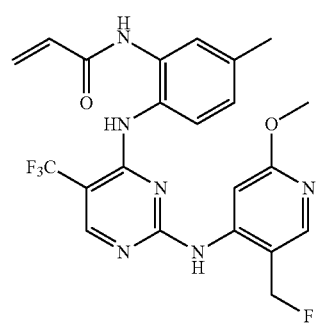
I-426
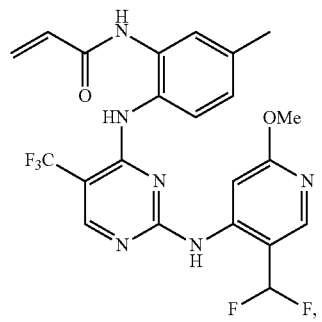
I-427
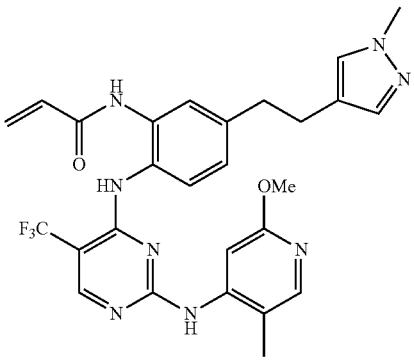
I-428
I-429
I-430
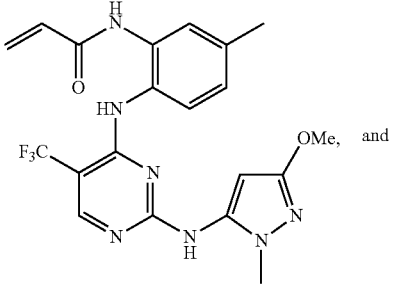
and
I-431
or a pharmaceutically acceptable salt thereof.